US012686692B2

(12) United States Patent
Wang et al.

(10) Patent No.: US 12,686,692 B2
(45) Date of Patent: Jul. 21, 2026

(54) KRas G12D INHIBITORS

(71) Applicants: Mirati Therapeutics, Inc., Princeton, NJ (US); Array BioPharma Inc., Boulder, CO (US)

(72) Inventors: Xiaolun Wang, San Diego, CA (US); Matthew Arnold Marx, San Diego, CA (US); Shelley Allen, Loveland, CO (US); Mark Joseph Chicarelli, Boulder, CO (US); Joshua Ryan Dahlke, Longmont, CO (US); Donghua Dai, Superior, CO (US); Jay Bradford Fell, Longmont, CO (US); John Peter Fischer, Longmont, CO (US); Michael Christopher Hilton, Fort Collins, CO (US); Dean Russell Kahn, Boulder, CO (US); Macedonio Junior Mejia, Denver, CO (US); Phong Nguyen, Boulder, CO (US); Spencer Pajk, Boulder, CO (US); Martha E. Rodriguez, Boulder, CO (US); Pavel Yu Savechenkov, Boulder, CO (US); Tony Pisal Tang, Boulder, CO (US)

(73) Assignees: MIRATI THERAPEUTICS, INC., Princeton, NJ (US); ARRAY BIOPHARMA INC., Boulder, CO (US)

( * ) Notice: Subject to any disclaimer, the term of this patent is extended or adjusted under 35 U.S.C. 154(b) by 560 days.

(21) Appl. No.: 18/027,300

(22) PCT Filed: Sep. 21, 2021

(86) PCT No.: PCT/US2021/051315

§ 371 (c)(1),
(2) Date: Mar. 20, 2023

(87) PCT Pub. No.: WO2022/066646

PCT Pub. Date: Mar. 31, 2022

(65) Prior Publication Data

US 2023/0357277 A1 Nov. 9, 2023

Related U.S. Application Data

(60) Provisional application No. 63/081,757, filed on Sep. 22, 2020.

(51) Int. Cl.
*C07D 519/00* (2006.01)
*A61P 35/00* (2006.01)

(52) U.S. Cl.
CPC ............ *C07D 519/00* (2013.01); *A61P 35/00* (2018.01)

(58) Field of Classification Search
CPC .................................................... C07D 519/00
See application file for complete search history.

(56) References Cited

U.S. PATENT DOCUMENTS

| | | | | |
|---|---|---|---|---|
| 6,924,284 B2 | 8/2005 | Beaton et al. | | |
| 8,163,763 B2 | 4/2012 | Bergeron et al. | | |
| 8,426,401 B2 | 4/2013 | Bian et al. | | |
| 9,562,019 B2 | 2/2017 | Djaballah et al. | | |
| 9,840,516 B2 | 12/2017 | Li et al. | | |
| 10,125,134 B2 * | 11/2018 | Blake | C07D 519/00 | |
| 10,633,381 B2 * | 4/2020 | Blake | C07D 519/00 | |
| 11,267,812 B2 * | 3/2022 | Fischer | C07D 471/04 | |
| 11,999,753 B2 * | 6/2024 | Wang | C07D 519/00 | |
| 12,421,253 B2 * | 9/2025 | Wang | C07D 519/00 | |
| 2003/0191143 A1 | 10/2003 | Pitts et al. | | |
| 2006/0229307 A1 | 10/2006 | Blurton et al. | | |
| 2007/0021445 A1 | 1/2007 | Berthel et al. | | |
| 2009/0312342 A1 | 12/2009 | Wilson et al. | | |
| 2010/0081654 A1 | 4/2010 | Stockwell et al. | | |
| 2011/0269244 A1 | 11/2011 | Petter et al. | | |
| 2013/0029978 A1 | 1/2013 | Kamino et al. | | |
| 2014/0288045 A1 | 9/2014 | Ren et al. | | |
| 2015/0175558 A1 | 6/2015 | Stockwell et al. | | |
| 2015/0239900 A1 | 8/2015 | Li et al. | | |
| 2016/0031898 A1 | 2/2016 | Ren et al. | | |
| 2016/0108019 A1 | 4/2016 | Li et al. | | |
| 2016/0166571 A1 | 6/2016 | Janes et al. | | |
| 2016/0229836 A1 | 8/2016 | Stockwell et al. | | |
| 2016/0264627 A1 | 9/2016 | Henning et al. | | |
| 2016/0297774 A1 | 10/2016 | Li et al. | | |
| 2017/0022184 A1 | 1/2017 | Li et al. | | |

(Continued)

FOREIGN PATENT DOCUMENTS

| | | | |
|---|---|---|---|
| CN | 113999226 A | 2/2022 | |
| WO | 02/053558 A1 | 7/2002 | |

(Continued)

OTHER PUBLICATIONS

Figueras, A. et al., "The impact of KRAS mutations on VEGF-A production and tumour vascular network", BMC Cancer 2013, 13:125.
Janes, M. et al., "Targeting KRAS Mutant Cancers with a Covalent G12C-Specific Inhibitor", 2018, Cell 172, 578-589, Jan. 25, 2018, Elsevier Inc.
Matikas, A. et al., "Targeting KRAS mutated non-small cell lung cancer: A history of failures and a future of hope for a diverse entity", Cretical Reviews in Oncology/Hematology 110 (2017) 1-12, Elsevier Ireland Ltd.

(Continued)

*Primary Examiner* — John S Kenyon
*Assistant Examiner* — Rehana Ismail
(74) *Attorney, Agent, or Firm* — Mintz, Levin, Cohn, Ferris, Glovsky and Popeo, P.C.

(57) ABSTRACT

The present invention relates to compounds that inhibit KRas G12D. In particular, the present invention relates to compounds that inhibit the activity of KRas G12D, pharmaceutical compositions comprising the compounds and methods of use therefor.

22 Claims, No Drawings

(56) References Cited

U.S. PATENT DOCUMENTS

| | | | |
|---|---|---|---|
| 2017/0115303 | A1 | 4/2017 | Cravatt et al. |
| 2017/0190672 | A1 | 7/2017 | Mani et al. |
| 2017/0197945 | A1 | 7/2017 | Li et al. |
| 2017/0275289 | A1 | 9/2017 | Albrecht et al. |
| 2018/0015087 | A1 | 1/2018 | Liu et al. |
| 2018/0072723 | A1 | 3/2018 | Blake et al. |
| 2018/0118757 | A1 | 5/2018 | Li et al. |
| 2018/0118761 | A1 | 5/2018 | Sebti et al. |
| 2018/0127396 | A1 | 5/2018 | Li et al. |
| 2018/0141927 | A1 | 5/2018 | Li et al. |
| 2018/0155348 | A1 | 6/2018 | Li et al. |
| 2018/0162812 | A1 | 6/2018 | Ren et al. |
| 2018/0177767 | A1 | 6/2018 | Lanman et al. |
| 2018/0194748 | A1 | 7/2018 | Li et al. |
| 2018/0201610 | A1 | 7/2018 | Tao et al. |
| 2018/0273515 | A1 | 9/2018 | Li et al. |
| 2018/0273523 | A1 | 9/2018 | Li et al. |
| 2018/0273577 | A1 | 9/2018 | Revenko et al. |
| 2018/0282307 | A1 | 10/2018 | Li et al. |
| 2018/0282308 | A1 | 10/2018 | Li et al. |
| 2018/0289683 | A1 | 10/2018 | Mccormick et al. |
| 2019/0144444 | A1 | 5/2019 | Blake et al. |
| 2019/0374542 | A1 | 12/2019 | Allen et al. |
| 2020/0069657 | A1 | 3/2020 | Lanman et al. |
| 2020/0262837 | A1 | 8/2020 | Marx et al. |
| 2020/0331911 | A1 | 10/2020 | Marx et al. |
| 2020/0399297 | A1 | 12/2020 | Campbell et al. |
| 2021/0024501 | A1 | 1/2021 | Liansheng et al. |
| 2021/0139517 | A1 | 5/2021 | Gill et al. |

FOREIGN PATENT DOCUMENTS

| | | | |
|---|---|---|---|
| WO | 02/087513 | A2 | 11/2002 |
| WO | 2007/146122 | A2 | 12/2007 |
| WO | 2008/009078 | A2 | 1/2008 |
| WO | 2009/047255 | A1 | 4/2009 |
| WO | 2010/014939 | A1 | 2/2010 |
| WO | 2010/120996 | A1 | 10/2010 |
| WO | 2013/155223 | A1 | 10/2013 |
| WO | 2014/143659 | A1 | 9/2014 |
| WO | 2014/152588 | A1 | 9/2014 |
| WO | 2016/049568 | A1 | 3/2015 |
| WO | 2015/054572 | A1 | 4/2015 |
| WO | 2016/025650 | A1 | 2/2016 |
| WO | 2016/044772 | A1 | 3/2016 |
| WO | 2016/049565 | A1 | 3/2016 |
| WO | 2016130460 | A2 | 8/2016 |
| WO | 2016/164675 | A1 | 10/2016 |
| WO | 2016/168540 | A1 | 10/2016 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/079864 | A1 | 5/2017 |
| WO | 2017/080980 | A1 | 5/2017 |
| WO | 2017/087528 | A1 | 5/2017 |
| WO | 2017/100546 | A1 | 6/2017 |
| WO | 2017201161 | A1 | 11/2017 |
| WO | 2018/064510 | A1 | 4/2018 |
| WO | 2018/068017 | A1 | 4/2018 |
| WO | 2018/102452 | A2 | 6/2018 |
| WO | 2018/102453 | A1 | 6/2018 |
| WO | 2018/112420 | A1 | 6/2018 |
| WO | 2018/115380 | A1 | 6/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/195439 | A2 | 10/2018 |
| WO | 2018218070 | A2 | 11/2018 |
| WO | 2019/051291 | A1 | 3/2019 |
| WO | 2019099524 | A1 | 5/2019 |
| WO | 202063594 | | 4/2020 |
| WO | 202098488 | | 5/2020 |
| WO | 2020097537 | A2 | 5/2020 |
| WO | 2020118066 | A1 | 6/2020 |
| WO | 2020146613 | A1 | 7/2020 |
| WO | 202027202 | | 8/2020 |
| WO | 2020163598 | | 8/2020 |
| WO | 2020165670 | | 8/2020 |
| WO | 2020169838 | | 8/2020 |
| WO | 2020171499 | | 8/2020 |
| WO | 2020172332 | | 8/2020 |
| WO | 2020123395 | A1 | 9/2020 |
| WO | 2020176693 | | 9/2020 |
| WO | 2020176963 | | 9/2020 |
| WO | 2020177629 | | 9/2020 |
| WO | 2020178282 | | 9/2020 |
| WO | 2020181142 | | 9/2020 |
| WO | 2020198125 | | 10/2020 |
| WO | 2020204359 | | 10/2020 |
| WO | 2020205473 | | 10/2020 |
| WO | 2020205486 | | 10/2020 |
| WO | 2020212895 | | 10/2020 |
| WO | 2020214537 | | 10/2020 |
| WO | 2020221239 | | 11/2020 |
| WO | 2020230028 | | 11/2020 |
| WO | 2020230091 | | 11/2020 |
| WO | 2020231806 | | 11/2020 |
| WO | 2020231808 | | 11/2020 |
| WO | 2020232130 | | 11/2020 |
| WO | 2020233592 | | 11/2020 |
| WO | 2020234103 | | 11/2020 |
| WO | 2020236940 | | 11/2020 |
| WO | 2020236947 | | 11/2020 |
| WO | 2020236948 | | 11/2020 |
| WO | 2020247914 | | 12/2020 |
| WO | 2020252336 | | 12/2020 |
| WO | 2020252353 | | 12/2020 |
| WO | 2021000885 | | 1/2021 |
| WO | 2021023154 | | 2/2021 |
| WO | 2021023247 | | 2/2021 |
| WO | 2021027911 | | 2/2021 |
| WO | 2021027943 | | 2/2021 |
| WO | 2021031952 | | 2/2021 |
| WO | 2021034992 | | 2/2021 |
| WO | 2021037018 | | 3/2021 |
| WO | 2021041671 | | 3/2021 |
| WO | 2021043322 | | 3/2021 |
| WO | 2021045279 | | 3/2021 |
| WO | 2021050732 | | 3/2021 |
| WO | 2021051034 | | 3/2021 |
| WO | 2021052499 | | 3/2021 |
| WO | 2021055728 | | 3/2021 |
| WO | 2021057832 | | 4/2021 |
| WO | 2021058018 | | 4/2021 |
| WO | 2021061515 | | 4/2021 |
| WO | 2021061749 | | 4/2021 |
| WO | 2021063346 | | 4/2021 |
| WO | 2021068898 | | 4/2021 |
| WO | 2021075147 | | 4/2021 |
| WO | 2021076655 | | 4/2021 |
| WO | 2021078285 | | 4/2021 |
| WO | 2021078312 | | 4/2021 |
| WO | 2021080359 | | 4/2021 |
| WO | 2021081212 | | 4/2021 |
| WO | 2021083167 | | 5/2021 |
| WO | 2021084765 | | 5/2021 |
| WO | 2021085653 | | 5/2021 |
| WO | 2021086833 | | 5/2021 |
| WO | 2021088458 | | 5/2021 |
| WO | 2021088938 | | 5/2021 |
| WO | 2021091956 | | 5/2021 |
| WO | 2021091967 | | 5/2021 |
| WO | 2021091982 | | 5/2021 |
| WO | 2021093758 | A1 | 5/2021 |

(56) References Cited

FOREIGN PATENT DOCUMENTS

| | | | |
|---|---|---|---|
| WO | 2021104431 | A1 | 6/2021 |
| WO | 2021106230 | A1 | 6/2021 |
| WO | 2021106231 | A1 | 6/2021 |
| WO | 2021107160 | A1 | 6/2021 |
| WO | 2021108683 | A1 | 6/2021 |
| WO | 2021109737 | A1 | 6/2021 |
| WO | 2021113595 | A1 | 6/2021 |
| WO | 2021120045 | A1 | 6/2021 |
| WO | 2021121330 | A1 | 6/2021 |
| WO | 2021121367 | A1 | 6/2021 |
| WO | 2021121371 | A1 | 6/2021 |
| WO | 2021121397 | A1 | 6/2021 |
| WO | 2021126120 | A1 | 6/2021 |
| WO | 2021126799 | A1 | 6/2021 |
| WO | 2021127404 | A1 | 6/2021 |
| WO | 2021129820 | A1 | 7/2021 |
| WO | 2021129824 | A1 | 7/2021 |
| WO | 2021139678 | A1 | 7/2021 |
| WO | 2021139748 | A1 | 7/2021 |
| WO | 2021141628 | A1 | 7/2021 |
| WO | 2021142252 | A1 | 7/2021 |
| WO | 2021143693 | A1 | 7/2021 |
| WO | 2021145520 | A1 | 7/2021 |
| WO | 2021145521 | A1 | 7/2021 |
| WO | 2021147965 | A1 | 7/2021 |
| WO | 2021147967 | A1 | 7/2021 |
| WO | 2021150613 | A1 | 7/2021 |
| WO | 2021152149 | A1 | 8/2021 |
| WO | 2021168193 | A1 | 8/2021 |
| WO | 2021169963 | A1 | 9/2021 |
| WO | 2021169990 | A1 | 9/2021 |
| WO | 2021173923 | A1 | 9/2021 |
| WO | 2021175199 | A1 | 9/2021 |
| WO | 2021177721 | A1 | 9/2021 |
| WO | 2021178740 | A2 | 9/2021 |
| WO | 2021178741 | A1 | 9/2021 |
| WO | 2021180181 | A1 | 9/2021 |
| WO | 2021185233 | A1 | 9/2021 |
| WO | 2021190467 | A2 | 9/2021 |
| WO | 2021197499 | A1 | 10/2021 |
| WO | 2021203768 | A1 | 10/2021 |
| WO | 2021207172 | A1 | 10/2021 |
| WO | 2021211864 | A1 | 10/2021 |
| WO | 2021215544 | A1 | 10/2021 |
| WO | 2021216770 | A1 | 10/2021 |
| WO | 2021217019 | A1 | 10/2021 |
| WO | 2021090855 | A1 | 11/2021 |
| WO | 2021218110 | A1 | 11/2021 |
| WO | 2021219072 | A1 | 11/2021 |
| WO | 2021219090 | A2 | 11/2021 |
| WO | 2021219091 | A1 | 11/2021 |
| WO | 2021228161 | A1 | 11/2021 |
| WO | 2021231526 | A1 | 11/2021 |
| WO | 2021236475 | A1 | 11/2021 |
| WO | 2021239058 | A1 | 12/2021 |
| WO | 2021243280 | A1 | 12/2021 |
| WO | 2021244603 | A1 | 12/2021 |
| WO | 2021245051 | A1 | 12/2021 |
| WO | 2021245055 | A1 | 12/2021 |
| WO | 2021245499 | A1 | 12/2021 |
| WO | 2021248079 | A1 | 12/2021 |
| WO | 2021248082 | A1 | 12/2021 |
| WO | 2021248083 | A1 | 12/2021 |
| WO | 2021248090 | A1 | 12/2021 |
| WO | 2021248095 | A1 | 12/2021 |
| WO | 2021249563 | A1 | 12/2021 |
| WO | 2021252339 | A1 | 12/2021 |
| WO | 2021257828 | A1 | 12/2021 |
| WO | 2021259331 | A1 | 12/2021 |
| WO | 2022002102 | A1 | 1/2022 |
| WO | 2022015375 | A1 | 1/2022 |
| WO | 2022017339 | A1 | 1/2022 |
| WO | 2022028346 | A1 | 2/2022 |
| WO | 2022028492 | A1 | 2/2022 |
| WO | 2022031678 | A1 | 2/2022 |
| WO | 2022036176 | A1 | 2/2022 |
| WO | 2022258974 | A1 | 12/2022 |
| WO | 2023039240 | A1 | 3/2023 |

OTHER PUBLICATIONS

McCormick, F., "Targeting KRAS Directly", Annual Review of Cancer Biology, 2018, 2:81, 81-90.

Misalee, S. et al., KRAS G12C NSCLC models are sensitive to direct targeting of KRAS in combination with PI3K inhibition, Downloaded from clincancerres.aacrjournals.org on Oct. 22, 2018. © 2018 American Association for Cancer Research.

Nabet, B. et al., "It Takes Two To Target: A Study in KRAS Dimerization", pubs.acs.org/biochemistry, DOI: 10.1021.

O'Bryan, J., "Pharmacological Targeting of RAS: Recent Success with Direct Inhibitors", Pharmacological Research (2018), https://doi.org/10.1016/j.phrs.2018.10.021.

Ross, S. et al., "Targeting KRAS-dependent tumors with AZD4785, a high-affinity therapeutic antisense oligonucleotide inhibitor of KRAS", Sci. Transl. Med. 9, eaal5253 (2017) Jun. 14, 2017.

Ruess, D. et al., "Mutant KRAS-driven cancers depend on PTPN11/SHP2 phosphatase", Nature Medicine, Letters, https://doi.org/10.1038/s41591-018-0024-8.

Simanshu, D. et al., "RAS Proteins and Their Regulators in Human Disease", Cell 170, 17-33, Jun. 29, 2017.

Suzawa, K., et al., "Activation of KRAS mediates resistance to targeted therapy in MET exon 14 mutant non-small cell lung cancer", Author Manuscript Published OnlineFirst on Oct. 23, 2018; DOI: 10.1158/1078-0432. CCR-18-1640, Downloaded from clincancerres.aacrjournals.org on Oct. 29, 2018. © 2018 American Association for Cancer Research.

Wijeratne, A. et al., "Chemical Proteomic Characterization of a covalent KRASG12C inhibitor", ACS Med. Chem. Ltter., DOI: 10.1021/acsmedchemlett.8b00110, May 21, 2018.

Wood, K. et al., "Prognostic and Predictive Value in KRAS in Non-Small-Cell Lung Cancer A Review", JAMA Oncol. 2016:2(6), 805-812, Apr. 21, 2016.

Yen, I. et al., "Pharmacological Induction of RAS-GTP Confers RAF Inhibitor Sensitivity in KRAS Mutant Tumors", Cancer Cell 34, 611-625, Oct. 8, 2018, Elsevier Inc.

Ziemke, E. et al., "Sensitivity of KRAS-Mutant Colorectal Cancers to Combination Therapy That Cotargets MEK and CDK4/6", Clin Cancer Res; 22(2) Jan. 15, 2016.

Ambrogio, C. et al., "KRAS Dimerization Impacts MEK Inhibitor Sensitivity and Oncogenic Activity of Mutant KRAS", Cell 172, 1-12, Feb. 8, 2018, Elsevier Inc.

Hansen, R. et al., "An Internally Controlled Quantitative Target Occupancy Assay for Covalent Inhibitors", Scientific Reports, 8:14312 (2018), DOI: 10.1038/s41598-018-32683-w.

Pantar, T. et al., "Assessment of mutation probabilities of KRAS G12 missense mutants and their long-timescale dynamics by atomistic molecular simulations and Markov state modeling", PLOS Computational Biology, Sep. 10, 2018.

Skoulidis, F. et al., "STK11/LKB1 Mutations and PD-1 Inhibitor Resistance in KRAS-Mutant Lung Adenocarcinoma", Downloaded from cancerdiscovery.aacrjournals.org on May 21, 2018. © 2018 American Association for Cancer Research.

Yuan, T. et al., "Differential Effector Engagement by Oncogenic KRAS", Cell Reports 22, 1889-1902, Feb. 13, 2018, Cell Press.

(2017) "AACR Project GENIE: Powering Precision Medicine through an International Consortium", Cancer discovery, 7 (8):818-831.

Extended European Search Report Issued in European Patent Application No. 21873279.0, mailed on Oct. 7, 2024, 9 Pages.

International Search Report Issued in PCT Application No. PCT/US21/51315, mailed on Feb. 15, 2022, 4 Pages.

(May 24, 2018) "SID 364182955", Database Pubchem, 5 Pages.

(Dec. 6, 2019) "SID 395425028", Database PubChem Substance Anonymous, 5 Pages.

Alamgeer et al. (2013) "Novel Therapeutic Targets in Non-small Cell Lung Cancer", Current Opinion in Pharmacology, 13(3):394-401.

Mccormick, Frank (2015) "KRAS as a Therapeutic Target", Clinical Cancer Research, 21(8):1797-1801.

(56) References Cited

OTHER PUBLICATIONS

Santos et al. (1984) "Malignant Activation of a K-Ras Oncogene in Lung Carcinoma but Not in Normal Tissue of the Same Patient", Science, 223(4637):661-664.
Sung, Y. et al., "Mutagenesis of the H-ras p21 at Glycine-60 Residue Disrupts GTP-Induced Conformational Change", Biochemistry 1995, 34, 3470-3477, American Chemical Society.
Tape, C. et al., "Oncogenic KRAS Regulates Tumor Cell Signaling via Stromal Reciprocation", Cell 165, 1-11May 5, 2016.
Thierry, A. et al., "Clinical validation of the detection of KRAS and BRAF mutations from circulating tumor DNA", Nature Medicine, vol. 20, No. 4, pp. 430-436 , Apr. 2014.
Tran, E. et al., "T-Cell Transfer Therapy Targeting Mutant KRAS in Cancer", N Engl J Med 2016;375:2255-62., Dec. 8, 2016; DOI: 10.1056/NEJMoa1609279.
Wang, Y. et al., "Targeting Mutant KRAS for Anticancer Therapeutics: A Review of Novel Small Molecule Modulators", J. Med. Chem. 2013, 56, 5219-5230, dx.doi.org/10.1021/jm3017706; 2013 American Chemical Society, ACS Publications.
Wang, Y. et al., "Ezh2 Acts as a Tumor Suppressor in Kras-driven Lung Adenocarcinoma", International Journal of Biological Sciences 2017; 13(5): 652-659. doi: 10.7150/ijbs.19108.
Welsch, M. et al., "Multivalent Small-Molecule Pan-RAS Inhibitors", Welsch et al., 2017, Cell 168, 878-889 Feb. 23, 2017; 2017 Elsevier Inc. http://dx.doi.org/10.1016/j.cell.2017.02.006.
Winter, J. et al., "Small Molecule Binding Sites on the Ras:SOS Complex Can Be Exploited for Inhibition of Ras Activation", J. Med. Chem. 2015, 58, 2265-2274; DOI: 10.1021/jm501660t; 2015 American Chemical Society, ACS Publications.
Wood, K. et al., "Reply" Comments & Response, Letters JAMA Oncology Published online Jul. 21, 2016, American Medical Association.
Xiong, Y. et al., "Development of covalent guanosine mimetic inhibitors of G12C KRAS", ACS Med. Chem. Lett., Just Accepted Manuscript • DOI: 10.1021/acsmedchemlett.6b00373 • Publication Date (Web): Nov. 30, 2016 Downloaded from http://pubs.acs.org on Dec. 1, 2016.
Xiong, Y. et al., "Covalent Guanosine Mimetic Inhibitors of G12C KRAS" ACS Med. Chem. Lett. 2017, 8, 61-66, DOI: 10.1021/acsmedchemlett.6b00373; 2016 American Chemical Society, ACS Publications.
Janes et al., "Targeting KRAS Mutant Cancers with a Covalent G12C-Specific Inhibitor", Cell 172, 578-589, Jan. 25, 2018.
Singh et al., "A Gene Expression Signature Associated with K-Ras Addiction" Reveals Regulators of EMT and Tumor Cell Survival, Cancer Cell 15, p. 489-500, Jun. 2, 2009.
Stephen et al., "Dragging Ras Back in the Ring", Cancer Cell 25, p. 272, Mar. 17, 2014.
Zhu et al., "Inhibition of KRAS-driven tumorigenicity by interruption of an autocrine cytokine circuit", doi:10.1158/2159-8290.CD-13-0646; Cancer Discovery Published OnlineFirst Jan. 20, 2014.
Simanshu et al., "RAS Proteins and Their Regulators in Human Disease", Cell 170, p. 17, Jun. 29, 2017.
Pacold et al., "Crystal Structure and Functional Analysis of Ras Binding to Its Effector Phosphoinositide 3-Kinase gamma", Cell, vol. 103, p. 931-943, Dec. 8, 2000.
Lech-Gustav et al., "The Renaissance of Ras", ACS Chem. Biol., 2014, 9, 2447-2458.
Karachaliou et al., "KRAS Mutations in Lung Cancer", Clinical Lung Cancer, vol. 14, No. 3, p. 2015-14, 2013.
Schwartz et al., "Covalent EGFR inhibitor analysis reveals importance of reversible interactions to potency and mechanisms of drug resistance", PNAS, vol. 111, No. 1, p. 173-178, Jan. 7, 2014.
Sun et al., "A method for the second-site screening of K-Ras in the presence of a covalently attached first-site ligand", J. Biomol. NMR (2014) vol. 60 p. 11-14.
Kyriakis, J., "Thinking Outside the Box about Ras", J. Biol. Chem. 2009, 284:10993-10994, published online Dec. 17, 2008.
Sunaga et al., "Knockdown of Oncogenic KRAS in Non-Small Cell Lung Cancers Suppresses Tumor Growth and Sensitizes Tumor Cells to Targeted Therapy", Mol. Cancer Ther. 2011; 10:336-346.
Serafimova et al., "Reversible targeting of noncatalytic cysteines with chemically tuned electrophiles", Nat Chem Biol.; 8(5):471-476. doi:10.1038/nchembio.925.
Walker et al., "Structural insights into phosphoinositide 3-kinase catalysis and signalling", Nature vol. 402, p. 18 Nov. 1999; www.nature.com.
Barbie et al., "Systematic RNA interference reveals that oncogenic KRAS-driven cancers require TBK1", Nature, vol. 462, p. 108, Nov. 5, 2009; doi:10.1038/nature08460.
Zimmermann et al., "Small molecule inhibition of the KRAS-PDEdelta interaction impairs oncogenic KRAS signalling", Nature, vol. 497, p. 638, May 30, 2013.
Karnoub et al., "Ras oncogenes: split personalities", Nature Reviews, molecular Cell Biology, vol. 9, Jul. 2008 p. 517.
Nassar et al., "Ras/Rap effector specificity determined by charge reversal", Nature Structural Biology, vol. 3, No. 8, Aug. 1996.
De Rooij et al., "Minimal Ras-binding domain of Raf1 can be used as an activation-specific probe for Ras", Oncogene (1997) 14, 623-625, 1997 Stockton Press.
Cox et al., "The dark side of RAs: regulation of apoptosis", Oncogene (2003) 22, 8999-9006, 2003 Nature Publishing Group.
Tanaka et al., "Interfering with RAS-effector protein interactions prevent RAS-dependent tumour initiation and causes stop-start control of cancer growth", Oncogene (2010) 29, 6064-6070, 2010 Macmillan Publishers Limited.
Grant et al., "Novel Allosteric Sites on Ras for Lead Generation", PLOS ONE, vol. 6, Issue 10, Oct. 2011.
Maegley et al., "Ras-catalyzed hydrolysis of GTP: A new perspective from model studies", Proc. Natl. Acad. Sci. USA, vol. 93, pp. 8160-8166, Aug. 1996.
Ahmadian et al., "Guanosine triphosphatase stimulation of oncogenic Ras mutants", Proc. Natl. Acad. Sci. USA, vol. 96, pp. 7065-7070, Jun. 1999.
Kiel et al., "Electrostatically optimized Ras-binding Ral guanine dissociation stimulator mutants increase the rate of association by stabilizing the encounter complex", PNAS, vol. 101, No. 25, p. 9223-9228, Jun. 22, 2004.
Kotting et al., "The GAP arginine finger movement into the catalytic site of Ras increases the activation entropy", PNAS, vol. 105, No. 17, p. 6260-6265, Apr. 29, 2008.
Shaw et al., "Selective killing of K-ras mutant cancer cells by small molecule inducers of oxidative stress", PNAS, vol. 108, No. 21, p. 8773-8778, May 24, 2011.
Ischenko et al., "Direct reprogramming by oncogenic Ras and Myc", PNAS early edition 1, 2013.
Smith et al., "NMR-based functional profiling of RASopathies and oncogenic RAS mutations", PNAS, vol. 110, No. 12, p. 4574-4579, Mar. 19, 2013.
Shima, et al., "In silico discovery of small-molecule Ras inhibitors that display antitumor activity by blocking the Ras-effector interaction", PNAS, vol. 110, No. 20, p. 8182-8187, May 14, 2013.
Burns et al., "Approach for targeting Ras with small molecules that activate SOS-mediated nucleotide exchange", PNAS, vol. 111, No. 9, p. 3401-3406, Mar. 4, 2014.
Zeng et al., "Design of inhibitors of Ras-Raf interaction using a computational combinatorial algorithm", Protein Engineering, vol. 14, No. 1, p. 39-45, 2001.
Scheffzek et al., "The Ras-RasGAP Complex: Structural Basis for GTPAse Activation and Its Loss in Oncogenic Ras Mutants", Science, vol. 277, Jul. 18, 1997.
Taylor et al., "Protein Kinases: Evolution of Synamic Regulatory Proteins", Trends Biochem Sci. Feb. 2011; 36 (2): 65-77. doi:10.1016/j.tibs.2010.09.006.
Fell et al. 'Discovery of Tetrahydropyridopyrimidines as Irreversible Covalent Inhibitors of KRAS-G12C with In Vivo Activity', ACS Medicinal Chemistry Letters, Nov. 7, 2018 (Nov. 7, 2018), vol. 9, pp. 1230-1234.
International Search Report and Written Opinion for corresponding PCT application No. PCT/US18/61060 mailed Feb. 7, 2019.

(56) References Cited

OTHER PUBLICATIONS

Martin, James S. et al., "Characterising covalent warhead reactivity", Bioorganic & Medicinal Chemistry, 27 (2019) 2066-2074.
Palkowitz, Maximilian D. et al., "Synthesis of Diverse N-Acryloyl Azetidines and Evaluation of Their Enhanced Thiol Reactivities", ACS Publications Mar. 16, 2017, 9, 9, 2270-2273.
Sunaga, N. et al., "Oncogenic KRAS-induced epiregulin overexpression contributes to aggressive phenotype and is a promising therapeutic target in non-small-cell lung cancer", Oncogene (2013) 32, 4034-4042& 2013 Macmillan Publishers Limited.
Blake et al., "Discovery of 5,6,7,8-tetrahydropyrido[3,4-d]pyrimidine inhibitors of Erk2" Bioorganic & Medicinal Chemistry Letters, Jun. 15, 2014, vol. 24, p. 2635-2639; p. 2635, Figure 1, p. 2637, right col, Para 2.
Ambrogio, C. et al., "Combined inhibition of DDR1 and Notch signaling is a therapeutic strategy for KRAS-driven lung adenocarcinoma", Nature Medicine, vol. 22, No. 3, pp. 270-279, Mar. 2016.
Araki, M. et al., "Solution Structure of the State 1 Conformer of GTP-bound H-Ras Protein and Distinct Dynamic Properties between the State 1 and State 2 Conformers" The Journal of Biological Chemistry vol. 286, No. 45, pp. 39644-39653, Nov. 11, 2011.
Broutin, S. et al., "Insights into significance of combined inhibition of MEK and m-TOR signalling output in KRAS mutant non-small-cell lung cancer", British Journal of Cancer (2016), 1-4 | doi: 10.1038/bjc.2016.220.
Burgess, M. et al., "KRAS Allelic Imbalance Enhances Fitness and Modulates MAP Kinase Dependence in Cancer", Cell 168, 817-829, Feb. 23, 2017, Elsevier Inc.
Cammarata, M. et al., "Impact of G12 Mutations on the Structure of K-Ras Probed by Ultraviolet Photodissociation Mass Spectrometry", . Am. Chem. Soc., 2016, 138 (40), pp. 13187-13196.
Costa-Cabral, S. et al., "CDK1 Is a Synthetic Lethal Target for KRAS Mutant Tumours", PLOS ONE | DOI: 10.1371/journal.pone.0149099 Feb. 16, 2016.
Cully, "Closing the door on KRAS-mutant lung cancer", Nature Reviews Drug Discovery | Published online Nov. 3, 2016; doi:10.1038/nrd.2016.216, MacMillan Publishers.
Dharmaiah, S. et al., "Structural basis of recognition of farnesylated and methylated KRAS4b by PDEδ", E6766-E6775, PNAS, Published online Oct. 17, 2016.
Fiala, O. et al., "The dominant role of G12C over other KRAS mutation types in the negative prediction of efficacy of epidermal growth factor receptor tyrosine kinase inhibitors in nonesmall cell lung cancer", Cancer Genetics 206 (2013) 26-31.
Ford, B. et al., "Structure of the G60A Mutant of Ras Implications for the Dominant Negative Effect", J. Biol. Chem., vol. 280, No. 27, Issue of Jul. 8, pp. 25697-25705, 2005.
Hall, B. et al., "The structural basis for the transition from Ras-GTP to Ras-GDP", PNAS, vol. 99, No. 19, pp. 12138-12142, Sep. 17, 2002.
Hunter, J. et al., "In situ selectivity profiling and crystal structure of SML-8-73-1, an active site inhibitor of oncogenic K-Ras G12C", PNAS, vol. 111, No. 24, pp. 8895-8900, Jun. 17, 2014.
Ihle, N. et al., "Effect of KRAS Oncogene Substitutions on Protein Behavior: Implications for Signaling and Clinical Outcome", JNCI, Oxford Journals, vol. 104, Issue 3, Feb. 8, 2012.
Jarvis, L., "Have drug hunters finally cracked KRas?", c&en, vol. 94, Issue 23, pp. 28-33, Jun. 6, 2016.
Kamerkar, S. et al., "Exosomes facilitate therapeutic targeting of oncogenic KRAS in pancreatic cancer", Nature 546, 498-503 (Jun. 22, 2017) doi:10.1038/nature22341.
Kaufman, J. et al., "Treatment of KRAS-Mutant Non-Small Cell Lung Cancer The End of the Beginning for Targeted Therapies", JAMA May 9, 2017 vol. 317, No. 18.
Kerr, E. et al., "Mutant Kras copy number defines metabolic reprogramming and therapeutic susceptibilities", Nature 531, 110-113, (Mar. 3, 2016) doi:10.1038/nature16967.
Kim, J. et al., "CPS1 maintains pyrimidine pools and DNA synthesis in KRAS/LKB1-mutant lung cancer cells", Nature 546, 168-172, (Jun. 1, 2017) doi:10.1038/nature22359.
Kim, J. et al., "XPO1-dependent nuclear export is a druggable vulnerability in KRAS-mutant lung cancer", Nature 538, 114-117 (Oct. 6, 2016) doi:10.1038/nature19771.
Kitai, H. et al., "Key roles of EMT for adaptive resistance to MEK inhibitor in KRAS mutant lung cancer", SSN: 2154-1248 (Print) 2154-1256 (Online) Journal homepage: http://www.tandfonline.com/loi/ksgt20.
Kosloff, M. et al., "GTPase Catalysis by Ras and Other G-proteins: Insights from Substrate Directed SuperImposition", J. Mol. Biol. (2003) 331, 1157-1170, doi:10.1016/S0022-2836(03)00847-7.
Ledford, H., "Thirty years of pursuit have failed to yield a drug to take on one of the deadliest families of cancer-causing proteins. Now some researchers are taking another shot." The RAS Renaissance, Nature, vol. 520, 278-280, Apr. 16, 2015.
Lim, S et all., "Therapeutic Targeting of Oncogenic K-Ras by a Covalent Catalytic Site Inhibitor", Angew. Chem. Int. Ed. 2014, 53, 199-204.
Loncle, C. et al., "The pancreatitis-associated protein VMP1, a key regulator of inducible autophagy, promotes KrasG12D-mediated pancreatic cancer initiation", Cell Death and Disease (2016) 7, e2295; doi:10.1038/cddis.2016.202 Official journal of the Cell Death Differentiation Association.
Manchado, E. et al., "A combinatorial strategy for treating KRAS-mutant lung cancer", Nature 534, 647-651 (Jun. 30, 2016) doi:10.1038/nature18600.
Maurer, T. et al., "Small-molecule ligands bind to a distinct pocket in Ras and inhibit SOS-mediated nucleotide exchange activity", PNAS, Apr. 3, 2012, vol. 109, No. 14, pp. 5299-5304.
Muller, M. et al., "Nucleotide based covalent inhibitors of KRas can only be efficient in vivo if they bind reversibly with GTP-like affinity", Scientific Reports, 7: 3687 | DOI:10.1038/s41598-017-03973-6.
Nadal, E. et al., "Abstract C141: KRAS G12C mutation is prognostic of poor outcome in resected lung adenocarcinomas and predictive of poor response to MEK inhibition in vitro", Mol Cancer Ther Nov. 2013 12; C141, doi: 10.1158/1535-7163.TARG-13-C141.
Nussinov, R. et al., "Independent and core pathways in oncogenic KRAS signaling", Journal: Expert Review of Proteomics, DOI: 10.1080/14789450.2016.1209417, Published by Taylor & Francis.
Ostrem, J. et al., "Direct small-molecule inhibitors of KRAS: from structural insights to mechanism-based design", Nature Reviews Drug Discovery 15, 771-785 (2016) doi:10.1038/nrd.2016.139.
Ostrem, J et al., "K-Ras(G12C) inhibitors allosterically control GTP affinity and effector interactions", Nature, vol. 503: 548, Nov. 28, 2013.
Papke, B. et al., "Drugging RAS: Know the enemy", Science 355, 1158-1163 (2017) Mar. 17, 2017.
Park, K. et al., "The HSP90 inhibitor, NVP-AUY922, sensitizes KRAS-mutant non-small cell lung cancer with intrinsic resistance to MEK inhibitor, trametinib", Cancer Letters 372 (2016) 75-81.
Patricelli, M. et al., "Selective Inhibition of Oncogenic KRAS Output with Small Molecules Targeting the Inactive State", OnlineFirst on Jan. 6, 2016; DOI: 10.1158/2159-8290.CD-15-1105.
Perara, D. et al., "Oncogenic KRAS triggers MAPK-dependent errors in mitosis and MYC-dependent sensitivity to anti-mitotic agents", Scientific Reports, 6:29741, DOI: 10.1038/srep29741.
Renaud, S. et al., "KRAS in Non-Small-Cell Lung Cancer: Oncogenic Addiction and Epidermal Growth Factor Receptor Tyrosine Kinase Inhibitors", JAMA Oncology Published online Jul. 21, 2016.
Riquelme, E. et al., "Modulation of EZH2 expression by MEK-ERK or PI3K-AKT signaling in lung cancer is dictated by different KRAS oncogene mutations", Author Manuscript Published OnlineFirst on Dec. 16, 2015; DOI: 10.1158/0008-5472.CAN-15-1141, American Association for Cancer Research.
Rudoni, S. et al., "Role of guanine nucleotides in the regulation of the Ras/cAMP pathway in *Saccharomyces cerevisiae*", Biochimica et Biophysica Acta 1538 (2001) 181^189.

(56) References Cited

OTHER PUBLICATIONS

Samatar, A. et al., "Targeting Ras-Erk signalling in cancer: promises and challenges", Nature Reviews Drug Discovery, vol. 13, pp. 928-942, Dec. 2014.
Sautier, B. et al., "Latest advances towards Ras inhibition—A medicinal chemistry perspective", Angewandte Chemie International Edition, 10.1002/anie.201608270.
Serresi, M. et al., "Polycomb Repressive Complex 2 Is a Barrier to KRAS-Driven Inflammation and Epithelial-Mesenchymal Transition in Non-Small-Cell Lung Cancer", Cancer Cell 29, 17-31, Jan. 11, 2016, 2016 Elsevier Inc. 17.
Shima, F. et al., "Structural Basis for Conformational Dynamics of GTP-bound Ras Protein", The Journal of Biological Chemistry, vol. 285, No. 29, pp. 22696-22705, Jul. 16, 2010.
Shipman, L., "Putting the brakes on KRAS-G12C nucleotide cycling", Nature Reviews Cancer, Published online Feb. 19, 2016; doi:10.1038/nrc.2016.13.
Spoerner, M. et al., "Dynamic properties of the Ras switch I region and its importance for binding to effectors", PNAS, vol. 98, No. 9, pp. 4944-4949, Apr. 24, 2001.
Sun, Q. et al., "Discovery of Small Molecules that Bind to K-Ras and Inhibit Sos-Mediated Activation**", Angew. Chem. Int. Ed. 2012, 51, 1-5, 2012 Wiley-VCH Verlag GmbH & Co. KGaA, Weinheim.
Sun, Q., et al., "A method for the second-site screening of K-Ras in the presence of a covalently attached first-site ligand", J Biomol NMR (2014) 60:11-14 DOI 10.1007/s10858-014-9849-8.
PubChem-SID-132593111, Modify Date: May 31, 2019 (May 31, 2019), p. 2, figure, this is a purchasable chemical.
JP 2015-124211 A (Dainippon Sumitomo Pharma Co L td) Jul. 6, 2015 (Jul. 6, 2015), especially: original document, p. 58, Table, formula 93.
Bakalova et al. "Electronic absorption and emission spectra and computational studies of some 2-aryl, 2-styryl, and 2-(40-aryl)butadienyl quinazolin-4-ones", Journal of Molecular Structure (Theochem). 2004. 710, 229-234, especially: p. 230, Scheme 2.
Orlov et al. "Rapid Improvement of the Performance Status and Reduction of the Tumor Size in KRAS-Mutated Colorectal Cancer Patient Receiving Binimetinib, Hydroxychloroquine, and Bevacizumab", Case Rep Oncol. 2020. 13: pp. 985-989, para 3; p. 988, para 4.
Canon et al. "The clinical KRAS(G12C) inhibitor AMG 510 drives anti-tumour immunity", Nature. 2019. vol. 575, pp. 217-223, especially: abstract; p. 218, Fig. 1a, formula AMG 510; p. 220, col. 2, para 2.
Lanman et al. "Discovery of a Covalent Inhibitor of KRASG12C (Amg 510) for the Treatment of Solid Tumors" Journal of Medicinal Chemistry. Dec. 10, 2019 (Dec. 10, 2019) vol. 63, p. 52-65; p. 52, abstract.
Abe, H et al. Discovery of a Highly Potent and Selective MEK Inhibitor: GSK1120212 (JTP-74057 DMSO Solvate). ACS Medicinal Chemistry Letters, vol. 2, No. 4, Feb. 28, 2011, doi: 10.1021/ml200004g, pp. 320-324; p. 321, figure 1.

* cited by examiner

KRas G12D INHIBITORS

FIELD OF THE INVENTION

The present invention relates to compounds that inhibit KRas G12D. In particular, the present invention relates to compounds that inhibit the activity of KRas G12D, pharmaceutical compositions comprising the compounds and methods of use therefor.

BACKGROUND OF THE INVENTION

Kirsten Rat Sarcoma 2 Viral Oncogene Homolog ("KRas") is a small GTPase and a member of the Ras family of oncogenes. KRas serves as a molecular switch cycling between inactive (GDP-bound) and active (GTP-bound) states to transduce upstream cellular signals received from multiple tyrosine kinases to downstream effectors to regulate a wide variety of processes, including cellular proliferation (e.g., see Alamgeer et al., (2013) Current Opin Pharmcol. 13:394-401).

The role of activated KRas in malignancy was observed over thirty years ago (e.g., see Santos et al., (1984) Science 223:661-664). Aberrant expression of KRas accounts for up to 20% of all cancers and oncogenic KRas mutations that stabilize GTP binding and lead to constitutive activation of KRas and downstream signaling have been reported in 25-30% of lung adenocarcinomas. (e.g., see Samatar and Poulikakos (2014) Nat Rev Drug Disc 13(12): 928-942 doi: 10.1038/nrd428). Single nucleotide substitutions that result in missense mutations at codons 12 and 13 of the KRas primary amino acid sequence comprise approximately 40% of these KRas driver mutations in lung adenocarcinoma. KRAS G12D mutation is present in 25.0% of all pancreatic ductal adenocarcinoma patients, 13.3% of all colorectal carcinoma patients, 10.1% of all rectal carcinoma patients, 4.1% of all non-small cell lung carcinoma patients and 1.7% of all small cell lung carcinoma patients (e.g., see The AACR Project GENIE Consortium, (2017) Cancer Discovery; 7(8):818-831. Dataset Version 4).

The well-known role of KRas in malignancy and the discovery of these frequent mutations in KRas in various tumor types made KRas a highly attractive target of the pharmaceutical industry for cancer therapy. Notwithstanding thirty years of large-scale discovery efforts to develop inhibitors of KRas for treating cancer, no KRas inhibitor has yet demonstrated sufficient safety and/or efficacy to obtain regulatory approval (e.g., see McCormick (2015) Clin Cancer Res. 21 (8):1797-1801).

Compounds that inhibit KRas activity are still highly desirable and under investigation, including those that disrupt effectors such as guanine nucleotide exchange factors (e.g., see Sun et al., (2012) Agnew Chem Int Ed Engl. 51(25):6140-6143 doi: 10.1002/anie201201358) as well recent advances in the covalent targeting of an allosteric pocket of KRas G12C (e.g., see Ostrem et al., (2013) Nature 503:548-551 and Fell et al., (2018) ACS Med. Chem. Lett. 9:1230-1234). Clearly there remains a continued interest and effort to develop inhibitors of KRas, particularly inhibitors of activating KRas mutants, especially KRas G12D.

Thus, there is a need to develop new KRas G12D inhibitors that demonstrate sufficient efficacy for treating KRas G12D-mediated cancer.

SUMMARY OF THE INVENTION

In one aspect of the invention, compounds are provided that inhibit KRas G12D activity.

In certain embodiments, the compounds are represented by Formula (I):

Formula (I)

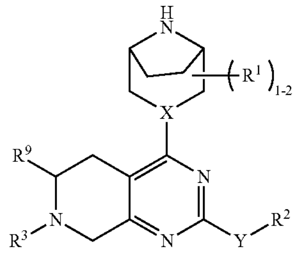

or a pharmaceutically acceptable salt thereof:

wherein:

each $R^1$ is independently hydrogen, hydroxy, halogen, C1-C3 haloalkyl, C1-C3 alkyl, C1-C3 alkoxy, (C1-C3 alkoxy)-C1-C3 alkyl, C1-C3 alkyl-$N(R^5)_2$, cyano, C1-C3 cyanoalkyl, C2-C4 cyanoalkenyl, C1-C3 hydroxyalkyl, HC(=O)—, —$CO_2R^5$, or —$CO^2$ $N(R^5)_2$;

X is N or $CR^5$;

Y is a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-$N(R^5)_2$, -L-NHC(=NH)$NH_2$, -L-C(O)$N(R^5)_2$, -L-C1-C6 haloalkyl, -L-$OR^5$, -L-($CH_2OR^5$)$(CH_2)_nOR^5$, -L-$NR^5$C(O)-aryl or -L-COOH, wherein the heterocyclyl, the aryl portion of -L-$NR^5$C(O)-aryl, the heterocyclyl portion of -L-heterocyclyl and the cycloalkyl portion of the -L-cycloalkyl is optionally substituted with one or more $R^6$, and wherein the aryl portion of -L-aryl and heteroaryl portion of -L-heteroaryl is optionally substituted with one or more $R^7$;

$R^3$ is -L-aryl, aryl -L-heteroaryl or heteroaryl, wherein the aryl or the heteroaryl is optionally substituted with one or more $R^8$;

each L is independently a C1-C4 alkylene optionally substituted with hydroxy, C1-C4 hydroxyalkyl or heteroaryl;

each $R^5$ is independently hydrogen, C1-C3 alkyl or C1-C3hydroxyalkyl, or two $R^5$ together with the atom to which they are both attached optionally join to form a heterocyclyl ring, wherein the heterocyclic ring formed by two $R^5$ is optionally substituted with one or more substituents independently selected from C1-C3 alkyl, hydroxy and C1-C3 alkoxy;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2$F, —NHC(O)phenyl, —NHC(O)phenyl$SO_2$F, C1-C3 alkyl substituted pyrazolyl, C1-C3 aralkyl, tert-butyldimethylsilyloxy$CH_2$—, —$N(R^5)_2$, (C1-C3 alkoxy)C1-C3 alkyl-, (C1-C3 alkyl)C(=O)—, oxo, (C1-C3 haloalkyl)C(=O)—, —$SO_2$F, or (C1-C3 alkoxy)C1-C3 alkoxy, (C1-C3)alkyl-O(C=O)—$N(R^5)_2$ or (C1-C3)alkyl-O(C=O)—N($OR^5$)$R^5$;

Q is a bond or O;

each $R^7$ is independently halogen, hydroxy, HC(=O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, cyclopropyl, $N(R^5)_2$, C1-C4 hydroxyalkyl, —S—C1-C3 haloalkyl or —O—C1-C3alkyl; and $R^9$ is hydrogen or oxo.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting KRas G12D activity in a in a cell, comprising contacting the cell with a compound of Formula (I), or a pharmaceutically acceptable salt thereof, or a pharmaceutical composition thereof as defined herein. In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method of treating a KRas G12D-associated disease or disorder in a patient in need of such treatment, the method comprising administering to the patient a therapeutically effective amount of a compound of Formula (I), or a pharmaceutically acceptable salt thereof, or a pharmaceutical composition thereof as defined herein.

Also provided herein is a compound of Formula (I), or a pharmaceutically acceptable salt thereof, or a pharmaceutical composition thereof as defined herein for use in therapy.

Also provided herein is a compound of Formula (I), or a pharmaceutically acceptable salt thereof or a pharmaceutical composition thereof as defined herein for use in the treatment of cancer.

Also provided herein is a compound of Formula (I), or a pharmaceutically acceptable salt thereof for use in the inhibition of KRas G12D.

Also provided herein is a compound of Formula (I), or a pharmaceutically acceptable salt thereof or a pharmaceutical composition thereof as defined herein, for use in the treatment of a KRas G12D-associated disease or disorder.

Also provided herein is the use of a compound of Formula (I), or a pharmaceutically acceptable salt thereof, as defined herein in the manufacture of a medicament for the treatment of cancer.

Also provided herein is a use of a compound of Formula (I), or a pharmaceutically acceptable salt thereof, as defined herein in the manufacture of a medicament for the inhibition of activity of KRas G12D.

Also provided herein is the use of a compound of Formula (I), or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that the cancer is associated with a KRas G12D mutation (i.e., a KRas G12D-associated cancer); and (b) administering to the patient a therapeutically effective amount of a compound of Formula (I), or a pharmaceutically acceptable salt thereof, or a pharmaceutical composition thereof.

Also provided herein is a process for preparing a compound of Formula (I), or a pharmaceutically acceptable salt thereof.

Also provided herein is a compound of Formula (I), or a pharmaceutically acceptable salt thereof obtained by a process of preparing the compound as defined herein.

DETAILED DESCRIPTION OF THE INVENTION

The present invention relates to inhibitors of KRas G12D. In particular, the present invention relates to compounds that inhibit the activity of KRas G12D, pharmaceutical compositions comprising a therapeutically effective amount of the compounds and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference.

As used herein, "KRas G12D" refers to a mutant form of a mammalian KRas protein that contains an amino acid substitution of an aspartic acid for a glycine at amino acid position 12. The assignment of amino acid codon and residue positions for human KRas is based on the amino acid sequence identified by UniProtKB/Swiss-Prot P01116: Variantp.Gly12Asp.

As used herein, a "KRas G12D inhibitor" refers to compounds of the present invention that are represented by Formula (I), as described herein. These compounds are capable of negatively modulating or inhibiting all or a portion of the enzymatic activity of KRas G12D.

A "KRas G12D-associated disease or disorder" as used herein refers to diseases or disorders associated with or mediated by or having a KRas G12D mutation. A non-limiting example of a KRas G12D-associated disease or disorder is a KRas G12D-associated cancer.

As used herein, the term "subject," "individual," or "patient," used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer having a KRas G12D mutation (e.g., as determined using a regulatory agency-approved, e.g., FDA-approved, assay or kit). In some embodiments, the subject has a tumor that is positive for a KRas G12D mutation (e.g., as determined using a regulatory agency-approved assay or kit). The subject can be a subject with a tumor(s) that is positive for a KRas G12D mutation (e.g., identified as positive using a regulatory agency-approved, e.g., FDA-approved, assay or kit). The subject can be a subject whose tumors have a KRas G12D mutation (e.g., where the tumor is identified as such using a regulatory agency-approved, e.g., FDA-approved, kit or assay). In some embodiments, the subject is suspected of having a KRas G12D gene-associated cancer. In some embodiments, the subject has a clinical record indicating that the subject has a tumor that has a KRas G12D mutation (and optionally the clinical record indicates that the subject should be treated with any of the compositions provided herein).

In some embodiments of any of the methods or uses described herein, an assay is used to determine whether the patient has KRas G12D mutation using a sample (e.g., a biological sample or a biopsy sample (e.g., a paraffin-embedded biopsy sample) from a patient (e.g., a patient suspected of having a KRas G12D-associated cancer, a patient having one or more symptoms of a KRas G12D-associated cancer, and/or a patient that has an increased risk of developing a KRas G12D-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof.

The term "regulatory agency" is a country's agency for the approval of the medical use of pharmaceutical agents with the country. For example, a non-limiting example of a regulatory agency is the U.S. Food and Drug Administration (FDA).

The terms "C1-C6 alkyl", "C1-C4 alkyl" and "C1-C3 alkyl" as employed herein refers to straight and branched chain aliphatic groups having from 1-6 carbon atoms, or 1-4 carbon atoms, or 1-3 carbon atoms, respectively. Examples of alkyl groups include, without limitation, methyl, ethyl, propyl, isopropyl, butyl, isobutyl, sec-butyl, tert-butyl, pentyl, and hexyl.

The terms "C1-C3 haloalkyl", "C1-C4 haloalkyl" and "C1-C6 haloalkyl" refer to a C1-C3 alkyl, a C1-C4 alkyl or a C1-C6 alkyl, respectively, as defined herein in which one or more hydrogen has been replaced by a halogen. Examples include trifluoromethyl, difluoromethyl and fluoromethyl.

An "C1-C4 alkylene," group is a C1-C4 alkyl group, as defined hereinabove, that is positioned between and serves to connect two other chemical groups. Exemplary alkylene groups include, without limitation, methylene, ethylene, propylene, and butylene.

The terms "C1-C3 alkoxy" and "C1-C4 alkoxy" refer to —OC1-C3 alkyl and —OC1-C4 alkyl, respectively, wherein the alkyl portion is as defined herein above.

The term "cycloalkyl" as employed herein includes saturated and partially unsaturated cyclic hydrocarbon groups having 3 to 12 carbons, for example 3 to 8 carbons, and as a further example 3 to 6 carbons, wherein the cycloalkyl group additionally is optionally substituted with one or more $R^6$ groups as defined herein. Examples of cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkyl" also includes bridged cycloalkyls, such as bicyclo[1.1.1]pentanyl.

As used herein, the terms "C1-C3 hydroxyalkyl" and "C1-C4 hydroxyalkyl" refer to —C1-C3 alkylene-OH and —C1-C4 alkylene-OH, respectively.

As used herein, the term "C2-C4 hydroxyalkynyl" refers to —C2-C4 alkynylene-OH.

An "aryl" group is a $C_6$-$C_{14}$ aromatic moiety comprising one to three aromatic rings, which is optionally substituted as defined herein. As one embodiment, the aryl group is a $C_6$-$C_{10}$ aryl group. Examples of aryl groups include, without limitation, phenyl, naphthyl, anthracenyl, fluorenyl, and dihydrobenzofuranyl. "Aryl" also refers to bicyclic or tricyclic ring systems in which one or two rings, respectively, of said aryl ring system may be saturated or partially saturated, and wherein if said ring system includes two saturated rings, said saturated rings may be fused or spirocyclic. An example of an aryl ring system comprising two saturated rings wherein the rings are spirocyclic includes the following ring system:

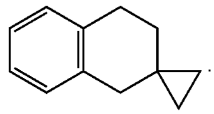 [SMILES: c1ccc2c(c1)CCC1(CC1)C2]

An "araC1-C6 alkyl" or "arylalkyl" group comprises an aryl group covalently linked to an alkyl group, either of which may independently be optionally substituted or unsubstituted. An example of an aralkyl group is ($C_6$-$C_{10}$) aryl($C_1$-$C_6$)alkyl-, including, without limitation, benzyl, phenethyl, and naphthylmethyl. An example of a substituted araC1-C6 alkyl is wherein the alkyl group is substituted with hydroxyalkyl.

A "heterocyclyl" or "heterocyclic" group is a ring structure having from 3 to 12 atoms, for example 4 to 8 atoms, wherein one or more atoms are selected from the group consisting of N, O, and S wherein the ring N atom may be oxidized to N—O, and the ring S atom may be oxidized to SO or $SO_2$, the remainder of the ring atoms being carbon. The heterocyclyl may be a monocyclic, a bicyclic, a spirocyclic or a bridged ring system. The heterocyclic group is optionally substituted with one or more $R^6$ on ring carbon or ring nitrogen at one or more positions, wherein $R^6$ is as defined for Formula (I). The heterocyclic group is also independently optionally substituted on a ring nitrogen atom with alkyl, aralkyl, alkylcarbonyl, or on sulfur with lower alkyl. Examples of heterocyclic groups include, without limitation, epoxy, azetidinyl, aziridinyl, tetrahydrofuranyl, tetrahydropyranyl, pyrrolidinyl, pyrrolidinonyl, piperidinyl, piperazinyl, imidazolidinyl, imidazopyridinyl, thiazolidinyl, dithianyl, trithianyl, dioxolanyl, oxazolidinyl, oxazolidinonyl, decahydroquinolinyl, piperidonyl, 4-piperidinonyl, quinuclidinyl, thiomorpholinyl, thiomorpholinyl 1,1 dioxide, morpholinyl, azepanyl, oxazepanyl, azabicyclohexanyls, azabicycloheptanyl, azabicyclooctanyls, azabicyclononanyls (e.g., octahydroindolizinyl), azaspiroheptanyls, dihydro-1H,3H,5H-oxazolo[3,4-c]oxazolyl, tetrahydro-1'H,3'H-spiro[cyclopropane-1,2'-pyrrolizine], hexahydro-1H-pyrrolizinyl, hexahydro-1H-pyrrolo[2,1-c][1,4]oxazinyl, octahydroindolizinyl, oxaazaspirononanyls, oxaazaspirooctanyls, diazaspirononanyls, oxaazabiocycloheptanyls, hexahydropyrrolizinyl 4(1H)-oxide, tetrahydro-2H-thiopyranyl 1-oxide and tetrahydro-2H-thiopyranyl 1,1-dioxide. Specifically excluded from the scope of this term are compounds having adjacent annular O and/or S atoms.

As used herein, the term "heteroaryl" refers to groups having 5 to 14 ring atoms, preferably 5, 6, 9, or 10 ring atoms; having 6, 10, or 14π electrons shared in a cyclic array having one to three heteroaromatic rings; and having, in addition to carbon atoms, from one to three heteroatoms in at least one ring selected from the group consisting of N, O, and S. Examples of heteroaryl groups include acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, 6,7-dihydro-5H-pyrrolo[1,2-a]imidazole, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. "Heteroaryl" also refers to bicyclic ring systems having, in addition to carbon atoms, from one to three heteroatoms in at least one aromatic ring selected from the group consisting of N, O, and S in which one ring in the bicyclic ring system may be saturated or partially saturated. "Heteroaryl" ring systems are optionally substituted as defined herein.

As used herein, "an effective amount" of a compound is an amount that is sufficient to negatively modulate or inhibit the activity of KRas G12D. Such amount may be administered as a single dosage or may be administered according to a regimen, whereby it is effective.

As used herein, a "therapeutically effective amount" of a compound is an amount that is sufficient to ameliorate, or in some manner reduce a symptom or stop or reverse progression of a condition, or negatively modulate or inhibit the activity of KRas G12D. Such amount may be administered as a single dosage or may be administered according to a regimen, whereby it is effective.

As used herein, treatment means any manner in which the symptoms or pathology of a condition, disorder or disease are ameliorated or otherwise beneficially altered. Treatment also encompasses any pharmaceutical use of the compositions herein.

As used herein, amelioration of the symptoms of a particular disorder by administration of a particular pharmaceutical composition refers to any lessening, whether permanent or temporary, lasting or transient that can be attributed to or associated with administration of the composition.

Compounds

In one aspect of the invention, compounds are provided represented by Formula (I):

Formula (I)

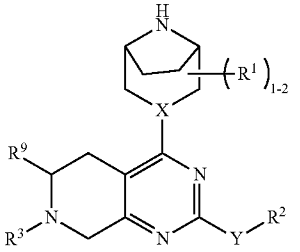

or a pharmaceutically acceptable salt thereof:

wherein:

each $R^1$ is independently hydrogen, hydroxy, halogen, C1-C3 haloalkyl, C1-C3 alkyl, C1-C3 alkoxy, (C1-C3 alkoxy)-C1-C3alkyl-, C1-C3-alkylN$(R^5)_2$, cyano, C1-C3 cyanoalkyl, C2-C4 cyanoalkenyl, C1-C3 hydroxyalkyl, HC(═O)—, —$CO_2R^5$, or —$CO^2$ N$(R^5)_2$;

X is N or $CR^5$;

Y is a bond, O or $NR^5$;

$R^2$ is hydrogen, —N$(R^5)_2$, heterocyclyl, C1-C6 alkyl, -L-heterocyclyl, -L-aryl, -L-heteroaryl, -L-cycloalkyl, -L-N$(R^5)_2$, -L-NHC(═NH)$NH_2$, -L-C(O)N$(R^5)_2$, -L-C1-C6 haloalkyl, -L-$OR^5$, -L-$(CH_2OR^5)(CH_2)_nOR^5$, -L-$NR^5$C(O)-aryl or -L-COOH, wherein the heterocyclyl, the aryl portion of -L-$NR^5$C(O)-aryl, the heterocyclyl portion of -L-heterocyclyl and the cycloalkyl portion of -L-cycloalkyl is optionally substituted with one or more $R^6$, and wherein the aryl portion of -L-aryl and heteroaryl portion of -L-heteroaryl is optionally substituted with one or more $R^7$;

$R^3$ is -L-aryl, aryl -L-heteroaryl or heteroaryl, wherein the aryl or the heteroaryl is optionally substituted with one or more $R^8$;

each L is independently a C1-C4 alkylene optionally substituted with hydroxy, C1-C4 hydroxyalkyl or heteroaryl;

each $R^5$ is independently hydrogen, C1-C3 alkyl or C1-C3hydroxyalkyl, or two $R^5$ together with the atom to which they are both attached optionally join to form a heterocyclyl ring, wherein the heterocyclic ring formed by two $R^5$ is optionally substituted with one or more substituents independently selected from C1-C3 alkyl, hydroxy and C1-C3 alkoxy;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2F$, —NHC(O)phenyl, —NHC(O)phenyl$SO_2F$, C1-C3 alkyl substituted pyrazolyl, C1-C3 aralkyl, tert-butyldimethylsilyloxy $CH_2$—, —N$(R^5)_2$, (C1-C3 alkoxy)C1-C3 alkyl-, (C1-C3 alkyl)C(═O)—, oxo, (C1-C3 haloalkyl)C(═O)—, —$SO_2F$, (C1-C3 alkoxy)C1-C3 alkoxy, (C1-C3)alkyl-O(C═O)—N$(R^5)_2$ or (C1-C3)alkyl-O(C═O)—N$(OR^5)R^5$;

Q is a bond or O;

each $R^7$ is independently halogen, hydroxy, HC(═O)—, C1-C4 alkyl, C1-C4 alkoxy, C1-C4 haloalkyl, C1-C4 hydroxyalkyl, or —N$(R^5)_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, cyclopropyl, N$(R_5)^2$, C1-C4hydroxyalkyl, —S—C1-C3 haloalkyl or —O—C1-C3 alkyl; and $R^9$ is hydrogen or oxo.

In certain embodiments there is provided a compound or salt as herein described wherein each $R^1$ is independently hydrogen, hydroxy, halogen, C1-C3 alkoxy, C1-C3-alkylN$(R^5)_2$, C1-C3 cyanoalkyl, dihalo-C1-C3alkyl, C1-C3 alkyl, cyano, C2-C4 cyanoalkenyl, C1-C3 hydroxyalkyl, hydroxy or (C1-C3alkyl)-C1-C3alkoxy.

In certain embodiments, X is N.

In certain embodiments, X is $CR^5$, $R^5$ is hydrogen or C1-C3 alkyl, and each $R^1$ is independently hydrogen or hydroxy.

In other embodiments, Y is O (oxygen).

In still other embodiments, $R^2$ is heterocyclyl or -L-heterocyclyl. In certain of these embodiments, L, if present, is methylene optionally substituted with methyl, and $R^2$ is heterocyclyl optionally substituted with one or more $R^6$. In certain of these embodiments, heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4(1H)-oxide, azetidinyl, pyrrolidinyl, pyrrolidin-2-one, oxetanyl, piperidinyl, 1-azabicyclo[2.2.1]heptanyl, morpholinyl, oxa-5-azabicyclo[2.2.1]heptan-5-yl, thiopyranyl, 6-oxa-2λ 2-azaspiro[3.4]octanyl, 7-oxa-2λ 2-azaspiro[3.5]nonanyl, 2',3'-dihydrospiro[cyclopropane-1,1'-indenyl], (2S)-1-azabicyclo[2.2.1]heptan-2-yl, or tetrahydrofuranyl, each optionally substituted with one or more $R^6$. In certain of these embodiments, heterocyclyl is pyrrolidinyl or hexahydro-1H-pyrrolizinyl, each optionally substituted with one or more $R^6$.

In certain embodiments one or more $R^6$ groups are each independently selected from halogen, hydroxy, C1-C3 hydroxyalkyl, C1-C3 alkyl, C1-C3 haloalkyl, C1-C3 alkoxy, (C1-C3 alkoxy)C1-C3 alkoxy, (C1-C3)alkyl-O(C═O)—N$(R^5)_2$ and (C1-C3)alkyl-O(C═O)—N$(OR^5)R^5$.

In certain embodiments one or more $R^6$ groups are each independently selected from halogen, C1-C3 hydroxyalkyl, C1-C3 alkyl, C1-C3 haloalkyl, (C1-C3)alkyl-O(C═O)—N$(R^5)_2$ and (C1-C3)alkyl-O(C═O)—N$(OR^5)R^5$.

In certain embodiments, two $R^5$ together with the atom to which they are both attached join to form a heterocycle. In certain of these embodiments, the formed heterocycle is piperidine, piperazine or morpholine. In other embodiments, each $R^5$ is independently hydrogen, C1-C3 alkyl or C1-C3hydroxyalkyl.

In certain embodiments, $R^9$ is hydrogen. In other embodiments, $R^9$ is oxo.

In certain embodiments, $R^3$ is -L-aryl or aryl, wherein the aryl is phenyl, naphthyl, 1,2,3,4-tetrahydronaphthalenyl or 2,3-dihydro-1H-indenyl, each optionally substituted with one or more $R^8$. In certain of these embodiments, each $R^8$ is independently halogen, hydroxy, C1-C4 alkyl, C1-C3 haloalkyl, —O—C1-C3 haloalkyl, cyclopropyl or —O—C1-C3 alkyl.

In certain embodiments, $R^3$ is -L-heteroaryl or heteroaryl, wherein heteroaryl is isoquinoline or quinazoline, each optionally substituted with one or more $R^8$. In certain of these embodiments, each $R^8$ is independently halogen, $N(R^5)_2$, hydroxy, C1-C4 alkyl, C1-C3 haloalkyl, —O—C1-C3 haloalkyl or cyclopropyl. In certain of these embodiments, each $R^8$ is independently halogen or $N(R^5)_2$.

In certain embodiments the present invention provides a pharmaceutical composition comprising a therapeutically effective amount of any of the compounds described herein, or a pharmaceutically acceptable salt thereof, and a pharmaceutically acceptable excipient.

Embodiments of the invention also include a method for inhibiting KRas G12D activity in a cell, comprising contacting the cell in which inhibition of KRas G12D activity is desired with an effective amount of a compound of any compound described herein, or a pharmaceutically acceptable salt thereof, or related pharmaceutical compositions described herein.

The invention includes an embodiment which is a method for treating cancer comprising administering to a patient having cancer a therapeutically effective amount of a compound described herein, or a pharmaceutically acceptable salt thereof, or a pharmaceutical composition described herein. In certain embodiments that cancer is a KRas G12D-associated cancer. In certain embodiments, that cancer is non-small cell lung cancer, small cell lung cancer, colorectal cancer, rectal cancer or pancreatic cancer.

In certain embodiments of the invention, a compound for cancer treatment described herein is provided in a therapeutically effective amount of between about 0.01 to 100 mg/kg per day. In certain other embodiments, the therapeutically effective amount of the compound is between about 0.1 to 50 mg/kg per day.

The invention further includes an embodiment which is a method for treating cancer in a patient in need thereof, the method comprising (a) determining that the cancer is associated with a KRas G12D mutation (e.g., a KRas G12D-associated cancer); and (b) administering to the patient a therapeutically effective amount of a compound as described herein, or a pharmaceutically acceptable salt thereof, or a pharmaceutical composition described herein.

In another embodiment there is one $R^1$ and $R^9$ is H.

In another embodiment, there are two $R^1$.

In one embodiment of the compounds of Formula (I), at least $R^1$ is halogen, hydroxy, C1-C3 alkyl, C1-C3 cyanoalkyl, C1-C3 hydroxyalkyl, HC(═O)—, —$CO_2R^5$, —$CO_2N(R^5)_2$, C1-C3 alkoxy, (C1-C3 alkoxy)-C1-C3 alkyl, C1-C3-$N(R^5)_2$, cyano or C2-C4 cyanoalkenyl;

In certain embodiments, each $R^1$ is hydrogen.

In certain embodiments one or two $R^1$ are hydroxy.

In certain embodiments one $R^1$ is hydroxy and one $R^1$ is C1-C3 halo-alkyl.

In other embodiments, one $R^1$ is —$CO_2R^5$. In certain embodiments, $R^5$ is hydrogen. In other embodiments, $R^5$ is C1-C3 alkyl.

In another embodiment, one $R^1$ is —$C(O)_2N(R^5)_2$.

In certain embodiments, each $R^5$ is hydrogen, each $R^5$ is an independently selected C1-C3 alkyl, or one $R^5$ is hydrogen and the second $R^5$ is C1-C3 alkyl.

In certain embodiments, two $R^5$ together with the atom to which they are both attached optionally join to form a heterocyclic ring, wherein the heterocyclic ring formed by two $R^5$ is optionally substituted with one or more substituents independently selected from C1-C3 alkyl, hydroxy and C1-C3 alkoxy;

In another embodiment, one or two $R^1$ are C1-C3 hydroxy-alkyl or (C1-C3alkoxy)-C1-C3 alkyl.

In another embodiment, one or two $R^1$ are C1-C3 alkyl.

In another embodiment, one or two $R^1$ are 2-aminoethyl.

In another embodiment, one or two $R^1$ are cyano, alkylcyano or cyano-alkenyl.

In another embodiment one $R^1$ is hydroxy and the other is halogen or C1-C3 halo-alkyl.

In one embodiment, Y is a bond.

In one embodiment, Y is methyl or ethyl;

In one embodiment, Y is O (oxygen);

In one embodiment of the compounds of Formula (I), Y is a bond and $R^2$ is hydrogen, —$N(R^5)_2$, or heterocyclyl optionally substituted with one or more $R^6$.

In certain embodiments, $R^2$ is —$N(R^5)_2$. In one embodiment, each $R^5$ is hydrogen.

In one embodiment, each $R^5$ is an independently selected C1-C3 alkyl. In one embodiment, one $R^5$ is hydrogen and the second $R^5$ is C1-C3 alkyl. In certain embodiments, Y is a bond and $R^2$ is —$N(R^5)_2$.

In other embodiments, $R^2$ is heterocyclyl. In one embodiment $R^2$ is heterocyclyl and the heterocyclyl is azetidinyl, pyrrolidinyl, tetrahydro-2H-thiopyran 1,1-dioxide or 1,6λ $^2$-diazaspiro[3.3]heptanyl. In certain embodiments, Y is a bond and $R^2$ is heterocyclyl.

In certain embodiments, the heterocyclyl is azetidinyl substituted with one $R^6$. In certain embodiments, the heterocyclyl is azetidinyl substituted with one $R^6$, wherein $R^6$ is hydroxy, hydroxyalkyl, or —$N(R^5)_2$. In certain embodiments, the heterocyclyl is azetidinyl substituted with two $R^6$ groups independently selected from —$N(R^5)_2$ and C1-C3 alkyl. In certain embodiments, Y is a bond and the heterocyclyl is azetidinyl substituted with one $R^6$, wherein $R^6$ is hydroxy, hydroxyalkyl, or —$N(R^5)_2$. In certain embodiments, Y is a bond and the heterocyclyl is azetidinyl substituted with two $R^6$ groups independently selected from —$N(R^5)_2$ and C1-C3 alkyl.

In one embodiment, Y is O.

In one embodiment, Y is O and $R^2$ is C1-C6 alkyl, -L-heterocyclyl wherein the heterocyclyl portion is optionally substituted with one or more $R^6$, -L-heteroaryl wherein the heteroaryl portion is optionally substituted with one or more $R^7$, -L-aryl wherein the aryl portion is optionally substituted with one or more $R^7$, -L-cycloalkyl wherein the cycloalkyl portion is optionally substituted with one or more $R^6$, -L-$N(R^5)_2$, -L-NC(=NH)—$NH_2$, -L-C(O)$N(R^5)_2$, -L-C1-C6 haloalkyl, -L-$COR^5$, -L-$(CH_2OR^5)(CH_2)_nOR^5$ or -L-$NR^5$C(O)-aryl.

In one embodiment of the compounds of Formula (I), Y is O and $R^2$ is C1-C6 alkyl. In certain embodiments, the C1-C6 alkyl is methyl, ethyl, isopropyl or isobutyl.

In one embodiment of the compounds of Formula (I), Y is O and $R^2$ is -L-heterocyclyl optionally substituted with one or more $R^6$.

In one embodiment, Y is O and $R^2$ is heterocyclyl wherein the heterocyclyl is tetrahydropyranyl optionally substituted with two halogens. In certain embodiment, the two halogens are both fluoro.

In another embodiment, Y is O and $R^2$ is -L-heterocyclyl wherein L is methylene and the heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4(1H)-oxide, azetidinyl, pyrrolidinyl, pyrrolidin-2-one, oxetanyl, piperidinyl, 1-azabicyclo[2.2.1]heptanyl, morpholinyl, oxa-5-azabicyclo[2.2.1]heptan-5-yl, thiopyranyl, 6-oxa-2$\lambda^2$-azaspiro[3.4]octanyl, 7-oxa-2$\lambda^2$-azaspiro[3.5]nonanyl, 2',3'-dihydrospiro[cyclopropane-1,1'-indenyl], (2S)-1-azabicyclo[2.2.1]heptan-2-yl or tetrahydrofuranyl.

In certain embodiments, Y is O and $R^2$ is -L-heterocyclyl wherein L is methylene and the heterocyclyl is hexahydro-1H-pyrrolizinyl.

In certain embodiments, Y is O and $R^2$ is -L-heterocyclyl wherein L is methylene and the heterocyclyl is hexahydro-1H-pyrrolizinyl substituted with C1-C3alkyl-O—C(O)—$N(R^5)_2$ or C1-C3alkyl-O—C(O)—$N(OR^5)R^5$.

In certain embodiments, Y is O and $R^2$ is -L-heterocyclyl wherein L is methylene and the heterocyclyl is hexahydro-1H-pyrrolizinyl optionally substituted with one $R^6$, wherein $R^6$ is halogen, hydroxy, hydroxyalkyl, C1-C3 haloalkyl, C1-C3 alkyl, C1-C3 alkoxy, phenyl, tert-butyldimethylsilyloxy$CH_2$— or pyrazolyl, wherein the pyrazolyl is optionally substituted with C1-C3 alkyl. In one embodiment, the C1-C3 haloalkyl is chloromethyl. In another embodiment, the pyrazolyl is substituted with C1-C3 alkyl. In other embodiments, the hexahydro-1H-pyrrolizinyl is substituted with two $R^6$ groups, wherein each $R^6$ is an independently selected C1-C3 alkyl. In certain embodiments, the heterocyclyl is hexahydro-1H-pyrrolizinyl which is unsubstituted.

In certain embodiments, Y is O and $R^2$ is -L-heterocyclyl wherein L is methylene and the heterocyclyl is azetidinyl substituted with one $R^6$, wherein $R^6$ is C1-C3 alkyl.

In certain embodiments, Y is O and $R^2$ is -L-heterocyclyl wherein L is methylene and the heterocyclyl is pyrrolidinyl substituted with one $R^6$, wherein $R^6$ is C1-C3 hydroxyalkyl, C1-C3 haloalkyl, C1-C3 alkyl, C1-C3 alkoxy, C1-C3 aralkyl, or -Q-phenyl, wherein Q is O, and —NHC(O)phenyl. In one embodiment, the phenyl group of the -Q-phenyl is substituted with $SO_2F$. In another embodiment, the phenyl group of the —NHC(O)phenyl is substituted with $SO_2F$.

In one embodiment, the C1-C3 aralkyl is benzyl.

In other embodiments, Y is O and $R^2$ is -L-heterocyclyl wherein L is methylene and the pyrrolidinyl is substituted with two $R^6$ groups, wherein one $R^6$ is C1-C3 alkyl and the other $R^6$ is C1-C3 alkoxy or halogen.

In certain embodiments, Y is O and $R^2$ is -L-heterocyclyl wherein L is methylene and the heterocyclyl is pyrrolidin-2-one substituted with one $R^6$, wherein $R^6$ is C1-C3 alkyl.

In certain embodiments, Y is O and $R^2$ is -L-heterocyclyl wherein L is methylene and the heterocyclyl is piperidinyl substituted with one $R^6$, wherein $R^6$ is acetyl, (C1-C3 alkoxy)C1-C3 alkoxy, or —C(O)$CH_2$C1.

In certain embodiments, Y is O and $R^2$ is -L-heterocyclyl wherein L is methylene and the heterocyclyl is (2S)-1-azabicyclo[2.2.1]heptan-2-yl.

In one embodiment of the compounds of Formula (I), Y is O, $R^2$ is -L-heterocyclyl wherein L is ethylene or propylene and the heterocyclyl is morpholinyl or oxa-5-azabicyclo[2.2.1]heptan-5-yl.

In one embodiment of the compounds of Formula (I), Y is O and $R^2$ is -L-heteroaryl, wherein the heteroaryl portion is optionally substituted with one or more $R^7$. In certain embodiments, L is ethylene and the heteroaryl is benzimidazolyl, optionally substituted with one or more $R^7$. In one embodiment, $R^7$ is C1-C4 alkyl.

In certain embodiments, Y is O and $R^2$ is -L-heteroaryl.

In certain embodiments, Y is O and $R^2$ is -L-heteroaryl, wherein L is methylene or ethylene. In certain embodiments, Y is O and $R^2$ is -L-heteroaryl, wherein L is methylene or ethylene and the heteroaryl is pyridyl, pyrazolyl, imidazolyl, triazolyl, 4,5,6,7-tetrahydro-1H-indazolyl, benzimidazolyl, imidazo[1,2-a]pyridinyl, or pyrimidinyl.

In certain embodiments, Y is O and $R^2$ is -L-heteroaryl, wherein the heteroaryl is pyridyl substituted with one $R^7$. In certain embodiments, Y is O and $R^2$ is -L-heteroaryl, wherein the heteroaryl is pyridyl substituted with one $R^7$ wherein $R^7$ is halogen, C1-C4 haloalkyl, C1-C4 hydroxyalkyl, C1-C4 alkyl, —$N(R^5)_2$, or C1-C4 alkoxy.

In certain embodiments, Y is O and $R^2$ is -L-heteroaryl, wherein L is methylene or ethylene and the heteroaryl is pyrazolyl substituted with one $R^7$. In certain embodiments, Y is O and $R^2$ is -L-heteroaryl, wherein L is methylene or ethylene and the heteroaryl is pyrazolyl substituted with one $R^7$ wherein $R^7$ is halogen, C1-C4 haloalkyl, C1-C4 hydroxyalkyl, C1-C4 alkyl, alkoxy or —$N(R^5)_2$.

In certain embodiments, Y is O and $R^2$ is -L-heteroaryl, wherein L is methylene or ethylene and the heteroaryl is imidazolyl substituted with one $R^7$. In certain embodiments, Y is O and $R^2$ is -L-heteroaryl, wherein L is methylene or ethylene and the heteroaryl is imidazolyl substituted with one $R^7$ wherein $R^7$ is C1-C4 alkyl, C1-C4 haloalkyl, or C1-C4 hydroxyalkyl.

In certain embodiments, Y is O and $R^2$ is -L-heteroaryl, wherein L is methylene or ethylene and the heteroaryl is triazolyl substituted with one $R^7$. In certain embodiments, Y is O and $R^2$ is -L-heteroaryl, wherein L is methylene or ethylene and the heteroaryl is triazolyl substituted with one $R^7$, wherein $R^7$ is C1-C4 alkyl.

In one embodiment of the compounds of Formula (I), Y is O and $R^2$ is -L-aryl, wherein the aryl portion is optionally substituted with one or more $R^7$. In certain embodiments, L is ethylene and the aryl is phenyl. In one embodiment, the phenyl is substituted with one $R^7$. In one embodiment, the phenyl is substituted with one $R^7$, wherein $R^7$ is halogen. In one embodiment, the phenyl is substituted with two $R^7$ groups. In one embodiment, the phenyl is substituted with two $R^7$ groups. In one embodiment, the phenyl is substituted with two $R^7$ groups wherein one $R^7$ is hydroxy and one $R^7$ is HC(═O)—.

In one embodiment of the compounds of Formula (I), Y is O and $R^2$ is -L-cycloalkyl, wherein the cycloalkyl portion is optionally substituted with one or more $R^6$. In one embodiment, L is methylene. In one embodiment, the cycloalkyl is cyclopropyl, cyclobutyl, cyclopentyl or cyclohexyl. In certain embodiments, the cyclopropyl and cyclopentyl are each substituted with one $R^6$. In certain embodiments, the cyclopropyl and cyclopentyl are each substituted with one $R^6$, wherein $R^6$ is haloalkyl. In certain embodiments, the cyclobutyl and cyclohexyl are each substituted with two $R^6$ groups. In certain embodiments, the cyclobutyl and cyclohexyl are each substituted with two $R^6$ groups, wherein each $R^6$ group is halogen.

In one embodiment of the compounds of Formula (I), Y is O, and $R^2$ is -L-N($R^5$)$_2$. In certain embodiments, L is ethylene. In certain embodiments, $R^5$ is C1-C3 alkyl.

In one embodiment of the compounds of Formula (I), Y is O, and $R^2$ is -L-NC(═NH)—$NH_2$. In certain embodiments, L is ethylene or propylene.

In one embodiment of the compounds of Formula (I), Y is O, and $R^2$ is -L-C(O)N($R^5$)$_2$. In certain embodiments, L is ethylene and each $R^5$ is C1-C3 alkyl.

In one embodiment of the compounds of Formula (I), Y is O, and $R^2$ is -L-C1-C6 haloalkyl. In certain embodiments, L is methylene. In certain embodiments, the haloalkyl is 1,1,3,3-tetrafluoropropanyl or trifluoromethyl. In other embodiments, L is ethylene or propylene and the haloalkyl is trifluoromethyl.

In one embodiment of the compounds of Formula (I), Y is O, and $R^2$ is -L-COR$^5$. In certain embodiments, L is propylene and $R^5$ is hydrogen or C1-C3 alkyl. In certain embodiments, L is propylene that is substituted with hydroxy, hydroxyalkyl or heteroaryl and $R^5$ is hydrogen or C1-C3 alkyl. In one embodiment, the heteroaryl is pyridyl.

In one embodiment of the compounds of Formula (I), Y is O, and $R^2$ is -L-($CH_2OR^5$)($CH_2$)$_n$OR$^5$. In certain embodiments, L is methylene, each $R^5$ is independently hydrogen or C1-C3 alkyl, and n is one or two.

In one embodiment of the compounds of Formula (I), Y is O, and $R^2$ is -L-NR$^5$C(O)-aryl. In certain embodiments, L is methylene, $R^5$ is hydrogen. In one embodiment the aryl is phenyl. In one embodiment, the phenyl is substituted with one $R^6$, wherein $R^6$ is —$SO_2F$.

In one embodiment of the compounds of Formula (I), $R^3$ is aryl or -L-aryl, where the aryl is optionally substituted with one or more $R^8$. In certain embodiments, the aryl is selected from the group consisting of phenyl, naphthyl, 1,2,3,4-tetrahydronaphthalenyl and 2,3-dihydro-1H-indenyl, wherein each is optionally substituted with one or more $R^8$.

In one embodiment, the aryl is phenyl substituted with one or more $R^8$ groups. In one embodiment, the aryl is phenyl substituted with one or more $R^8$ groups independently selected from halogen, C1-C3 haloalkyl and —O—C1-C3 haloalkyl. In certain embodiments the phenyl is substituted with two $R^8$ groups. In certain embodiments the phenyl is substituted with two $R^8$ groups, wherein the two $R^8$ groups are two independently selected C1-C3 haloalkyl groups, or —O—C1-C3 haloalkyl and halogen.

In one embodiment, the aryl is 2,3-dihydro-1H-indenyl optionally substituted with one or more $R^8$. In one embodiment, the aryl is 2,3-dihydro-1H-indenyl optionally substituted with one $R^8$. In one embodiment, $R^8$ is C1-C alkyl. In one embodiment $R^8$ is cyclopropyl.

In one embodiment, the aryl is naphthyl substituted with one or more $R^8$ groups. In one embodiment, the aryl is naphthyl substituted with one or more $R^8$ groups independently selected from halogen, cyano, hydroxy, C1-C3 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl and —O—C1-C3 haloalkyl.

In one embodiment, the aryl is naphthyl substituted with hydroxy. In one embodiment, the aryl is naphthyl substituted with halogen. In certain embodiments, the halogen is chlorine, fluorine or bromine. In other embodiments, the halogen is chlorine.

In one embodiment, the aryl is naphthyl substituted with C1-C3 alkyl, wherein the C1-C3 alkyl is methyl or ethyl.

In one embodiment, the aryl is naphthyl substituted with C2-C4 alkenyl. In certain embodiments, the C2-C4 alkenyl is prop-2-enyl.

In one embodiment, the aryl is naphthyl substituted with C2-C4 alkynyl. In certain embodiments, the C2-C4 alkynyl is ethyne or prop-2-ynyl.

In one embodiment, the aryl is naphthyl substituted with one or two $R^8$, wherein each $R^8$ is halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, or triazolyl. In one embodiment, the aryl is naphthyl substituted with two $R^8$ groups independently selected from halogen, hydroxy, C1-C3 alkyl, C2-C4 alkynyl and cyclopropyl.

In one embodiment of the compounds of Formula (I), $R^3$ is -L-heteroaryl or heteroaryl, where the heteroaryl is optionally substituted with one or more $R^8$. In one embodiment, the heteroaryl is isoquinolinyl, indazolyl, or benzo[d][1,3]dioxolyl optionally substituted with one or more $R^8$. In one embodiment, the heteroaryl is indazolyl optionally substituted with one or more $R^8$. In one embodiment, the heteroaryl is indazolyl optionally substituted with C1-C3 alkyl. In other embodiments, the heteroaryl is isoquinolinyl optionally substituted with one or more $R^8$. In other embodiments, the heteroaryl is isoquinolinyl optionally substituted with halogen or C2-C4 alkynyl. In certain embodiments, the heteroaryl is benzo[d][1,3]dioxolyl optionally substituted with two $R^8$ groups. In certain embodiments, the heteroaryl is benzo[d][1,3]dioxolyl optionally substituted with two $R^8$ groups, wherein each $R^8$ group is an independently selected halogen. In one embodiment, the two halogens are gem-difluoro substitutions.

Nonlimiting examples of compounds of Formula (I) are selected from the group consisting of:

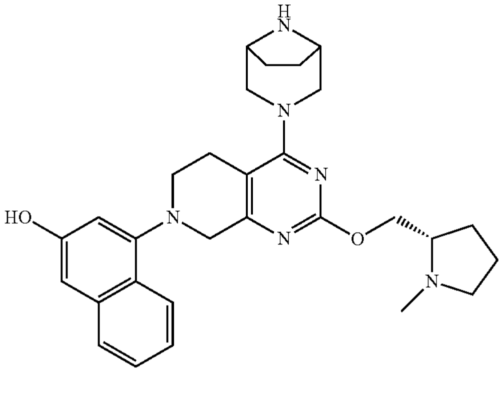
,

-continued
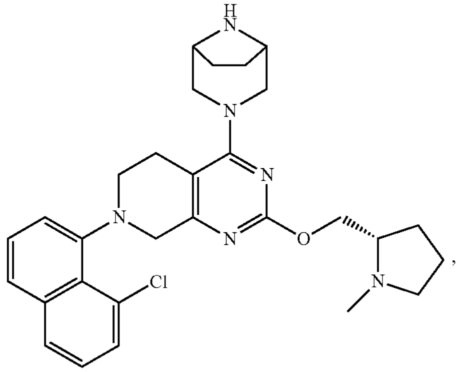
,
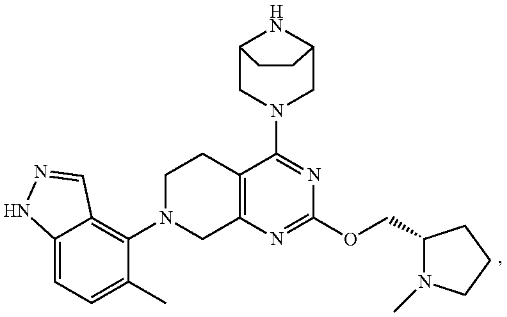
,
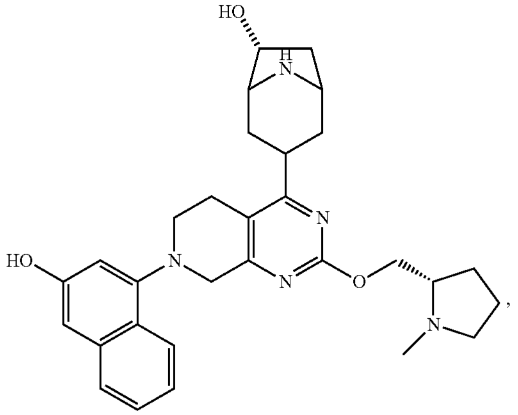
,
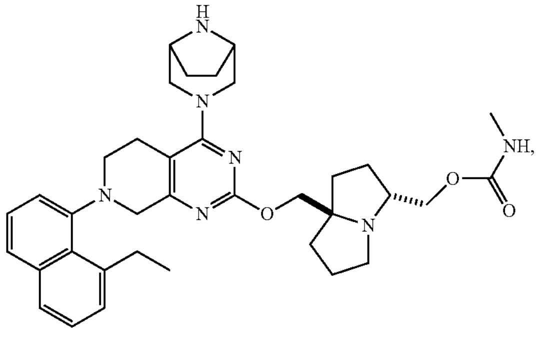
,
-continued
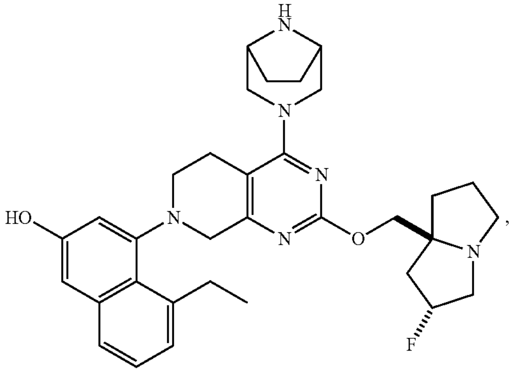
,
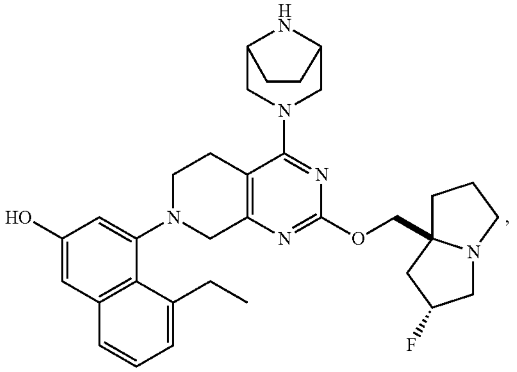
,
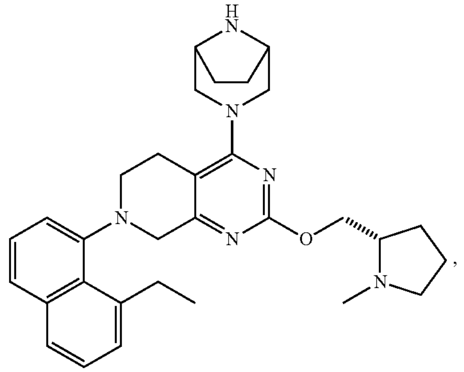
,
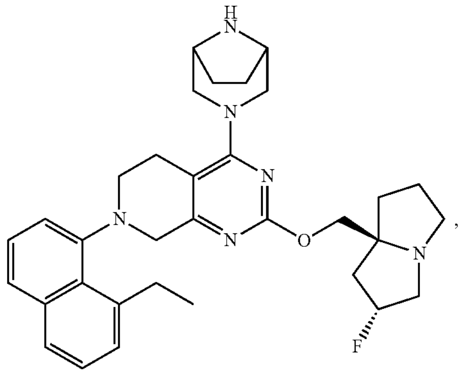
,

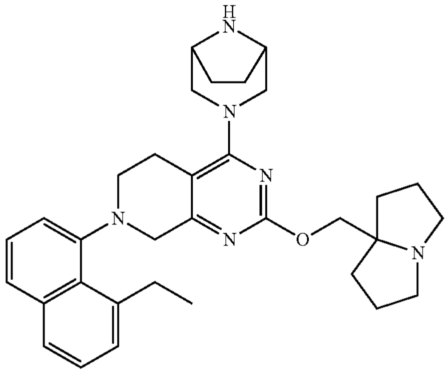
,
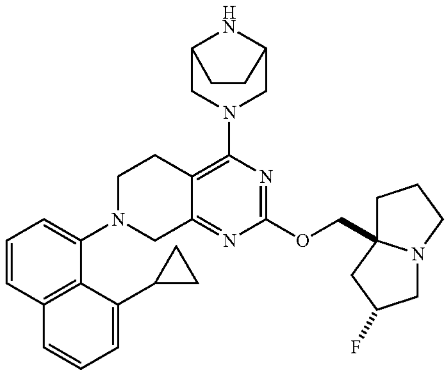
,
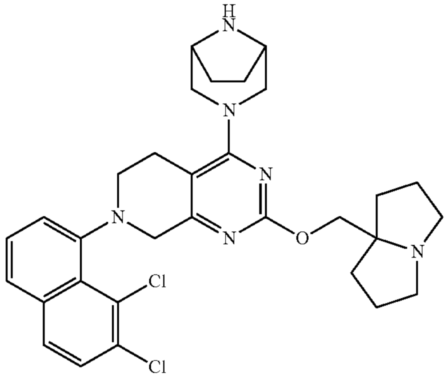
,
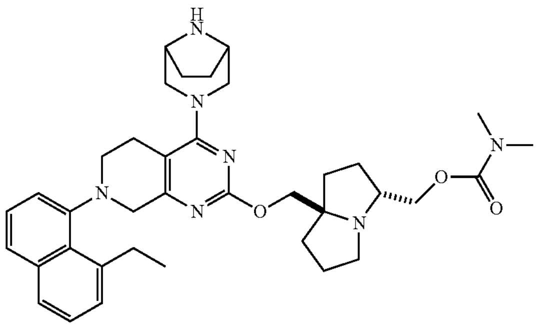
,
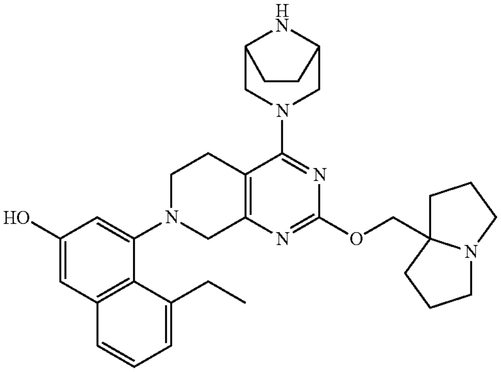
,
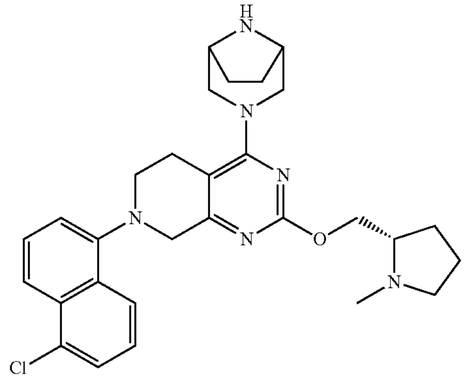
,
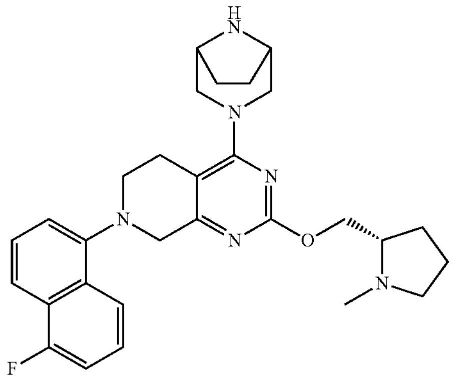
,
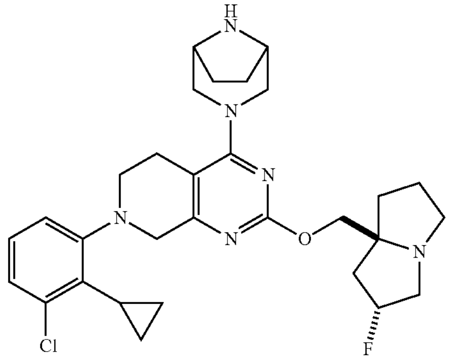
, -continued
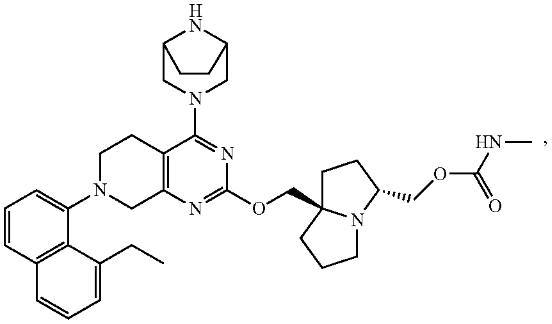
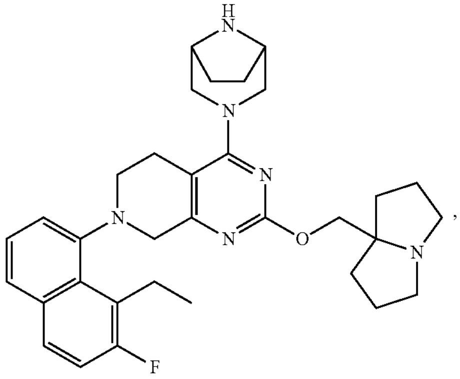
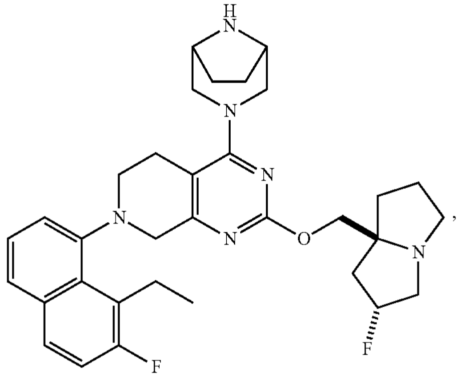
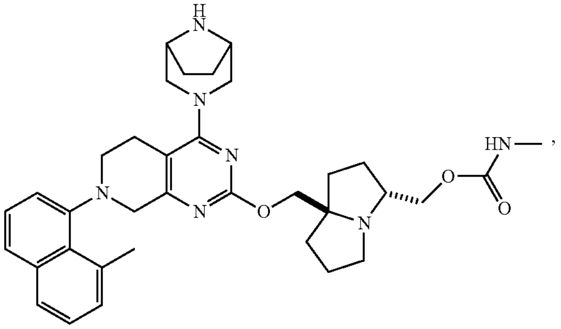
-continued
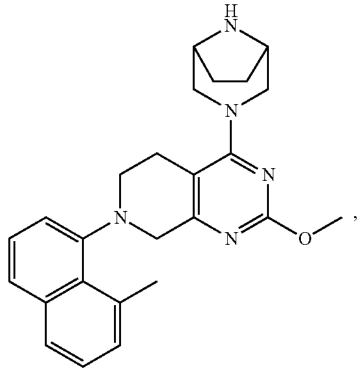
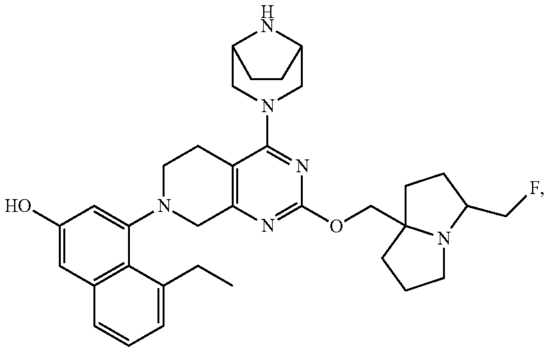
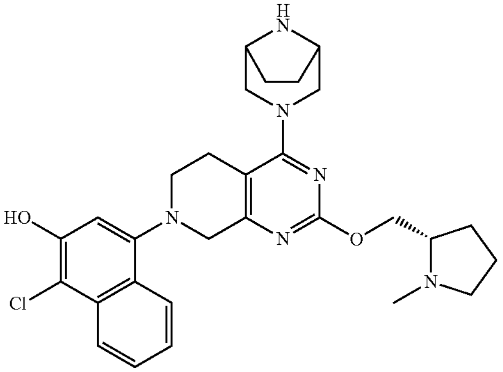
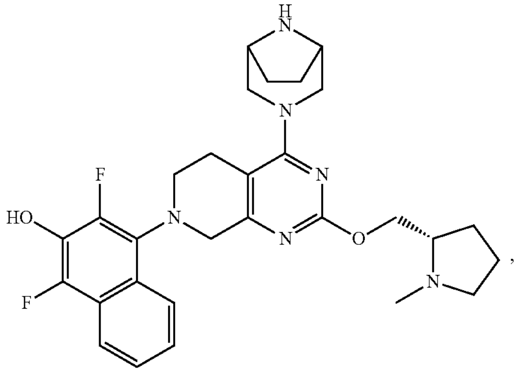

-continued
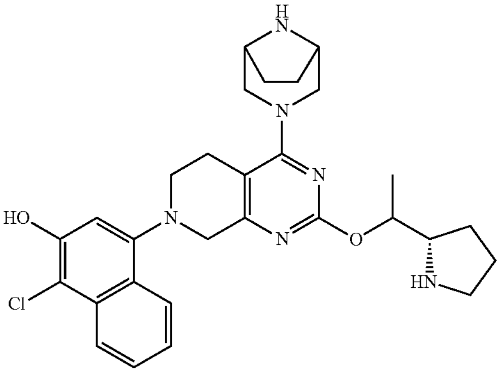
,
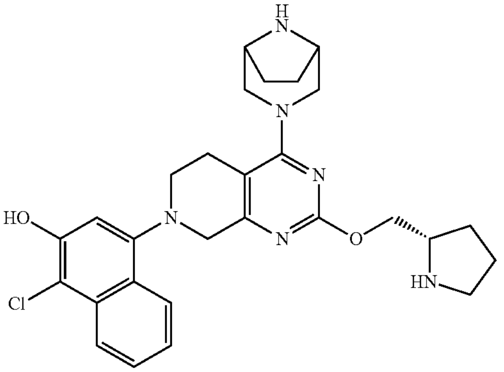
,
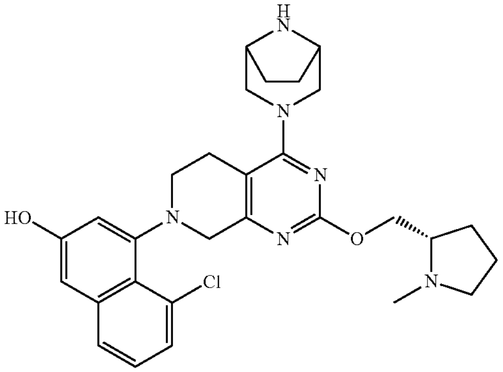
,
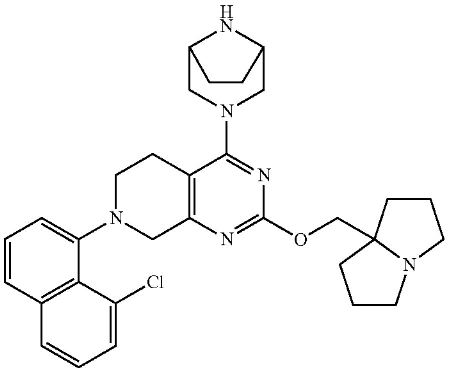
,
-continued
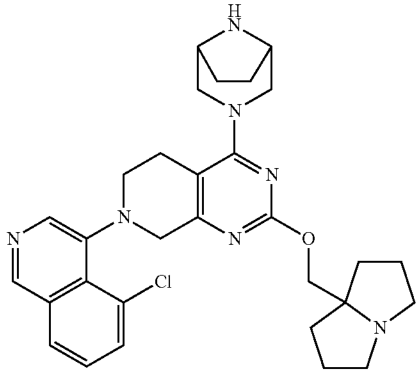
,
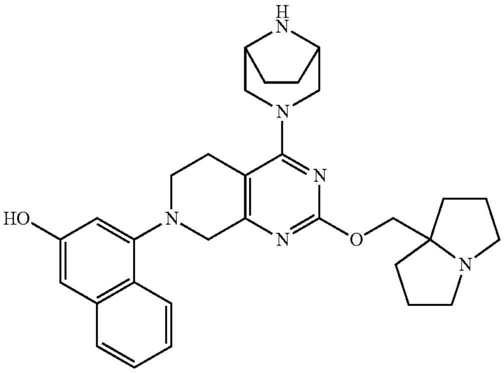
,
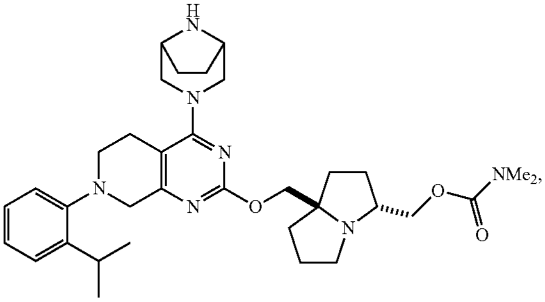
,
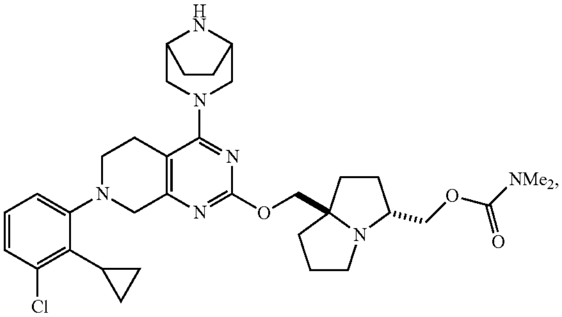
,
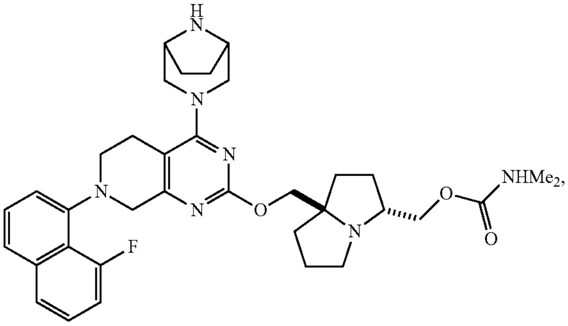
, -continued
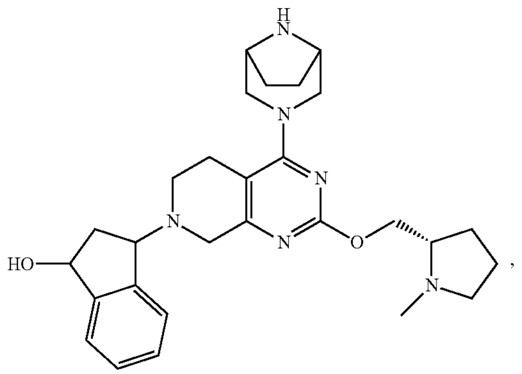
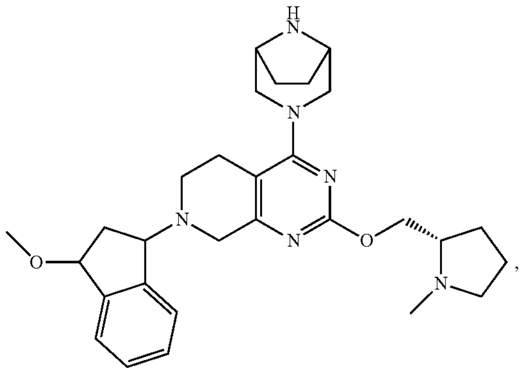
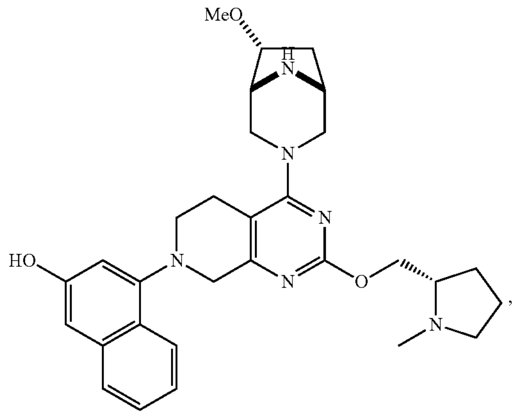
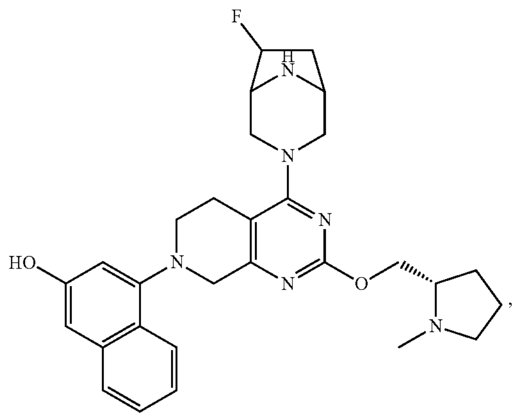
-continued
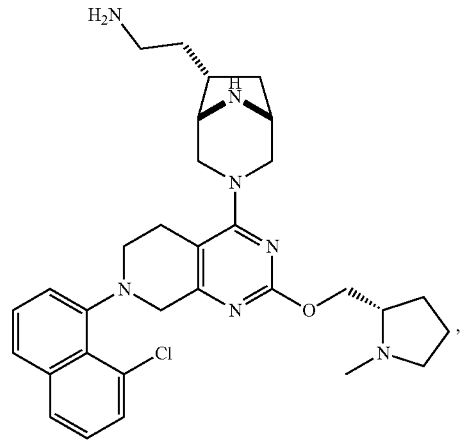
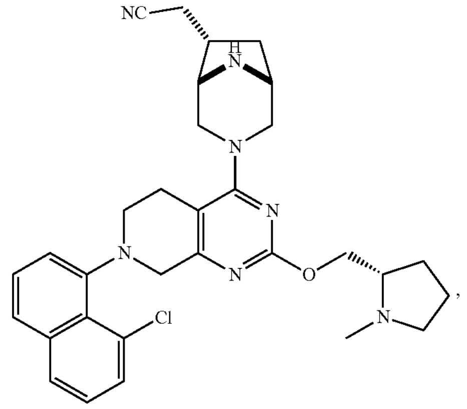
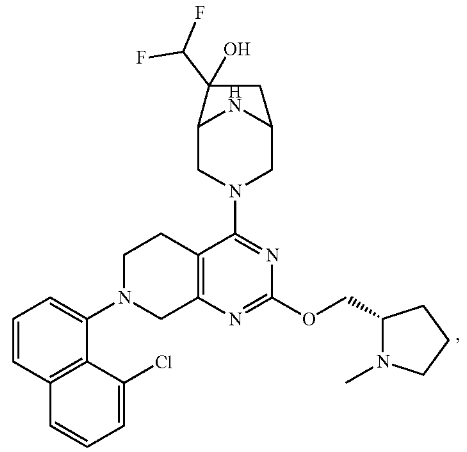
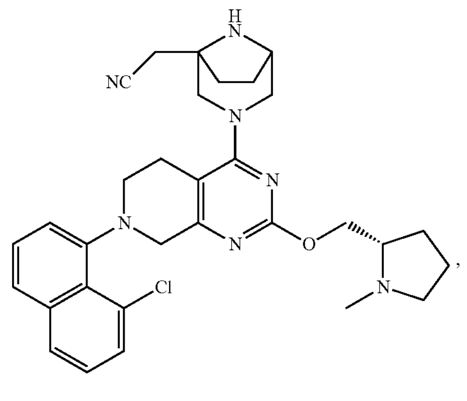

-continued
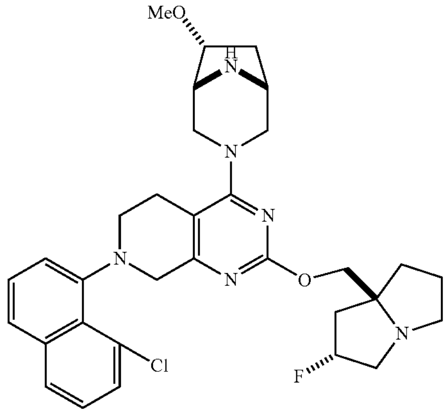
,
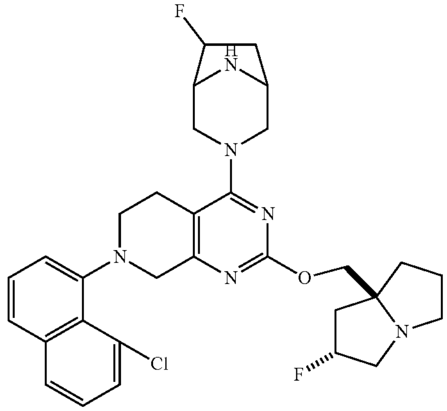
,
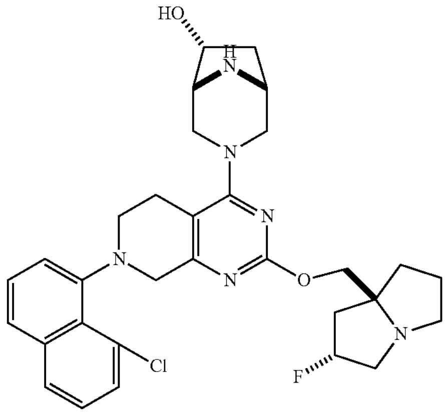
,
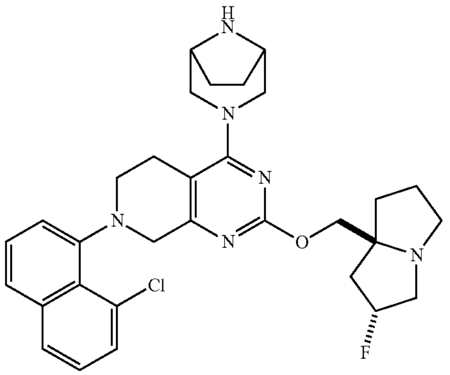
,
-continued
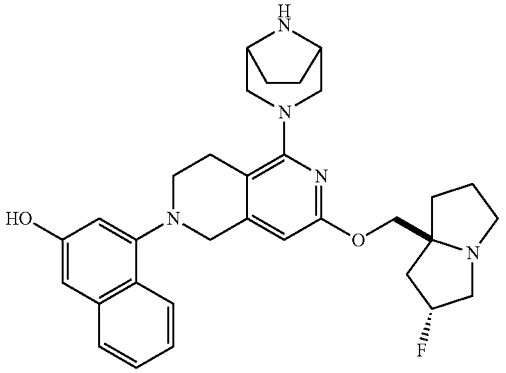
,
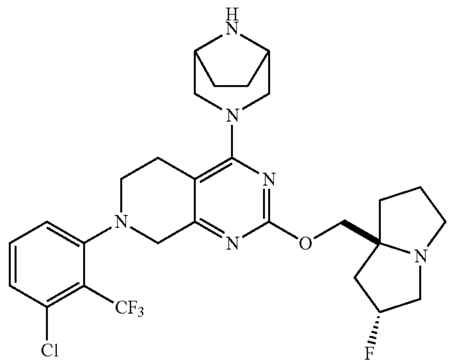
,
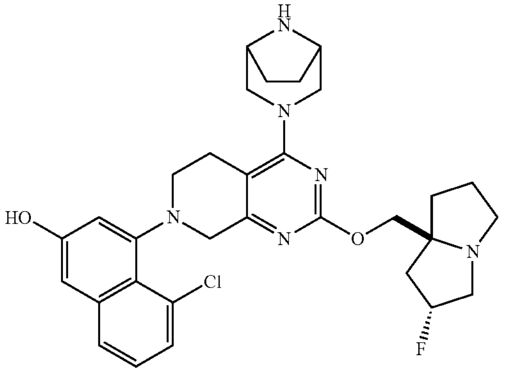
,
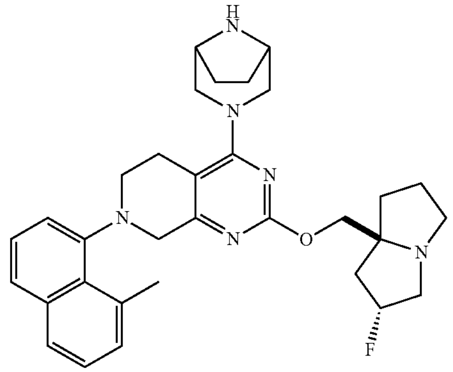
,

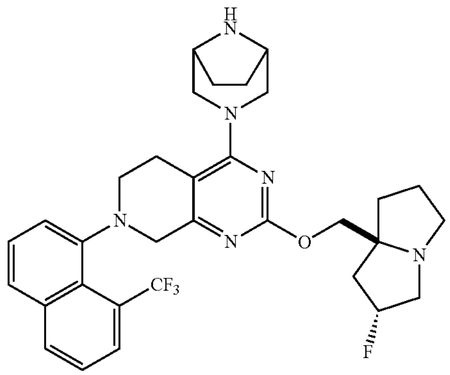
,
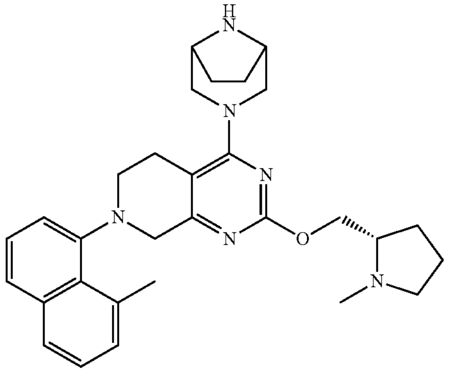
,
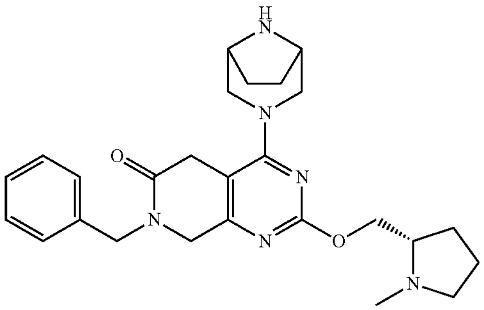
,
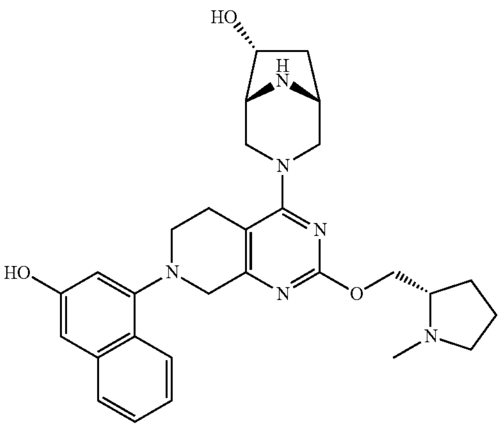
,
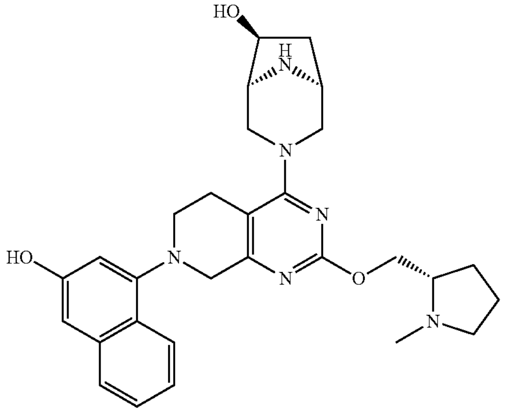
,
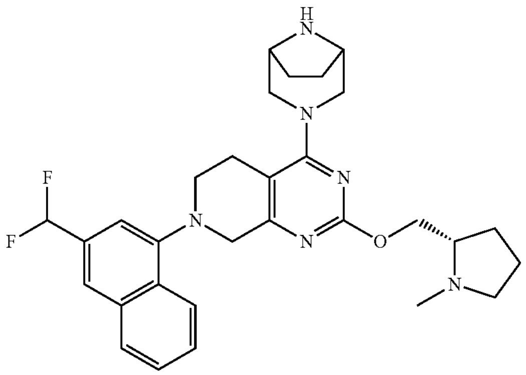
,
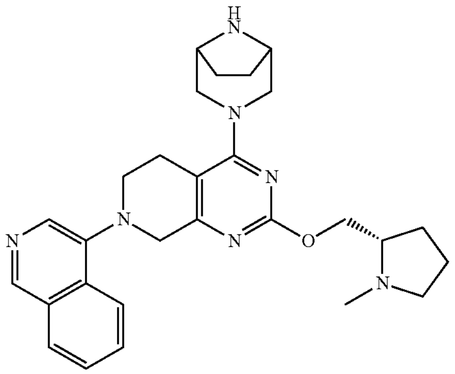
,
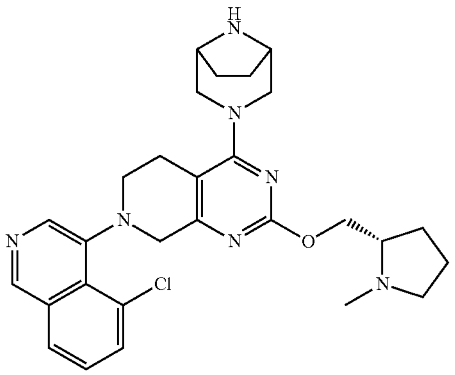
, -continued
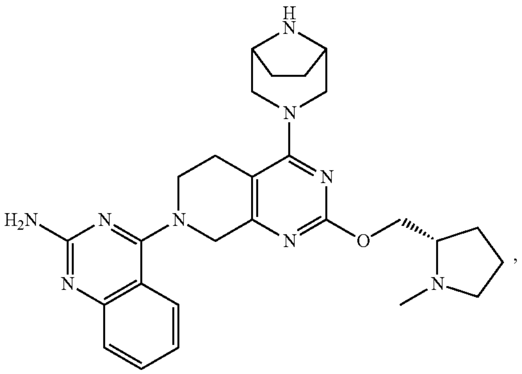
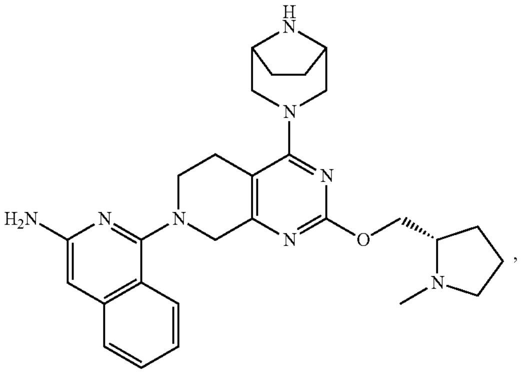
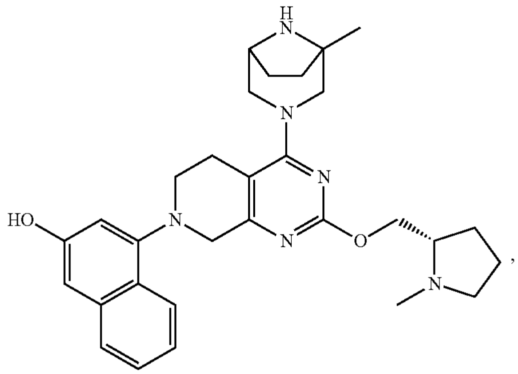
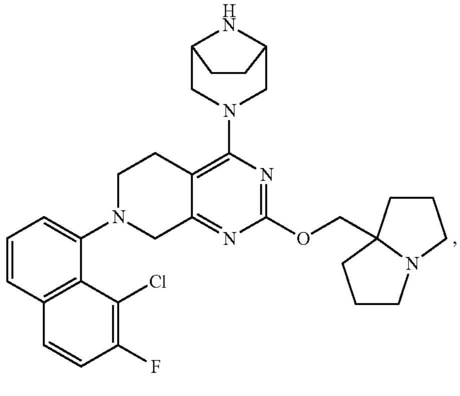
-continued
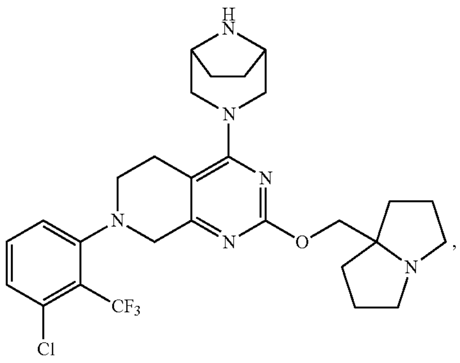
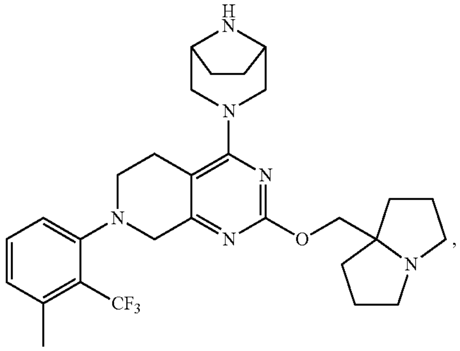
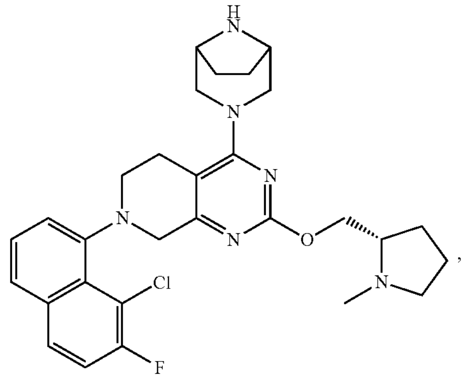
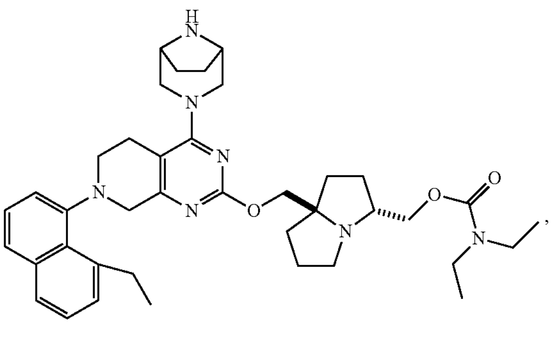

-continued
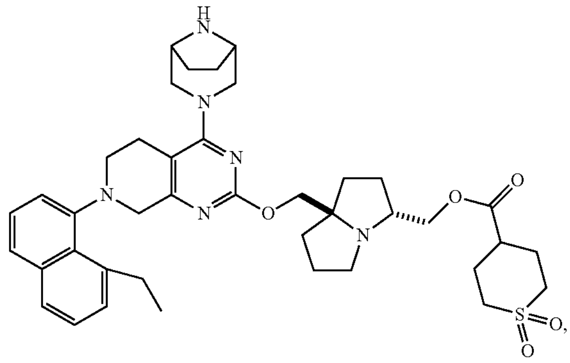
,
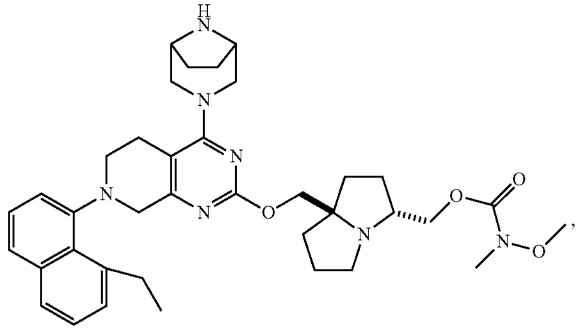
,
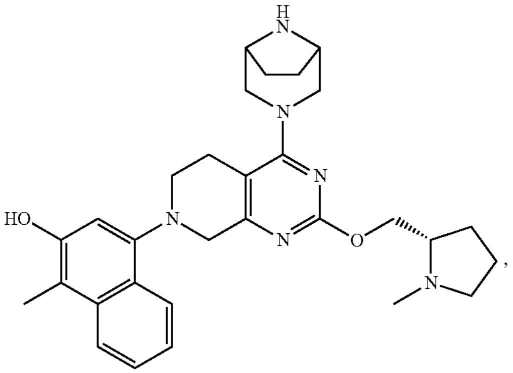
,
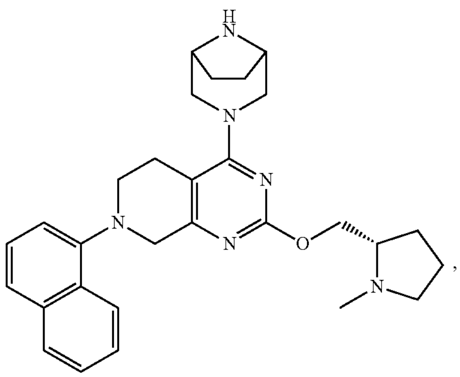
,
-continued
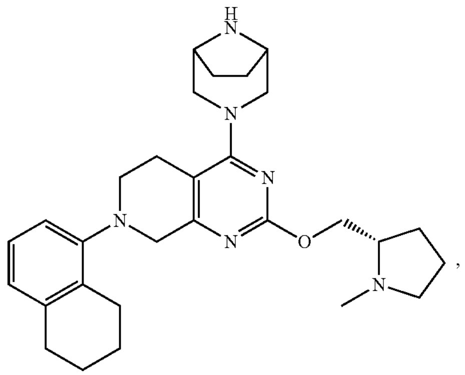
,
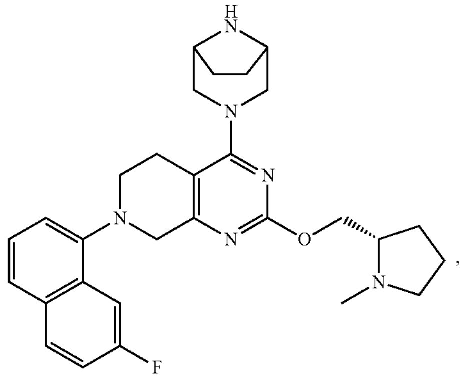
,
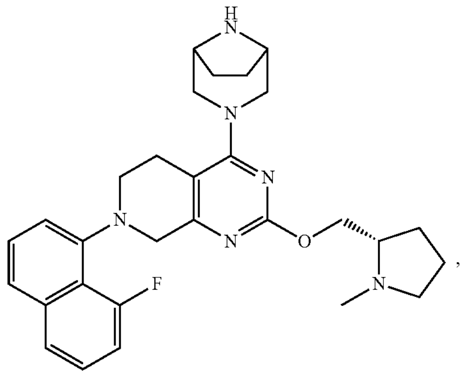
,
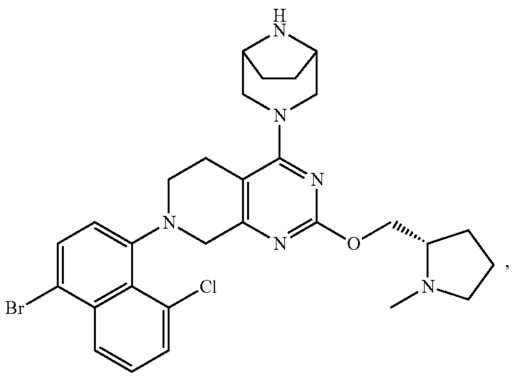
, -continued
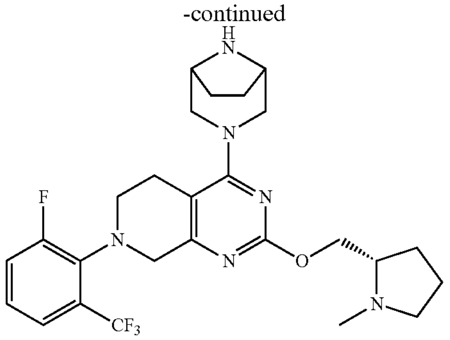
,
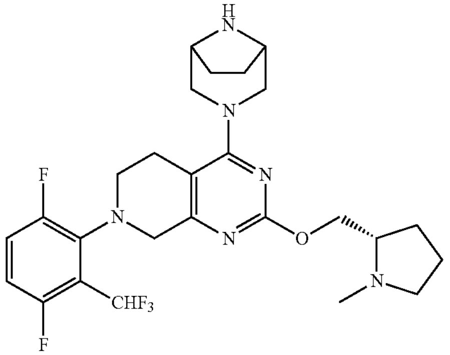
,
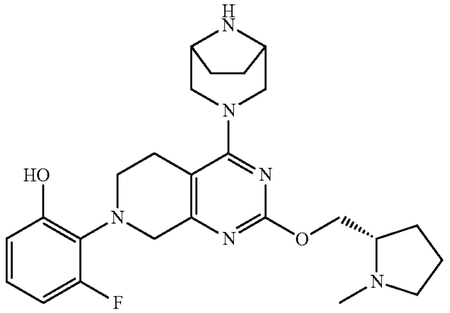
,
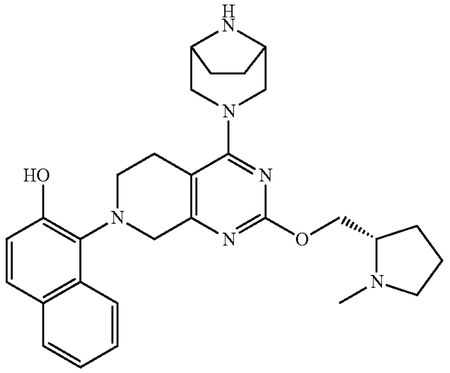
,
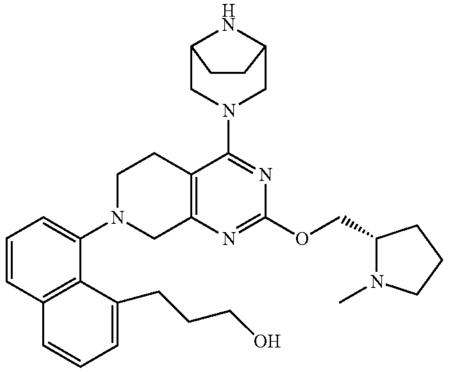
,
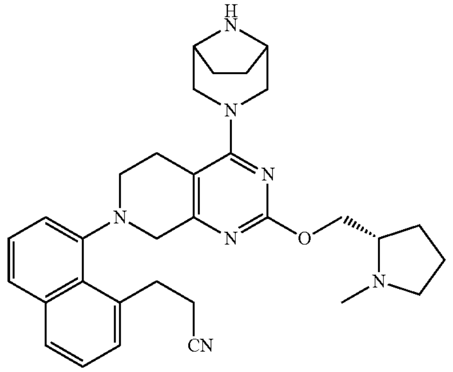
,
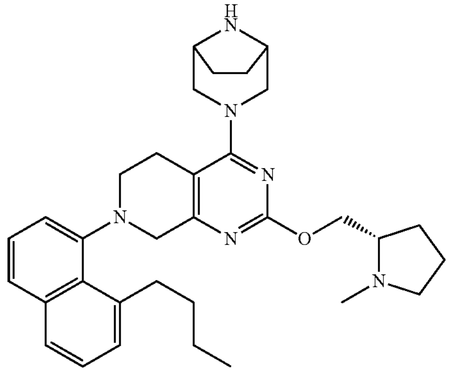
,
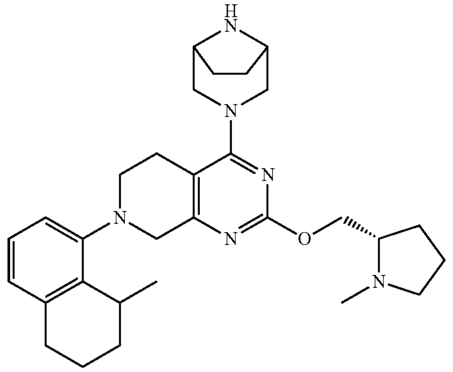
,
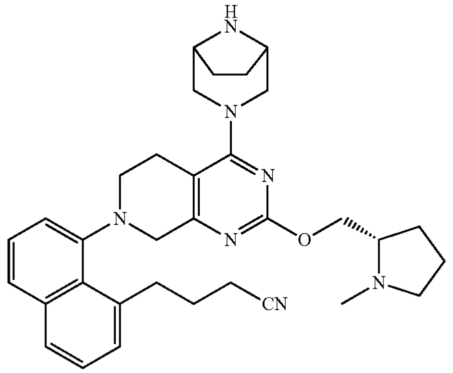
, -continued
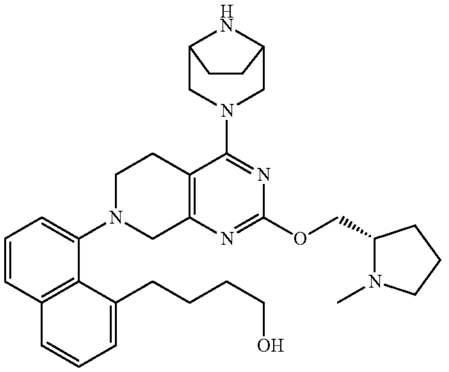,
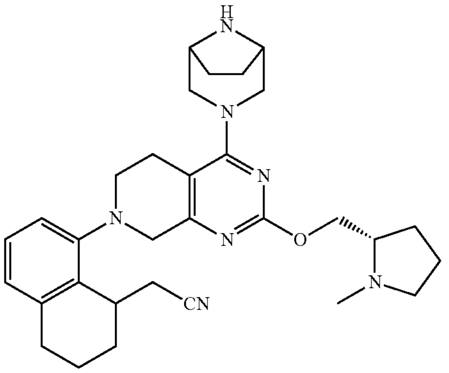,
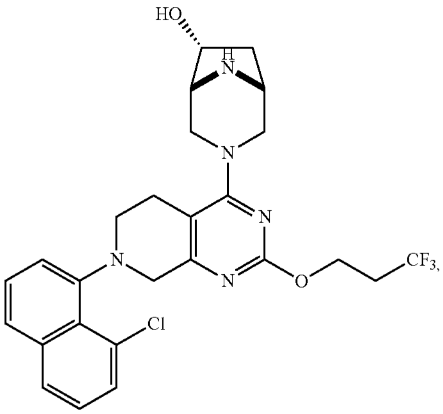
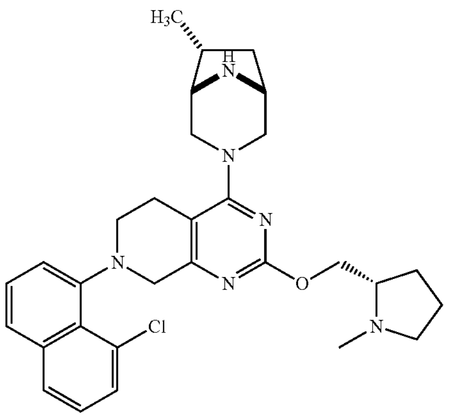,
-continued
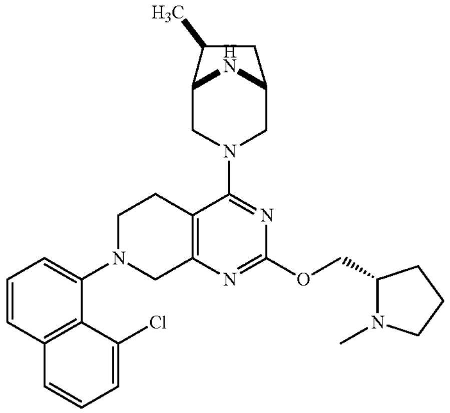,
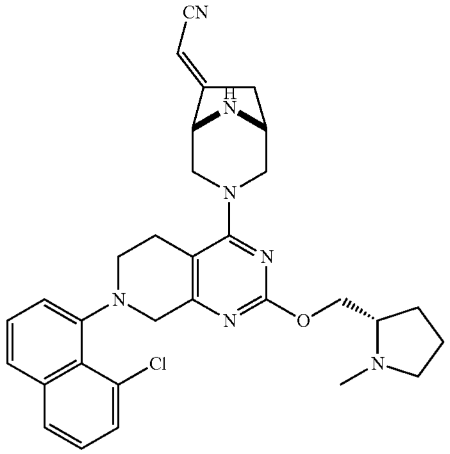,
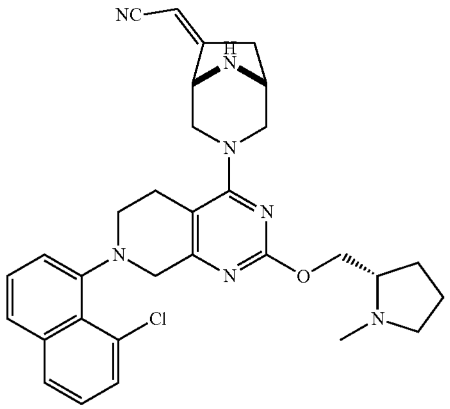,
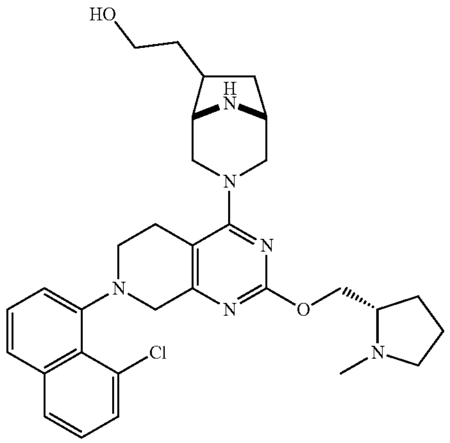, -continued
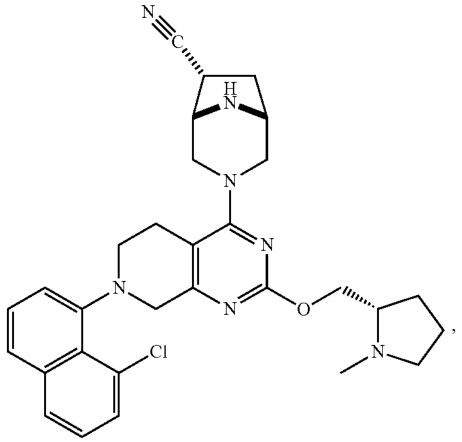
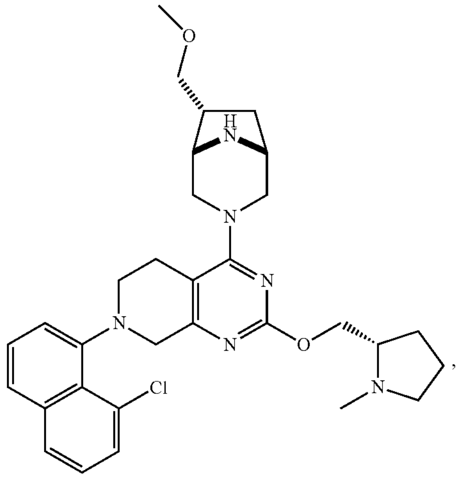
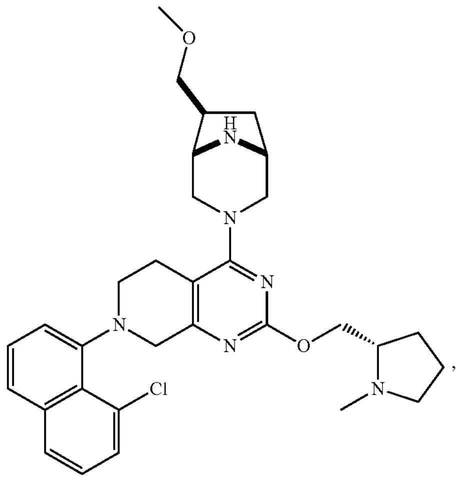
-continued
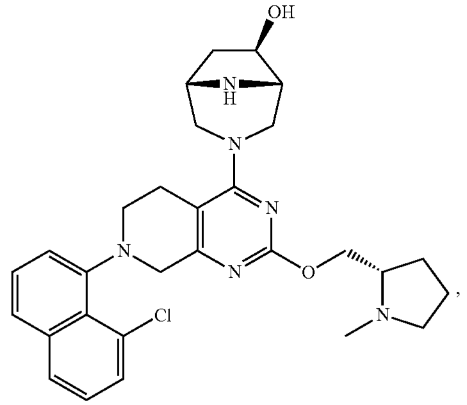
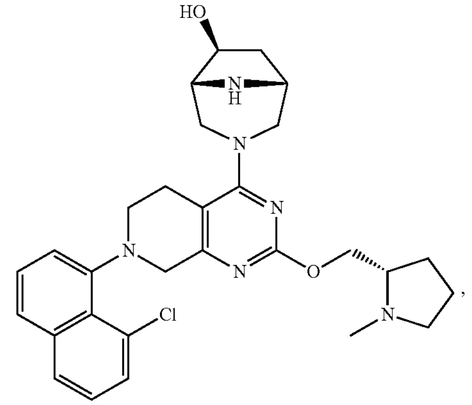
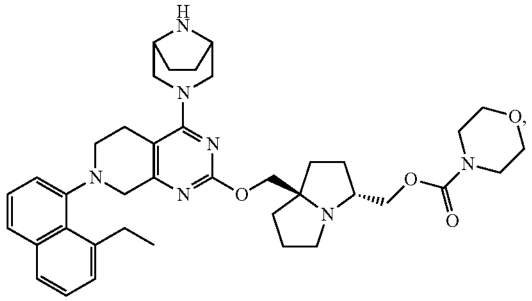
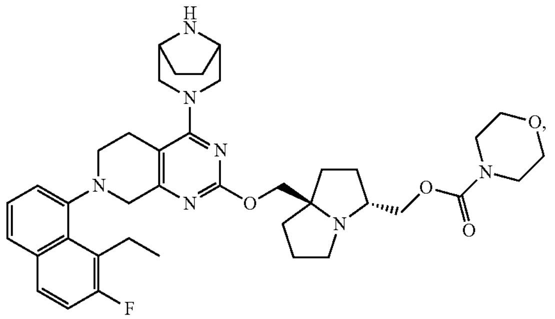

-continued
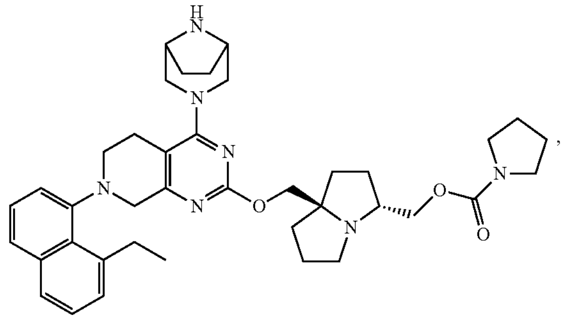
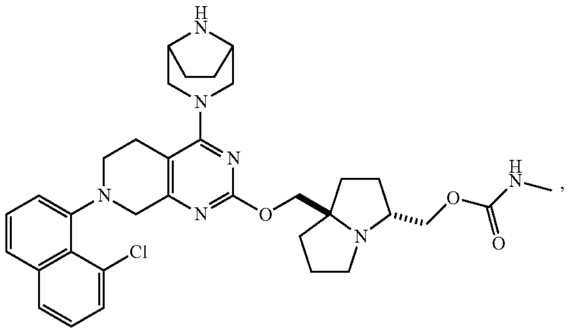
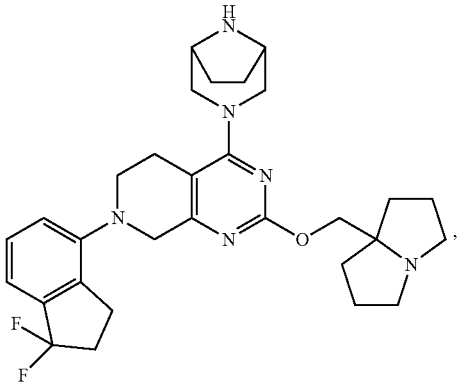
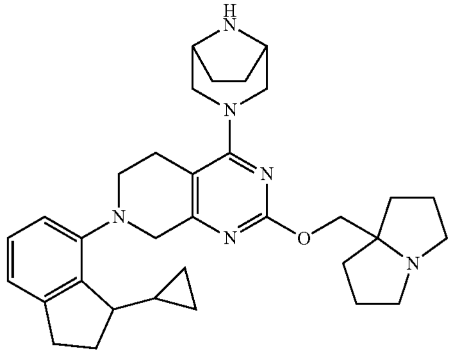
-continued
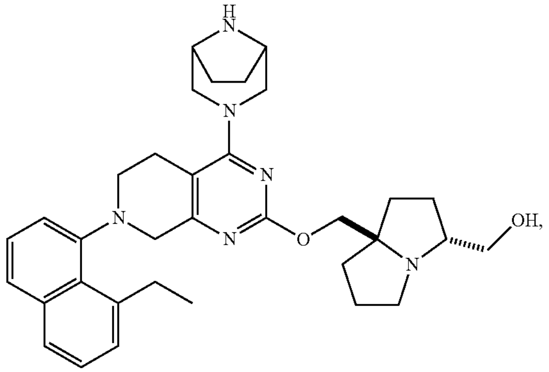
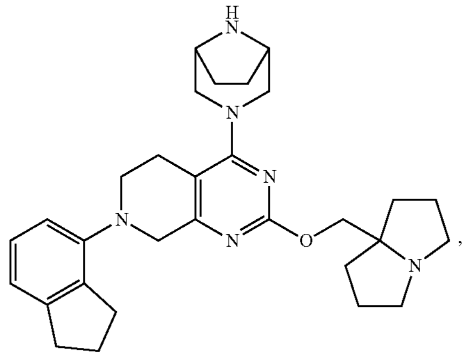
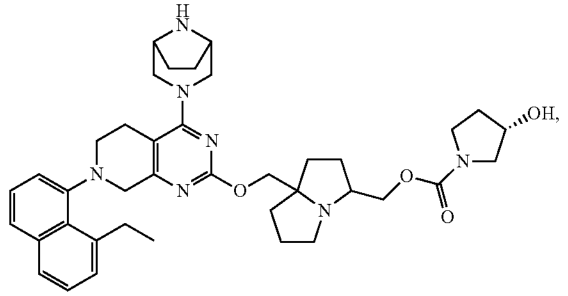
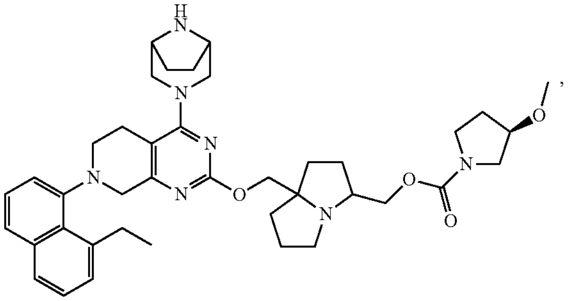
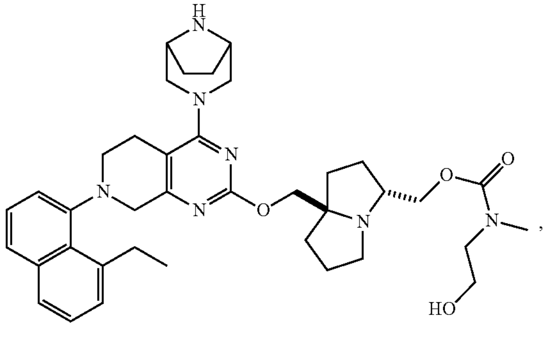

-continued
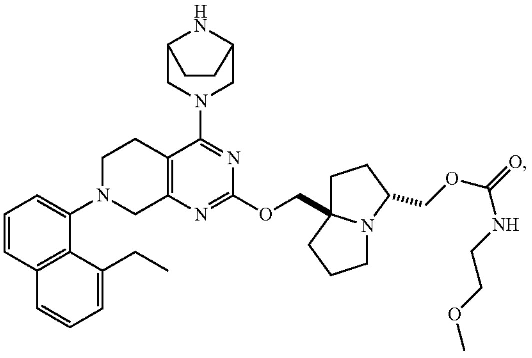
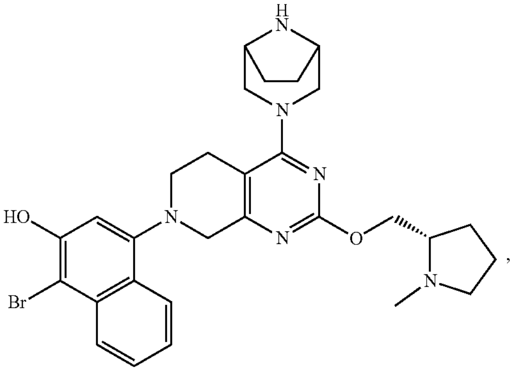
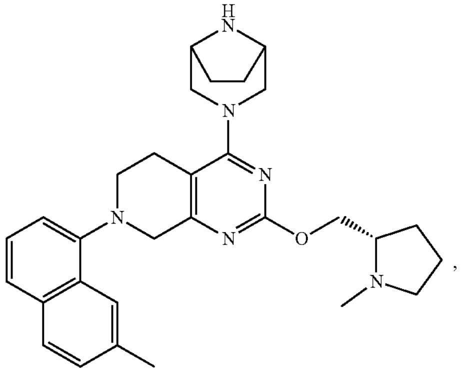
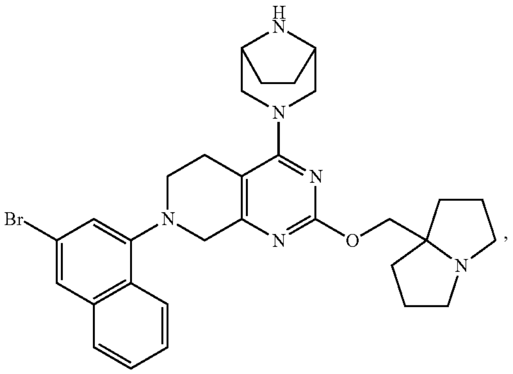
-continued
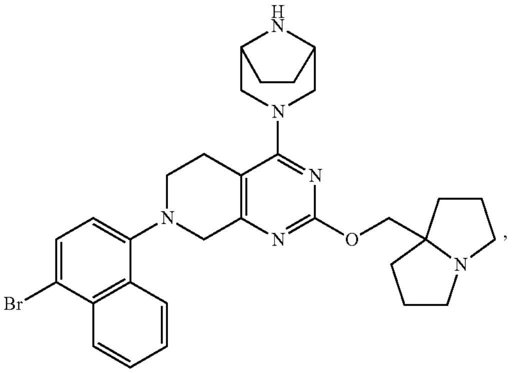
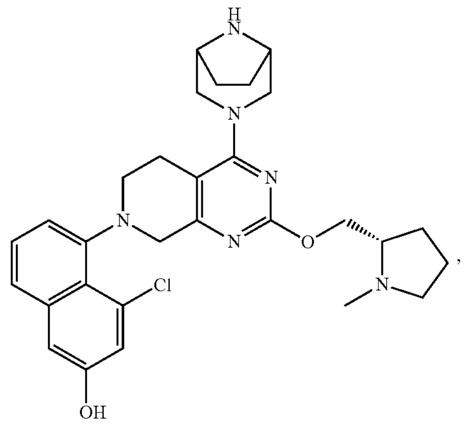
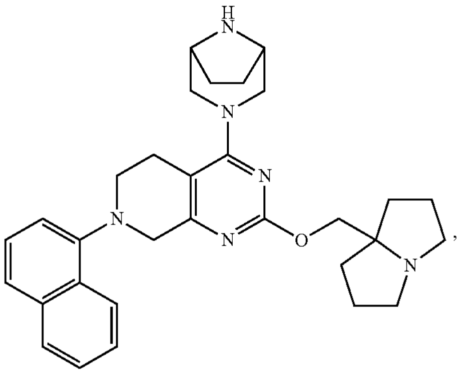
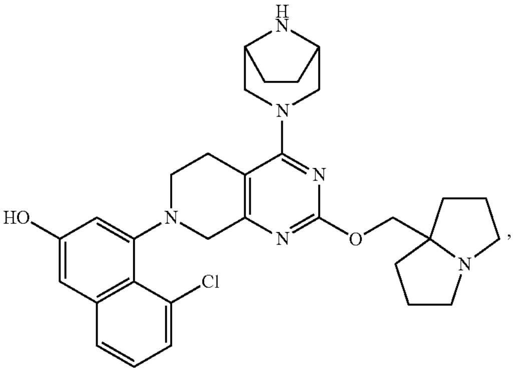

-continued

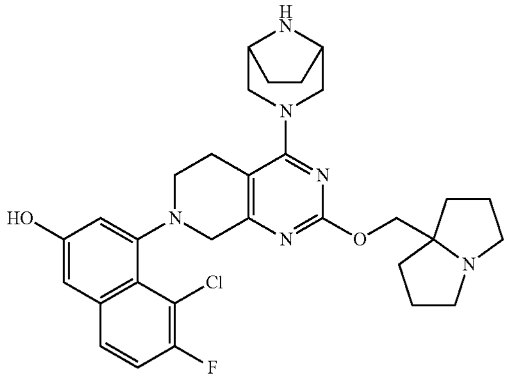

,

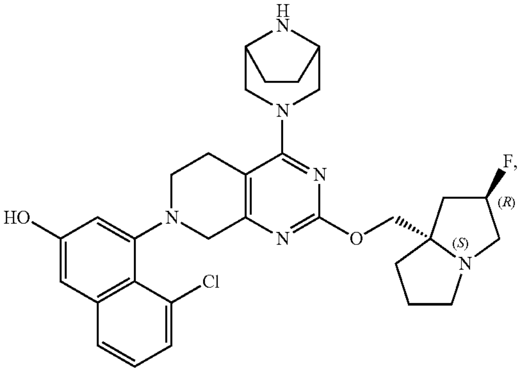

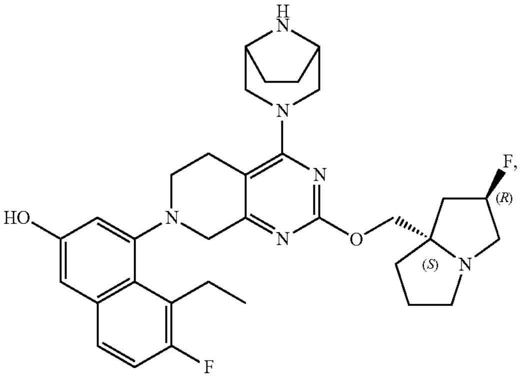

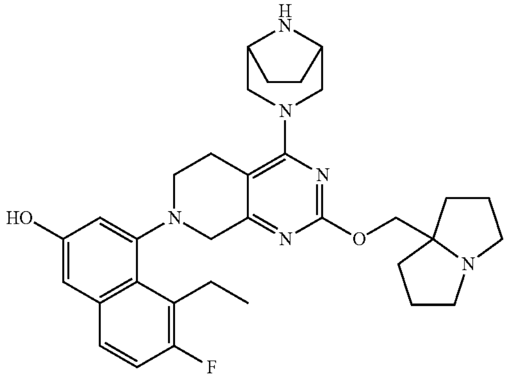

,

-continued

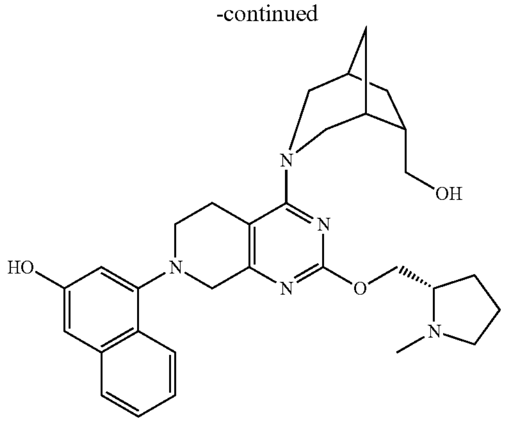

,

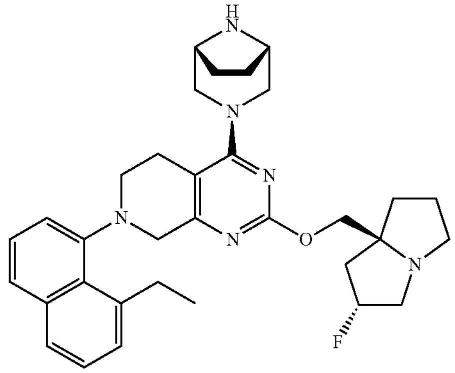

,

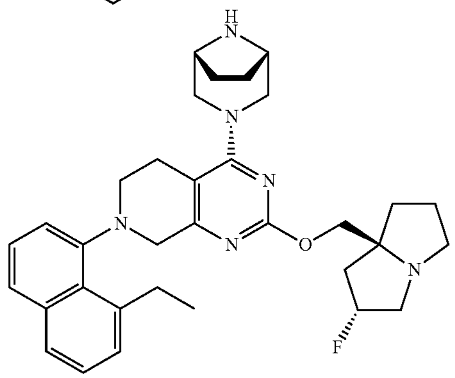

, and

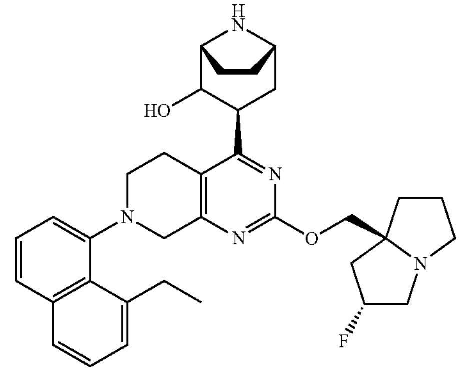

and pharmaceutically acceptable salts thereof. In one embodiment, the compounds of Formula (I) include bis-hydrochloride, tris-hydrochloride, trifluoroacetic acid, bis-trifluoroacetic acid, and tris-trifluoracetic acid salts of the above compounds. The compounds of Formula (I) or pharmaceutically acceptable salt thereof may be formulated into pharmaceutical compositions.

Pharmaceutical Compositions

In another aspect, the invention provides pharmaceutical compositions comprising a KRas G12D inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In one embodiment, administration may be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term pharmaceutically acceptable salt refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. In one embodiment, a dose of the active compound for all of the above-mentioned conditions is in the range from about 0.01 to 300 mg/kg, for example 0.1 to 100 mg/kg per day, and as a further example 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods of use described herein.

Methods of Use

In yet another aspect, the invention provides for methods for inhibiting KRas G12D activity in a cell, comprising contacting the cell in which inhibition of KRas G12D activity is desired with an effective amount of a compound of Formula (I), pharmaceutically acceptable salts thereof, or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a KRas G12D with a compound provided herein includes the administration of a compound provided herein to an individual or patient, such as a human, having KRas G12D, as well as, for example, introducing a compound provided herein into a sample containing a cellular or purified preparation containing the KRas G12D.

In one embodiment, a cell in which inhibition of KRas G12D activity is desired is contacted with an effective amount of a compound of Formula (I) or pharmaceutically acceptable salt thereof to negatively modulate the activity of KRas G12D.

By negatively modulating the activity of KRas G12D, the methods described herein are designed to inhibit undesired cellular proliferation resulting from enhanced KRas G12D activity within the cell. The cells may be contacted in a single dose or multiple doses in accordance with a particular treatment regimen to effect the desired negative modulation of KRas G12D. The ability of compounds to bind KRas G12D may be monitored in vitro using well known methods, including those described in Examples A and B below. In addition, the inhibitory activity of exemplary compounds in cells may be monitored, for example, by measuring the inhibition of KRas G12D activity of the amount of phosphorylated ERK, for example using the method described in Example C below.

In another aspect, methods of treating cancer in a patient in need thereof, comprising administering to said patient a therapeutically effective amount of a compound of Formula (I) or a pharmaceutically acceptable salt thereof, or a pharmaceutical composition comprising the compound or pharmaceutically acceptable salt thereof are provided.

The compositions and methods provided herein may be used for the treatment of a KRas G12D-associated cancer in a patient in need thereof, comprising administering to said patient a therapeutically effective amount of a compound of Formula (I), a pharmaceutically acceptable salt thereof, or a pharmaceutical composition comprising the compound or pharmaceutically acceptable salt thereof are provided. In one embodiment, the KRas G12D-associated cancer is lung cancer.

The compositions and methods provided herein may be used for the treatment of a wide variety of cancers including tumors such as lung, prostate, breast, brain, skin, cervical carcinomas, testicular carcinomas, etc. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is non-small cell lung cancer, small cell lung cancer, colorectal cancer, rectal cancer or pancreatic cancer. In certain embodiments, the cancer is non-small cell lung cancer.

The concentration and route of administration to the patient will vary depending on the cancer to be treated. The compounds, pharmaceutically acceptable salts thereof and pharmaceutical compositions comprising such compounds and salts also may be co-administered with other anti-neoplastic compounds, e.g., chemotherapy, or used in combination with other treatments, such as radiation or surgical intervention, either as an adjuvant prior to surgery or post-operatively.

Also provided herein is a compound of Formula (I) or a pharmaceutically acceptable salt thereof, or a pharmaceutical composition thereof as defined herein for use in therapy.

Also provided herein is a compound of Formula (I) or a pharmaceutically acceptable salt thereof, or a pharmaceutical composition thereof as defined herein for use in the treatment of cancer.

Also provided herein is a compound of Formula (I) or a pharmaceutically acceptable salt thereof, or a pharmaceutical composition thereof for use in the inhibition of KRas G12D.

Also provided herein is a compound of Formula (I) or a pharmaceutically acceptable salt thereof, or a pharmaceutical composition thereof as defined herein, for use in the treatment of a KRas G12D-associated disease or disorder.

Also provided herein is the use of a compound of Formula (I) or a pharmaceutically acceptable salt thereof, as defined herein in the manufacture of a medicament for the treatment of cancer.

Also provided herein is a use of a compound of Formula (I) or a pharmaceutically acceptable salt thereof, as defined herein in the manufacture of a medicament for the inhibition of activity of KRas G12D.

Also provided herein is the use of a compound of Formula (I) or a pharmaceutically acceptable salt thereof, as defined herein, in the manufacture of a medicament for the treatment of a KRas G12D-associated disease or disorder.

Also provided herein is a method for treating cancer in a patient in need thereof, the method comprising (a) determining that cancer is associated with a KRas G12D mutation (e.g., a KRas G12D-associated cancer) (e.g., as determined using a regulatory agency-approved, e.g., FDA-approved, assay or kit); and (b) administering to the patient a therapeutically effective amount of a compound of Formula (I), or a pharmaceutically acceptable salt thereof, or a pharmaceutical composition thereof.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

REACTION SCHEMES AND EXAMPLES

The compounds of the present invention may be prepared from commercially available reagents using the synthetic methods and reaction schemes described herein, or using other reagents and conventional methods well known to those skilled in the art.

For instance, compounds of the present invention may be prepared according to the General Reaction Schemes I-IV.

General Reaction Schemes

SCHEME I

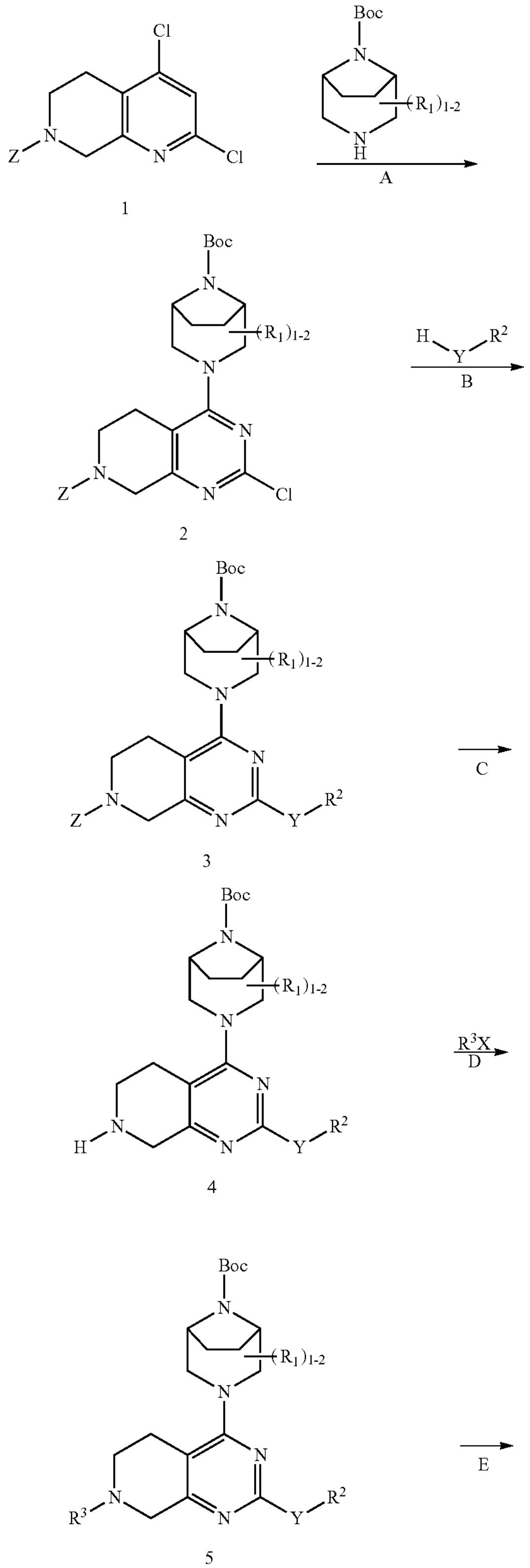

1

2

3

4

5

-continued

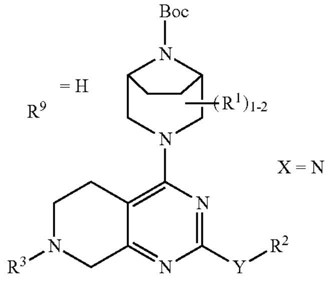
I

Compounds of Formula (I) wherein all of the substituents are as defined for Formula (I), with the exception that —Y—$R^2$ is not hydrogen, $R^9$ is hydrogen, and X is nitrogen, can be prepared according to Scheme I. In step A, the N-protected 2,4-dichloro-5,6,7,8-tetrahydropyrido[3,4-d]pyrimidine (1) undergoes a $S_NAr$ with an amine in the presence of a base such as N-ethyl-N-isopropylpropan-2-amine to give compound (2). In step B, compound (2) reacts with H—Y—$R^2$ through another $S_NAr$ or Palladium catalyzed coupling in the presences of a base such as Cesium carbonate to provide compound (3). In step C, the protective group (Z) is removed under either hydrogenation or acidic hydrolysis conditions to yield compound (4). In step D, $R^3$ is introduced through a C—N coupling catalyzed by Palladium in the presence of a phosphine ligand and a base such as Cesium carbonate. In step E, the Boc group of compound (5) is removed using conditions known in the art, for example with cold 4 N HCl in a solvent such as dioxane, to provide compound (I). In some cases, the species $R^1$, $R^2$ and/or $R^3$ will also contain protecting group(s) or require further transformation(s), which can be removed or done before or after step E in the synthetic sequence.

Compounds (1), (2), (3), (4), and (5) as shown and described above for Scheme I are useful as intermediates for preparing compounds of Formula (I) and are provided as further aspects of the invention.

SCHEME II

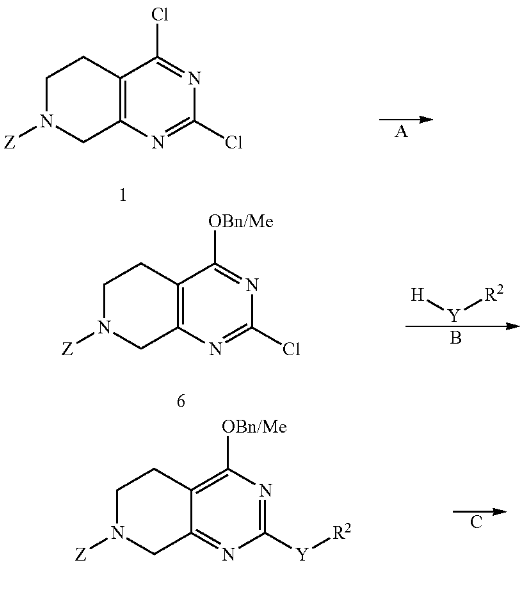

1

6

7

-continued

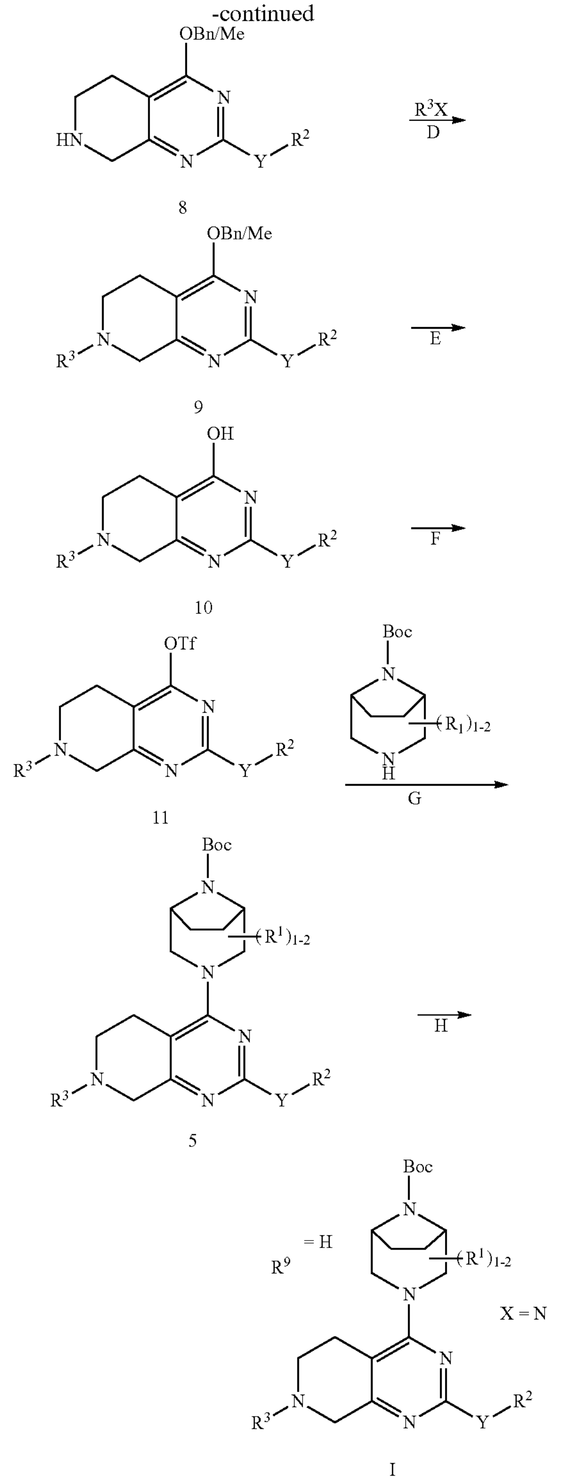

Compounds of Formula (I) wherein all of the substituents are as defined for Formula (I), with the exception that —Y—$R^2$ is not hydrogen, $R^9$ is hydrogen, and X is nitrogen, can be prepared according to Scheme II. In step A, the N-protected 2,4-dichloro-5,6,7,8-tetrahydropyrido[3,4-d] pyrimidine (1) undergoes a $S_NAr$ with benzyl alcohol or methanol in the presence of a base such as Cesium carbonate and in a polar solvent such dioxane to give compound (6). In step B, compound (6) reacts with H—Y—$R^2$ through another $S_NAr$ or Palladium catalyzed coupling in the presences of a base such as Cesium carbonate to provide compound (7). In step C, the protective group (Z) is removed under either hydrogenation or acidic hydrolysis conditions to yield compound (8). In step D, $R^3$ is introduced through a C—N coupling catalyzed by Palladium in the presence of a phosphine ligand and a base such as cesium carbonate. In step E, the benzyl or methyl group of compound (9) is removed with hydrogenation or sodium thiomethoxide. In step F, compound (10) is converted to the triflate with Trifluoromethanesulfonic anhydride in the presence of a base such as N-ethyl-N-isopropylpropan-2-amine. In step G, the triflate is replaced with an amine in a solvent such as dichloromethane. In step H, the Boc group of compound (5) is removed using conditions known in the art, for example with cold 4 N HCl in a solvent such as dioxane, to provide compound (I). In some cases, the species $R^1$, $R^2$ and/or $R^3$ will also contain protecting group(s) or require further transformation(s), which can be removed or done before or after step H in the synthetic sequence.

Compounds (6), (7), (8), (9), (10) and (11) as shown and described above for Scheme II are useful as intermediates for preparing compounds of Formula (I) and are provided as further aspects of the invention.

SCHEME III

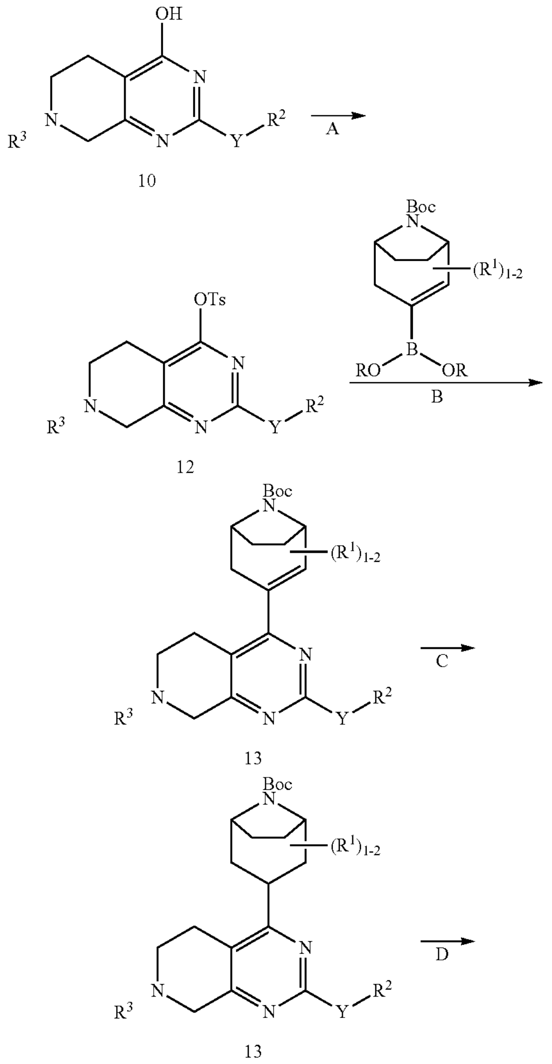

-continued

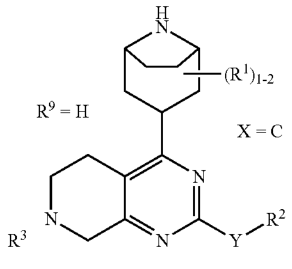

I

Compounds of Formula (I) wherein all of the substituents are as defined for Formula (I), with the exception that —Y—$R^2$ is not hydrogen, $R^9$ is hydrogen, and X is carbon, can be prepared according to Scheme III. In step A, compound (10) is converted to tosylate (12) through the reaction with tosyl chloride in the presence of a base such as triethylamine and catalytical amount of DMAP in dichloromethane. In step B, compound (12) undergoes a Suzuki coupling reaction to give compound (13) in a solvent such as dioxane and in the presence of a base such as potassium carbonate and a catalyst such as $Pd(PPh_3)_4$. In step C, compound (13) is hydrogenated under the catalysis of $Pd(OH)_2$. In step D, the Boc group of compound (14) is removed using conditions known in the art, for example with TFA in a solvent such as dichloromethane, to provide compound (I). In some cases, the species $R^1$, $R^2$ and/or $R^3$ will also contain protecting group(s) or require further transformation(s), which can be removed or done before or after step D in the synthetic sequence.

Compounds (12), (13), and (14) as shown and described above for Scheme III are useful as intermediates for preparing compounds of Formula (I) and are provided as further aspects of the invention.

SCHEME IV

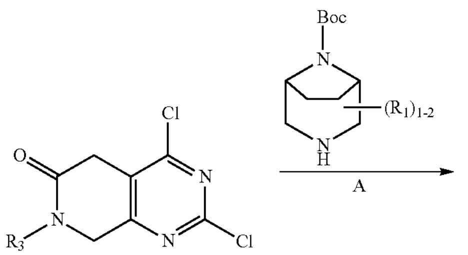

15

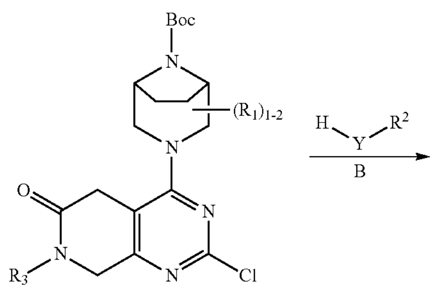

16

-continued

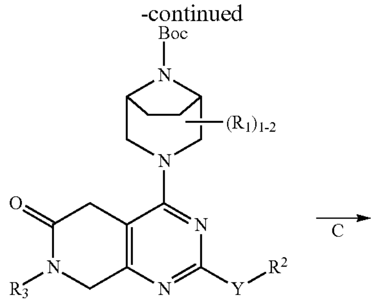

17

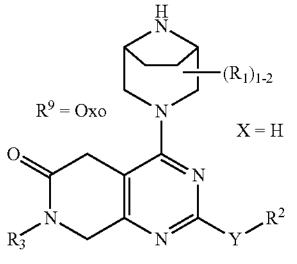

I

Compounds of Formula (I) wherein all of the substituents are as defined for Formula (I), with the exception that —Y—$R^2$ is not hydrogen, $R^9$ is oxo, and X is nitrogen, can be prepared according to Scheme IV. In step A, compound (15) undergoes a $S_NAr$ with an amine in the presence of a base such as triethylamine to give compound (16). In step B, compound (16) reacts with H—Y—$R^2$ through another $S_NAr$ in the presences of a base such as Cesium carbonate to provide compound (17). In step C, the Boc group of compound (17) is removed using conditions known in the art, for example with TFA in a solvent such as dichloromethane, to provide compound (I). In some cases, the species $R^1$, $R^2$ and/or $R^3$ will also contain protecting group(s) or require further transformation(s), which can be removed or done before or after step C in the synthetic sequence.

Compounds (15), (16), and (17) as shown and described above for Scheme III are useful as intermediates for preparing compounds of Formula (I) and are provided as further aspects of the invention.

The compounds of the present invention may have one or more chiral center and may be synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic IPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention. Unless otherwise indicated, whenever the specification, including the claims, refers to compounds of the invention, the term "compound" is to be understood to encompass all chiral (enantiomeric and diastereomeric) and racemic forms.

The compounds of the present invention may be in anhydrous, solvated or hydrated forms, and all such forms are included within the scope of the invention.

The following Intermediates are intended to illustrate further certain embodiments of the invention and are not intended to limit the scope of the invention.

Intermediate 1

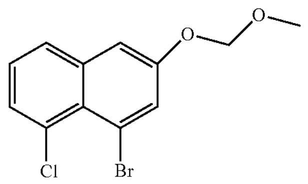 [SMILES: COCOc1cc(Br)c2c(Cl)cccc2c1]

1-bromo-8-chloro-3-(methoxymethoxy)naphthalene

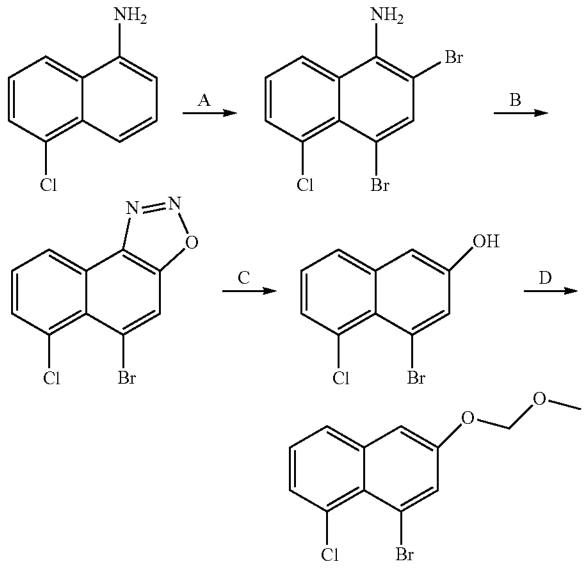

Step A. 2,4-dibromo-5-chloronaphthalen-1-amine: To a solution of 5-chloronaphthalen-1-amine (1.0 g, 5.6 mmol) in chloroform (30 mL) was added bromine (0.58 mL, 11 mmol) in chloroform (30 mL) dropwise. The mixture was heated at 50° C. overnight. Additional bromine (0.58 mL, 11 mmol) in 30 mL of chloroform was added dropwise at room temperature and the mixture was heated to 50° C. for 4 hours. The reaction was cooled to rt and concentrated in vacuo. Water was added to the residue and the aqueous layer was extracted three times with ethyl acetate. The pooled organic layers were dried over magnesium sulfate, filtered, and concentrated. The residue was purified by a silica gel column to give 2,4-dibromo-5-chloronaphthalen-1-amine as a brown solid. 1H NMR 400 MHz, (CDC13): δ 7.94 (s, 1H), 7.76 (d, J=8.0 Hz, 1H), 7.64 (d, J=8.0 Hz, 1H), 7.36 (t, J=8.0 Hz, 1H), 4.46 (bs, 2H).

Step B. 5-bromo-6-chloronaphtho[1,2-d][1,2,3]oxadiazole: 2,4-Dibromo-5-chloronaphthalen-1-amine (0.90 g, 2.7 mmol) was dissolved in acetic acid (22 mL) and propionic acid (2.2 mL). The solution was cooled in an ice bath, sodium nitrite (0.28 g, 4.0 mmol) was added, and the reaction was stirred at 0° C. for one hour and at rt for one hour. Water was added to the reaction and the aqueous layer was extracted three times with ethyl acetate. The pooled organic layers were dried over magnesium sulfate, filtered, and concentrated. The crude product was purified by a silica gel column to give 5-bromo-6-chloronaphtho[1,2-d][1,2,3]oxadiazole as a brown/yellow solid. 1H NMR 400 MHz, (CDC13): δ 7.45-7.38 (m, 2H), 7.31 (s, 1H), 7.22 (dd, J=8.0, 4.0 Hz, 1H).

Step C. 4-bromo-5-chloronaphthalen-2-ol: 5-Bromo-6-chloronaphtho[1,2-d][1,2,3]oxadiazole (0.28 g, 0.99 mmol) was dissolved in ethanol (15 mL) and THF (15 mL) at 0° C. Sodium borohydride (86 mg, 2.3 mmol) was added and the reaction was warmed to rt over 2 hours. The solvent was removed, and water was added to the residue. The mixture was acidified with 2 M HCl (aq.) and extracted two times with ethyl acetate. The pooled organics were dried over magnesium sulfate, filtered, and concentrated. The crude product was purified by a silica gel column to give 4-bromo-5-chloronaphthalen-2-ol as a yellow solid. 1H NMR 500 MHz, (CDC13) δ 7.61-7.58 (m, 2H), 7.48 (d, J=10.0 Hz, 1H), 7.30 (d, 1H, J=10.0 Hz, 1H), 7.15 (s, 1H), 5.02 (s, 1H).

Step D. 1-bromo-8-chloro-3-(methoxymethoxy)naphthalene: To a solution of 4-bromo-5-chloronaphthalen-2-ol (0.20 g, 0.79 mmol) in THE (4 mL) at 0° C. was added sodium hydride (47 mg, 1.2 mmol). The mixture was stirred at 0° C. for 30 minutes, chloromethyl methyl ether (78 μL, 1.0 mmol) was added, and the reaction was warmed to room temperature over 2 hours. The reaction was concentrated in vacuo, the residue was partitioned between EtOAc and water, and the layers were separated. The aqueous layer was extracted with ethyl acetate. The pooled organic layers were dried over magnesium sulfate, filtered, and concentrated. The crude material was purified by a silica gel column to give 1-bromo-8-chloro-3-(methoxymethoxy)naphthalene as a solid. $^1$H NMR 500 MHz, ($CDCl_3$) δ 7.68 (s, 1H), 7.65 (d, J=10.0 Hz, 1H), 7.49 (d, J=10.0 Hz, 1H), 7.36 (s, 1H), 7.29 (t, J=10.0 Hz, 1H), 5.26 (s, 2H), 3.51 (s, 3H).

Intermediate 2

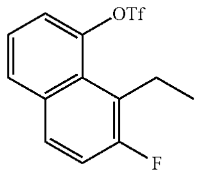 [SMILES: CCc1c(F)ccc2cccc(OS(=O)(=O)C(F)(F)F)c12]

8-ethyl-7-fluoronaphthalen-1-yl trifluoromethanesulfonate

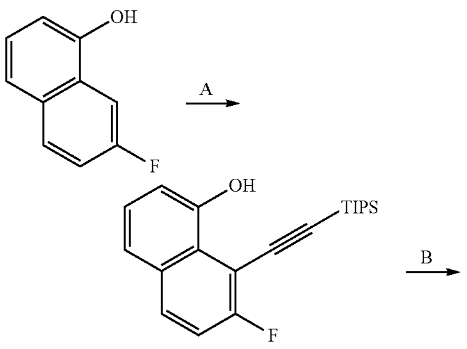

-continued

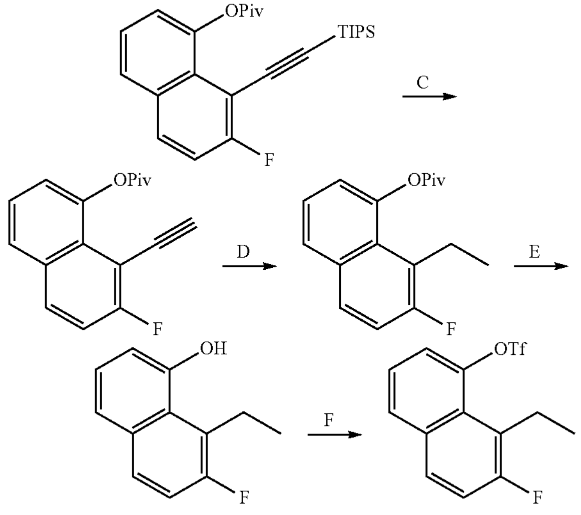

Step A. 7-fluoro-8-((triisopropylsilyl)ethynyl)naphthalen-1-ol. 7-Fluoronaphthalen-1-ol (0.32 g, 2.0 mmol), (bromoethynyl)triisopropylsilane (0.63 g, 2.4 mmol), potassium carbonate (0.28 g, 2.0 mmol), and sodium acetate (33 mg, 0.40 mmol) were added to a vial with a stir bar and septa cap. The vial was degassed and purged with $N_2$ 3 times before dry DCE (8.0 mL) was added followed by dichloro(p-cymene)ruthenium(II) dimer (0.12 g, 0.20 mmol). The reaction was heated to 40° C. for 21 hours before being diluted with water and extracted with DCM 2 times. The DCM layers were combined, dried with $Na_2SO_4$, filtered, and concentrated. The residue was purified by flash chromatography (silica, 0-10% EtOAc/hexanes) to yield 7-fluoro-8-((triisopropylsilyl)ethynyl)naphthalen-1-ol as an orange solid (0.51 g, 75%). $^1H$ NMR ($CDCl_3$, 400 MHz): δ 9.09 (s, 1H), 7.78 (dd, J=9.3, 5.9 Hz), 7.39-7.34 (m, 2H), 7.22 (t, J=8.7 Hz, 1H), 7.06-7.00 (m, 1H), 1.22-1.16 (m, 21H).

Step B. 7-fluoro-8-((triisopropylsilyl)ethynyl)naphthalen-1-yl pivalate. 7-Fluoro-8-((triisopropylsilyl)ethynyl)naphthalen-1-ol (0.51 g, 1.5 mmol), N,N-dimethylpyridin-4-amine (0.18 g, 1.5 mmol), N-ethyl-N-isopropylpropan-2-amine (0.78 mL, 4.5 mmol), and DCM (10 mL) were added to a vial with a stir bar and septa cap. The vial was cooled to 0° C. and pivaloyl chloride (0.54 mL, 4.5 mmol) was added dropwise. The reaction was stirred at 0° C. for 1 hour. The reaction was diluted with water and extracted with DCM. The DCM layer was dried with $Na_2SO_4$, filtered, and concentrated. The residue was purified by flash chromatography (silica, 0-10% EtOAc in hexanes) to yield 7-fluoro-8-((triisopropylsilyl)ethynyl)naphthalen-1-yl pivalate as an orange solid (0.53 g, 84%). $^1H$ NMR ($CDCl_3$, 400 MHz): δ 7.76 (dd, J=8.9, 5.7 Hz, 1H), 7.65 (d, J=8.2 Hz, 1H), 7.39 (t, J=7.8 Hz, 1H), 7.25 (t, J=8.8 Hz, 1H), 7.06 (d, J=7.5 Hz, 1H), 1.48 (s, 9H), 1.20-1.14 (m, 21H).

Step C. 8-ethynyl-7-fluoronaphthalen-1-yl pivalate. 7-Fluoro-8-((triisopropylsilyl)ethynyl)naphthalen-1-yl pivalate (0.53 g, 1.3 mmol) was added to a vial with a stir bar and septa cap. THE (4 mL) was added and the vial was cooled to 0° C. 1M TBAF in THE (1.9 mL, 1.9 mmol) was added dropwise at 0° C. The reaction was stirred at 0° C. for 1 hour and at room temperature for 15 minutes. The reaction was diluted with water and extracted with DCM. The DCM layer was dried with $Na_2SO_4$, filtered, and concentrated. The residue was purified by flash chromatography (silica, 0-10% EtOAc in hexanes) to yield 8-ethynyl-7-fluoronaphthalen-1-yl pivalate as an orange solid (0.28 g, 83%). $^1H$ NMR ($CDCl_3$, 400 MHz): δ 7.83 (dd, J=8.9, 5.7 Hz, 1H), 7.70 (d, J=8.2 Hz, 1H), 7.43 (t, J=7.8 Hz, 1H), 7.28 (t, J=8.8 Hz, 1H), 7.09 (d, J=7.6 Hz, 1H), 3.59 (s, 1H), 1.45 (s, 9H).

Step D. 8-ethyl-7-fluoronaphthalen-1-yl pivalate. 8-Ethynyl-7-fluoronaphthalen-1-yl pivalate (0.28 g, 1.0 mmol) and MeOH (7 mL) were added to a vial with a stir bar and septa cap. The vial was degassed with $N_2$ for 10 minutes before 10% Pd on carbon (0.11 g, 0.10 mmol) was added in one portion. The reaction was stirred at room temperature under a $H_2$ atmosphere for 2 hours. The reaction mixture was filtered through Celite with MeOH and the filtrate was concentrated to yield 8-ethyl-7-fluoronaphthalen-1-yl pivalate (0.22 g, 77%). $^1H$ NMR ($CDCl_3$, 400 MHz): δ 7.70-7.64 (m, 2H), 7.35 (t, J=7.8 Hz, 1H), 7.22 (t, J=9.3 Hz, 1H), 7.00 (d, J=7.5 Hz, 1H), 3.16 (qd, J=7.5, 2.9 Hz, 2H), 1.45 (s, 9H), 1.24 (t, J=7.5 Hz, 3H).

Step E. 8-ethyl-7-fluoronaphthalen-1-ol. 8-Ethyl-7-fluoronaphthalen-1-yl pivalate (0.22 g, 0.80 mmol) and methanol (4 mL) were added to a round bottom flask with a stir bar. 6M NaOH (0.66 mL, 4.0 mmol) was added and the reaction was stirred at room temperature for 30 minutes. 2M HCl was added until the reaction mixture reached a pH of 5. The reaction mixture was extracted with DCM 2 times. The DCM layers were combined, dried with $Na_2SO_4$, filtered, and concentrated. The residue was purified by flash chromatography (silica, 0-20% EtOAc in hexanes) to yield 8-ethyl-7-fluoronaphthalen-1-ol as a pink oil (0.13 g, 83%). $^1H$ NMR ($CDCl_3$, 400 MHz): δ 7.59 (dd, J=9.0, 5.8 Hz, 1H), 7.37 (d, J=8.2 Hz, 1H), 7.24-7.15 (m, 2H), 6.72 (d, J=7.4 Hz, 1H), 5.42 (s, 1H), 3.37 (qd, J=7.4, 3.2 Hz, 2H), 1.31 (t, J=7.4 Hz, 3H).

Step F. 8-ethyl-7-fluoronaphthalen-1-yl trifluoromethanesulfonate. 8-Ethyl-7-fluoronaphthalen-1-ol (0.13 g, 0.66 mmol), N,N-diisopropylethylamine (0.15 mL, 1.1 mmol), and DCM (7 mL) were added to a round bottom flask with a stir bar and septa. The round bottom flask was cooled to −78° C. before the addition of $Tf_2O$ (0.20 mL, 0.86 mmol). The reaction was stirred at −78° C. for 15 minutes before being warmed to room temperature. The reaction was diluted with water and extracted with DCM 2 times. The DCM layers were combined, dried with $Na_2SO_4$, filtered, and concentrated. The residue was purified by flash chromatography (silica, 0-10% EtOAc in hexanes) to yield 8-ethyl-7-fluoronaphthalen-1-yl trifluoromethanesulfonate as a colorless oil (0.18 g, 86%). $^1H$ ($CDCl_3$, 400 MHz): δ 7.84 (d, J=8.1 Hz, 1H), 7.75 (dd, J=9.0, 5.7 Hz, 1H), 7.57 (d, J=7.8 Hz, 1H), 7.42 (t, J=8.0 Hz, 1H), 7.34 (t, J=9.2 Hz, 1H), 3.30 (qd, J=7.5, 2.8 Hz, 2H), 1.26 (t, J=7.5 Hz, 3H).

Intermediate 3

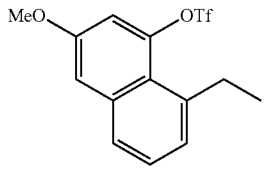 [SMILES: CCc1cccc2cc(OC)cc(OS(=O)(=O)C(F)(F)F)c12]

8-ethyl-3-methoxynaphthalen-1-yl trifluoromethanesulfonate

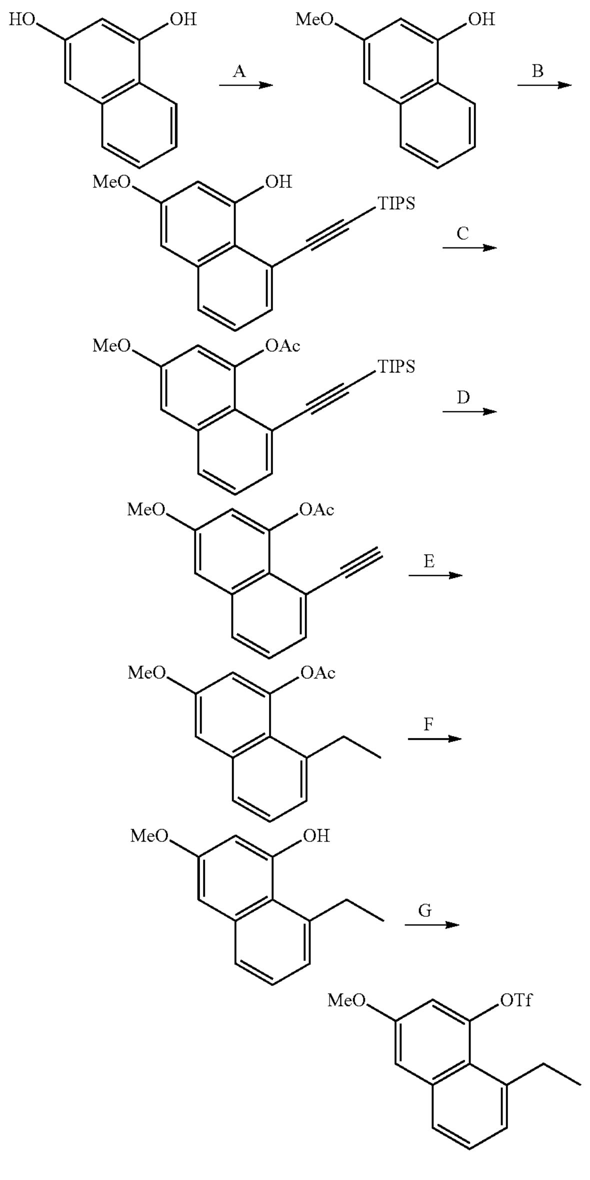

Step A: 3-methoxynaphthalen-1-ol. A solution of naphthalene-1,3-diol (2.0 g, 12 mmol) in MeOH (21 mL) and a 4.0 M hydrochloric acid solution in 1,4-dioxane (22 mL, 88 mmol) was stirred at room temperature. The solution was concentrated and purified by silica gel chromatography eluting with 5-75% EtOAc/Hex to give 3-methoxynaphthalen-1-ol (2.0 g, 92% yield). LCMS (MM-ES+APCI, Pos): m/z 175.1 (M+H).

Step B: 3-methoxy-8-((triisopropylsilyl)ethynyl)naphthalen-1-ol. A mixture of 3-methoxynaphthalen-1-ol (2.0 g, 12 mmol), (bromoethynyl)triisopropylsilane (3.5 g, 13 mmol), potassium carbonate (1.6 g, 12 mmol), sodium acetate (0.19 g, 2.3 mmol), and dichloro(p-cymene)ruthenium(II) dimer (0.35 g, 0.57 mmol) in 1,2-dichloroethane (46 mL) was sparged with argon and heated to 40° C. under nitrogen overnight. The mixture was concentrated and purified by silica gel chromatography (5-50% EtOAc/Hex) to give 3-methoxy-8-((triisopropylsilyl)ethynyl)naphthalen-1-ol (3.2 g, 79% yield). LCMS (MM-ES+APCI, Pos): m/z 355.2 (M+H).

Step C: 3-methoxy-8-((triisopropylsilyl)ethynyl)naphthalen-1-yl acetate. To a solution of 3-methoxy-8-((triisopropylsilyl)ethynyl)naphthalen-1-ol (0.20 g, 0.56 mmol) in dichloromethane (3.7 mL) was added acetic anhydride (69 μL, 0.73 mmol) and DMAP (7 mg, 0.06 mmol) and the reaction was stirred for 90 minutes. The solution was partitioned between dichloromethane and saturated $NaHCO_3$. The organics were concentrated and purified by silica gel chromatography (5-30% EtOAc/Hex) to give 3-methoxy-8-((triisopropylsilyl)ethynyl)naphthalen-1-yl acetate (0.21 g, 94% yield). LCMS (MM-ES+APCI, Pos): m/z 397.2 (M+H).

Step D: 8-ethynyl-3-methoxynaphthalen-1-yl acetate. To a solution of 3-methoxy-8-((triisopropylsilyl)ethynyl)naphthalen-1-yl acetate (0.21 g, 0.53 mmol) in tetrahydrofuran (5 mL) at 0° C. was added TBAF (1.0 mL, 1.0 mmol) and the reaction was stirred for 30 minutes. The solution was partitioned between dichloromethane and water. The organics were concentrated and purified by silica gel chromatography (5-50% EtOAc/Hex) to give 8-ethynyl-3-methoxynaphthalen-1-yl acetate (78 mg, 61% yield). LCMS (MM-ES+APCI, Pos): m/z 241.1 (M+H).

Step E: 8-ethyl-3-methoxynaphthalen-1-yl acetate. A mixture of 8-ethynyl-3-methoxynaphthalen-1-yl acetate (78 mg, 0.32 mmol) and Pd/C (35 mg, 0.032 mmol) in methanol (2 mL) was stirred under hydrogen for 1 hour. The mixture was filtered and the filtrate was concentrated to give 8-ethyl-3-methoxynaphthalen-1-yl acetate (75 mg, 95% yield). LCMS (MM-ES+APCI, Pos): m/z 245.1 (M+H).

Step F: 8-ethyl-3-methoxynaphthalen-1-ol. A mixture of 8-ethyl-3-methoxynaphthalen-1-yl acetate (75 mg, 0.31 mmol) in methanol (1.5 mL) and 6 M NaOH (0.25 mL) was stirred for 15 minutes. The mixture was brought to pH ~5 and partitioned with DCM.

The organics were concentrated and purified by silica gel chromatography (5-95% EtOAc/Hex) to give 8-ethyl-3-methoxynaphthalen-1-ol (47 mg, 76% yield). LCMS (MM-ES+APCI, Pos): m/z 203.2 (M+H).

Step G: 8-ethyl-3-methoxynaphthalen-1-yl trifluoromethanesulfonate. To a solution of 8-ethyl-3-methoxynaphthalen-1-ol (47 mg, 0.23 mmol) in DCM (2.3 mL) was added DIEA (61 μL, 0.35 mmol). The solution was cooled to −78° C., triflic anhydride (47 μL, 0.28 mmol) was added, and the solution was warmed to room temperature and stirred for 30 minutes. The solution was partitioned between dichloromethane and saturated $NaHCO_3$. The organics were concentrated and purified by silica gel chromatography (5-50% EtOAc/Hex) to give 8-ethyl-3-methoxynaphthalen-1-yl trifluoromethanesulfonate (58 mg, 75% yield). LCMS (MM-ES+APCI, Pos): m/z 334.0 (M+H).

Intermediate 4

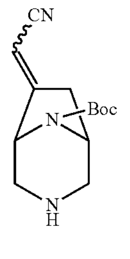 [SMILES: CC(C)(C)OC(=O)N1C2CNCC1C(=CC#N)C2]

tert-butyl 6-(cyanomethylene)-3,8-diazabicyclo [3.2.1]octane-8-carboxylate

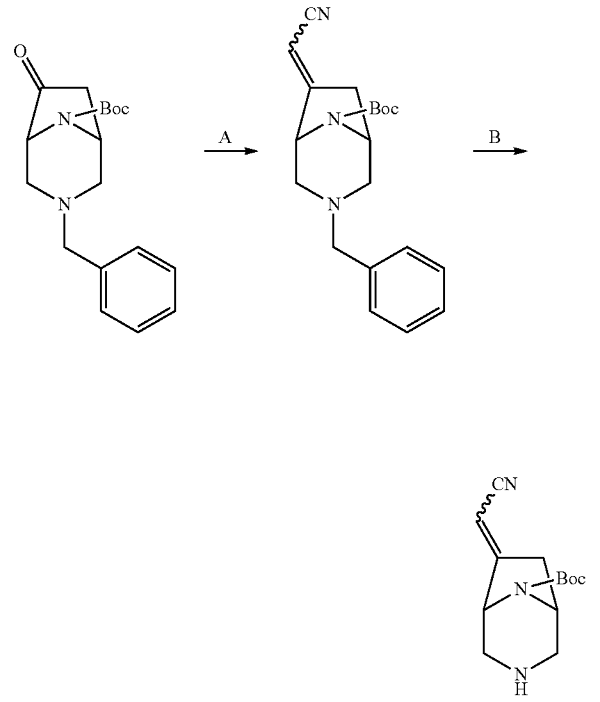

Step A. tert-butyl 3-benzyl-6-(cyanomethylene)-3,8-diazabicyclo[3.2.1]octane-8-carboxylate. To a stirred suspension of (cyanomethyl)trimethylphosphanium iodide (0.42 g, 1.7 mmol) in tetrahydrofuran (11 mL) under $N_2$ was added NaH (60%, 71 mg, 1.8 mmol) in one portion. The mixture was stirred at rt for 1 h. To the mixture was added tert-butyl (1R,5R)-3-benzyl-6-oxo-3,8-diazabicyclo[3.2.1]octane-8-carboxylate (0.36 g, 1.1 mmol). The mixture was stirred at rt for 1 h. The reaction mixture was quenched with $NH_4Cl$ (sat.) and extracted with ethyl acetate. The extract was dried over $Na_2SO_4$, concentrated, and purified by flash chromatography eluting with 0>30% ethyl acetate/hexanes to give the title compound (0.38 g, 98%) as a colorless oil. LCMS (MM-ES+APCI, Pos): m/z 340.3 (M+H).

Step B. tert-butyl 6-(cyanomethylene)-3,8-diazabicyclo [3.2.1]octane-8-carboxylate hydrochloride. To a solution of tert-butyl (1R,5S)-3-benzyl-6-(cyanomethylene)-3,8-diazabicyclo[3.2.1]octane-8-carboxylate (25 mg, 0.074 mmol) in 1,2-dichloroethane (0.74 mL) in a vial was added 1-chloroethyl chloroformate (40 µL, 0.37 mmol). The vial was heated at 90° C. for 5 h. The solution was cooled to rt and 1-chloroethyl chloroformate (40 µL, 0.37 mmol) was added. The mixture was heated at 90° C. for 7 h. The mixture was cooled to rt and concentrated to dryness. The residue was treated with methanol (1.5 mL) at rt for 2 h and at 35° C. for 2 h. The solution was concentrated and triturated with hexanes to give the crude title compound (28 mg, 133%) as the HCl salt. LCMS (MM-ES+APCI, Pos): m/z 250.2 (M+H).

Intermediate 5

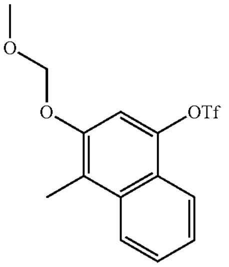 [SMILES: COCOc1cc(OS(=O)(=O)C(F)(F)F)c2ccccc2c1C]

3-(methoxymethoxy)-4-methylnaphthalen-1-yl trifluoromethanesulfonate

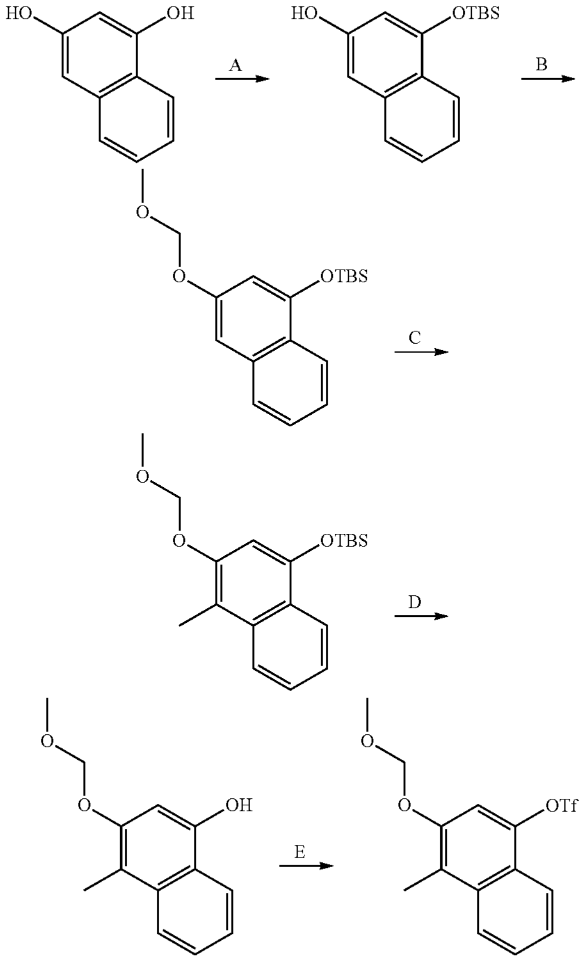

Step A. 4-((tert-butyldimethylsilyl) oxy) naphthalen-2-ol. Naphthalene-1,3-diol (2.0 g, 13 mmol), imidazole (1.0 g, 15 mmol) and TBS-Cl (1.9 g, 13 mmol) were placed in THE (25 mL) and the reaction was stirred for 3 hours. The reaction was quenched with water and the mixture was extracted with DCM. The organic layers were combined, concentrated, and the residue was purified by normal phase chromatography (0-15% EtOAc/hexane) to provide 4-((tert-butyldimethylsilyl) oxy) naphthalen-2-ol (0.58 g, 17% yield). $^1$H NMR ($CDCl_3$, 400 MHz): δ 8.08-8.05 (m, 1H), 7.61 (d, J=8.2 Hz, 1H), 7.43-7.38 (m, 1H), 7.32-7.26 (m, 1H), 6.77 (d, J=2.3 Hz, 1H), 6.52 (d, J=2.3 Hz, 1H), 1.09 (s, 9H), 0.92 (s, 6H).

Step B. tert-butyl((3-(methoxymethoxy) naphthalen-1-yl) oxy) dimethylsilane. A solution of 4-((tert-butyldimethylsilyl)oxy)naphthalen-2-ol (0.58 g, 2.1 mmol) and N-ethyl-N-isopropylpropan-2-amine (0.55 mL, 3.2 mmol) in DCM (1 mL) was cooled to 0° C., chloro (methoxy) methane (0.18 mL, 2.3 mmol) was added, and the reaction was stirred at 0° C. for 1 hour. Water was added and the mixture was extracted with DCM. The organics were concentrated and the residue was purified by silica gel (0-20% EtOAc/hexane) to provide tert-butyl((3-(methoxymethoxy) naphthalen-1-yl) oxy) dimethylsilane (0.36 g, 53% yield). $^1$H NMR ($CDCl_3$, 400 MHz): δ 8.07 (d, J=8.4 Hz, 1H), 7.67 (d, J=8.2 Hz, 1H), 7.45-7.39 (m, 1H), 7.34-7.29 (m, 1H), 7.02 (d, J=2.1 Hz, 1H), 6.63 (d, J=2.3 Hz, 1H), 5.26 (s, 2H), 3.52 (s, 3H), 1.09 (s, 9H), 0.3 (s, 6H).

Step C. tert-butyl((3-(methoxymethoxy)-4-methylnaphthalen-1-yl) oxy) dimethylsilane. Tert-butyl((3-(methoxymethoxy) naphthalen-1-yl)oxy)dimethylsilane (0.30 g, 0.95 mmol) was placed in THF (5 mL) and was cooled to −78° C. BuLi (1.0 mL, 1.0 mmol) was added and the reaction was stirred at 0° C. for 1 hour. The reaction was cooled to −78° C. and MeI (0.12 mL, 1.9 mmol) was added. The reaction was stirred for 20 minutes and quenched with water. The mixture was extracted with ether. The extracts were combined and concentrated in vacuo. The residue was purified by silica gel (hexanes) to provide tert-butyl((3-(methoxymethoxy)-4-methylnaphthalen-1-yl) oxy) dimethylsilane (0.22 g, 71% yield). NMR $^1$H ($CDCl_3$, 400 MHz): δ 8.13 (d, J=9.1 Hz, 1H), 7.9 (d, J=8.5 Hz, 1H), 7.51-7.46 (m, 1H), 7.37-7.34 (m, 1H), 6.88 (s, 1H), 5.21 (s, 2H), 3.54 (s, 3H), 2.5 (s, 3H), 1.09 (s, 9H), 0.28 (s, 6H).

Step D. 3-(methoxymethoxy)-4-methylnaphthalen-1-ol. Tert-butyl((3-(methoxymethoxy)-4-methylnaphthalen-1-yl) oxy) dimethylsilane (92 mg, 0.28 mmol) was placed in THE (5 mL) and cooled to O ° C. TBAF (0.11 g, 0.42 mmol) was added and the reaction was stirred at 0° C. for 1 hour. Water was added and the reaction was extracted with DCM. The organic layers were concentrated, and the residue purified by silica gel (0-25% EtOAc in hex) to provide 3-(methoxymethoxy)-4-methylnaphthalen-1-ol (45 mg, 75% yield). $^1$H NMR ($CDCl_3$, 400 MHz): δ 8.11 (d, J=8.3 Hz, 1H), 7.91 (d, J=8.4 Hz, 1H), 7.54-7.49 (m, 1H), 7.4-7.36 (m, 1H), 6.84 (s, 1H), 5.29 (s, 1H), 5.23 (s, 2H), 3.55 (s, 3H), 2.5 (s, 3H).

Step E. 3-(methoxymethoxy)-4-methylnaphthalen-1-yl trifluoromethanesulfonate. 3-(Methoxymethoxy)-4-methylnaphthalen-1-ol (45 mg, 0.21 mmol) and Hunig's base (71 μL, 0.41 mmol) were placed in DCM (2 mL) and the mixture was cooled to −78° C. $Tf_2O$ (52 μL, 0.31 mmol) was added and the reaction was stirred for 1 hour. Water was added and the mixture was extracted with DCM. The extracts were combined and concentrated. The residue was purified by silica gel (0-20% EtOAc in hex) to provide 3-(methoxymethoxy)-4-methylnaphthalen-1-yl trifluoromethanesulfonate (61 mg, 85% yield).

Intermediate 6

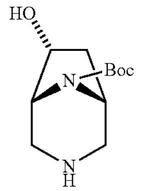 [SMILES: CC(C)(C)OC(=O)N1[C@H]2CNC[C@@H]1[C@H](O)C2]

tert-butyl 6-hydroxy-3,8-diazabicyclo[3.2.1]octane-8-carboxylate

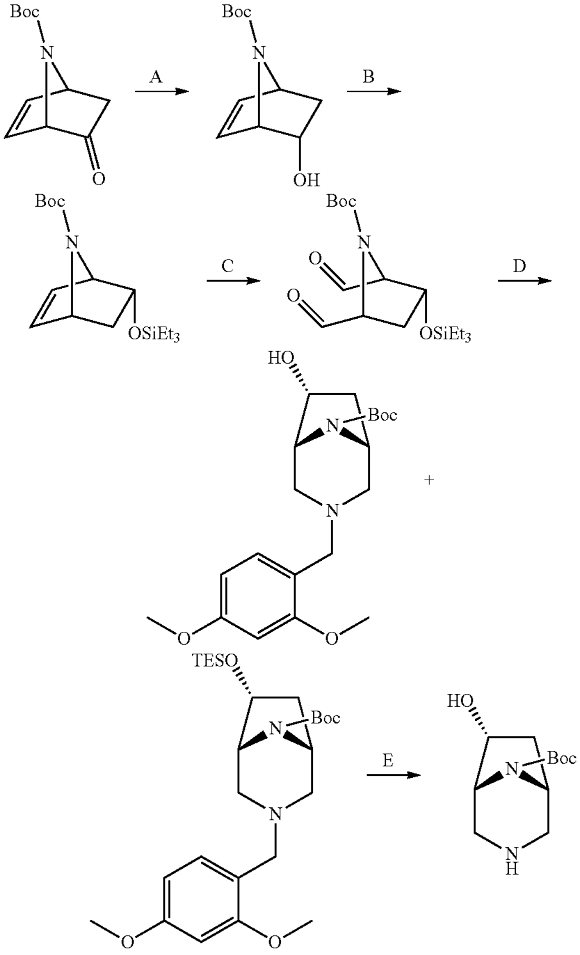

Step A. tert-butyl (1S,4S,5S)-5-hydroxy-7-azabicyclo[2.2.1]hept-2-ene-7-carboxylate. To a stirred solution of tert-butyl-5-oxo-7-azabicyclo[2.2.1]hept-2-ene-7-carboxylate (0.50 g, 24 mmol) in ethanol (5 mL) was added solid sodium borohydride (45 mg, 1.2 mmol) in several portions. The suspension was stirred at rt for 1 h. The reaction was partitioned between water (20 mL) and EtOAc (30 mL), and the layers were separated. The organic layer was washed with brine (5 mL), dried over $Na_2SO_4$ and concentrated in vacuo. The colorless solid was dried over a stream of air and washed with 20% EtOAc/hexane (3×0.5 mL). The combined aqueous phases were extracted with EtOAc, dried over $Na_2SO_4$, concentrated in vacuo, combined with washings from the main material, and chromatographed on silica gel eluting with 20 to 50% EtOAc/hex. The fractions containing product were combined with the initially obtained solid to give tert-butyl 5-hydroxy-7-azabicyclo[2.2.1]hept-2-ene-7-carboxylate (0.50 g, 99%). $^1$H NMR (400 MHz, $CDCl_3$): 6.59 (s, 1H), 6.32 (s, 1H), 4.71 (s, 1H), 4.68 (s, 1H), 4.55-4.45 (m, 1H), 2.35 (ddd, J=11.9, 8.0, 5.4 Hz, 1H), 1.49 (brs, 1H), 1.40 (m, 10H).

Step B tert-butyl 5-((triethylsilyl)oxy)-7-azabicyclo[2.2.1]hept-2-ene-7-carboxylate. To a stirred solution tert-butyl 5-hydroxy-7-azabicyclo[2.2.1]hept-2-ene-7-carboxylate (0.50 g, 2.4 mmol) and triethylamine (0.66 mL, 4.7 mmol) in dichloromethane (5 mL) was added chlorotriethylsilane (0.60 mL, 3.6 mmol) dropwise. The reaction mixture was stirred at rt overnight. The reaction was partitioned between water (10 mL) and MTBE (15 mL), and the organic layer was separated. The organics were washed with brine (5 mL), dried over $Na_2SO_4$, and concentrated in vacuo. The residue was chromatographed on silica gel using 10 to 40% EtOAc/hexane as eluent to give tert-butyl 5-((triethylsilyl)oxy)-7-azabicyclo[2.2.1]hept-2-ene-7-carboxylate (0.72 g, 93%) as a colorless liquid. LCMS (MM-ES+APCI, Pos): m/z 226.3 $(M\text{-}Boc+H)^+$. $^1$H NMR (400 MHz, $CDCl_3$): 6.47 (s, 1H), 6.23 (s, 1H), 4.57 (brs, 2H), 4.45-4.39 (m, 1H), 2.22 (ddd, J=11.5, 7.8, 4.5 Hz, 1H), 1.40 (s, 9H), 0.92 (t, J=7.8 Hz, 9H), 0.87 (dd, J=11.5, 2.3 Hz, 1H), 0.57 (q, J=7.9 Hz, 6H).

Step C. tert-butyl (2R,3S,5S)-2,5-diformyl-3-((triethylsilyl)oxy)pyrrolidine-1-carboxylate. A stirred solution of tert-butyl (1S,4S,5S)-5-((triethylsilyl)oxy)-7-azabicyclo[2.2.1]hept-2-ene-7-carboxylate (0.72 g, 2.2 mmol) in dichloromethane (11 mL) was cooled in a dry ice-ethanol bath and ozone (~1% in $O_2$, ~3 mL/s) was introduced. After ~45 min. a solution of triphenylphosphane (1.4 g, 5.5 mmol) in DCM (5 mL) was added dropwise. The reaction mixture was warmed to 0° C. and used in the next stage immediately.

Step D. tert-butyl 3-(2,4-dimethoxybenzyl)-6-((triethylsilyl)oxy)-3,8-diazabicyclo[3.2.1]octane-8-carboxylate and tert-butyl 3-(2,4-dimethoxybenzyl)-6-hydroxy-3,8-diazabicyclo[3.2.1]octane-8-carboxylate. To a solution of crude tert-butyl (2R,3S,5S)-2,5-diformyl-3-((triethylsilyl)oxy)pyrrolidine-1-carboxylate (0.78 g, 2.2 mmol) in dichloromethane (44 mL) was added sodium triacetoxyborohydride (1.2 g, 5.5 mmol) followed by a solution of (2,4-dimethoxyphenyl)methanamine (0.37 g, 2.2 mmol) in DCM (1 mL). The reaction was stirred for 2 hours at r.t., 2M $Na_2CO_3$ (10 mL) was added, and the reaction was stirred for one hour. The layers were separated, the organic phase was washed with water (10 mL), washed with brine (10 mL), dried over $Na_2SO_4$, and evaporated in vacuo. The residue was chromatographed on silica gel in 10 to 40% EtOAc/hex. to yield tert-butyl 3-(2,4-dimethoxybenzyl)-6-((triethylsilyl)oxy)-3,8-diazabicyclo[3.2.1]octane-8-carboxylate (0.25 g, 23%) and tert-butyl 3-(2,4-dimethoxybenzyl)-6-hydroxy-3,8-diazabicyclo[3.2.1]octane-8-carboxylate (0.16 g, 19%). LCMS (MM-ES+APCI, Pos): 0-TES alcohol m/z 493.3 (M+H), free alcohol. LCMS (MM-ES+APCI, Pos): m/z 379.3 (M+H).

Step E. tert-butyl (1R,5R,6R)-6-hydroxy-3,8-diazabicyclo[3.2.1]octane-8-carboxylate: To a stirred solution of tert-butyl (1R,5R,6R)-3-(2,4-dimethoxybenzyl)-6-hydroxy-3,8-diazabicyclo[3.2.1]octane-8-carboxylate (0.30 g, 0.79 mmol) in methanol (8 mL) was added 20% palladium hydroxide on carbon (0.10 g, 0.14 mmol). The reaction mixture was degassed with $H_2$ and a hydrogen atmosphere (from a balloon) was introduced. The reaction was stirred under $H_2$ for 3 hours. The reaction mixture was filtered through Celite and the Celite was washed with MeOH (3*2 mL). The filtrate was evaporated in vacuo, the residue was dissolved in MTBE and filtered through a cotton plug. The filtrate was evaporated under a stream of nitrogen to give tert-butyl (1R,5R,6R)-6-hydroxy-3,8-diazabicyclo[3.2.1]octane-8-carboxylate which was used crude in the next reaction. LCMS (MM-ES+APCI, Pos): m/z 229.3 (M+H).

Intermediate 7

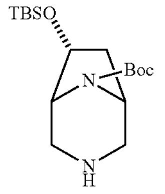 [SMILES: CC(C)(C)OC(=O)N1C2CNCC1[C@H](O[Si](C)(C)C(C)(C)C)C2]

tert-butyl (6R)-6-((tert-butyldimethylsilyl)oxy)-3,8-diazabicyclo[3.2.1]octane-8-carboxylate

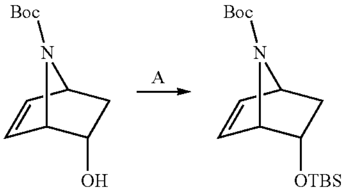

Step A. tert-butyl (1S,4S,5S)-5-((tert-butyldimethylsilyl)oxy)-7-azabicyclo[2.2.1]hept-2-ene-7-carboxylate. A mixture of tert-butyl (1S,4S,5S)-5-hydroxy-7-azabicyclo[2.2.1]hept-2-ene-7-carboxylate (4.1 g, 19 mmol), imidazole (2.0 g, 29 mmol), and tert-butylchlorodimethylsilane (3.5 g, 23 mmol) in N,N-dimethylformamide (8 mL) was stirred at 30° C. for 1 hour and at r.t. overnight. The reaction mixture was quenched with MeOH (2 mL), stirred for 1 h at r.t., and partitioned between water (50 mL) and MTBE (100 mL). The organic layer was washed with brine (5 mL), dried over $Na_2SO_4$, evaporated in vacuo, and chromatographed on silica gel eluting with 10 to 40% EtOAc/hexane to yield the desired material as a colorless oil (5.6 g, 89%).

tert-butyl (6R)-6-((tert-butyldimethylsilyl)oxy)-3,8-diazabicyclo[3.2.1]octane-8-carboxylate. Synthesized according to intermediate 9, steps C-E substituting tert-butyl (1S,4S,5S)-5-((tert-butyldimethylsilyl)oxy)-7-azabicyclo[2.2.1]hept-2-ene-7-carboxylate for tert-butyl (1S,4S,5S)-5-((triethylsilyl)oxy)-7-azabicyclo[2.2.1]hept-2-ene-7-carboxylate in Step C. LCMS (MM-ES+APCI, Pos): m/z 343.2 (M+H).

Intermediate 8

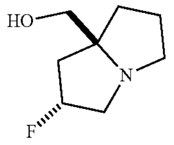 [SMILES: OC[C@@]12CCCN1C[C@H](F)C2]

(2-fluorotetrahydro-1H-pyrrolizin-7a(5H)-yl)methanol (racemic, trans)

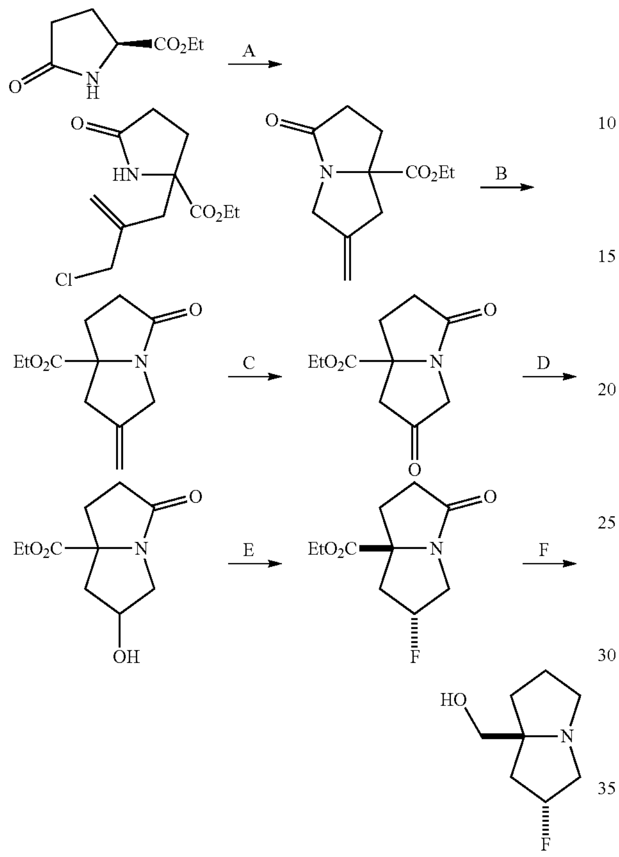

Step A. ethyl 2-(2-(chloromethyl)allyl)-5-oxopyrrolidine-2-carboxylate. To a stirred solution of ethyl (S)-5-oxopyrrolidine-2-carboxylate (5.7 g, 36 mmol) and 3-chloro-2-(chloromethyl)prop-1-ene (17 mL, 150 mmol) in THE (36 mL) at −40° C. under nitrogen was added LiHMDS (76 mL, 76 mmol) (1M in THF) by slow cannulation. After 15 minutes, the cooling bath was removed. The reaction was warmed to room temperature and stirred for 2 hours. The reaction was quenched with a saturated ammonium chloride solution (20 mL) and concentrated to about 60 mL. The residual material was partitioned between ethyl acetate (100 mL) and water (100 mL) and the layers were separated. The organics were washed 1×100 mL with brine, dried over $MgSO_4$, filtered, and concentrated. The crude product was purified by flash chromatography eluting with an ethyl acetate/hexanes gradient (20 to 80% ethyl acetate). The crude product (5.6 g) contained a mixture (approximately 2.7:1) of ethyl 2-(2-(chloromethyl)allyl)-5-oxopyrrolidine-2-carboxylate and ethyl 2-methylene-5-oxotetrahydro-1H-pyrrolizine-7a(5H)-carboxylate (product of the step B) and was carried on crude without further purification.

Step B. ethyl 2-methylene-5-oxotetrahydro-1H-pyrrolizine-7a(5H)-carboxylate. To a stirred suspension of NaH (0.14 g, 3.5 mmol) in THF (40 mL) at 0° C. under nitrogen was added a 2.7:1 mixture of ethyl 2-(2-(chloromethyl)allyl)-5-oxopyrrolidine-2-carboxylate and ethyl 2-methylene-5-oxotetrahydro-1H-pyrrolizine-7a(5H)-carboxylate (0.71 g) as a solution in THE (20 mL) by syringe. The mixture was heated to reflux overnight. The reaction was cooled to room temperature and quenched with water (20 mL). The majority of the THF was removed by rotary evaporation and the residual mixture was partitioned between ethyl acetate (50 mL) and water (50 mL). The organics were dried over MgSO4, filtered, and concentrated to yield ethyl 2-methylene-5-oxotetrahydro-1H-pyrrolizine-7a(5H)-carboxylate an orange oil which was carried on crude without further purification.

Step C. ethyl 2,5-dioxotetrahydro-1H-pyrrolizine-7a(5H)-carboxylate. To a stirred solution of crude ethyl 2-methylene-5-oxotetrahydro-1H-pyrrolizine-7a(5H)-carboxylate (1.1 g, 5.3 mmol) in dichloromethane (14 mL) at −78° C. was added ozone gas via a pipet inserted into the solution. Ozone was continuously passed through the solution until a light blue color appeared (about 15 minutes). The ozone generator was turned off and oxygen was passed through the reaction for about 5 minutes. Nitrogen gas was passed through the solution for another 5 minutes. Polymer-bound triphenylphosphine (3.50 g, 10.5 mmol) was added neat as a solid at −78° C. The reaction was warmed to rt and slowly stirred overnight. The reaction mixture was filtered and concentrated to yield 1 g of a light-yellow oil which was carried on crude without further purification.

Step D. ethyl 2-hydroxy-5-oxotetrahydro-1H-pyrrolizine-7a(5H)-carboxylate. Ethyl 2,5-dioxotetrahydro-1H-pyrrolizine-7a(5H)-carboxylate (1.1 g, 5.1 mmol) was charged to a 50 mL round bottom flask equipped with a stir bar and nitrogen inlet with methanol (17 mL). To the stirred solution was added sodium borohydride neat (0.14 g, 3.8 mmol). After 5 minutes the mixture was quenched slowly with 10% aqueous $K_2CO_3$ and the aqueous layer was extracted with 5 portions of 25% IPA/DCM. The combined organics were dried over $Na_2SO_4$ and concentrated in vacuo to yield 0.97 g of a white solid which was carried on crude without further purification.

Step E. ethyl 2-fluoro-5-oxotetrahydro-1H-pyrrolizine-7a(5H)-carboxylate. To a stirred solution of crude ethyl 2-hydroxy-5-oxotetrahydro-1H-pyrrolizine-7a(5H)-carboxylate (4.8:1 cis:trans isomers) (1 g, 4.7 mmol) in dichloromethane (14 mL) at −78° C. was added Deoxo-Fluor (0.86 mL, 4.7 mmol) neat by syringe. The reaction was stirred overnight and warmed to rt. The mixture was partitioned between 25% IPA/DCM and water and the layers were separated. The aqueous layer was extracted 3× with 25% IPA/DCM and the organics were combined and dried over $Na_2SO_4$. The crude product was concentrated and purified by flash chromatography eluting with an ethyl acetate/hexanes gradient (0% to 60% ethyl acetate) to yield ethyl 2-fluoro-5-oxotetrahydro-1H-pyrrolizine-7a(5H)-carboxylate as a clear oil containing a single racemic trans diastereomer (0.21 g, 21%). $^1H$ NMR (400 MHz, $CDCl_3$) δ 5.30, (m, 1H), 4.21 (m, 2H), 3.16 (m, 1H), 2.73 (m, 4H), 2.45 (m, 1H), 2.19 (m, 2H), 1.28 (m, 3H).

Step F. (2-fluorotetrahydro-1H-pyrrolizin-7a(5H)-yl)methanol. Ethyl 2-fluoro-5-oxotetrahydro-1H-pyrrolizine-7a(5H)-carboxylate (0.21 g, 0.99 mmol) and dry THE (2 mL) were charged to a 25 mL pear shaped flask equipped with a stir bar. The mixture was cooled to 0° C. and LAH (1M in THF) (3.0 mL, 3.0 mmol) was added dropwise. The vessel was equipped with a cold-water condenser and heated to 70° C. for 4 hours. The mixture was diluted with ethyl ether, cooled to 0 followed by water (330 μL). The vessel was warmed to room temperature and stirred for 15 minutes. To the mixture was added anhydrous magnesium sulfate. The mixture stirred for 15 minutes before being filtered and concentrated in vacuo to give product (0.16 g, 100%). LCMS (MM-ES+APCI, Pos): m/z 160.2 (M+H).

Intermediate 9

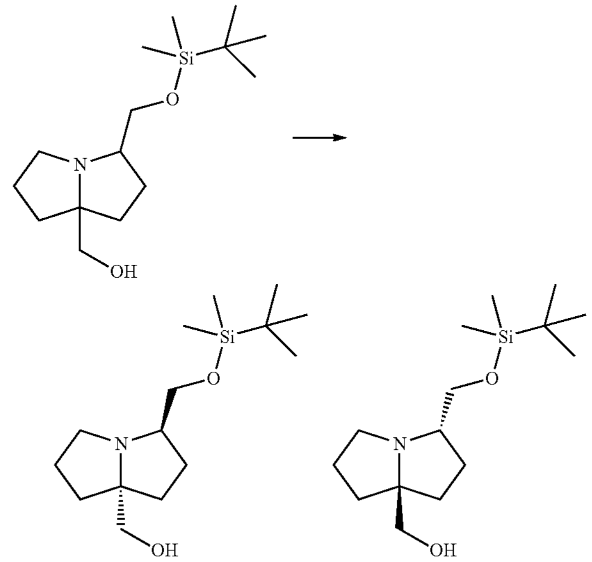

((3R,7aR)-3-(((tert-butyldimethylsilyl)oxy)methyl) tetrahydro-1H-pyrrolizin-7a(5H)-yl)methanol and ((3S,7aS)-3-(((tert-butyldimethylsilyl)oxy)methyl) tetrahydro-1H-pyrrolizin-7a(5H)-yl)methanol A mixture of (3-(((tert-butyldimethylsilyl)oxy)methyl)tetrahydro-1H-pyrrolizin-7a(5H)-yl)methanol was separated by Lotus Separations using chiral SFC using an AD-H (3×25 cm) column injecting with 1 mL of a 20 mg/mL solution of compound in methanol eluting with 20% methanol/$CO_2$ at 100 bar of pressure with 70 mL/min. flow rate and monitoring 220 nM.

Intermediate 10

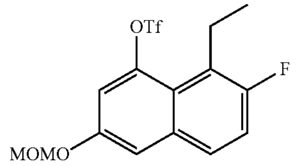

8-ethyl-7-fluoro-3-(methoxymethoxy)naphthalen-1-yl trifluoromethane sulfonate

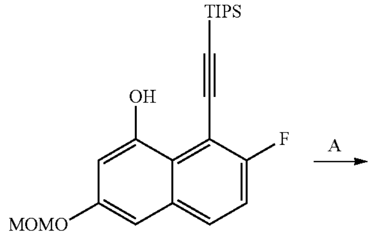

-continued

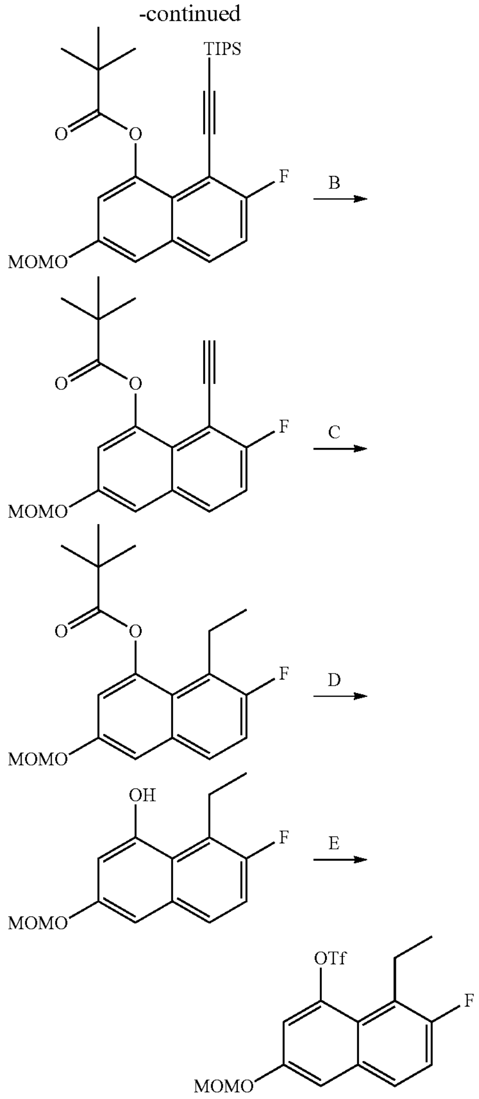

Step A. 7-fluoro-3-(methoxymethoxy)-8-((triisopropylsilyl)ethynyl)naphthalen-1-yl pivalate. To the solution of 7-fluoro-3-(methoxymethoxy)-8-((triisopropylsilyl)ethynyl) naphthalen-1-ol (2.00 g, 4.97 mmol, 1.0 eq), DMAP (122 mg, 999 μmol, 0.2 eq), TEA (1.51 g, 14.9 mmol, 3.0 eq) in DCM (20 mL) was added 2,2-dimethylpropanoyl chloride (1.80 g, 14.9 mmol, 3.0 eq) dropwise at 0° C., and then the mixture was stirred at 20° C. for 1 hour. After completion, the reaction mixture was diluted with DCM (15 mL) and water (15 mL), and then the aqueous layer was extracted with DCM (10 mL), The combined organic phase was dried over $Na_2SO_4$ and concentrated. The residue was purified by column chromatography ($SiO_2$, Petroleum ether/Ethyl acetate=I/O to 15/1) to give the title compound (3.00 g, crude). Yellow oil. LCMS [ESI, M+1]:487.2.

Step B. 8-ethynyl-7-fluoro-3-(methoxymethoxy)naphthalen-1-yl pivalate. To the solution of 7-fluoro-3-(methoxymethoxy)-8-((triisopropylsilyl)ethynyl)naphthalen-1-yl pivalate (3.00 g, 6.16 mmol, 1.0 eq) in DMF (50 mL) was added CsF (9.36 g, 61.6 mmol, 10 eq), and the mixture was stirred at 20° C. for 0.25 hour. After completion, to the reaction mixture was added water (250 mL), and then the mixture was extracted with ethyl acetate (2×120 mL). The combined organic phase was washed with brine 100 mL, dried over $Na_2SO_4$ and concentrated to give the title compound (2.20 g, crude). Yellow oil. LCMS [ESI, M+1]: 331.1.

Step C. 8-ethyl-7-fluoro-3-(methoxymethoxy)naphthalen-1-yl pivalate. To the solution of 8-ethynyl-7-fluoro-3-(methoxymethoxy)naphthalen-1-yl pivalate (2.00 g, 6.05 mmol, 1.0 eq) in MeOH (20 mL) was added Pd/C (200 mg, 10% purity) under $N_2$. The suspension was degassed under vacuum and purged with $H_2$ several times. The mixture was stirred under $H_2$ (15 psi) at 20° C. for 20 minutes. After completion, the mixture was filtered and concentrated to give the title compound (1.06 g, crude). LCMS [ESI, M+1]: 335.1.

Step D. 8-ethyl-7-fluoro-3-(methoxymethoxy)naphthalen-1-ol. To the solution of 8-ethyl-7-fluoro-3-(methoxymethoxy)naphthalen-1-yl pivalate (1.00 g, 2.99 mmol, 1.0 eq) in MeOH (15 mL) was added KOH (504 mg, 8.98 mmol, 3.0 eq), and the mixture was stirred at 20° C. for 0.5 hour. After completion, the reaction solution was adjusted to pH=4 with 0.5 M HCl at 0° C. and extracted with ethyl acetate (80 mL×2), the combined organic phase was washed with brine 50 mL, dried over anhydrous sodium sulfate, filtered and concentrated. The residue was purified by column chromatography ($SiO_2$, Petroleum ether/Ethyl acetate=50/1 to 10/1) to give the title compound (570 mg, four steps 51% yield). Yellow solid. $^1H$ NMR (400 MHz, $CDCl_3$) δ=7.55-7.43 (m, 1H), 7.18 (t, J=9.2 Hz, 1H), 6.98 (d, J=2.4 Hz, 1H), 6.57 (d, J=2.0 Hz, 1H), 5.32 (s, 1H), 5.25 (s, 2H), 3.52 (s, 3H), 3.40-3.25 (m, 2H), 1.30 (t, J=7.6 Hz, 3H).

Step E. 8-ethyl-7-fluoro-3-(methoxymethoxy)naphthalen-1-yl trifluoromethane sulfonate. To the solution of 8-ethyl-7-fluoro-3-(methoxymethoxy)naphthalen-1-ol (520 mg, 2.08 mmol, 1.0 eq), DIEA (806 mg, 6.24 mmol, 3.0 eq) in DCM (10 mL), trifluoromethylsulfonyl trifluoromethanesulfonate (879 mg, 3.12 mmol, 1.5 eq) was added dropwise at −40° C., and then the mixture was stirred at −40° C. for 0.5 hr. After completion, the reaction mixture was quenched with ice-water (15 mL), and then extracted with DCM (2×15 mL). The combined organic phase was dried over $Na_2SO_4$ and concentrated. The residue was purified by column chromatography ($SiO_2$, Petroleum ether/Ethyl acetate=100/1 to 30/1) to give the title compound (620 mg, 78% yield). Yellow oil. $^1H$ NMR (400 MHz, $CDCl_3$) δ=7.67-7.59 (m, 1H), 7.43 (d, J=2.4 Hz, 1H), 7.37 (d, J=2.4 Hz, 1H), 7.33-7.27 (m, 1H), 5.29 (s, 2H), 3.53 (s, 3H), 3.33-3.14 (m, 2H), 1.25 (t, J=7.6 Hz, 3H).

Intermediate 11

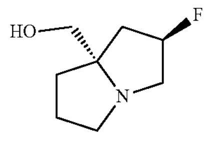 [SMILES: OC[C@@]12CCCN1C[C@H](F)C2]

((2R,7aS)-2-fluorotetrahydro-1H-pyrrolizin-7a(5H)-yl)methanol

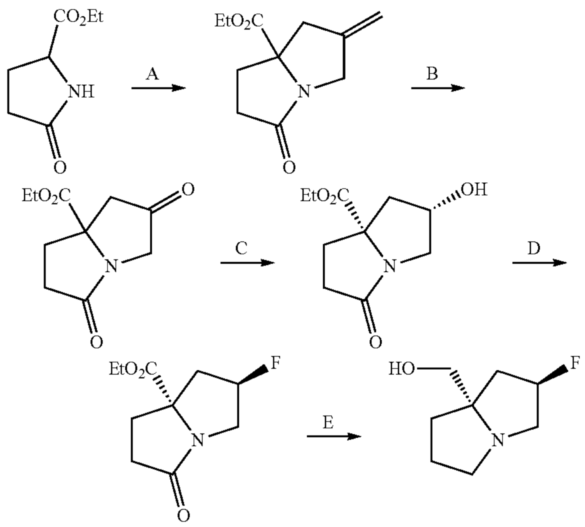

Step A. Ethyl 2-methylene-5-oxotetrahydro-1H-pyrrolizine-7a(5H)-carboxylate. To a mixture of ethyl 5-oxopyrrolidine-2-carboxylate (1.50 kg, 9.54 mol, 1.00 eq) and 3-chloro-2-(chloromethyl)prop-1-ene (1.91 kg, 15.3 mol, 1.77 L, 1.60 eq) in THE (7.50 L) was added LiHMDS (1 M, 19.1 L, 2.00 eq) drop-wise at −40° C. under $N_2$. The mixture was stirred at 25° C. for 20 hrs. The reaction mixture was poured into HCl (1 M, 2.50 L) and pH was adjusted to 7 with HCl (2 M) at 0° C. The mixture was extracted with EtOAc (4.50 L×3). The combined organic layers were washed with brine (4.50 L), dried over $Na_2SO_4$, filtered and concentrated under reduced pressure to give a residue. The residue was purified by column chromatography ($SiO_2$, Petroleum ether/Ethyl acetate=10/1 to 1/1, Rf=0.40) to afford the title compound (898 g, 3.88 mol, 40.6% yield, 82% purity) as a yellow oil. LCMS: Rt=0.716 min, m/z=210.1 (M+H). $^1H$ NMR: 400 MHz $CDCl_3$ δ: 5.02-5.07 (m, 2H), 4.28 (m, 1H), 4.16-4.22 (m, 2H), 3.71 (dd, J=15.6, 1.6 Hz, 1H), 3.04 (m, 1H), 2.73-2.80 (m, 1H), 2.57-2.64 (m, 1H), 2.41-2.49 (m, 2H), 2.03-2.17 (m, 2H), 1.24-1.30 (m, 3H).

Step B. ethyl 2,5-dioxotetrahydro-1H-pyrrolizine-7a(5H)-carboxylate. To a mixture of ethyl 2-methylene-5-oxotetrahydro-1H-pyrrolizine-7a(5H)-carboxylate (165 g, 646 mmol, 1.00 eq) in DCM (1650 mL) and MeOH (165 mL) was added $O_3$ (15 psi) at −70° C. under $N_2$. The solution became pale blue, and then the mixture was purged by $N_2$ for 30 min. $Me_2S$ (80.4 g, 1.29 mol, 95.0 mL, 2.00 eq) was added to the mixture at −70° C. The mixture was stirred at 25° C. for 16 hours. The reaction mixture was concentrated under reduced pressure to give a residue. The residue was purified by column chromatography ($SiO_2$, Petroleum ether/Ethyl acetate=10/1 to 1/1, Rf=0.50) to afford the title compound (821 g, 3.62 mol, 93.3% yield, 93.1% purity) as a yellow oil. LCMS: Rt=0.543 min, m/z=212.1 (M+H). $^1H$ NMR: 400 MHz $CDCl_3$ δ: 4.23 (m, 2H), 4.12 (m, 1H), 3.56 (m, 1H), 2.96-3.01 (m, 2H), 2.77-2.86 (m, 1H), 2.43-2.50 (m, 2H), 2.14-2.22 (m, 1H), 1.28 (m, 1H).

Step C. ethyl 2-hydroxy-5-oxotetrahydro-1H-pyrrolizine-7a(5H)-carboxylate. To a solution of ethyl 2,5-dioxotetrahydro-1H-pyrrolizine-7a(5H)-carboxylate (257 g, 1.22 mol, 1.00 eq) in EtOH (1300 mL) was slowly added $NaBH_4$ (13.8 g, 365 mmol, 0.30 eq) at 0° C. under $N_2$. The mixture was stirred at 0° C. for 10 min. The reaction was quenched with saturated $NH_4Cl$ (65.0 mL) at 5° C. and stirred at 5° C. for 0.5 hr, then the mixture was concentrated under reduced pressure to give a residue. The residue was purified by column chromatography ($SiO_2$, Petroleum ether/Ethyl acetate=10/1 to 1/1) to afford the title compound (56.8% yield) as a yellow oil. $^1H$ NMR: 400 MHz $CDCl_3$ $_{δ:}$ 4.65 (s, 1H), 4.14 (q, J=7.2 Hz, 2H), 3.95 (dd, J=12.8, 6.0 Hz, 1H), 3.10 (d, J=12.8 Hz, 1H), 2.75-2.84 (m, 2H), 2.49-2.49 (m, 2H), 2.39-2.45 (m, 1H), 2.02-2.10 (m, 1H), 1.84 (dd, J=13.6, 6.0 Hz, 1H), 1.30 (t, J=7.2 Hz, 1H).

Step D. ethyl (2S,7aR)-2-fluoro-5-oxotetrahydro-1H-pyrrolizine-7a(5H)-carboxylate. To a solution of ethyl 2-hydroxy-5-oxotetrahydro-1H-pyrrolizine-7a(5H)-carboxylate (150 g, 642 mmol, 1.00 eq) in DCM (750 mL) was added a solution of DAST (131 g, 813 mmol, 107 mL, 1.50 eq) drop-wise at −70° C. under $N_2$. The reaction mixture was warmed to 25° C. stirred at 25° C. for 16 hours. The reaction mixture was quenched with MeOH (40.0 mL) at 10° C., then diluted with water (750 mL) and extracted with DCM (750 mL×3). The combined organic layers were washed with brine (750 mL), dried over $Na_2SO_4$, filtered and concentrated under reduced pressure to give a residue. The residue was purified by column chromatography ($SiO_2$, Petroleum ether/Ethyl acetate=I/O to 0/1, Rf=0.30) to afford ethyl 2-fluoro-5-oxotetrahydro-1H-pyrrolizine-7a(5H)-carboxylate (50.6% yield, 74.7% purity) as a yellow oil. This compound (61 g, 283.43 mmol, 1.00 eq) was further purified by HPLC (column: Welch ultimate XB—$NH_2$ 250*50*10 um; mobile phase: [Heptane-EtOH (0.1% NH3$H_2O$)]; B %: 10%-10%,10 min) to give a yellow oil (49.0 g, 226.08 mmol, 99.3% purity). $^1H$ NMR: 400 MHz $CDCl_3$ δ: 5.30 (m, 1H), 4.10-4.23 (m, 3H), 3.11-3.14 (m, 1H), 2.67-2.76 (m, 3H), 2.41-2.45 (m, 1H), 2.03-2.12 (m, 2H), 1.23-1.29 (m, 3H). SFC separation (column: DAICEL CHIRALPAK IC (250 mm*50 mm, 10 um); mobile phase: [0.1%$_0$$NH_3$·$H_2O$ IPA]; B %: 40%-40%, 4.7 min; 200 minmin, desired product: Peak 2, Rt=1.959 min) of the racemic material (280 g, 1.22 mol, 1 eq) gave the title compound (114 g, 96.0% purity).

Step E. ((2R,7aS)-2-fluorotetrahydro-1H-pyrrolizin-7a(5H)-yl)methanol. To a suspension of $LiAlH_4$ (33.1 g, 871 mmol, 1.50 eq) in THE (625 mL) was added a solution of ethyl (2S,7aR)-2-fluoro-5-oxotetrahydro-1H-pyrrolizine-7a(5H)-carboxylate (125 g, 581 mmol, 1.00 eq) in THE (375 mL) drop-wise at 0° C. under $N_2$. The reaction mixture was warmed to 70° C. and stirred at 70° C. for 3 hours. The mixture was cooled to 0° C. Then to the mixture was added water (33.0 mL), NaOH (15%, 99.0 mL) and water (99 mL) dropwise in sequence 0° C. After addition, the mixture was stirred at 0° C. stirred for 5 min. The mixture was filtered, and the filtered cake was washed with EtOAc (1000 mL×2). The filtrate was dried with $MgSO_4$, filtered, and concentrated under reduced pressure to give a residue. The residue was purified by column chromatography ($SiO_2$, DCM: MeOH=100/1 to 10/1) to afford the title compound (180 g, 1.10 mol, 94.7% yield, 97.3% purity) as a yellow oil. $^1H$ NMR: 400 MHz $CDCl_3$ $_{δ:}$ 5.12-5.27 (m, 1H), 3.25 (s, 2H), 3.14-3.18 (m, 2H), 3.12-3.13 (m, 1H), 3.02-3.09 (m, 1H), 2.01-2.11 (m, 2H), 1.75-1.86 (m, 4H).

Intermediate 12

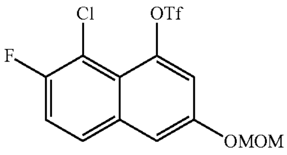

8-chloro-7-fluoro-3-(methoxymethoxy)naphthalen-1-yl trifluoromethanesulfonate

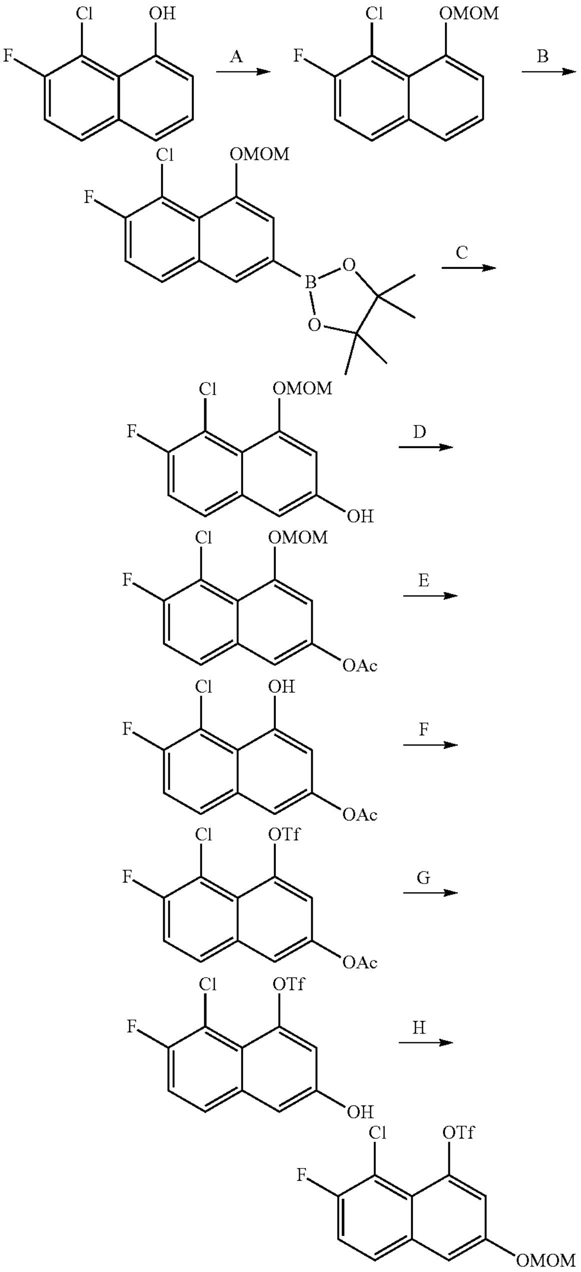

Step A. 1-chloro-2-fluoro-8-(methoxymethoxy)naphthalene. To a mixture of 8-chloro-7-fluoronaphthalen-1-ol (50.0 g, 254 mmol, 1.0 eq) and DCM (1000 mL) were added DIEA (98.7 g, 763 mmol, 3.0 eq) and chloro(methoxy) methane (41.0 g, 509 mmol, 2.0 eq) in one portion at 0° C. under $N_2$. The mixture was stirred at 25° C. for 1 hour. After completion, the mixture was quenched with water (800 mL). The organic phase was separated, and concentrated. To the residue was added saturated $NH_4Cl$ solution (600 mL). The mixture was extracted with ethyl acetate (500 mL×2). The combined organic phase was dried over anhydrous sodium sulfate, filtered, concentrated, and purified by column chromatography ($SiO_2$, Petroleum ether/Ethyl acetate=30/1 to 10/1) to give the title compound (52.0 g, 82% yield). Colorless oil. $^1H$ NMR (400 MHz, CHLOROFORM-d) δ=7.66 (dd, J=5.6, 9.2 Hz, 1H), 7.45 (dd, J=0.8, 8.4 Hz, 1H), 7.33 (t, J=8.0 Hz, 1H), 7.29-7.24 (m, 1H), 7.19 (d, J=7.6 Hz, 1H), 5.30 (s, 2H), 3.57 (s, 3H).

Step B. 2-[5-chloro-6-fluoro-4-(methoxymethoxy)-2-naphthyl]-4,4,5,5-tetramethyl-1,3,2-dioxaborolane. A mixture of 1-chloro-2-fluoro-8-(methoxymethoxy)naphthalene (25.0 g, 104 mmol, 1.0 eq), 4,4,4',4',5,5,5',5'-octamethyl-2,2'-bi(1,3,2-dioxaborolane) (26.4 g, 104 mmol, 1.0 eq), $Ir(OMe)(cod))_2$ (3.44 g, 5.19 mmol, 0.05 eq), dtbbpy (3.35 g, 12.5 mmol, 0.12 eq) in THE (500 mL) was degassed, and then the mixture was stirred at 60° C. for 1 hour. After completion, the mixture was concentrated to give a residue. The residue was purified by column chromatography ($SiO_2$, Petroleum ether/Ethyl acetate=20/1 to 8/1) to give the title compound (40.0 g, crude). Yellow oil.

Step C. 5-chloro-6-fluoro-4-(methoxymethoxy)naphthalen-2-ol. To a solution of 2-[5-chloro-6-fluoro-4-(methoxymethoxy)-2-naphthyl]-4,4,5,5-tetramethyl-1,3,2-dioxaborolane (40.0 g, crude) in THF (400 mL) and $H_2O$ (200 mL) were added $H_2O_2$ (100 g, 882 mmol, 30% purity, 8.08 eq) and AcOH (328 g, 5.46 mol, 50.0 eq) at 10° C. The mixture was stirred at 25° C. for 1 hour. After completion, the mixture was quenched with saturated $Na_2SO_3$ solution (800 mL×2) and extracted with ethyl acetate (500 mL×2). The combined organic phases were washed with saturated brine (800 mL), dried over anhydrous sodium sulfate, filtered and concentrated to give a residue. The residue was purified by column chromatography ($SiO_2$, Petroleum ether/Ethyl acetate=20/1 to 8/1) to give the title compound (3.95 g, two steps 15% yield). Off-white solid. $^1H$ NMR (400 MHz, CHLOROFORM-d) δ=7.49 (dd, J=5.2, 8.8 Hz, 1H), 7.24 (t, J=8.8 Hz, 1H), 6.89 (d, J=2.0 Hz, 1H), 6.82 (d, J=2.4 Hz, 1H), 5.32 (s, 2H), 5.27 (br s, 1H), 3.60 (s, 3H). LCMS [ESI, M+1]: 257

Step D. [5-chloro-6-fluoro-4-(methoxymethoxy)-2-naphthyl] acetate. To the solution of 5-chloro-6-fluoro-4-(methoxymethoxy)naphthalen-2-ol (0.500 g, 1.95 mmol, 1.0 eq), TEA (394 mg, 3.90 mmol, 2.0 eq), DMAP (23.8 mg, 195 μmol, 0.1 eq) in DCM (10 mL) was added dropwise acetyl chloride (229 mg, 2.92 mmol, 1.5 eq) at 0° C. The reaction mixture was then warmed to 25° C. and stirred for 0.5 hour. After completion, the mixture was diluted with water (20 mL). The organic layer was separated, and the aqueous phase was extracted with DCM (30 mL×2). The combined organic phase was washed with brine, dried over anhydrous sodium sulfate, filtered and concentrated. The residue was purified by column chromatography ($SiO_2$, Petroleum ether/Ethyl acetate=20/1 to 6/1) to give the title compound (540 mg, 93% yield). White solid; $^1H$ NMR (400 MHz, CHLOROFORM-d) δ=7.64 (dd, J=5.2, 8.8 Hz, 1H), 7.32 (t, J=8.8 Hz, 1H), 7.25 (d, J=2.0 Hz, 1H), 7.01 (d, J=2.0 Hz, 1H), 5.34 (s, 2H), 3.59 (s, 3H), 2.35 (s, 3H).

Step E. (5-chloro-6-fluoro-4-hydroxy-2-naphthyl) acetate. To the solution of [5-chloro-6-fluoro-4-(methoxymethoxy)-2-naphthyl] acetate (540 mg, 1.81 mmol, 1.0 eq) in ACN (5 mL) was added HCl·dioxane (4 M, 5 mL, 11.1 eq) at 0° C., and then the mixture was stirred at 0° C. for 1 hr. After completion, the mixture was concentrated. The residue was quenched with saturated $NaHCO_3$ solution (15 mL) and extracted with ethyl acetate (30 mL×2). The combined organic phase was washed with brine 50 mL, dried over anhydrous sodium sulfate, filtered and concentrated to give the title compound (400 mg, 86% yield) which was used in the next step without further purification. White solid; $^1H$ NMR (400 MHz, CHLOROFORM-d) δ=8.06 (s, 1H), 7.70 (dd, J=5.2, 9.2 Hz, 1H), 7.31 (t, J=8.8 Hz, 1H), 7.19 (d, J=2.4 Hz, 1H), 6.87 (d, J=2.0 Hz, 1H), 2.35 (s, 3H).

Step F. [5-chloro-6-fluoro-4-(trifluoromethylsulfonyloxy)-2-naphthyl] acetate. To the solution of (5-chloro-6-fluoro-4-hydroxy-2-naphthyl) acetate (400 mg, 1.57 mmol, 1 eq), DIPEA (609 mg, 4.71 mmol, 3.0 eq) in DCM (8 mL) was added dropwise trifluoromethylsulfonyl trifluoromethanesulfonate (665 mg, 2.36 mmol, 1.5 eq) at −40° C., and then the reaction was warmed to 25° C. and stirred for 0.5 hour. After completion, the mixture was quenched with water (15 mL) and extracted with DCM (20 mL×2). The combined organic phase was washed with brine 30 mL, dried over anhydrous sodium sulfate, filtered and concentrated to give a residue. The residue was purified by column chromatography ($SiO_2$, Petroleum ether/Ethyl acetate=15/1 to 3/1) to give the title compound (270 mg, 44% yield). Yellow solid. $^1H$ NMR (400 MHz, CHLOROFORM-d) δ=7.79 (dd, J=5.2, 9.0 Hz, 1H), 7.71 (d, J=2.0 Hz, 1H), 7.50-7.40 (m, 2H), 2.39 (s, 3H).

Step G. (8-chloro-7-fluoro-3-hydroxy-1-naphthyl) trifluoromethanesulfonate. To the mixture of [5-chloro-6-fluoro-4-(trifluoromethylsulfonyloxy)-2-naphthyl] acetate (1.70 g, 4.40 mmol, 1.0 eq), $H_2O$ (8 mL) and THE (30 mL) was added LiOH (211 mg, 8.79 mmol, 2.0 eq) at 0° C. The mixture was stirred at 0° C. for 1 hr. After completion, the mixture was concentrated, and its pH was adjusted to 6 with AcOH. The resulting mixture was extracted with ethyl acetate (60 mL×2), and the combined organic phase was washed with brine 50 mL, dried over anhydrous sodium sulfate, filtered and concentrated to give the title compound (1.80 g, crude). Brown oil; $^1H$ NMR (400 MHz, CHLOROFORM-d) δ=7.62 (dd, J=5.2, 8.8 Hz, 1H), 7.35 (t, J=8.8 Hz, 1H), 7.28 (d, J=2.4 Hz, 1H), 7.23 (d, J=2.4 Hz, 1H)

Step H. 8-chloro-7-fluoro-3-(methoxymethoxy)naphthalen-1-yl trifluoromethanesulfonate. To the solution of (8-chloro-7-fluoro-3-hydroxy-1-naphthyl) trifluoromethanesulfonate (1.80 g, crude) and DIEA (2.02 g, 15.7 mmol, 3.0 eq) in DCM (40 mL) was added MOMCl (841 mg, 10.5 mmol, 2.0 eq) at 0° C., the mixture was stirred at 0° C. for 1 hr. After completion, the reaction was quenched by water 40 mL at 0° C., and then extracted with DCM 100 mL. The organic layer was washed with brine 60 mL, dried over $Na_2SO_4$, filtered and concentrated under reduced pressure to give a residue. The residue was purified by column chromatography ($SiO_2$, Petroleum ether/Ethyl acetate=10/1 to 6/1) to give the title compound (920 mg, two steps 54% yield) as a yellow oil. $^1H$ NMR (400 MHz, CHLOROFORM-d) δ=7.70 (dd, J=5.2, 8.8 Hz, 1H), 7.47 (d, J=2.4 Hz, 1H), 7.42-7.35 (m, 2H), 5.30 (s, 2H), 3.53 (s, 3H).

Intermediate 13

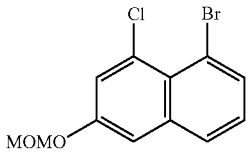

8-bromo-1-chloro-3-(methoxymethoxy)naphthalene

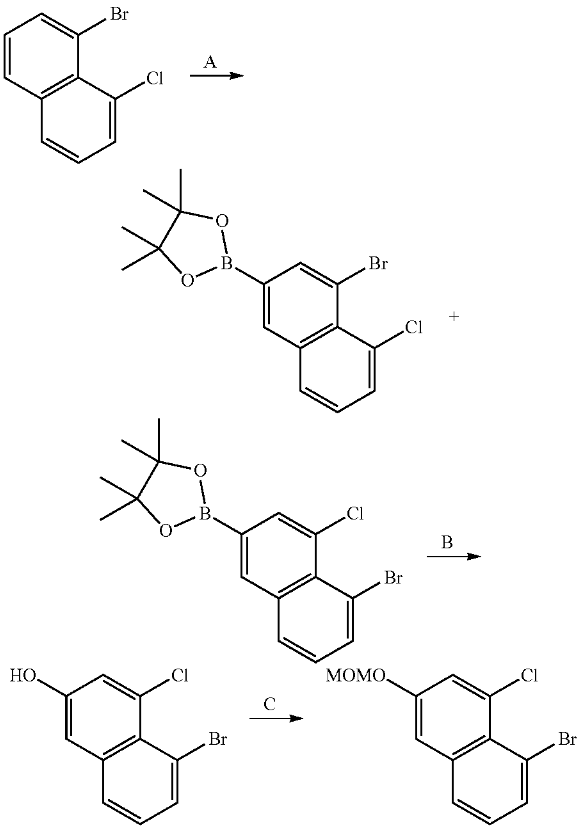

Step A: 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane. A mixture of 1-bromo-8-chloro-naphthalene (1.5 g, 6.21 mmol, 1.0 eq), 4,4,5,5-tetramethyl-1,3,2-dioxaborolane (2.38 g, 18.6 mmol, 2.70 mL, 3.0 eq), (1Z,5Z)-cycloocta-1,5-diene; 2,4-dimethyl-BLAHbicyclo[1.1.0]butane (205 mg, 310 μmol, 0.05 eq), 4-tert-butyl-2-(4-tert-butyl-2-pyridyl)pyridine (100 mg, 372 μmol, 0.06 eq) in THE (20 mL) was degassed and purged with $N_2$ for 3 times, and then the mixture was stirred at 60° C. for 10 hours under $N_2$ atmosphere. The reaction mixture was concentrated under vacuum. The residue was purified by reversed phase flash [water (0.1% formic acid)/acetonitrile)] to give the title compounds (total 0.56 g) as brown oil.

Step B: 5-bromo-4-chloronaphthalen-2-ol. To a solution of 2-(4-bromo-5-chloronaphthalen-2-yl)-4,4,5,5-tetramethyl-1,3,2-dioxaborolane and 2-(5-bromo-4-chloronaphthalen-2-yl)-4,4,5,5-tetramethyl-1,3,2-dioxaborolane (3.5 g, 9.52 mmol, 1.0 eq) in $H_2O$ (35 mL) and THE (10 mL) was added AcOH (36.7 g, 611 mmol, 35.0 mL, 64.2 eq) and $H_2O_2$ (20.6 g, 182 mmol, 17.5 mL, 30% purity, 19.1 eq). The mixture was stirred at 10° C. for 1 hour.

The reaction mixture was quenched with saturated $NaHSO_3$ solution (30 mL) and extracted with ethyl acetate (3×50 mL). The combined organic layers were washed with brine (30 mL), dried over $Na_2SO_4$, filtered and concentrated under reduced pressure to give the residue. The residue was purified by column chromatography ($SiO_2$, petroleum ether/ethyl acetate=10/1 to 3/1) and further purified twice by SFC (column: DAICEL CHIRALPAK AD-H (250 mm*30 mm, 5 um); mobile phase: [0.1% $NH_3H_2O$ MEOH]; B %: 30%-30%, 3.4 min; 950 minmin) and (column: DAICEL CHIRALPAK AD-H (250 mm*30 mm, 5 um); mobile phase: [0.1% $NH_3H_2O$ MEOH]; B %: 35%-35%, 2.4 min, 680 minmin) to give the title compound (0.9 g, 37% yield) as a yellow solid. $^1$H NMR (400 MHz, chloroform-d) δ=7.74 (dd, J=1.2, 7.6 Hz, 1H), 7.63 (dd, J=0.8, 8.4 Hz, 1H), 7.33 (d, J=2.8 Hz, 1H), 7.20 (t, J=8.0 Hz, 1H), 7.12 (d, J=2.8 Hz, 1H), 5.42 (br s, 1H).

Step C: 8-bromo-1-chloro-3-(methoxymethoxy)naphthalene. To a solution of 5-bromo-4-chloronaphthalen-2-ol (300 mg, 1.16 mmol, 1.0 eq) in dichloromethane (5 mL) was added MOMCl (140 mg, 1.75 mmol, 132 uL, 1.5 eq) and DIEA (451 mg, 3.49 mmol, 608 uL, 3.0 eq) at 0° C. The mixture was stirred at 10° C. for 1 hour. The reaction mixture was diluted with water (5 mL) and extracted with dichloromethane (3×10 mL). The combined organic layers were washed with brine (10 mL), dried over $Na_2SO_4$, filtered and concentrated under reduced pressure to give a residue. The residue was purified by column chromatography ($SiO_2$, petroleum ether/ethyl acetate=50/1 to 3/1) to give the title compound (350 mg, 99% yield) as a white solid. $R_f$=0.43 (3:1 petroleum ether/ethyl acetate); $^1$H NMR (400 MHz, chloroform-d) δ=7.76 (dd, J=1.2, 7.6 Hz, 1H), 7.69 (d, J=8.4 Hz, 1H), 7.43 (d, J=2.8 Hz, 1H), 7.34 (d, J=2.8 Hz, 1H), 7.21 (t, J=7.6 Hz, 1H), 5.28 (s, 2H), 3.61-3.46 (m, 3H).

The following Examples are intended to illustrate further certain embodiments of the invention and are not intended to limit the scope of the invention.

Example 1

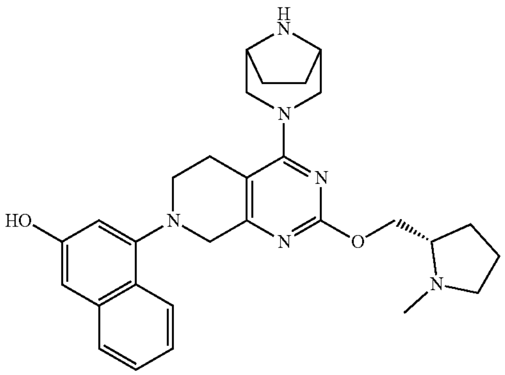 [SMILES: CN1CCC[C@H]1COc1nc2c(c(N3CC4CCC(C3)N4)n1)CCN(c1cc(O)cc3ccccc13)C2]

4-(4-((1R,5S)-3,8-diazabicyclo[3.2.1]octan-3-yl)-2-(((S)-1-methylpyrrolidin-2-yl)methoxy)-5,8-dihydro-pyrido[3,4-d]pyrimidin-7(6H)-yl)naphthalen-2-ol

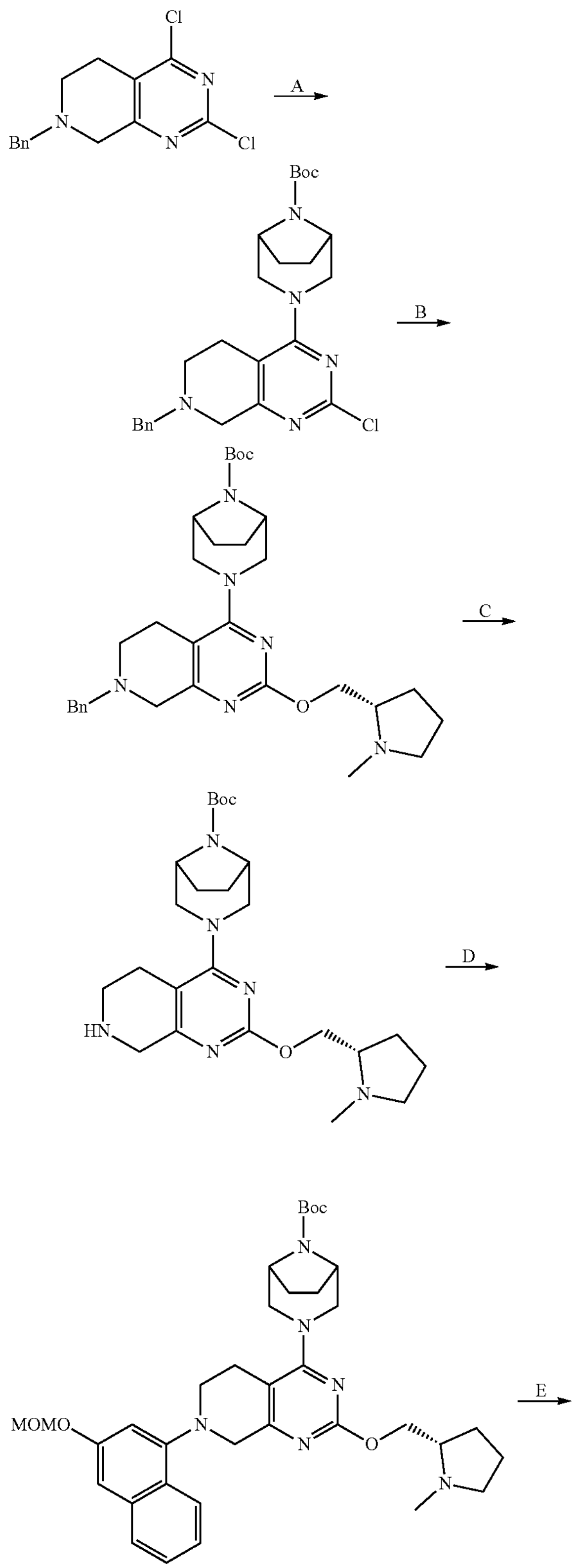

-continued

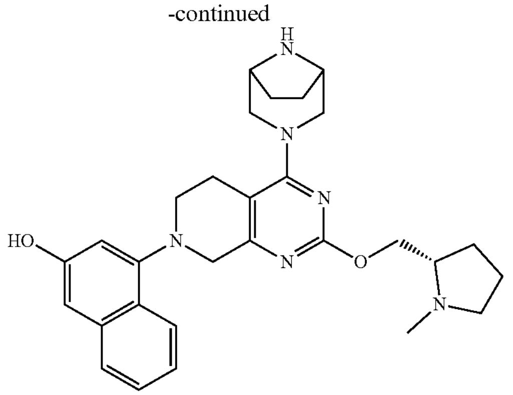

Step A. tert-butyl (1R,5S)-3-(7-benzyl-2-chloro-5,6,7,8-tetrahydropyrido[3,4-d]pyrimidin-4-yl)-3,8-diazabicyclo[3.2.1]octane-8-carboxylate. To a mixture of 8-Boc-3,8-diazabicyclo[3.2.1]octane (3.8 g, 18 mmol), N-ethyl-N-isopropylpropan-2-amine (3.6 mL, 20 mmol) in dichloromethane (20 mL) was added 7-benzyl 2,4-dichloro-5,6-dihydropyrido[3,4-d]pyrimidine (5.0 g, 17 mmol). The suspension was stirred on a cold water bath for 1 h and then at r.t. for 24 h. The reaction mixture was diluted with DCM (50 mL), washed with 1M $Na_2CO_3$ (20 mL), dried over $Na_2SO_4$, and evaporated in vacuo. The residue was chromatographed on silica gel in 2% MeOH/DCM. The target fractions were evaporated in vacuo, and the residue was crystallized from MTBE. The solid was washed with MTBE (7 mL) and dried over a stream of $N_2$ to yield the desired product as colorless crystalline solid (4.6 g, 58%). LCMS (MM-ES+APCI, Pos): m/z 470.2 (M+H).

Step B. tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A mixture of tert-butyl (1R,5S)-3-(7-benzyl-2-chloro-5,6,7,8-tetrahydropyrido[3,4-d]pyrimidin-4-yl)-3,8-diazabicyclo[3.2.1]octane-8-carboxylate (4.4 g, 9.4 mmol), cesium carbonate (9.2 g, 28 mmol), (S)-(1-methylpyrrolidin-2-yl)methanol (2.2 g, 19 mmol), BINAP Palladacycle Gen. 3 precatalyst (0.47 g, 0.47 mmol), racemic BINAP (0.31 g, 0.47 mmol), and dry toluene (25 mL) was degassed and stirred under a $N_2$ atmosphere at 90° C. overnight. The reaction mixture was cooled to r.t. and partitioned between water (50 mL) and EtOAc (100 mL). The organic phase was washed with water and brine (25 mL each), dried over $Na_2SO_4$, and evaporated in vacuo. The residue was chromatographed on silica gel in 4% MeOH+0.4% $NH_4OH$ in DCM to give the product (4.8 g, 93%). LCMS (MM-ES+APCI, Pos): m/z 549.4 (M+H).

Step C. tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a stirred solution of tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (4.8 g, 8.7 mmol) in methanol (100 mL) was added 20% palladium (II) hydroxide on carbon (1 g) and the reaction mixture was degassed and stirred under a $H_2$ atmosphere (rubber balloon) for 24 h. The slurry was filtered through Celite, the Celite was washed with MeOH (3*20 mL), and the filtrate was evaporated in vacuo. The material was used crude in the next reaction. LCMS (MM-ES+APCI, Pos): m/z 459.4 (M+H).

Step D. tert-butyl (1R,5S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A mixture of tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (0.10 g, 0.22 mmol), 3-(methoxymethoxy)naphthalen-1-yl trifluoromethanesulfonate (0.11 g, 0.33 mmol), $Cs_2CO_3$ (0.36 g, 1.1 mmol), BINAP Palladacycle Gen. 3 precatalyst (22 mg, 0.022 mmol), racemic BINAP (11 mg, 0.017 mmol), and toluene (1 mL) was degassed and stirred at 80° C. for 1 h and at r.t. overnight. The reaction mixture was diluted with EtOAc (3 mL), filtered through Celite, and the Celite was washed with EtOAc (3*3 mL). The filtrate was evaporated and the residue chromatographed on silica gel in 4% MeOH/DCM+0.4% $NH_4OH$ as modifier to give product (0.10 g, 72%). LCMS (MM-ES+APCI, Pos): m/z 645.3 (M+H).

Step E. 4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol. To a stirred solution of tert-butyl (1R,5S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (50 mg, 0.078 mmol) in a mixture of methanol (0.75 mL) and tetrahydrofuran (0.75 mL) was added 6M hydrogen chloride (0.25 mL, 1.5 mmol) and the reaction mixture was heated to 50° C. for 4.5 h. The reaction mixture was cooled to r.t., diluted with 2M phosphate buffer (pH~9), and extracted with 5% MeOH in DCM (4*10 mL). The combined organic phases were dried over $Na_2SO_4$, evaporated in vacuo, and chromatographed on silica gel in 7 to 10% MeOH/DCM+10% $NH_4OH$ as modifier to give the product (15 mg, 39%). LCMS (MM-ES+APCI, Pos): m/z 501.3 (M+H).

Example 2

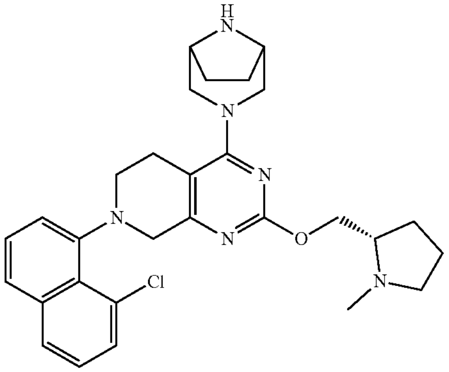 [SMILES: CN1CCC[C@H]1COc1nc2c(c(N3CC4CCC(C3)N4)n1)CCN(c1cccc3cccc(Cl)c13)C2]

4-((1R,5S)-3,8-diazabicyclo[3.2.1]octan-3-yl)-7-(8-chloronaphthalen-1-yl)-2-(((S)-1-methylpyrrolidin-2-yl)methoxy)-5,6,7,8-tetrahydropyrido[3,4-d]pyrimidine

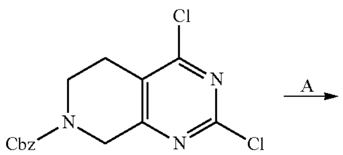

-continued

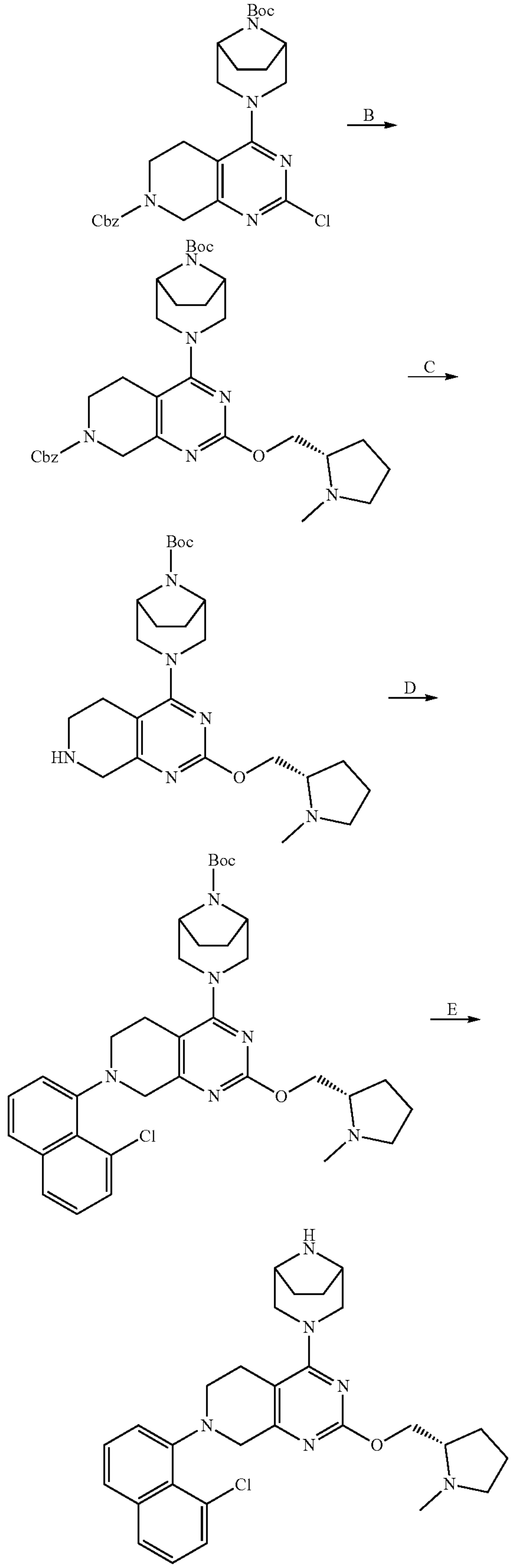

Step A. benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate. To a suspension of tert-butyl (1R,5S)-3,8-diazabicyclo[3.2.1]octane-8-carboxylate (1.3 g, 6.2 mmol) and N-ethyl-N-isopropylpropan-2-amine (1.2 mL, 7.1 mmol) in N,N-dimethylacetamide (5 mL) was added benzyl 2,4-dichloro-5,6-dihydropyrido[3,4-d]pyrimidine-7(8H)-carboxylate (2.0 g, 5.9 mmol) and the suspension was stirred on a cold water bath. The reaction mixture was partitioned between 0.5M $NaHCO_3$ (30 mL) and DCM (50 mL). The organic layer was dried over $Na_2CO_3$ and evaporated in vacuo. The residue was dissolved in MTBE (20 mL), filtered, and evaporated in vacuo. The material was used crude in the next reaction. LCMS (MM-ES+APCI, Pos): m/z 514.3 (M+H).

Step B. benzyl 4-((1R,5S)-8-(tert-butoxycarbonyl)-3,8-diazabicyclo[3.2.1]octan-3-yl)-2-(((S)-1-methylpyrrolidin-2-yl)methoxy)-5,8-dihydropyrido[3,4-d]pyrimidine-7(6H)-carboxylate. Synthesized according to Example 1, Step B substituting benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate in place of tert-butyl (1R,5S)-3-(7-benzyl-2-chloro-5,6,7,8-tetrahydropyrido[3,4-d]pyrimidin-4-yl)-3,8-diazabicyclo[3.2.1]octane-8-carboxylate. (1.6 g, 46%). LCMS (MM-ES+APCI, Pos): m/z 593.4 (M+H).

Step C. tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step C substituting benzyl 4-((1R,5S)-8-(tert-butoxycarbonyl)-3,8-diazabicyclo[3.2.1]octan-3-yl)-2-(((S)-1-methylpyrrolidin-2-yl)methoxy)-5,8-dihydropyrido[3,4-d]pyrimidine-7(6H)-carboxylate in place of tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The yield of the desired product was assumed to be quantitative. LCMS (MM-ES+APCI, Pos): m/z 459.3 (M+H).

Step D. tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 1-bromo-8-chloronaphthalene in place of 3-(methoxymethoxy)naphthalen-1-yl trifluoromethanesulfonate. (64 mg, 47%). LCMS (MM-ES+APCI, Pos): m/z 619.4 (M+H).

Step E. 4-((1R,5S)-3,8-diazabicyclo[3.2.1]octan-3-yl)-7-(8-chloronaphthalen-1-yl)-2-(((S)-1-methylpyrrolidin-2-yl)methoxy)-5,6,7,8-tetrahydropyrido[3,4-d]pyrimidine. Tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (64 mg, 0.10 mmol) was dissolved in DCM (0.5 mL), and cooled on an ice bath. Then cold 4M hydrogen chloride in dioxane (2.6 mL, 10 mmol) was added at once with stirring. The reaction mixture was warmed to r.t. over 30 min. and stirred at r.t. for 2 hr. The reaction was evaporated in vacuo. The residue was dissolved in water (2 mL) and basified by addition of 1M $NaHCO_3$ (2 mL). The emulsion was extracted with DCM (2*10 mL). The combined organic phases were dried over $Na_2CO_3$, evaporated in vacuo, and chromatographed on silica gel in 6 to 10% MeOH/DCM+10% $NH_4OH$ as a modifier to yield the product (3.4 mg, 6%). LCMS (MM-ES+APCI, Pos): m/z 519.5 (M+H).

Example 3

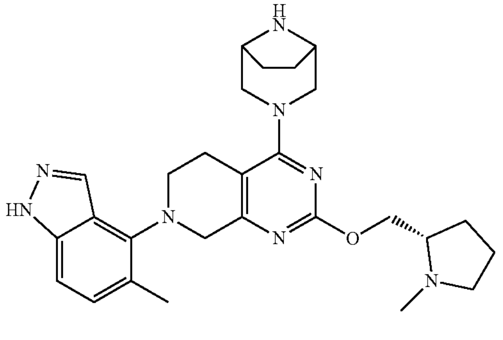 [SMILES: Cc1ccc2[nH]ncc2c1N1CCc2c(nc(OC[C@@H]3CCCN3C)nc2N2CC3CCC(C2)N3)C1]

4-((1R,5S)-3,8-diazabicyclo[3.2.1]octan-3-yl)-7-(5-methyl-1H-indazol-4-yl)-2-(((S)-1-methylpyrrolidin-2-yl)methoxy)-5,6,7,8-tetrahydropyrido[3,4-d]pyrimidine

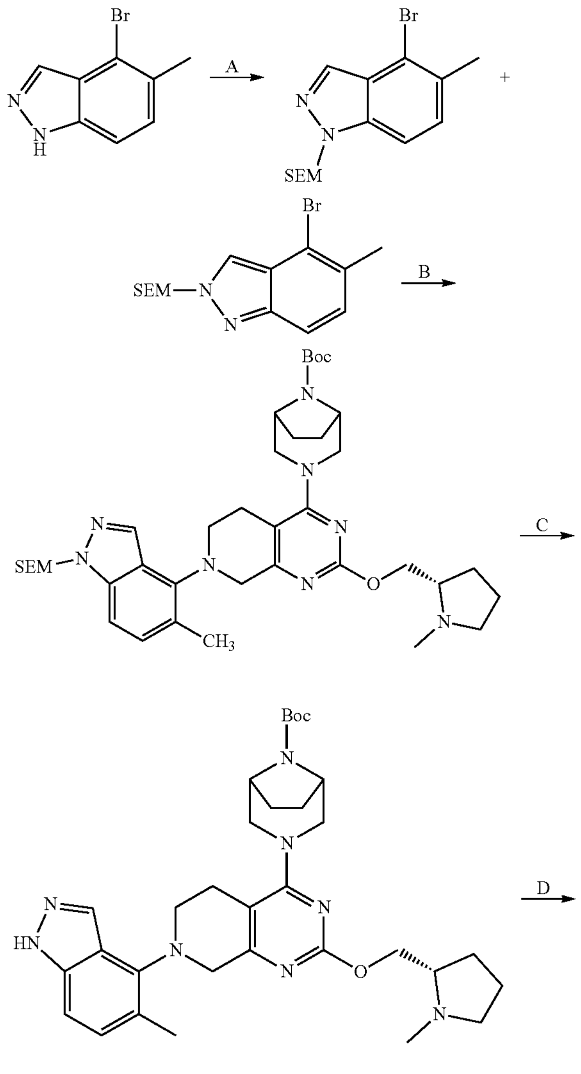

-continued

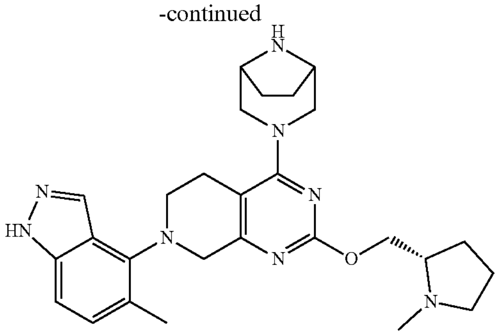

Step A. 4-bromo-5-methyl-1-((2-(trimethylsilyl)ethoxy)methyl)-1H-indazole and 4-bromo-5-methyl-2-((2-(trimethylsilyl)ethoxy)methyl)-2H-indazole. A stirred solution of 4-bromo-5-methyl-1H-indazole (0.50 g, 2.4 mmol) and N-ethyl-N-isopropylpropan-2-amine (0.83 mL, 4.7 mmol) in dichloromethane (5 mL) was cooled in an ice bath and (2-(chloromethoxy)ethyl)trimethylsilane (0.63 mL, 3.6 mmol) was added dropwise. The reaction mixture was warmed to r.t. over 2 hours and evaporated in vacuo. The residue was partitioned between MTBE (15 mL) and sat. $NaHCO_3$ (5 mL). The organic layer was washed with brine, dried over $Na_2SO_4$, evaporated in vacuo, and the residue chromatographed on silica gel in 5→10% EtOAc in hexane to give isomeric alkylation products. Isomer 1 (used in the next step) (0.35 g, 44%). $^1$H NMR ($CDCl_3$, 400 MHz): 7.97 (d, J=1.0 Hz, 1H), 7.42 (dd, J=8.5, 1.0 Hz, 1H), 7.27 (dd, J=8.5, 1.0 Hz, 1H), 5.70 (s, 2H), 3.53 (m, 2H), 2.50 (s, 3H), 0.87 (m, 2H), −0.07 (s, 9H). $2^{nd}$ isomer (292 mg, 32%). $^1$H NMR ($CDCl_3$, 400 MHz): 8.04 (d, J=1.0 Hz, 1H), 7.42 (ddd, J=8.8, 2.0, 1.0 Hz, 1H), 7.16 (d, J=9.0 Hz, 1H), 5.69 (s, 2H), 3.62 (m, 2H), 2.47 (s, 3H), 0.94 m, 2H), −0.03 (s, 9H).

Step B. tert-butyl (1R,5S)-3-(7-(5-methyl-1-((2-(trimethylsilyl)ethoxy)methyl)-1H-indazol-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 4-bromo-5-methyl-1-((2-(trimethylsilyl)ethoxy)methyl)-1H-indazole in place of 3-(methoxymethoxy)naphthalen-1-yl trifluoromethanesulfonate to yield the title product (45 mg, 52%). LCMS (MM-ES+APCI, Pos): m/z 719.4 (M+H).

Step C. tert-butyl (1R,5S)-3-(7-(5-methyl-1H-indazol-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(7-(5-methyl-1-((2-(trimethylsilyl)ethoxy)methyl)-1H-indazol-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (45 mg, 0.056 mmol) was dissolved in DCM (3 mL), and cooled on an ice bath. TFA (2 mL) was added dropwise with stirring. The reaction mixture was warmed to r.t. over 30 minutes and kept at r.t. for 2 h. The reaction was evaporated in vacuo, freebased with sat. $NaHCO_3$, and treated with an excess of di-tert-butyl dicarbonate. The mixture was dried under high vacuum and chromatographed on the reverse phase, Gilson, C18 25*250 mm, 5 to 95% MeCN+0.1% TFA to give the product (5 mg, 24%). LCMS (MM-ES+APCI, Pos): m/z 589.4 (M+H).

Step D. 4-((1R,5S)-3,8-diazabicyclo[3.2.1]octan-3-yl)-7-(5-methyl-1H-indazol-4-yl)-2-(((S)-1-methylpyrrolidin-2-yl)methoxy)-5,6,7,8-tetrahydropyrido[3,4-d]pyrimidine.

Synthesized according to Example 2, Step E substituting tert-butyl (1R,5S)-3-(7-(5-methyl-1H-indazol-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (4.2 mg, 92%). LCMS (MM-ES+APCI, Pos): m/z 489.4 (M+H).

Example 4

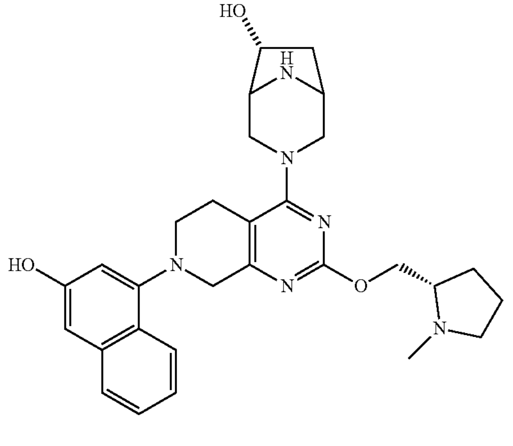 [SMILES: CN1CCC[C@H]1COc1nc2c(c(N3CC4C[C@@H](O)C(C3)N4)n1)CCN(c1cc(O)cc3ccccc13)C2]

3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol

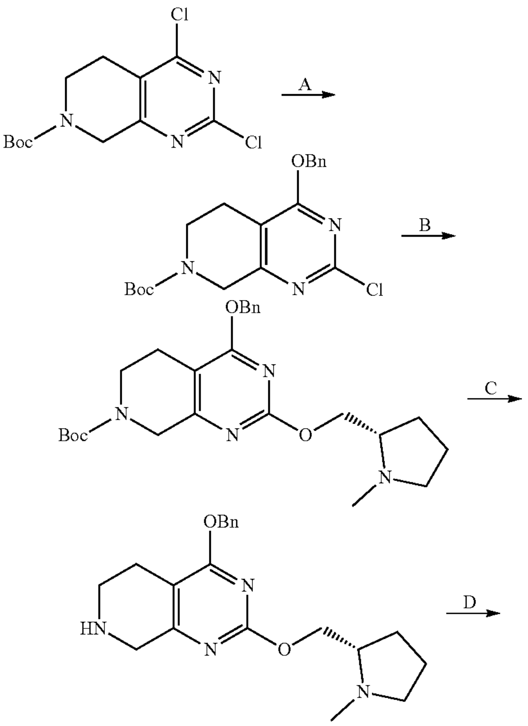

-continued

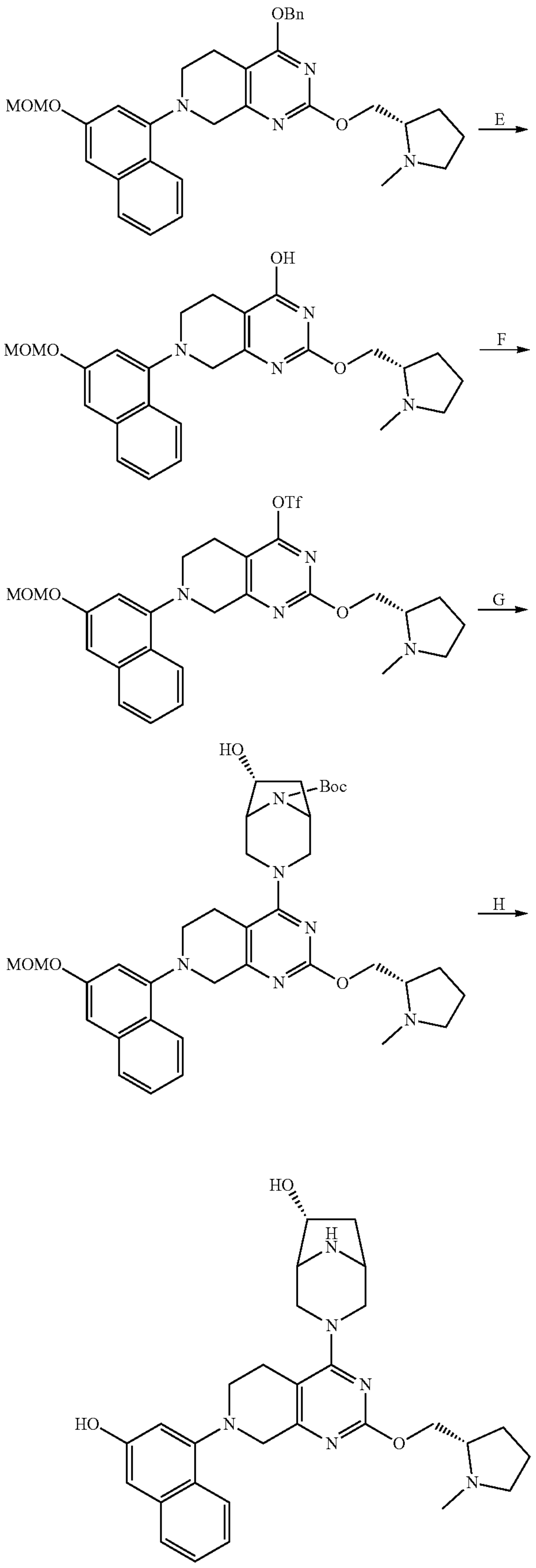

Step A. tert-butyl 4-(benzyloxy)-2-chloro-5,8-dihydropyrido[3,4-d]pyrimidine-7(6H)-carboxylate. To a stirred mixture of tert-butyl 2,4-dichloro-5,8-dihydropyrido[3,4-d]pyrimidine-7(6H)-carboxylate (25 g, 82 mmol) in dioxane (240 mL) were added phenylmethanol (26 mL, 250 mmol) and cesium carbonate (53 g, 160 mmol) and the mixture was heated to 80° C. for 8 hours. The reaction mixture was cooled to r.t., concentrated in vacuo to ~75 mL, and partitioned between ethyl acetate (200 mL) and water (200 mL). The organic layer was washed with brine (200 mL), dried over $MgSO_4$, filtered, and concentrated in vacuo. A portion of the residue was chromatographed on silica gel in 0-20% of ethyl acetate/hexanes to give pure crystalline material. The remaining crude product was diluted with ~20% ethyl acetate/hexanes, seeded with the crystals, and sonicated. The solid was filtered off, washed with 30% ethyl acetate/hexanes, and dried under a stream of $N_2$ to give the product. The mother liquor was concentrated, dried under high vacuum, and chromatographed on silica gel eluting with 0→20% EtOAc/hexane to give the product. Combined yield (7.3 g, 24%). LCMS (MM-ES+APCI, Pos): m/z 376.2 (M+H).

Step B. tert-butyl (S)-4-(benzyloxy)-2-((1-methylpyrrolidin-2-yl)methoxy)-5,8-dihydropyrido[3,4-d]pyrimidine-7(6H)-carboxylate. Synthesized according to Example 1, Step B, substituting tert-butyl 4-(benzyloxy)-2-chloro-5,8-dihydropyrido[3,4-d]pyrimidine-7(6H)-carboxylate (1.2 g, 3.3 mmol) in place of tert-butyl (1R,5S)-3-(7-benzyl-2-chloro-5,6,7,8-tetrahydropyrido[3,4-d]pyrimidin-4-yl)-3,8-diazabicyclo[3.2.1]octane-8-carboxylate to yield the title product as a yellow solid (1.0 g, 67%). LCMS (MM-ES+APCI, Pos): m/z 455.3 (M+H).

Step C. (S)-4-(benzyloxy)-2-((1-methylpyrrolidin-2-yl)methoxy)-5,6,7,8-tetrahydropyrido[3,4-d]pyrimidine. To a stirred solution of tert-butyl (S)-4-(benzyloxy)-2-((1-methylpyrrolidin-2-yl)methoxy)-5,8-dihydropyrido[3,4-d]pyrimidine-7(6H)-carboxylate (1.0 g, 2.2 mmol) in dichloromethane (6.6 mL) was added TFA (6.8 mL, 88 mmol). After 1 hour at r.t. the reaction was concentrated under a stream of nitrogen and under high vacuum. The residue was dissolved in dichloromethane (10 mL) and treated with a 20% sodium carbonate solution (10 mL). The layers were separated and the aqueous phase was extracted with 10% methanol in dichloromethane (2×10 mL). The combined organic layers were dried over MgSO4, filtered, and concentrated to a yellow oil that was used as crude in the next reaction. LCMS (MM-ES+APCI, Pos): m/z 355.2 (M+H).

Step D. (S)-4-(benzyloxy)-7-(3-(methoxymethoxy)naphthalen-1-yl)-2-((1-methylpyrrolidin-2-yl)methoxy)-5,6,7,8-tetrahydropyrido[3,4-d]pyrimidine. A mixture of $Cs_2CO_3$ (5.9 g, 18 mmol), (S)-4-(benzyloxy)-2-((1-methylpyrrolidin-2-yl)methoxy)-5,6,7,8-tetrahydropyrido[3,4-d]pyrimidine (2.1 g, 6.0 mmol), RuPhos (0.28 mg, 0.60 mmol), RuPhos-Pd-G4 precatalyst (0.51 mg, 0.60 mmol), 3-(methoxymethoxy)naphthalen-1-yl trifluoromethanesulfonate (3.0 g, 9.0 mmol) and 1,4-dioxane (20 mL) was degassed and stirred under $N_2$ at 75° C. for 1.5 hr. The reaction mixture was cooled and partitioned between EtOAc (50 mL) and water (20 mL). The organic layer was washed with 0.5M $NaHCO_3$ and brine (15 mL each), dried over $Na_2SO_4$, and evaporated in vacuo. The residue was chromatographed on silica gel eluting with 4% MeOH/DCM+0.4% $NH_4OH$ as a modifier to give the product (2.4 g, 74%). LCMS (MM-ES+APCI, Pos): m/z 541.3 (M+H).

Step E. (S)-7-(3-(methoxymethoxy)naphthalen-1-yl)-2-((1-methylpyrrolidin-2-yl)methoxy)-5,6,7,8-tetrahydropyrido[3,4-d]pyrimidin-4-ol. Synthesized according to Example 1, Step C substituting (S)-4-(benzyloxy)-7-(3-(methoxymethoxy)naphthalen-1-yl)-2-((1-methylpyrrolidin-2-yl)methoxy)-5,6,7,8-tetrahydropyrido[3,4-d]pyrimidine in place of tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. LCMS (MM-ES+APCI, Pos): m/z 451.2 (M+H).

Step F. (S)-7-(3-(methoxymethoxy)naphthalen-1-yl)-2-((1-methylpyrrolidin-2-yl)methoxy)-5,6,7,8-tetrahydropyrido[3,4-d]pyrimidin-4-yl trifluoromethanesulfonate. A stirred solution of (S)-7-(3-(methoxymethoxy)naphthalen-1-yl)-2-((1-methylpyrrolidin-2-yl)methoxy)-5,6,7,8-tetrahydropyrido[3,4-d]pyrimidin-4-ol (0.20 g, 0.44 mmol) and triethylamine (0.12 mL, 0.89 mmol) in dichloromethane (2 mL) under $N_2$ was cooled to −60° C. and trifluoromethanesulfonic anhydride (90 µL, 0.53 mmol) was added dropwise. The reaction was stirred at −60° C. for 2 hr and warmed to room temperature. The reaction was diluted with DCM (10 mL). The organics were washed with sat. $NaHCO_3$ (3 mL), dried over $Na_2SO_4$, and evaporated in vacuo. The material was used crude in the next reaction. LCMS (MM-ES+APCI, Pos): m/z 583.2 (M+H).

Step G. tert-butyl 6-hydroxy-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a stirred solution of crude tert-butyl 6-hydroxy-3,8-diazabicyclo[3.2.1]octane-8-carboxylate (33 mg, 0.086 mmol), in DCM (0.5 mL) was added a solution of (S)-7-(3-(methoxymethoxy)naphthalen-1-yl)-2-((1-methylpyrrolidin-2-yl)methoxy)-5,6,7,8-tetrahydropyrido[3,4-d]pyrimidin-4-yl trifluoromethanesulfonate (50 mg, 0.086 mmol) in DCM (0.5 mL) and the reaction mixture was stirred overnight at room temperature. The reaction was partitioned between EtOAc (10 mL) and sat. $NaHCO_3$, and the layers separated. The organic phase was washed with 1M $Na_2CO_3$, water, and brine (5 mL each), dried over $Na_2SO_4$, and evaporated in vacuo. The residue was chromatographed on silica gel eluting with 4 to 10% MeOH/DCM+10% $NH_4OH$ as modifier to give product (35 mg, 62%). LCMS (MM-ES+APCI, Pos): m/z 661.3 (M+H).

Step H. 3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol. Synthesized according to Example 1, Step E substituting tert-butyl 6-hydroxy-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The material was purified using a reverse phase C18 column eluting with 5-95% acetonitrile in water+0.1% TFA as a modifier to give the product (9.8 mg, 36%). LCMS (MM−ES+APCI, Pos): m/z 517.3 (M+H).

Example 5

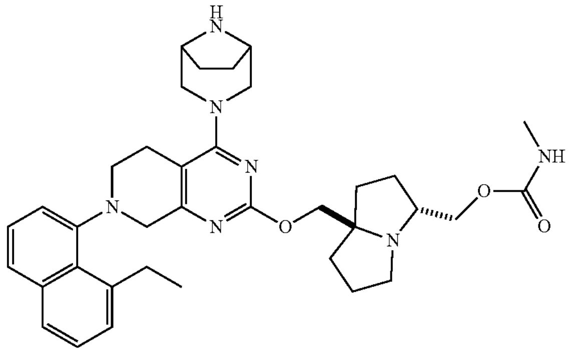

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers)

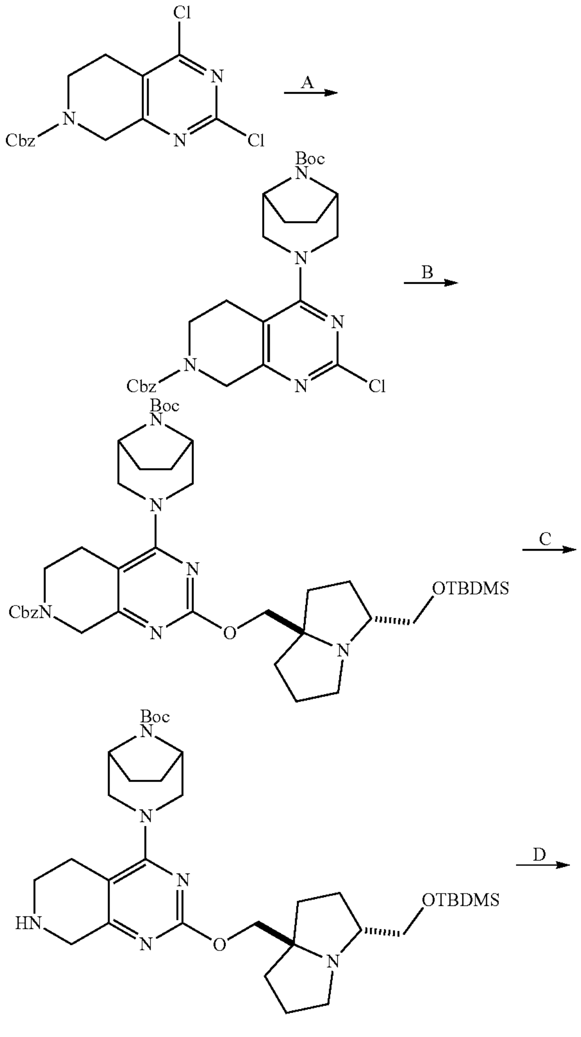

-continued

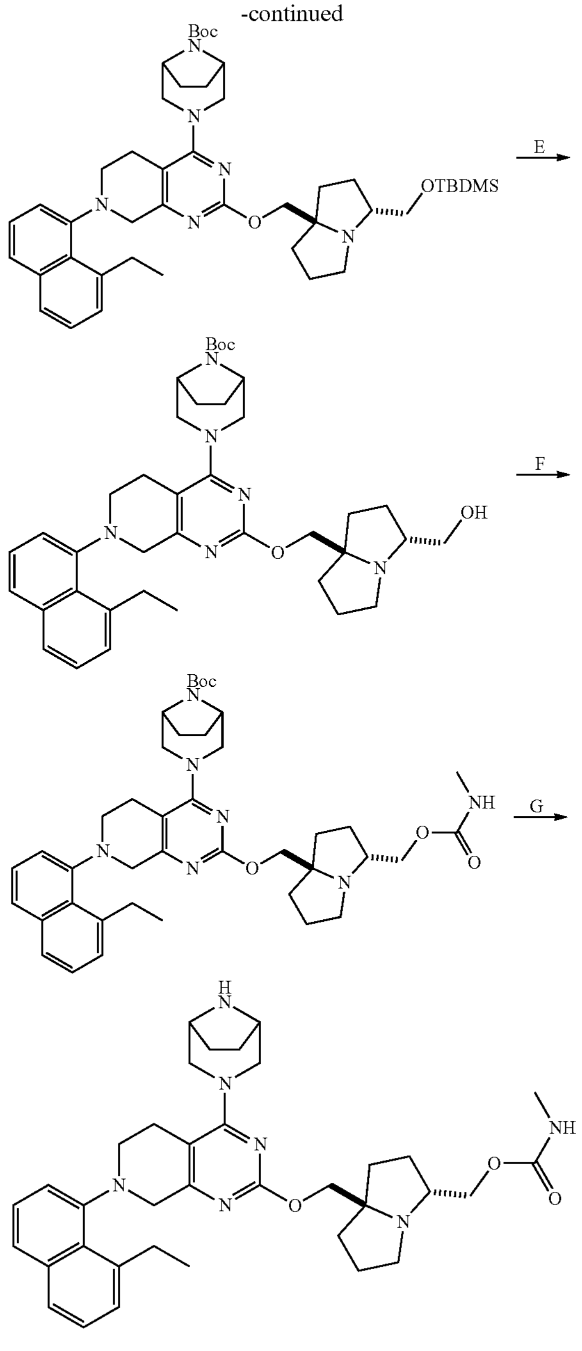

Step A. benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate. A solution of benzyl 2,4-dichloro-5,8-dihydropyrido[3,4-d]pyrimidine-7(6H)-carboxylate (2.0 g, 5.9 mmol) in DMA (10 mL) was added to a solution of 8-Boc-3,8-diazabicyclo[3.2.1]octane (1.3 g, 5.9 mmol) and DIEA (3.1 mL, 17 mmol) in DMA (5 mL). The reaction was stirred at room temperature overnight before being diluted with water and extracted with EtOAc. The organic layer was dried with $Na_2SO_4$, filtered, and concentrated. The residue was purified by flash chromatography (silica gel, 0-50% EtOAc/hexanes) to yield benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate as a white solid (1.4 g, 46%). LCMS (MM-ES+APCI, Pos): m/z 514.3 (M+H).

Step B. benzyl 4-((1R,5S)-8-(tert-butoxycarbonyl)-3,8-diazabicyclo[3.2.1]octan-3-yl)-2(3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers). Benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.50 g, 0.97 mmol), (3-(((tert-butyldimethylsilyl)oxy)methyl)tetrahydro-1H-pyrrolizin-7a(5H)-yl)methanol (trans enantiomers) (0.28 g, 0.97 mmol), BINAP (0.12 g, 0.19 mmol), $Cs_2CO_3$ (0.95 g, 2.9 mmol), and $Pd(OAc)_2$ (22 mg, 0.097 mmol) were added to a vial with a stir bar and septa cap. The vial was degassed and purged with $N_2$ 3 times before dry toluene (4.9 mL) was added. The vial was sparged with $N_2$ for 15 minutes and heated to 100° C. for 4 hours. The reaction was diluted with water and extracted with DCM 3 times. The DCM layers were combined, dried with $Na_2SO_4$, filtered, and concentrated. The residue was purified by flash chromatography (silica gel, 0-8% MeOH in DCM) to yield benzyl 4-((1R,5S)-8-(tert-butoxycarbonyl)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) as a white solid (0.53 g, 71%). LCMS (MM-ES+APCI, Pos): m/z 763.4 (M+H).

Step C. tert-butyl (1R,5S)-3-(2-((3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers). Benzyl 4-((1R,5S)-8-(tert-butoxycarbonyl)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) (0.53 g, 0.69 mmol) and MeOH (7 mL) were added to a round bottom flask which was sparged with $N_2$ for 15 minutes. 20% $Pd(OH)_2$ on carbon (50% water) (97 mg, 0.14 mmol) was added in one portion and the round bottom flask was sparged with $H_2$. The reaction was stirred at room temperature under $H_2$ for 4.5 hours. The reaction was filtered through Celite and the filtrate was concentrated to yield tert-butyl (1R,5S)-3-(2-((3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) as a white solid (0.40 g, 93%). LCMS (MM-ES+APCI, Pos): m/z 629.5 (M+H).

Step D. tert-butyl (1R,5S)-3-(2-((3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (trans enantiomers). Tert-butyl (1R,5S)-3-(2-((3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) (0.30 g, 0.48 mmol), 1-bromo-8-ethylnaphthalene (0.15 g, 0.62 mmol), tris(dibenzylideneacetone)dipalladium (0) (44 mg, 0.048 mmol), 9,9-dimethyl-4,5-bis(diphenyl-phosphino)xanthene (55 mg, 0.095 mmol), and $Cs_2CO_3$ (0.62 g, 1.9 mmol) were added to a vial with a stir bar and septa cap. The vial was degassed and purged with $N_2$ 3 times before dioxane (3.2 mL) was added. The vial was sparged with $N_2$ for 15 minutes and heated to 100° C. for 16 hours. The reaction was diluted with water and extracted with DCM 3 times. The DCM layers were combined, dried with $Na_2SO_4$, filtered, and concentrated. The residue was purified via reverse phase chromatography (C18, 0-100% MeCN in water with 0.1% TFA as a modifier). The fractions containing the product were combined, diluted with a saturated solution of $NaHCO_3$, and extracted with DCM two times. The DCM layers were combined, dried with $Na_2SO_4$, filtered, and concentrated to yield tert-butyl (1R,5S)-3-(2-((3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (trans enantiomers) as a pale yellow solid (0.20 g, 53%). LCMS (MM-ES+APCI, Pos): m/z 783.4 (M+H).

Step E. tert-butyl (1R,5S)-3-(7-(8-ethylnaphthalen-1-yl)-2-((3-(hydroxymethyl)tetrahydro-1H-pyrrolizin-7a(5H)-yl) methoxy)-5,6,7,8-tetrahydropyrido[3,4-d]pyrimidin-4-yl)-3,8-diazabicyclo[3.2.1]octane-8-carboxylate (trans enantiomers). Tert-butyl (1R,5S)-3-(2-((3-(((tert-butyldimethylsilyl)oxy)methyl)tetrahydro-1H-pyrrolizin-7a(5H)-yl) methoxy)-7-(8-ethylnaphthalen-1-yl)-5,6,7,8-tetrahydropyrido[3,4-d]pyrimidin-4-yl)-3,8-diazabicyclo[3.2.1] octane-8-carboxylate (trans enantiomers) (0.20 g, 0.25 mmol) was added to a vial with a stir bar and septa cap. The vial was degassed and purged with $N_2$ 3 times before THE (1.3 mL) was added. The vial was cooled to 0° C. and 1M TBAF in THE (0.38 mL, 0.38 mmol) was added. The reaction was warmed to room temperature and stirred for 1.5 hours. The reaction was diluted with water and extracted with DCM three times. The DCM layers were combined, dried with $Na_2SO_4$, filtered, and concentrated. The residue was purified via flash chromatography (silica, 0-20% MeOH in DCM with 2% $NH_4OH$ as a modifier). The fractions containing the product were combined and washed with water. The organic layer was dried with $Na_2SO_4$, filtered, and concentrated to yield tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d] pyrimidin-4-yl)-3,8-diazabicyclo[3.2.1]octane-8-carboxylate (trans enantiomers) as a pale yellow solid (0.13 g, 78%). LCMS (MM-ES+APCI, Pos): m/z 669.3 (M+H).

Step F. tert-butyl (1R,5S)-3-(7-(8-ethylnaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d] pyrimidin-4-yl)-3,8-diazabicyclo[3.2.1]octane-8-carboxylate (trans enantiomers). Tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate (trans enantiomers) (33 mg, 0.05 mmol), THE (1 mL), and triethylamine (14 μL, 0.1 mmol) were added to a vial with a stir bar and septa cap. The vial was degassed and purged with $N_2$ 3 times and 4-nitrophenyl carbonochloridate (12 mg, 0.060 mmol) was added in one portion at room temperature. The reaction was stirred at room temperature for 30 minutes before 2.0 M methylamine in methanol (0.15 mL, 0.30 mmol) was added dropwise. The reaction was stirred at room temperature for 1 hour. The reaction was concentrated and the residue was purified via flash chromatography (silica, 0-15% MeOH in DCM) followed by a second flash column (silica, 0-5% MeOH in DCM) to yield tert-butyl (1R,5S)-3-(7-(8-ethylnaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1] octane-8-carboxylate (trans enantiomers) as a colorless oil (9.6 mg, 26%). LCMS (MM-ES+APCI, Pos): m/z 726.4 (M+H).

Step G. (7a-(((4-((1R,5S)-3,8-diazabicyclo[3.2.1]octan-3-yl)-7-(8-ethylnaphthalen-1-yl)-5,6,7,8-tetrahydropyrido [3,4-d]pyrimidin-2-yl)oxy)methyl)hexahydro-1H-pyrrolizin-3-yl)methyl methylcarbamate (trans enantiomers). Tert-butyl (1R,5S)-3-(7-(8-ethylnaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) (9.6 mg, 0.013 mmol) was added to a round bottom flask with a stir bar. DCM (1.0 mL) and TFA (0.5 mL) were added next. The reaction was stirred at room temperature for 30 minutes before being concentrated. The residue was purified via reverse phase chromatography (C18, 0-80% MeCN in water with 0.1% TFA). The fractions containing the product were combined, frozen, and lyophilized. The TFA salt was passed through two PL-HCO3 ME Resin plugs with methanol and concentrated to yield (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl) methyl methylcarbamate (trans enantiomers) as a colorless oil (7.0 mg, 85%). LCMS (MM-ES+APCI, Pos): m/z 626.4 (M+H).

Example 6

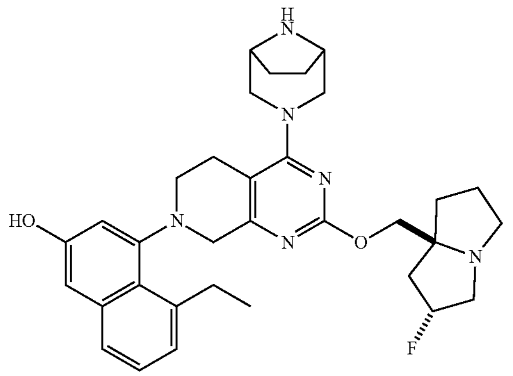

4-(4-((1R,5S)-3,8-diazabicyclo[3.2.1]octan-3-yl)-2-((2-fluorotetrahydro-1H-pyrrolizin-7a(5H)-yl) methoxy)-5,8-dihydropyrido[3,4-d]pyrimidin-7(6H)-yl)-5-ethylnaphthalen-2-ol (racemic, trans)

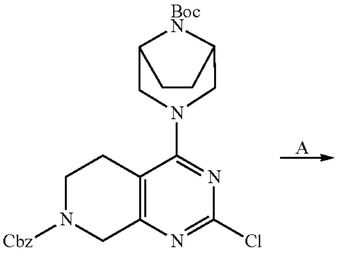

-continued

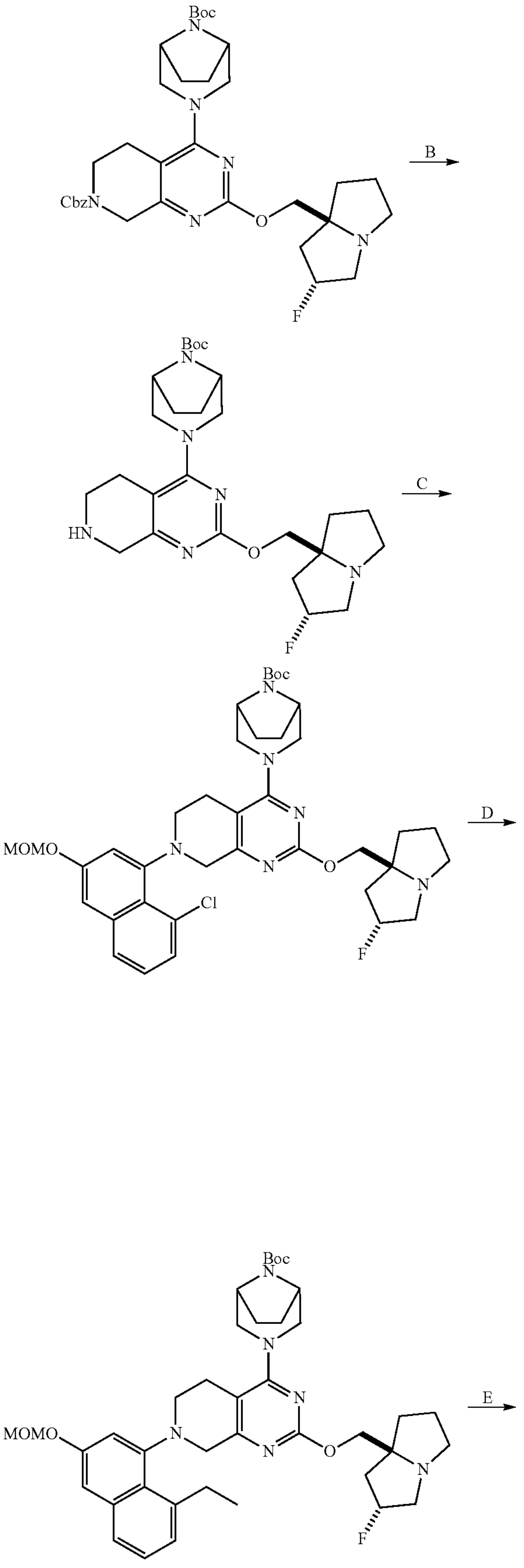

-continued

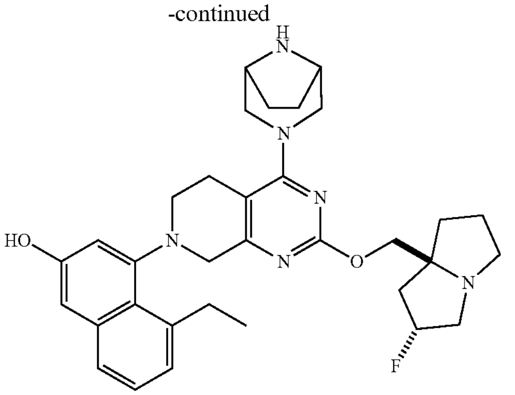

Step A. benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans). Benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.57 g, 1.1 mmol), (2-fluorotetrahydro-1H-pyrrolizin-7a(5H)-yl)methanol (racemic, trans) (0.26 g, 1.7 mmol), BINAP (0.14 g, 0.22 mmol), $Cs_2CO_3$ (1.1 g, 3.3 mmol), and $Pd(OAc)_2$ (25 mg, 0.11 mmol) were added to a vial with a stir bar and septa cap. The vial was degassed and purged with $N_2$ 3 times before dry toluene (5.5 mL) was added. The vial was sparged with $N_2$ and heated to 110° C. overnight. The reaction was diluted with water and extracted with DCM two times. The DCM layers were combined, dried with $Na_2SO_4$, and concentrated. The residue was purified via flash chromatography (silica, 0-20% MeOH in DCM) to yield benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans) as a grey solid (0.53 g, 76%). LCMS (MM-ES+APCI, Pos): m/z 637.4 (M+H).

Step B. tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans) (0.53 g, 0.84 mmol) and MeOH (12 mL) were added to a round bottom flask which was sparged with $N_2$ for 15 minutes. 20% $Pd(OH)_2$ on carbon (50% water) (0.12 g, 0.17 mmol) was added in one portion and the round bottom flask was sparged with $H_2$. The reaction was stirred at room temperature under $H_2$ for 7.5 hours. The reaction was filtered through Celite using methanol and the filtrate was concentrated to yield tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) as an off-white solid (0.33 g, 78%). LCMS (MM-ES+APCI, Pos): m/z 503.3 (M+H).

Step C. tert-butyl (1R,5S)-3-(7-(8-chloro-3-(methoxymethoxy)naphthalen-1-yl)-2-((2-fluorotetrahydro-1H-pyrrolizin-7a(5H)-yl)methoxy)-5,6,7,8-tetrahydro-pyrido[3,4-d]pyrimidin-4-yl)-3,8-diazabicyclo[3.2.1]octane-8-carboxylate (racemic, trans). Tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8- diazabicyclo[3.2.1]octane-8-carboxylate (racemic, trans) (0.20 g, 0.40 mmol), 1-bromo-8-chloro-3-(methoxymethoxy)naphthalene (0.18 g, 0.6 mmol), tris (dibenzylideneacetone)dipalladium (0) (37 mg, 0.04 mmol), 9,9-dimethyl-4,5-bis(dipheyl-phosphino)xanthene (46 mg, 0.08 mmol), $Cs_2CO_3$ (0.52 g, 1.6 mmol), and dioxane (3 mL) were added to a vial with a stir bar and septa cap. The vial was sparged with $N_2$ for 15 minutes and heated to 100° C. for 19 hours. The reaction was diluted with water and extracted with DCM 3 times. The DCM layers were combined, dried with $Na_2SO_4$, filtered, and concentrated. The residue was purified via flash chromatography (silica, 0-20% MeOH in DCM) to yield tert-butyl (1R,5S)-3-(7-(8-chloro-3-(methoxymethoxy)naphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1] octane-8-carboxylate (racemic, trans) as an orange solid. (0.30 g, 100%). LCMS (MM-ES+APCI, Pos): m/z 723.3 (M+H).

Step D. tert-butyl (1R,5S)-3-(7-(8-ethyl-3-(methoxymethoxy)naphthalen-1-yl)-2-((2-fluorotetrahydro-1H-pyrrolizin-7a(5H)-yl)methoxy)-5,6,7,8-tetrahydro-pyrido[3,4-d]pyrimidin-4-yl)-3,8-diazabicyclo[3.2.1] octane-8-carboxylate (racemic, trans). Tert-butyl (1R,5S)-3-(7-(8-chloro-3-(methoxymethoxy)naphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate (racemic, trans) (72 mg, 0.1 mmol), Pd(dppf)$Cl_2$ (7.3 mg, 0.01 mmol), and $Cs_2CO_3$ (65 mg, 0.2 mmol) were added to a vial with a stir bar and septa cap. The vial was degassed and purged with $N_2$ 3 times before dry toluene (0.5 mL) was added. The vial was sparged with $N_2$ for 15 minutes and 1 M triethylborane in THF (0.2 mL, 0.2 mmol) was added. The reaction was heated to 90° C. for 6 hours before additional Pd(dppf)$Cl_2$ (15 mg, 0.020 mmol) and 1 M triethylborane in THF (0.2 mL, 0.2 mmol) were added. The reaction was heated to 90° C. for another 15 hours before being diluted with water and extracted with DCM 3 times. The DCM layers were combined, dried with $Na_2SO_4$, filtered, and concentrated. The residue was purified twice via reverse phase chromatography (C18, 0-50% MeCN/water with 0.1% TFA) to yield tert-butyl (1R,5S)-3-(7-(8-ethyl-3-(methoxymethoxy)naphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) as a brown oil (8.7 mg, 12%). LCMS (MM-ES+APCI, Pos): m/z 717.4 (M+H).

Step E. 4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)-5-ethylnaphthalen-2-ol (racemic, trans). Tert-butyl (1R,5S)-3-(7-(8-ethyl-3-(methoxymethoxy)naphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate (racemic, trans) (8.7 mg, 0.012 mmol) was added to a round bottom flask with a stir bar. DCM (1.0 mL) and 4 M HCl in dioxane (1.0 mL) were added and the reaction was stirred at room temperature for 1 hour. The reaction was concentrated, and the residue was purified via reverse phase chromatography (C18, 0-60% MeCN/water with 0.1% TFA). The fractions containing the product were combined, frozen, and lyophilized. The acid salt was passed through two PL-HCO3 ME Resin plugs with methanol and concentrated to yield 4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)-5-ethylnaphthalen-2-ol (racemic, trans) as an off-white solid (1.4 mg, 20%). LCMS (MM-ES+APCI, Pos): m/z 573.3 (M+H).

Example 7

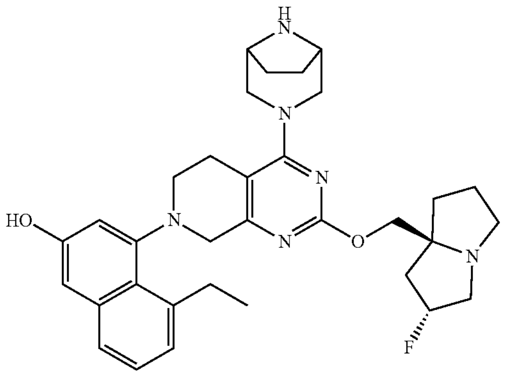 [SMILES: CCc1cccc2cc(O)cc(N3CCc4c(nc(OC[C@@]56CCCN5C[C@H](F)C6)nc4N4CC5CCC(C4)N5)C3)c12]

4-(4-((1R,5S)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethylnaphthalen-2-ol

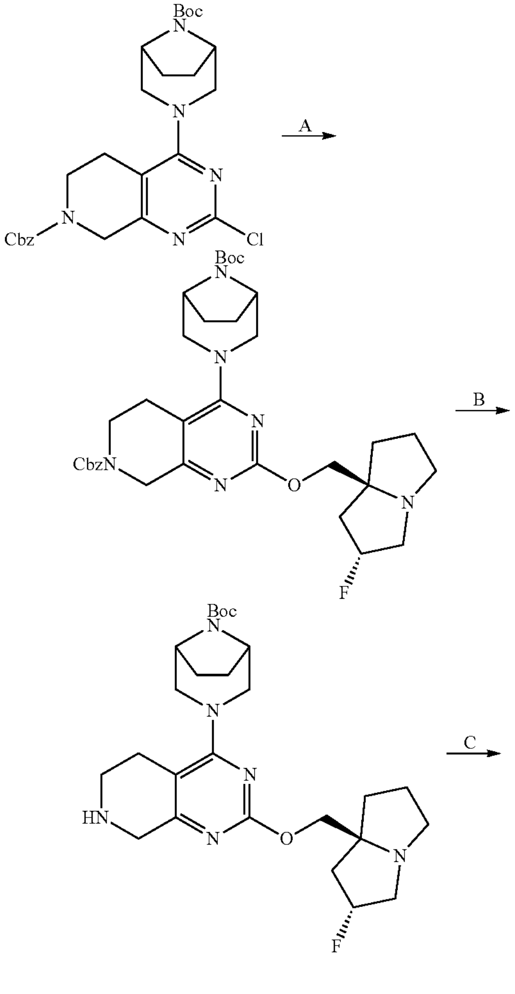

-continued

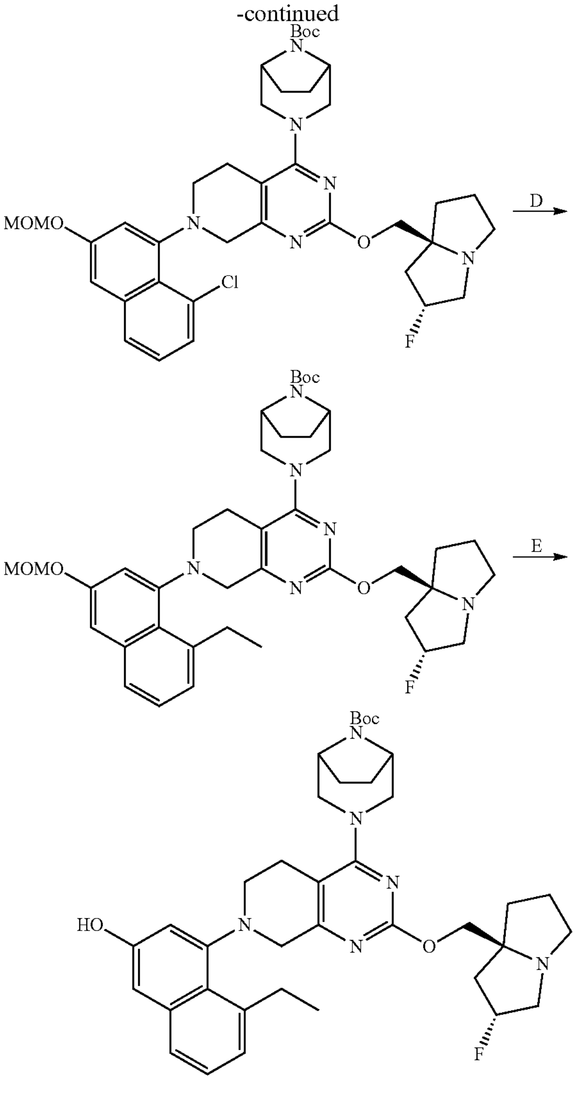

Step A. benzyl 4-((1R,5S)-8-(tert-butoxycarbonyl)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidine-7(6H)-carboxylate. Benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.37 g, 0.71 mmol), ((2R,7aS)-2-fluorotetrahydro-1H-pyrrolizin-7a(5H)-yl)methanol (0.17 g, 1.1 mmol), BINAP (89 mg, 0.14 mmol), $Cs_2CO_3$ (0.70 g, 2.1 mmol), and $Pd(OAc)_2$ (16 mg, 0.07 mmol) were added to a vial with a stir bar and septa cap. The vial was degassed and purged with $N_2$ 3 times before dry toluene (3.6 mL) was added. The vial was sparged with $N_2$ and heated to 100° C. for 15 hours. The reaction was diluted with water and extracted with DCM two times. The DCM layers were combined, dried with $Na_2SO_4$, and concentrated. The residue was purified via flash chromatography (silica, 0-20% MeOH/DCM with 2% $NH_4OH$) to yield benzyl 4-((1R,5S)-8-(tert-butoxycarbonyl)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidine-7(6H)-carboxylate as a grey solid (0.36 g, 79%). LCMS (MM-ES+APCI, Pos): m/z 637.3 (M+H).

Step B. tert-butyl (1R,5S)-3-(2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Benzyl 4-((1R,5S)-8-(tert-butoxycarbonyl)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidine-7(6H)-carboxylate (0.36 g, 0.56 mmol) and MeOH (5.6 mL) were added to a round bottom flask which was sparged with $N_2$ for 15 minutes. 20% $Pd(OH)_2$ on carbon (50% water) (79 mg, 0.11 mmol) was added in one portion and the round bottom flask was sparged with $H_2$. The reaction was stirred at room temperature under $H_2$ for 4.5 hours. The reaction was filtered through Celite and the filtrate was concentrated to yield tert-butyl (1R,5S)-3-(2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as an off-white solid (0.21 g, 74%). LCMS (MM-ES+APCI, Pos): m/z 503.3 (M+H).

Step C. tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.21 g, 0.042 mmol), 1-bromo-8-chloro-3-(methoxymethoxy)naphthalene (0.19 g, 0.62 mmol), tris(dibenzylideneacetone)dipalladium (0) (38 mg, 0.042 mmol), 9,9-dimethyl-4,5-bis(dipheyl-phosphino)xanthene (48 mg, 0.083 mmol), $Cs_2CO_3$ (0.54 g, 1.7 mmol), and dioxane (3 mL) were added to a vial with a stir bar and septa cap. The vial was sparged with $N_2$ for 15 minutes and heated to 100° C. for 19 hours. The reaction was diluted with water and extracted with DCM 3 times. The DCM layers were combined, dried with $Na_2SO_4$, filtered, and concentrated. The residue was purified via flash chromatography (silica, 0-15% MeOH/DCM) to yield tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a dark brown solid. (0.24 g, 78%). LCMS (MM-ES+APCI, Pos): m/z 723.3 (M+H).

Step D. tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.24 g, 0.33 mmol), Pd(dppf)$Cl_2$ (24 mg, 0.033 mmol), and $Cs_2CO_3$ (0.21 g, 0.65 mmol) were added to a vial with a stir bar and septa cap. The vial was degassed and purged with $N_2$ 3 times before dry toluene (1.6 mL) was added. The vial was sparged with $N_2$ for 15 minutes and 1 M triethylborane in THE (0.65 mL, 0.65 mmol) was added. The reaction was heated to 90° C. for 17 hours before additional Pd(dppf)$Cl_2$ (24 mg, 0.033 mmol) and 1 M triethylborane in THE (0.65 mL, 0.65 mmol) were added. The reaction was heated to 100° C. for 7.5 hours before being diluted with water and extracted with DCM 3 times. The DCM layers were combined, dried with $Na_2SO_4$, filtered, and concentrated. The residue was purified twice via reverse phase chromatography (C18, 0-60% MeCN/water with 0.1% TFA) to yield tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a brown oil (27 mg, 12%). LCMS (MM-ES+APCI, Pos): m/z 717.4 (M+H).

Step E. 4-(4-((1R,5S)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethylnaphthalen-2-ol. Tert-butyl (1R,5S)-3-(7-(8-chloro-3-(methoxymethoxy)naphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (27 mg, 0.038 mmol) was added to a round bottom flask with a stir bar. DCM (1.0 mL) and 4 M HCl in dioxane (1.0 mL) were added and the reaction was stirred at room temperature for 1 hour. The reaction was concentrated and the residue was purified via reverse phase chromatography (C18, 0-60% MeCN/water with 0.1% TFA). The fractions containing the product were combined, frozen, and lyophilized. The acid salt was passed through two PL-HCO3 ME Resin plugs with methanol and concentrated to yield 4-(4-((1R,5S)-3,8-diazabicyclo[3.2.1]octan-3-yl)-2-(((2R,7aS)-2-fluorotetrahydro-1H-pyrrolizin-7a(5H)-yl)methoxy)-5,8-dihydropyrido[3,4-d]pyrimidin-7(6H)-yl)-5-ethylnaphthalen-2-ol as an off-white solid (3.1 mg, 14%). LCMS (MM-ES+APCI, Pos): m/z 573.3 (M+H).

Example 8

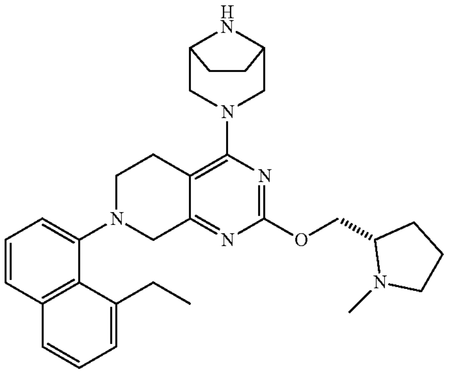

4-((1R,5S)-3,8-diazabicyclo[3.2.1]octan-3-yl)-7-(8-ethylnaphthalen-1-yl)-2-(((S)-1-methylpyrrolidin-2-yl)methoxy)-5,6,7,8-tetrahydropyrido[3,4-d]pyrimidine

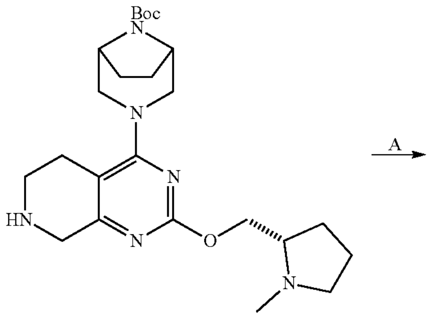

-continued

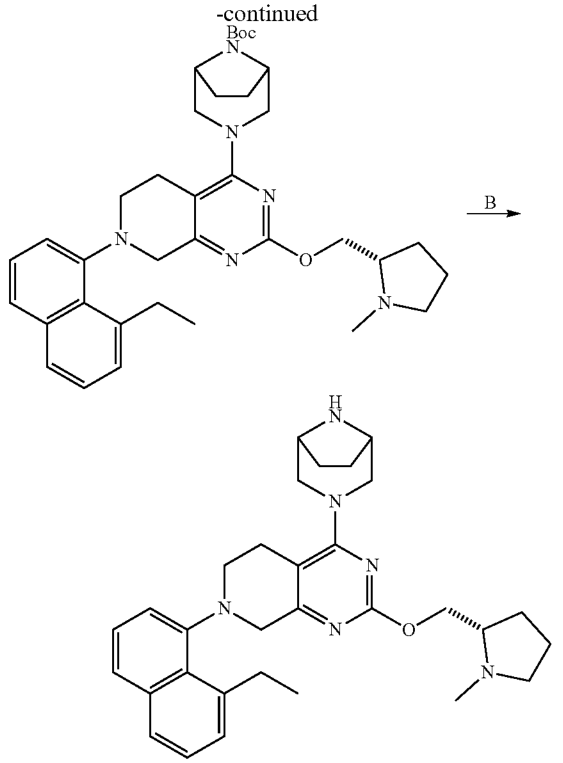

Step A. tert-butyl (1R,5S)-3-(7-(8-ethylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (46 mg, 0.10 mmol), 1-bromo-8-ethylnaphthalene (50 mg, 0.21 mmol), $Cs_2CO_3$ (0.13 g, 0.40 mmol) and dioxane (0.67 mL) were added to a vial with a stir bar. The vial was sparged with $N_2$ for 15 minutes before tris(dibenzylideneacetone)dipalladium (0) (9.2 mg, 0.01 mmol) and 9,9-dimethyl-4,5-bis(dipheyl-phosphino)xanthene (12 mg, 0.020 mmol) were added. The vial was degassed and purged with $N_2$ 3 times before the reaction was heated to 100° C. for 16 hours. The reaction was diluted with water and extracted with DCM 3 times. The DCM layers were combined, dried with $Na_2SO_4$, filtered, and concentrated. The residue was purified via flash chromatography (silica, 0-20% MeOH in DCM) to yield tert-butyl (1R,5S)-3-(7-(8-ethylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (9.7 mg, 16%). LCMS (MM-ES+APCI, Pos): m/z 613.4 (M+H).

Step B. 4-((1R,5S)-3,8-diazabicyclo[3.2.1]octan-3-yl)-7-(8-ethylnaphthalen-1-yl)-2-(((S)-1-methylpyrrolidin-2-yl)methoxy)-5,6,7,8-tetrahydropyrido[3,4-d]pyrimidine. Tert-butyl (1R,5S)-3-(7-(8-ethylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (9.7 mg, 0.016 mmol) was added to around bottom flask with a stir bar. DCM (1.0 mL) was added followed by TFA (0.5 mL). The reaction was stirred at room temperature for 2 hours before being concentrated to dryness. The residue was purified via reverse phase chromatography (C18, 0-60% MeCN/water with 0.1% TFA). The fractions containing the product were combined, frozen, and lyophilized to yield 4-((1R,5S)-3,8-diazabicyclo[3.2.1]octan-3-yl)-7-(8-ethylnaphthalen-1-yl)-2-(((S)-1-methylpyrrolidin-2-yl)methoxy)-5,6,7,8-tetrahydropyrido[3,4-d]pyrimidine as the TFA salt (7.7 mg, 65%). LCMS (MM-ES+APCI, Pos): m/z 513.3 (M+H).

Example 9

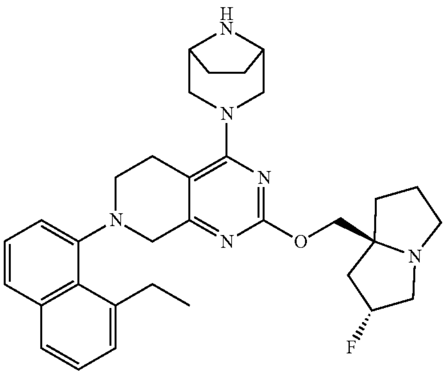 [SMILES: CCc1cccc2cccc(N3CCc4c(nc(OC[C@@]56CCCN5C[C@H](F)C6)nc4N4CC5CCC(C4)N5)C3)c12]

4-((1R,5S)-3,8-diazabicyclo[3.2.1]octan-3-yl)-7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans)

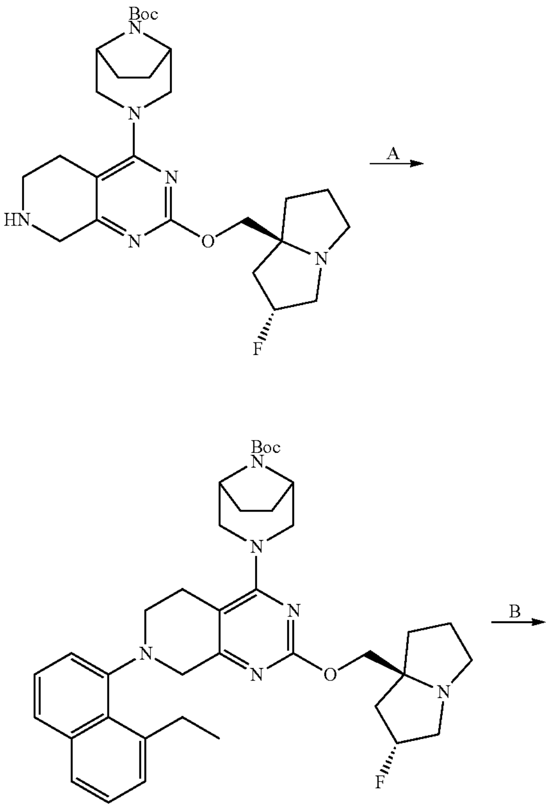

-continued

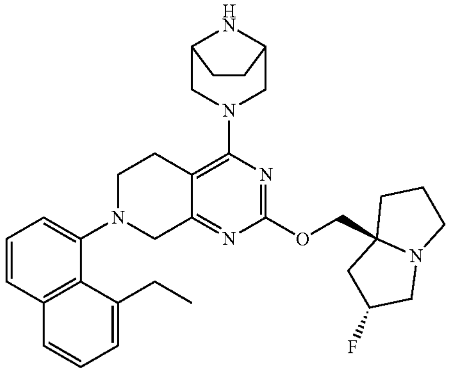

Step A. tert-butyl (1R,5S)-3-(7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (50 mg, 0.10 mmol), 1-bromo-8-ethylnaphthalene (35 mg, 0.15 mmol), tris(dibenzylideneacetone)dipalladium (0) (9.2 mg, 0.01 mmol), 9,9-dimethyl-4,5-bis(dipheyl-phosphino)xanthene (12 mg, 0.02 mmol), $Cs_2CO_3$ (0.13 g, 0.40 mmol), and dioxane (0.7 mL) were added to a vial with a stir bar. The vial was sparged with $N_2$ for 15 minutes before the reaction was heated to 100° C. overnight. The reaction was diluted with water and extracted with DCM 3 times. The DCM layers were combined, dried with $Na_2SO_4$, filtered, and concentrated. The residue was purified via flash chromatography (silica, 0-20% MeOH/DCM) to yield tert-butyl (1R,5S)-3-(7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (17 mg, 25%). LCMS (MM-ES+APCI, Pos): m/z 657.4 (M+H).

Step B. 4-((1R,5S)-3,8-diazabicyclo[3.2.1]octan-3-yl)-7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans). Tert-butyl (1R,5S)-3-(7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (17 mg, 0.025 mmol) was added to a round bottom flask with a stir bar. DCM (1 mL) was added followed by TFA (0.5 mL). The reaction was stirred at room temperature for 1 hour before being concentrated to dryness. The residue was purified via reverse phase chromatography (C18, 0-80% MeCN/water with 0.1% TFA). The fractions containing the product were combined, frozen, and lyophilized to yield 4-((1R,5S)-3,8-diazabicyclo[3.2.1]octan-3-yl)-7-(8-ethylnaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans) as the TFA salt (17 mg, 86%). LCMS (MM-ES+APCI, Pos): m/z 557.4 (M+H).

Example 10

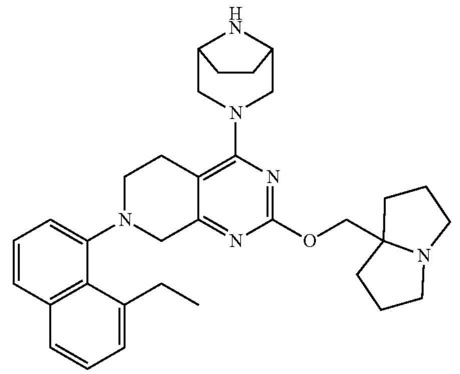 [SMILES: CCc1cccc2cccc(N3CCc4c(nc(OCC56CCCN5CCC6)nc4N4CC5CCC(C4)N5)C3)c12]

4-((1R,5S)-3,8-diazabicyclo[3.2.1]octan-3-yl)-7-(8-ethylnaphthalen-1-yl)-2-((tetrahydro-1H-pyrrolizin-7a(5H)-yl)methoxy)-5,6,7,8-tetrahydropyrido[3,4-d] pyrimidine

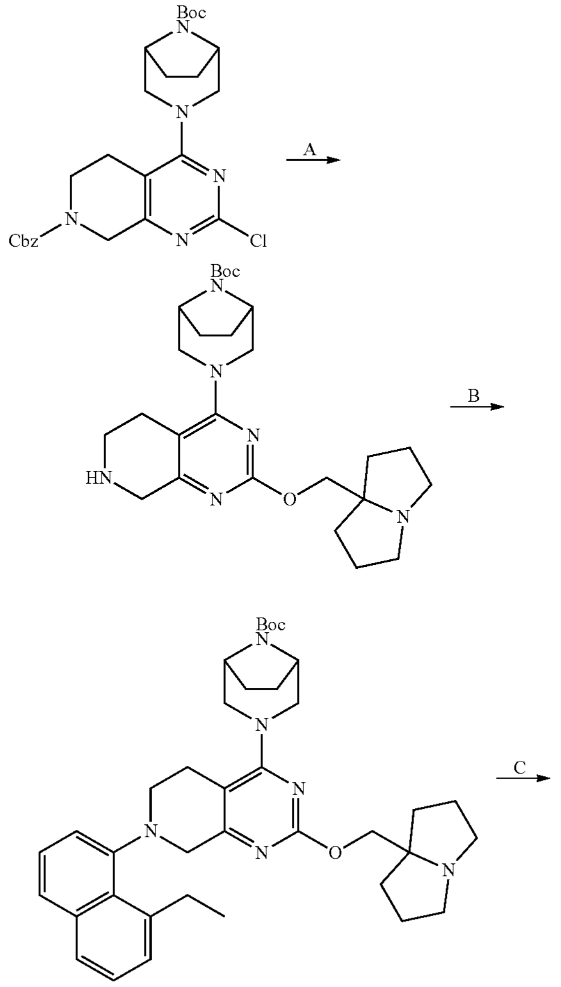

-continued

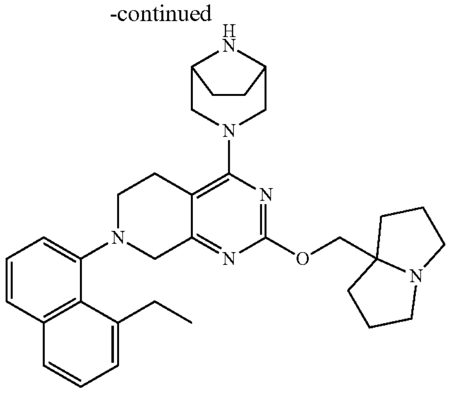

Step A. tert-butyl (1R,5S)-3-(2-((tetrahydro-1H-pyrrolizin-7a(5H)-yl)methoxy)-5,6,7,8-tetrahydropyrido[3,4-d] pyrimidin-4-yl)-3,8-diazabicyclo[3.2.1]octane-8-carboxylate. Synthesized according to Example 6 step A-B, substituting (tetrahydro-1H-pyrrolizin-7a(5H)-yl)methanol for (2-fluorotetrahydro-1H-pyrrolizin-7a(5H)-yl)methanol and using the deprotection step B. (0.23 g, 84%). LCMS (MM-ES+APCI, Pos): m/z 485.4 (M+H).

Step B. tert-butyl (1R,5S)-3-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate. Tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate (72 mg, 0.15 mmol), 1-bromo-8-ethylnaphthalene (52 mg, 0.22 mmol), tris (dibenzylideneacetone)dipalladium (0) (13 mg, 0.015 mmol), 9,9-dimethyl-4,5-bis(dipheyl-phosphino)xanthene (17 mg, 0.03 mmol), $Cs_2CO_3$ (0.20 g, 0.60 mmol), and dioxane (1 mL) were added to a vial with a stir bar. The vial was sparged with $N_2$ for 15 minutes before the reaction was heated to 100° C. overnight. The reaction was diluted with water and extracted with DCM 3 times. The combined DCM layers were dried with $Na_2SO_4$, filtered, and concentrated. The residue was purified via flash chromatography (silica, 0-20% MeOH/DCM) to yield tert-butyl (1R,5S)-3-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (37 mg, 38%). LCMS (MM-ES+APCI, Pos): m/z 639.4 (M+H).

Step C. 4-((1R,5S)-3,8-diazabicyclo[3.2.1]octan-3-yl)-7-(8-ethylnaphthalen-1-yl)-2-((tetrahydro-1H-pyrrolizin-7a (5H)-yl)methoxy)-5,6,7,8-tetrahydropyrido[3,4-d]pyrimidine. Tert-butyl (1R,5S)-3-(7-(8-ethylnaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo [3.2.1]octane-8-carboxylate (37 mg, 0.058 mmol) was added to a round bottom flask with a stir bar. DCM (1.0 mL) was added followed by TFA (0.5 mL). The reaction was stirred at room temperature for 2 hours before being concentrated to dryness. The residue was purified via reverse phase chromatography (C18, 0-80% MeCN/water with 0.1% TFA). The fractions containing the product were combined, frozen, and lyophilized to yield 4-((1R,5S)-3,8-diazabicyclo[3.2.1]octan-3-yl)-7-(8-ethylnaphthalen-1-yl)-2-((tetrahydro-1H-pyrrolizin-7a(5H)-yl)methoxy)-5,6,7,8-tetrahydropyrido[3,4-d]pyrimidine as the TFA salt (24 mg, 54%). LCMS (MM-ES+APCI, Pos): m/z 539.3 (M+H).

Example 11

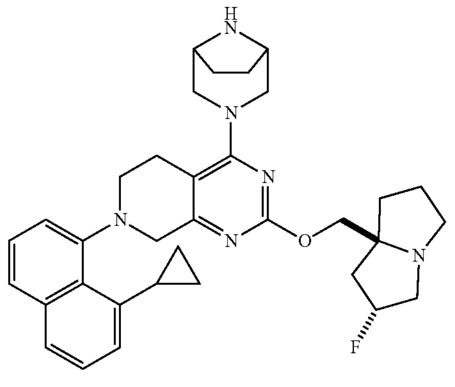

4-((1R,5S)-3,8-diazabicyclo[3.2.1]octan-3-yl)-7-(8-cyclopropylnaphthalen-1-yl)-2-((2-fluorotetrahydro-1H-pyrrolizin-7a(5H)-yl)methoxy)-5,6,7,8-tetrahydropyrido[3,4-d]pyrimidine) (racemic, trans)

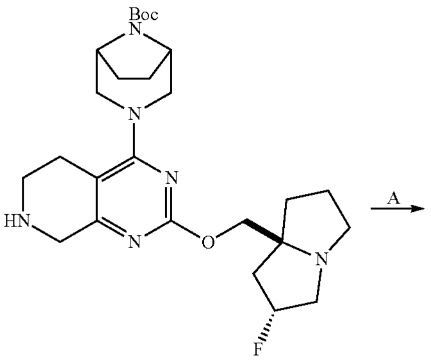

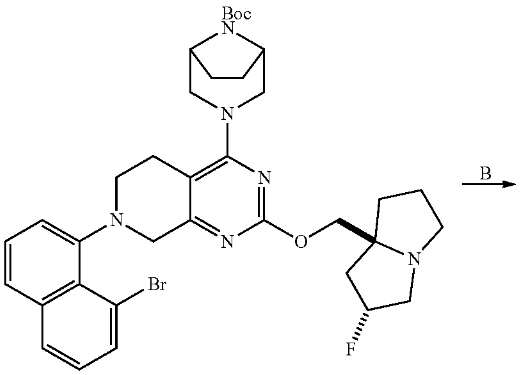

-continued

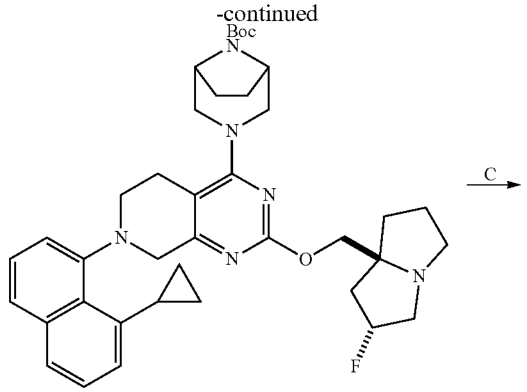

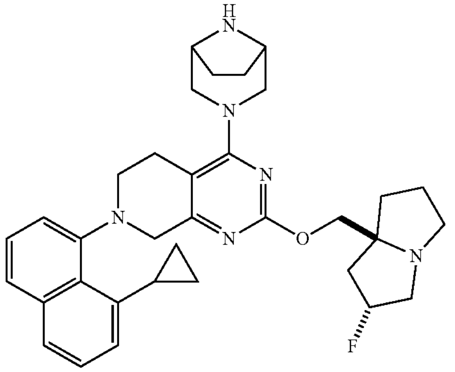

Step A. tert-butyl (1R,5S)-3-(7-(8-bromonaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (0.30 g, 0.59 mmol), 9,9-dimethyl-4,5-bis(dipheyl-phosphino)xanthene (68 mg, 0.11 mmol), tris(dibenzylideneacetone)dipalladium (0) (54 mg, 0.059 mmol), 1,8-dibromonaphthalene (0.51 g, 1.8 mmol), and $Cs_2CO_3$ (0.96 g, 3.0 mmol) were added to a vial with a stir bar and septa cap. The vial was degassed and purged with $N_2$ 3 times before toluene (2.4 mL) was added. The vial was sparged with $N_2$ for 15 minutes before the reaction was heated to 105° C. for 23 hours. The reaction was diluted with water and extracted with DCM 3 times. The combined DCM layers were dried with $Na_2SO_4$, filtered, and concentrated. The residue was purified twice via flash chromatography (silica, 0-10% MeOH in DCM) to yield tert-butyl (1R,5S)-3-(7-(8-bromonaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (0.15 g, 35%). LCMS (MM-ES+APCI, Pos): m/z 707.3 (M+H).

Step B. tert-butyl (1R,5S)-3-(7-(8-cyclopropylnaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Tert-butyl (1R,5S)-3-(7-(8-bromonaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (35 mg, 0.049 mmol) and dichloro[1,1'-bis(diphenylphosphino)ferrocene]palladium (II) dichloromethane adduct (16 mg, 0.020 mmol) were added to a vial with a stir bar and septa cap. The vial was degassed and purged with $N_2$ 3 times before 0.5 M cyclopropylzine bromide (0.3 mL, 0.15 mmol) was added. The reaction was heated to 90° C. for 15 hours before being diluted with water and extracted with DCM three times. The DCM layers were combined, dried with $Na_2SO_4$, filtered, and concentrated. The residue was purified via flash chromatography (silica, 0-20% MeOH/DCM) to yield tert-butyl (1R,5S)-3-(7-(8-cyclopropylnaphthalen-1-yl)-2-((2-fluorotetrahydro-1H-pyrrolizin-7a(5H)-yl) methoxy)-5,6,7,8-tetrahydropyrido[3,4-d]pyrimidin-4-yl)-3,8-diazabicyclo[3.2.1]octane-8-carboxylate (racemic, trans) (10 mg, 30%). LCMS (MM-ES+APCI, Pos): m/z 669.4 (M+H).

Step C. 4-((1R,5S)-3,8-diazabicyclo[3.2.1]octan-3-yl)-7-(8-cyclopropylnaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans). Tert-butyl (1R,5S)-3-(7-(8-cyclopropylnaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (10 mg, 0.015 mmol) was added to a round bottom flask with a stir bar. DCM (1.0 mL) was added followed by TFA (0.5 mL). The reaction was stirred at room temperature for 1 hour before being concentrated to dryness. The residue was purified via reverse phase chromatography (C18, 0-80% MeCN/water with 0.1% TFA). The fractions containing the product were combined, frozen, and lyophilized to yield 4-((1R,5S)-3,8-diazabicyclo[3.2.1]octan-3-yl)-7-(8-cyclopropylnaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans) as the TFA salt (6 mg, 50%). LCMS (MM-ES+APCI, Pos): m/z 569.3 (M+H).

Example 12

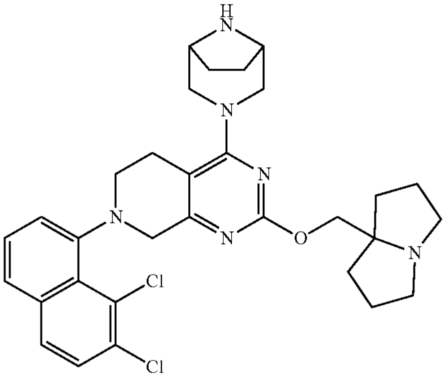 [SMILES: Clc1ccc2cccc(N3CCc4c(nc(OCC56CCCN5CCC6)nc4N4CC5CCC(C4)N5)C3)c2c1Cl]

4-((1R,5S)-3,8-diazabicyclo[3.2.1]octan-3-yl)-7-(7,8-dichloronaphthalen-1-yl)-2-((tetrahydro-1H-pyrrolizin-7a(5H)-yl)methoxy)-5,6,7,8-tetrahydropyrido[3,4-d]pyrimidine

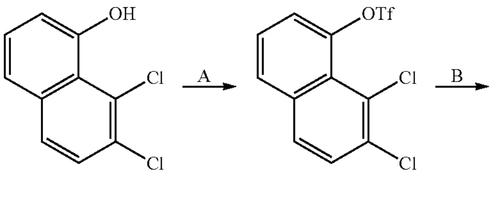

-continued

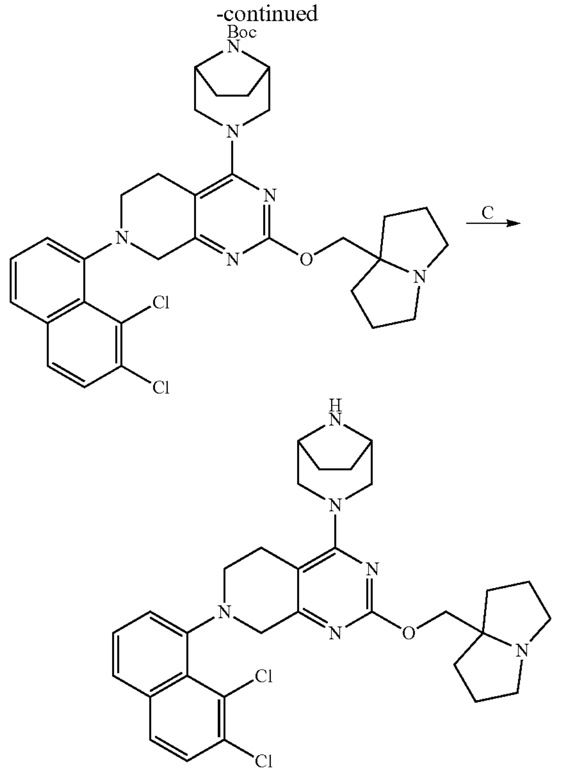

Step A. 7,8-dichloronaphthalen-1-yl trifluoromethanesulfonate. 7,8-Dichloronaphthalen-1-ol (0.10 g, 0.47 mmol) was added to a vial with a stir bar and septa cap. DCM (4.7 mL) and DIPEA (0.12 mL, 0.70 mmol) were added and the vial was cooled to −78° C. $Tf_2O$ (96 μL, 0.59 mmol) was added and the reaction was warmed to room temperature. The reaction was diluted with water and extracted with DCM. The DCM layer was dried with $Na_2SO_4$, filtered, and concentrated. The residue was purified via flash chromatography (silica, 0-10% EtOAc/hexanes) to yield 7,8-dichloronaphthalen-1-yl trifluoromethanesulfonate as a pale-yellow oil (0.16 g, purity 85%). $^1H$ NMR ($CDCl_3$, 400 MHz): δ 8.40 (dd, J=7.6, 2.1 Hz, 1H), 7.67-7.53 (m, 4H).

Step B. tert-butyl (1R,5S)-3-(7-(7,8-dichloronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (24 mg, 0.05 mmol), 7,8-dichloronaphthalen-1-yl trifluoromethanesulfonate (25 mg, 0.075 mmol), tris(dibenzylideneacetone)dipalladium (0) (5 mg, 0.005 mmol), 9,9-dimethyl-4,5-bis(diphenyl-phosphino) xanthene (6 mg, 0.01 mmol), and $Cs_2CO_3$ (65 mg, 0.2 mmol) were added to a vial with a stir bar and septa cap. The vial was degassed and purged with $N_2$ 3 times before dioxane (0.33 mL) was added. The vial was sparged with $N_2$ for 15 minutes and the reaction was heated to 100° C. for 4 hours. The reaction was diluted with water and extracted with DCM 3 times. The DCM layers were combined, dried with $Na_2SO_4$, filtered, and concentrated. The residue was purified via flash chromatography (silica, 0-20% MeOH/DCM with 2% $NH_4OH$). The fractions containing the product were diluted with water and extracted with 3:1 DCM:IPA. The organic layer was dried with $Na_2SO_4$, filtered, and concentrated to yield tert-butyl (1R,5S)-3-(7-(7,8-dichloronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as an orange oil (19 mg, 55%). LCMS (MM-ES+APCI, Pos): m/z 679.3 (M+H).

Step C. 4-((1R,5S)-3,8-diazabicyclo[3.2.1]octan-3-yl)-7-(7,8-dichloronaphthalen-1-yl)-2-((tetrahydro-1H-pyrrolizin-7a(5H)-yl)methoxy)-5,6,7,8-tetrahydropyrido[3,4-d]pyrimidine. Tert-butyl (1R,5S)-3-(7-(7,8-dichloronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (19 mg, 0.028 mmol) was added to a round bottom flask with a stir bar. DCM (1.0 mL) and TFA (0.5 mL) were added next. The reaction was stirred at room temperature for 30 minutes before being concentrated. The residue was purified via reverse phase chromatography (C18, 0-80% MeCN/water with 0.1% TFA). The fractions containing the product were combined, frozen, and lyophilized. The TFA salt was passed through two PL-HCO3 ME Resin plugs with methanol and concentrated to yield 4-((1R,5S)-3,8-diazabicyclo[3.2.1]octan-3-yl)-7-(7,8-dichloronaphthalen-1-yl)-2-((tetrahydro-1H-pyrrolizin-7a(5H)-yl)methoxy)-5,6,7,8-tetrahydropyrido[3,4-d]pyrimidine as a tan oil (3.8 mg, 24%). LCMS (MM-ES+APCI, Pos): m/z 579.2 (M+H).

Example 13

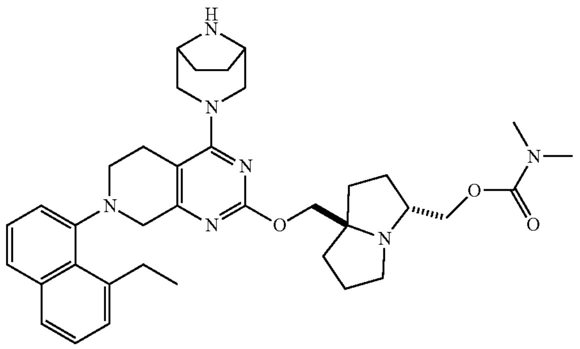

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl dimethylcarbamate (trans enantiomers)

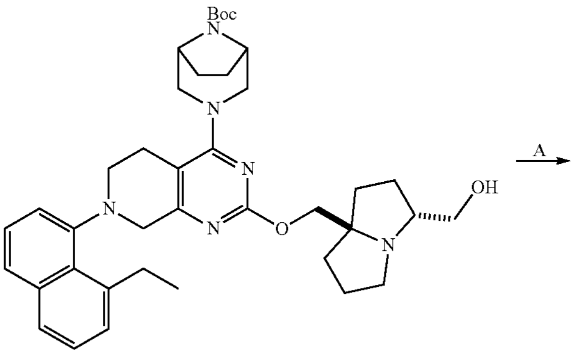

-continued

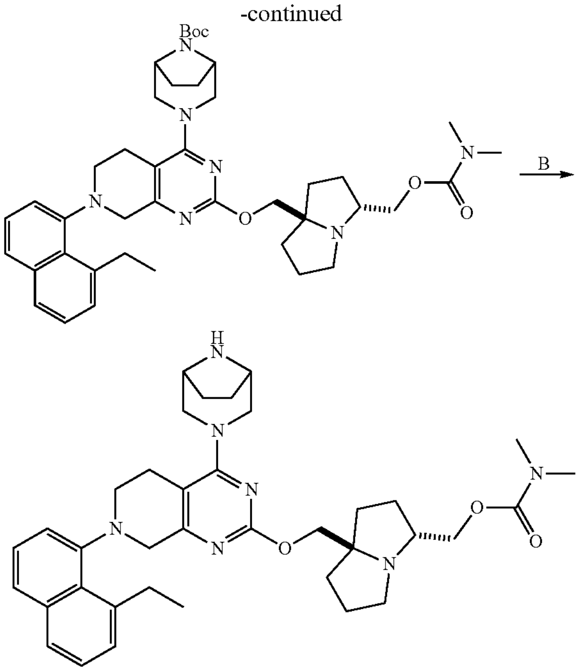

Step A. tert-butyl (1R,5S)-3-(2-((3-(((dimethylcarbamoyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (trans enantiomers). Tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) (33 mg, 0.05 mmol) was added to a vial with a stir bar and septa cap. The vial was degassed and purged with $N_2$ 3 times before THE (1 mL) and triethylamine (21 μL, 0.15 mmol) were added. 4-Nitrophenyl carbonochloridate (15 mg, 0.075 mmol) was added in one portion at room temperature. The reaction was stirred at room temperature for 30 minutes before 2.0 M dimethylamine in THE (0.15 mL, 0.30 mmol) was added dropwise. The reaction was stirred at room temperature for 1 hour. The reaction was concentrated to dryness and the residue was purified via flash chromatography (silica, 0-10% MeOH/DCM) followed by a second flash column (silica, 0-5% MeOH/DCM) to yield tert-butyl (1R,5S)-3-(2-((3-(((dimethylcarbamoyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (trans enantiomers) (5.2 mg, 14%). LCMS (MM-ES+APCI, Pos): m/z 740.3 (M+H).

Step B. (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl dimethylcarbamate (trans enantiomers). Tert-butyl (1R,5S)-3-(2-((3-(((dimethylcarbamoyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (trans enantiomers) (5.2 mg, 0.007 mmol) was added to a round bottom flask with a stir bar. DCM (1.0 mL) and TFA (0.5 mL) were added next. The reaction was stirred at room temperature for 30 minutes before being concentrated. The residue was purified via reverse phase chromatography (C18, 0-80% MeCN in water with 0.1% TFA). The fractions containing the product were combined, frozen, and lyophilized. The TFA salt was passed through two PL-HCO3 ME Resin plugs with methanol and concentrated to yield (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl) methyl dimethylcarbamate (trans enantiomers) as a colorless oil (2.6 mg, 58%). LCMS (MM-ES+APCI, Pos): m/z 640.5 (M+H).

Example 14

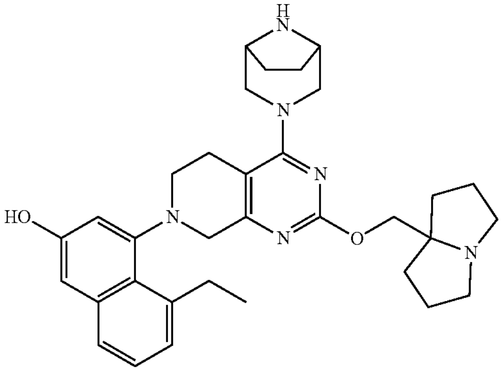 [SMILES: CCc1cccc2cc(O)cc(N3CCc4c(nc(OCC56CCCN5CCC6)nc4N4CC5CCC(C4)N5)C3)c12]

4-(4-((1R,5S)-3,8-diazabicyclo[3.2.1]octan-3-yl)-2-((tetrahydro-1H-pyrrolizin-7a(5H)-yl)methoxy)-5,8-dihydropyrido[3,4-d]pyrimidin-7(6H)-yl)-5-ethyl-naphthalen-2-ol

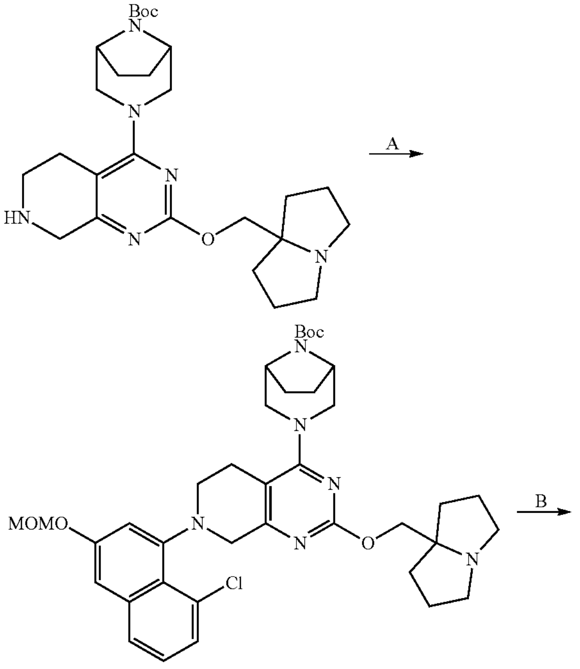

-continued

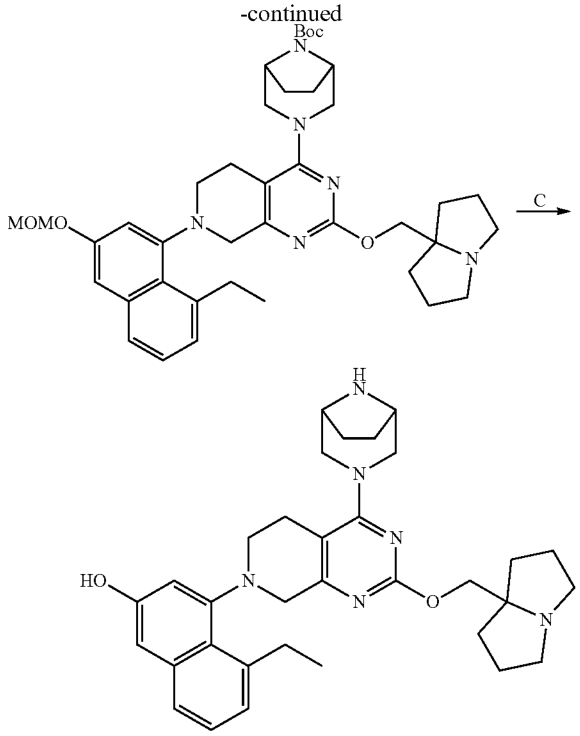

Step A. tert-butyl (1R,5S)-3-(7-(8-chloro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.13 g, 0.27 mmol), 1-bromo-8-chloro-3-(methoxymethoxy)naphthalene (0.12 g, 0.40 mmol), tris (dibenzylideneacetone)dipalladium (0) (24 mg, 0.027 mmol), 9,9-dimethyl-4,5-bis(dipheyl-phosphino)xanthene (30 mg, 0.053 mmol), $Cs_2CO_3$ (0.35 g, 1.1 mmol), and dioxane (2 mL) were added to a vial with a stir bar and septa cap. The vial was sparged with $N_2$ for 15 minutes and the reaction was heated to 100° C. for 21 hours. The reaction was diluted with water and extracted with DCM 3 times. The DCM layers were combined, dried with $Na_2SO_4$, filtered, and concentrated. The residue was purified via flash chromatography (silica, 0-20% MeOH/DCM) to yield tert-butyl (1R,5S)-3-(7-(8-chloro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (75 mg, 40%). LCMS (MM-ES+APCI, Pos): m/z 705.4 (M+H).

Step B. tert-butyl (1R,5S)-3-(7-(8-ethyl-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(7-(8-chloro-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (75 mg, 0.11 mmol), Pd(dppf)$Cl_2$ (13 mg, 0.016 mmol), and $Cs_2CO_3$ (0.10 g, 0.32 mmol) were added to a vial with a stir bar and septa cap. The vial was degassed and purged with $N_2$ 3 times before toluene (1.7 mL) was added. The vial was sparged with $N_2$ for 15 minutes before 1M triethylborane (0.53 mL, 0.53 mmol) was added. The reaction was heated to 90° C. for 17 hours and 100° C. for 4 hours. Additional Pd(dppf)$Cl_2$ (13 mg, 0.016 mmol) was added and the vial was sparged with $N_2$ for 15 minutes. Additional 1M triethylborane (0.5 mL, 0.5 mmol) was added and the reaction was heated to 120° C. for 17 hours. Additional Pd(dppf)$Cl_2$ (26 mg, 0.032 mmol) was added before the vial was sparged with $N_2$ for 15 minutes. Additional 1M triethylborane (0.5 mL, 0.5 mmol) was added and the reaction was heated to 120° C. for 4 hours. The reaction was diluted with water and extracted with DCM 3 times. The DCM layers were combined, dried with $Na_2SO_4$, filtered, and concentrated. The residue was purified via flash chromatography (silica, 0-20% MeOH/DCM) followed by a reverse phase column (C18, 0-80% MeCN/water with 0.1% TFA) to yield tert-butyl (1R,5S)-3-(7-(8-ethyl-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (6.3 mg, 8%). LCMS (MM-ES+APCI, Pos): m/z 699.4 (M+H).

Step C. 4-(4-((1R,5S)-3,8-diazabicyclo[3.2.1]octan-3-yl)-2-((tetrahydro-1H-pyrrolizin-7a(5H)-yl)methoxy)-5,8-dihydropyrido[3,4-d]pyrimidin-7(6H)-yl)-5-ethylnaphthalen-2-ol. Tert-butyl (1R,5S)-3-(7-(8-ethyl-3-(methoxymethoxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (6.3 mg,) was added to a round bottom flask with a stir bar. DCM (1.0 mL) and 4M HCl in dioxanes (1.0 mL) were added and the reaction was stirred at room temperature for 1 hour before being concentrated to dryness. The residue was purified via a reverse phase column (C18, 0-80% MeCN/water with 0.1% TFA). The fractions containing the product were combined, frozen, and lyophilized. The product was passed through three PL-HCO3 ME Resin plugs with methanol and concentrated to yield 4-(4-((1R,5S)-3,8-diazabicyclo[3.2.1]octan-3-yl)-2-((tetrahydro-1H-pyrrolizin-7a(5H)-yl)methoxy)-5,8-dihydropyrido[3,4-d]pyrimidin-7(6H)-yl)-5-ethylnaphthalen-2-ol as an off-white solid (1.8 mg, 32%) LCMS (MM-ES+APCI, Pos): m/z 555.3 (M+H).

Example 15

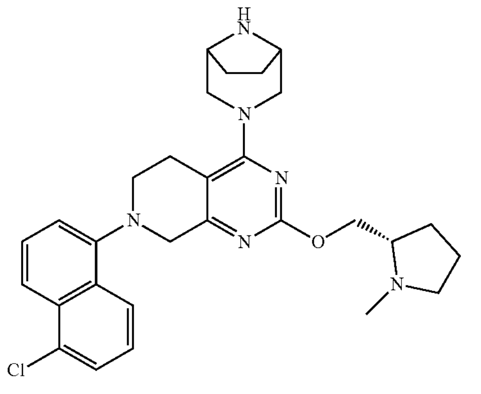 [SMILES: CN1CCC[C@H]1COc1nc2c(c(N3CC4CCC(C3)N4)n1)CCN(c1cccc3c(Cl)cccc13)C2]

4-((1R,5S)-3,8-diazabicyclo[3.2.1]octan-3-yl)-7-(5-chloronaphthalen-1-yl)-2-(((S)-1-methylpyrrolidin-2-yl)methoxy)-5,6,7,8-tetrahydropyrido[3,4-d]pyrimidine

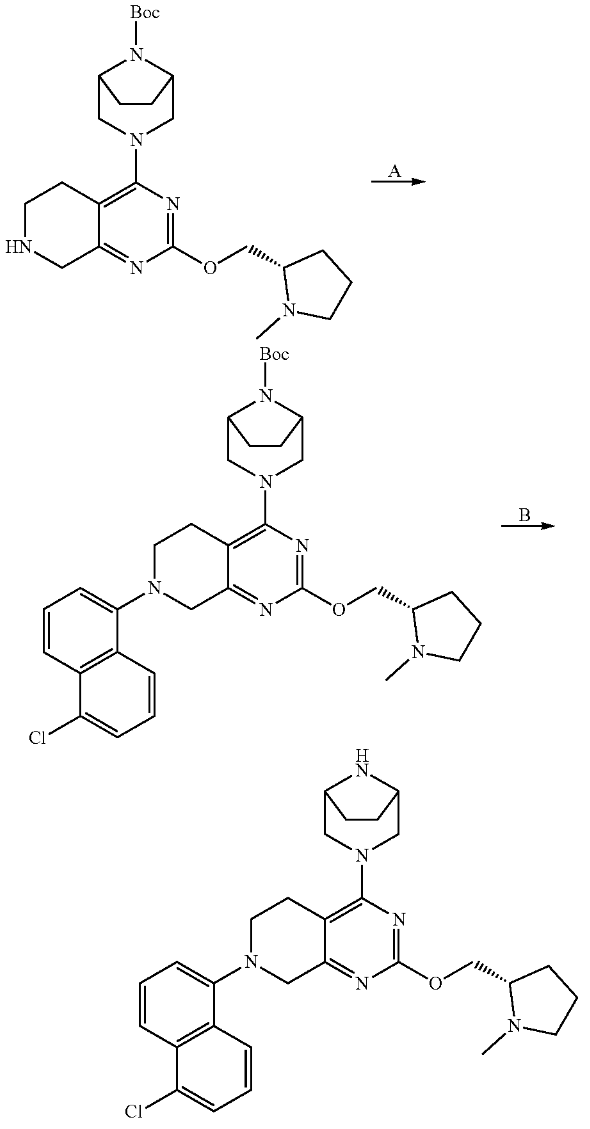

Step A. tert-butyl (1R,5S)-3-(7-(5-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (69 mg, 0.15 mmol), 1-bromo-5-chloronaphthalene (54 mg, 0.23 mmol), tris (dibenzylideneacetone)dipalladium (0) (14 mg, 0.015 mmol), 9,9-dimethyl-4,5-bis(dipheyl-phosphino)xanthene (17 mg, 0.03 mmol), $Cs_2CO_3$ (0.20 g, 0.6 mmol) and dioxane (1.0 mL) were added to a vial with a stir bar and septa cap. The vial was sparged with $N_2$ for 15 minutes before the reaction was heated to 100° C. for 15 hours. The reaction was diluted with water and extracted with DCM 3 times. The DCM layers were combined, dried with $Na_2SO_4$, filtered, and concentrated. The residue was purified via flash chromatography (silica, 0-20% MeOH/DCM with 2% $NH_4OH$) followed by a reverse phase column (C18, 0-80% MeCN/water with 0.1% TFA) to yield tert-butyl (1R,5S)-3-(7-(5-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (35 mg, 37%). LCMS (MM-ES+APCI, Pos): m/z 619.3 (M+H).

Step B. 4-((1R,5S)-3,8-diazabicyclo[3.2.1]octan-3-yl)-7-(5-chloronaphthalen-1-yl)-2-(((S)-1-methylpyrrolidin-2-yl)methoxy)-5,6,7,8-tetrahydropyrido[3,4-d]pyrimidine. Tert-butyl (1R,5S)-3-(7-(5-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (35 mg, 0.056 mmol) was added to a round bottom flask with a stir bar. DCM (1 mL) and TFA (0.5 mL) were added. The reaction was stirred at room temperature for 1 hour before being concentrated to dryness. The residue was purified via a reverse phase column (C18, 0-80% MeCN/water with 0.1% TFA). The fractions containing the product were combined, frozen, and lyophilized. The TFA salt was passed through two PL-HCO3 ME Resin plugs with methanol and concentrated to yield 4-((1R,5S)-3,8-diazabicyclo[3.2.1]octan-3-yl)-7-(5-chloronaphthalen-1-yl)-2-(((S)-1-methylpyrrolidin-2-yl)methoxy)-5,6,7,8-tetrahydropyrido[3,4-d]pyrimidine as an off-white solid (8.0 mg, 28%). LCMS (MM-ES+APCI, Pos): m/z 519.3 (M+H).

Example 16

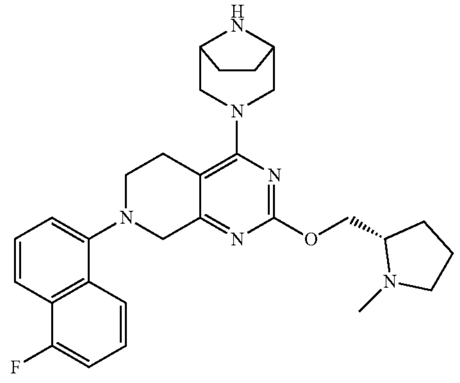 [SMILES: CN1CCC[C@H]1COc1nc2c(c(N3CC4CCC(C3)N4)n1)CCN(c1cccc3c(F)cccc13)C2]

4-((1R,5S)-3,8-diazabicyclo[3.2.1]octan-3-yl)-7-(5-fluoronaphthalen-1-yl)-2-(((S)-1-methylpyrrolidin-2-yl)methoxy)-5,6,7,8-tetrahydropyrido[3,4-d]pyrimidine

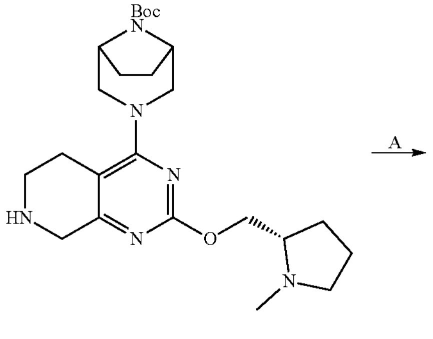

-continued

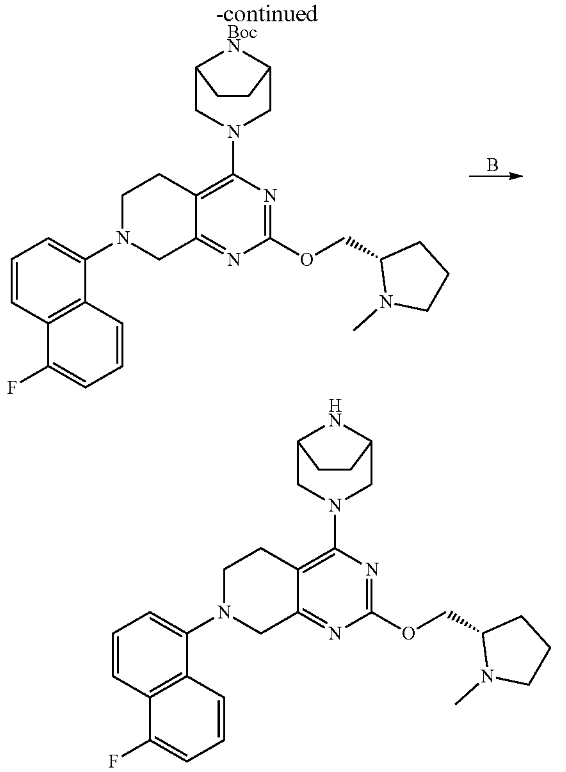

Step A. tert-butyl (1R,5S)-3-(7-(5-fluoronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (46 mg, 0.1 mmol), 1-bromo-5-fluoronaphthalene (34 mg, 0.15 mmol), tris(dibenzylideneacetone)dipalladium (0) (9 mg, 0.01 mmol), 9,9-dimethyl-4,5-bis(dipheyl-phosphino)xanthene (12 mg, 0.020 mmol), $Cs_2CO_3$ (0.13 g, 0.40 mmol), and dioxane (0.67 mL) were added to a vial with a stir bar and septa cap. The vial was sparged with $N_2$ for 15 minutes before the reaction was heated to 100° C. for 19 hours. The reaction was diluted with water and extracted with DCM 3 times. The DCM layers were combined, dried with $Na_2SO_4$, filtered, and concentrated. The residue was purified via flash chromatography (silica, 0-20% MeOH/DCM with 2% $NH_4OH$) to yield tert-butyl (1R,5S)-3-(7-(5-fluoronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate as an orange oil (6.9 mg, 11%). LCMS (MM-ES+APCI, Pos): m/z 603.3 (M+H).

Step B. 4-((1R,5S)-3,8-diazabicyclo[3.2.1]octan-3-yl)-7-(5-fluoronaphthalen-1-yl)-2-(((S)-1-methylpyrrolidin-2-yl)methoxy)-5,6,7,8-tetrahydropyrido[3,4-d]. Tert-butyl (1R,5S)-3-(7-(5-fluoronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (6.9 mg, 0.011 mmol) was added to a round bottom flask with a stir bar. DCM (1.0 mL) and TFA (0.5 mL) were added. The reaction was stirred at room temperature for 30 minutes before being concentrated to dryness. The residue was purified via a reverse phase column (C18, 0-80% MeCN/water with 0.1% TFA). The fractions containing the product were combined, frozen, and lyophilized to yield 4-((1R,5S)-3,8-diazabicyclo[3.2.1]octan-3-yl)-7-(5-fluoronaphthalen-1-yl)-2-(((S)-1-methylpyrrolidin-2-yl)methoxy)-5,6,7,8-tetrahydropyrido[3,4-d]pyrimidine as the TFA salt (3.2 mg, 40%). LCMS (MM-ES+APCI, Pos): m/z 503.3 (M+H).

Example 17

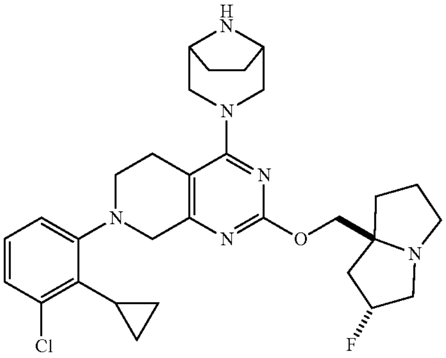

4-((1R,5S)-3,8-diazabicyclo[3.2.1]octan-3-yl)-7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidine (racemic, trans)

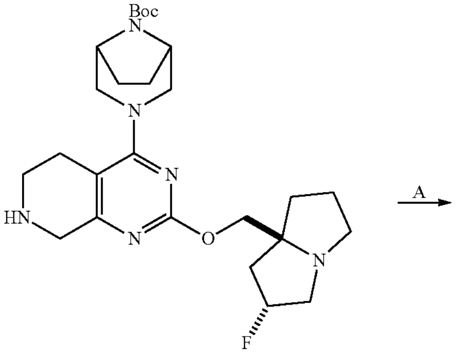

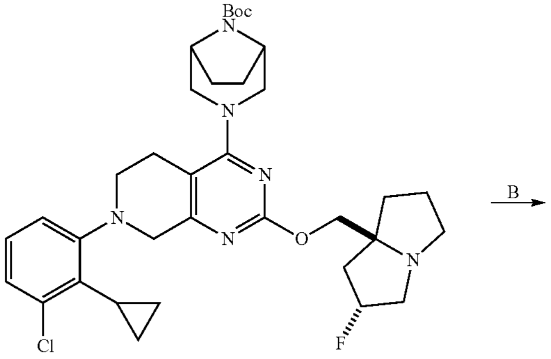

-continued

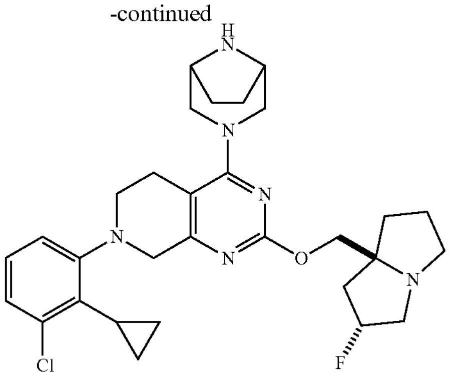

Step A. tert-butyl (1R,5S)-3-(7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (25 mg, 0.05 mmol), tris(dibenzylideneacetone)dipalladium (0) (7 mg, 0.008 mmol), racemic-2,2'-bis(diphenylphosphino)-1,1'-binaphthyl (10 mg, 0.016 mmol), and toluene (0.15 mL) were added to a vial with a stir bar and septa cap. The vial was sparged with $N_2$ for 10 minutes. The vial was heated to 100° C. for 15 minutes before sodium tert-butoxide (10 mg, 0.1 mmol) was added followed by 1-bromo-3-chloro-2-cyclopropylbenzene (23 mg, 0.1 mmol). The vial was degassed and purged with $N_2$ 3 times and the reaction was heated to 100° C. for 2 hours. The reaction mixture was filtered through Celite with DCM washing and the filtrate was concentrated. The residue was purified via a reverse phase column (C18, 0-80% MeCN/water with 0.1% TFA). The fractions containing the product were combined and washed with saturated $Na_2CO_3$. The DCM layer was dried with $Na_2SO_4$, filtered, and concentrated to yield tert-butyl (1R,5S)-3-(7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) as an orange oil (17 mg, 52%). LCMS (MM-ES+APCI, Pos): m/z 653.3 (M+H).

Step B. 4-((1R,5S)-3,8-diazabicyclo[3.2.1]octan-3-yl)-7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidine (racemic, trans). Tert-butyl (1R,5S)-3-(7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (17 mg, 0.026 mmol) was added to a round bottom flask with a stir bar. DCM (1.0 mL) was added followed by TFA (0.5 mL). The reaction was stirred at room temperature for 1 hour before being concentrated. The residue was purified via a reverse phase column (C18, 0-80% MeCN/water with 0.1% TFA). The fractions containing the product were combined, frozen, and lyophilized. The acid salt was passed through two PL-HCO3 ME Resin plugs with methanol and concentrated to yield 4-((1R,5S)-3,8-diazabicyclo[3.2.1]octan-3-yl)-7-(3-chloro-2-cyclopropylphenyl)-2-((2-fluorotetrahydro-1H-pyrrolizin-7a(5H)-yl)methoxy)-5,6,7,8-tetrahydropyrido[3,4-d]pyrimidine (racemic, trans) as a colorless oil (8.5 mg, 59%). LCMS (MM-ES+APCI, Pos): m/z 553.3 (M+H).

Example 18

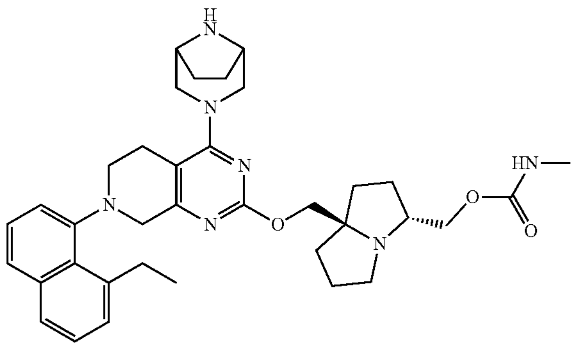 [SMILES: CCc1cccc2cccc(N3CCc4c(nc(OC[C@]56CCCN5[C@@H](COC(=O)NC)CC6)nc4N4CC5CCC(C4)N5)C3)c12]

((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate

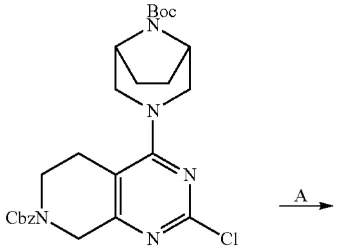

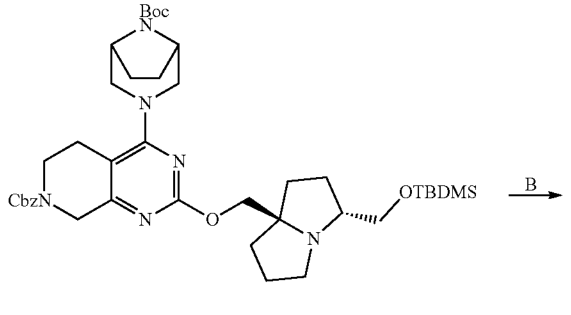

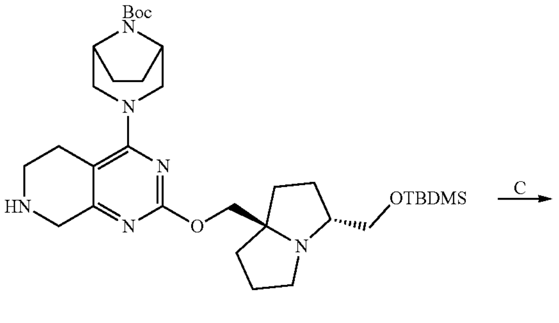

-continued

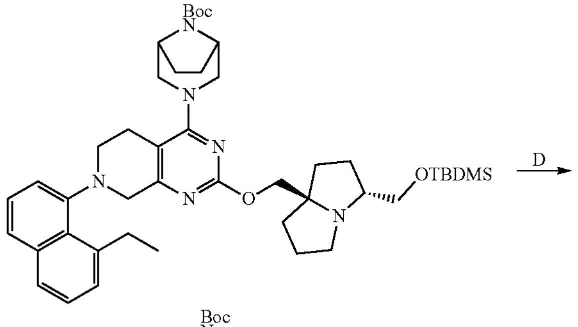

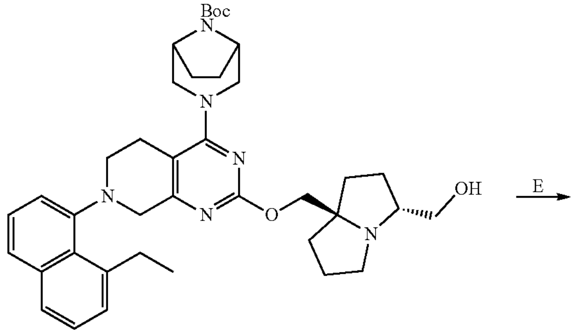

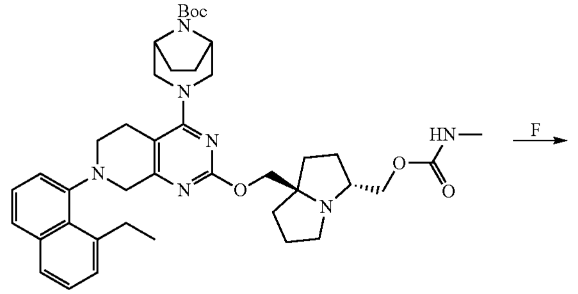

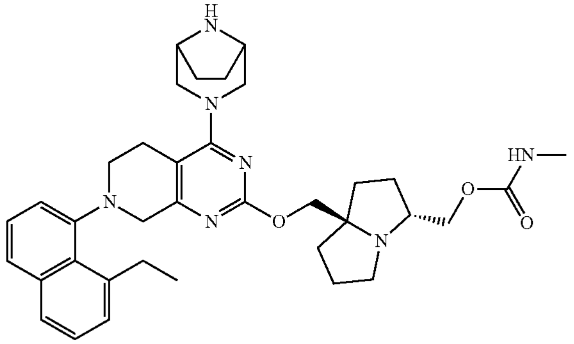

Step A. benzyl 4-((1R,5S)-8-(tert-butoxycarbonyl)-3,8-diazabicyclo[3.2.1]octan-3-yl)-2-(((3R,7aR)-3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate. Benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.50 g, 0.97 mmol), ((3R,7aR)-3-(((tert-butyldimethylsilyl)oxy)methyl)tetrahydro-1H-pyrrolizin-7a(5H)-yl)methanol (0.28 g, 0.97 mmol), BINAP (0.12 g, 0.19 mmol), $Cs_2CO_3$ (0.95 mg, 2.9 mmol), and $Pd(OAc)_2$ (22 mg, 0.097 mmol) were added to a vial with a stir bar and septa cap. The vial was degassed and purged with $N_2$ 3 times before dry toluene (5 mL) was added. The vial was sparged with $N_2$ for 15 minutes before the reaction was heated to 100° C. for 6 hours. Additional $Pd(OAc)_2$ (22 mg, 0.097)

was added and the vial was sparged with $N_2$ for 15 minutes. The reaction was heated to 100° C. overnight. The reaction was diluted with water and extracted with DCM 3 times. The DCM layers were combined, dried with $Na_2SO_4$, filtered, and concentrated. The residue was purified via flash chromatography (silica, 0-20% MeOH/DCM) to yield benzyl 4-((1R,5S)-8-(tert-butoxycarbonyl)-3,8-diazabicyclo[3.2.1]octan-3-yl)-2-(((3R,7aR)-3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate as a pale orange solid (0.41 g, 55%). LCMS (MM-ES+APCI, Pos): m/z 763.5 (M+H).

Step B. tert-butyl (1R,5S)-3-(2-(((3R,7aR)-3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Benzyl 4-((1R,5S)-8-(tert-butoxycarbonyl)-3,8-diazabicyclo[3.2.1]octan-3-yl)-2-(((3R,7aR)-3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (0.41 g, 0.53 mmol) and MeOH (6 mL) were added to a round bottom flask. The flask was sparged with $N_2$ for 15 minutes before 20% $Pd(OH)_2$ on carbon (50% water) (74 mg, 0.11 mmol) was added in one portion. The round bottom flask was stirred at room temperature under a $H_2$ atmosphere for 2 hours. The reaction mixture was filtered through Celite with MeOH and the filtrate was concentrated to yield tert-butyl (1R,5S)-3-(2-(((3R,7aR)-3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.31 g, 95%). LCMS (MM-ES+APCI, Pos): m/z 629.5 (M+H).

Step C. tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((3R,7aR)-3-(((tert-butyldimethylsilyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.31 g, 0.50 mmol), 1-bromo-8-ethylnaphthalene (0.18 g, 0.75 mmol), tris(dibenzylideneacetone)dipalladium (0) (46 mg, 0.050), 9,9-dimethyl-4,5-bis(dipheyl-phosphino)xanthene (58 mg, 0.10 mmol), $Cs_2CO_3$ (0.66 g, 2.0 mmol), and dioxane (4 mL) were added to a vial with a stir bar and septa cap. The vial was sparged with $N_2$ for 15 minutes before the reaction was heated to 100° C. for 23 hours. The reaction was diluted with water and extracted with DCM 3 times. The DCM layers were combined, dried with $Na_2SO_4$, filtered, and concentrated. The residue was purified by flash chromatography (silica, 0-20% MeOH/DCM) to yield tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate as a brown solid (0.12 g, 29%). LCMS (MM-ES+APCI, Pos): m/z 783.5 (M+H).

Step D. tert-butyl (1R,5S)-3-(7-(8-ethylnaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate (0.12 g, 0.15 mmol) was added to a vial with a stir bar and septa cap. The vial was degassed and purged with $N_2$ 3 times before dry THF (0.7 mL) was added. The vial was cooled to 0° C. and 1 M TBAF in THF (0.22 mL, 0.22 mmol) was added. The reaction was warmed to room temperature and stirred for 1.5 hours. The reaction was diluted with water and extracted with DCM 3 times. The DCM layers were combined, dried with $Na_2SO_4$, filtered, and concentrated. The residue was purified by flash chromatography (silica, 0-20% MeOH/DCM) to yield tert-butyl (1R,5S)-3-(7-(8-ethylnaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a tan solid (38 mg, 38%). LCMS (MM-ES+APCI, Pos): m/z 669.5 (M+H).

Step E. tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. tert-butyl (1R,5S)-3-(7-(8-ethylnaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (38 mg, 0.057 mmol) was added to a vial with a stir bar and septa cap. The vial was degassed and purged with $N_2$ 3 times before THF (1 mL) and triethylamine (16 μL, 0.11 mmol) were added. 4-Nitrophenyl carbonochloridate (13 mg, 0.068 mmol) was added in one portion as a solid. The reaction was stirred at room temperature for 30 minutes before 2.0 M methylamine in THF (0.43 mL) was added dropwise. The reaction was stirred at room temperature for 1 hour before being concentrated to dryness. The residue was purified by flash chromatography (silica, 0-20% MeOH/DCM) to yield tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (22 mg, 54%). LCMS (MM-ES+APCI, Pos): m/z 726.4 (M+H).

Step F. ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate. Tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (22 mg, 0.031 mmol) was added to a round bottom flask with a stir bar. DCM (1 mL) and TFA (0.5 mL) were added next. The reaction was stirred at room temperature for 30 minutes before being concentrated to dryness. The residue was purified via a reverse phase column (C18, 0-80% MeCN/water with 0.1% TFA). The fractions containing the product were combined, frozen, and lyophilized. The product was passed through two PL-HCO3 ME Resin plugs with methanol and concentrated to yield ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate as a white solid (10 mg, 50%). LCMS (MM-ES+APCI, Pos): m/z 626.4 (M+H).

Example 19

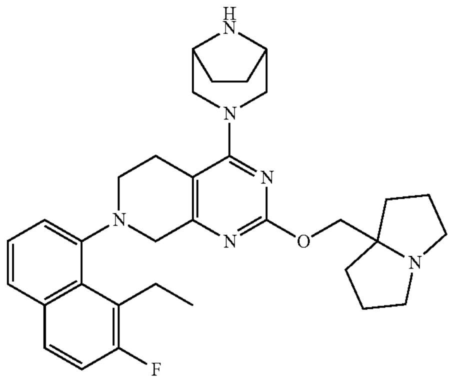 [SMILES: CCc1c(F)ccc2cccc(N3CCc4c(nc(OCC56CCCN5CCC6)nc4N4CC5CCC(C4)N5)C3)c12]

4-((1R,5S)-3,8-diazabicyclo[3.2.1]octan-3-yl)-7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidine

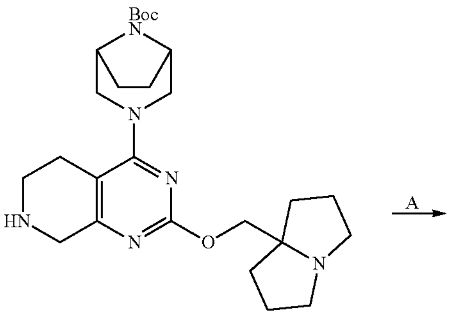

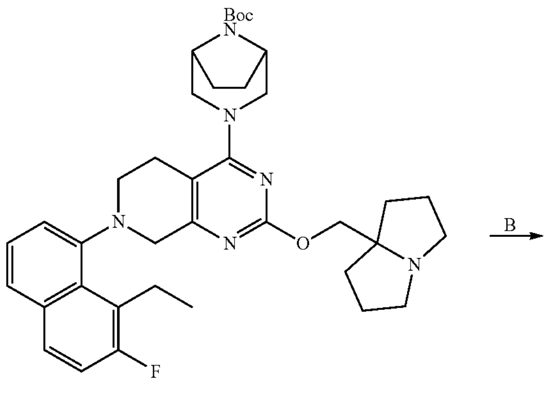

-continued

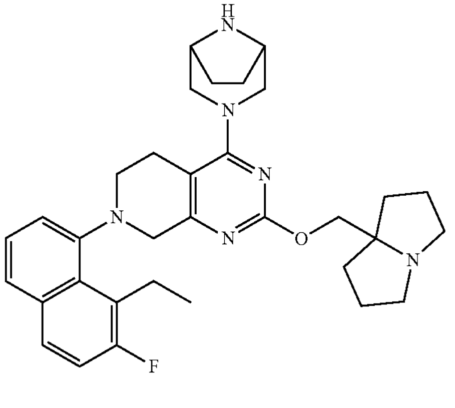

Step A. tert-butyl (1R,5S)-3-(7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (48 mg, 0.1 mmol), 8-ethyl-7-fluoronaphthalen-1-yl trifluoromethanesulfonate (48 mg, 0.15 mmol), tris(dibenzylideneacetone) dipalladium (0) (9 mg, 0.01 mmol), 9,9-dimethyl-4,5-bis(diphenyl-phosphino)xanthene (11 mg, 0.02 mmol), $Cs_2CO_3$ (0.13 g, 0.40 mmol), and dioxane (0.7 mL) were added to a vial with a stir bar and septa cap. The vial was sparged with $N_2$ for 15 minutes before the reaction was heated to 100° C. for 7.5 hours. The reaction was diluted with water and extracted with DCM 3 times. The DCM layers were combined, dried with $Na_2SO_4$, filtered, and concentrated. The residue was purified by flash chromatography (silica, 0-20% MeOH/DCM) to yield tert-butyl (1R,5S)-3-(7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a colorless oil (30 mg, 46%). LCMS (MM-ES+APCI, Pos): m/z 657.4 (M+H).

Step B. 4-((1R,5S)-3,8-diazabicyclo[3.2.1]octan-3-yl)-7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidine. Tert-butyl (1R,5S)-3-(7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (30 mg, 0.046 mmol) was added to a round bottom flask with a stir bar. DCM (1.0 mL) and TFA (0.5 mL) were added. The reaction was stirred at room temperature for 30 minutes before being concentrated to dryness. The residue was purified via a reverse phase column (C18, 0-80% MeCN/water with 0.1% TFA). The fractions containing the product were combined, frozen, and lyophilized. The acid salt was passed through two PL-HCO3 ME Resin plugs with MeOH and concentrated to yield 4-((1R,5S)-3,8-diazabicyclo[3.2.1]octan-3-yl)-7-(8-ethyl-7-fluoronaphthalen-1-yl)-2-((tetrahydro-1H-pyrrolizin-7a(5H)-yl)methoxy)-5,6,7,8-tetrahydropyrido[3,4-d]pyrimidine as a white solid (15 mg, 61%). LCMS (MM-ES+APCI, Pos): m/z 557.3 (M+H).

Example 20

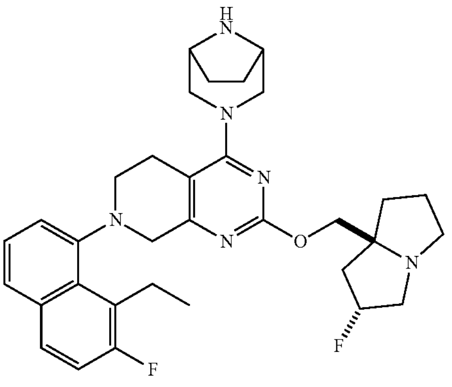

4-((1R,5S)-3,8-diazabicyclo[3.2.1]octan-3-yl)-7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans)

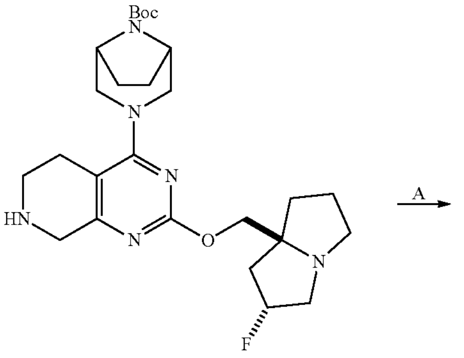

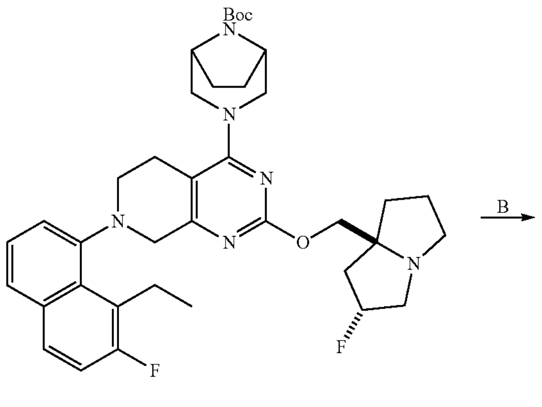

-continued

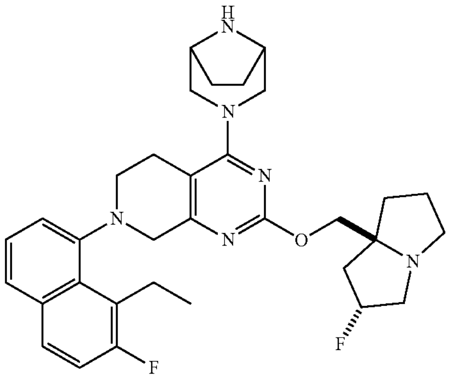

Step A. tert-butyl (1R,5S)-3-(7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). Tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (25 mg, 0.05 mmol), 8-ethyl-7-fluoronaphthalen-1-yl trifluoromethanesulfonate (24 mg, 0.075 mmol), tris(dibenzylideneacetone)dipalladium (0) (4 mg, 0.005 mmol), 9,9-dimethyl-4,5-bis(dipheyl-phosphino) xanthene (6 mg, 0.01 mmol), $Cs_2CO_3$ (65 mg, 0.2 mmol), and dioxane (0.33 mL) were added to a vial with a stir bar and septa cap. The vial was degassed with $N_2$ for 15 minutes before the reaction was heated to 100° C. for 7.5 hours. The reaction was diluted with water and extracted with DCM 3 times. The DCM layers were combined, dried with $Na_2SO_4$, filtered, and concentrated. The residue was purified by flash chromatography (silica, 0-20% MeOH/DCM) to yield tert-butyl (1R,5S)-3-(7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) as a colorless oil (21 mg, 62%). LCMS (MM-ES+APCI, Pos): m/z 675.4 (M+H).

Step B. 4-((1R,5S)-3,8-diazabicyclo[3.2.1]octan-3-yl)-7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans). Tert-butyl (1R,5S)-3-(7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (21 mg, 0.031 mmol) was added to a round bottom flask with a stir bar. DCM (1.0 mL) and TFA (0.5 mL) were added next. The reaction was stirred at room temperature for 30 minutes before being concentrated to dryness. The residue was purified via a reverse phase column (0-80% MeCN/water with 0.1% TFA). The fractions containing the product were combined, frozen, and lyophilized. The acid salt was passed through two PL-HCO3 ME Resin plugs with methanol and concentrated to yield 4-((1R,5S)-3,8-diazabicyclo[3.2.1]octan-3-yl)-7-(8-ethyl-7-fluoronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans) as a white solid (9.2 mg, 49%). LCMS (MM-ES+APCI, Pos): m/z 575.4 (M+H).

Example 21

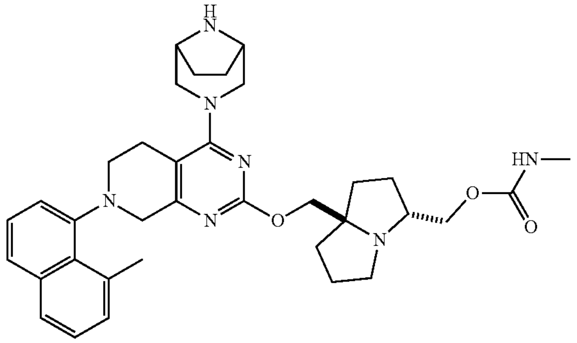

(7a-(((4-((1R,5S)-3,8-diazabicyclo[3.2.1]octan-3-yl)-7-(8-methylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers)

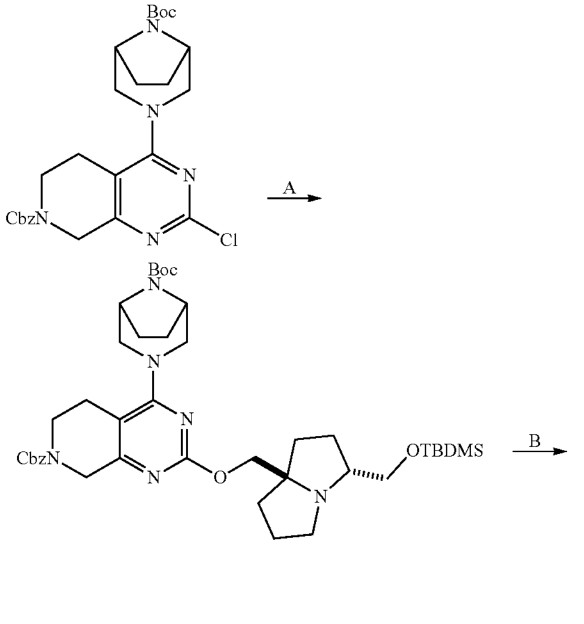

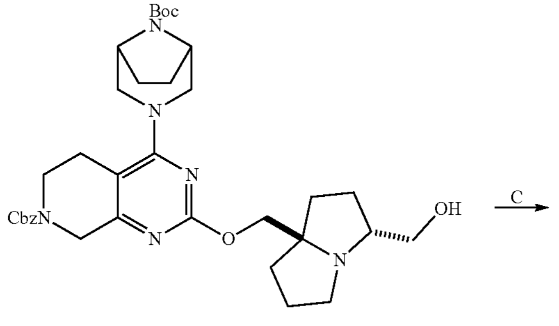

-continued

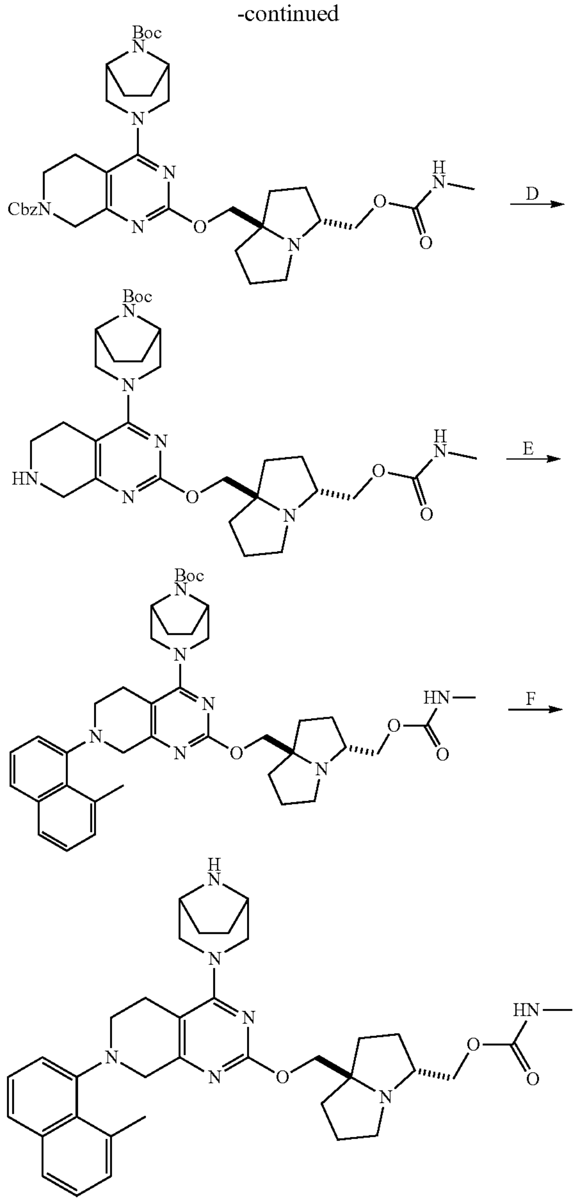

Step A. benzyl 4-((1R,5S)-8-(tert-butoxycarbonyl)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers). Benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (1.5 g, 3.0 mmol), (3-(((tert-butyldimethylsilyl)oxy)methyl)tetrahydro-1H-pyrrolizin-7a(5H)-yl)methanol (trans enantiomers) (1.1 g, 3.9 mmol), BINAP (0.37 g, 0.59 mmol), $Cs_2CO_3$ (2.9 g, 8.9 mmol), and $Pd(OAc)_2$ (67 mg, 0.30 mmol) were added to a vial with a stir bar and septa cap. The vial was degassed and purged with $N_2$ 3 times before dry toluene (15 mL) was added. The vial was sparged with $N_2$ for 15 minutes and the reaction was heated to 100° C. for 22 hours. The reaction was diluted with water and extracted with DCM 3 times. The DCM layers were combined, dried with $Na_2SO_4$, filtered, and concentrated. The residue was purified twice by flash chromatography (silica, 0-8% MeOH in DCM) to yield benzyl 4-((1R,5S)-8-(tert-butoxycarbonyl)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) as a light tan solid (1.2 g, 54%). LCMS (MM-ES+APCI, Pos): m/z 763.4 (M+H).

Step B. benzyl 4-((1R,5S)-8-(tert-butoxycarbonyl)-3,8-diazabicyclo[3.2.1]octan-3-yl)-2-((3-(hydroxymethyl)tetrahydro-1H-pyrrolizin-7a(5H)-yl)methoxy)-5,8-dihydropyrido[3,4-d]pyrimidine-7(6H)-carboxylate (trans enantiomers). Benzyl 4-((1R,5S)-8-(tert-butoxycarbonyl)-3,8-diazabicyclo[3.2.1]octan-3-yl)-2-((3-(((tert-butyldimethylsilyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) (1.2 g, 1.6 mmol) was added to a vial with a stir bar and septa cap. The vial was degassed and purged with $N_2$ 3 times before dry THE (8 mL) was added. The vial was cooled to 0° C. and 1M TBAF in THF (4.0 mL, 4.0 mmol) was added. The reaction was warmed to room temperature and stirred for 22 hours. The reaction was diluted with water and extracted with DCM 3 times. The DCM layers were combined, dried with $Na_2SO_4$, filtered, and concentrated. The residue was purified by flash chromatography (silica, 0-20% MeOH in DCM with 2% $NH_4OH$) to yield benzyl 4-((1R,5S)-8-(tert-butoxycarbonyl)-3,8-diazabicyclo[3.2.1]octan-3-yl)-2-((3-(hydroxymethyl)tetrahydro-1H-pyrrolizin-7a(5H)-yl)methoxy)-5,8-dihydropyrido[3,4-d]pyrimidine-7(6H)-carboxylate (trans enantiomers) as a white solid (0.93 g, 89%). LCMS (MM-ES+APCI, Pos): m/z 649.3 (M+H).

Step C. benzyl 4-((1R,5S)-8-(tert-butoxycarbonyl)-3,8-diazabicyclo[3.2.1]octan-3-yl)-2-((3-(((methylcarbamoyl)oxy)methyl)tetrahydro-1H-pyrrolizin-7a(5H)-yl)methoxy)-5,8-dihydropyrido[3,4-d]pyrimidine-7(6H)-carboxylate (trans enantiomers). Benzyl 4-((1R,5S)-8-(tert-butoxycarbonyl)-3,8-diazabicyclo[3.2.1]octan-3-yl)-2-((3-(hydroxymethyl)tetrahydro-1H-pyrrolizin-7a(5H)-yl)methoxy)-5,8-dihydropyrido[3,4-d]pyrimidine-7(6H)-carboxylate (trans enantiomers) (0.93 g, 1.4 mmol) was added to a round bottom flask with a stir bar and septa. The vial was degassed and purged with $N_2$ 3 times before THE (14 mL) and triethylamine (0.4 mL, 2.9 mmol) were added. 4-Nitrophenyl carbonochloridate (0.35 g, 1.7 mmol) was added in one portion as a solid. The reaction was stirred at room temperature for 30 minutes before additional triethylamine (0.20 mL, 1.4 mmol) and 4-nitrophenyl carbonochloridate (0.17 mL, 0.86 mmol) were added. The reaction was stirred for 30 minutes and 2.0 M methylamine in THE (5.0 mL, 10 mmol) was added dropwise. The reaction was stirred at room temperature for 1 hour before being diluted with water and extracted with DCM 3 times. The DCM layers were combined, dried with $Na_2SO_4$, filtered, and concentrated. The residue was purified by flash chromatography (silica, 0-15% MeOH in DCM with 2% $NH_4OH$) to yield benzyl 4-((1R,5S)-8-(tert-butoxycarbonyl)-3,8-diazabicyclo[3.2.1]octan-3-yl)-2-((3-(((methylcarbamoyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) as a colorless oil (0.89 g, 88%). LCMS (MM-ES+APCI, Pos): m/z 706.5 (M+H).

Step D. tert-butyl (1R,5S)-3-(2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers). Benzyl 4-((1R,5S)-8-(tert-butoxycarbonyl)-3,8-diazabicyclo[3.2.1]octan-3-yl)-2-((3-(((methylcarbamoyl)oxy)methyl)tetrahydro-1H-pyrrolizin-7a(5H)-yl)methoxy)-5,8-dihydropyrido[3,4-d]pyrimidine-7(6H)-carboxylate (trans enantiomers) (0.89 g, 1.3 mmol) and MeOH (13 mL) were added to a round bottom flask which was sparged with $N_2$ for 15 minutes. 20% $Pd(OH)_2$ on carbon (50% water) (0.18 g, 0.25 mmol) was added in one portion. The reaction was stirred at room temperature under a $H_2$ atmosphere overnight. The reaction mixture was filtered through Celite and the filtrate was concentrated to yield tert-butyl (1R,5S)-3-(2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) (0.63 g, 87%). LCMS (MM-ES+APCI, Pos): m/z 572.4 (M+H).

Step E. tert-butyl (1R,5S)-3-(2-((3-(((methylcarbamoyl)oxy)methyl)tetrahydro-1H-pyrrolizin-7a(5H)-yl)methoxy)-7-(8-methylnaphthalen-1-yl)-5,6,7,8-tetrahydropyrido[3,4-d]pyrimidin-4-yl)-3,8-diazabicyclo[3.2.1]octane-8-carboxylate (trans enantiomers). Tert-butyl (1R,5S)-3-(2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (trans enantiomers) (35 mg, 0.061 mmol), 1-bromo-8-methylnaphthalene (20 mg, 0.092 mmol), tris(dibenzylideneacetone)dipalladium (0) (5.6 mg, 0.006 mmol), 9,9-dimethyl-4,5-bis(dipheyl-phosphino)xanthene (7.1 mg, 0.012 mmol), and $Cs_2CO_3$ (79 mg, 0.25 mmol) were added to a vial with a stir bar and septa cap. The vial was degassed and purged with $N_2$ 3 times before dioxane was added. The vial was sparged with $N_2$ for 15 minutes before the reaction was heated to 100° C. overnight. Additional tris(dibenzylideneacetone)dipalladium (0) (11 mg, 0.012 mmol), 9,9-dimethyl-4,5-bis(dipheyl-phosphino)xanthene (14 mg, 0.024 mmol), and dioxane (0.4 mL) were added. The vial was sparged with $N_2$ for 15 minutes before the reaction was heated to 110° C. overnight. The reaction was diluted with water and extracted with DCM 3 times. The DCM layers were combined, dried with $Na_2SO_4$, filtered, and concentrated. The residue was purified by flash chromatography (silica, 0-20% MeOH in DCM) to yield tert-butyl (1R,5S)-3-(2-((3-(((methylcarbamoyl)oxy)methyl)tetrahydro-1H-pyrrolizin-7a(5H)-yl)methoxy)-7-(8-methylnaphthalen-1-yl)-5,6,7,8-tetrahydropyrido[3,4-d]pyrimidin-4-yl)-3,8-diazabicyclo[3.2.1]octane-8-carboxylate (trans enantiomers) as an orange oil (11 mg, 24%). LCMS (MM-ES+APCI, Pos): m/z 712.4 (M+H).

Step F. (7a-(((4-((1R,5S)-3,8-diazabicyclo[3.2.1]octan-3-yl)-7-(8-methylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers). Tert-butyl (1R,5S)-3-(2-((3-(((methylcarbamoyl)oxy)methyl)tetrahydro-1H-pyrrolizin-7a(5H)-yl)methoxy)-7-(8-methylnaphthalen-1-yl)-5,6,7,8-tetrahydropyrido[3,4-d]pyrimidin-4-yl)-3,8-diazabicyclo[3.2.1]octane-8-carboxylate (trans enantiomers) (11 mg, 0.015 mmol) was added to a vial with a stir bar. DCM (1.0 mL) was added followed by TFA (0.5 mL). The reaction was stirred at room temperature for 30 minutes before being concentrated to dryness. The residue was purified via a reverse phase column (C18, 0-80% MeCN in water with 0.1% TFA). The fractions containing the product were combined, frozen, and lyophilized. The product was passed through a PL-HCO3 ME Resin plug with methanol and concentrated to yield (7a-(((4-((1R,5S)-3,8-diazabicyclo[3.2.1]octan-3-yl)-7-(8-methylnaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers) as a tan solid (2.1 mg, 21%). LCMS (MM-ES+APCI, Pos): m/z 612.4 (M+H).

Example 22

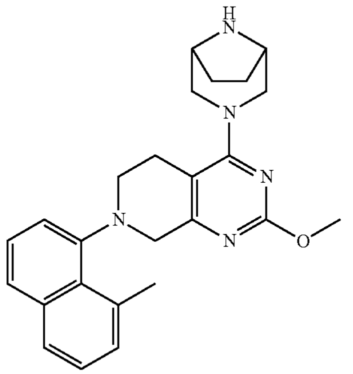 [SMILES: COc1nc2c(c(N3CC4CCC(C3)N4)n1)CCN(c1cccc3cccc(C)c13)C2]

4-((1R,5S)-3,8-diazabicyclo[3.2.1]octan-3-yl)-2-methoxy-7-(8-methylnaphthalen-1-yl)-5,6,7,8-tetrahydropyrido[3,4-d]pyrimidine

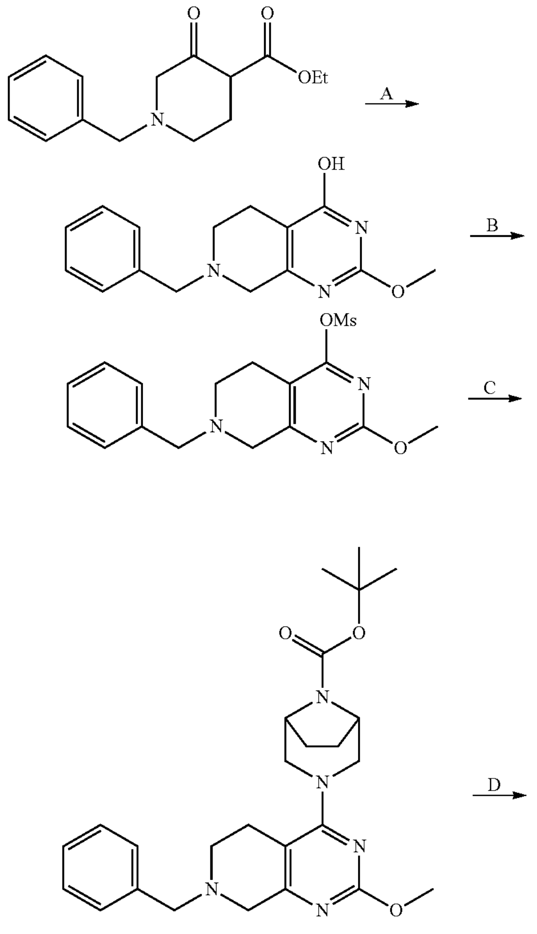

-continued

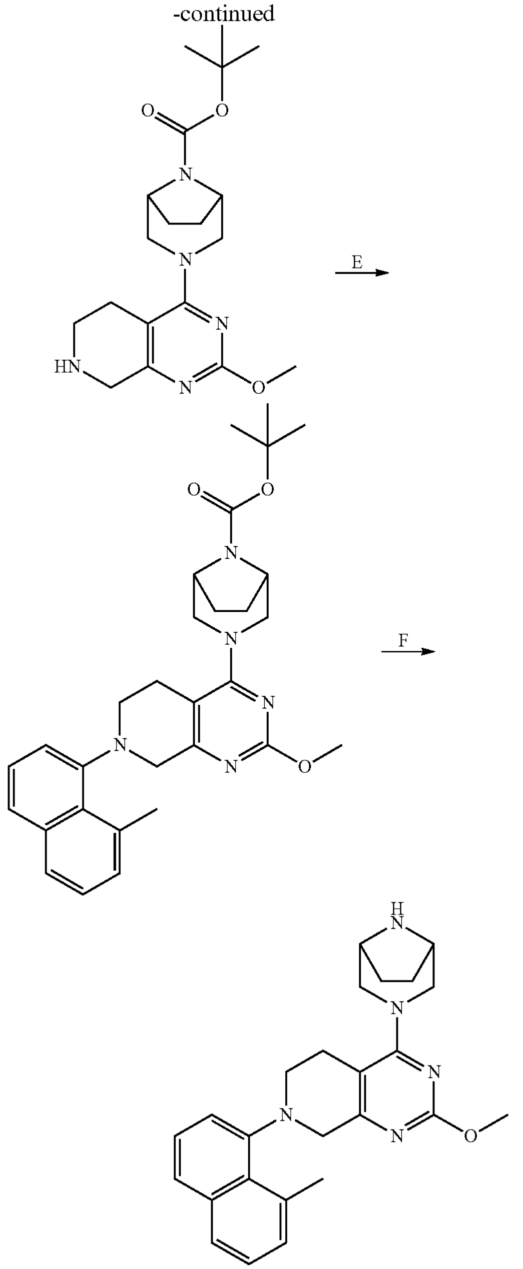

Step A. 7-benzyl-2-methoxy-5,6,7,8-tetrahydropyrido[3,4-d]pyrimidin-4-ol. To a solution of ethyl 1-benzyl-3-oxopiperidine-4-carboxylate hydrochloride (1.0 g, 3.4 mmol) in EtOH (6 mL) was added methyl carbamimidate hydrochloride (0.48 g, 4.3 mmol) followed by a 1 M solution of $K_2CO_3$ (4.5 mL, 4.4 mmol). The reaction mixture was stirred at room temperature for 4 days. The reaction was filtered with DCM and concentrated. The aqueous mixture was extracted with DCM, dried with $MgSO_4$, and concentrated in vacuo. The residue was purified via flash chromatography (silica, 0-100% EtOAc in hexanes) to yield 7-benzyl-2-methoxy-5,6,7,8-tetrahydropyrido[3,4-d]pyrimidin-4-ol as a beige powder (99 mg, 11%). LCMS (MM-ES+APCI, Pos): m/z 272.1 (M+H).

Step B. 7-benzyl-2-methoxy-5,6,7,8-tetrahydropyrido[3,4-d]pyrimidin-4-yl methanesulfonate. To a solution of 7-benzyl-2-methoxy-5,6,7,8-tetrahydropyrido[3,4-d]pyrimidin-4-ol (0.24 g, 0.87 mmol) in DCM (5 mL) were added triethylamine (0.30 mL, 2.2 mmol) and methanesulfonyl chloride (0.10 mL, 1.3 mmol). The mixture was stirred at room temperature for 1 hour. The reaction mixture was diluted with saturated $NaHCO_3$ (50 mL) and washed with EtOAc (3×20 mL). The combined organic layers were washed with brine (15 mL), dried over $Na_2SO_4$, filtered, and concentrated in vacuo to yield 7-benzyl-2-methoxy-5,6,7,8-tetrahydropyrido[3,4-d]pyrimidin-4-yl methanesulfonate as an orange oil (0.30 g, 99%). LCMS (MM-ES+APCI, Pos): m/z 350.1 (M+H).

Step C. tert-butyl (1R,5S)-3-(7-benzyl-2-methoxy-5,6,7,8-tetrahydropyrido[3,4-d]pyrimidin-4-yl)-3,8-diazabicyclo[3.2.1]octane-8-carboxylate. To a solution of 7-benzyl-2-methoxy-5,6,7,8-tetrahydropyrido[3,4-d]pyrimidin-4-yl methanesulfonate (0.30 g, 0.86 mmol) in THE (2.5 mL) was added tert-butyl (1R,5S)-3,8-diazabicyclo[3.2.1]octane-8-carboxylate (0.37 g, 1.7 mmol). The solution was heated to reflux for 16 hours. The mixture was diluted with EtOAc (10 mL) and saturated $NaHCO_3$ (20 mL). The aqueous layer was extracted with EtOAc (2×10 mL). The combined organic layers were washed with brine (10 mL), dried over $Na_2SO_4$, filtered, and concentrated in vacuo. The residue was purified via flash chromatography (silica, 0-7% MeOH in DCM) to yield tert-butyl (1R,5S)-3-(7-benzyl-2-methoxy-5,6,7,8-tetrahydropyrido[3,4-d]pyrimidin-4-yl)-3,8-diazabicyclo[3.2.1]octane-8-carboxylate as an orange foam (0.16 g, 39%). LCMS (MM-ES+APCI, Pos): m/z 466.2 (M+H).

Step D. tert-butyl (1R,5S)-3-(2-methoxy-5,6,7,8-tetrahydropyrido[3,4-d]pyrimidin-4-yl)-3,8-diazabicyclo[3.2.1]octane-8-carboxylate. To a mixture of tert-butyl (1R,5S)-3-(7-benzyl-2-methoxy-5,6,7,8-tetrahydropyrido[3,4-d]pyrimidin-4-yl)-3,8-diazabicyclo[3.2.1]octane-8-carboxylate (0.16 g, 0.34 mmol) and 20% palladium hydroxide on carbon (76 mg, 0.11 mmol) under nitrogen was added methanol (4 mL). The mixture was sparged with nitrogen for 5 minutes. The mixture was stirred under hydrogen for 16 hours and was filtered through G/F paper. The filter paper was washed with MeOH, and the filtrate concentrated in vacuo to yield tert-butyl (1R,5S)-3-(2-methoxy-5,6,7,8-tetrahydropyrido[3,4-d]pyrimidin-4-yl)-3,8-diazabicyclo[3.2.1]octane-8-carboxylate as a grey foam (0.12 g, 94%). LCMS (MM-ES+APCI, Pos): m/z 376.2 (M+H).

Step E. tert-butyl (1R,5S)-3-(2-methoxy-7-(8-methylnaphthalen-1-yl)-5,6,7,8-tetrahydropyrido[3,4-d]pyrimidin-4-yl)-3,8-diazabicyclo[3.2.1]octane-8-carboxylate. Tris(dibenzylideneacetone)dipalladium(0) (59 mg, 0.064 mmol) and 9,9-dimethyl-4,5-bis(diphenylphosphino)xanthene (74 mg, 0.13 mmol) were dissolved in 1,4-dioxane (3 mL), and purged under argon for 5 minutes. The reaction mixture was stirred at 100° C. for 15 minutes. To the reaction was added tert-butyl (1R,5S)-3-(2-methoxy-5,6,7,8-tetrahydropyrido[3,4-d]pyrimidin-4-yl)-3,8-diazabicyclo[3.2.1]octane-8-carboxylate (0.12 g, 0.32 mmol), 1-bromo-8-methylnaphthalene (0.21 g, 0.96 mmol), and cesium carbonate (0.31 g, 0.96 mmol). The reaction was stirred at 100° C. for 16 hours. The mixture was diluted with water (50 mL) and extracted with EtOAc (3×20 mL). The combined organic layers were washed with brine (30 mL), dried over $Na_2SO_4$, filtered, and concentrated in vacuo. The residue was purified via flash chromatography eluting with 0-30% EtOAc/hexanes to yield tert-butyl (1R,5S)-3-(2-methoxy-7-(8-methylnaphthalen-1-yl)-5,6,7,8-tetrahydropyrido[3,4-d]pyrimidin-4-yl)-3,8-diazabicyclo[3.2.1]octane-8-carboxylate as an orange foam (0.17 g, 103%). LCMS (MM-ES+APCI, Pos): m/z 516.3 (M+H).

Step F. 4-((1R,5S)-3,8-diazabicyclo[3.2.1]octan-3-yl)-2-methoxy-7-(8-methylnaphthalen-1-yl)-5,6,7,8-tetrahydropyrido[3,4-d]pyrimidine. To a solution of tert-butyl (1R,5S)-3-(2-methoxy-7-(8-methylnaphthalen-1-yl)-5,6,7,8-tetrahydropyrido[3,4-d]pyrimidin-4-yl)-3,8-diazabicyclo[3.2.1]octane-8-carboxylate (0.17 g, 0.33 mmol) in DCM (6.5 mL,) was added TFA (0.5 mL, 6.6 mmol). The mixture was stirred at room temperature for 3 hours. The solution was poured into a mixture of saturated bicarbonate (40 mL) and EtOAc (20 mL). The aqueous layer was washed with EtOAc (2×20 mL). The combined organic layers were washed with saturated bicarbonate (2×30 mL), brine (30 mL), dried over $Na_2SO_4$, and concentrated in vacuo. The residue was purified via flash chromatography eluting with 0-20% MeOH/DCM to yield 4-((1R,5S)-3,8-diazabicyclo[3.2.1]octan-3-yl)-2-methoxy-7-(8-methylnaphthalen-1-yl)-5,6,7,8-tetrahydropyrido[3,4-d]pyrimidine as a tan solid (59 mg, 42%). LCMS (MM-ES+APCI, Pos): m/z 416.2 (M+H).

Example 23

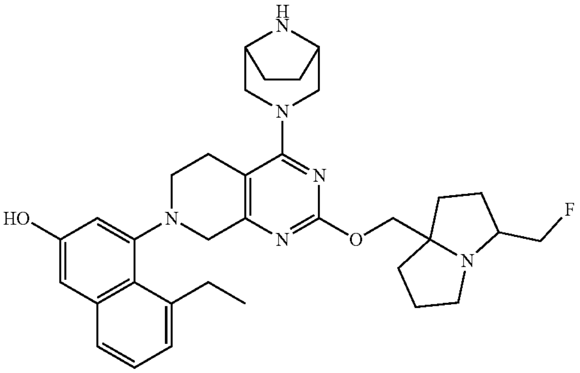 [SMILES: CCc1cccc2cc(O)cc(N3CCc4c(nc(OCC56CCCN5C(CF)CC6)nc4N4CC5CCC(C4)N5)C3)c12]

4-(4-((1R,5S)-3,8-diazabicyclo[3.2.1]octan-3-yl)-2-((3-(fluoromethyl)tetrahydro-1H-pyrrolizin-7a(5H)-yl)methoxy)-5,8-dihydropyrido[3,4-d]pyrimidin-7(6H)-yl)-5-ethylnaphthalen-2-ol (mixture or isomers)

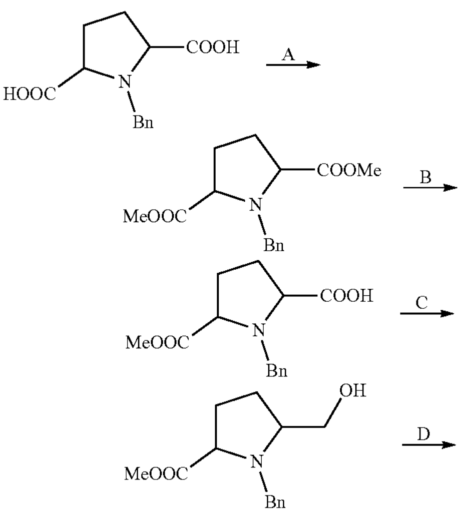

-continued

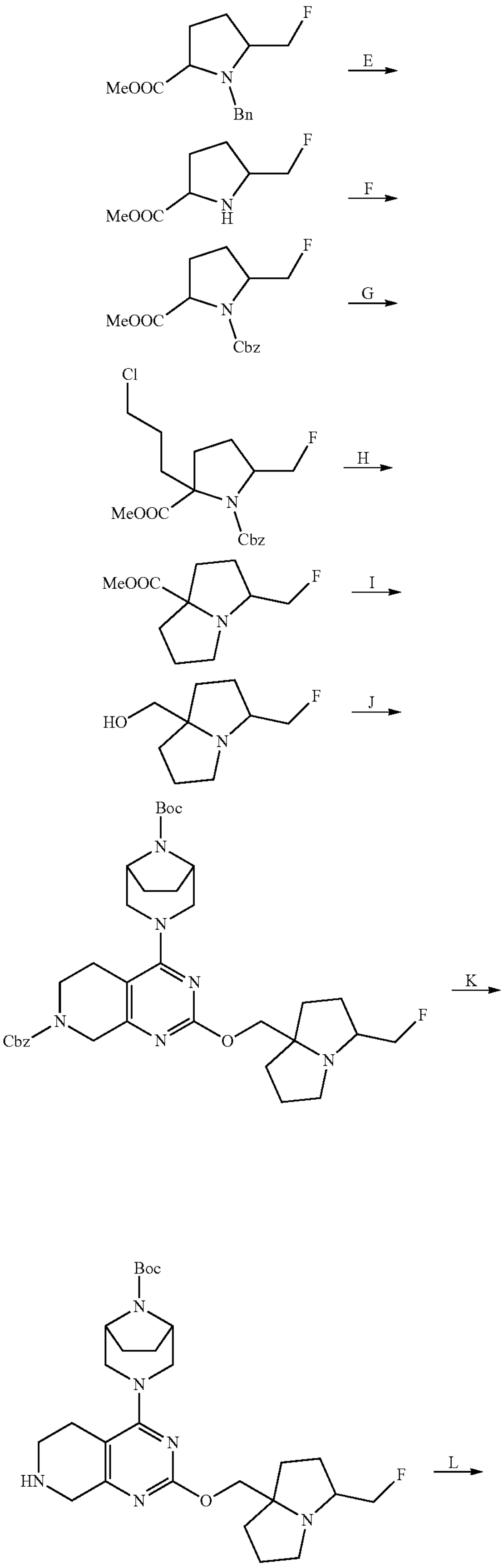

-continued

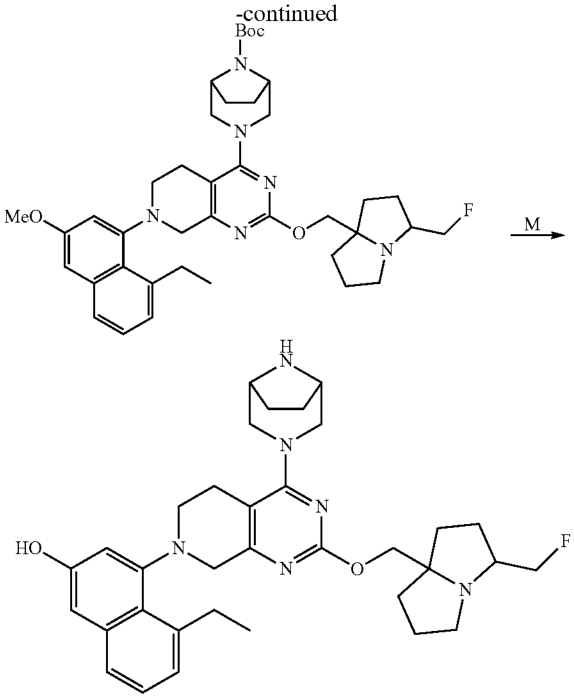

Step A. dimethyl 1-benzylpyrrolidine-2,5-dicarboxylate (mixture of isomers). To a solution of 1-benzylpyrrolidine-2,5-dicarboxylic acid hydrochloride (1.5 g, 5.2 mmol) in tetrahydrofuran (21 mL) and methanol (5 mL) at 0° C. was added (diazomethyl)trimethylsilane (13 mL, 26 mmol) and the reaction was stirred at room temperature for 45 minutes. The mixture was partitioned between dichloromethane and saturated $NaHCO_3$. The organics were washed with brine, dried with $Na_2SO_4$, filtered, concentrated, and purified by silica gel chromatography (5-95% EtOAc/hex) to give dimethyl 1-benzylpyrrolidine-2,5-dicarboxylate (mixture of isomers) (0.9 g, 62%). LCMS (MM-ES+APCI, Pos): m/z 278.1 (M+H).

Step B. 1-benzyl-5-(methoxycarbonyl)pyrrolidine-2-carboxylic acid (mixture of isomers). To a mixture of dimethyl 1-benzylpyrrolidine-2,5-dicarboxylate (mixture of isomers) (0.73 g, 2.6 mmol) in methanol (4 mL) and water (4 mL) was added 2M NaOH (1.3 mL, 2.6 mmol) and the reaction was stirred overnight. The reaction mixture was concentrated to remove the MeOH and the aqueous mixture was washed with EtOAc. The aqueous layer's pH was adjusted to 5 with 4.0 M HCl and was extracted with EtOAc. The EtOAc layer was dried with $Na_2SO_4$, filtered, and concentrated to give 1-benzyl-5-(methoxycarbonyl)pyrrolidine-2-carboxylic acid (mixture of isomers) (0.19 g, 28%). LCMS (MM-ES+APCI, Pos): m/z 264.1 (M+H).

Step C. methyl 1-benzyl-5-(hydroxymethyl)pyrrolidine-2-carboxylate (mixture of isomers). To a solution of 1-benzyl-5-(methoxycarbonyl)pyrrolidine-2-carboxylic acid (mixture of isomers) (19 mg, 0.73 mmol) in tetrahydrofuran (7 mL) at 0° C. were added triethylamine (0.11 mL, 0.80 mmol) and ethyl chloroformate (76 μL, 0.80 mmol). The reaction was stirred for 90 minutes. The reaction mixture was filtered and the filtrate was added to a suspension of sodium borohydride (0.11 g, 2.9 mmol) in water (0.4 mL). The reaction was stirred for 1 hour at 0° C. The mixture was partitioned with EtOAc. The organics were dried with $Na_2SO_4$, filtered, and concentrated to give methyl 1-benzyl- 5-(hydroxymethyl)pyrrolidine-2-carboxylate (mixture of isomers) (0.17 g, 92%). LCMS (MM-ES+APCI, Pos): m/z 250.1 (M+H).

Step D. methyl 1-benzyl-5-(fluoromethyl)pyrrolidine-2-carboxylate (mixture of isomers). To a solution of 4-(trifluoro-$\lambda^4$-sulfanyl)morpholine (37 μL, 0.31 mmol) in dichloromethane (1.5 mL) at 0° C. was added methyl 1-benzyl-5-(hydroxymethyl)pyrrolidine-2-carboxylate (0.97 g, 3.9 mmol). The reaction was slowly warmed to room temperature over 2 hours. The solution was partitioned between dichloromethane and saturated $NaHCO_3$. The organics were concentrated and purified by silica gel chromatography (5-15% EtOAc/Hex) to give methyl 1-benzyl-5-fluoropiperidine-2-carboxylate (23 mg, 44%) and methyl 1-benzyl-5-(fluoromethyl)pyrrolidine-2-carboxylate (mixture of isomers) (24 mg, 46%). LCMS (MM-ES+APCI, Pos): m/z 251.3 (M+H).

Step E. methyl 5-(fluoromethyl)pyrrolidine-2-carboxylate (mixture of isomers). A mixture of methyl 1-benzyl-5-(fluoromethyl)pyrrolidine-2-carboxylate (mixture of isomers) (15 mg, 0.060 mmol) and Pd/C Degussa type (6.4 mg, 0.006 mmol) in methanol (0.4 mL) was stirred under a balloon of hydrogen for 4 hours. The mixture was filtered and concentrated to give methyl 5-(fluoromethyl)pyrrolidine-2-carboxylate (mixture of isomers) (9 mg, 94%). LCMS (MM-ES+APCI, Pos): m/z 161.2 (M+H).

Step F. 1-benzyl 2-methyl 5-(fluoromethyl)pyrrolidine-1,2-dicarboxylate (mixture of isomers). To a solution of methyl 5-(fluoromethyl)pyrrolidine-2-carboxylate (mixture of isomers) (35 mg, 0.22 mmol) and triethylamine (0.12 mL, 0.87 mmol) in dichloromethane (1 mL) was added benzyl carbonochloridate (61 μL, 0.43 mmol). The reaction was stirred for 1 hour. The solution was partitioned between dichloromethane and saturated $NaHCO_3$. The organics were washed with brine, dried with $Na_2SO_4$, filtered, concentrated, and purified by silica gel chromatography (5-95% EtOAc/Hex) to give 1-benzyl 2-methyl 5-(fluoromethyl) pyrrolidine-1,2-dicarboxylate (mixture of isomers) (61 mg, 95%). LCMS (MM-ES+APCI, Pos): m/z 296.2 (M+H).

Step G. 1-benzyl 2-methyl 2-(3-chloropropyl)-5-(fluoromethyl)pyrrolidine-1,2-dicarboxylate (mixture of isomers). To a solution of 1-benzyl 2-methyl 5-(fluoromethyl) pyrrolidine-1,2-dicarboxylate (mixture of isomers) (0.11 g, 0.38 mmol) in tetrahydrofuran (2 mL) at −70° C. was added LDA (1 mL, 1.9 mmol) and stirred for 1 hour at −75° C. 1-Chloro-3-iodopropane (0.29 mL, 2.7 mmol) was added and the solution stirred for 1 hour at room temperature. The mixture was partitioned between dichloromethane and saturated $NaHCO_3$. The organics were concentrated and purified by silica gel chromatography (5-95% EtOAc/hex) to give 1-benzyl 2-methyl 2-(3-chloropropyl)-5-(fluoromethyl)pyrrolidine-1,2-dicarboxylate (mixture of isomers) (55 mg, 39%). LCMS (MM-ES+APCI, Pos): m/z 372.2 (M+H).

Step H. methyl 3-(fluoromethyl)tetrahydro-1H-pyrrolizine-7a(5H)-carboxylate (mixture of isomers). A mixture of 1-benzyl 2-methyl 2-(3-chloropropyl)-5-(fluoromethyl)pyrrolidine-1,2-dicarboxylate (mixture of isomers) (3.6 mg, 0.0097 mmol) and Pd/C Degussa (1 mg, 0.001 mmol) in methanol (0.1 mL) was stirred under a balloon of hydrogen for 3 hours. The reaction mixture was filtered and concentrated to give methyl 3-(fluoromethyl)tetrahydro-1H-pyrrolizine-7a(5H)-carboxylate (mixture of isomers) (1.8 mg, 92%). LCMS (MM-ES+APCI, Pos): m/z 202.1 (M+H).

Step I. (3-(fluoromethyl)tetrahydro-1H-pyrrolizin-7a(5H)-yl)methanol (mixture of isomers). To a solution of methyl 3-(fluoromethyl)tetrahydro-1H-pyrrolizine-7a(5H)-carboxylate (mixture of isomers) (29 mg, 0.14 mmol) in tetrahydrofuran (0.4 mL) at 0° C. was added 1M $LiAlH_4$ (0.58 mL, 0.58 mmol). The reaction stirred at 0° C. for 30 minutes and was diluted with ether (0.3 mL). The mixture was cooled to 0° C. and water (30 L) was added followed by 15% NaOH (30 L) and additional water (90 μL). The slurry was stirred at room temperature for 15 minutes. $MgSO_4$ was added and the mixture was stirred for 15 minutes. The mixture was filtered and the filtrate was evaporated under a stream of $N_2$ to give (3-(fluoromethyl)tetrahydro-1H-pyrrolizin-7a(5H)-yl)methanol (mixture of isomers) (23 mg, 92%). LCMS (MM-ES+APCI, Pos): m/z 174.1 (M+H).

Step J. benzyl 4-((1R,5S)-8-(tert-butoxycarbonyl)-3,8-diazabicyclo[3.2.1]octan-3-yl)-2-((3-(fluoromethyl)tetrahydro-1H-pyrrolizin-7a(5H)-yl)methoxy)-5,8-dihydropyrido[3,4-d]pyrimidine-7(6H)-carboxylate (mixture of isomers). A mixture of (3-(fluoromethyl)tetrahydro-1H-pyrrolizin-7a(5H)-yl)methanol (mixture of isomers) (20 mg, 0.10 mmol), benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (89 mg, 0.17 mmol), palladium(II) acetate (2.6 mg, 0.011 mmol), BINAP (14 mg, 0.023 mmol) and $Cs_2CO_3$ (0.11 g, 0.35 mmol) in dioxanes was sparged with argon and heated to 95° C. overnight in a sealed vial. The mixture was purified by silica gel chromatography (1-15% MeOH/DCM with 1% $NH_4OH$ as modifier) to give benzyl 4-((1R,5S)-8-(tert-butoxycarbonyl)-3,8-diazabicyclo[3.2.1]octan-3-yl)-2-((3-(fluoromethyl) tetrahydro-1H-pyrrolizin-7a(5H)-yl)methoxy)-5,8-dihydropyrido[3,4-d]pyrimidine-7(6H)-carboxylate (mixture of isomers) (49 mg, 65% yield). LCMS (MM-ES+APCI, Pos): m/z 651.4 (M+H).

Step K: tert-butyl (1R,5S)-3-(2-((3-(fluoromethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers). A mixture of benzyl 4-((1R,5S)-8-(tert-butoxycarbonyl)-3,8-diazabicyclo[3.2.1]octan-3-yl)-2-((3-(fluoromethyl)tetrahydro-1H-pyrrolizin-7a(5H)-yl)methoxy)-5,8-dihydropyrido[3,4-d]pyrimidine-7(6H)-carboxylate (mixture of isomers) (49 mg, 0.075 mmol) and Pd/C (10 mg) in methanol (0.8 mL) was stirred under $H_2$ for 1 hour. The mixture was filtered and concentrated to give tert-butyl (1R,5S)-3-(2-((3-(fluoromethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (27 mg, 69% yield). LCMS (MM-ES+APCI, Pos): m/z 517.3 (M+H).

Step L. tert-butyl (1R,5S)-3-(7-(8-ethyl-3-methoxynaphthalen-1-yl)-2-((3-(fluoromethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers). A mixture of tert-butyl (1R,5S)-3-(2-((3-(fluoromethyl)tetrahydro-1H-pyrrolizin-7a(5H)-yl) methoxy)-5,6,7,8-tetrahydropyrido[3,4-d]pyrimidin-4-yl)-3,8-diazabicyclo[3.2.1]octane-8-carboxylate (mixture of isomers) (17 mg, 0.033 mmol), 8-ethyl-3-methoxynaphthalen-1-yl trifluoromethanesulfonate (16 mg, 0.049 mmol), $Pd_2(dba)_3$ (3.0 mg, 0.0033 mmol), Xantphos (3.8 mg, 0.0066 mmol), and $Cs_2CO_3$ (43 mg, 0.13 mmol) in dioxanes was sparged with argon and heated in a sealed tube at 100° C. overnight. The mixture was purified by silica gel chromatography (1-15% MeOH/DCM with 1% $NH_4OH$ as modifier) to give 10 mg of impure product which was taken forward crude. LCMS (MM-ES+APCI, Pos): m/z 701.4 (M+H).

Step M. 4-(4-((1R,5S)-3,8-diazabicyclo[3.2.1]octan-3-yl)-2-((3-(fluoromethyl)tetrahydro-1H-pyrrolizin-7a(5H)- yl)methoxy)-5,8-dihydropyrido[3,4-d]pyrimidin-7(6H)-yl)-5-ethylnaphthalen-2-ol (mixture of isomers). To a solution of tert-butyl (1R,5S)-3-(7-(8-ethyl-3-methoxynaphthalen-1-yl)-2-((3-(fluoromethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (10 mg, 0.014 mmol) in DCM (0.15 mL) at −78° C. was added $BBr_3$ (71 μL, 0.071 mmol) and stirred at 0° C. for 1 hour. The mixture was stirred at room temperature for 45 minutes, concentrated, and purified by reverse-phase chromatography (5-95% MeCN/water with 0.1% TFA as modifier). The fractions containing the product were pooled, frozen, and lyophilized to give 4-(4-((1R,5S)-3,8-diazabicyclo[3.2.1]octan-3-yl)-2-((3-(fluoromethyl)tetrahydro-1H-pyrrolizin-7a(5H)-yl)methoxy)-5,8-dihydropyrido[3,4-d]pyrimidin-7(6H)-yl)-5-ethylnaphthalen-2-ol (mixture of isomers) as the TFA salt (1.1 mg, 9.5% yield). LCMS (MM-ES+APCI, Pos): m/z 587.3 (M+H).

Example 24

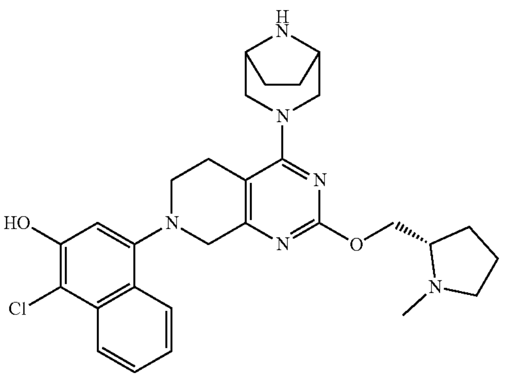 [SMILES: CN1CCC[C@H]1COc1nc2c(c(N3CC4CCC(C3)N4)n1)CCN(c1cc(O)c(Cl)c3ccccc13)C2]

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-chloronaphthalen-2-ol

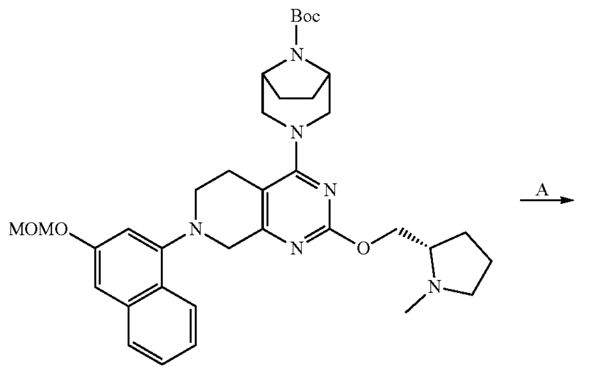

-continued

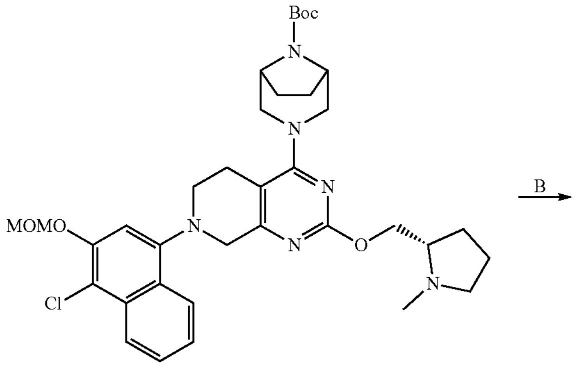

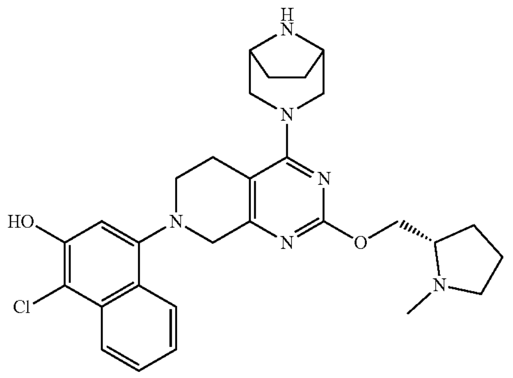

Step A. tert-butyl (1R,5S)-3-(7-(4-chloro-3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A solution of N-chlorosuccinimide (0.026 g, 0.19 mmol) and tert-butyl (1R,5S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (0.12 g, 0.18 mmol) in DMF (0.9 mL) was stirred at room temperature for two days. Water was added to the mixture and the aqueous layer was extracted two times with ethyl acetate. The pooled organic layers were washed with water (2×), brine, and dried over magnesium sulfate. The mixture was filtered, and the filtrate was concentrated. The residue was purified by silica gel column (0 to 15% MeOH/DCM) to give the crude product (70 mg, 58%). LCMS (MM-ES+APCI, Pos): m/z 679.3 (M+H).

Step B. 4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-chloronaphthalen-2-ol. A solution of tert-butyl (1R,5S)-3-(7-(4-chloro-3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (70 mg, 0.10 mmol) in dichloromethane and trifluoroacetic acid (2 mL, 3:1 DCM to TFA) was stirred at rt for 90 minutes. The solution was concentrated, and the residue was purified by prep-HPLC (5 to 50% $CH_3CN/H_2O$ with 0.1% TFA) to give the desired product as the bis TFA salt (24 mg, 43%). LCMS (MM-ES+APCI, Pos): m/z 535.3 (M+H).

Example 25

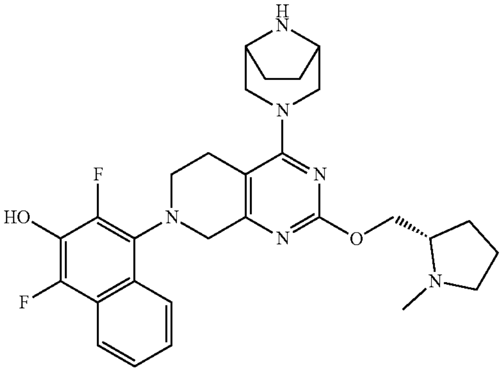 [SMILES: CN1CCC[C@H]1COc1nc2c(c(N3CC4CCC(C3)N4)n1)CCN(c1c(F)c(O)c(F)c3ccccc13)C2]

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1,3-difluoronaphthalen-2-ol Synthesized according to Example 24 substituting Selectfluor® for N-chlorosuccinimide in step A to give the title product (0.80 mg, 1.4% yield). LCMS (MM-ES+APCI, Pos): m/z 537.2 (M+H).

Example 26

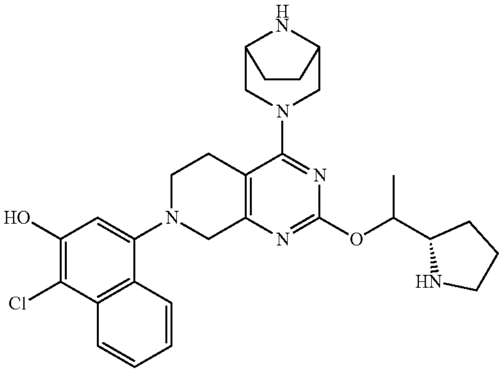 [SMILES: CC(Oc1nc2c(c(N3CC4CCC(C3)N4)n1)CCN(c1cc(O)c(Cl)c3ccccc13)C2)[C@@H]1CCCN1]

4-(4-((1R,5S)-3,8-diazabicyclo[3.2.1]octan-3-yl)-2-(1-((S)-pyrrolidin-2-yl)ethoxy)-5,8-dihydropyrido[3,4-d]pyrimidin-7(6H)-yl)-1-chloronaphthalen-2-ol Synthesized according to Example 1, step B-D substituting tert-butyl (2S)-2-(1-hydroxyethyl)pyrrolidine-1-carboxylate for (S)-(1-methylpyrrolidin-2-yl)methanol in step B followed by using Example 24 step A and B to give title product (3.0 mg, 11% yield). LCMS (MM-ES+APCI, Pos): m/z 535.2 (M+H).

Example 27

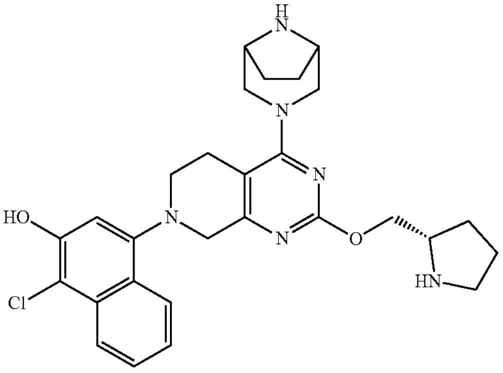 [SMILES: Oc1cc(N2CCc3c(nc(OC[C@@H]4CCCN4)nc3N3CC4CCC(C3)N4)C2)c2ccccc2c1Cl]

4-(4-((1R,5S)-3,8-diazabicyclo[3.2.1]octan-3-yl)-2-(((S)-pyrrolidin-2-yl)methoxy)-5,8-dihydropyrido[3,4-d]pyrimidin-7(6H)-yl)-1-chloronaphthalen-2-ol Synthesized according to Example 1, steps B-D substituting tert-butyl (S)-2-(hydroxymethyl)pyrrolidine-1-carboxylate for (S)-(1-methylpyrrolidin-2-yl)methanol in step B, followed by using Example 24 steps A and B to give title product (13 mg, 49% yield). LCMS (MM-ES+APCI, Pos): m/z 521.1 (M+H).

Example 28

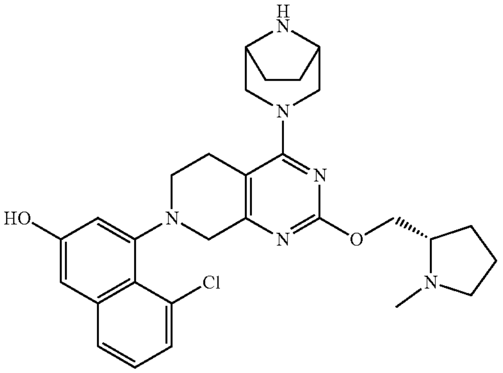 [SMILES: CN1CCC[C@H]1COc1nc2c(c(N3CC4CCC(C3)N4)n1)CCN(c1cc(O)cc3cccc(Cl)c13)C2]

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-5-chloronaphthalen-2-ol Synthesized according to Example 6, steps A-C substituting (S)-(1-methylpyrrolidin-2-yl)methanol for (2-fluorotetrahydro-1H-pyrrolizin-7a(5H)-yl)methanol in step B followed by using Example 24 step B to give the title product (14 mg, 32% yield). LCMS (MM-ES+APCI, Pos): m/z 535.2 (M+H).

Example 29

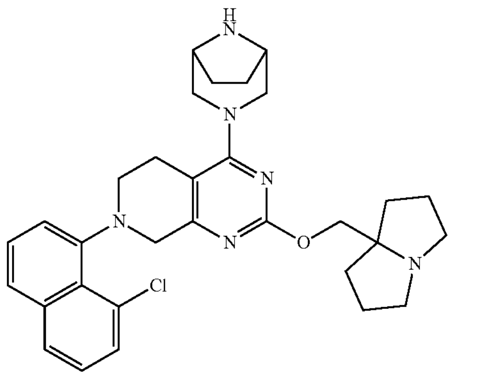 [SMILES: Clc1cccc2cccc(N3CCc4c(nc(OCC56CCCN5CCC6)nc4N4CC5CCC(C4)N5)C3)c12]

4-((1R,5S)-3,8-diazabicyclo[3.2.1]octan-3-yl)-7-(8-chloronaphthalen-1-yl)-2-((tetrahydro-1H-pyrrolizin-7a(5H)-yl)methoxy)-5,6,7,8-tetrahydropyrido[3,4-d]pyrimidine

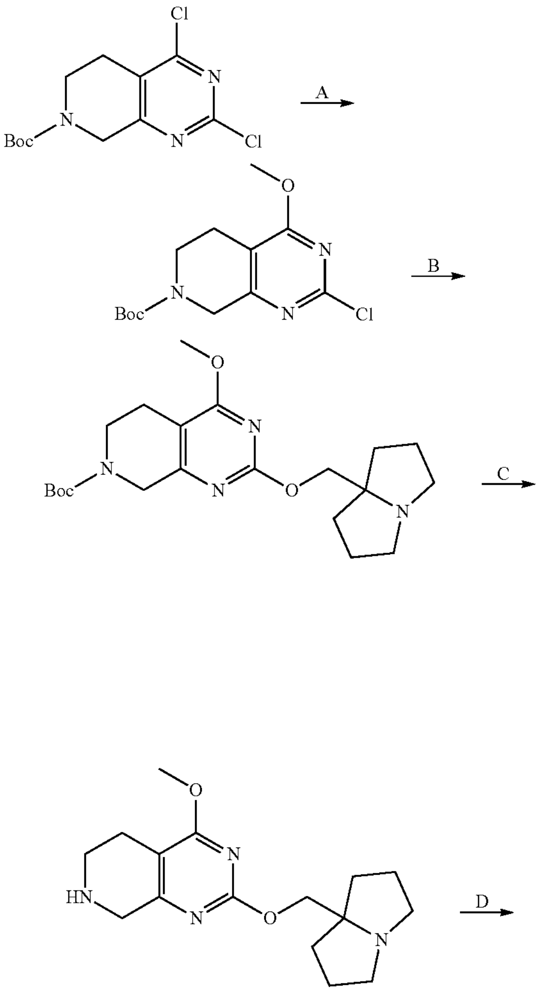

-continued

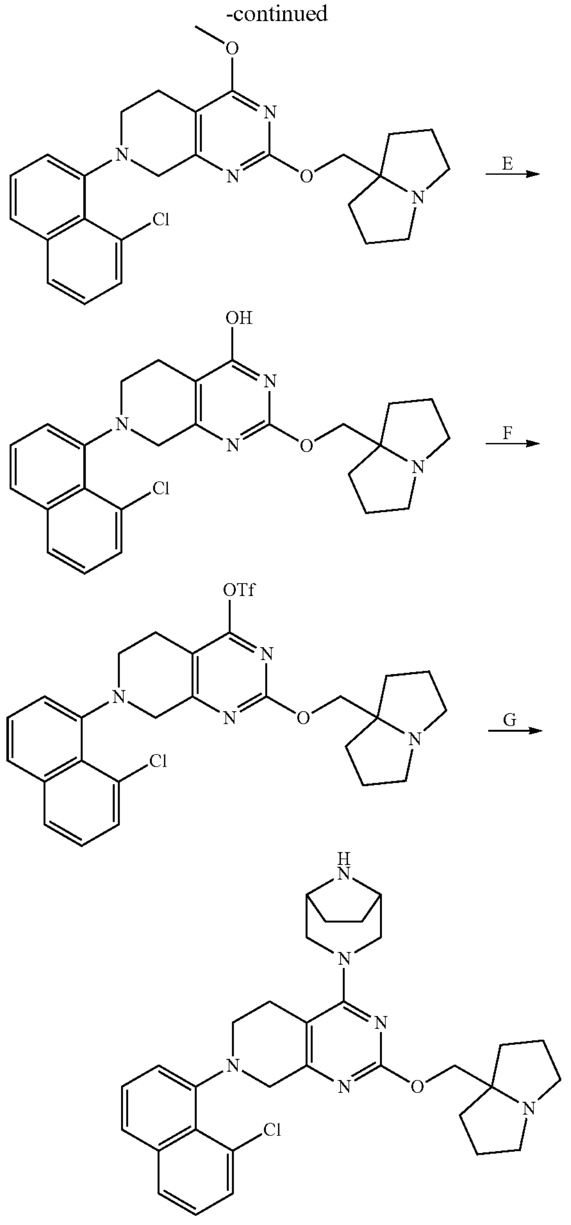

Step A. tert-butyl 2-chloro-4-methoxy-5,8-dihydropyrido[3,4-d]pyrimidine-7(6H)-carboxylate. Tert-butyl 2,4-dichloro-5,8-dihydropyrido[3,4-d]pyrimidine-7(6H)-carboxylate (15 g, 49 mmol) was dissolved in methanol (490 mL) and the solution was cooled to 0° C. To this mixture was added sodium methoxide (11 mL, 49 mmol) and the reaction was stirred for 1 hour. The reaction was concentrated in vacuo and resuspended in EtOAc. The organics were washed with water and the aqueous layer extracted with EtOAc. The combined organics were filtered through 1PS paper and concentrated in vacuo to give crude tert-butyl 2-chloro-4-methoxy-5,8-dihydropyrido[3,4-d]pyrimidine-7(6H)-carboxylate (15 g, 99% yield). LCMS (MM-ES+APCI, Pos): m/z 200.0 $(M+H-Boc)^+$.

Step B. tert-butyl 4-methoxy-2-((tetrahydro-1H-pyrrolizin-7a(5H)-yl)methoxy)-5,8-dihydropyrido[3,4-d]pyrimidine-7(6H)-carboxylate. (Tetrahydro-1H-pyrrolizin-7a(5H)-yl)methanol (0.29 g, 2.1 mmol), tert-butyl 2-chloro-4-methoxy-5,8-dihydropyrido[3,4-d]pyrimidine-7(6H)- carboxylate (0.41 g, 1.4 mmol), 2,2'-bis(diphenylphosphanyl)-1,1'-binaphthalene (0.17 g, 0.27 mmol), toluene (7 mL), and cesium carbonate (1.3 g, 4.1 mmol) were charged to a 75 mL glass pressure vessel and sparged with argon for 5 minutes. Diacetoxypalladium (0.030 g, 0.13 mmol) was added to the mixture and the vessel was sealed and heated to 110° C. with stirring for 16 hours. The mixture was cooled to room temperature and filtered through Celite. The filtrate was concentrated in vacuo and purified by column chromatography (5 to 10% MeOH/DCM with 1% $NH_4OH$) to give the product (0.39 g, 71%). LCMS (MM-ES+APCI, Pos): m/z 405.3 (M+H).

Step C. 4-methoxy-2-((tetrahydro-1H-pyrrolizin-7a(5H)-yl)methoxy)-5,6,7,8-tetrahydropyrido[3,4-d]pyrimidine. To a solution of tert-butyl 4-methoxy-2-((tetrahydro-1H-pyrrolizin-7a(5H)-yl)methoxy)-5,8-dihydropyrido[3,4-d]pyrimidine-7(6H)-carboxylate (0.39 g, 0.97 mmol) in dichloromethane (3.3 mL) was added dropwise 2,2,2-trifluoroacetic acid (0.12 mL). The mixture was stirred at room temperature for 30 minutes and the reaction was quenched with sat. aq. $NaHCO_3$. The aqueous layer was extracted 5 times with 25% IPA/DCM, the combined organics were dried over $Na_2SO_4$, and concentrated in vacuo to furnish the product as an orange oil, used without further purification (0.29 g, 99%). LCMS (MM-ES+APCI, Pos): m/z 305.2 (M+H).

Step D. 7-(8-chloronaphthalen-1-yl)-4-methoxy-2-((tetrahydro-1H-pyrrolizin-7a(5H)-yl)methoxy)-5,6,7,8-tetrahydropyrido[3,4-d]pyrimidine. XantPhos (0.17 g, 0.29 mmol), 4-methoxy-2-((tetrahydro-1H-pyrrolizin-7a(5H)-yl)methoxy)-5,6,7,8-tetrahydropyrido[3,4-d]pyrimidine (0.29 g, 0.97 mmol), 1-bromo-8-chloronaphthalene (0.47 g, 1.9 mmol), and cesium carbonate (1.3 g, 3.7 mmol) were charged to a 75 mL glass pressure vessel with 1,4-dioxane (6.5 mL) and a stir bar. The mixture was purged with argon for 5 minutes and $Pd_2(dba)_3$ (0.13 g, 0.15 mmol) was added. The vessel was sealed and heated to 100° C. with stirring for 20 hours. The mixture was cooled to room temperature, filtered through Celite, and the filtrate was concentrated in vacuo. The crude material was purified by column chromatography (0 to 10% methanol/DCM with 1% $NH_4OH$) to furnish the product as a colorless oil (0.22 g, 50%). LCMS (MM-ES+APCI, Pos): m/z 465.2 (M+H).

Step E. 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-ol. To a solution of 7-(8-chloronaphthalen-1-yl)-4-methoxy-2-((tetrahydro-1H-pyrrolizin-7a(5H)-yl)methoxy)-5,6,7,8-tetrahydropyrido[3,4-d]pyrimidine (0.22 g, 0.48 mmol) in DMA (2.4 mL) was added sodium methanethiolate (0.035 g, 0.50 mmol) at rt. The mixture was stirred at 75° C. for 2 h. An additional portion of sodium methanethiolate (0.035 g, 0.50 mmol) was added to the mixture and the mixture was stirred for 2 hours at 85° C. The mixture was cooled to room temperature, quenched with saturated aqueous sodium bicarbonate, and diluted with 25% IPA/DCM. The aqueous layer was extracted with 6 portions of 25% IPA/DCM. The combined organics were dried over $Na_2SO_4$ and concentrated in vacuo. The material was purified by column chromatography (5% to 10% MeOH/DCM) to furnish the product as a brown powder (0.22 g, 44%). LCMS (MM-ES+APCI, Pos): m/z 451.2 (M+H).

Step F. 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl trifluoromethanesulfonate. 7-(8-Chloronaphthalen-1-yl)-2-((tetrahydro-1H-pyrrolizin-7a(5H)-yl)methoxy)-5,6,7,8-tetrahydropyrido[3,4-d]pyrimidin-4-ol (0.096 g, 0.21 mmol) and dichloromethane (2.2 mL) were charged to a 25 mL pear shaped flask equipped with a stir bar. The vessel was placed under an $N_2$ atmosphere and cooled to −40° C. diisopropylethylamine (0.43 mmol) was added dropwise and the mixture was stirred for 5 minutes. Trifluoromethanesulfonic anhydride (0.039 mL, 0.23 mmol) was added dropwise and the mixture was stirred for 20 minutes. The mixture was diluted with DCM and sat. aq. $NaHCO_3$. The aqueous layer was extracted 3× with DCM. The combined organics were dried with $Na_2SO_4$, concentrated in vacuo, and purified by column chromatography (0 to 10% MeOH/DCM with 1% $NH_4OH$) to furnish the product (0.075 g, 45%). LCMS (MM-ES+APCI, Pos): m/z 583.2 (M+H).

Step G. 4-((1R,5S)-3,8-diazabicyclo[3.2.1]octan-3-yl)-7-(8-chloronaphthalen-1-yl)-2-((tetrahydro-1H-pyrrolizin-7a(5H)-yl)methoxy)-5,6,7,8-tetrahydropyrido[3,4-d]pyrimidine. Tert-butyl (1R,5S)-3,8-diazabicyclo[3.2.1]octane-8-carboxylate (0.082 g, 0.39 mmol), triethylamine (0.054 mL, 0.39 mmol), 7-(8-chloronaphthalen-1-yl)-2-((tetrahydro-1H-pyrrolizin-7a(5H)-yl)methoxy)-5,6,7,8-tetrahydropyrido[3,4-d]pyrimidin-4-yl trifluoromethanesulfonate (0.075 g, 0.13 mmol), and dichloromethane (0.7 mL) were charged to a 25 mL pear shaped flask. The mixture was stirred at room temperature for 1 hour. Volatiles were removed in vacuo and the mixture was constituted in DCM (0.5 mL). Trifluoroacetic acid (0.5 mL, 0.13 mmol) was added dropwise and the mixture was stirred for 30 minutes at room temperature. The mixture was concentrated in vacuo and the crude material was purified by reverse-phase preparatory HPLC (5 to 95% water/ACN with 0.1% TFA over 20 minutes). Product-containing fractions were concentrated in vacuo, constituted in 25% DCM/IPA and filtered through Agilent StartoSpheres SPE PL-HCO3 M 2 times. The filtrate was concentrated in vacuo to furnish the title compound (0.010 g, 10%). LCMS (MM-ES+APCI, Pos): m/z 545.3 (M+H).

Example 30

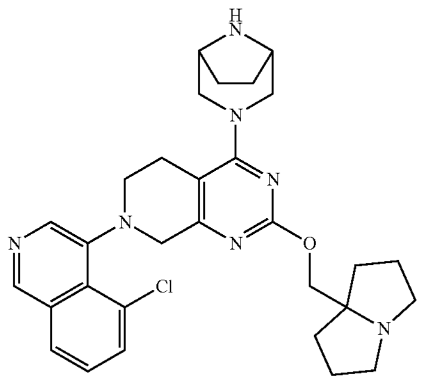 [SMILES: Clc1cccc2cncc(N3CCc4c(nc(OCC56CCCN5CCC6)nc4N4CC5CCC(C4)N5)C3)c12]

4-((1R,5S)-3,8-diazabicyclo[3.2.1]octan-3-yl)-7-(5-chloroisoquinolin-4-yl)-2-((tetrahydro-1H-pyrrolizin-7a(5H)-yl)methoxy)-5,6,7,8-tetrahydropyrido[3,4-d]pyrimidine

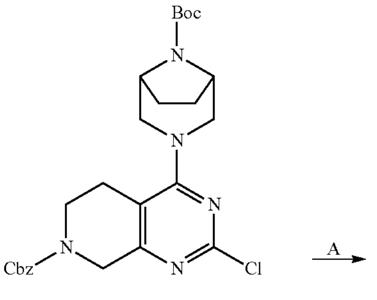

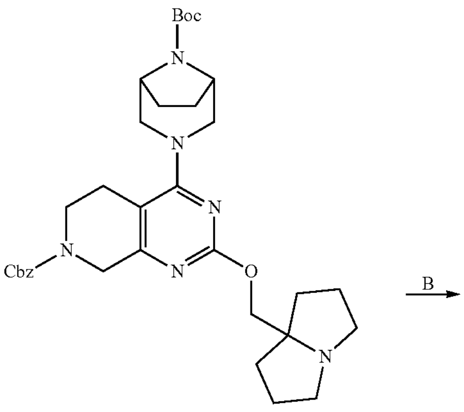

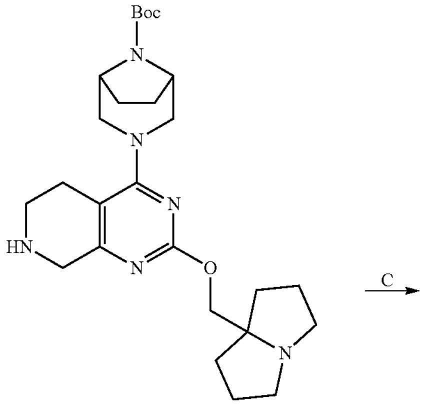

-continued

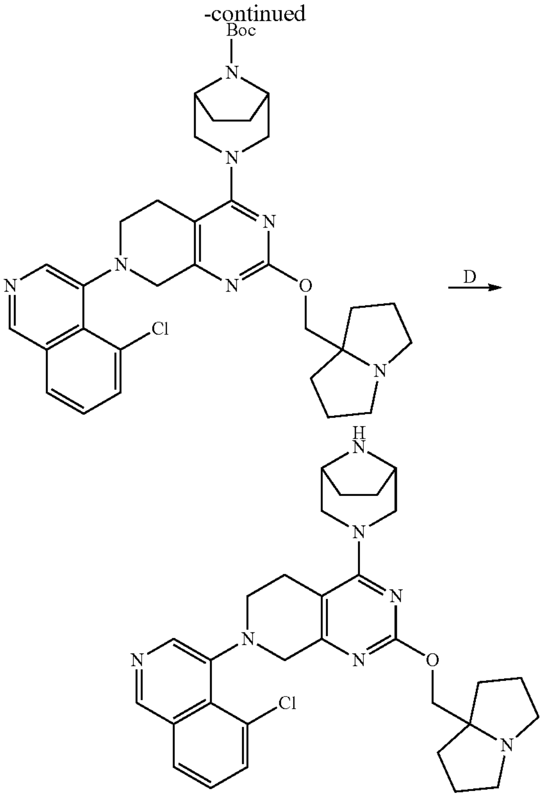

Step A. benzyl 4-((1R,5S)-8-(tert-butoxycarbonyl)-3,8-diazabicyclo[3.2.1]octan-3-yl)-2-((tetrahydro-1H-pyrrolizin-7a(5H)-yl)methoxy)-5,8-dihydropyrido[3,4-d]pyrimidine-7(6H)-carboxylate. (Tetrahydro-1H-pyrrolizin-7a(5H)-yl)methanol (0.082 g, 0.58 mmol), benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.20 g, 0.38 mmol), diacetoxypalladium (0.009 g, 0.04 mmol), 2,2'-bis(diphenylphosphanyl)-1,1'-binaphthalene (0.049 g, 0.078 mmol), cesium carbonate (0.38 g, 1.17 mmol), and toluene (2 mL) were combined in a 10 mL glass pressure vessel equipped with a stir bar. The mixture was sparged with argon for 5 minutes, sealed and heated to 110° C. for 8 hours. An additional 1 equivalent of alcohol was added, and the mixture was stirred at 110° C. for 4 hours. The mixture was filtered through Celite, concentrated in vacuo, and purified by column chromatography (0 to 10% MeOH/DCM) to furnish the product as a yellow oil. (0.14 g, 59% yield). LCMS (MM-ES+APCI, Pos): m/z 619.4 (M+H).

Step B. tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Benzyl 4-((1R,5S)-8-(tert-butoxycarbonyl)-3,8-diazabicyclo[3.2.1]octan-3-yl)-2-((tetrahydro-1H-pyrrolizin-7a(5H)-yl)methoxy)-5,8-dihydropyrido[3,4-d]pyrimidine-7(6H)-carboxylate (0.14 g, 0.23 mmol), methanol (2.3 mL), and dihydroxypalladium (0.16 g, 0.23 mmol) were charged to a 25 mL pear shaped flask equipped with a stir bar. The mixture was placed under a $N_2$ atmosphere and stirred at room temperature. The mixture was purged with $H_2$ via a balloon for 2 minutes. The mixture was stirred at room temperature for 30 minutes under a $H_2$ atmosphere. The vessel was purged with nitrogen. The reaction mixture was diluted with methanol and filtered under a nitrogen atmosphere. The filtered solution was concentrated in vacuo and used without further purification (0.095 g, 69%).

Step C. tert-butyl (1R,5S)-3-(7-(5-chloroisoquinolin-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. 4-Bromo-5-chloroisoquinoline (0.019 g, 0.077 mmol), tert-butyl (1R,5S)-3-(2-((tetrahydro-1H-pyrrolizin-7a(5H)-yl)methoxy)-5,6,7,8-tetrahydro-pyrido[3,4-d]pyrimidin-4-yl)-3,8-diazabicyclo[3.2.1]octane-8-carboxylate (0.025 g, 0.052 mmol), cesium carbonate (0.067 g, 0.21 mmol), 1,4-dioxane (0.4 mL), and XantPhos (0.0090 g, 0.015 mmol) were charged to a 10 mL glass pressure vessel equipped with a stir bar. The mixture was purged with argon for 5 minutes and $Pd_2(dba)_3$ (0.007 g, 0.008 mmol) was added. The vessel was sealed and heated to 100° C. for 14 hours. To the mixture were added 4-bromo-5-chloroisoquinoline (19 mg), $Pd_2(dba)_3$ (7 mg), and Xantphos (9 mg). The mixture was heated to 110° C. for 24 hours. The mixture was cooled to rt and filtered through Celite, concentrated in vacuo, and purified by column chromatography (0 to 10% MeOH/DCM with 1% $NH_4OH$) to furnish the product as a yellow solid (0.019 g, 57%). LCMS (MM-ES+APCI, Pos): m/z 646.3 (M+H).

Step D. 4-((1R,5S)-3,8-diazabicyclo[3.2.1]octan-3-yl)-7-(5-chloroisoquinolin-4-yl)-2-((tetrahydro-1H-pyrrolizin-7a(5H)-yl)methoxy)-5,6,7,8-tetrahydropyrido[3,4-d]pyrimidine. Tert-butyl (1R,5S)-3-(7-(5-chloroisoquinolin-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.013 g, 0.020 mmol) was constituted in dichloromethane (0.5 mL) and the mixture was stirred at room temperature. 2,2,2-Trifluoroacetic acid (0.5 mL, 0.068 mmol) was added dropwise to the vessel and the mixture was stirred at room temperature for 30 minutes. The mixture was diluted with water, concentrated in vacuo, and purified with a Gilson reverse-phase preparatory HPLC (5 to 95% water/ACN with 0.1% TFA as modifier). The isolated product was reconstituted in 25% IPA/DCM and 10% aq. $K_2CO_3$ and the layers were separated. The aqueous layer was extracted with 6 portions of 25% IPA/DCM. The combined organics were combined, dried over $Na_2SO_4$, and concentrated in vacuo to furnish the title compound (0.0080 g, 73%). LCMS (MM-ES+APCI, Pos): m/z 546.3 (M+H).

Example 31

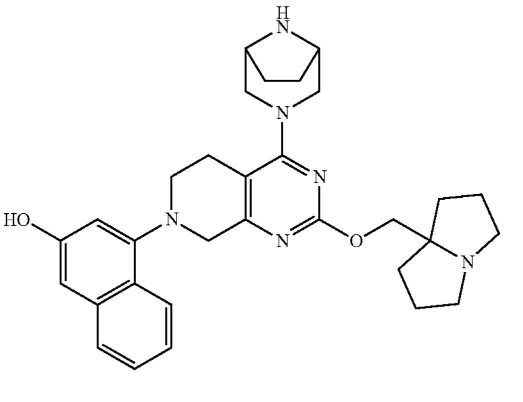

4-(4-((1R,5S)-3,8-diazabicyclo[3.2.1]octan-3-yl)-2-((tetrahydro-1H-pyrrolizin-7a(5H)-yl)methoxy)-5,8-dihydropyrido[3,4-d]pyrimidin-7(6H)-yl)naphthalen-2-ol

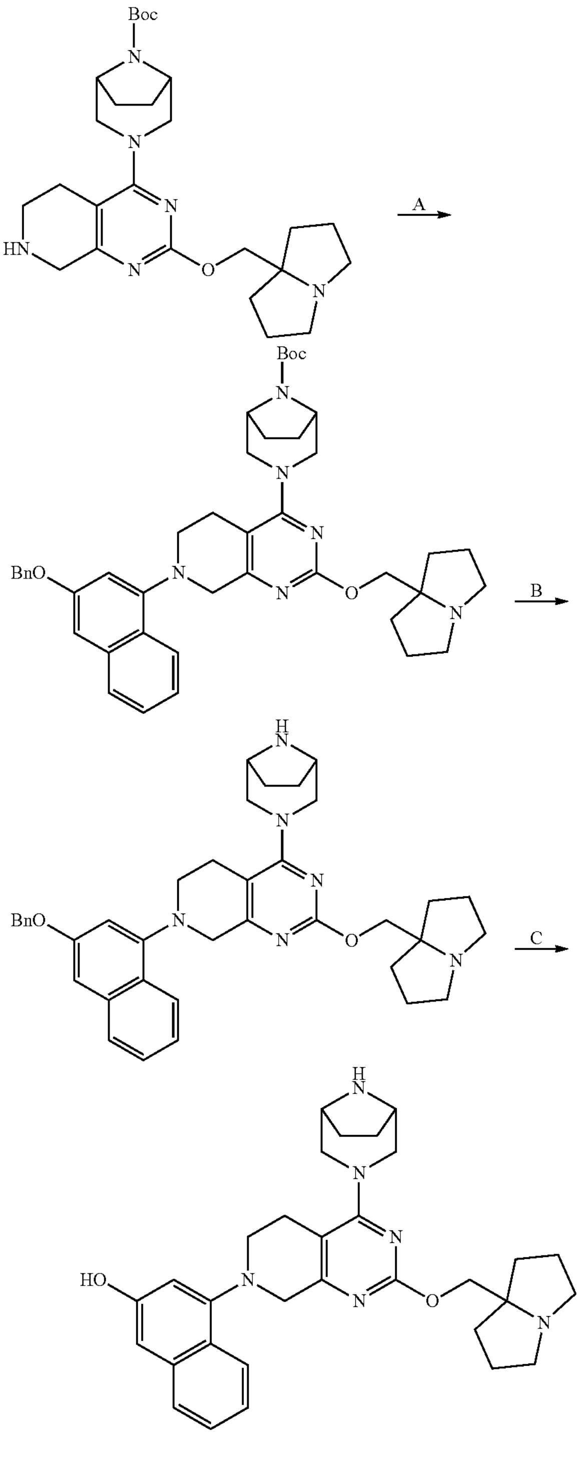

Step A. tert-butyl (1R,5S)-3-(7-(3-(benzyloxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. 3-(Benzyloxy)-1-bromonaphthalene (0.039 g, 0.12 mmol), tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.030 g, 0.062 mmol), cesium carbonate (0.081 g, 0.25 mmol), XantPhos (0.011 g, 0.019 mmol) and 1,4-dioxane (0.4 mL) were charged to a 10 mL glass pressure vessel equipped with a stir bar. The mixture was purged with argon for 5 minutes and $Pd_2(dba)_3$ (0.009 g, 0.009 mmol) was added. The vessel was sealed and heated to 100° C. with stirring. Additional portions of $Pd_2(dba)_3$ (0.0085 g, 0.0093 mmol) and XantPhos (0.011 g, 0.019 mmol) were added and the mixture was heated for 4 hours. The mixture was cooled to room temperature, filtered through Celite, and concentrated in vacuo. The crude material was purified by column chromatography (0 to 20% methanol/DCM with 1% $NH_4OH$) to furnish the product as a yellow oil (0.044 g, 27%). LCMS (MM-ES+APCI, Pos): m/z 717.4 (M+H).

Step B. 7-(3-(benzyloxy)naphthalen-1-yl)-4-((1R,5S)-3,8-diazabicyclo[3.2.1]octan-3-yl)-2-((tetrahydro-1H-pyrrolizin-7a(5H)-yl)methoxy)-5,6,7,8-tetrahydropyrido[3,4-d]pyrimidine bis-(2,2,2-trifluoroacetate). Tert-butyl (1R,5S)-3-(7-(3-(benzyloxy)naphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (0.012 g, 0.017 mmol) was charged to a 25 mL pear shaped flask with DCM (0.5 mL). To the stirred solution was added TFA (0.5 mL) dropwise. The mixture was stirred at room temperature for 30 minutes, diluted with 2 mL of DCM, and quenched with 10% aqueous $K_2CO_3$. The aqueous layer was extracted 5 times with 25% IPA/DCM and the combined organics were concentrated in vacuo. The crude material was purified with a Gilson reverse-phase preparatory HPLC (5 to 95% water/ACN with 0.1% TFA). The material was slurried with Silicycle Si-TRI resin in 2 mL of DCM and stirred at room temperature for 30 minutes. The mixture was filtered, and the solids were washed with 20% MeOH/DCM with 1% $NH_4OH$. The combined filtrate was concentrated in vacuo to furnish the product as an orange solid (0.010 g, 87%). LCMS (MM-ES+APCI, Pos): m/z 617.4 (M+H).

Step C. 4-(4-((1R,5S)-3,8-diazabicyclo[3.2.1]octan-3-yl)-2-((tetrahydro-1H-pyrrolizin-7a(5H)-yl)methoxy)-5,8-dihydropyrido[3,4-d]pyrimidin-7(6H)-yl)naphthalen-2-ol. 7-(3-(Benzyloxy)naphthalen-1-yl)-4-((1R,5S)-3,8-diazabicyclo[3.2.1]octan-3-yl)-2-((tetrahydro-1H-pyrrolizin-7a(5H)-yl)methoxy)-5,6,7,8-tetrahydropyrido[3,4-d]pyrimidine (0.006 g, 0.009 mmol), methanol (0.1 mL), and dihydroxypalladium (0.002 g, 0.002 mmol) were charged to a 10 mL round bottom flask equipped with a stir bar. The mixture was placed under a $N_2$ atmosphere and stirred at room temperature. The mixture was purged with $H_2$ via a balloon for 2 minutes. The mixture was stirred at room temperature for 22 hours under a $H_2$ atmosphere. The vessel was purged with nitrogen. The reaction mixture was diluted with methanol and filtered under a nitrogen atmosphere. The mixture was concentrated in vacuo and purified by Gilson reverse-phase preparatory HPLC (5 to 95% water/ACN with 0.1% TFA as modifier). The fractions containing the product were filtered through a HCO3 resin and concentrated in vacuo to give the product (0.0040 g, 54%). LCMS (MM-ES+APCI, Pos): m/z 527.4 (M+H).

Example 32

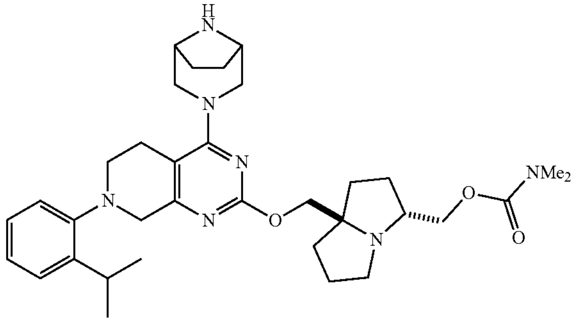

(7a-(((4-((1R,5S)-3,8-diazabicyclo[3.2.1]octan-3-yl)-7-(2-isopropylphenyl)-5,6,7,8-tetrahydropyrido[3,4-d]pyrimidin-2-yl)oxy)methyl)hexahydro-1H-pyrrolizin-3-yl)methyl dimethylcarbamate (trans enantiomers)

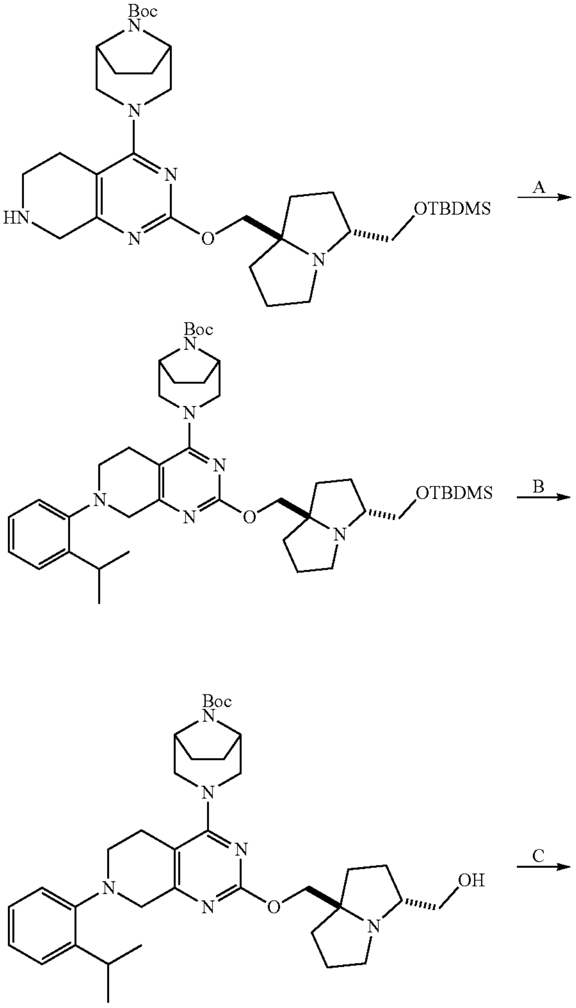

-continued

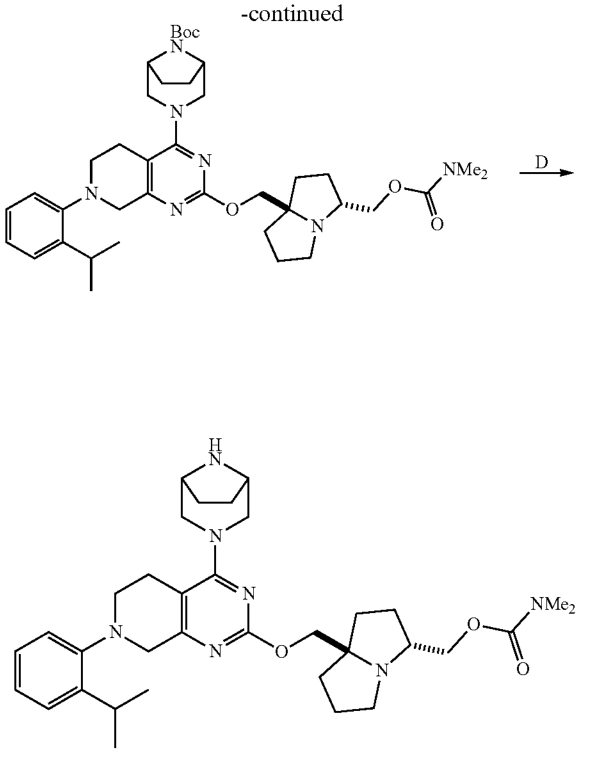

Step A. tert-butyl (1R,5S)-3-(2-((3-(((tert-butyldimethylsilyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step D substituting 1-bromo-2-isopropylbenzene in place of 1-bromo-8-ethylnaphthalene to afford tert-butyl (1R,5S)-3-(2-((3-(((tert-butyldimethylsilyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) (64 mg, 54%). LCMS (MM-ES+APCI, Pos): m/z 747.5 [M+H].

Step B. tert-butyl (1R,5S)-3-(2-((3-(hydroxymethyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step E substituting tert-butyl (1R,5S)-3-(2-((3-(((tert-butyldimethylsilyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(2-((3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate to afford tert-butyl (1R,5S)-3-(2-((3-(hydroxymethyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) (54 mg, 100%). LCMS (MM-ES+APCI, Pos): m/z 633.4 [M+H].

Step C. tert-butyl (1R,5S)-3-(2-((3-(((dimethylcarbamoyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step F substituting tert-butyl (1R,5S)-3-(2-((3-(hydroxymethyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate and 2.0 M dimethylamine in THE in place of 2.0 M methylamine in methanol to afford tert-butyl (1R,5S)-3-(2-((3-(((dimethylcarbamoyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) (31 mg, 52%). LCMS (MM-ES+APCI, Pos): m/z 704.4 [M+H].

Step D. (7a-(((4-((1R,5S)-3,8-diazabicyclo[3.2.1]octan-3-yl)-7-(2-isopropylphenyl)-5,6,7,8-tetrahydropyrido[3,4-d]pyrimidin-2-yl)oxy)methyl)hexahydro-1H-pyrrolizin-3-yl)methyl dimethylcarbamate (mixture of isomers). Tert-butyl (1R,5S)-3-(2-((3-(((dimethylcarbamoyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) (31 mg, 0.044 mmol) was dissolved in DCM (1.0 mL). A 4 N solution of HCl in 1,4-dioxane (1.0 mL, 4.0 mmol) was added and the mixture was stirred for 30 minutes at room temperature. The mixture was condensed and the residue was purified by prep HPLC (5-50% MeCN/$H_2O$ with 0.1% TFA as modifier). The fraction containing the desired product was pooled, lyophilized to afford (7a-(((4-((1R,5S)-3,8-diazabicyclo[3.2.1]octan-3-yl)-7-(2-isopropylphenyl)-5,6,7,8-tetrahydropyrido[3,4-d]pyrimidin-2-yl)oxy)methyl)hexahydro-1H-pyrrolizin-3-yl)methyl dimethylcarbamate (mixture of isomers) as the TFA salt (18 mg, 49%). LCMS (MM-ES+APCI, Pos): m/z 604.4 [M+H].

Example 33

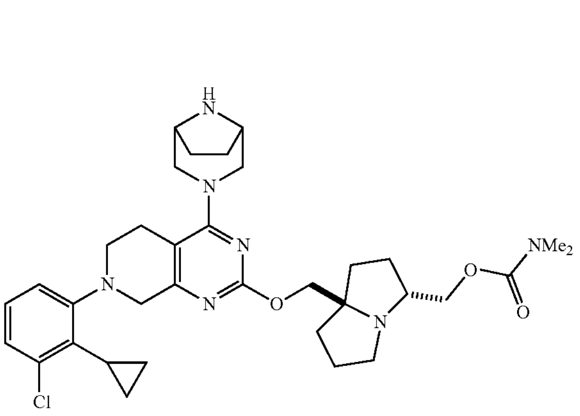

(7a-(((4-((1R,5S)-3,8-diazabicyclo[3.2.1]octan-3-yl)-7-(3-chloro-2-cyclopropylphenyl)-5,6,7,8-tetrahydropyrido[3,4-d]pyrimidin-2-yl)oxy)methyl)hexahydro-1H-pyrrolizin-3-yl)methyl dimethylcarbamate (trans enantiomers)

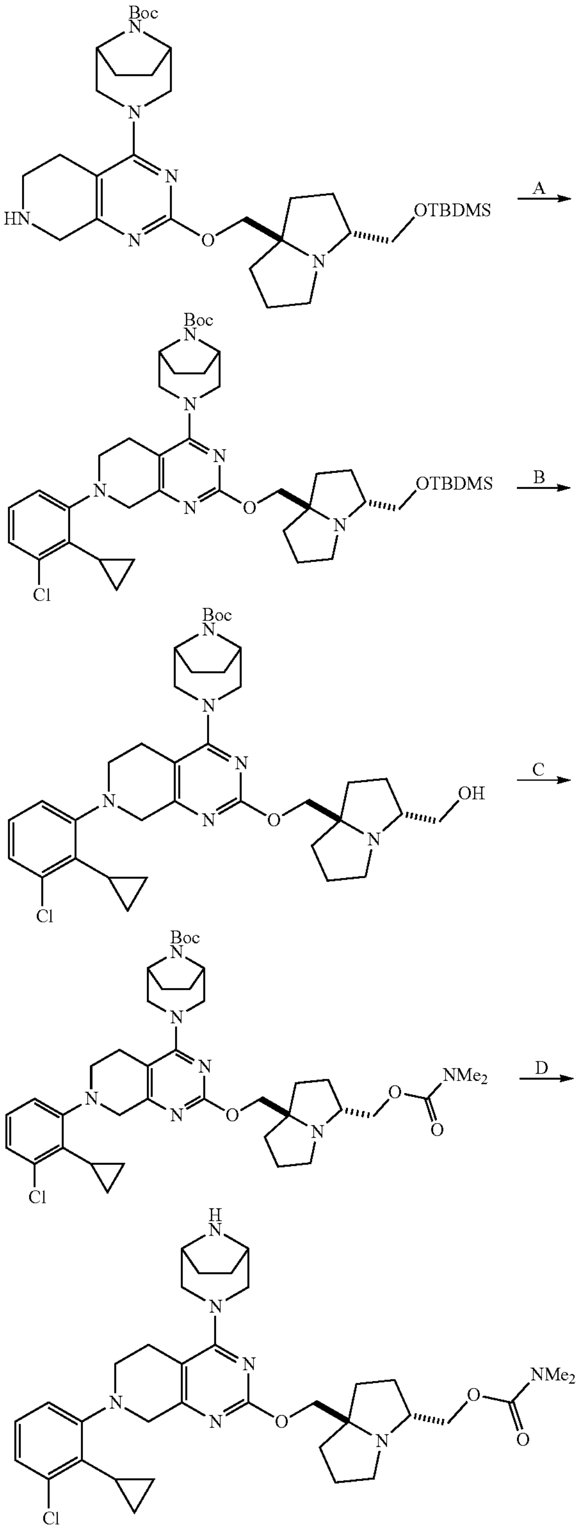

Step A. tert-butyl (1R,5S)-3-(2-((3-(((tert-butyldimethylsilyl)oxy)methyl)tetrahydro-1H-pyrrolizin-7a(5H)-yl)methoxy)-7-(3-chloro-2-cyclopropylphenyl)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step D substituting 1-bromo-3-chloro-2-cyclopropylbenzene in place of 1-bromo-8-ethylnaphthalene to afford tert-butyl (1R,5S)-3-(2-((3-(((tert-butyldimethylsilyl)oxy)methyl)tetrahydro-1H-pyrrolizin-7a(5H)-yl)methoxy)-7-(3-chloro-2-cyclopropylphenyl)-5,6,7,8-tetrahydropyrido[3,4-d]pyrimidin-4-yl)-3,8-diazabicyclo[3.2.1]octane-8-carboxylate (mixture of isomers) (66 mg, 53%). LCMS (MM-ES+APCI, Pos): m/z 779.4 [M+H].

Step B. tert-butyl (1R,5S)-3-(7-(3-chloro-2-cyclopropylphenyl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step E substituting tert-butyl (1R,5S)-3-(2-((3-(((tert-butyldimethylsilyl)oxy)methyl)tetrahydro-1H-pyrrolizin-7a(5H)-yl)methoxy)-7-(3-chloro-2-cyclopropylphenyl)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(2-((3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate to afford tert-butyl (1R,5S)-3-(7-(3-chloro-2-cyclopropylphenyl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (56 mg, 100%). LCMS (MM-ES+APCI, Pos): m/z 665.3 [M+H].

Step C. tert-butyl (1R,5S)-3-(7-(3-chloro-2-cyclopropylphenyl)-2-((3-(((dimethylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step F substituting tert-butyl (1R,5S)-3-(7-(3-chloro-2-cyclopropylphenyl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate and 2.0 M dimethylamine in THE in place of 2.0 M methylamine in methanol to afford tert-butyl (1R,5S)-3-(7-(3-chloro-2-cyclopropylphenyl)-2-((3-(((dimethylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (18 mg, 29%). LCMS (MM-ES+APCI, Pos): m/z 736.4 [M+H].

Step D. (7a-(((4-((1R,5S)-3,8-diazabicyclo[3.2.1]octan-3-yl)-7-(3-chloro-2-cyclopropylphenyl)-5,6,7,8-tetrahydropyrido[3,4-d]pyrimidin-2-yl)oxy)methyl)hexahydro-1H-pyrrolizin-3-yl)methyl dimethylcarbamate (mixture of isomers). Synthesized according to Example 32, Step D substituting tert-butyl (1R,5S)-3-(7-(3-chloro-2-cyclopropylphenyl)-2-((3-(((dimethylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(2-((3-(((dimethylcarbamoyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin- 4-yl)-3,8-diazabicyclo[3.2.1]octane-8-carboxylate (mixture of isomers) to afford (7a-(((4-((1R,5S)-3,8-diazabicyclo[3.2.1]octan-3-yl)-7-(3-chloro-2-cyclopropylphenyl)-5,6,7,8-tetrahydropyrido[3,4-d]pyrimidin-2-yl)oxy)methyl)hexahydro-1H-pyrrolizin-3-yl)methyl dimethylcarbamate (mixture of isomers) as the TFA salt (14 mg, 66%). LCMS (MM-ES+APCI, Pos): m/z 636.4 [M+H].

Example 34

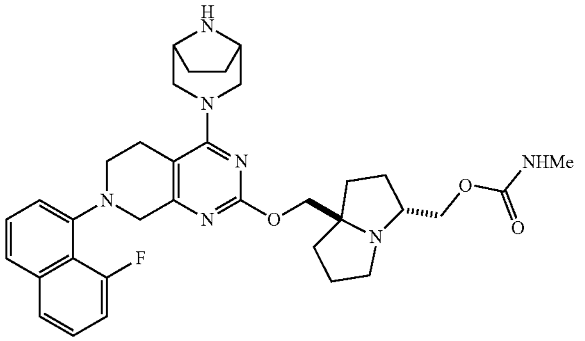

(7a-(((4-((1R,5S)-3,8-diazabicyclo[3.2.1]octan-3-yl)-7-(8-fluoronaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers)

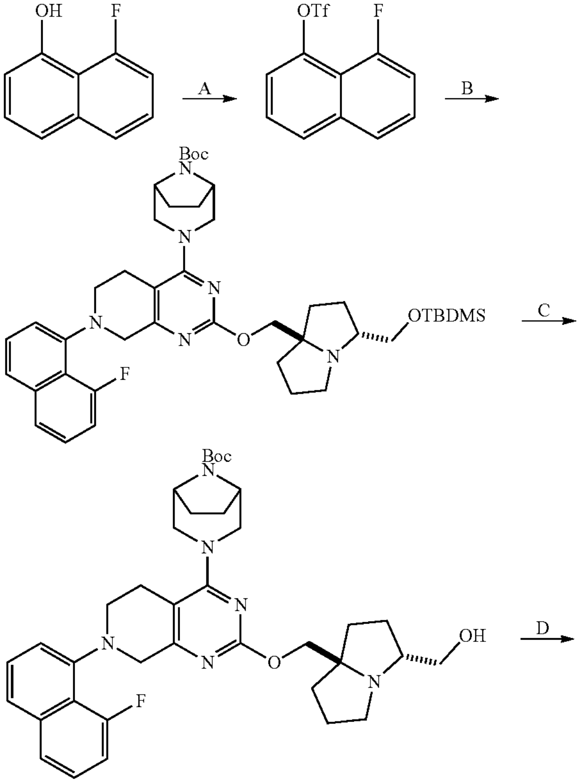

-continued

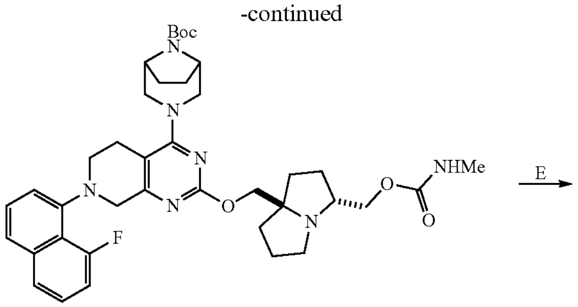

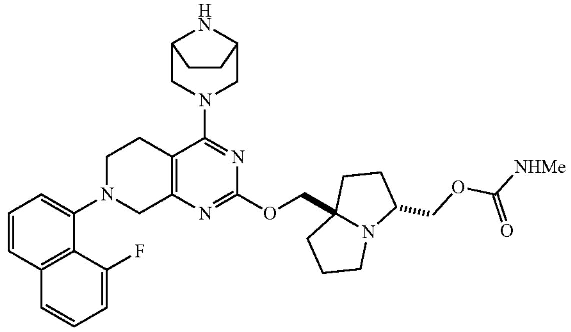

Step A. 8-fluoronaphthalen-1-yl trifluoromethanesulfonate. 8-Fluoronaphthalen-1-ol (0.50 g, 3.1 mmol) and N,N-diisopropylethylamine (0.81 mL, 4.6 mmol) were dissolved in DCM (31 mL). The solution was cooled to −40° C., trifluoromethanesulfonic anhydride (0.62 mL, 3.7 mmol) was added dropwise, and the reaction was stirred for 2 hrs. The reaction mixture was warmed to 0° C. and quenched by addition of saturated aqueous $NaHCO_3$. The organics were separated, and the aqueous was extracted twice with DCM. The organics were dried over magnesium sulfate and condensed. The residue was purified by flash chromatography (0-10% EtOAc/hexane) to afford 8-fluoronaphthalen-1-yl trifluoromethanesulfonate (0.70 g, 77%). $^1$H NMR (400 MHz, $CDCl_3$) δ 7.90 (d, J=8.2 Hz, 1H), 7.71 (d, J=8.4 Hz, 1H), 7.54-7.49 (m, 2H), 7.45 (d, J=7.9 Hz, 1H), 7.31 (dd, J=12.5, 7.5 Hz, 1H).

Step B. tert-butyl (1R,5S)-3-(2-((3-(((tert-butyldimethylsilyl)oxy)methyl)tetrahydro-1H-pyrrolizin-7a(5H)-yl)methoxy)-7-(8-fluoronaphthalen-1-yl)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step D substituting 8-fluoronaphthalen-1-yl trifluoromethanesulfonate in place of 1-bromo-8-ethylnaphthalene to afford tert-butyl (1R,5S)-3-(2-((3-(((tert-butyldimethylsilyl)oxy)methyl)tetrahydro-1H-pyrrolizin-7a(5H)-yl)methoxy)-7-(8-fluoronaphthalen-1-yl)-5,6,7,8-tetrahydropyrido[3,4-d]pyrimidin-4-yl)-3,8-diazabicyclo[3.2.1]octane-8-carboxylate (mixture of isomers) (32 mg, 52%). LCMS (MM-ES+APCI, Pos): m/z 773.4 [M+H].

Step C. tert-butyl (1R,5S)-3-(7-(8-fluoronaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4- yl)-3,8-diazabicyclo[3.2.1]octane-8-carboxylate (mixture of isomers). Synthesized according to Example 5, Step E substituting tert-butyl (1R,5S)-3-(2-((3-(((tert-butyldimethylsilyl)oxy)methyl)tetrahydro-1H-pyrrolizin-7a(5H)-yl)methoxy)-7-(8-fluoronaphthalen-1-yl)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(2-((3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate to afford tert-butyl (1R,5S)-3-(7-(8-fluoronaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (27 mg, quantitative). LCMS (MM-ES+APCI, Pos): m/z 659.3 [M+H].

Step D. tert-butyl (1R,5S)-3-(7-(8-fluoronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers). Synthesized according to Example 5, Step F substituting tert-butyl (1R,5S)-3-(7-(8-fluoronaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(7-(8-ethylnaphthalen-1-yl)-2-((3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate and 2.0 M methylamine in THE in place of 2.0 M methylamine in methanol to afford tert-butyl (1R,5S)-3-(7-(8-fluoronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) (8.0 mg, 27%). LCMS (MM-ES+APCI, Pos): m/z 716.3 [M+H].

Step E. (7a-(((4-((1R,5S)-3,8-diazabicyclo[3.2.1]octan-3-yl)-7-(8-fluoronaphthalen-1-yl)-5,6,7,8-tetrahydropyrido[3,4-d]pyrimidin-2-yl)oxy)methyl)hexahydro-1H-pyrrolizin-3-yl)methyl methylcarbamate (mixture of isomers). Synthesized according to Example 32, Step D substituting tert-butyl (1R,5S)-3-(7-(8-fluoronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) in place of tert-butyl (1R,5S)-3-(2-((3-(((dimethylcarbamoyl)oxy)methyl)tetrahydro-1H-pyrrolizin-7a(5H)-yl)methoxy)-7-(2-isopropylphenyl)-5,6,7,8-tetrahydropyrido[3,4-d]pyrimidin-4-yl)-3,8-diazabicyclo[3.2.1]octane-8-carboxylate (mixture of isomers) to afford tert-butyl (1R,5S)-3-(7-(8-fluoronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (mixture of isomers) as the TFA salt (4.0 mg, 42%). LCMS (MM-ES+APCI, Pos): m/z 616.3 [M+H].

Example 35

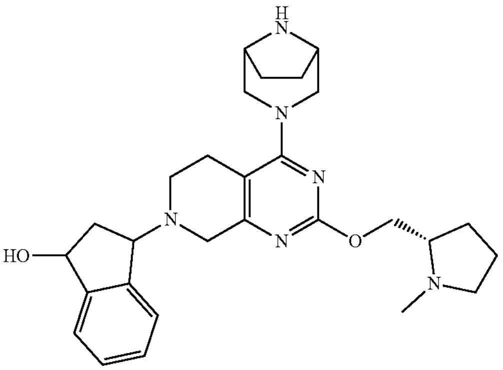 [SMILES: CN1CCC[C@H]1COc1nc2c(c(N3CC4CCC(C3)N4)n1)CCN(C1CC(O)c3ccccc31)C2]

3-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-2,3-dihydro-1H-inden-1-ol

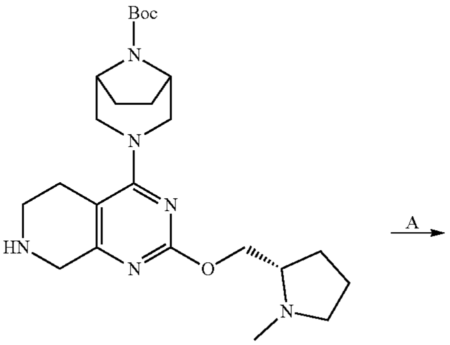

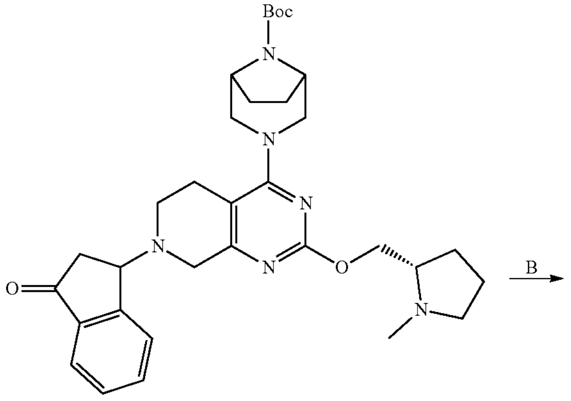

-continued

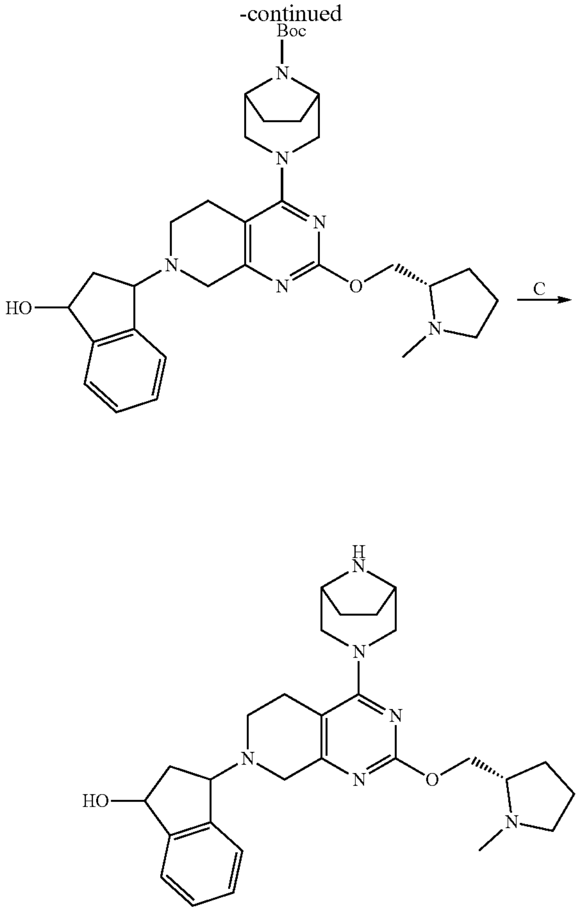

Step A. tert-butyl (1R,5S)-3-(2-(((S)-1-methylpyrrolidin-2-yl)methoxy)-7-(3-oxo-2,3-dihydro-1H-inden-1-yl)-5,6,7,8-tetrahydropyrido[3,4-d]pyrimidin-4-yl)-3,8-diazabicyclo[3.2.1]octane-8-carboxylate. To a solution of 3-bromo-2,3-dihydro-1H-inden-1-one (25 mg, 0.12 mmol) in toluene (1.0 mL) at rt was added tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (46 mg, 0.10 mmol). The mixture was stirred at rt for 30 min, quenched with $NaHCO_3$ (sat.), and extracted with DCM. The combined extracts were dried over $Na_2SO_4$, concentrated, and purified by flash chromatography eluting with MeOH/DCM (0-20%) to give the title compound (46 mg, 78%) as a white foam. LCMS (MM-ES+APCI, Pos): m/z 589.3 (M+H).

Step B. tert-butyl (1R,5S)-3-(7-(3-hydroxy-2,3-dihydro-1H-inden-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of tert-butyl (1R,5S)-3-(2-(((S)-1-methylpyrrolidin-2-yl)methoxy)-7-(3-oxo-2,3-dihydro-1H-inden-1-yl)-5,6,7,8-tetrahydropyrido[3,4-d]pyrimidin-4-yl)-3,8-diazabicyclo[3.2.1]octane-8-carboxylate (59 mg, 0.10 mmol) in MeOH (1 mL) at rt was added $NaBH_4$ (22 mg, 0.60 mmol) in three equal portions over 20 min. The mixture was purified by preparative C18 HPLC (Gilson, 0-95% $CH_3CN/H_2O$ with 0.1% TFA). The desired fractions were combined, basified with $NaHCO_3$ (sat.), and extracted with ethyl acetate. The ethyl acetate extract was dried over $Na_2SO_4$ and concentrated to give the title compound (36 mg, 61%) as a white solid. LCMS (MM-ES+APCI, Pos): m/z 591.3 (M+H).

Step C. 3-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-2,3-dihydro-1H-inden-1-ol. To a solution of tert-butyl (1R,5S)-3-(7-(3-hydroxy-2,3-dihydro-1H-inden-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (36 mg, 0.061 mmol) in DCM (1 mL) was added TFA (0.4 mL). The solution was stirred at rt for 1 h, and concentrated. The residue was purified by preparative C18 HPLC (Gilson, 0-95% $CH_3CN/H_2O$ with 0.1% TFA). The desired fractions were combined and concentrated to give a solid. The solid was dissolved in dioxane (1 mL) and treated with $NH_3{\cdot}H_2O$ (28%, 0.2 mL) at rt for 1.5 h. The mixture was concentrated to dryness. The residue was extracted with DCM/MeOH (3:1) 3 times. The combined extract was concentrated to yield the title compound (30 mg, 100%) as a white solid. LCMS (MM-ES+APCI, Pos): m/z 491.3 (M+H).

Example 36

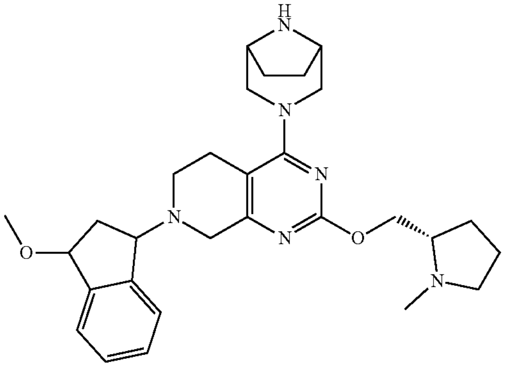 [SMILES: COC1CC(N2CCc3c(nc(OC[C@@H]4CCCN4C)nc3N3CC4CCC(C3)N4)C2)c2ccccc21]

4-((1R,5S)-3,8-diazabicyclo[3.2.1]octan-3-yl)-7-(3-methoxy-2,3-dihydro-1H-inden-1-yl)-2-(((S)-1-methylpyrrolidin-2-yl)methoxy)-5,6,7,8-tetrahydropyrido[3,4-d]pyrimidine

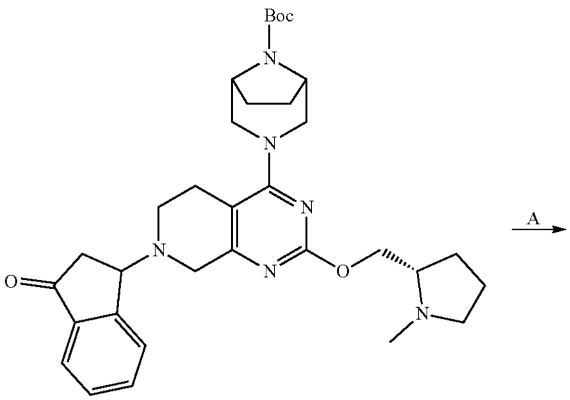

-continued

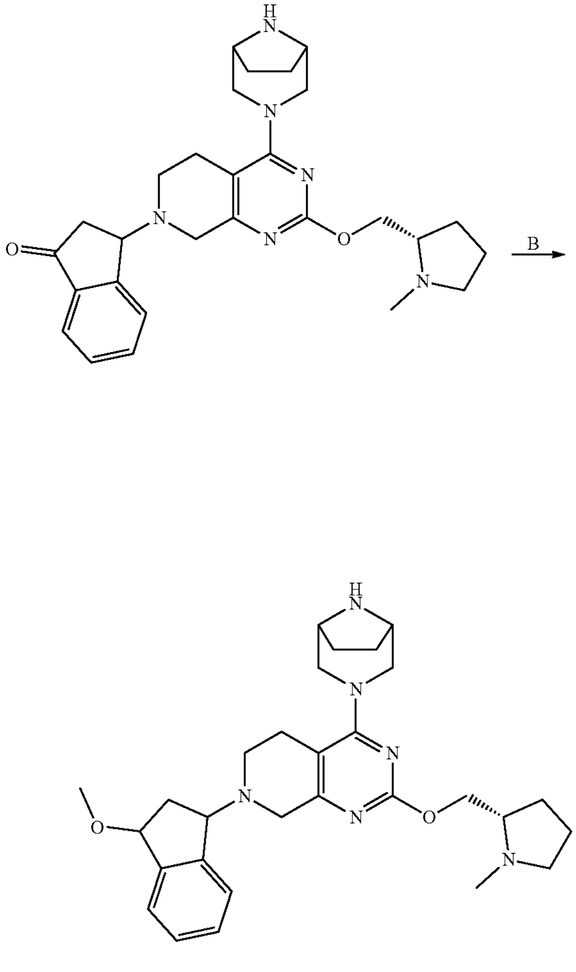

Step A. 3-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-2,3-dihydro-1H-inden-1-one bis(2,2,2-trifluoroacetate). To a solution of tert-butyl (1R,5S)-3-(2-(((S)-1-methylpyrrolidin-2-yl)methoxy)-7-(3-oxo-2,3-dihydro-1H-inden-1-yl)-5,6,7,8-tetrahydropyrido[3,4-d]pyrimidin-4-yl)-3,8-diazabicyclo[3.2.1]octane-8-carboxylate (25 mg, 0.042 mmol) in DCM (0.9 mL) was added TFA (0.2 mL). The solution was stirred at rt for 1 h and concentrated to dryness to give the crude title compound as a white solid. LCMS (MM-ES+APCI, Pos): m/z 489.3 (M+H).

Step B. 4-((1R,5S)-3,8-diazabicyclo[3.2.1]octan-3-yl)-7-(3-methoxy-2,3-dihydro-1H-inden-1-yl)-2-(((S)-1-methylpyrrolidin-2-yl)methoxy)-5,6,7,8-tetrahydropyrido[3,4-d]pyrimidine. To a solution of 3-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-2,3-dihydro-1H-inden-1-one tris(2,2,2-trifluoroacetate) (31 mg, 0.037 mmol) in MeOH (1.2 mL) was added $NaBH_4$ (10 mg, 0.27 mmol) in two portions over 10 min. The mixture was stirred at rt for 30 min and was concentrated to dryness. The residue was purified by preparative C18 HPLC (Gilson, 0-70% $CH_3CN/H_2O$ with 0.1% TFA). The desired fractions were combined and lyophilized to give the title compound (25 mg, 90%) as the TFA salt. LCMS (MM-ES+APCI, Pos): m/z 505.3 (M+H).

Example 37

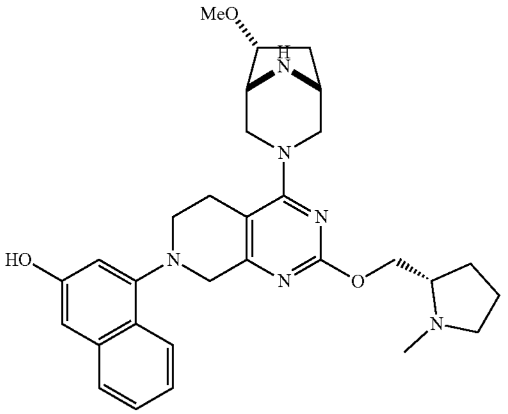

4-(4-((1R,5R,6R)-6-methoxy-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol

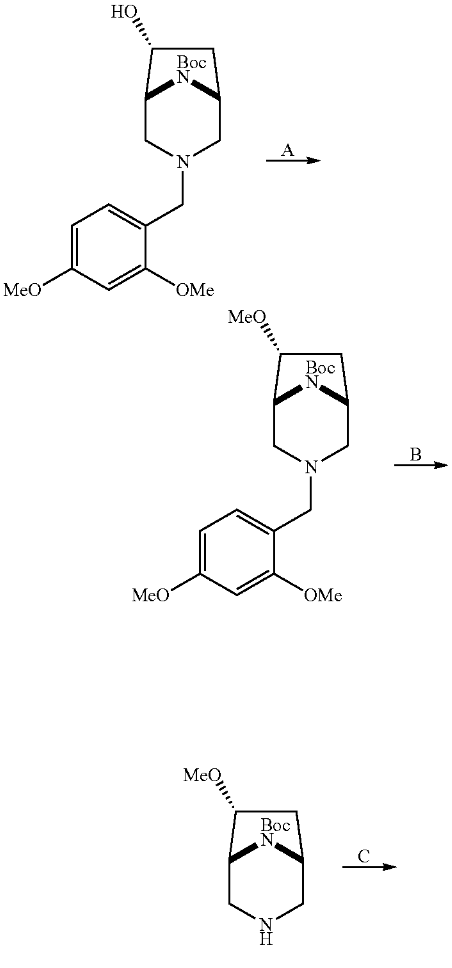

-continued

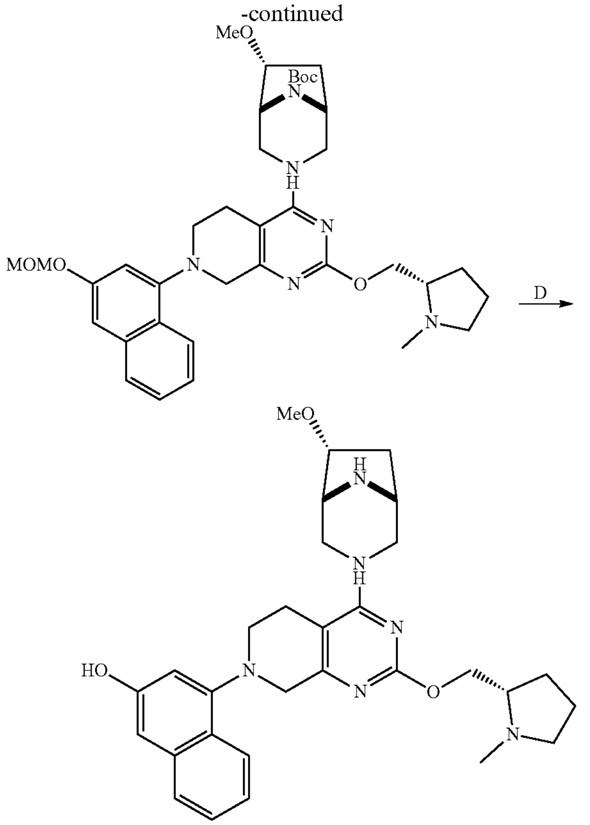

Step A. tert-butyl (1R,5R,6R)-3-(2,4-dimethoxybenzyl)-6-methoxy-3,8-diazabicyclo[3.2.1]octane-8-carboxylate. To a solution of tert-butyl (1S,5S,6S)-3-(2,4-dimethoxybenzyl)-6-hydroxy-3,8-diazabicyclo[3.2.1]octane-8-carboxylate (58 mg, 0.15 mmol) and MeI (48 μL, 0.76 mmol) in DMF (1.5 mL) at 0° C. under $N_2$ was added NaH (60%, 24 mg, 0.62 mmol). The mixture was stirred at 0° C. for 1 h, quenched with water and extracted with ethyl acetate. The extract was dried over $Na_2SO_4$, and concentrated. The residue was purified by flash chromatography eluting with ethyl acetate/hexanes (0-40%) to give the title compound (32 mg, 53%) as a colorless oil. LCMS (MM-ES+APCI, Pos): m/z 393.3 (M+H).

Step B. tert-butyl (1R,5R,6R)-6-methoxy-3,8-diazabicyclo[3.2.1]octane-8-carboxylate. A mixture of tert-butyl (1S,5S,6S)-3-(2,4-dimethoxybenzyl)-6-methoxy-3,8-diazabicyclo[3.2.1]octane-8-carboxylate (30 mg, 0.076 mmol), $Pd(OH)_2$ (30% on carbon, 7.2 mg, 0.015 mmol), and MeOH (1.9 mL) was stirred under a balloon of $H_2$ at rt for 2 h. The mixture was filtered through a pad of Celite and the Celite pad was rinsed with MeOH. The combined filtrate was concentrated to give the crude title compound as a colorless oil. LCMS (MM-ES+APCI, Pos): m/z 243.3 (M+H).

Step C. tert-butyl (1R,5R,6R)-6-methoxy-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of (S)-7-(3-(methoxymethoxy)naphthalen-1-yl)-2-((1-methylpyrrolidin-2-yl)methoxy)-5,6,7,8-tetrahydropyrido[3,4-d]pyrimidin-4-yl trifluoromethanesulfonate (37 mg, 0.063 mmol) in DCM (1.3 mL) was added tert-butyl (1S,5S,6S)-6-methoxy-3,8-diazabicyclo[3.2.1]octane-8-carboxylate (18 mg, 0.076 mmol) in DCM (1.3 mL) followed by $Et_3N$ (8.8 μL, 0.063 mmol). The mixture was stirred at rt for 16 h, concentrated, and purified by flash chromatography eluting with ethyl acetate/hexanes (0-100% with 5% $Et_3N$) to give the title compound (25 mg, 58%) as a brown solid. LCMS (MM-ES+APCI, Pos): m/z 675.3 (M+H).

Step D. 4-(4-((1R,5R,6R)-6-methoxy-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol. To a solution of 4-((1R,5R,6R)-6-methoxy-3,8-diazabicyclo[3.2.1]octan-3-yl)-7-(3-(methoxymethoxy)naphthalen-1-yl)-2-(((S)-1-methylpyrrolidin-2-yl)methoxy)-5,6,7,8-tetrahydropyrido[3,4-d]pyrimidine (25 mg, 0.037 mmol) in THE (0.75 mL) and MeOH (0.75 mL) was added HCl (6.0 M, 0.50 mL, 3.0 mmol). The mixture was stirred at 50° C. for 1 h, cooled to rt, basified with $Na_2CO_3$ (2.0 M), and extracted with DCM. The combined extracts were dried over $Na_2SO_4$, concentrated, and purified by preparative C18 HPLC (Gilson, 0-95% $CH_3CN/H_2O$ with 0.1% TFA). The desired fractions were combined and lyophilized to give the title compound (23 mg, 82%) as the TFA salt. LCMS (MM-ES+APCI, Pos): m/z 531.3 (M+H).

Example 38

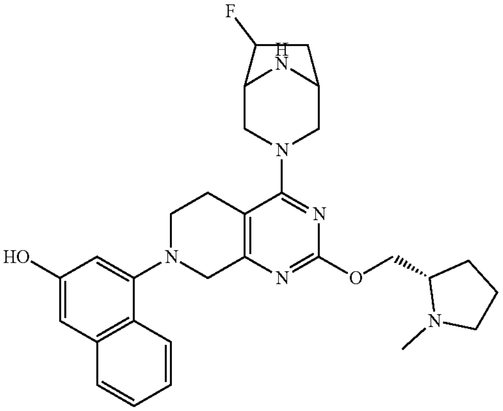 [SMILES: CN1CCC[C@H]1COc1nc2c(c(N3CC4CC(F)C(C3)N4)n1)CCN(c1cc(O)cc3ccccc13)C2]

4-(4-(6-fluoro-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol)

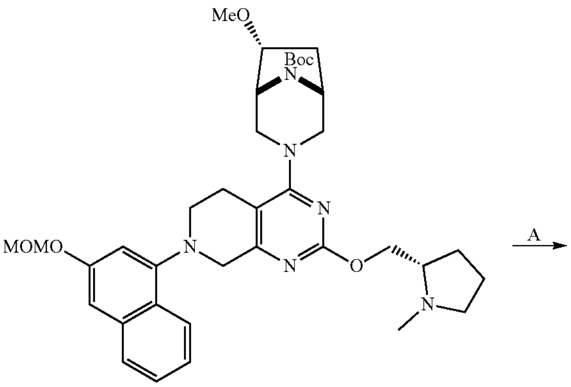

-continued

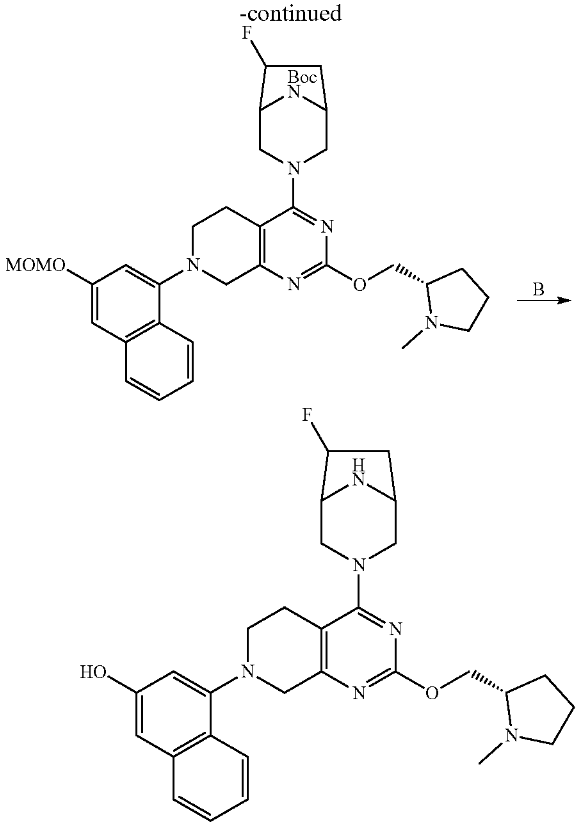

Step A. tert-butyl 6-fluoro-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of tert-butyl (1R,5R,6R)-6-hydroxy-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (16 mg, 0.024 mmol) in DCM (0.48 mL) at rt was added DAST (13 μL, 0.097 mmol). The mixture was stirred at rt for 4 h and concentrated. The residue was purified by preparative C18 HPLC (Gilson, 0-95% $CH_3CN/H_2O$ with 0.1% TFA). The desired fractions were combined, basified with $NaHCO_3$ (sat.), and extracted with DCM. The combined extracts were washed with brine, dried over $Na_2SO_4$, and concentrated to give the title compound (12 mg, 75%) as a brown solid. LCMS (MM-ES+APCI, Pos): m/z 663.3 (M+H).

Step B. 4-(4-(6-fluoro-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol. To a solution of tert-butyl (1R,5R,6R)-6-fluoro-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (15 mg, 0.023 mmol) in THE (0.75 mL) and MeOH (0.75 mL) was added HCl (6.0 M, 0.25 mL, 1.5 mmol). The mixture was stirred at 50° C. for 1 h, cooled to rt, and basified with $Na_2CO_3$ (2.0 M). The mixture was extracted with DCM/IPA (5:1) 4 times. The combined extracts were dried over $Na_2SO_4$, concentrated, and purified by preparative C18 HPLC (Gilson, 0-95% $CH_3CN/H_2O$ with 0.1% TFA). The desired fractions were combined and lyophilized to give the title compound (23 mg, 99%) as the TFA salt. LCMS (MM-ES+APCI, Pos): m/z 519.3 (M+H).

Example 39

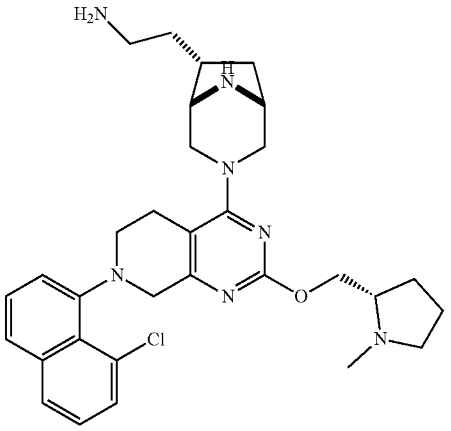

2-((1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)ethan-1-amine

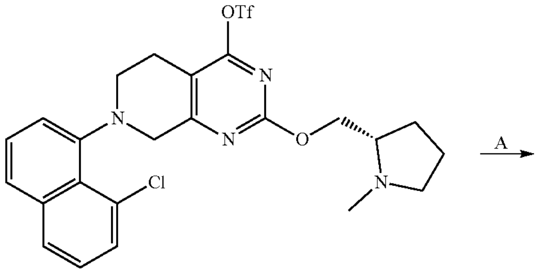

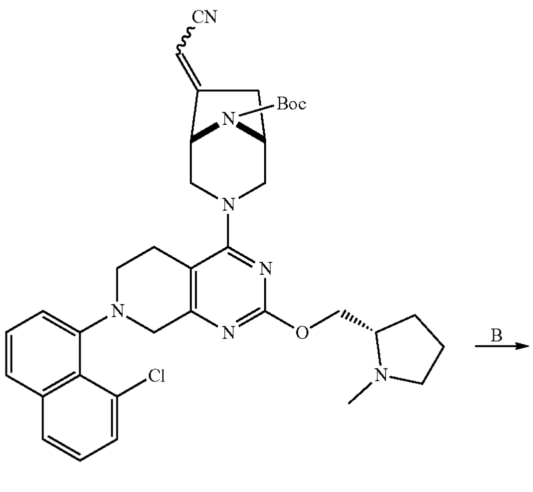

-continued

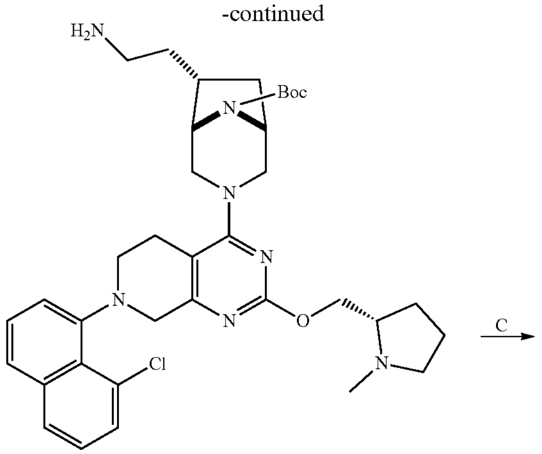

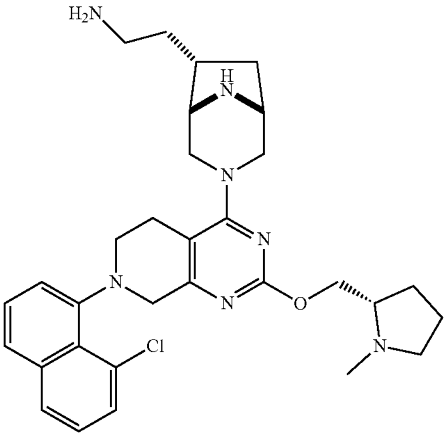

Step A. tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethylene)-3,8-diazabicyclo[3.2.1]octane-8-carboxylate. To a solution of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (17 mg, 0.025 mmol) in DCM (1.0 mL) were added tert-butyl (1R,5S)-6-(cyanomethylene)-3,8-diazabicyclo[3.2.1]octane-8-carboxylate hydrochloride (29 mg, 0.050 mmol) and $Et_3N$ (17 μL, 0.13 mmol). The mixture was stirred at rt for 14 h and heated in a closed vial at 45° C. for 5 h. The reaction was cooled to rt and purified by flash chromatography eluting with MeOH/EtOAc (0-10% with 3% $Et_3N$) to give the title compound (8.0 mg, 49%). LCMS (MM-ES+APCI, Pos): m/z 656.3 (M+H).

Step B. tert-butyl (1R,5S,6R)-6-(2-aminoethyl)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethylene)-3,8-diazabicyclo[3.2.1]octane-8-carboxylate (8.0 mg, 0.012 mmol) in THE (0.40 mL) at −40° C. was added L-Selectride (1.0 M in THF, 0.10 mL, 0.10 mmol). The mixture was stirred while maintaining a temperature between −35° C. and −45° C. for 1.5 h. The reaction was quenched with MeOH and concentrated to give the crude title compound as a yellow solid. LCMS (MM-ES+APCI, Pos): m/z 662.3 (M+H).

Step C. 2-((1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)ethan-1-amine. To crude tert-butyl (1R,5S,6R)-6-(2-aminoethyl)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate was added TFA (1.0 mL). The solution was stirred at rt for 15 min, concentrated, and purified by preparative C18 HPLC (Gilson, 0-95% $CH_3CN/H_2O$ with 0.1% TFA). The desired fractions were combined and lyophilized to give the title compound (5 mg, 50%) as a yellow solid as the TFA salt. LCMS (MM-ES+APCI, Pos): m/z 562.3 (M+H).

Example 40

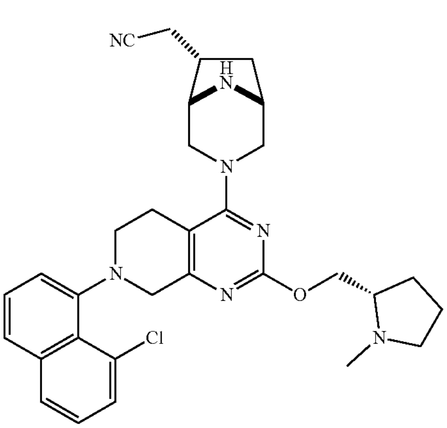

2-((1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)

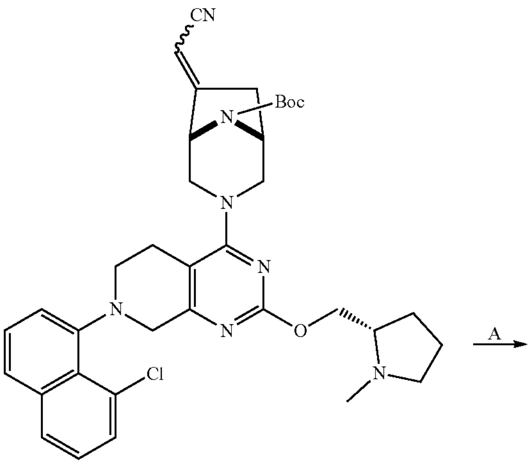

-continued

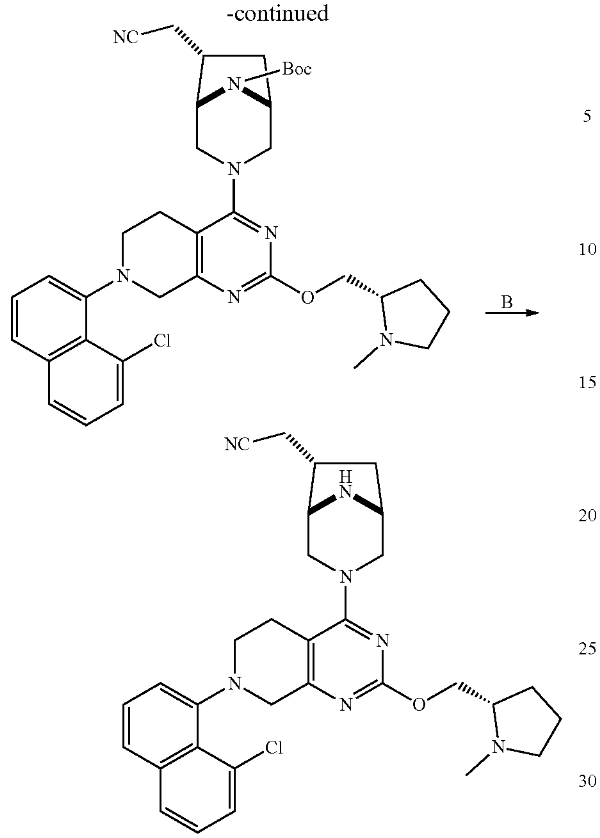

Step A. tert-butyl (1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethyl)-3,8-diazabicyclo[3.2.1]octane-8-carboxylate. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethylene)-3,8-diazabicyclo[3.2.1]octane-8-carboxylate (20 mg, 0.030 mmol) in THE (1.0 mL) at −60° C. was added dropwise of L-Selectride (1.0 M, 90 μL, 0.090 mmol). The mixture was warmed to −30° C. over 1 h and stirred between −30 and −20° C. for 0.5 h before quenching with MeOH. The mixture was concentrated and purified by preparative C18 HPLC (Gilson, 0-95% $CH_3CN/H_2O$ with 0.1% TFA). The desired fractions were combined and concentrated to remove $CH_3CN$, basified with $NaHCO_3$, and extracted with DCM. The combined extract was dried over $Na_2SO_4$ and concentrated to give the title compound (18 mg, 90%) as a white solid. LCMS (MM-ES+APCI, Pos): m/z 658.4 (M+H).

Step B. 2-((1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)acetonitrile. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethyl)-3,8-diazabicyclo[3.2.1]octane-8-carboxylate (18 mg, 0.027 mmol) in DCM (1.0 mL) was added TFA (1.0 mL). The solution was stirred at rt for 1 h, concentrated, and purified by preparative C18 HPLC (Gilson, 0-95% $CH_3CN/H_2O$ with 0.1% TFA). The desired fractions were combined and lyophilized to give the title compound (10 mg, 47%) the TFA salt. LCMS (MM-ES+APCI, Pos): m/z 558.3 (M+H).

Example 41

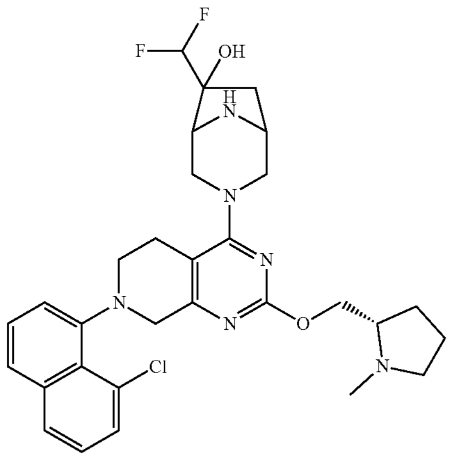 [SMILES: CN1CCC[C@H]1COc1nc2c(c(N3CC4CC(O)(C(F)F)C(C3)N4)n1)CCN(c1cccc3cccc(Cl)c13)C2]

3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(difluoromethyl)-3,8-diazabicyclo[3.2.1]octan-6-ol

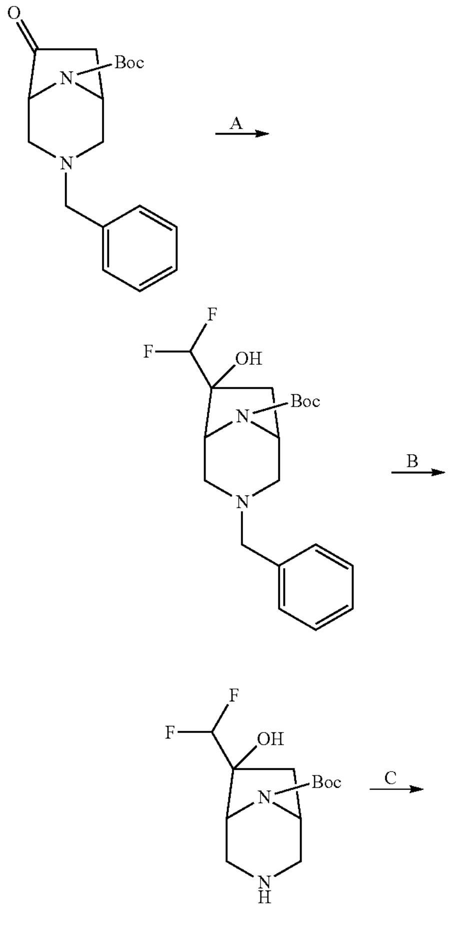

-continued

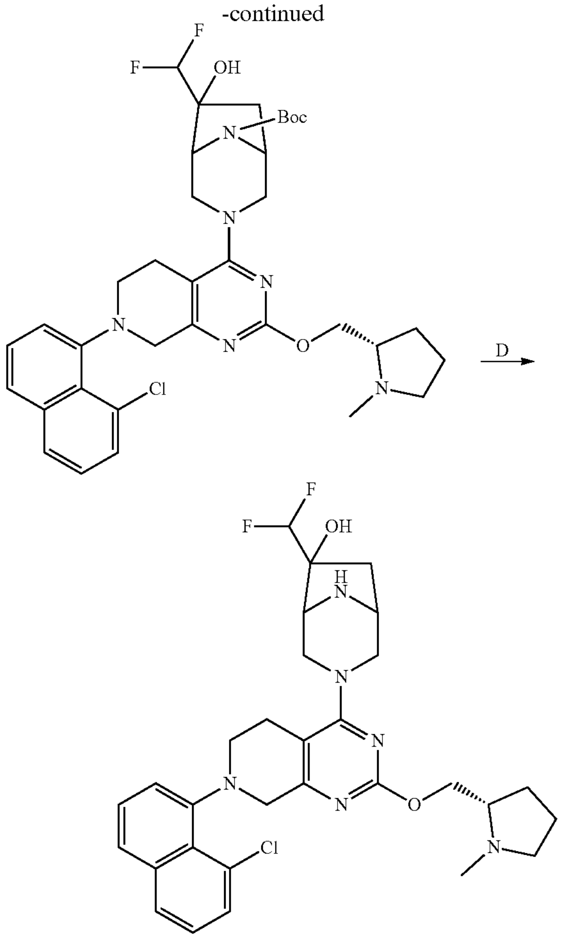

Step A. tert-butyl 3-benzyl-6-(difluoromethyl)-6-hydroxy-3,8-diazabicyclo[3.2.1]octane-8-carboxylate. To a solution of diethyl (difluoromethyl)phosphonate (0.32 mL, 2.0 mmol) in tetrahydrofuran (5.0 mL) at −75° C. was added LDA (2.0 M in THF, 1.0 mL, 2.00 mmol) dropwise. The mixture was stirred at −75° C. for 10 min and tert-butyl (1R,5R)-3-benzyl-6-oxo-3,8-diazabicyclo[3.2.1]octane-8-carboxylate (0.16 g, 0.50 mmol) was added. The mixture was stirred at −70° C. for 30 min, warmed to rt, and heated at 65° C. for 15 h. The mixture was cooled, concentrated, and purified by preparative C18 HPLC (Gilson, 0-95% $CH_3CN/H_2O$ with 0.1% TFA). The desired fractions were combined, basified with $NaHCO_3$ (sat.), and extracted with ethyl acetate. The extract was washed with water, washed with brine, dried with $Na_2SO_4$, and concentrated to give the title compound (100 mg, 54%) as a colorless oil. LCMS (MM-ES+APCI, Pos): m/z 369.3 (M+H).

Step B. tert-butyl 6-(difluoromethyl)-6-hydroxy-3,8-diazabicyclo[3.2.1]octane-8-carboxylate. A mixture of tert-butyl (1R,5R)-3-benzyl-6-(difluoromethyl)-6-hydroxy-3,8-diazabicyclo[3.2.1]octane-8-carboxylate (43 mg, 0.12 mmol), Pd (10% on carbon, 37 mg, 0.035 mmol) and MeOH (2.3 mL) was stirred under a balloon of $H_2$ at rt for 6 h. The reaction was quenched with Celite and the mixture was filtered through a short pad of Celite. The filtrate was concentrated to give the crude title compound (33 mg, 102%) as a colorless oil. LCMS (MM-ES+APCI, Pos): m/z 279.2 (M+H).

Step C. tert-butyl 3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(difluoromethyl)-6-hydroxy-3,8-diazabicyclo[3.2.1]octane-8-carboxylate. To a solution of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (30 mg, 0.043 mmol) in DCM (1.4 mL) at rt was added $Et_3N$ (18 μL, 0.13 mmol) followed by tert-butyl (1R,5R)-6-(difluoromethyl)-6-hydroxy-3,8-diazabicyclo[3.2.1]octane-8-carboxylate (24 mg, 0.086 mmol). The mixture was stirred at rt for 14 h and heated in a closed vial at 45° C. for 3 h. The reaction was cooled to rt, concentrated, and purified by flash chromatography eluting with 0→10% MeOH/DCM with 5% $NH_3{\cdot}H_2O$ as a modifier to give the title compound (16 mg, 54%) as a yellow solid. LCMS (MM-ES+APCI, Pos): m/z 685.3 (M+H).

Step D. 3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(difluoromethyl)-3,8-diazabicyclo[3.2.1]octan-6-ol. To a solution of tert-butyl (1R,5R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(difluoromethyl)-6-hydroxy-3,8-diazabicyclo[3.2.1]octane-8-carboxylate (19 mg, 0.028 mmol) in DCM (1.0 mL) was added TFA (1.0 mL). The solution was stirred at rt for 1 h, concentrated, and purified by preparative C18 HPLC (Gilson, 0-95% $CH_3CN/H_2O$ with 0.1% TFA). The desired fractions were combined and lyophilized to give the title compound (5 mg, 31%) as the TFA salt. LCMS (MM-ES+APCI, Pos): m/z 585.3 (M+H).

Example 42

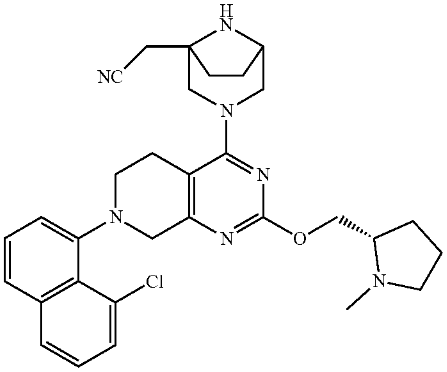 [SMILES: CN1CCC[C@H]1COc1nc2c(c(N3CC4CCC(CC#N)(C3)N4)n1)CCN(c1cccc3cccc(Cl)c13)C2]

2-(3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-1-yl)acetonitrile

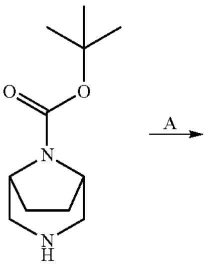

-continued

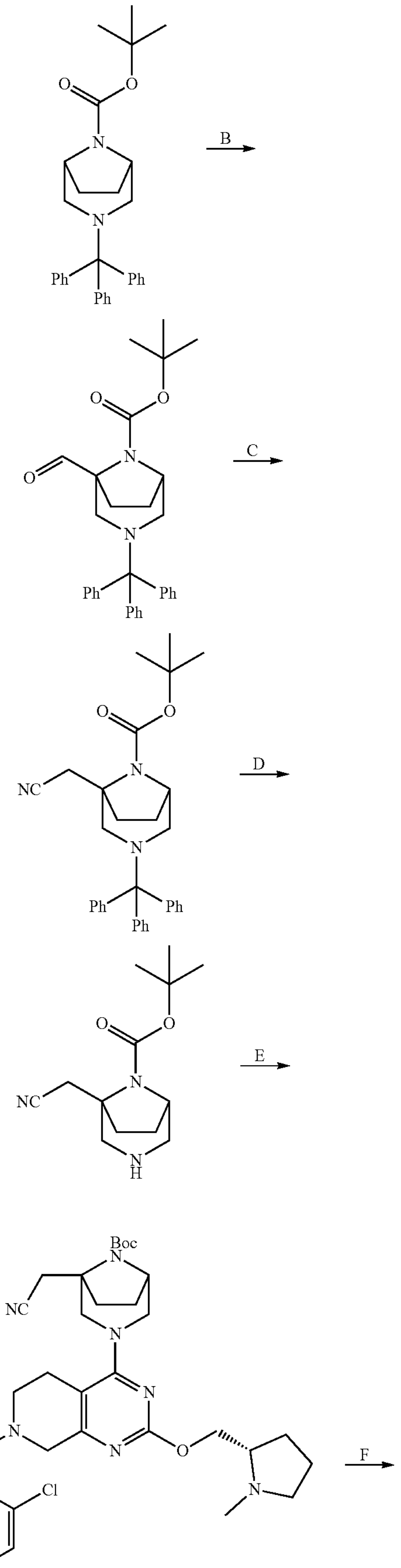

-continued

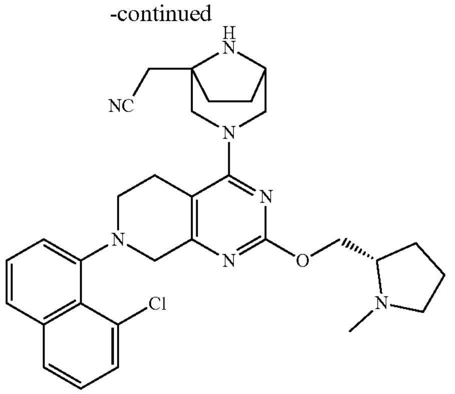

Step A. tert-butyl (1R,5S)-3-trityl-3,8-diazabicyclo[3.2.1]octane-8-carboxylate. To a solution of tert-butyl (1R,5S)-3,8-diazabicyclo[3.2.1]octane-8-carboxylate (1.0 g, 4.7 mmol) and triethyl amine (0.79 ml, 5.6 mmol) in DCM (23 mL) was added Trityl-Cl (1.4 g, 5.0 mmol) and the reaction stirred at rt for 1 day. Additional tert-butyl (1R,5S)-3,8-diazabicyclo[3.2.1]octane-8-carboxylate (0.40 g) was added and the reaction stirred for 8 h. The reaction diluted with DCM and washed with water and brine. The organics were concentrated to a residue and purified by flash chromatography eluting with 0→50% EtOAc/Hex to give product (2.0 g, 93%).

Step B. tert-butyl 1-formyl-3-trityl-3,8-diazabicyclo[3.2.1]octane-8-carboxylate. To a suspension of tert-butyl (1R,5S)-3-trityl-3,8-diazabicyclo[3.2.1]octane-8-carboxylate (1.4 g, 3.0 mmol) and N,N,N',N'-tetramethylethylenediamine (0.77 mL, 5.1 mmol) in diethyl ether (20 mL) at 0° C. was added s-BuLi (3.6 mL, 5.1 mmol). The mixture was stirred at 0° C. for 1.5 h to give an orange suspension. Ethyl formate (0.73 mL, 9.0 mmol) was added and the mixture was stirred at 0° C. for 15 min before the reaction was quenched with $NH_4Cl$ (sat.). The mixture was diluted with EtOAc and washed with water. The organic layer was dried over $Na_2SO_4$, filtered, concentrated, and purified by flash chromatography eluting with 0-20% ethyl acetate/hexanes to give the desired product (0.69 g, 48%) as a white solid. LCMS (MM-ES+APCI, Pos): m/z 185.2 $(M+H-Ph_3C\text{-}isobutene)^+$.

Step C. tert-butyl 1-(cyanomethyl)-3-trityl-3,8-diazabicyclo[3.2.1]octane-8-carboxylate. To a flask containing KOtBu (1.0 M in THF, 0.88 mL, 0.88 mmol) at −50° C. was added tosylmethyl isocyanide (98 mg, 0.50 mmol). The mixture was stirred at this temperature for 15 min and a solution of tert-butyl 1-formyl-3-trityl-3,8-diazabicyclo[3.2.1]octane-8-carboxylate (0.12 g, 0.25 mmol) in THE (2.5 mL) was added. The mixture was stirred at −50° C. for 1 h and MeOH (0.10 mL) was added. The mixture was warmed to rt, stirred at rt for 1 h, and heated at 60° C. for 30 min. The mixture was cooled to rt, quenched with $NH_4Cl$ (sat.), and extracted with ethyl acetate. The extract was dried over $Na_2SO_4$, concentrated, and purified by flash chromatography eluting with ethyl acetate/hexanes (0-30%) to give the title compound (0.11 g, 85%) as a colorless oil. LCMS (MM-ES+APCI, Pos): m/z 196.0 $(M+3H—CPh_3\text{-}tBu)$.

Step D. tert-butyl 1-(cyanomethyl)-3,8-diazabicyclo[3.2.1]octane-8-carboxylate.

To a solution of tert-butyl 1-(cyanomethyl)-3-trityl-3,8-diazabicyclo[3.2.1]octane-8-carboxylate (0.10 g, 0.20 mmol) in 1,4-dioxane (4 mL) at rt was added HCl (1.0 M, 1.2 mL, 1.2 mmol). The mixture was stirred at rt for 2 h, quenched with solid $NaHCO_3$ (102 mg, 1.2 mmol), and stirred at rt for 10 min. The mixture was concentrated, and the residue was extracted with DCM and filtered. The filtrate was concentrated to give the crude title compound (83 mg, 80%) as a white solid.

Step E. tert-butyl 3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(cyanomethyl)-3,8-diazabicyclo[3.2.1]octane-8-carboxylate. To a solution of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (25 mg, 0.045 mmol) in DCM (0.90 mL) at rt was added tert-butyl 1-(cyanomethyl)-3,8-diazabicyclo[3.2.1]octane-8-carboxylate (34 mg, 0.067 mmol) followed by $Et_3N$ (19 μL, 0.13 mmol). The mixture was stirred at 40° C. for 2 h, concentrated, and purified by preparative C18 HPLC (Gilson, 0-95% $CH_3CN/H_2O$ with 0.1% TFA). The desired fractions were combined and lyophilized to give the title compound (8 mg, 23%) as a yellow solid. LCMS (MM-ES+APCI, Pos): m/z 658.3 (M+H).

Step F. 2-(3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-1-yl)acetonitrile. To a solution of tert-butyl (1R,5R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(cyanomethyl)-3,8-diazabicyclo[3.2.1]octane-8-carboxylate 2,2,2-trifluoroacetate (8.0 mg, 0.012 mmol) in DCM (1 mL) was added TFA (0.5 mL). The solution was stirred at rt for 1 h, concentrated, and purified by preparative C18 HPLC (Gilson, 0-95% $CH_3CN/H_2O$ with 0.1% TFA). The desired fractions were combined and lyophilized to give the title compound (5 mg, 53%) as the TFA salt. LCMS (MM-ES+APCI, Pos): m/z 558.3 (M+H).

Example 43

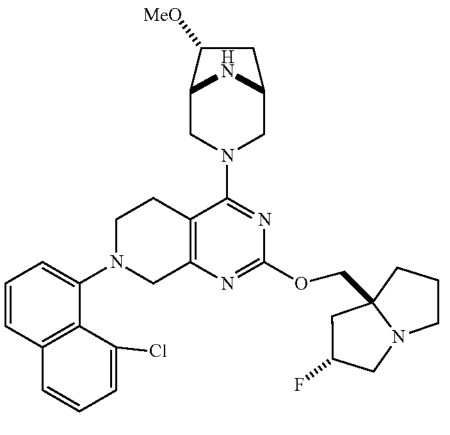

7-(8-chloronaphthalen-1-yl)-2-((2-fluorotetrahydro-1H-pyrrolizin-7a(5H)-yl)methoxy)-4-((1R,5R,6R)-6-methoxy-3,8-diazabicyclo[3.2.1]octan-3-yl)-5,6,7,8-tetrahydropyrido[3,4-d]pyrimidine (racemic, trans)

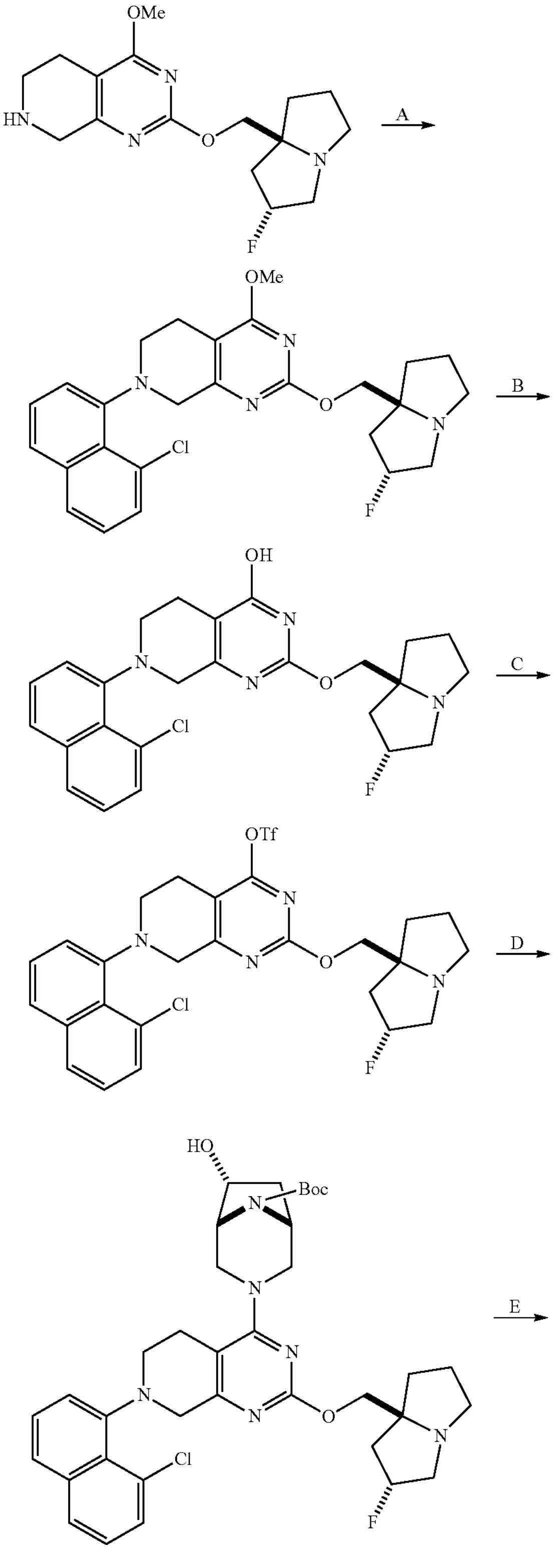

-continued

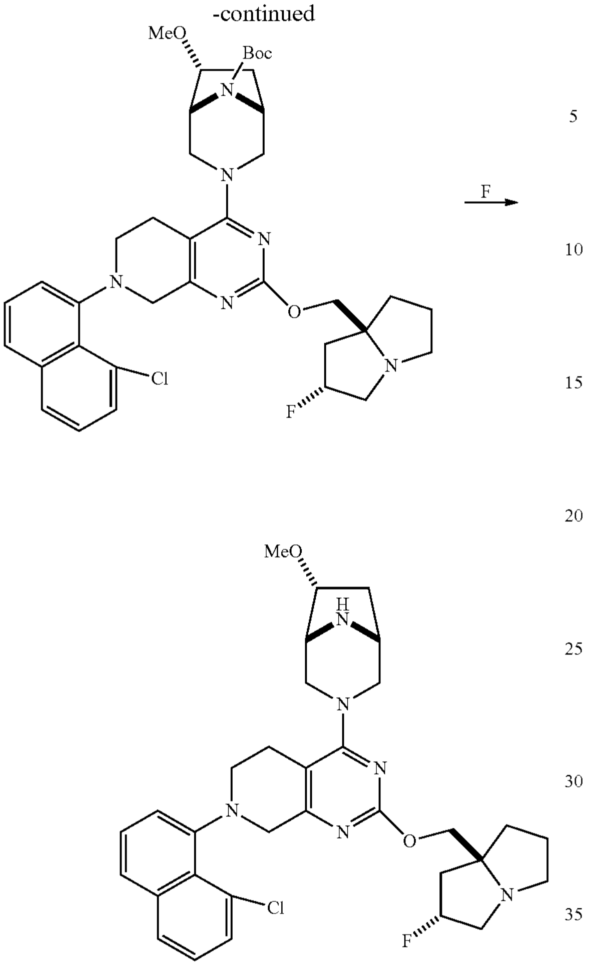

Step A. 7-(8-chloronaphthalen-1-yl)-2-((2-fluorotetrahydro-1H-pyrrolizin-7a(5H)-yl)methoxy)-4-methoxy-5,6,7,8-tetrahydropyrido[3,4-d]pyrimidine (racemic, trans). A mixture of 2-((2-fluorotetrahydro-1H-pyrrolizin-7a(5H)-yl)methoxy)-4-methoxy-5,6,7,8-tetrahydropyrido[3,4-d]pyrimidine (racemic, trans) (0.59 g, 1.8 mmol), $Cs_2CO_3$ (1.2 g, 3.7 mmol), and 1-bromo-8-chloronaphthalene (0.88 g, 3.7 mmol) in 1,4-dioxane (18 mL) was sparged with $N_2$. $Pd_2(dba)_3$ (0.17 g, 0.18 mmol) and Xantphos (0.21 g, 0.37 mmol) were added and the mixture was stirred at 95° C. for 17 h. The reaction mixture was cooled to rt, quenched with ethyl acetate, and filtered. The filtrate was concentrated and purified by flash chromatography eluting with 0→20% MeOH/DCM with 2% $NH_4OH$ as a modifier to give the title compound (0.45 g, 51%) as a brown solid. LCMS (MM-ES+APCI, Pos): m/z 483.2 (M+H).

Step B. 7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-ol (racemic, trans). A mixture of 7-(8-chloronaphthalen-1-yl)-2-((2-fluorotetrahydro-1H-pyrrolizin-7a(5H)-yl)methoxy)-4-methoxy-5,6,7,8-tetrahydropyrido[3,4-d]pyrimidine (racemic, trans) (0.44 g, 0.91 mmol), NaSMe (0.26 g, 3.6 mmol), and DMA (13 mL) was heated at 80° C. for 4 h, cooled to rt, quenched with water (70 mL), and extracted with ethyl acetate/IPA (5:1). The combined extracts were washed with water, washed with brine, dried over $Na_2SO_4$, and concentrated to give the crude title compound. LCMS (MM-ES+APCI, Pos): m/z 469.3 (M+H).

Step C. 7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl trifluoromethanesulfonate (racemic, trans). To a solution of 7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-ol (racemic, trans) (0.28 g, 0.60 mmol) in DCM (6.0 mL) at −50° C. was added DIPEA (0.21 mL, 1.2 mmol), followed by dropwise addition of $Tf_2O$ (0.15 mL, 0.90 mmol). The mixture was warmed to −30° C. over 1 h, quenched with $NaHCO_3$ (sat.), and extracted with DCM. The extract was dried over $Na_2SO_4$, concentrated, and purified by flash chromatography eluting with ethyl acetate/hexanes (0-100%) to give the title compound (0.28 g, 77%) as a white solid. LCMS (MM-ES+APCI, Pos): m/z 601.2 (M+H).

Step D. tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-hydroxy-3,8-diazabicyclo[3.2.1]octane-8-carboxylate (racemic, trans). To a solution of 7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl trifluoromethanesulfonate (racemic, trans) (0.11 g, 0.18 mmol) in DMA (1.8 mL) at rt was added tert-butyl (1R,5R,6R)-6-hydroxy-3,8-diazabicyclo[3.2.1]octane-8-carboxylate (40 mg, 0.18 mmol) followed by $Et_3N$ (37 μL, 0.26 mmol). The mixture was stirred at rt for 15 h, diluted with ethyl acetate, and washed with $NaHCO_3$ (sat.), water, and brine. The ethyl acetate layer was dried over $Na_2SO_4$ and concentrated to give crude the title compound (0.13 g, 109%) as a light orange solid. LCMS (MM-ES+APCI, Pos): m/z 679.3 (M+H).

Step E. tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-methoxy-3,8-diazabicyclo[3.2.1]octane-8-carboxylate. To a solution of tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-hydroxy-3,8-diazabicyclo[3.2.1]octane-8-carboxylate (racemic, trans) (20 mg, 0.029 mmol) in DMA (1 mL) at 0° C. was added MeI (7.4 μL, 0.12 mmol) followed by NaH (60%, 3.5 mg, 0.088 mmol). The mixture was stirred at 0° C. for 1 h and quenched with ethyl acetate. The organics were washed with water, washed with brine, and dried over $Na_2SO_4$. The solution was concentrated to give the crude title compound as a yellow oil. LCMS (MM-ES+APCI, Pos): m/z 693.3 (M+H).

Step F. 7-(8-chloronaphthalen-1-yl)-2-((2-fluorotetrahydro-1H-pyrrolizin-7a(5H)-yl)methoxy)-4-((1R,5R,6R)-6-methoxy-3,8-diazabicyclo[3.2.1]octan-3-yl)-5,6,7,8-tetrahydropyrido[3,4-d]pyrimidine (racemic, trans). To a solution of crude tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-methoxy-3,8-diazabicyclo[3.2.1]octane-8-carboxylate (racemic, trans) (0.020 g, 0.029 mmol) in DCM (1.0 mL) was added TFA (0.5 mL). The solution was stirred at rt for 30 min, concentrated, and purified by preparative C18 HPLC (Gilson, 0-95% $CH_3CN/H_2O$ with 0.1% TFA). The desired fractions were combined and lyophilized to give the title compound (8 mg, 32% over 2 steps) as the TFA salt. LCMS (MM-ES+APCI, Pos): m/z 593.2 (M+H).

Example 44

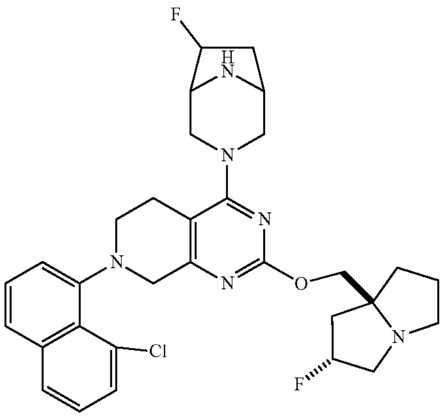

7-(8-chloronaphthalen-1-yl)-4-(6-fluoro-3,8-diazabicyclo[3.2.1]octan-3-yl)-2-((2-fluorotetrahydro-1H-pyrrolizin-7a(5H)-yl)methoxy)-5,6,7,8-tetrahydropyrido[3,4-d]pyrimidine (racemic, trans)

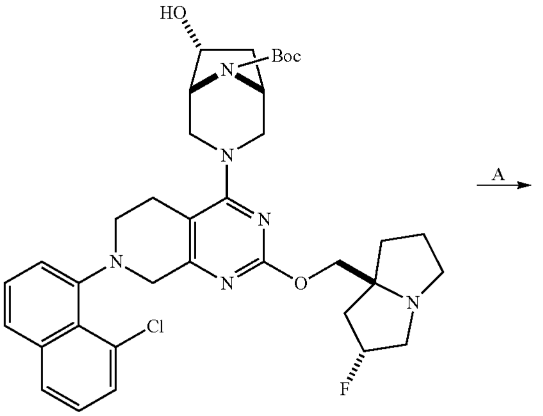

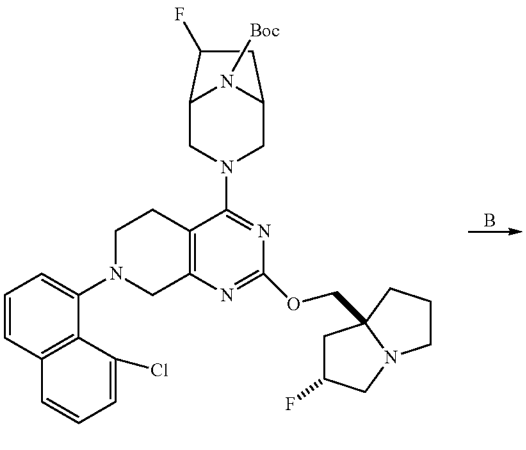

-continued

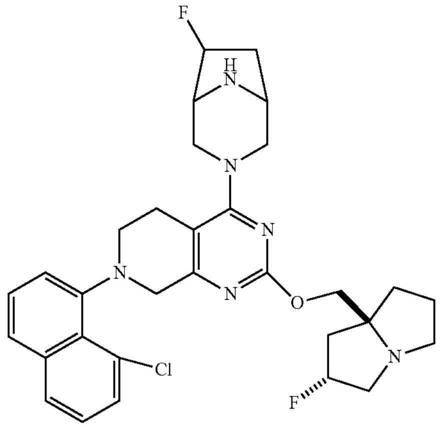

Step A. tert-butyl 3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-fluoro-3,8-diazabicyclo[3.2.1]octane-8-carboxylate (racemic, trans). To a solution of tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-hydroxy-3,8-diazabicyclo[3.2.1]octane-8-carboxylate (racemic, trans) (35 mg, 0.052 mmol) in DCM (1 mL) in a Teflon vial at rt was added DAST (27 μL, 0.21 mmol). The mixture was stirred at rt for 4 h and quenched with $NaHCO_3$ (sat.). The mixture was extracted with DCM and the extract was dried over $Na_2SO_4$. The residue was concentrated to give a crude mixture of starting material and title compound as a light brown solid. LCMS (MM-ES+APCI, Pos): m/z 681.3 (M+H).

Step B. 7-(8-chloronaphthalen-1-yl)-4-(6-fluoro-3,8-diazabicyclo[3.2.1]octan-3-yl)-2-((2-fluorotetrahydro-1H-pyrrolizin-7a(5H)-yl)methoxy)-5,6,7,8-tetrahydropyrido[3,4-d]pyrimidine (racemic, trans). To a solution of a mixture of tert-butyl (1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-hydroxy-3,8-diazabicyclo[3.2.1]octane-8-carboxylate (racemic, trans) and tert-butyl 3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-6-fluoro-3,8-diazabicyclo[3.2.1]octane-8-carboxylate (racemic, trans) in DCM (1.0 mL) was added TFA (0.50 mL). The solution was stirred at rt for 30 min, concentrated, and purified by preparative C18 HPLC (Gilson, 0-95% $CH_3CN/H_2O$ with 0.1% TFA). The desired fractions were combined and lyophilized to give the title compound (4 mg, 10%) as the TFA salt. LCMS (MM-ES+APCI, Pos): m/z 581.2 (M+H).

Example 45

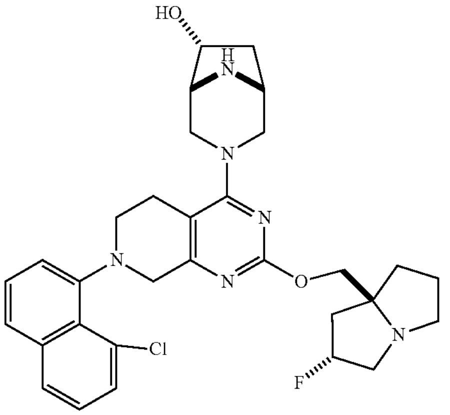

(1R,5R,6R)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octan-6-ol (racemic, trans)

Isolated in Synthesis of Example 44, Step B (28 mg, 67%) as the TFA salt. LCMS (MM-ES+APCI, Pos): m/z 579.3 (M+H).

Example 46

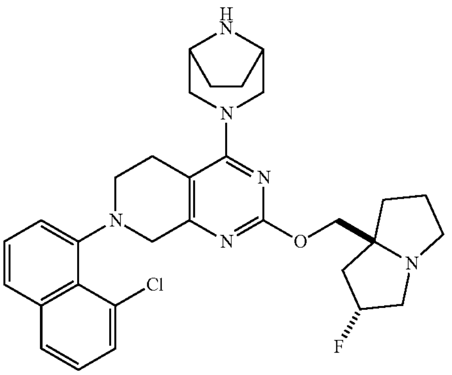

4-((1R,5S)-3,8-diazabicyclo[3.2.1]octan-3-yl)-7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans)

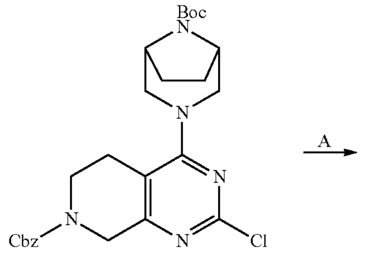

-continued

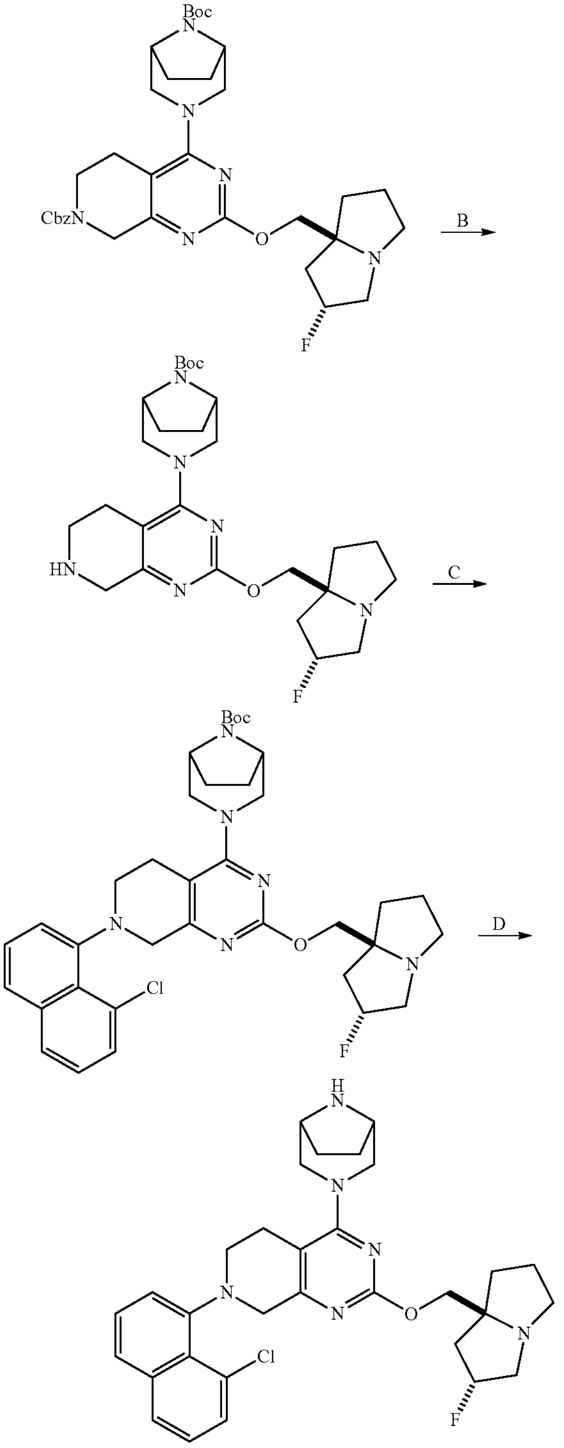

Step A. benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans). To a stirred mixture of benzyl 4-((1R,5S)-8-(tert-butoxycarbonyl)-3,8-diazabicyclo[3.2.1]octan-3-yl)-2-chloro-5,8-dihydropyrido[3,4-d]pyrimidine-7(6H)-carboxylate (0.50 g, 0.97 mmol), (2-fluorotetrahydro-1H-pyrrolizin-7a(5H)-yl)methanol (racemic, trans) (0.23 g, 1.5 mmol), and BINAP (0.12 g, 0.19 mmol) in toluene (5 mL) at room temperature under argon was added Cs2CO3 (0.95 g, 2.9 mmol). The reaction was sparged with argon for 5 minutes and palladium (II) acetate (22 mg, 0.10 mmol) was added. The mixture was heated to 100° C. and stirred for 3 hours. After cooled to room temperature, the reaction mixture was partitioned between EtOAc and water. The organics were washed with brine, dried over Na2SO4, and concentrated in vacuo. The concentrate was purified by normal phase chromatography (0→20% MeOH/DCM with 2% $NH_4OH$ as a modifier) to give benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans) (0.49 g, 79% yield). LCMS (MM-ES+APCI, Pos): m/z 637.4 (M+H).

Step B. tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). A solution of benzyl 4-((1R,5S)-8-(tert-butoxycarbonyl)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidine-7(6H)-carboxylate (racemic, trans) (0.49 g, 0.77 mmol) in EtOH (7.6 mL) and THE (7.6 mL) was purged with $N_2$ for 5 minutes. To this solution was added palladium 10 wt. % (dry basis, activated carbon, wet, Degussa) (40 mg, 0.38 mmol). The reaction was capped and purged with $N_2$ for 5 minutes. The mixture was stirred under a $H_2$ atmosphere overnight. The mixture was diluted with MeOH and filtered through packed Celite. The filtrate was concentrated in vacuo and purified by normal phase chromatography (0→20% MeOH/DCM with 2% $NH_4OH$ as modifier) to give tert-butyl(1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (0.18 g, 47% yield). LCMS (MM-ES+APCI, Pos): m/z 503.3 (M+H).

Step C. tert-butyl (1R,5S)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans). A mixture of tert-butyl (1R,5S)-3-(2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (90 mg, 0.18 mmol), 1-bromo-8-chloronaphthalene (87 mg, 0.36 mmol), $Cs_2CO_3$ (0.23 g, 0.72 mmol) in 1,4-dioxane (1.2 mL) was sparged with nitrogen for 15 minutes and treated with tris(dibenzylideneacetone)dipalladium (0) (16 mg, 0.02 mmol) and 9,9-dimethyl-4,5-bis(dipheyl-phosphino)xanthene (21 mg, 0.04 mmol). The mixture was stirred at 100° C. for 6 hours, cooled to room temperature, and was partitioned between EtOAc and water. The combined organics were washed with brine, dried over $Na_2SO_4$, and concentrated in vacuo. The concentrate was purified by normal phase chromatography (0%→15% DCM/MeOH+2% $NH_4OH$) to give tert-butyl (1R,5S)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (71 mg, 60% yield). LCMS (MM-ES+APCI, Pos): m/z 663.3 (M+H).

Step D. 4-((1R,5S)-3,8-diazabicyclo[3.2.1]octan-3-yl)-7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans). Tert-butyl (1R,5S)-3-(7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (racemic, trans) (71 mg, 0.12 mmol) was dissolved in methanol (1 mL) and treated with hydrochloric acid (4.0 M in 1,4-dioxane) (0.21 mL, 0.86 mmol). The reaction was stirred at room temperature for 3 hours. The reaction was concentrated in vacuo and purified by prep HPLC (Gilson, 5>95% ACN/TFA with 0.1% TFA as a modifier). The fractions containing the desired product were lyophilized to give 4-((1R,5S)-3,8-diazabicyclo[3.2.1]octan-3-yl)-7-(8-chloronaphthalen-1-yl)-2-((2-fluorotetrahydro-1H-pyrrolizin-7a(5H)-yl)methoxy)-5,6,7,8-tetrahydropyrido[3,4-d]pyrimidine (racemic, trans) (30 mg, 35% yield) as the TFA salt. LCMS (MM-ES+APCI, Pos): m/z 563.3 (M+H).

Example 47

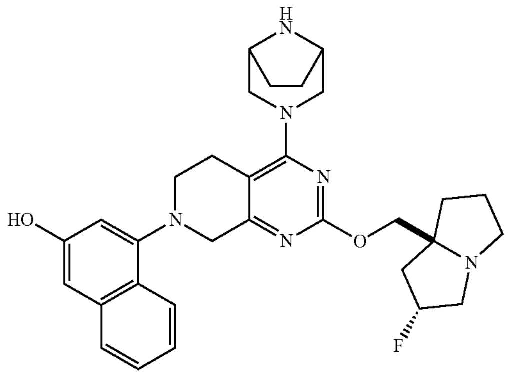

4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)naphthalen-2-ol (racemic, trans)

Synthesized according to Example 46 substituting 3-(methoxymethoxy)naphthalen-1-yl trifluoromethanesulfonate in place of 1-bromo-8-chloronaphthalene in step C to afford 4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)naphthalen-2-ol (racemic, trans) (51 mg 49% yield) as the TFA salt. LCMS (MM-ES+APCI, Pos): m/z 545.3 (M+H).

Example 48

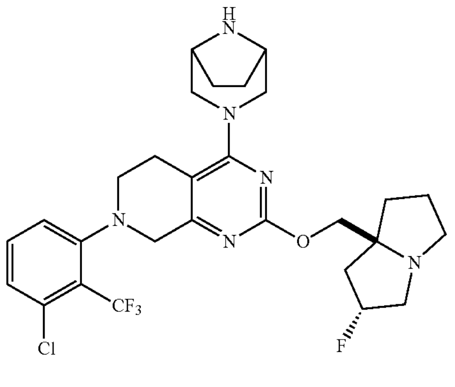

4-((1R,5S)-3,8-diazabicyclo[3.2.1]octan-3-yl)-7-(3-chloro-2-(trifluoromethyl)phenyl)-2-((2-fluorotetrahydro-1H-pyrrolizin-7a(5H)-yl)methoxy)-5,6,7,8-tetrahydropyrido[3,4-d]pyrimidine (racemic, trans)

Synthesized according to Example 46 substituting 1-bromo-3-chloro-2-(trifluoromethyl)benzene in place of 1-bromo-8-chloronaphthalene in step C to afford 4-((1R,5S)-3,8-diazabicyclo[3.2.1]octan-3-yl)-7-(3-chloro-2-(trifluoromethyl)phenyl)-2-((2-fluorotetrahydro-1H-pyrrolizin-7a(5H)-yl)methoxy)-5,6,7,8-tetrahydropyrido[3,4-d]pyrimidine (racemic, trans) as the TFA salt (18 mg, 39% yield). LCMS (MM-ES+APCI, Pos): m/z 581.3 (M+H).

Example 49

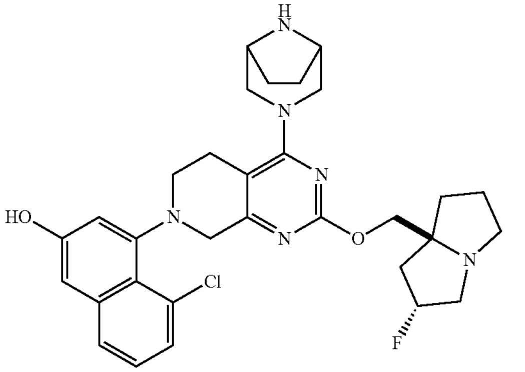

4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)-5-chloronaphthalen-2-ol (racemic, trans)

Synthesized according to Example 46 substituting 1-bromo-8-chloro-3-(methoxymethoxy)naphthalene in place of 1-bromo-8-chloronaphthalene in step C to afford 4-(4-((1R,5S)-3,8-diazabicyclo[3.2.1]octan-3-yl)-2-((2-fluorotetrahydro-1H-pyrrolizin-7a(5H)-yl)methoxy)-5,8-dihydropyrido[3,4-d]pyrimidin-7(6H)-yl)-5-chloronaphthalen-2-ol (racemic, trans) as the TFA salt (12 mg, 30% yield). LCMS (MM-ES+APCI, Pos): m/z 579.3 (M+H).

Example 50

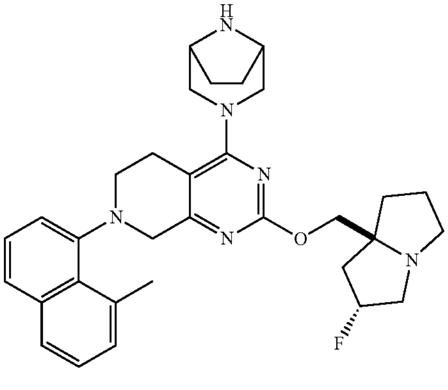

4-((1R,5S)-3,8-diazabicyclo[3.2.1]octan-3-yl)-2-((2-fluorotetrahydro-1H-pyrrolizin-7a(5H)-yl)methoxy)-7-(8-methylnaphthalen-1-yl)-5,6,7,8-tetrahydropyrido[3,4-d]pyrimidine (racemic, trans)

Synthesized according to Example 46 substituting 1-bromo-8-methylnaphthalene in place of 1-bromo-8-chloronaphthalene in step C to afford 4-((1R,5S)-3,8-diazabicyclo[3.2.1]octan-3-yl)-2-((2-fluorotetrahydro-1H-pyrrolizin-7a(5H)-yl)methoxy)-7-(8-methylnaphthalen-1-yl)-5,6,7,8-tetrahydropyrido[3,4-d]pyrimidine (racemic, trans) as the TFA salt (19 mg, 33% yield). LCMS (MM-ES+APCI, Pos): m/z 543.3 (M+H).

Example 51

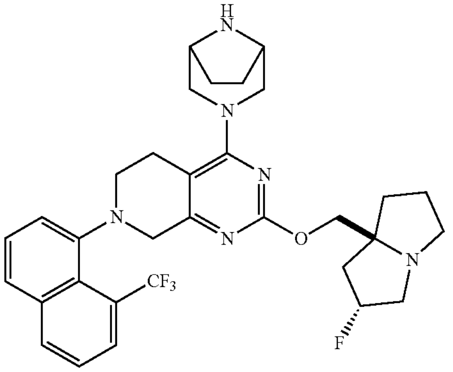

4-((1R,5S)-3,8-diazabicyclo[3.2.1]octan-3-yl)-2-((2-fluorotetrahydro-1H-pyrrolizin-7a(5H)-yl)methoxy)-7-(8-(trifluoromethyl)naphthalen-1-yl)-5,6,7,8-tetrahydropyrido[3,4-d]pyrimidine (racemic, trans)

Synthesized according to Example 46 substituting 8-(trifluoromethyl)naphthalen-1-yl trifluoromethanesulfonate in place of 1-bromo-8-chloronaphthalene in step C to afford 4-((1R,5S)-3,8-diazabicyclo[3.2.1]octan-3-yl)-2-((2-fluorotetrahydro-1H-pyrrolizin-7a(5H)-yl)methoxy)-7-(8-(trifluoromethyl)naphthalen-1-yl)-5,6,7,8-tetrahydropyrido[3,4-d]pyrimidine (racemic, trans) as the TFA salt (2.3 mg, 9% yield). LCMS (MM-ES+APCI, Pos): m/z 597.4 (M+H).

Example 52

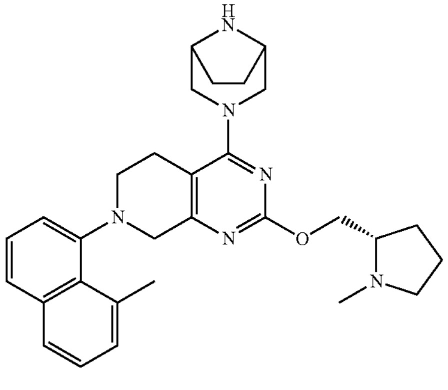 [SMILES: Cc1cccc2cccc(N3CCc4c(nc(OC[C@@H]5CCCN5C)nc4N4CC5CCC(C4)N5)C3)c12]

4-((1R,5S)-3,8-diazabicyclo[3.2.1]octan-3-yl)-7-(8-methylnaphthalen-1-yl)-2-(((S)-1-methylpyrrolidin-2-yl)methoxy)-5,6,7,8-tetrahydropyrido[3,4-d]pyrimidine

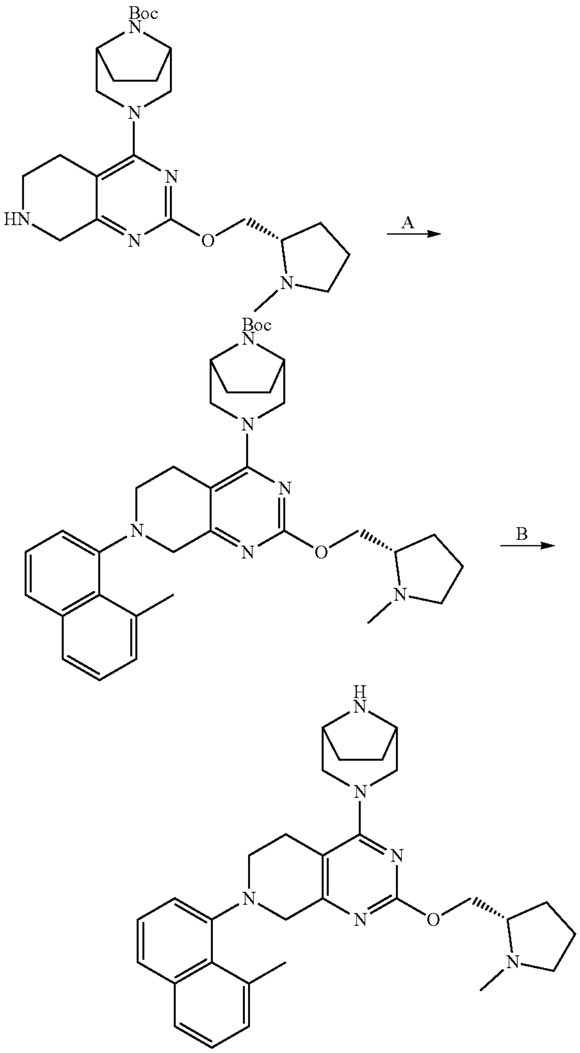

Step A. tert-butyl (1R,5S)-3-(7-(8-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Tris(dibenzylideneacetone)dipalladium(0) (20 mg, 0.22 mmol) and 9,9-dimethyl-4,5-bis(diphenylphosphino)xanthene (25 mg, 0.44 mmol) were dissolved in 1,4-dioxane (1 mL) and purged under argon for 5 minutes. The reaction was stirred at 100° C. under argon for 15 minutes and cooled to room temperature. To the reaction was added tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (50 mg, 0.11 mmol), 1-bromo-8-methylnaphthalene (72 mg, 0.33 mmol), and cesium carbonate (0.11 g, 0.33 mmol) under argon. The reaction was capped and stirred at 100° C. overnight. The reaction was cooled to room temperature and filtered through GF/F paper. The filtrate was concentrated in vacuo and purified by normal phase chromatography 2 times using 0→75% Hexanes/EtOAc as eluent to give tert-butyl (1R,5S)-3-(7-(8-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (35 mg, 54% yield). LCMS (MM-ES+APCI, Pos): m/z 599.3 (M+H).

Step B. 4-((1R,5S)-3,8-diazabicyclo[3.2.1]octan-3-yl)-7-(8-methylnaphthalen-1-yl)-2-(((S)-1-methylpyrrolidin-2-yl)methoxy)-5,6,7,8-tetrahydropyrido[3,4-d]pyrimidine. To a solution of tert-butyl (1R,5S)-3-(7-(8-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (35 mg, 0.060 mmol) in dichloromethane (0.6 mL) was added hydrochloric acid (4.0 M in 1,4-dioxane) (73 μL, 0.29 mmol). The mixture was stirred at room temperature for 6 hours. The mixture was concentrated in vacuo and purified by prep HPLC (Gilson, 5495% ACN/water with 0.1% TFA as a modifier). The fractions containing the desired product were lyophilized to give 4-((1R,5S)-3,8-diazabicyclo[3.2.1]octan-3-yl)-7-(8-methylnaphthalen-1-yl)-2-(((S)-1-methylpyrrolidin-2-yl)methoxy)-5,6,7,8-tetrahydropyrido[3,4-d]pyrimidine (6.3 mg, 22% yield) as the TFA salt. LCMS (MM-ES+APCI, Pos): m/z 499.4 (M+H).

Example 53

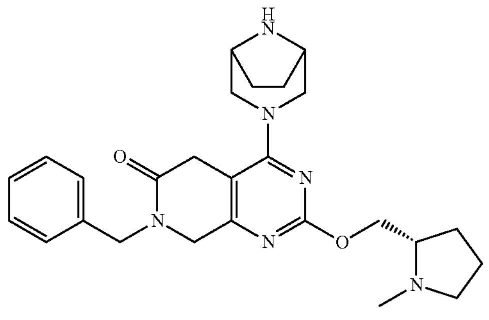 [SMILES: CN1CCC[C@H]1COc1nc2c(c(N3CC4CCC(C3)N4)n1)CC(=O)N(Cc1ccccc1)C2]

7-benzyl-4-((1R,5S)-3,8-diazabicyclo[3.2.1]octan-3-yl)-2-(((S)-1-methylpyrrolidin-2-yl)methoxy)-7,8-dihydropyrido[3,4-d]pyrimidin-6(5H)-one

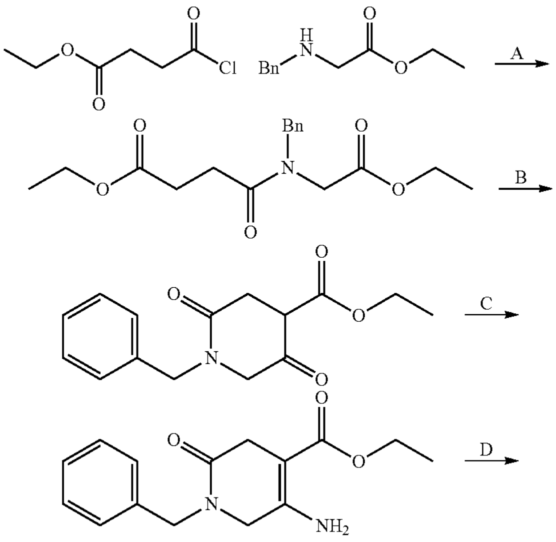

-continued

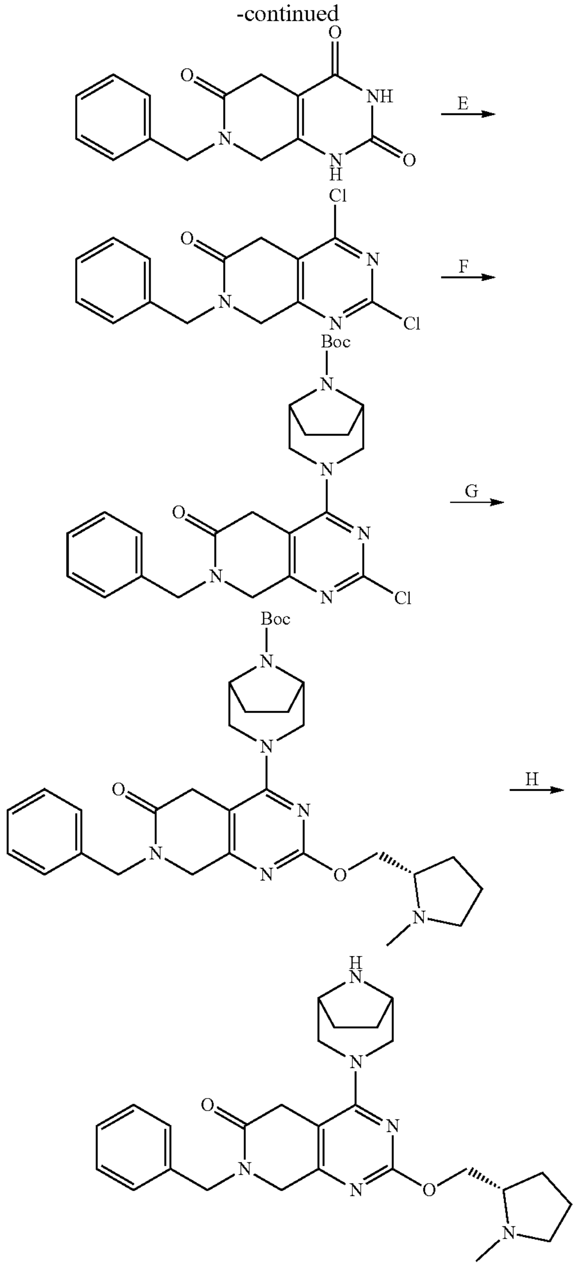

Step A. ethyl 4-(benzyl(2-ethoxy-2-oxoethyl)amino)-4-oxobutanoate. A solution of ethyl 4-chloro-4-oxobutanoate (25.0 g, 152 mmol) in toluene (240 mL) was added to ethyl benzyl glycinate (24 g, 122 mmol) in toluene (243 mL) at 0° C. To this mixture was added a 15% aq. $K_2CO_3$ solution (182 mL, 365 mmol). The mixture was warmed to RT and the pH was adjusted to 11-12 using a solution of $K_2CO_3$. The reaction was stirred at RT overnight. The reaction was acidified with 2N HCl and extracted with EtOAc (3×). The organic layer was dried over MgSO4 and concentrated to give ethyl 4-(benzyl(2-ethoxy-2-oxoethyl)amino)-4-oxobutanoate (30 g, 77%) as an oil that was used without purification. LCMS (MM-ES+APCI, Pos): m/z 322.1 (M+H).

Step B. ethyl 1-benzyl-5-hydroxy-2-oxo-1,2,3,6-tetrahydropyridine-4-carboxylate. A mixture of ethyl 4-(benzyl(2-ethoxy-2-oxoethyl)amino)-4-oxobutanoate (30 g, 93 mmol) and sodium ethoxide (21 wt %, 33 g, 103 mmol) in ethanol (470 mL) was heated at 100° C. for 24 hrs. The reaction mixture was cooled to ambient temperature, transferred to a separatory funnel, acidified with 2N HCl, and extracted with EtOAc 3 times. The combined organic layers were dried over $MgSO_4$ and concentrated to give ethyl 1-benzyl-5-hydroxy-2-oxo-1,2,3,6-tetrahydropyridine-4-carboxylate (30.0 g, 117%). LCMS (MM-ES+APCI, Pos): m/z 276.1 (M+H).

Step C. ethyl 5-amino-1-benzyl-2-oxo-1,2,3,6-tetrahydropyridine-4-carboxylate. A solution of ethyl 1-benzyl-2,5-dioxopiperidine-4-carboxylate (30 g, 110 mmol), ammonium acetate (25 g, 330 mmol) in ethanol (550 mL) was stirred at RT over 1 week. The reaction mixture was concentrated and partitioned between DCM/water. The layers were separated. The aqueous layer was extracted with DCM. The combined organic layers were dried over $MgSO_4$ and concentrated to give ethyl 5-amino-1-benzyl-2-oxo-1,2,3,6-tetrahydropyridine-4-carboxylate (25 g, 84%). LCMS (MM-ES+APCI, Pos): m/z 275.1 (M+H).

Step D. 7-benzyl-1,5,7,8-tetrahydropyrido[3,4-d]pyrimidine-2,4,6(3H)-trione. To a solution of ethyl 5-amino-1-benzyl-2-oxo-1,2,3,6-tetrahydropyridine-4-carboxylate (25 g, 91 mmol) in acetonitrile (460 mL) was added 2,2,2-trichloroacetyl isocyanate (17 g, 91 mmol) and the mixture was stirred at RT for 2 h. To this mixture was added ammonia (65 mL, 460 mmol) and the mixture was heated to 70° C. for 2 h. To the mixture at 70° C. was added 103 g of a 21 wt % of NaOEt in EtOH. The reaction mixture was cooled to RT and partitioned between DCM and water. The aqueous layer was acidified with 2N HCl and extracted with EtOAc 3 times. The combined organic layers were washed with brine, dried over $MgSO_4$, and concentrated to give 7-benzyl-1,5,7,8-tetrahydropyrido[3,4-d]pyrimidine-2,4,6(3H)-trione (8.6 g, 35%). LCMS (MM-ES+APCI, Pos): m/z 272.2 (M+H).

Step E. 7-benzyl-2,4-dichloro-7,8-dihydropyrido[3,4-d]pyrimidin-6(5H)-one. To a solution of 7-benzyl-1,5,7,8-tetrahydropyrido[3,4-d]pyrimidine-2,4,6(3H)-trione (1.0 g, 3.7 mmol) and DIEA (1.9 mL, 11 mmol) in DCE (37 mL) was added $POCl_3$ (1.4 mL, 15 mmol) and the reaction was heated to 70° C. overnight. The reaction mixture was concentrated to remove excess $POCl_3$. The residue was diluted with EtOAc and washed with water, $NaHCO_3$, and brine. The organic layer was dried over $MgSO_4$ and concentrated to give 7-benzyl-2,4-dichloro-7,8-dihydropyrido[3,4-d]pyrimidin-6(5H)-one (0.9 g, 79%). LCMS (MM-ES+APCI, Pos): m/z 308.0 (M+H).

Step F. tert-butyl (1R,5S)-3-(7-benzyl-2-chloro-6-oxo-5,6,7,8-tetrahydropyrido[3,4-d]pyrimidin-4-yl)-3,8-diazabicyclo[3.2.1]octane-8-carboxylate. A solution of 7-benzyl-2,4-dichloro-7,8-dihydropyrido[3,4-d]pyrimidin-6(5H)-one (0.90 g, 2.92 mmol), tert-butyl (1R,5S)-3,8-diazabicyclo[3.2.1]octane-8-carboxylate (0.62 g, 2.9 mmol) and triethylamine (1.2 mL, 8.8 mmol) in 1,2-dichloroethane (29 mL) was stirred at RT overnight. The reaction mixture was purified by column chromatography eluting with EtOAc/Hex to give tert-butyl (1R,5S)-3-(7-benzyl-2-chloro-6-oxo-5,6,7,8-tetrahydropyrido[3,4-d]pyrimidin-4-yl)-3,8-diazabicyclo[3.2.1]octane-8-carboxylate (0.31 g, 22%). LCMS (MM-ES+APCI, Pos): m/z 484.2 (M+H).

Step G. tert-butyl (1R,5S)-3-(7-benzyl-2-(((S)-1-methylpyrrolidin-2-yl)methoxy)-6-oxo-5,6,7,8-tetrahydropyrido[3,4-d]pyrimidin-4-yl)-3,8-diazabicyclo[3.2.1]octane-8-carboxylate. A mixture of tert-butyl (1R,5S)-3-(7-benzyl-2-chloro-6-oxo-5,6,7,8-tetrahydropyrido[3,4-d]pyrimidin-4-yl)-3,8-diazabicyclo[3.2.1]octane-8-carboxylate (0.11 g, 0.23 mmol), (S)-(1-methylpyrrolidin-2-yl)methanol (0.13 g, 1.2 mmol) and $Cs_2CO_3$ (0.60 g, 1.8 mmol) in dioxane (2.3 mL) was stirred at 95° C. for 4 days. The reaction mixture was purified by column chromatography eluting with 0-20% DCM/MeOH+0-2% $NH_4OH$ as a modifier to afford tert-butyl (1R,5S)-3-(7-benzyl-2-(((S)-1-methylpyrrolidin-2-yl)methoxy)-6-oxo-5,6,7,8-tetrahydropyrido[3,4-d]pyrimidin-4-yl)-3,8-diazabicyclo[3.2.1]octane-8-carboxylate (0.10 g, 78%). LCMS (MM-ES+APCI, Pos): m/z 563.3 (M+H).

Step H. 7-benzyl-4-((1R,5S)-3,8-diazabicyclo[3.2.1]octan-3-yl)-2-(((S)-1-methylpyrrolidin-2-yl)methoxy)-7,8-dihydropyrido[3,4-d]pyrimidin-6(5H)-one. A solution of tert-butyl (1R,5S)-3-(7-benzyl-2-(((S)-1-methylpyrrolidin-2-yl)methoxy)-6-oxo-5,6,7,8-tetrahydropyrido[3,4-d]pyrimidin-4-yl)-3,8-diazabicyclo[3.2.1]octane-8-carboxylate (50 mg, 0.089 mmol) in TFA (0.30 mL) and DCM (0.5 mL) was stirred at RT for 1 day. The reaction mixture was concentrated and the residue was partitioned between EtOAc and 2M $K_2CO_3$ (aq.). The aqueous layer was extracted with EtOAc 3 times. The combined organic layers were dried over MgSO4 and concentrated to give 7-benzyl-4-((1R,5S)-3,8-diazabicyclo[3.2.1]octan-3-yl)-2-(((S)-1-methylpyrrolidin-2-yl)methoxy)-7,8-dihydropyrido[3,4-d]pyrimidin-6(5H)-one (9 mg, 22%). LCMS (MM-ES+APCI, Pos): m/z 463.2 (M+H).

Example 54 and 55

Peak 1

EXAMPLE 54

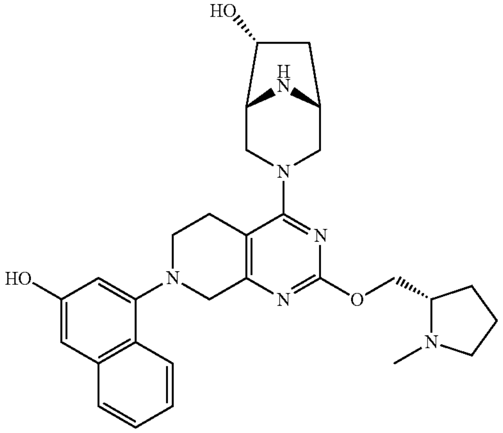

Peak 2

EXAMPLE 55

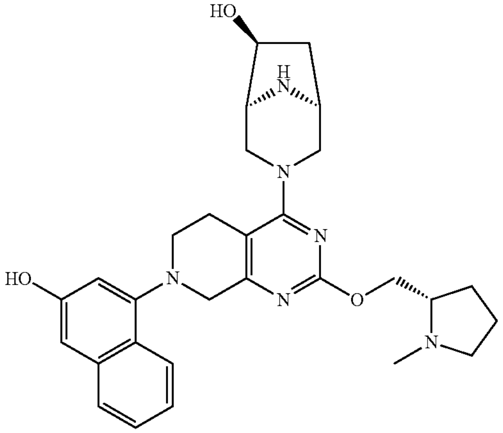

(1R,5R,6R)-3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol and (1S,5S,6S)-3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol A 5 mg sample of 3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol (Example 4) was purified by SFC chromatography using an OD-H 2×25 cm eluting with 50% ethanol (0.1% DEA)/$CO_2$ at 100 bar, 50 mL/min, monitoring at 220 nm. Peak 1 eluted at 7 min, Peak 2 eluted at 11.5 min of a 20 min run. Peak 1: (1R,5R,6R)-3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol. Peak 2: (1S,5S,6S)-3-(7-(3-hydroxynaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol.

Example 56

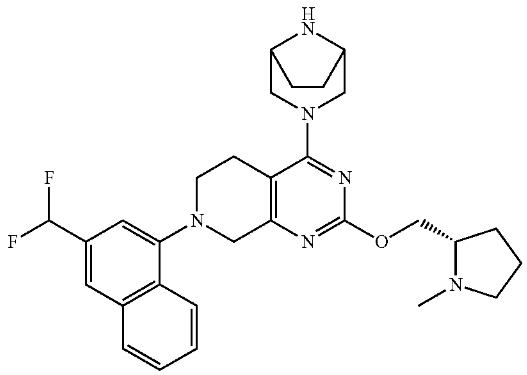 [SMILES: CN1CCC[C@H]1COc1nc2c(c(N3CC4CCC(C3)N4)n1)CCN(c1cc(C(F)F)cc3ccccc13)C2]

4-((1R,5S)-3,8-diazabicyclo[3.2.1]octan-3-yl)-7-(3-(difluoromethyl)naphthalen-1-yl)-2-(((S)-1-methylpyrrolidin-2-yl)methoxy)-5,6,7,8-tetrahydropyrido[3,4-d]pyrimidine

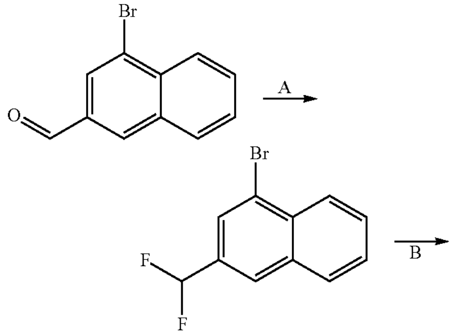

-continued

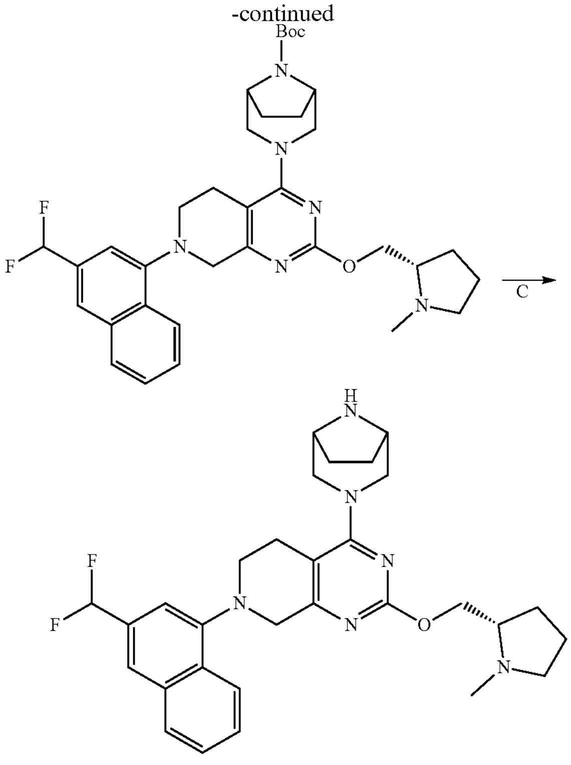

Step A. 1-bromo-3-(difluoromethyl)naphthalene. To a 5 mL Teflon bottle was added 4-bromo-2-naphthaldehyde (0.20 g, 0.85 mmol) followed by $CH_2Cl_2$ (4 mL). 1,1,1-Trifluoro-N,N-bis(2-methoxyethyl)-$\lambda^4$-sulfanamine (0.47 mL, 2.6 mmol) was added and the vial was capped. The mixture was warmed to 35° C. for 7 hours. The mixture was cooled to ambient temperature and a saturated aqueous $NaHCO_3$ solution was added while stirring until bubbling ceased. The mixture was extracted with $CH_2Cl_2$ (3×10 mL). The combined organic layers were dried over $Na_2SO_4$, filtered, and concentrated. The crude product was purified by column chromatography (2-5% EtOAc/hexanes) to afford 1-bromo-3-(difluoromethyl)naphthalene as a colorless oil (0.21 g, 95% yield).

Step B. tert-butyl (1R,5S)-3-(7-(3-(difluoromethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a vial were added tris (dibenzylideneacetone)dipalladium (0) (3.2 mg, 0.004 mmol), racemic-2,2'-bis(diphenylphosphino)-1,1'-binaphthyl (4.3 mg, 0.007 mmol) and toluene (0.2 mL). Argon was bubbled through the mixture for 5 minutes, the vial was capped, and the mixture was heated to 100° C. for 15 minutes. The mixture was cooled to ambient temperature and sodium tert-butoxide (8.4 mg, 0.087 mmol) was added followed by tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (20 mg, 0.044 mmol) and 1-bromo-3-(difluoromethyl)naphthalene (22 mg, 0.087 mmol). The vial was capped and the mixture was heated to 100° C. with stirring for 18 hours. The mixture was washed with water. The organics was separated, filtered through 1PS paper, concentrated, and purified by silica gel (0-20% MeOH in DCM with 0.25% $NH_4OH$ as a modifier) to provide tert-butyl (1R,5S)-3-(7-(3-(difluoromethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (8 mg, 29% yield). LCMS (MM-ES+APCI, Pos): m/z 635.4 (M+H).

Step C. 4-((1R,5S)-3,8-diazabicyclo[3.2.1]octan-3-yl)-7-(3-(difluoromethyl)naphthalen-1-yl)-2-(((S)-1-methylpyrrolidin-2-yl)methoxy)-5,6,7,8-tetrahydropyrido[3,4-d]pyrimidine. To a solution of tert-butyl (1R,5S)-3-(7-(3-(difluoromethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (6 mg, 0.01 mmol) in MeOH (1 mL) was added HCl 4.0 M in 1,4-dioxane (0.12 mL). The mixture was stirred at room temperature for 18 hours. The mixture was evaporated in vacuo and purified by C18 reverse phase chromatography (Gilson, 5-95% ACN/$H_2O$ with 0.1% TFA as a modifier) to afford 4-((1R,5S)-3,8-diazabicyclo[3.2.1]octan-3-yl)-7-(3-(difluoromethyl)naphthalen-1-yl)-2-(((S)-1-methylpyrrolidin-2-yl)methoxy)-5,6,7,8-tetrahydropyrido[3,4-d]pyrimidine (6 mg, 83% yield) as the TFA salt. LCMS (MM-ES+APCI, Pos): m/z 535.3 [M+H].

Example 57

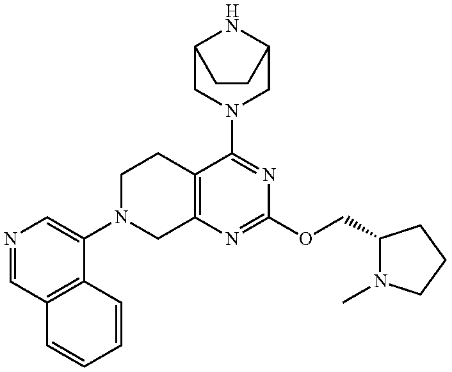 [SMILES: CN1CCC[C@H]1COc1nc2c(c(N3CC4CCC(C3)N4)n1)CCN(c1cncc3ccccc13)C2]

4-((1R,5S)-3,8-diazabicyclo[3.2.1]octan-3-yl)-7-(isoquinolin-4-yl)-2-(((S)-1-methylpyrrolidin-2-yl)methoxy)-5,6,7,8-tetrahydropyrido[3,4-d]pyrimidine

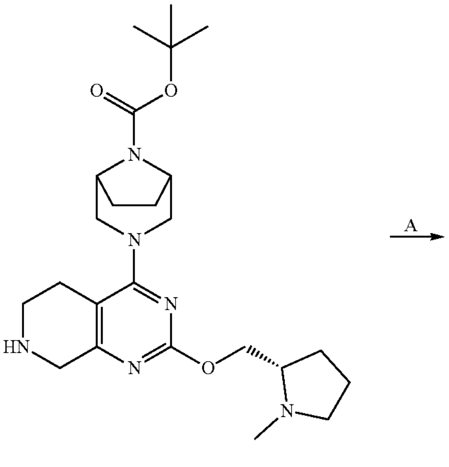

-continued

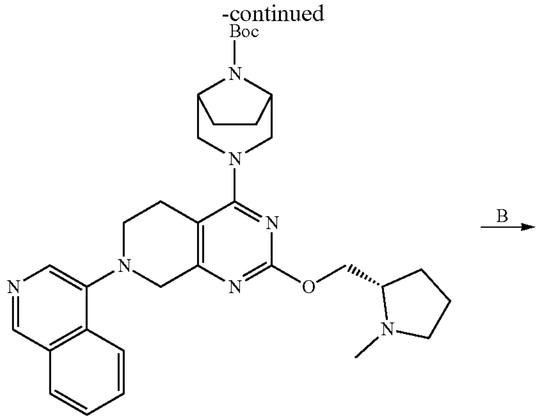

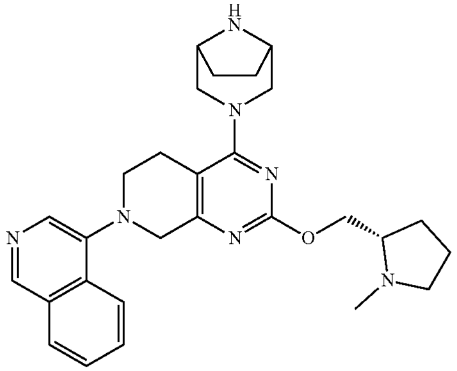

Step A. tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a vial were added cesium carbonate (77 mg, 0.24 mmol), tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (36 mg, 0.078 mmol), methanesulfonato(2-dicyclohexylphosphino-2',6'-di-1-propoxy-1,1'-biphenyl)(2'-methylamino-1,1'-biphenyl-2-yl)palladium(II) (13 mg, 0.016 mmol), 4-bromoisoquinoline (41 mg, 0.20 mmol) and 1,4-dioxane (0.5 mL). The vial was degassed with argon, sealed, and heated to 90° C. for 2 days. Water and saturated $NH_4Cl$ were added and the mixture extracted with EtOAc. The organic layers were combined, filtered through 1PS paper, concentrated, and purified by silica gel (0-20% MeOH in DCM w/0.25% $NH_4OH$) to provide tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (21 mg, 46% yield). LCMS (MM-ES+APCI, Pos): m/z 586.3 (M+H).

Step B. 4-((1R,5S)-3,8-diazabicyclo[3.2.1]octan-3-yl)-7-(isoquinolin-4-yl)-2-(((S)-1-methylpyrrolidin-2-yl)methoxy)-5,6,7,8-tetrahydropyrido[3,4-d]pyrimidine bis(2,2,2-trifluoroacetate). To a solution of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (21 mg, 0.029 mmol) in DCM (0.3 mL) was added TFA (0.6 mL) at 0° C. The mixture was stirred at room temperature for 2 hours. The mixture was evaporated in vacuo and purified by C18 (Gilson, 5-95% ACN/$H_2O$ with 0.1% TFA as modifier) to afford 4-((1R,5S)-3,8-diazabicyclo[3.2.1]octan-3-yl)-7-(isoquinolin-4-yl)-2-(((S)-1-methylpyrrolidin-2-yl)methoxy)-5,6,7,8-tetrahydropyrido[3,4-d]pyrimidine (27 mg, 100% yield) as the TFA salt. LCMS (MM-ES+APCI, Pos): m/z 486.3 (M+H).

Example 58

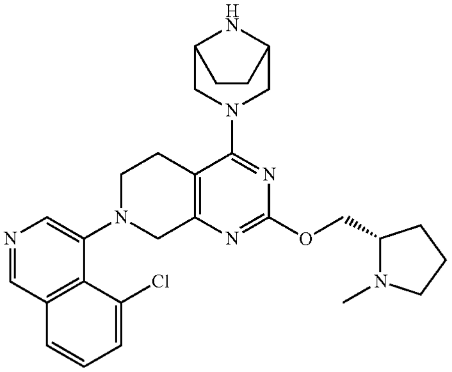 [SMILES: CN1CCC[C@H]1COc1nc2c(c(N3CC4CCC(C3)N4)n1)CCN(c1cncc3cccc(Cl)c13)C2]

4-((1R,5S)-3,8-diazabicyclo[3.2.1]octan-3-yl)-7-(5-chloroisoquinolin-4-yl)-2-(((S)-1-methylpyrrolidin-2-yl)methoxy)-5,6,7,8-tetrahydropyrido[3,4-d]pyrimidine

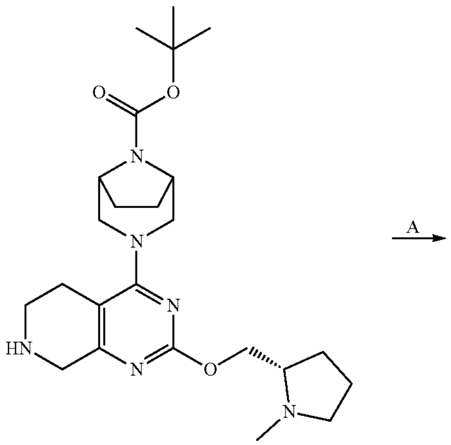

-continued

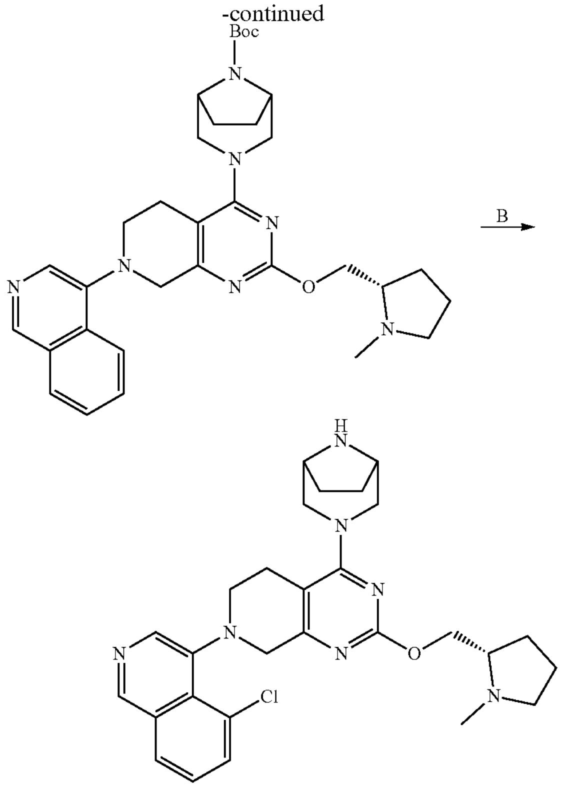

Step A. tert-butyl (1R,5S)-3-(7-(5-chloroisoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. $Pd_2(dba)_3$ (19 mg, 0.021 mmol) and Xantphos (25 mg, 0.043 mmol) were diluted with toluene (1 mL) and purged with argon. The reaction was sealed and heated to 100° C. for 15 minutes. The reaction was cooled and tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (65 mg, 0.14 mmol) was added followed by cesium carbonate (185 mg, 0.57 mmol) and 4-bromo-5-chloroisoquinoline. The reaction was purged with argon, sealed, and heated to 100° C. for 18 h. The reaction was cooled to room temperature, and then diluted with ethyl acetate and aq. saturated sodium bicarbonate. The layers were separated, and the organics were dried over $MgSO_4$, filtered, and concentrated. The material was purified on silica gel eluting with 1-20% methanol/DCM with 0.25% $NH_4OH$ as modifier to afford tert-butyl (1R,5S)-3-(7-(5-chloroisoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (48 mg, 55% yield). LCMS (MM-ES+APCI, Pos): m/z 621.3 (M+H).

Step B. 4-((1R,5S)-3,8-diazabicyclo[3.2.1]octan-3-yl)-7-(5-chloroisoquinolin-4-yl)-2-(((S)-1-methylpyrrolidin-2-yl)methoxy)-5,6,7,8-tetrahydropyrido[3,4-d]pyrimidine bis(2,2,2-trifluoroacetate). Synthesized according to Example 57, Step B substituting tert-butyl (1R,5S)-3-(7-(5-chloroisoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (48 mg, 83%). LCMS (MM-ES+APCI, Pos): m/z 520.2 (M+H).

Example 59

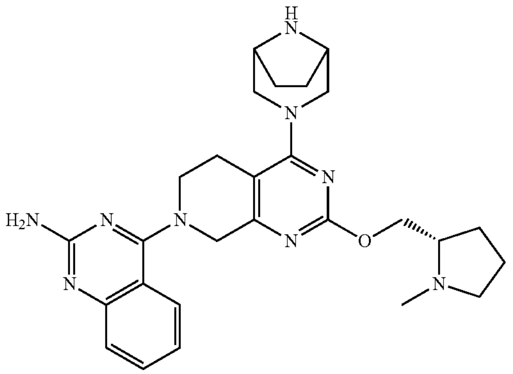 [SMILES: CN1CCC[C@H]1COc1nc2c(c(N3CC4CCC(C3)N4)n1)CCN(c1nc(N)nc3ccccc13)C2]

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)quinazolin-2-amine

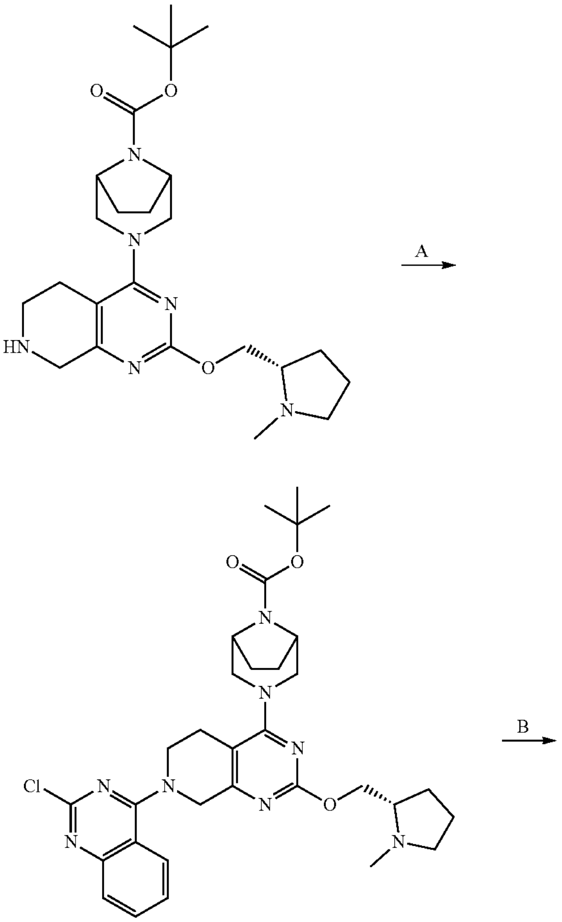

-continued

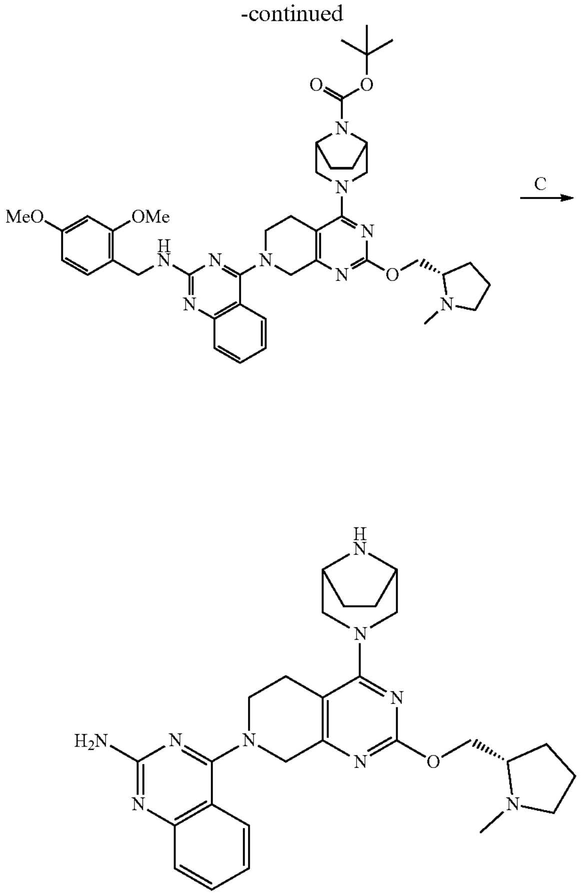

Step A. tert-butyl (1R,5S)-3-(7-(2-chloroquinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (19 mg, 0.041 mmol) in DMA (0.8 mL) was added 2,4-dichloroquinazoline (9.1 mg, 0.05 mmol) followed by DIEA (0.14 mL, 0.083 mmol) and the mixture was stirred at room temperature for 18 h. The mixture was evaporated in vacuo and purified by column chromatography eluting with 0-20% MeOH/DCM with 0.25% $NH_4OH$ as a modifier to give tert-butyl (1R,5S)-3-(7-(2-chloroquinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (15 mg, 58% yield). LCMS (MM-ES+APCI, Pos): m/z 621.3 (M+H).

Step B. tert-butyl (1R,5S)-3-(7-(2-((2,4-dimethoxybenzyl)amino)quinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A mixture of tert-butyl (1R,5S)-3-(7-(2-chloroquinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (15 mg, 0.024 mmol) in dioxane (0.1 mL) was treated with 2,4-dimethoxybenzylamine (4.0 mg, 0.024 mmol) and cesium carbonate (16 mg, 0.048 mmol) at room temperature. The mixture was stirred at 80° C. for 4 days. The mixture was diluted with aqueous saturated $NaHCO_3$ and extracted with EtOAc. The organics were filtered through 1PS paper and evaporated in vacuo to give tert-butyl (1R,5S)-3-(7-(2-((2,4-dimethoxybenzyl)amino)quinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (15 mg, 50% yield). LCMS (MM-ES+APCI, Pos): m/z 752.4 (M+H).

Step C. 4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)quinazolin-2-amine. Synthesized according to Example 57, Step B substituting tert-butyl (1R,5S)-3-(7-(2-((2,4-dimethoxybenzyl)amino)quinazolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (8 mg, 92%) as the TFA salt. LCMS (MM-ES+APCI, Pos): m/z 502.3 (M+H).

Example 60

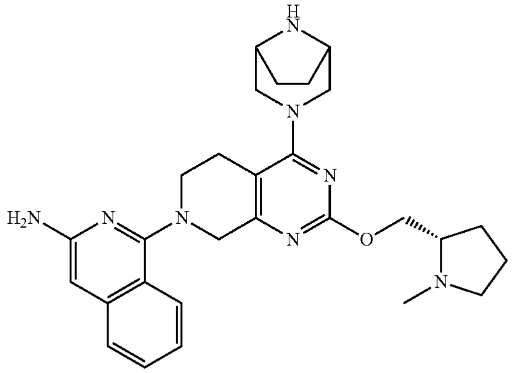 [SMILES: CN1CCC[C@H]1COc1nc2c(c(N3CC4CCC(C3)N4)n1)CCN(c1nc(N)cc3ccccc13)C2]

1-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)isoquinolin-3-amine

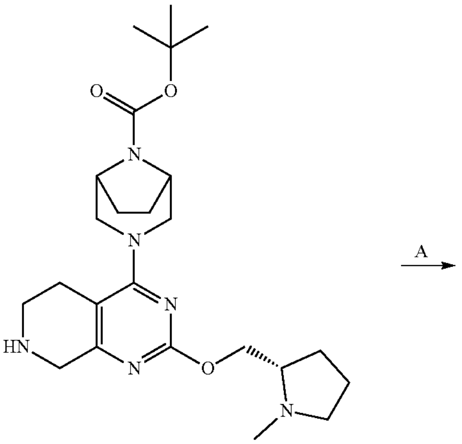

-continued

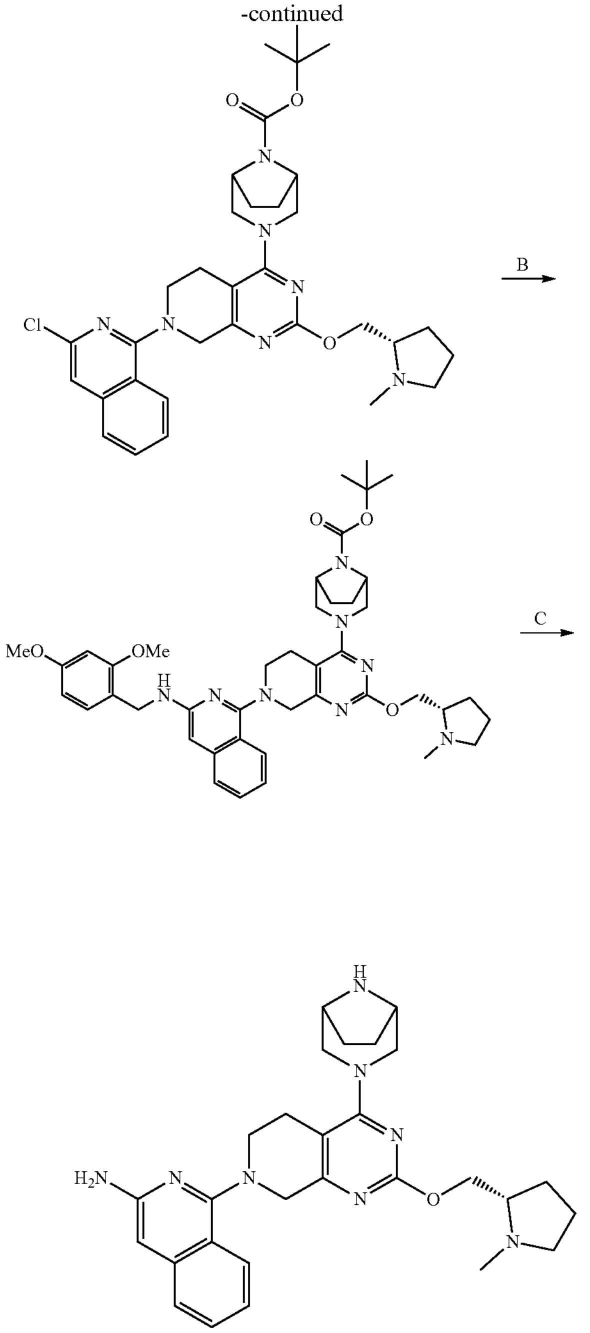

Step A. tert-butyl (1R,5S)-3-(7-(3-chloroisoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A solution of tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (44 mg, 0.096 mmol) in DMA (0.2 mL) was treated with 2,4-dichloroquinazoline (21 mg, 0.11 mmol) followed by DIEA (0.34 mL, 0.19 mmol) at 0° C. The mixture was stirred at 60° C. for 4 h. The mixture was diluted with water and the aqueous layer was extracted with EtOAc 3 times. The combined organics were filtered through 1PS paper, evaporated in vacuo, and purified by column chromatography eluting with 0-20% MeOH/DCM with 0.25% $NH_4OH$ to afford tert-butyl (1R,5S)-3-(7-(3-chloroisoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (22 mg, 37% yield). LCMS (MM-ES+APCI, Pos): m/z 620.3 (M+H).

Step B. tert-butyl (1R,5S)-3-(7-(3-((2,4-dimethoxybenzyl)amino)isoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A mixture of tert-butyl (1R,5S)-3-(7-(3-chloroisoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (10 mg, 0.016 mmol) in dioxane (0.2 mL) was purged with argon and treated with (2,4-dimethoxyphenyl)methanamine (3.2 mg, 0.019 mmol), sodium t-butoxide (2.3 mg, 0.024 mmol), $Pd_2(dba)_3$ (0.44 mg, 0.0005 mmol), and rac-BINAP (0.001 mmol). The reaction was sealed and heated to 100° C. for 2 d. The reaction was cooled to room temperature and diluted with ethyl acetate and saturated sodium bicarbonate. The layers were separated and the ethyl acetate layer was dried over $MgSO_4$, filtered, and concentrated. The residue was purified on silica gel eluting with 1-20% methanol/DCM with 0.25% $NH_4OH$ as modifier to afford tert-butyl (1R,5S)-3-(7-(3-((2,4-dimethoxybenzyl)amino)isoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (3 mg, 25% yield). LCMS (MM-ES+APCI, Pos): m/z 751.5 (M+H).

Step C. 1-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)isoquinolin-3-amine. Synthesized according to Example 57, Step B substituting tert-butyl (1R,5S)-3-(7-(3-((2,4-dimethoxybenzyl)amino)isoquinolin-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to yield 1-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)isoquinolin-3-amine (5 mg, 31%) as the TFA salt. LCMS (MM-ES+APCI, Pos): m/z 501.2 (M+H).

Example 61

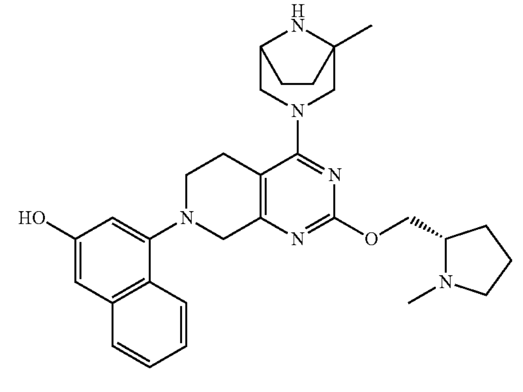 [SMILES: CN1CCC[C@H]1COc1nc2c(c(N3CC4CCC(C)(C3)N4)n1)CCN(c1cc(O)cc3ccccc13)C2]

4-(4-(1-methyl-3,8-diazabicyclo[3.2.1]octan-3-yl)-2-(((S)-1-methylpyrrolidin-2-yl)methoxy)-5,8-dihydro-pyrido[3,4-d]pyrimidin-7(6H)-yl)naphthalen-2-ol

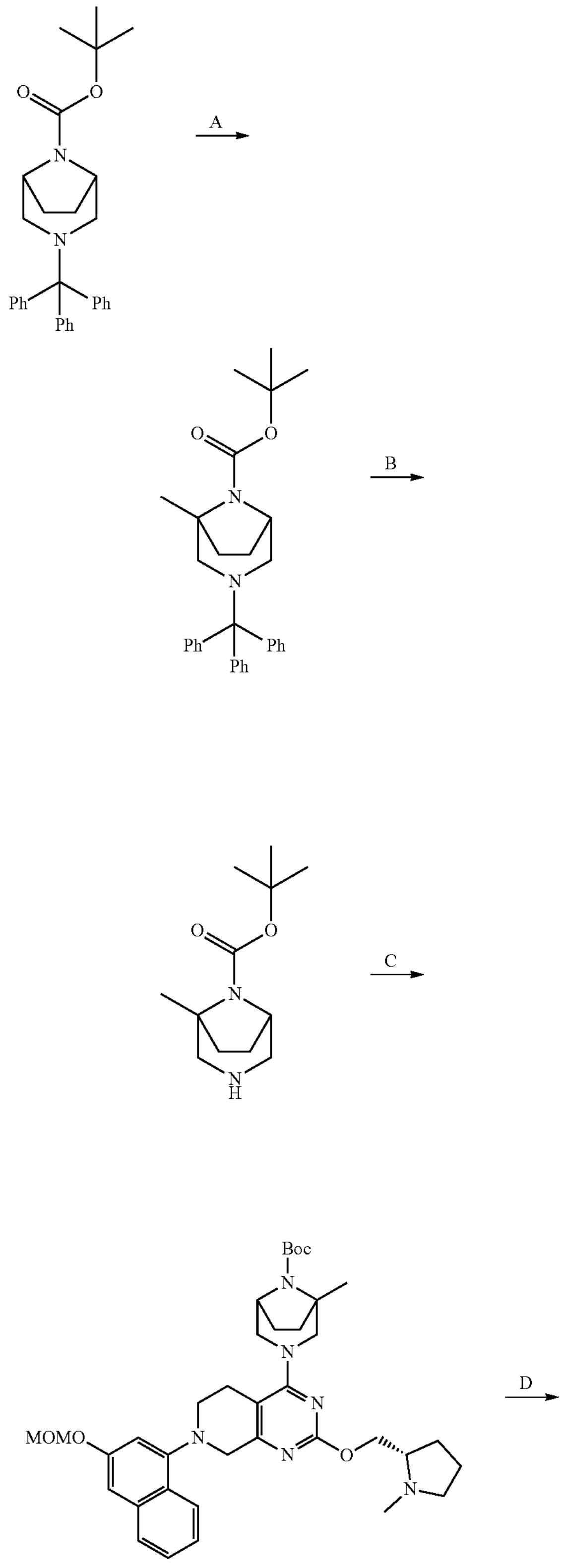

-continued

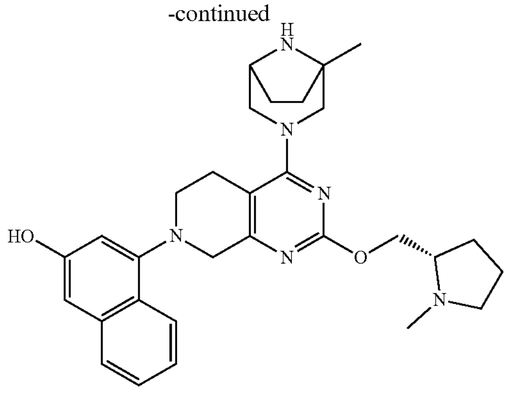

Step A. tert-butyl 1-methyl-3-trityl-3,8-diazabicyclo[3.2.1]octane-8-carboxylate. To a suspension of tert-butyl-3-trityl-3,8-diazabicyclo[3.2.1]octane-8-carboxylate (0.30 g, 0.66 mmol) and N,N,N',N'-tetramethylethylenediamine (0.23 mL, 1.5 mmol) in diethyl ether (4.4 mL) at −30° C. under $N_2$ was added s-BuLi (1.4 M in cyclohexane, 1.1 mL, 1.5 mmol). The mixture was slowly warmed to 0° C. to give a yellow suspension. The mixture was stirred at 0° C. for 30 min and iodomethane (0.041 mL, 0.66 mmol) was added. The mixture was stirred at 0° C. for 15 min and quenched with NH4Cl (sat.). The mixture was extracted with DCM and the DCM extract was dried over $Na_2SO_4$ and concentrated to give the crude desired product (0.29 g, 94%) as a white solid. LCMS (MM-ES+APCI, Pos): m/z 227.3 (M+H-Ph3C)+.

Step B. tert-butyl 1-methyl-3,8-diazabicyclo[3.2.1]octane-8-carboxylate. To a solution of tert-butyl 1-methyl-3-trityl-3,8-diazabicyclo[3.2.1]octane-8-carboxylate (0.28 g, 0.60 mmol) in 1,4-dioxane (6.0 mL) at rt was added HCl (1.0 N, 1.8 mL, 1.8 mmol). The mixture was stirred at rt for 1 h and treated with solid $NaHCO_3$(0.15 g, 1.8 mmol). The mixture was stirred at rt for 10 min. The resulting mixture was concentrated to dryness to give a white solid. The solid was extracted with DCM (10 mL) and the suspension was passed through a short pad of Celite. The filtrate was concentrated to give the crude desired product (0.31 g) as a white semi-solid.

Step C. tert-butyl 3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-1-methyl-3,8-diazabicyclo[3.2.1]octane-8-carboxylate. Synthesized according to Example 4, Step G substituting tert-butyl 1-methyl-3,8-diazabicyclo[3.2.1]octane-8-carboxylate in place of tert-butyl 6-hydroxy-3,8-diazabicyclo[3.2.1]octane-8-carboxylate (14 mg, 21%). LCMS (MM-ES+APCI, Pos): m/z 659.4 (M+H).

Step D. 4-(4-(1-methyl-3,8-diazabicyclo[3.2.1]octan-3-yl)-2-(((S)-1-methylpyrrolidin-2-yl)methoxy)-5,8-dihydro-pyrido[3,4-d]pyrimidin-7(6H)-yl)naphthalen-2-ol. Synthesized according to Example 56, Step C substituting tert-butyl 3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-1-methyl-3,8-diazabicyclo[3.2.1]octane-8-carboxylate in place of tert-butyl (1R,5S)-3-(7-(3-(difluoromethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give product (3 mg, 19%) as the TFA salt. LCMS (MM-ES+APCI, Pos): m/z 515.3 (M+H).

Example 62

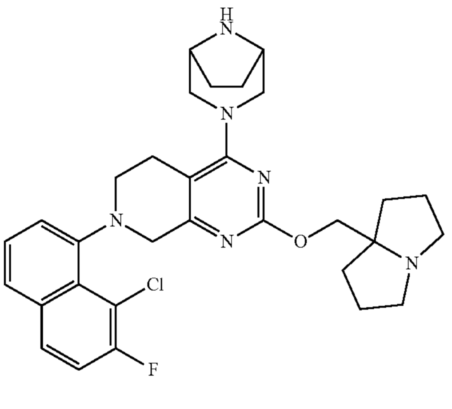 [SMILES: Fc1ccc2cccc(N3CCc4c(nc(OCC56CCCN5CCC6)nc4N4CC5CCC(C4)N5)C3)c2c1Cl]

4-((1R,5S)-3,8-diazabicyclo[3.2.1]octan-3-yl)-7-(8-chloro-7-fluoronaphthalen-1-yl)-2-((tetrahydro-1H-pyrrolizin-7a(5H)-yl)methoxy)-5,6,7,8-tetrahydro-pyrido[3,4-d]pyrimidine

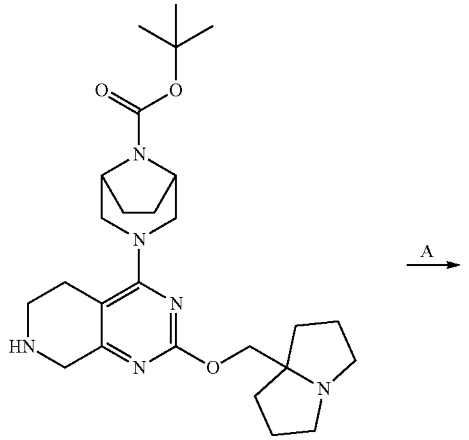

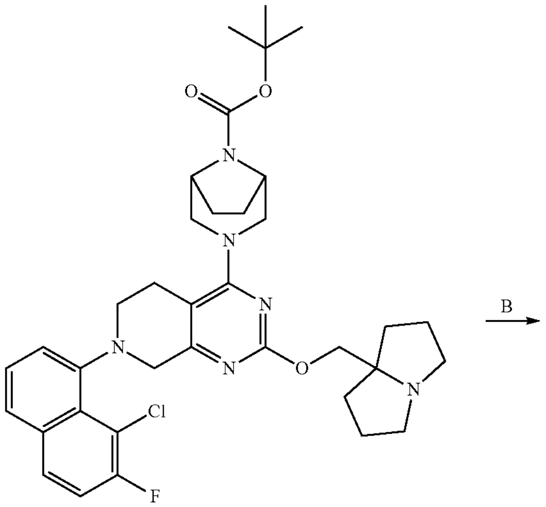

-continued

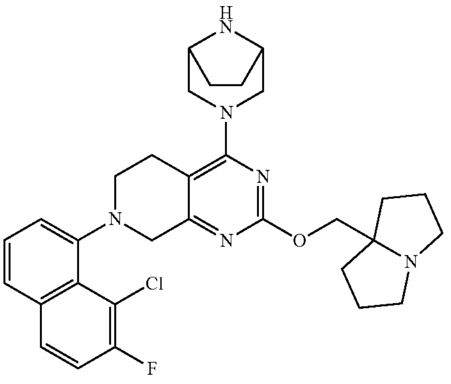

Step A. tert-butyl (1R,5S)-3-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 10, Step B substituting 8-chloro-7-fluoronaphthalen-1-yl trifluoromethanesulfonate in place of 1-bromo-8-ethylnaphthalene (13 mg, 30%). LCMS (MM-ES+APCI, Pos): m/z 663.3 (M+H).

Step B. 4-((1R,5S)-3,8-diazabicyclo[3.2.1]octan-3-yl)-7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidine. Synthesized according to Example 57, Step B substituting tert-butyl (1R,5S)-3-(7-(8-chloro-7-fluoronaphthalen-1-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to yield the title compound (4 mg, 37%) as the TFA salt. LCMS (MM-ES+APCI, Pos): m/z 563.3 (M+H).

Example 63

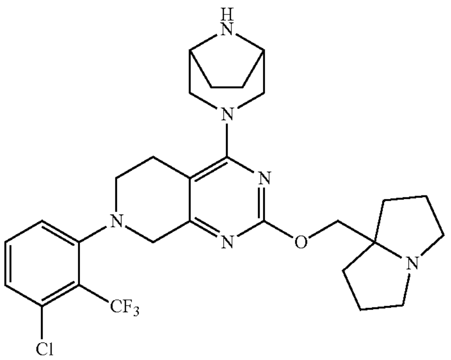 [SMILES: FC(F)(F)c1c(Cl)cccc1N1CCc2c(nc(OCC34CCCN3CCC4)nc2N2CC3CCC(C2)N3)C1]

4-((1R,5S)-3,8-diazabicyclo[3.2.1]octan-3-yl)-7-(3-chloro-2-(trifluoromethyl)phenyl)-2-((tetrahydro-1H-pyrrolizin-7a(5H)-yl)methoxy)-5,6,7,8-tetrahydropyrido[3,4-d]pyrimidine

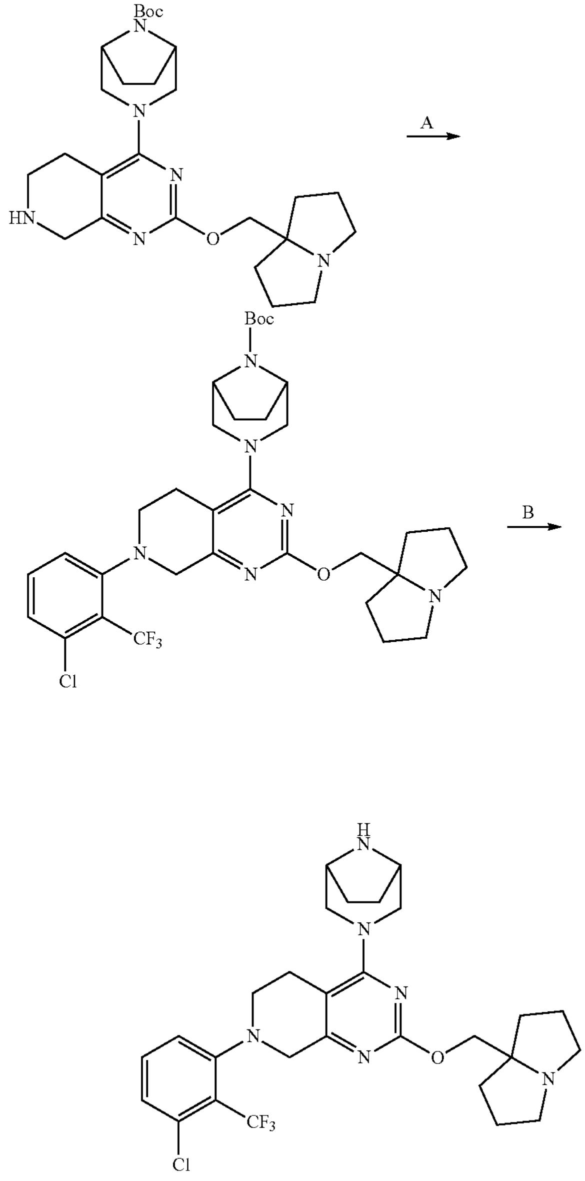

Step A. tert-butyl (1R,5S)-3-(7-(3-chloro-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 10, Step B substituting 1-bromo-3-chloro-2-(trifluoromethyl)benzene in place of 1-bromo-8-ethylnaphthalene (10 mg, 26%). LCMS (MM-ES+APCI, Pos): m/z 663.3 (M+H).

Step B. 4-((1R,5S)-3,8-diazabicyclo[3.2.1]octan-3-yl)-7-(3-chloro-2-(trifluoromethyl)phenyl)-2-((tetrahydro-1H-pyrrolizin-7a(5H)-yl)methoxy)-5,6,7,8-tetrahydropyrido[3,4-d]pyrimidine. Synthesized according to Example 57, Step B substituting tert-butyl (1R,5S)-3-(7-(3-chloro-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to yield the title compound (7 mg, 52%) as the TFA salt. LCMS (MM-ES+APCI, Pos): m/z 563.3 (M+H).

Example 64

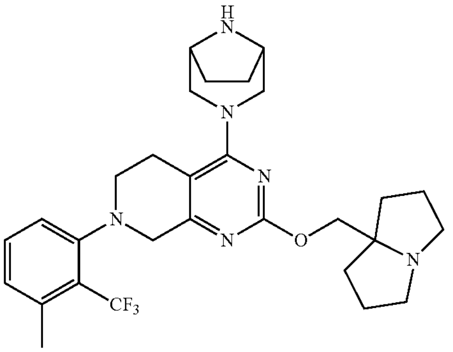 [SMILES: Cc1cccc(N2CCc3c(nc(OCC45CCCN4CCC5)nc3N3CC4CCC(C3)N4)C2)c1C(F)(F)F]

4-((1R,5S)-3,8-diazabicyclo[3.2.1]octan-3-yl)-7-(3-methyl-2-(trifluoromethyl)phenyl)-2-((tetrahydro-1H-pyrrolizin-7a(5H)-yl)methoxy)-5,6,7,8-tetrahydropyrido[3,4-d]pyrimidine

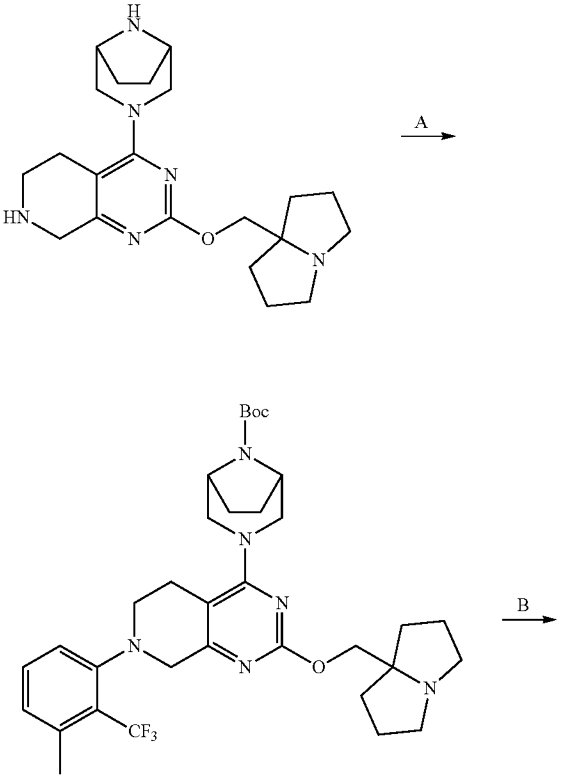

-continued

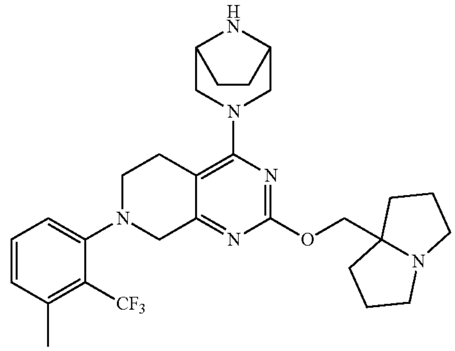

Step A. tert-butyl (1R,5S)-3-(7-(3-methyl-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 10, Step B substituting 2-bromo-6-methylbenzotrifluoride in place of 1-bromo-8-ethylnaphthalene (7 mg, 18%). LCMS (MM-ES+APCI, Pos): m/z 643.3 (M+H).

Step B. 4-((1R,5S)-3,8-diazabicyclo[3.2.1]octan-3-yl)-7-(3-methyl-2-(trifluoromethyl)phenyl)-2-((tetrahydro-1H-pyrrolizin-7a(5H)-yl)methoxy)-5,6,7,8-tetrahydropyrido[3,4-d]pyrimidine. Synthesized according to Example 57, Step B substituting tert-butyl (1R,5S)-3-(7-(3-methyl-2-(trifluoromethyl)phenyl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product (3 mg, 51%) as the TFA salt. LCMS (MM-ES+APCI, Pos): m/z 543.3 (M+H).

Example 65

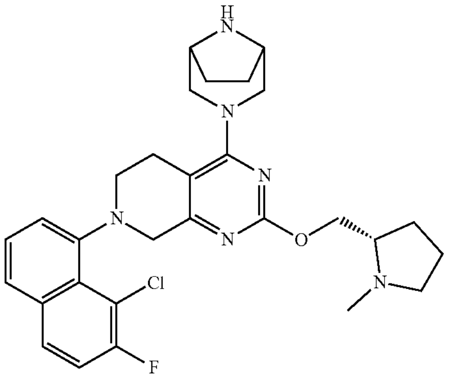 [SMILES: CN1CCC[C@H]1COc1nc2c(c(N3CC4CCC(C3)N4)n1)CCN(c1cccc3ccc(F)c(Cl)c13)C2]

4-((1R,5S)-3,8-diazabicyclo[3.2.1]octan-3-yl)-7-(8-chloro-7-fluoronaphthalen-1-yl)-2-(((S)-1-methylpyrrolidin-2-yl)methoxy)-5,6,7,8-tetrahydropyrido[3,4-d]pyrimidine

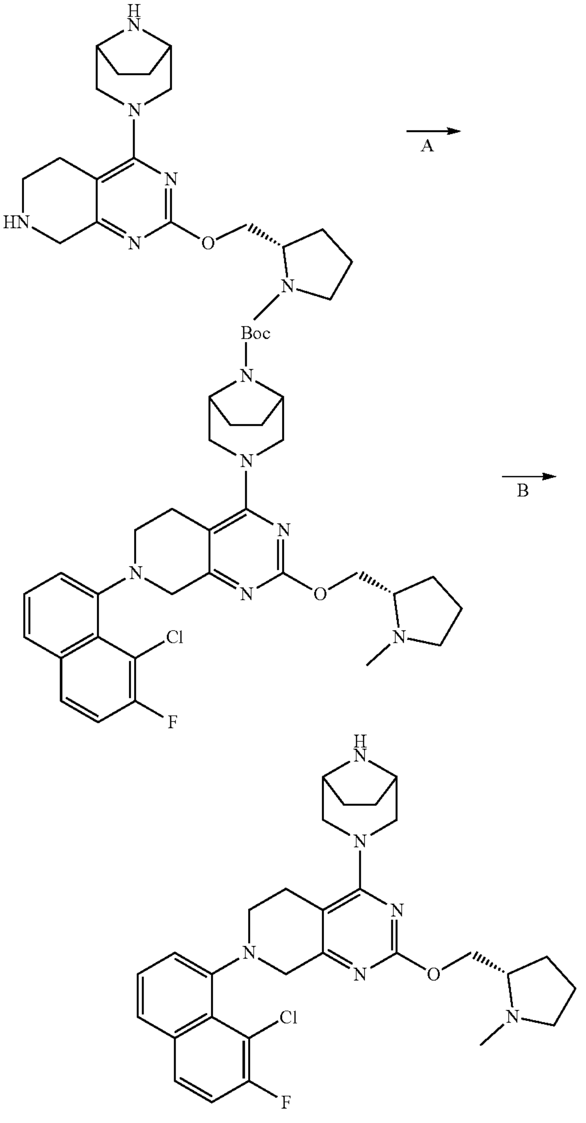

Step A. tert-butyl (1R,5S)-3-(7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 58, Step A substituting 8-chloro-7-fluoronaphthalen-1-yl trifluoromethanesulfonate in place of 4-bromo-5-chloroisoquinoline (26 mg, 45%). LCMS (MM-ES+APCI, Pos): m/z 637.3 (M+H).

Step B. 4-((1R,5S)-3,8-diazabicyclo[3.2.1]octan-3-yl)-7-(8-chloro-7-fluoronaphthalen-1-yl)-2-(((S)-1-methylpyrrolidin-2-yl)methoxy)-5,6,7,8-tetrahydropyrido[3,4-d]pyrimidine. Synthesized according to Example 57, Step B substituting tert-butyl (1R,5S)-3-(7-(8-chloro-7-fluoronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R, 5S)-3-(7-(isoquinolin-4-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product (8 mg, 46%). LCMS (MM-ES+APCI, Pos): m/z 537.2 (M+H).

Example 66

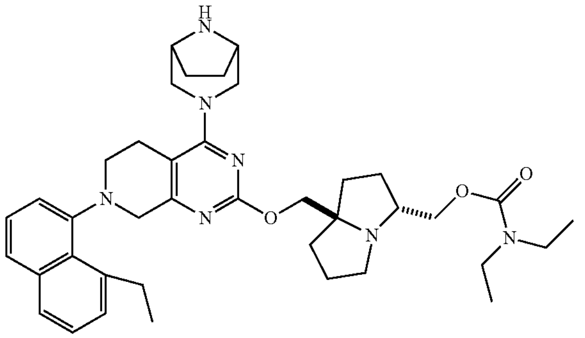

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl diethylcarbamate (trans enantiomers)

Synthesized according to example 5 substituting diethylamine in place of methylamine in Step F to give the product as the TFA salt. LCMS (MM-ES+APCI, Pos): m/z 668.4 [M+H].

Example 67

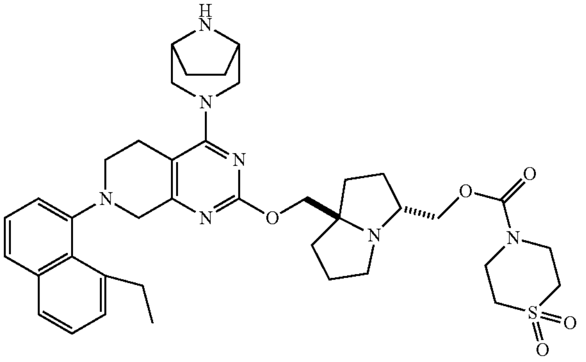

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl thiomorpholine-4-carboxylate 1,1-dioxide (trans enantiomers)

Synthesized according to example 5, substituting thiomorpholine 1,1-dioxide in place of methylamine in Step F to give the product as the TFA salt. LCMS (MM-ES+APCI, Pos): m/z 730.4 [M+H].

Example 68

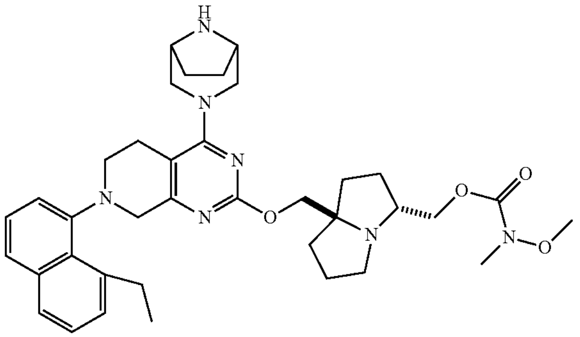

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl methoxy(methyl)carbamate (trans enantiomers)

Synthesized according to example 5, substituting N,O-dimethylhydroxylamine hydrochloride in place of methylamine in Step F to give the product as the TFA salt. LCMS (MM-ES+APCI, Pos): m/z 656.4 [M+H].

Example 69

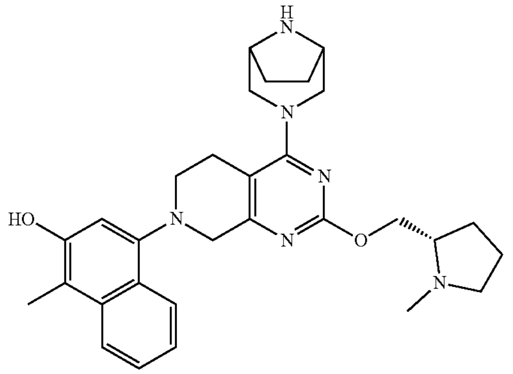

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-methylnaphthalen-2-ol

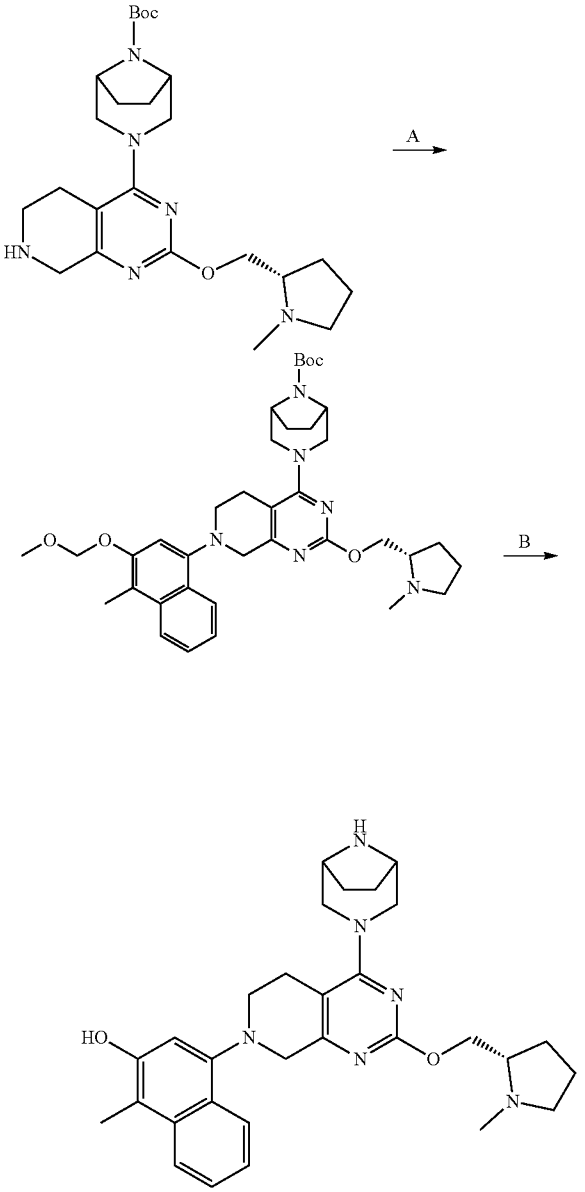

Step A. tert-butyl (1R,5S)-3-(7-(3-(methoxymethoxy)-4-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a vial were added cesium carbonate (64 mg, 0.2 mmol), tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (30 mg, 0.07 mmol), methanesulfonato(2-dicyclohexylphosphino-2',6'-di-1-propoxy-1,1'-biphenyl)(2'-methylamino-1,1'-biphenyl-2-yl)palladium(II) (11 mg, 0.01 mmol), 3-(methoxymethoxy)-4-methylnaphthalen-1-yl trifluoromethanesulfonate (62 mg, 0.18 mmol), and 1,4-dioxane (0.5 mL). The vial was degassed with argon, sealed, and heated to 90° C. for 24 hours. Water and saturated $NH_4Cl$ were added and the mixture was extracted with DCM. The organic layers were combined and concentrated. The residue was purified by silica gel (0-14% MeOH/DCM with 0.25% $NH_4OH$ as modifier) to provide tert-butyl (1R,5S)-3-(7-(3-(methoxymethoxy)-4-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (42 mg, 97% yield). LCMS (MM-ES+APCI, Pos): m/z 659.4 (M+H).

Step B. 4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-methylnaphthalen-2-ol. Tert-butyl (1R,5S)-3-(7-(3-(methoxymethoxy)-4-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (42 mg, 0.06 mmol) was placed in 3:1 DCM:TFA (2 mL) and was stirred for 90 minutes at room temperature. The reaction was concentrated, and the residue was purified by reverse phase chromatography (0-50% ACN/$H_2O$ with 0.1% TFA) to provide the TFA salt which was brought up in 10% MeOH/DCM and stirred with saturated bicarb for 10 minutes. The layers were separated and the aqueous was extracted with DCM. The organic layers were combined, dried, filtered, and concentrated to provide 4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-methylnaphthalen-2-ol (13 mg, 42% yield). LCMS (MM-ES+APCI, Pos): m/z 515.3 (M+H).

Example 70

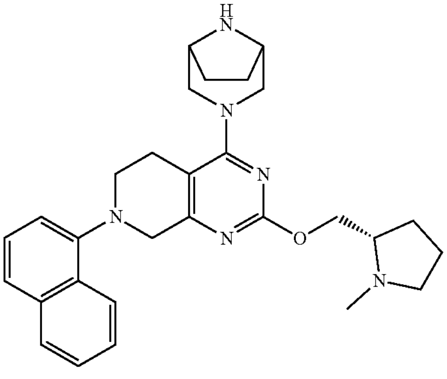 [SMILES: CN1CCC[C@H]1COc1nc2c(c(N3CC4CCC(C3)N4)n1)CCN(c1cccc3ccccc13)C2]

4-((1R,5S)-3,8-diazabicyclo[3.2.1]octan-3-yl)-2-(((S)-1-methylpyrrolidin-2-yl)methoxy)-7-(naphthalen-1-yl)-5,6,7,8-tetrahydropyrido[3,4-d]pyrimidine Synthesized according to Example 69 substituting 1-bromonaphthalene in place of 3-(methoxymethoxy)-4-methylnaphthalen-1-yl trifluoromethanesulfonate in step A to afford 4-((1R,5S)-3,8-diazabicyclo[3.2.1]octan-3-yl)-2-(((S)-1-methylpyrrolidin-2-yl)methoxy)-7-(naphthalen-1-yl)-5,6,7,8-tetrahydropyrido[3,4-d]pyrimidine as the TFA salt (43 mg, 99% yield). LCMS (MM-ES+APCI, Pos): m/z 485.3 (M+H).

Example 71

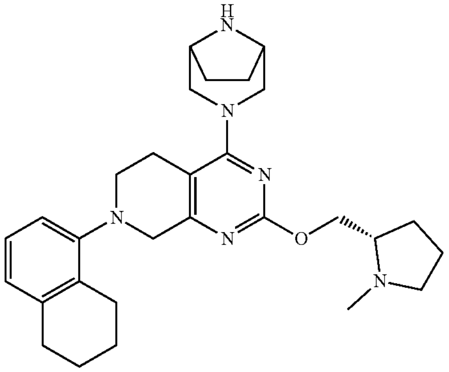 [SMILES: CN1CCC[C@H]1COc1nc2c(c(N3CC4CCC(C3)N4)n1)CCN(c1cccc3c1CCCC3)C2]

4-((1R,5S)-3,8-diazabicyclo[3.2.1]octan-3-yl)-2-(((S)-1-methylpyrrolidin-2-yl)methoxy)-7-(5,6,7,8-tetrahydronaphthalen-1-yl)-5,6,7,8-tetrahydropyrido[3,4-d]pyrimidine Synthesized according to Example 69 substituting 5-bromo-1,2,3,4-tetrahydronaphthalene in place of 3-(methoxymethoxy)-4-methylnaphthalen-1-yl trifluoromethanesulfonate in step A to afford 4-((1R,5S)-3,8-diazabicyclo[3.2.1]octan-3-yl)-2-(((S)-1-methylpyrrolidin-2-yl)methoxy)-7-(5,6,7,8-tetrahydronaphthalen-1-yl)-5,6,7,8-tetrahydropyrido[3,4-d]pyrimidine as the TFA salt (19 mg, 87% yield). LCMS (MM-ES+APCI, Pos): m/z 489.3 (M+H).

Example 72

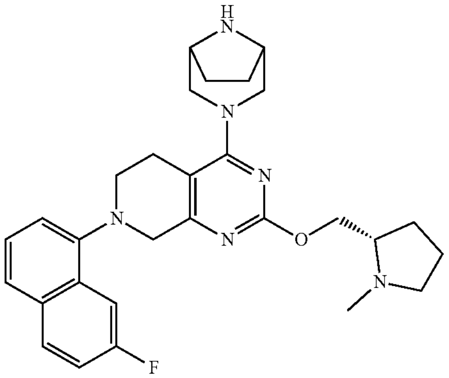 [SMILES: CN1CCC[C@H]1COc1nc2c(c(N3CC4CCC(C3)N4)n1)CCN(c1cccc3ccc(F)cc13)C2]

4-((1R,5S)-3,8-diazabicyclo[3.2.1]octan-3-yl)-7-(7-fluoronaphthalen-1-yl)-2-(((S)-1-methylpyrrolidin-2-yl)methoxy)-5,6,7,8-tetrahydropyrido[3,4-d]pyrimidine Synthesized according to Example 69 substituting 7-fluoronaphthalen-1-yl trifluoromethanesulfonate in place of 3-(methoxymethoxy)-4-methylnaphthalen-1-yl trifluoromethanesulfonate in step A to afford 4-((1R,5S)-3,8-diazabicyclo[3.2.1]octan-3-yl)-7-(7-fluoronaphthalen-1-yl)-2-(((S)-1-methylpyrrolidin-2-yl)methoxy)-5,6,7,8-tetrahydropyrido[3,4-d]pyrimidine (17 mg, 84% yield). LCMS (MM-ES+APCI, Pos): m/z 503.3 (M+H).

Example 73

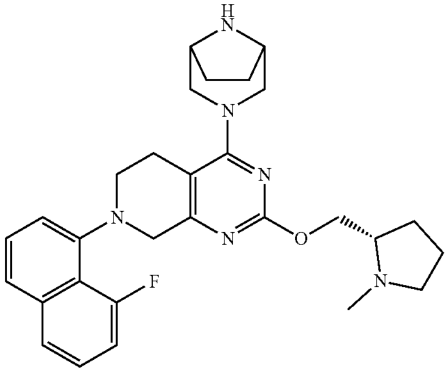 [SMILES: CN1CCC[C@H]1COc1nc2c(c(N3CC4CCC(C3)N4)n1)CCN(c1cccc3cccc(F)c13)C2]

4-((1R,5S)-3,8-diazabicyclo[3.2.1]octan-3-yl)-7-(8-fluoronaphthalen-1-yl)-2-(((S)-1-methylpyrrolidin-2-yl)methoxy)-5,6,7,8-tetrahydropyrido[3,4-d]pyrimidine Synthesized according to Example 69 substituting 1-bromo-8-fluoronaphthalene in place of 3-(methoxymethoxy)-4-methylnaphthalen-1-yl trifluoromethanesulfonate in step A to afford 4-((1R,5S)-3,8-diazabicyclo[3.2.1]octan-3-yl)-7-(8-fluoronaphthalen-1-yl)-2-(((S)-1-methylpyrrolidin-2-yl)methoxy)-5,6,7,8-tetrahydropyrido[3,4-d]pyrimidine (49 mg, 100% yield). LCMS (MM-ES+APCI, Pos): m/z 503.3 (M+H).

Example 74

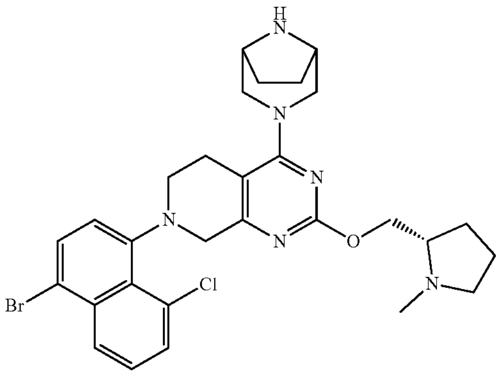 [SMILES: CN1CCC[C@H]1COc1nc2c(c(N3CC4CCC(C3)N4)n1)CCN(c1ccc(Br)c3cccc(Cl)c13)C2]

4-((1R,5S)-3,8-diazabicyclo[3.2.1]octan-3-yl)-7-(4-bromo-8-chloronaphthalen-1-yl)-2-(((S)-1-methylpyrrolidin-2-yl)methoxy)-5,6,7,8-tetrahydropyrido[3,4-d]pyrimidine

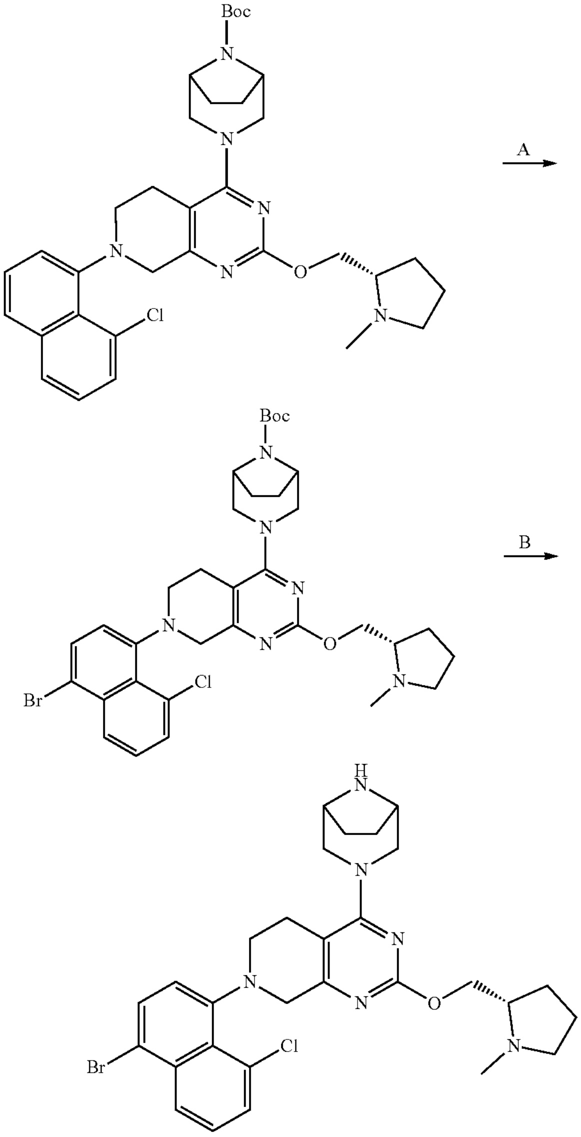

Step A. tert-butyl (1R,5S)-3-(7-(4-bromo-8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A stirred solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (10 mg, 0.016 mmol) in DCM (2 mL) was cooled to −78° C. and 2,4,4,6-tetrabromocyclohexa-2,5-dien-1-one (7.3 mg, 0.018 mmol) was added. The reaction mixture was warmed to r.t. and stirred for 3 h at room temperature. Tetrabromocyclohexadienone (12 mg, 0.030 mmol) and 1-bromopyrrolidine-2,5-dione (3.2 mg, 0.018 mmol) were added and the reaction mixture was stirred for 1 h. The reaction mixture was diluted with DCM (10 mL), washed with 1M NaOH (2 mL), dried over $Na_2CO_3$, and evaporated under $N_2$. The crude product was purified by reverse phase chromatography (Gilson) using 5-95% MeCN+0.1% TFA as modifier. The material was taken up in DCM and washed with aqueous $Na_2CO_3$ to yield the desired product (3.2 mg, 28%). LCMS (MM-ES+APCI, Pos): m/z 697.3 (M+H).

Step B. 4-((1R,5S)-3,8-diazabicyclo[3.2.1]octan-3-yl)-7-(4-bromo-8-chloronaphthalen-1-yl)-2-(((S)-1-methylpyrrolidin-2-yl)methoxy)-5,6,7,8-tetrahydropyrido[3,4-d]pyrimidine. Synthesized according to Example 2, Step E substituting tert-butyl (1R,5S)-3-(7-(4-bromo-8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The hydrochloride salt was taken up in DCM, washed with aqueous $Na_2CO_3$, and dried under vacuum to yield the target compound as a colorless solid (2.4 mg, 77%). LCMS (MM-ES+APCI, Pos): m/z 597.1 (M+H).

Example 75

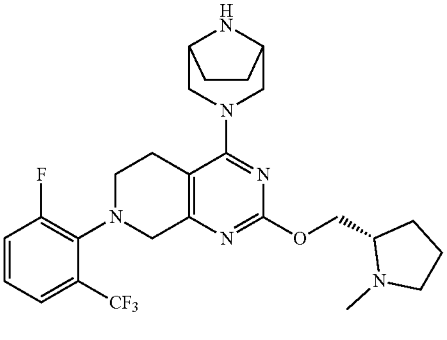 [SMILES: CN1CCC[C@H]1COc1nc2c(c(N3CC4CCC(C3)N4)n1)CCN(c1c(F)cccc1C(F)(F)F)C2]

4-((1R,5S)-3,8-diazabicyclo[3.2.1]octan-3-yl)-7-(2-fluoro-6-(trifluoromethyl)phenyl)-2-(((S)-1-methylpyrrolidin-2-yl)methoxy)-5,6,7,8-tetrahydropyrido[3,4-d]pyrimidine

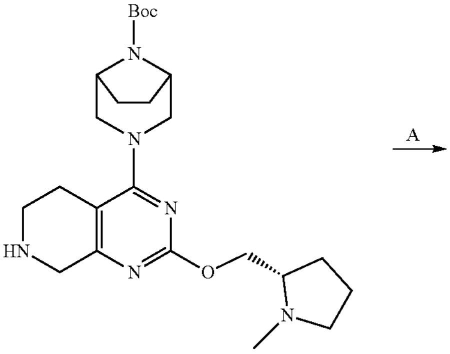

-continued

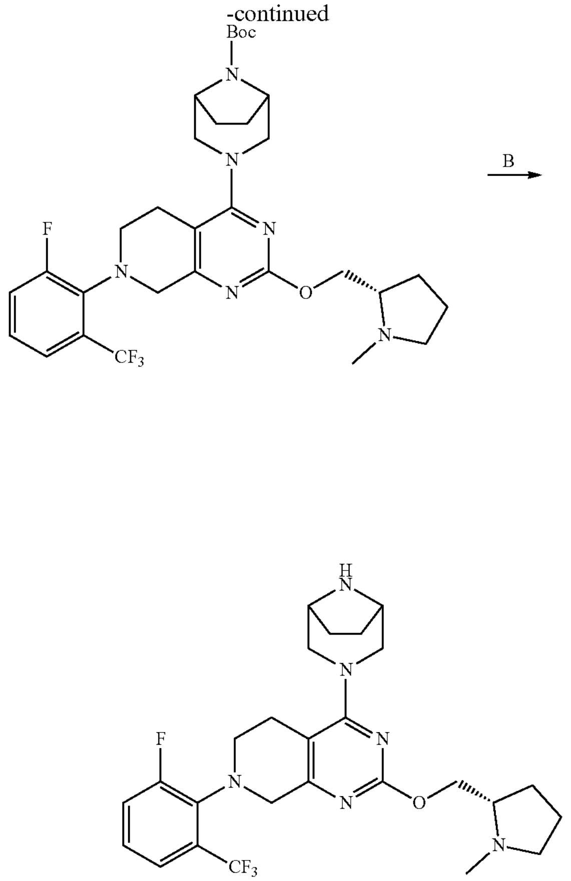

Step A. tert-butyl (1R,5S)-3-(7-(2-fluoro-6-(trifluoromethyl)phenyl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 2-bromo-1-fluoro-3-(trifluoromethyl)benzene in place of 3-(methoxymethoxy)naphthalen-1-yl trifluoromethanesulfonate to give the desired product (22 mg, 29%). LCMS (MM-ES+APCI, Pos): m/z 621.3 (M+H).

Step B. 4-((1R,5S)-3,8-diazabicyclo[3.2.1]octan-3-yl)-7-(2-fluoro-6-(trifluoromethyl)phenyl)-2-(((S)-1-methylpyrrolidin-2-yl)methoxy)-5,6,7,8-tetrahydropyrido[3,4-d]pyrimidine. Synthesized according to Example 2, Step E substituting tert-butyl (1R,5S)-3-(7-(2-fluoro-6-(trifluoromethyl)phenyl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The crude product was purified by reverse phase (C18, Gilson) eluting with 5 to 95% $MeCN/H_2O$+ 0.1% TFA as a modifier. The TFA salt was taken up in DCM, washed with aqueous $Na_2CO_3$, and dried under vacuum to yield the target compound as a colorless solid (15 mg, 81%). LCMS (MM-ES+APCI, Pos): m/z 521.5 (M+H).

Example 76

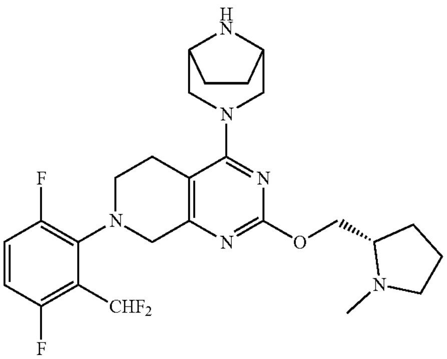 [SMILES: CN1CCC[C@H]1COc1nc2c(c(N3CC4CCC(C3)N4)n1)CCN(c1c(F)ccc(F)c1C(F)F)C2]

4-((1R,5S)-3,8-diazabicyclo[3.2.1]octan-3-yl)-7-(2-(difluoromethyl)-3,6-difluorophenyl)-2-(((S)-1-methylpyrrolidin-2-yl)methoxy)-5,6,7,8-tetrahydropyrido[3,4-d]pyrimidine

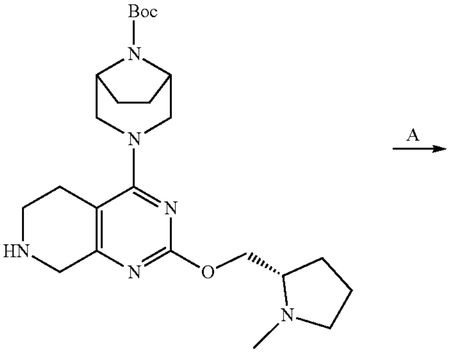

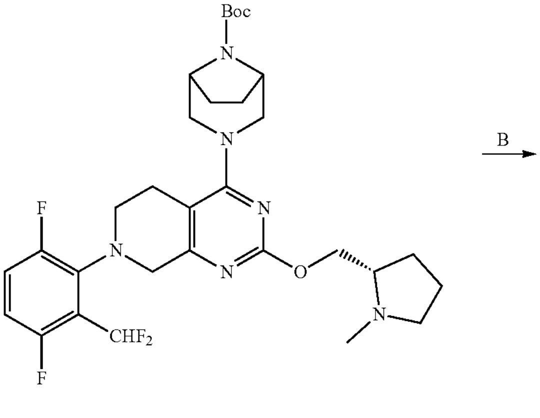

-continued

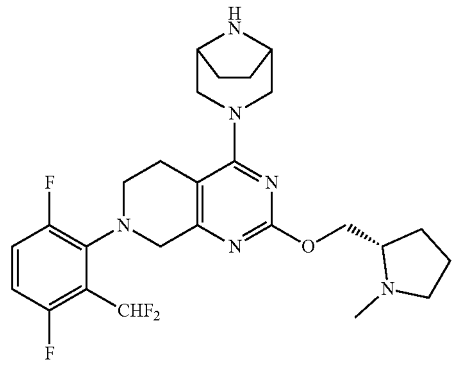

Step A. tert-butyl (1R,5S)-3-(7-(2-(difluoromethyl)-3,6-difluorophenyl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D, substituting 2-bromo-3-(difluoromethyl)-1,4-difluorobenzene in place of 3-(methoxymethoxy) naphthalen-1-yl trifluoromethanesulfonate. The crude product was chromatographed on silica gel eluting with 4% MeOH/DCM+0.4% $NH_4OH$ and purified on reverse phase (C18, Gilson) eluting with 5 to 95% MeCN/water+0.1% TFA as modifier. The TFA salt was taken up in DCM, washed with aqueous $Na_2CO_3$, and dried under vacuum to yield the desired product as a colorless solid (9 mg, 13%). LCMS (MM-ES+APCI, Pos): m/z 621.1 (M+H).

Step B. 4-((1R,5S)-3,8-diazabicyclo[3.2.1]octan-3-yl)-7-(2-(difluoromethyl)-3,6-difluorophenyl)-2-(((S)-1-methylpyrrolidin-2-yl)methoxy)-5,6,7,8-tetrahydropyrido[3,4-d] pyrimidine. Synthesized according to Example 2, Step E substituting tert-butyl (1R,5S)-3-(7-(2-(difluoromethyl)-3,6-difluorophenyl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R, 5S)-3-(7-(8-chloronaphthalen-1-yl)-2-(((S)-1-methylpyrrolidin-2-yl)methoxy)-5,6,7,8-tetrahydropyrido [3,4-d]pyrimidin-4-yl)-3,8-diazabicyclo[3.2.1]octane-8-carboxylate. The hydrochloride salt was taken up in DCM, washed with aqueous $Na_2CO_3$, and dried under vacuum to yield the target compound as a colorless solid (7.5 mg, 99%). LCMS (MM-ES+APCI, Pos): m/z 521.3 (M+H).

Example 77

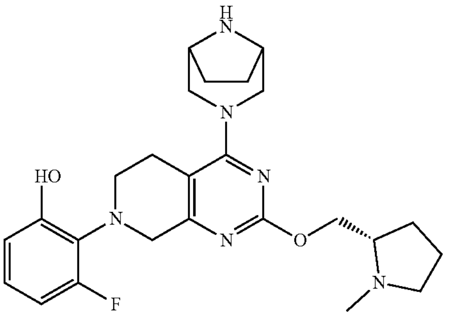 [SMILES: CN1CCC[C@H]1COc1nc2c(c(N3CC4CCC(C3)N4)n1)CCN(c1c(O)cccc1F)C2]

2-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-3-fluorophenol

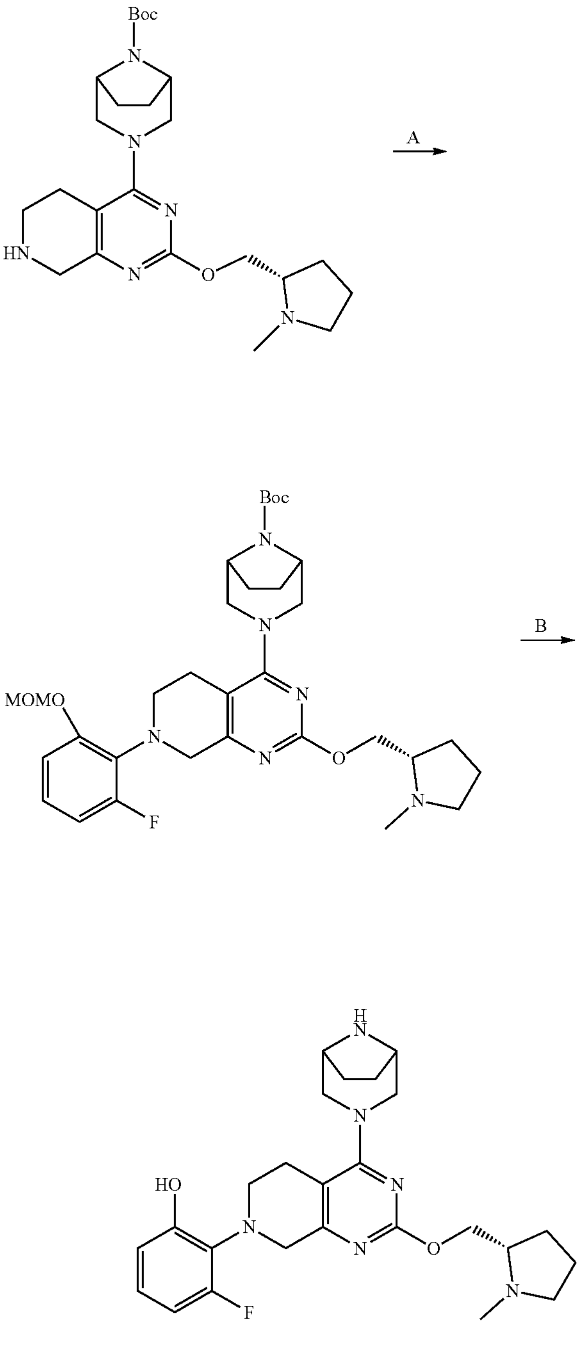

Step A. tert-butyl (1R,5S)-3-(7-(2-fluoro-6-(methoxymethoxy)phenyl)-2-(((S)-1-methylpyrrolidin-2-yl) methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 2-bromo-1-fluoro-3-(methoxymethoxy)benzene in place of 3-(methoxymethoxy)naphthalen-1-yl trifluoromethanesulfonate (28 mg, 30%). LCMS (MM-ES+APCI, Pos): m/z 613.3 (M+H).

Step B. 2-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-3-fluorophenol. Synthesized according to Example 2, Step E substituting tert-butyl (1R,5S)-3-(7-(2-fluoro-6-(methoxymethoxy)phenyl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The hydrochloride salt was taken up in DCM, washed with aqueous $Na_2CO_3$, and dried under vacuum to afford the target compound (21 mg, 98%). LCMS (MM-ES+APCI, Pos): m/z 469.3 (M+H).

Example 78

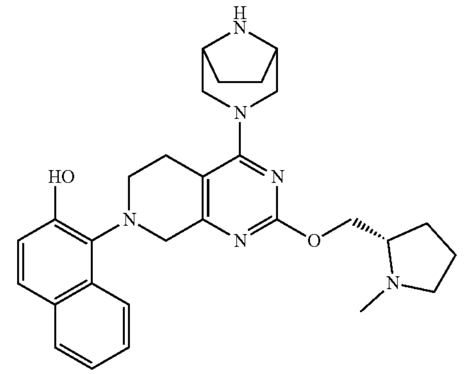 [SMILES: CN1CCC[C@H]1COc1nc2c(c(N3CC4CCC(C3)N4)n1)CCN(c1c(O)ccc3ccccc13)C2]

1-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol

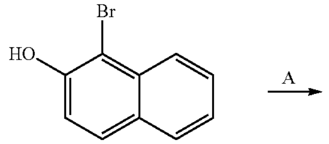

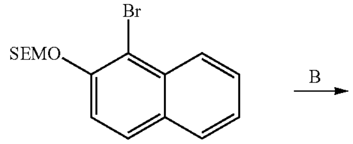

-continued

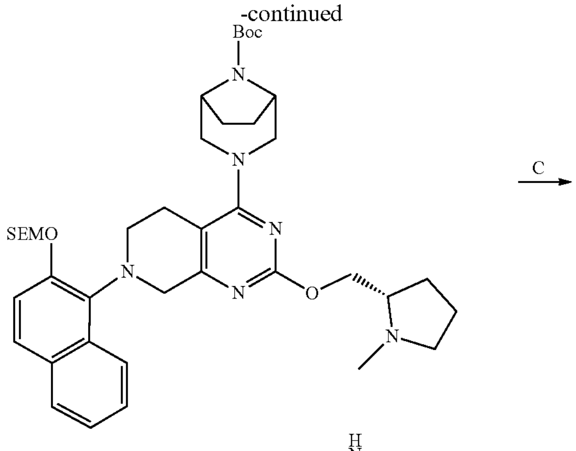

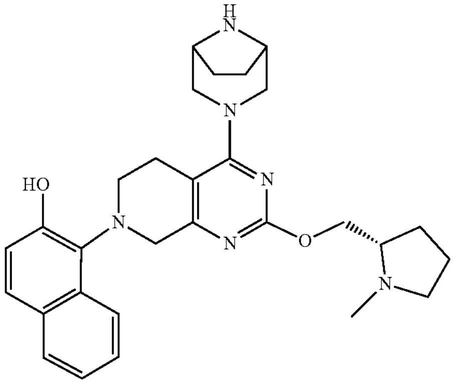

Step A. (2-(((1-bromonaphthalen-2-yl)oxy)methoxy)ethyl)trimethylsilane. To a solution of 1-Bromo-2-naphthol (1.0 g, 4.5 mmol), N-ethyl-N-isopropylpropan-2-amine (1.6 ml, 9.0 mmol) in dichloromethane (10 ml) cooled to 0° C. was added 2-(trimethylsilyl)ethoxymethyl chloride (1.2 ml, 6.7 mmol) and the reaction mixture was stirred for 2 hrs while warming to rt. The reaction was diluted with DCM (10 mL). The organics were washed with 0.5M $NaHCO_3$, dried over $Na_2SO_4$, and evaporated in vacuo. The material was used crude in the next reaction.

Step B. tert-butyl (1R,5S)-3-(2-(((S)-1-methylpyrrolidin-2-yl)methoxy)-7-(2-((2-(trimethylsilyl)ethoxy)methoxy)naphthalen-1-yl)-5,6,7,8-tetrahydropyrido[3,4-d]pyrimidin-4-yl)-3,8-diazabicyclo[3.2.1]octane-8-carboxylate. Synthesized according to Example 1, Step D substituting (2-(((1-bromonaphthalen-2-yl)oxy)methoxy)ethyl)trimethylsilane in place of 3-(methoxymethoxy)naphthalen-1-yl trifluoromethanesulfonate to give the desired product (54 mg, 34%) as a yellow solid. LCMS (MM-ES+APCI, Pos): m/z 731.5 (M+H).

Step C. 1-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol. Synthesized according to Example 2, Step E substituting tert-butyl (1R,5S)-3-(2-(((S)-1-methylpyrrolidin-2-yl)methoxy)-7-(2-((2-(trimethylsilyl)ethoxy)methoxy)naphthalen-1-yl)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to yield the product (2.1 mg, 3.4%) as the TFA salt. LCMS (MM-ES+APCI, Pos): m/z 501.3 (M+H).

Example 79

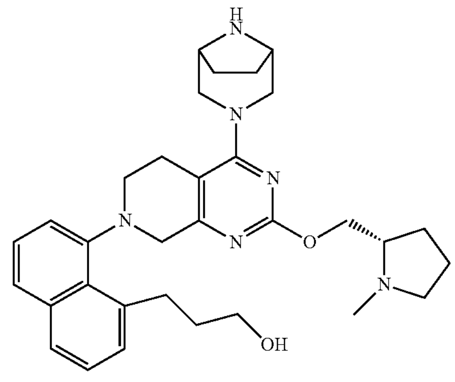 [SMILES: CN1CCC[C@H]1COc1nc2c(c(N3CC4CCC(C3)N4)n1)CCN(c1cccc3cccc(CCCO)c13)C2]

3-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)propan-1-ol

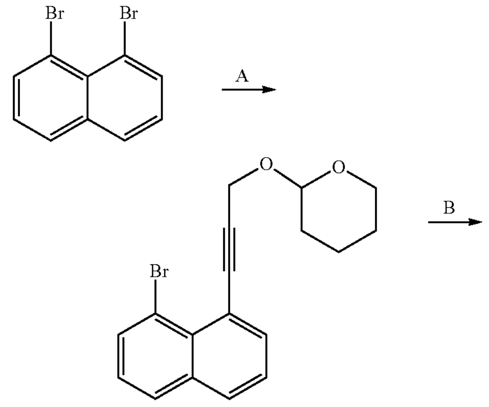

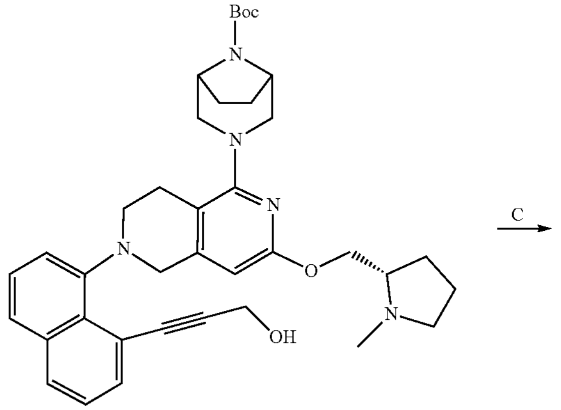

-continued

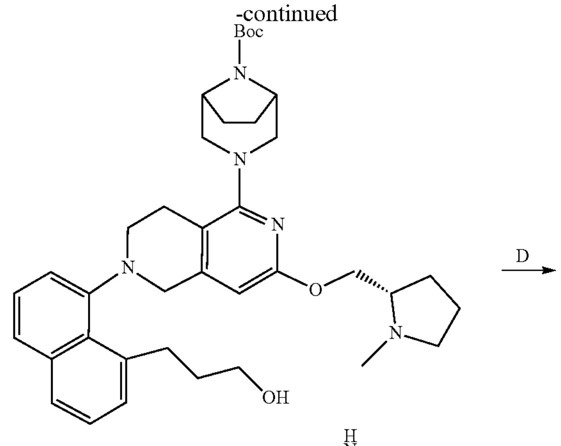

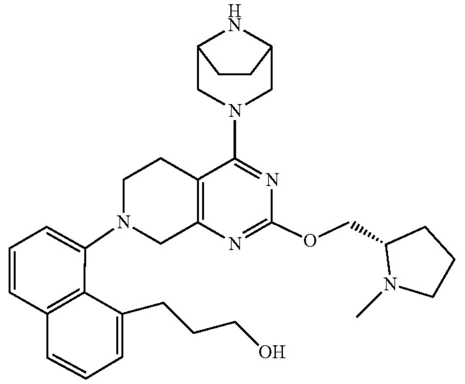

Step A. 2-((3-(8-bromonaphthalen-1-yl)prop-2-yn-1-yl)oxy)tetrahydro-2H-pyran. A mixture of 1,8-dibromonaphthalene (1.4 g, 5.0 mmol) and 2-(prop-2-yn-1-yloxy)tetrahydro-2H-pyran (0.84 g, 6.0 mmol) in diethylamine (5 mL) was sparged with $N_2$ for 5 minutes. A mixture of copper(I) iodide (0.019 g, 0.10 mmol) and $Pd(PPh_3)_4$(0.29 g, 0.25 mmol) was added in several portions. The reaction mixture was refluxed for 1 hour, stirred at 45° C. overnight, and refluxed for 3 more hours. The reaction was evaporated under $N_2$ and divided between MTBE (30 mL) and water (20 mL). The organic layer was washed with water (20 mL), washed with brine (10 mL), dried over $Na_2SO_4$, filtered, and concentrated in vacuo. The oil was chromatographed on silica gel eluting with 2→10% EtOAc/hexane to yield the desired product (0.40 g, 23%). LCMS (MM-ES+APCI, Pos): m/z 327.0 (M-OH).

Step B. tert-butyl (1R,5S)-3-(7-(8-(3-hydroxyprop-1-yn-1-yl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 2-((3-(8-bromonaphthalen-1-yl)prop-2-yn-1-yl)oxy)tetrahydro-2H-pyran in place of 3-(methoxymethoxy)naphthalen-1-yl trifluoromethanesulfonate. The product was stirred in 1% TFA in methanol (1 mL) overnight. The reaction mixture was chromatographed on a reverse phase column (C18, Gilson) 5-95% MeCN/$H_2O$+0.1% TFA as a modifier. The TFA salt was taken up in DCM, washed with aqueous $Na_2CO_3$, and dried under vacuum to give tert-butyl (1R,5S)-3-(7-(8-(3-hydroxyprop-1-yn-1-yl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (5 mg, 3.6%). LCMS (MM-ES+APCI, Pos): m/z 639.4 (M+H).

Step C. tert-butyl (1R,5S)-3-(7-(8-(3-hydroxypropyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step C substituting tert-butyl (1R,5S)-3-(7-(8-(3-hydroxyprop-1-yn-1-yl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product (3 mg, 60%). LCMS (MM-ES+APCI, Pos): m/z 643.5 (M+H).

Step D. 3-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)propan-1-ol. Synthesized according to Example 2, Step E substituting tert-butyl (1R,5S)-3-(7-(8-(3-hydroxypropyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the target compound (3.8 mg, 100%) as the HCl salt. LCMS (MM-ES+APCI, Pos): m/z 543.4 (M+H).

Example 80

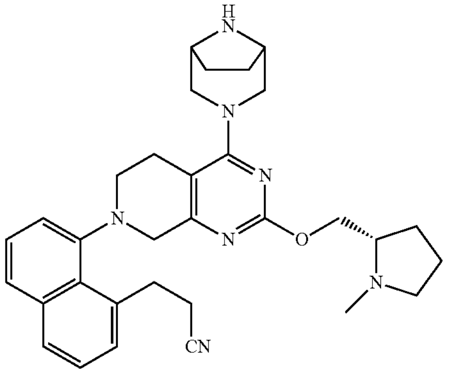 [SMILES: CN1CCC[C@H]1COc1nc2c(c(N3CC4CCC(C3)N4)n1)CCN(c1cccc3cccc(CCC#N)c13)C2]

3-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)propanenitrile

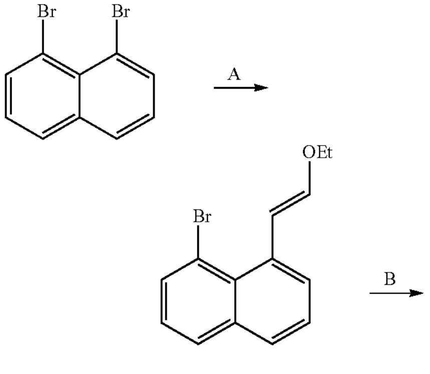

-continued

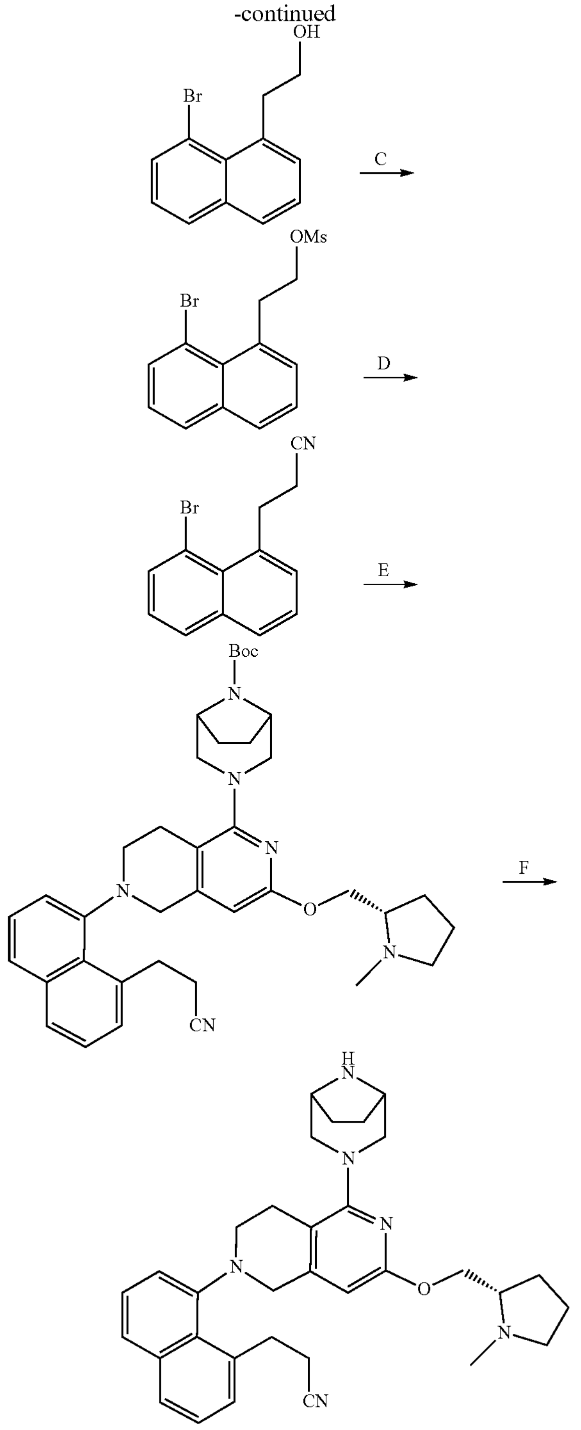

Step A. (E)-1-bromo-8-(2-ethoxyvinyl)naphthalene. A mixture of 1,8-dibromonaphthalene (1.0 g, 3.5 mmol), $Pd(PPh_3)_4$(0.40 g, 0.35 mmol), 2M $Na_2CO_3$ (5.3 mL, 11 mmol) and 1,4-dioxane (20 mL) was degassed under $N_2$. (E)-2-(2-ethoxyvinyl)-4,4,5,5-tetramethyl-1,3,2-dioxaborolane (0.83 g, 4.2 mmol) was added and the reaction mixture was stirred at 95° C. for 72 hours. The reaction mixture was cooled to r.t. and divided between EtOAc and water (100 mL each). The organic layer was washed with brine, dried over $Na_2SO_4$, and concentrated in vacuo. The crude material was chromatographed on silica gel eluting with 0-2% EtOAc/hexane to afford the desired (0.27 g, 28%). $^1H$ NMR ($CDCl_3$, 400 MHz): 7.82 (dd, J=7.5, 1.4 Hz, 1H), 7.77 (ddd, J=8.3, 3.4, 1 Hz, 1H), 7.75-7.69 (m, 1H), 7.41-7.35 (m, 2H), 7.22 (dd, J=8.0, 7.4 Hz, 1H), 7.11 (d, J=12.5 Hz, 1H), 6.56 (d, J=12.5 Hz, 1H), 4.02 (q, J=7.0 Hz, 2H), 1.40 (t, J=7.0 Hz, 3H).

Step B. 2-(8-bromonaphthalen-1-yl)ethan-1-ol. To a stirred solution of (E)-1-bromo-8-(2-ethoxyvinyl)naphthalene (0.20 g, 0.72 mmol) in tetrahydrofuran (2.5 mL) was added 6M aq. hydrogen chloride (0.5 mL, 3 mmol) and the reaction mixture was stirred for 1 hour. The mixture was divided between EtOAc (20 mL) and water (10 mL), and the organic layer was washed with 0.5M $NaHCO_3$. The organic layer was treated with $NaBH_4$ (0.27 g, 7.2 mmol) and stirred for 1 hour. The organic layer was decanted, washed with sat. $NaHCO_3$, brine (5 mL each), dried over $Na_2SO_4$, and evaporated in vacuo to give the desired product (0.18 g, 100%) which was used without further purification. $^1H$ NMR ($CDCl_3$, 400 MHz): 7.85 (dd, J=7.4, 1.1 Hz, 1H), 7.81 (dd, J=8.0, 0.9 Hz, 1H), 7.76 (dd, J=7.8, 1.7 Hz, 1H), 7.46-7.37 (m, 2H), 7.26-7.20 (m, 1H), 4.01 (t, J=6.8 Hz, 2H), 3.85 (t, J=6.8 Hz, 2H), 1.50 (br s, 1H).

Step C. 2-(8-bromonaphthalen-1-yl)ethyl methanesulfonate. A stirred solution of crude 2-(8-bromonaphthalen-1-yl)ethan-1-ol (0.18 g, 0.72 mmol) and N-ethyl-N-isopropylpropan-2-amine (0.19 mL, 1.1 mmol) in dichloromethane (5 mL) was cooled to 0° C. and methanesulfonyl chloride (0.067 mL, 0.87 mmol) was added dropwise. The reaction mixture was warmed to r.t. over 2 hours and partitioned between hexane/EtOAc (1:1, 15 mL) and 0.5M $NaHCO_3$ (5 mL). The organic phase was washed with brine, dried over $Na_2SO_4$, and evaporated in vacuo. The material was dissolved in MTBE (2 mL), filtered, and evaporated under $N_2$ to give the crude product (0.22 g, 93%).

Step D. 3-(8-bromonaphthalen-1-yl)propanenitrile. A mixture of crude 2-(8-bromonaphthalen-1-yl)ethyl methanesulfonate (0.22 g, 0.67 mmol), sodium cyanide (49 mg, 1.00 mmol) and N,N-dimethylacetamide (1.3 mL) was stirred at r.t. over 72 hours and heated to 50° C. for 5 hours. The reaction mixture was cooled and divided between EtOAc (15 mL) and water (10 mL). The organic phase was washed with brine, dried over $Na_2SO_4$, and evaporated in vacuo. The residue was chromatographed on silica gel eluting with 10% EtOAc/hexane to yield the product (0.17 g, 98%).

Step E. tert-butyl (1R,5S)-3-(7-(8-(2-cyanoethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 3-(8-bromonaphthalen-1-yl)propanenitrile in place of 3-(methoxymethoxy)naphthalen-1-yl trifluoromethanesulfonate to give the desired product (87 mg, 63%). LCMS (MM-ES+APCI, Pos): m/z 638.5 (M+H).

Step F. 3-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)propanenitrile. Synthesized according to Example 2, Step E substituting tert-butyl (1R,5S)-3-(7-(8-(2-cyanoethyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The crude product was chromatographed on silica gel eluting with 7→10% MeOH/DCM+10% $NH_4OH$ as a modifier to yield the target compound as a colorless solid (25 mg, 52%). LCMS (MM-ES+APCI, Pos): m/z 538.4 (M+H).

Example 81

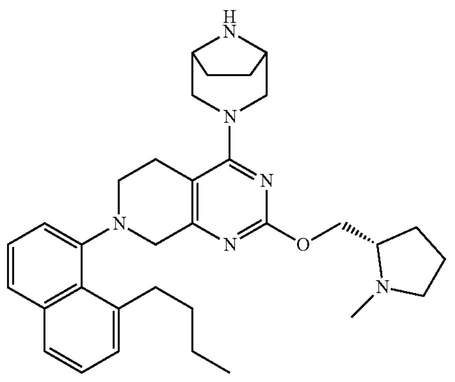 [SMILES: CCCCc1cccc2cccc(N3CCc4c(nc(OC[C@@H]5CCCN5C)nc4N4CC5CCC(C4)N5)C3)c12]

4-((1R,5S)-3,8-diazabicyclo[3.2.1]octan-3-yl)-7-(8-butylnaphthalen-1-yl)-2-(((S)-1-methylpyrrolidin-2-yl)methoxy)-5,6,7,8-tetrahydropyrido[3,4-d]pyrimidine

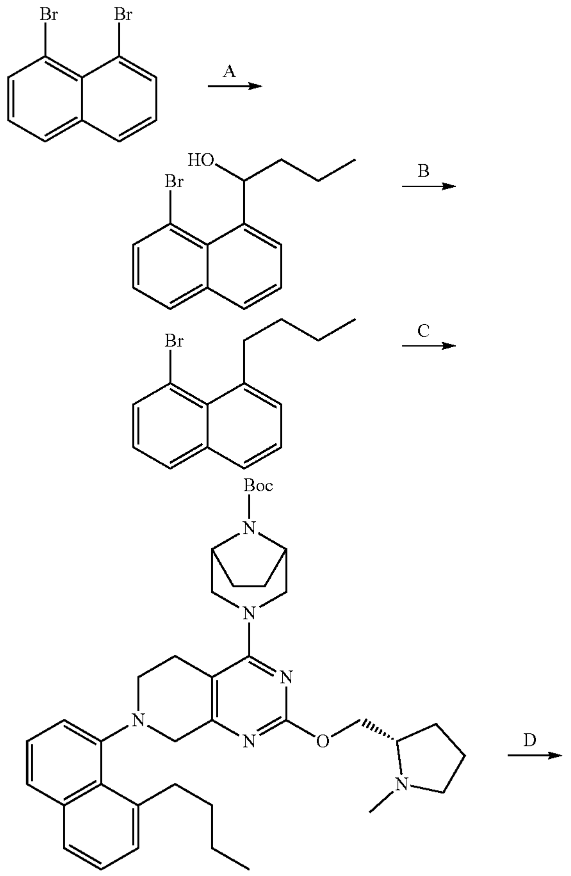

-continued

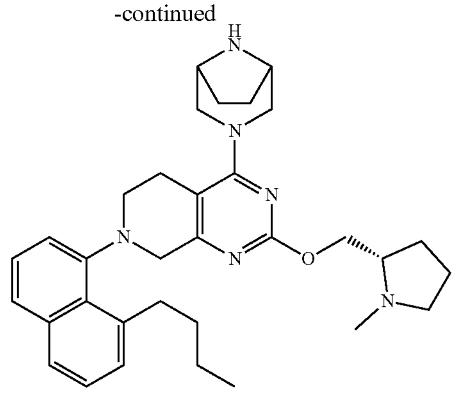

Step A. 1-(8-bromonaphthalen-1-yl)butan-1-ol. A stirred solution of 1,8-dibromonaphthalene (0.29 g, 1.0 mmol) in tetrahydrofuran (4 mL) was cooled to −78° C., and 2.5 M butyllithium (0.40 mL, 1.00 mmol) in hexanes was added dropwise over 5 min. The mixture was stirred for 15 min and butyraldehyde (0.11 mL, 1.2 mmol) was added. The reaction mixture was warmed to r.t. and divided between MTBE (15 mL) and water (10 mL). The organic layer was washed with water and brine (5 mL each), dried over $Na_2SO_4$, evaporated in vacuo, and chromatographed on silica gel in 5 to 10% EtOAc/hexane to yield the desired product as a colorless solid (0.19 g, 66%).

Step B. 1-bromo-8-butylnaphthalene. To a stirred solution of 1-(8-bromonaphthalen-1-yl)butan-1-ol (0.19 g, 0.66 mmol) in dichloromethane (2 mL) was added triethylsilane (0.32 mL, 2.0 mmol) followed by 2,2,2-trifluoroacetic acid (0.10 mL, 1.3 mmol). The reaction mixture was stirred for 10 min at r.t., diluted with hexane (10 mL), washed with water (5 mL) and then 1M NaOH (5 mL), dried over $Na_2SO_4$, and concentrated in vacuo. The residue was chromatographed on silica gel using hexanes to yield the desired product as a colorless oil (0.11 g, 63%).

Step C. tert-butyl (1R,5S)-3-(7-(8-butylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 1-bromo-8-butylnaphthalene in place of 3-(methoxymethoxy)naphthalen-1-yl trifluoromethanesulfonate (98 mg, 70%). LCMS (MM-ES+APCI, Pos): m/z 641.5 (M+H).

Step D. 4-((1R,5S)-3,8-diazabicyclo[3.2.1]octan-3-yl)-7-(8-butylnaphthalen-1-yl)-2-(((S)-1-methylpyrrolidin-2-yl)methoxy)-5,6,7,8-tetrahydropyrido[3,4-d]pyrimidine. Synthesized according to Example 2, Step E, substituting tert-butyl (1R,5S)-3-(7-(8-butylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product as the HCl salt (0.10 g, 100%). LCMS (MM-ES+APCI, Pos): m/z 541.4 (M+H).

Example 82

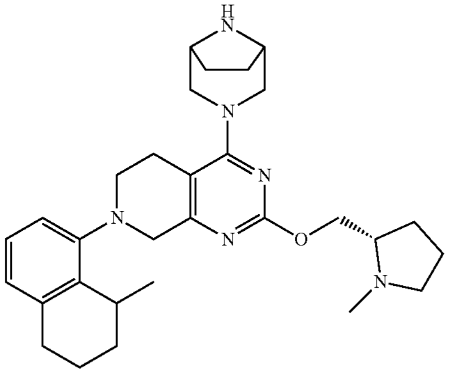 [SMILES: CC1CCCc2cccc(N3CCc4c(nc(OC[C@@H]5CCCN5C)nc4N4CC5CCC(C4)N5)C3)c21]

4-((1R,5S)-3,8-diazabicyclo[3.2.1]octan-3-yl)-7-(8-methyl-5,6,7,8-tetrahydronaphthalen-1-yl)-2-(((S)-1-methylpyrrolidin-2-yl)methoxy)-5,6,7,8-tetrahydropyrido[3,4-d]pyrimidine

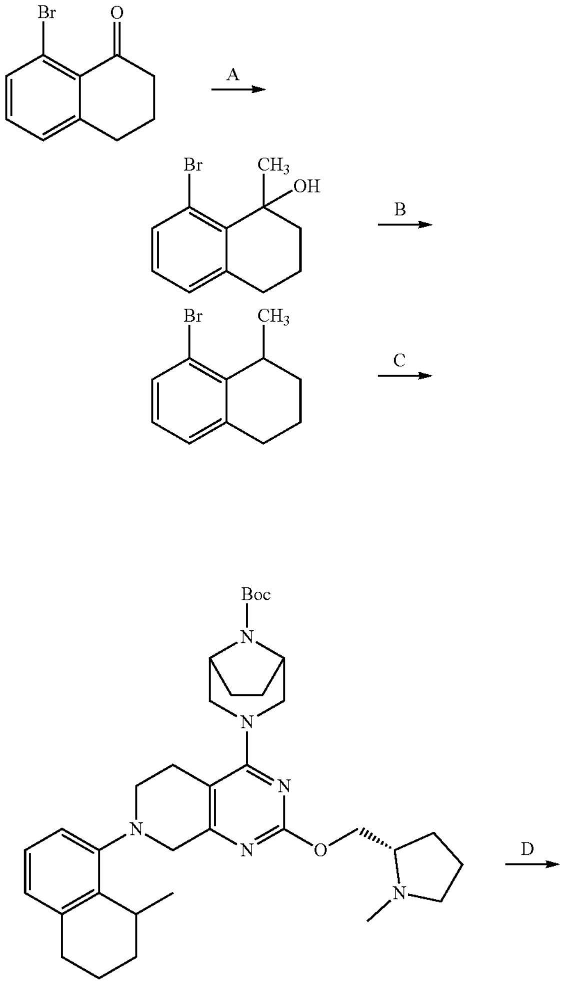

-continued

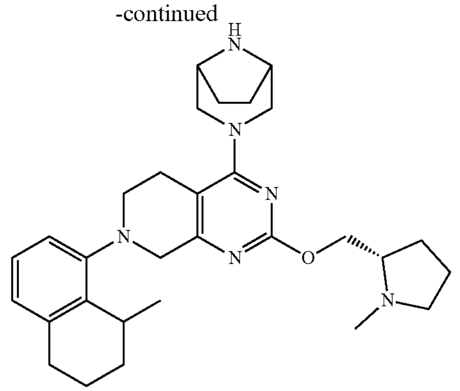

Step A. 8-bromo-1-methyl-1,2,3,4-tetrahydronaphthalen-1-ol. A stirred solution of 8-bromo-3,4-dihydro-2H-naphthalen-1-one (0.50 g, 2.22 mmol) in tetrahydrofuran (11 mL) was cooled to −20° C. and 3M methyl magnesium bromide (0.89 mL, 2.7 mmol) in ether was added dropwise. The reaction mixture was stirred at −20° C. for 1 hour, warmed to r.t., treated with methyl magnesium bromide (11 mmol), and stirred overnight at room temperature. The reaction mixture was cooled to 0° C., and added dropwise to a stirred mixture of ice (50 g) and acetic acid (10 mL). The emulsion was extracted with EtOAc (20 mL). The organic layer was washed with water, 2M $Na_2CO_3$, and brine (20 mL each), dried over $Na_2SO_4$, and evaporated in vacuo. The residue was dissolved in EtOH (3 mL), treated with 35% hydrazine (1 mL), heated to reflux for 40 min, and stirred at r.t. overnight. Additional 35% hydrazine (1 mL) was added and the reaction was heated to reflux for 2 hours. The reaction mixture was cooled, and divided between MTBE and water (30 mL each). The layers were separated. The organic phase was washed with brine (10 mL), dried over $Na_2SO_4$, concentrated in vacuo, and chromatographed on silica gel in 10% EtOAc/hexane to yield the desired product as a colorless solid (0.31 g, 59%). Step B. 8-bromo-1-methyl-1,2,3,4-tetrahydronaphthalene. A stirred solution of 8-bromo-1-methyl-1,2,3,4-tetrahydronaphthalen-1-ol (0.30 g, 1.2 mmol) and triethylsilane (1.0 mL, 6.2 mmol) in dichloromethane (12 mL) was cooled to −20° C. and treated with by 2,2,2-trifluoroacetic acid (0.29 mL). The reaction mixture warmed to r.t. over 3 hours and divided between water (10 mL) and hexane (30 mL). The organic phase was washed with sat. $NaHCO_3$, dried over $Na_2SO_4$, and concentrated in vacuo. Chromatography on silica gel in pentane afforded the desired product as a colorless oil (0.19 g, 69%).

Step C. tert-butyl (1R,5S)-3-(7-(8-methyl-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 8-bromo-1-methyl-1,2,3,4-tetrahydronaphthalene in place of 3-(methoxymethoxy)naphthalen-1-yl trifluoromethanesulfonate (45 mg, 34%). LCMS (MM-ES+APCI, Pos): m/z 603.3 (M+H).

Step D. 4-((1R,5S)-3,8-diazabicyclo[3.2.1]octan-3-yl)-7-(8-methyl-5,6,7,8-tetrahydronaphthalen-1-yl)-2-(((S)-1-methylpyrrolidin-2-yl)methoxy)-5,6,7,8-tetrahydropyrido[3,4-d]pyrimidine. Synthesized according to Example 2, Step E, substituting tert-butyl (1R,5S)-3-(7-(8-methyl-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product as the HCl salt (38 mg, 88%). LCMS (MM-ES+APCI, Pos): m/z 503.3 (M+H).

Example 83

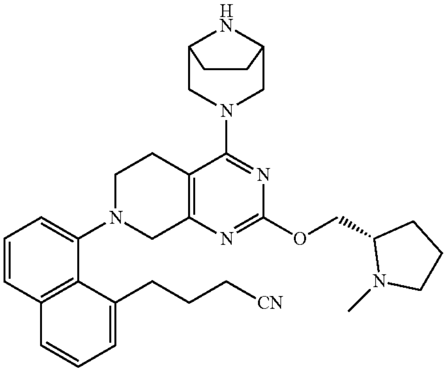 [SMILES: CN1CCC[C@H]1COc1nc2c(c(N3CC4CCC(C3)N4)n1)CCN(c1cccc3cccc(CCCC#N)c13)C2]

4-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)butanenitrile

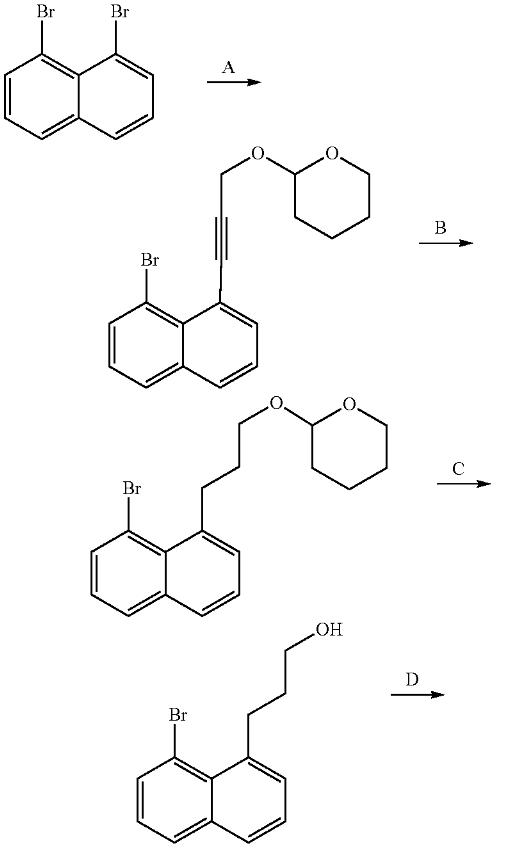

-continued

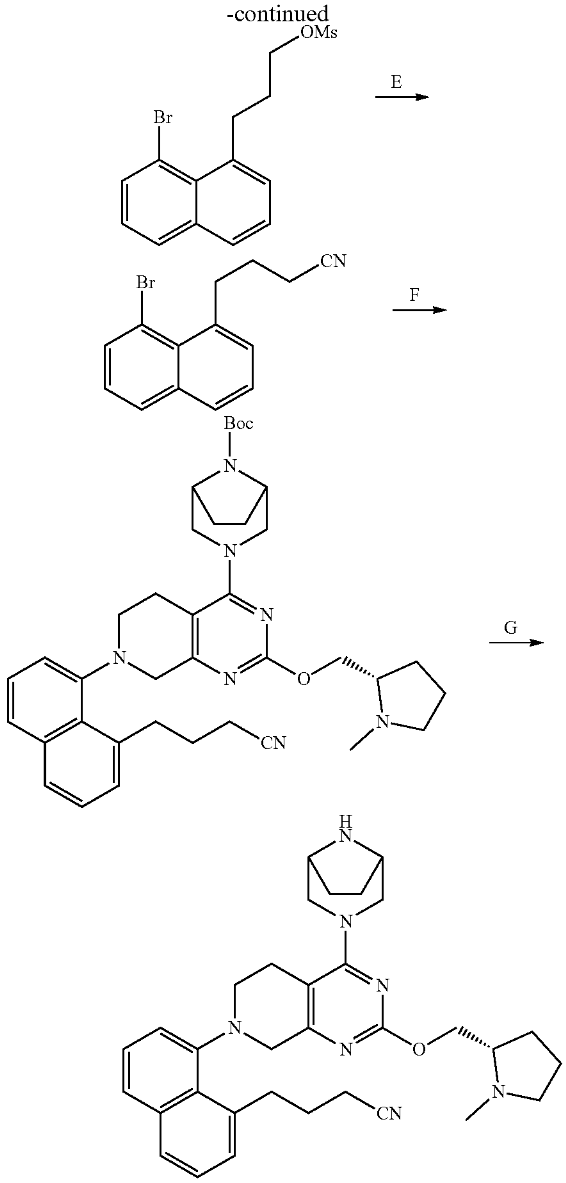

Step A. 2-((3-(8-bromonaphthalen-1-yl)prop-2-yn-1-yl)oxy)tetrahydro-2H-pyran. A mixture of 1,8-dibromonaphthalene (10 g, 35 mmol) and 2-(prop-2-yn-1-yloxy)tetrahydro-2H-pyran (5.9 g, 42 mmol) in diethylamine (20 mL) was sparged with $N_2$ flow for 5 minutes. Copper(I) iodide (0.13 g, 0.70 mmol) and $Pd(PPh_3)_4$(2.0 g, 1.8 mmol) were added and the reaction mixture was refluxed for one week under $N_2$. The reaction was cooled to r.t., diluted with hexane (50 mL), filtered, and the filter cake was washed with 10% MTBE/hexane. The combined filtrate was evaporated in vacuo and chromatographed on silica gel eluting with 2→20% EtOAc/hexane to yield the desired product as a viscous colorless oil (4.0 g, 33%). LCMS (MM-ES+APCI, Pos): m/z 327.1 $(M-H_2O)^+$.

Step B. 2-(3-(8-bromonaphthalen-1-yl)propoxy)tetrahydro-2H-pyran. A stirred solution of 2-((3-(8-bromonaphthalen-1-yl)prop-2-yn-1-yl)oxy)tetrahydro-2H-pyran (0.50 g, 1.5 mmol) and 35% aq. hydrazine (1.3 mL, 10 eq.) in ethanol (7 mL) was heated under air at 70° C. for 5 days. The reaction mixture was cooled to r.t., concentrated in vacuo, and divided between MTBE/water (50 mL each). The organic layer was washed with water (30 mL),brine (15 mL), dried over $Na_2SO_4$, and evaporated in vacuo. Chromatography on silica gel eluting with 2 to 5% EtOAc/hexane afforded the desired product as a mixture with the des-Br compound (0.31 g, 42%).

Step C. 3-(8-bromonaphthalen-1-yl)propan-1-ol. To a stirred mixture of crude 2-(3-(8-bromonaphthalen-1-yl)propoxy)tetrahydro-2H-pyran (0.30 g, 0.61 mmol) in methanol (5 mL) was added 6M hydrogen chloride (0.02 mL, 0.120 mmol) and the solution was stirred at r.t. for 1 h. The reaction mixture was quenched with $NH_4OH$ and evaporated in vacuo. The residue was dissolved in DCM (5 mL), filtered through a cotton plug and used directly in the next stage.

Step D. 3-(8-bromonaphthalen-1-yl)propyl methanesulfonate. A stirred solution of crude 3-(8-bromonaphthalen-1-yl)propan-1-ol (0.16 g, 0.61 mmol) and N-ethyl-N-isopropylpropan-2-amine (0.21 mL, 1.2 mmol) in dichloromethane (3 mL) was cooled to −20° C. and methanesulfonyl chloride (0.071 mL, 0.92 mmol) was added dropwise. The reaction mixture was warmed to 0° C. over 1 hour and divided between MTBE (15 mL) and 0.5M $NaHCO_3$ (5 mL). The organic phase was washed with brine, dried over $Na_2SO_4$, and evaporated in vacuo. The residue was dissolved in MTBE (2 mL), filtered, and evaporated under $N_2$. The material was used crude in the next reaction.

Step E. 4-(8-bromonaphthalen-1-yl)butanenitrile. A mixture of crude 3-(8-bromonaphthalen-1-yl)propyl methanesulfonate (0.21 g, 0.43 mmol), sodium cyanide (45 mg, 0.92 mmol) and N,N-dimethylacetamide (1.2 mL) under $N_2$ was stirred at 40° C. for 2 hours and 50° C. overnight. The reaction mixture was cooled to r.t. and divided between MTBE (30 mL) and water (10 mL). The organic phase was washed with water and brine, dried over $Na_2SO_4$, and evaporated in vacuo. Chromatography on silica gel in 10% EtOAc/hexane afforded the desired product as a colorless oil (0.16 g, 85%).

Step F. tert-butyl (1R,5S)-3-(7-(8-(3-cyanopropyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 4-(8-bromonaphthalen-1-yl)butanenitrile in place of 3-(methoxymethoxy)naphthalen-1-yl trifluoromethanesulfonate to give the title product (37 mg, 26%). LCMS (MM-ES+APCI, Pos): m/z 652.4 (M+H).

Step G. 4-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)butanenitrile. Synthesized according to Example 2, Step E substituting tert-butyl (1R,5S)-3-(7-(8-(3-cyanopropyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The crude product was chromatographed on silica gel eluting with 7 to 10% MeOH/DCM+10% $NH_4OH$ as modifier to yield the target compound as a colorless glassy solid (20 mg, 64%). LCMS (MM-ES+APCI, Pos): m/z 552.3 (M+H).

Example 84

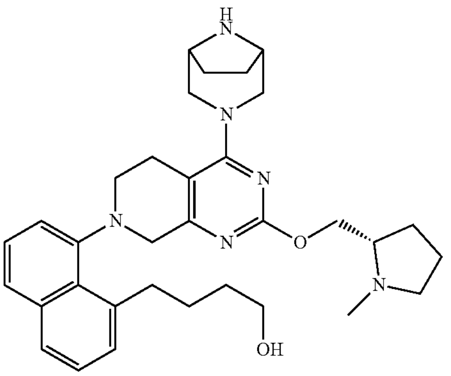 [SMILES: CN1CCC[C@H]1COc1nc2c(c(N3CC4CCC(C3)N4)n1)CCN(c1cccc3cccc(CCCCO)c13)C2]

4-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)butan-1-ol

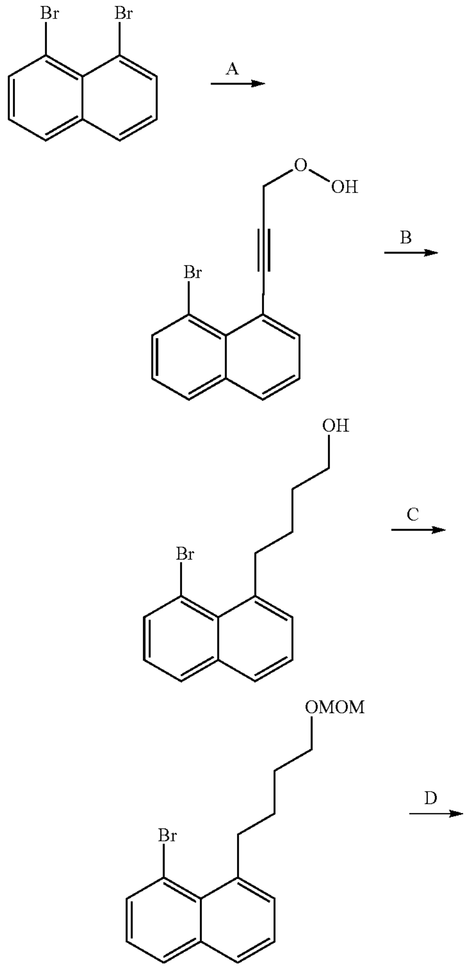

-continued

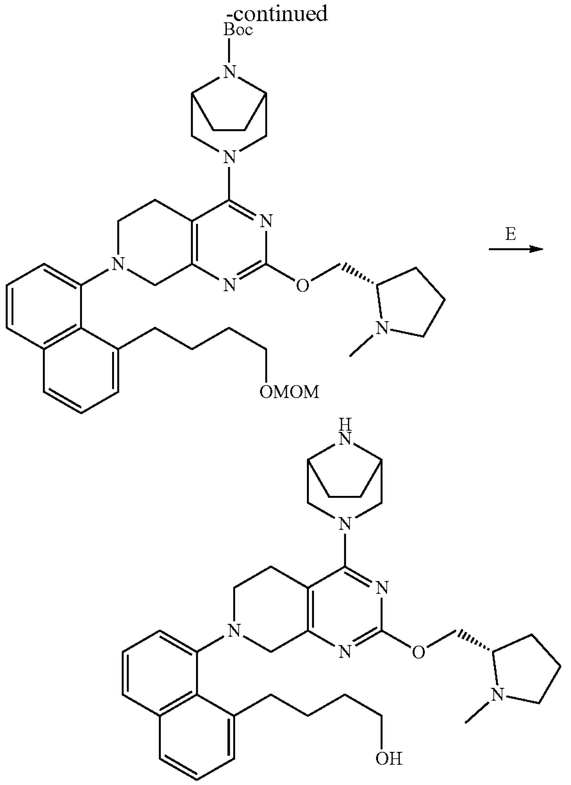

Step A. 4-(8-bromonaphthalen-1-yl)but-3-yn-1-ol. A mixture of 1,8-dibromonaphthalene (10 g, 35 mmol) and 3-butyn-1-ol (2.5 g, 35 mmol) in diethylamine (20 mL) was sparged with $N_2$ for 5 minutes. Copper(I) iodide (0.13 g, 0.70 mmol) and $Pd(PPh_3)_4$(2.0 g, 1.7 mmol) were added and the reaction mixture was refluxed for 40 hours. The reaction mixture was cooled to r.t. and divided between MTBE (200 mL) and water (150 mL). The organic phase was washed with water (100 mL), brine (50 mL), dried over $Na_2SO_4$, and concentrated in vacuo. Chromatography on silica gel eluting with 10→30% EtOAc/hexane yielded the crude product. A 1.0 g sample was dissolved in MTBE and EtOAc (20 mL each), 5% $H_2O_2$(30 mL) was added, and the mixture was stirred for 10 minutes. The organics were separated and a solution of NaI and $Na_2S_2O_3$ (2% each, 10 mL) was added. $FeCl_3$*$6H_2O$ (10 mg) was added and the reaction was stirred for 1.5 hours. The organics were separated, washed with brine (5 mL), dried over $Na_2SO_4$, and evaporated in vacuo. The material was chromatographed on silica gel eluting with 20% EtOAc/hex to yield the target compound as a colorless solid (0.86 g, 86%). LCMS (MM-ES+APCI, Pos): m/z 275.0 (M+H).

Step B. 4-(8-bromonaphthalen-1-yl)butan-1-ol. To a solution of 4-(8-bromonaphthalen-1-yl)but-3-yn-1-ol (0.86 g, 3.1 mmol) in ethanol (50 mL) was added 35% aq. hydrazine (2.9 g, 31 mmol) and the reaction mixture was stirred at 80° C. for 9 days with the addition of −1 mL of 35% $N_2H_4$ each day. The reaction mixture was cooled to r.t. and divided between water and MTBE (50 mL each). The organic layer was washed with water and brine (20 mL each), dried over $Na_2SO_4$, and evaporated in vacuo. The residue was chromatographed on silica gel eluting with 20% EtOAc/hexane to give the desired product as colorless oil (140 mg, 14%). $^1H$ NMR ($CDCl_3$, 400 MHz): 7.84 (dd, J=7.5, 1.4 Hz, 1H), 7.79 (ddd, J=8.0, 1.5, 0.6 Hz, 1H), 7.72 (dd, J=7.0, 2.7 Hz, 1H), 7.42-7.35 (m, 2H), 7.26-7.20 (d, J=8.0, 7.4 Hz, 1H), 3.69 (t, J=6.4 Hz, 2H), 3.57-3.51 (m, 2H), 1.89-1.66 (m, 4H), 1.36 (br s, 1H).

Step C. 1-bromo-8-(4-(methoxymethoxy)butyl)naphthalene. A solution of 4-(8-bromonaphthalen-1-yl)butan-1-ol (0.10 g, 0.32 mmol) and N-ethyl-N-isopropylpropan-2-amine (0.17 mL, 0.97 mmol) in dichloromethane (5 mL) was cooled to 0° C., treated with chloro(methoxy)methane (0.049 mL, 0.65 mmol), and stirred overnight. Additional chloro(methoxy)methane (0.049 mL) and N-ethyl-N-isopropylpropan-2-amine (0.7 mL) were added and the reaction mixture was stirred for 5 hours at r.t. The solution was stirred with excess $NH_4OH$ for 1 hour and the reaction was partitioned between MTBE and water (10 mL each). The organic phase was separated, washed with brine, dried over $Na_2SO_4$, and evaporated in vacuo. The residue was chromatographed on silica gel eluting with 5→20% EtOAc/hexane to give the desired product as colorless oil (85 mg, 82%).

Step D. tert-butyl (1R,5S)-3-(7-(8-(4-(methoxymethoxy)butyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. Synthesized according to Example 1, Step D substituting 1-bromo-8-(4-(methoxymethoxy)butyl)naphthalene in place of 3-(methoxymethoxy)naphthalen-1-yl trifluoromethanesulfonate to give the title product (0.10 g, 65%) as a colorless solid. LCMS (MM-ES+APCI, Pos): m/z 701.3 (M+H).

Step E. 4-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-1-yl)butan-1-ol. Synthesized according to Example 2, Step E substituting tert-butyl (1R,5S)-3-(7-(8-(4-(methoxymethoxy)butyl)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the product as the HCl salt (90 mg, 100%). LCMS (MM-ES+APCI, Pos): m/z 557.3 (M+H).

Example 85

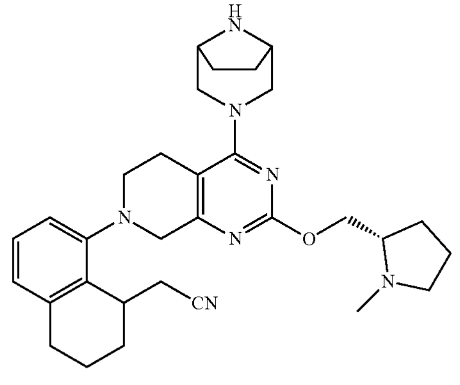 [SMILES: CN1CCC[C@H]1COc1nc2c(c(N3CC4CCC(C3)N4)n1)CCN(c1cccc3c1C(CC#N)CCC3)C2]

2-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1,2,3,4-tetrahydronaphthalen-1-yl)acetonitrile

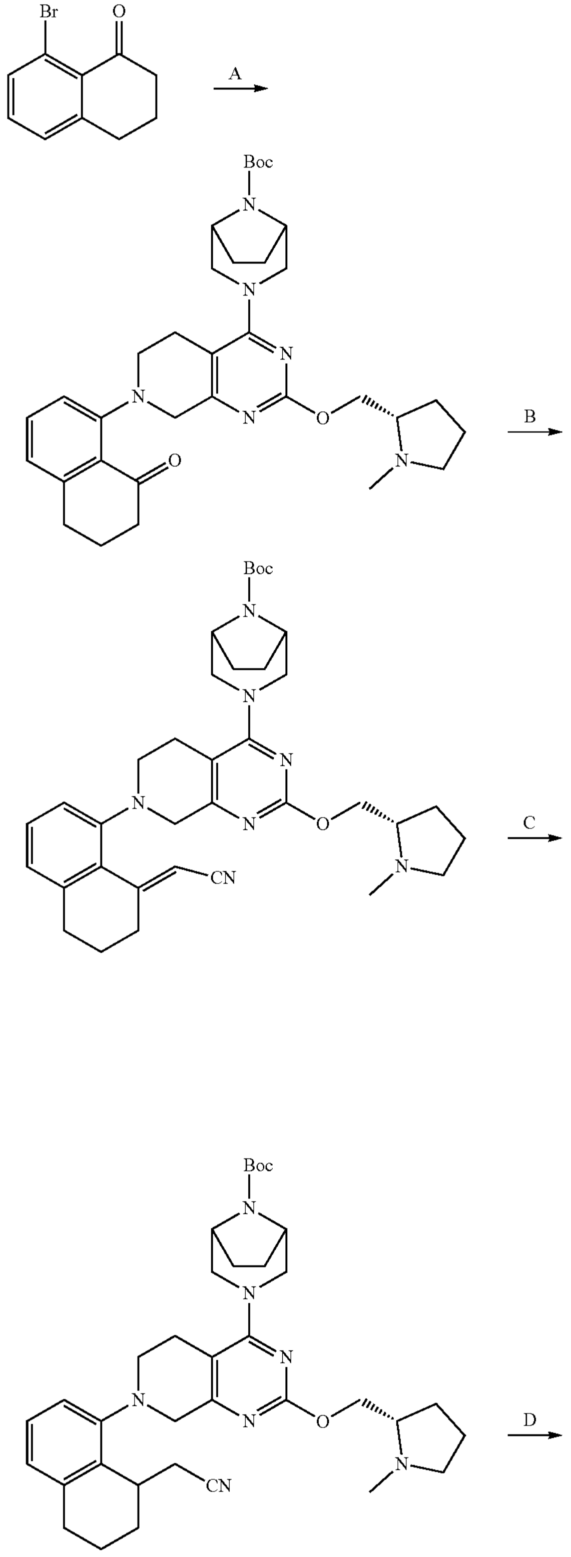

-continued

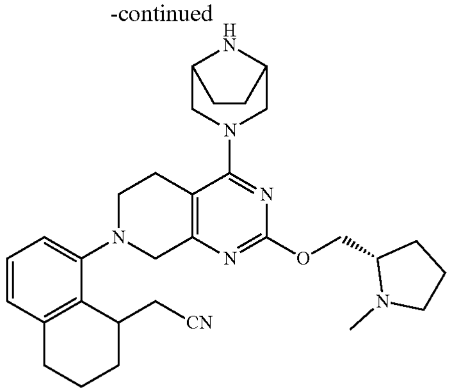

Step A. tert-butyl (1R,5S)-3-(2-(((S)-1-methylpyrrolidin-2-yl)methoxy)-7-(8-oxo-5,6,7,8-tetrahydronaphthalen-1-yl)-5,6,7,8-tetrahydropyrido[3,4-d]pyrimidin-4-yl)-3,8-diazabicyclo[3.2.1]octane-8-carboxylate. Synthesized according to Example 1, Step D substituting 8-bromo-3,4-dihydronaphthalen-1(2H)-one in place of 3-(methoxymethoxy)naphthalen-1-yl trifluoromethanesulfonate to give the product (24 mg, 18%). LCMS (MM-ES+APCI, Pos): m/z 603.3 (M+H).

Step B. tert-butyl (1R,5S)-3-(7-((Z)-8-(cyanomethylene)-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a stirred solution of diethyl cyanomethylphosphonate (64 μL, 0.40 mmol) in DMPU (0.4 mL) under $N_2$ was added sodium hydride (16 mg, 0.40 mmol). The reaction mixture was stirred for 1 hour and a solution of tert-butyl (1R,5S)-3-(2-(((S)-1-methylpyrrolidin-2-yl)methoxy)-7-(8-oxo-5,6,7,8-tetrahydronaphthalen-1-yl)-5,6,7,8-tetrahydropyrido[3,4-d]pyrimidin-4-yl)-3,8-diazabicyclo[3.2.1]octane-8-carboxylate (24 mg, 0.040 mmol) in DMPU (0.4 mL) was added. The reaction mixture was stirred at r.t. overnight and heated to 50° C. for 6 hours. The mixture was cooled to r.t., and divided between water and EtOAc (10 mL each). The organic layer was washed with water (2*5 mL) and brine (3 mL), dried over $Na_2SO_4$, and evaporated in vacuo. The combined aqueous phases were reextracted with EtOAc (10 mL). The organics were washed with brine and concentrated in vacuo. The residue was chromatographed on silica gel eluting with 3→4% MeOH/DCM+10% $NH_4OH$ as modifier to give the desired product as a mixture of isomers (10 mg, 40%). LCMS (MM-ES+APCI, Pos): m/z 626.3 (M+H).

Step C. tert-butyl (1R,5S)-3-(7-(8-(cyanomethyl)-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a stirred solution of tert-butyl (1R,5S)-3-(7-((Z)-8-(cyanomethylene)-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (10 mg, 0.016 mmol) in acetonitrile (3 mL) was added 10% Pd on carbon, (Degussa type, 1.7 mg). The reaction mixture was degassed, $H_2$ was introduced via balloon, and the mixture was stirred for 3 days at room temperature. Additional Pd/C (15 mg) was added and the reaction mixture was stirred for 8 hours. The reaction was filtered through Celite, evaporated in vacuo, and chromatographed on silica gel eluting with 4% MeOH+0.4% $NH_4OH$ in DCM to yield the desired product (7 mg, 70%). LCMS (MM-ES+APCI, Pos): m/z 628.3 (M+H).

Step D. 2-(8-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1,2,3,4-tetrahydronaphthalen-1-yl)acetonitrile. Synthesized according to Example 2, Step E substituting tert-butyl (1R,5S)-3-(7-(8-(cyanomethyl)-5,6,7,8-tetrahydronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The crude product was chromatographed on reverse phase (C18 prep HPLC) eluting with 5→95% MeCN/water with +0.1% TFA. The product was freebased by partitioning between aqueous $Na_2CO_3$ and DCM. The layers were separated and the organics dried under vacuum to yield the target compound (2.0 mg, 34%). LCMS (MM-ES+APCI, Pos): m/z 528.3 (M+H).

Example 86

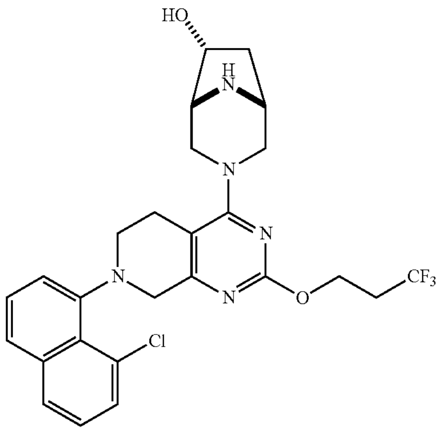

(1R,5R,6R)-3-(7-(8-chloronaphthalen-1-yl)-2-(3,3,3-trifluoropropoxy)-5,6,7,8-tetrahydropyrido[3,4-d]pyrimidin-4-yl)-3,8-diazabicyclo[3.2.1]octan-6-ol

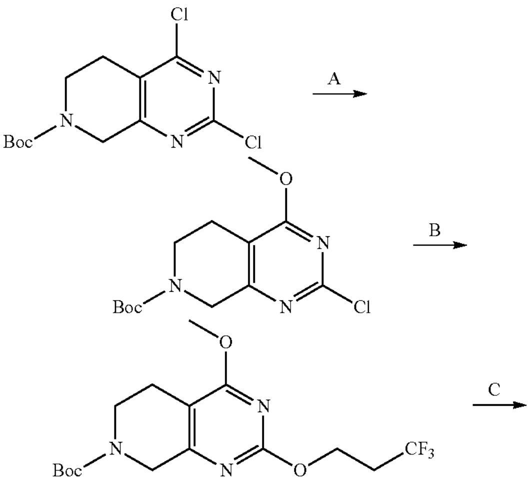

-continued

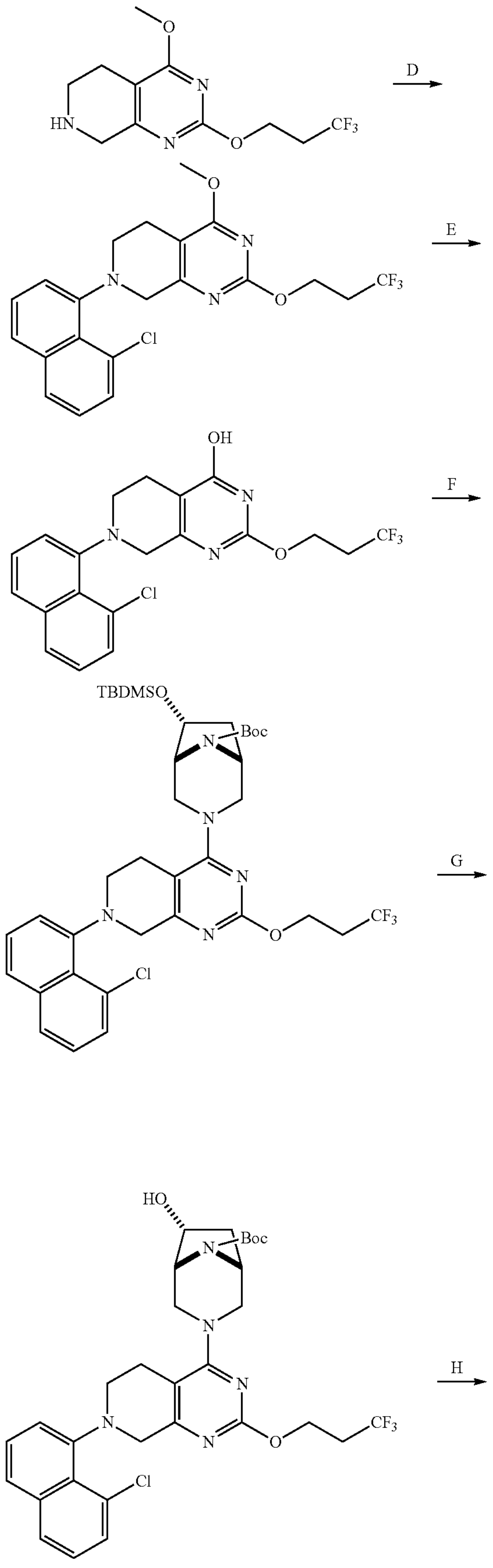

-continued

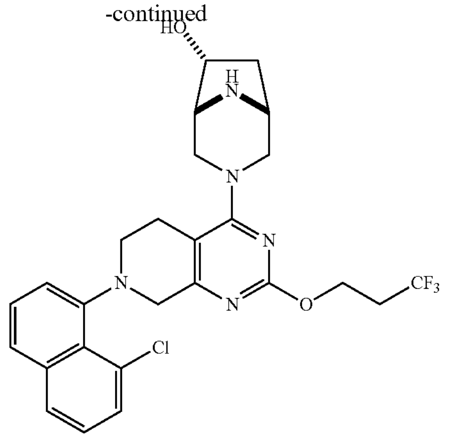

Step A. tert-butyl 2-chloro-4-methoxy-5,8-dihydropyrido[3,4-d]pyrimidine-7(6H)-carboxylate. A stirred solution of tert-butyl 2,4-dichloro-5,6-dihydropyrido[3,4-d]pyrimidine-7(8H)-carboxylate (20 g, 66 mmol) in methanol (330 mL) was cooled to 0° C. and 25% sodium methanolate in methanol (14 g, 66 mmol) was added. The reaction mixture was warmed to rt over 1 hour, evaporated in vacuo, and dried under high vacuum. The residue was partitioned between MTBE (200 mL) and water (100 mL) and the layers were separated. The organic layer was washed with brine, dried over $Na_2SO_4$, and evaporated in vacuo to yield the desired crude product (19.6 g, 100%). LCMS (MM-ES+APCI, Pos): m/z 300.2 (M+H).

Step B. tert-butyl 4-methoxy-2-(3,3,3-trifluoropropoxy)-5,8-dihydropyrido[3,4-d]pyrimidine-7(6H)-carboxylate. Synthesized according to Example 1, Step B substituting 3,3,3-trifluoropropan-1-ol in place of (S)-(1-methylpyrrolidin-2-yl)methanol and replacing tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate with tert-butyl 2-chloro-4-methoxy-5,8-dihydropyrido[3,4-d]pyrimidine-7(6H)-carboxylate. The crude product was chromatographed on silica gel eluting with 15 to 20% EtOAc/hexane to yield the title compound (1.1 g, 84%). LCMS (MM-ES+APCI, Pos): m/z 378.2 (M+H).

Step C. 4-methoxy-2-(3,3,3-trifluoropropoxy)-5,6,7,8-tetrahydropyrido[3,4-d]pyrimidine. Synthesized according to Example 4, Step C substituting tert-butyl 4-methoxy-2-(3,3,3-trifluoropropoxy)-5,8-dihydropyrido[3,4-d]pyrimidine-7(6H)-carboxylate in place of tert-butyl (S)-4-(benzyloxy)-2-((1-methylpyrrolidin-2-yl)methoxy)-5,8-dihydropyrido[3,4-d]pyrimidine-7(6H)-carboxylate. Yield of the desired product was assumed to be quantitative. LCMS (MM-ES+APCI, Pos): m/z 278.2 (M+H).

Step D. 7-(8-chloronaphthalen-1-yl)-4-methoxy-2-(3,3,3-trifluoropropoxy)-5,6,7,8-tetrahydropyrido[3,4-d]pyrimidine. Synthesized according to Example 1, Step D, substituting 1-bromo-8-chloronaphthalene in place of 3-(methoxymethoxy)naphthalen-1-yl trifluoromethanesulfonate and 4-methoxy-2-(3,3,3-trifluoropropoxy)-5,6,7,8-tetrahydropyrido[3,4-d]pyrimidine in place of tert-butyl (1R,5S)-3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give the title compound (0.48 g, 43%). LCMS (MM-ES+APCI, Pos): m/z 438.1 (M+H).

Step E. 7-(8-chloronaphthalen-1-yl)-2-(3,3,3-trifluoropropoxy)-5,6,7,8-tetrahydropyrido[3,4-d]pyrimidin-4-ol. A stirred mixture of 7-(8-chloronaphthalen-1-yl)-4-methoxy-2-(3,3,3-trifluoropropoxy)-5,6,7,8-tetrahydropyrido[3,4-d]pyrimidine (0.43 g, 0.99 mmol), sodium methanethiolate (0.21 g, 3.0 mmol), and N,N-dimethylacetamide (1 mL) under $N_2$ was heated to 50° C. for 1 hour. The reaction mixture was cooled to r.t. and divided between DCM (10 mL) and 0.5M $H_3PO_4$ (6 mL). The aqueous phase was acidified to pH 4 and extracted with DCM (2*10 mL). The combined organic phases were dried over $Na_2SO_4$ and evaporated under a stream of $N_2$ overnight. The residue was chromatographed on silica gel eluting with 30-50% EtOAc/hexane to yield the desired product as a yellow crystalline solid (0.32 g, 76%). LCMS (MM-ES+APCI, Pos): m/z 424.1 (M+H).

Step F. tert-butyl (1R,5R,6R)-6-((tert-butyldimethylsilyl)oxy)-3-(7-(8-chloronaphthalen-1-yl)-2-(3,3,3-trifluoropropoxy)-5,6,7,8-tetrahydropyrido[3,4-d]pyrimidin-4-yl)-3,8-diazabicyclo[3.2.1]octane-8-carboxylate. A suspension of 7-(8-chloronaphthalen-1-yl)-2-(3,3,3-trifluoropropoxy)-5,6,7,8-tetrahydropyrido[3,4-d]pyrimidin-4-ol (50 mg, 0.12 mmol) in toluene (1 mL) under $N_2$ was brought to reflux for 1 min., cooled to r.t., and diluted with dichloromethane (2.5 mL). The mixture was cooled to −78° C. and treated with triethylamine (41 μL, 0.29 mmol) followed by trifluoromethanesulfonic anhydride (37 mg, 0.13 mmol). The reaction mixture was warmed to −50° C. over 1 hour and treated with a solution of tert-butyl (1R,5R,6R)-6-((tert-butyldimethylsilyl)oxy)-3,8-diazabicyclo[3.2.1]octane-8-carboxylate (88 mg, 0.18 mmol) in MTBE. The reaction mixture was stirred under $N_2$ overnight and evaporated under a stream of $N_2$. The residue was diluted with triethylamine (41 μL) and dimethylacetamide (0.5 mL) and stirred at r.t. under $N_2$ over the weekend. The solution was evaporated in vacuo and chromatographed on silica gel eluting with 20 to 40% EtOAc/hexane to yield the desired product as a colorless solid (73 mg, 83%). LCMS (MM-ES+APCI, Pos): m/z 748.3 (M+H).

Step G. tert-butyl (1R,5R,6R)-3-(7-(8-chloronaphthalen-1-yl)-2-(3,3,3-trifluoropropoxy)-5,6,7,8-tetrahydropyrido[3,4-d]pyrimidin-4-yl)-6-hydroxy-3,8-diazabicyclo[3.2.1]octane-8-carboxylate. A stirred solution of tert-butyl (1R,5R,6R)-6-((tert-butyldimethylsilyl)oxy)-3-(7-(8-chloronaphthalen-1-yl)-2-(3,3,3-trifluoropropoxy)-5,6,7,8-tetrahydropyrido[3,4-d]pyrimidin-4-yl)-3,8-diazabicyclo[3.2.1]octane-8-carboxylate (73 mg, 0.098 mmol) in MTBE under $N_2$ was cooled to 0° C. and 1M tetrabutylammonium fluoride in THF (0.24 mL, 0.24 mmol) was added. The reaction mixture was stirred for 2 hours at 0° C. The reaction mixture was partitioned between MTBE and 0.5M $NaHCO_3$ (15 mL each) and the layers were separated. The organic layer was washed with brine, dried over $Na_2SO_4$, and evaporated in vacuo. The residue was chromatographed on silica gel eluting with 20 to 40% EtOAc/hexane to yield the desired product as a colorless solid (47 mg, 76%). LCMS (MM-ES+APCI, Pos): m/z 634.2 (M+H).

Step H. (1R,5R,6R)-3-(7-(8-chloronaphthalen-1-yl)-2-(3,3,3-trifluoropropoxy)-5,6,7,8-tetrahydropyrido[3,4-d]pyrimidin-4-yl)-3,8-diazabicyclo[3.2.1]octan-6-ol. Synthesized according to Example 4, Step H substituting tert-butyl (1R,5R,6R)-3-(7-(8-chloronaphthalen-1-yl)-2-(3,3,3-trifluoropropoxy)-5,6,7,8-tetrahydropyrido[3,4-d]pyrimidin-4-yl)-6-hydroxy-3,8-diazabicyclo[3.2.1]octane-8-carboxylate in place of tert-butyl 6-hydroxy-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. The crude product was chromatographed on silica gel in 4% MeOH+0.4% $NH_4OH$ in DCM to give the title product (9.2 mg, 23%) as a colorless solid. LCMS (MM-ES+APCI, Pos): m/z 534.2 (M+H).

Example 87

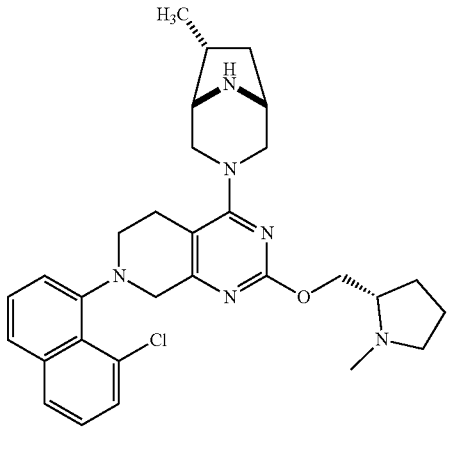

7-(8-chloronaphthalen-1-yl)-4-((1R,5S,6R)-6-methyl-3,8-diazabicyclo[3.2.1]octan-3-yl)-2-(((S)-1-methylpyrrolidin-2-yl)methoxy)-5,6,7,8-tetrahydropyrido[3,4-d]pyrimidine

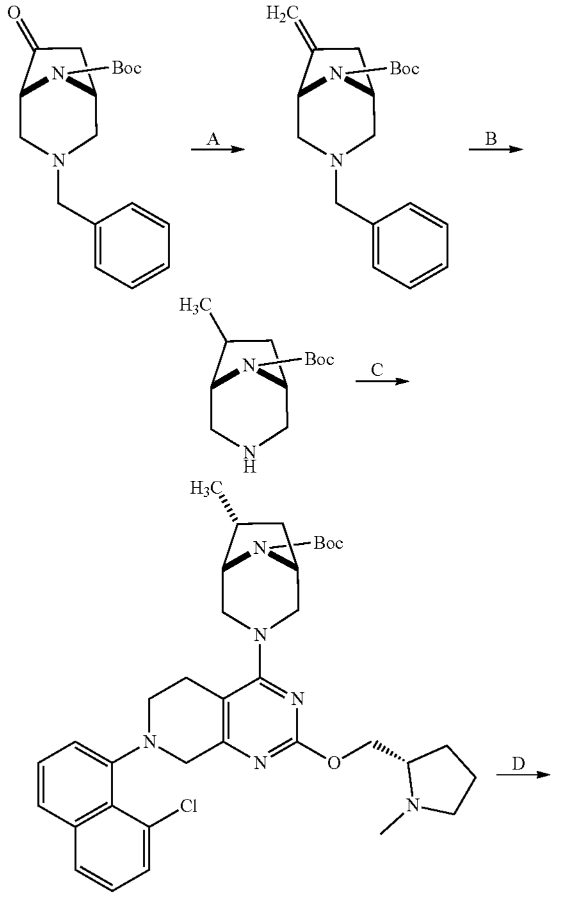

-continued

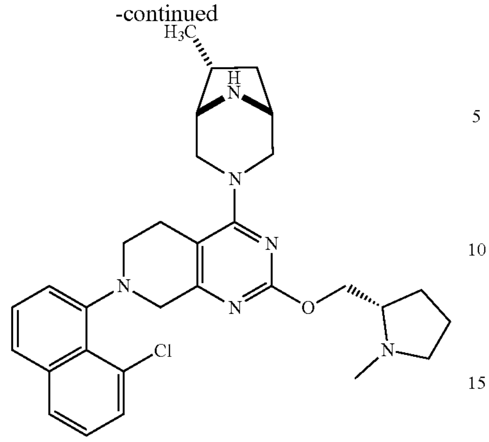

Step A. tert-butyl (1R,5S)-3-benzyl-6-methylene-3,8-diazabicyclo[3.2.1]octane-8-carboxylate. To a stirred suspension of methyltriphenylphosphonium bromide (0.17 g, 0.47 mmol) in ethoxyethane (3 mL) under $N_2$ was added methyllithium (0.24 mL, 0.38 mmol). The mixture was stirred at r.t. for 2 h followed by addition of tert-butyl (1R,5R)-3-benzyl-6-oxo-3,8-diazabicyclo[3.2.1]octane-8-carboxylate (0.10 g, 0.32 mmol). The reaction mixture was stirred at r.t. over the weekend and diluted with THF (1 mL). The mixture was heated to 40° C. for 2 hours, cooled to r.t., and filtered. The filter cake was washed with MTBE (3*1 mL). The combined organics were evaporated under $N_2$ and chromatographed on silica gel eluting with 10-20% EtOAc/hexane to yield the desired product as colorless oil (79 mg, 80%). LCMS (MM-ES+APCI, Pos): m/z 315.2 (M+H).

Step B. tert-butyl (1R,5S)-6-methyl-3,8-diazabicyclo[3.2.1]octane-8-carboxylate. A stirred mixture of tert-butyl (1R,5S)-3-benzyl-6-methylene-3,8-diazabicyclo[3.2.1]octane-8-carboxylate (79 mg, 0.25 mmol), 20% dihydroxypalladium on carbon (50 mg) in methanol (2.5 mL) was degassed and stirred under a hydrogen atmosphere via balloon for 1 h. The reaction mixture was filtered through Celite and evaporated in vacuo. The residue was dissolved in MTBE (2 mL), filtered through a cotton plug, and concentrated under a stream of $N_2$ to give desired product which was used crude in the next reaction. LCMS (MM-ES+APCI, Pos): m/z 227.3 (M+H).

Step C. tert-butyl (1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-methyl-3,8-diazabicyclo[3.2.1]octane-8-carboxylate and tert-butyl (1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-methyl-3,8-diazabicyclo[3.2.1]octane-8-carboxylate. A solution of (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (30 mg, 0.054 mmol), tert-butyl 6-methyl-3,8-diazabicyclo[3.2.1]octane-8-carboxylate (12 mg, 0.054 mmol) and triethylamine (15 µL, 0.11 mmol) in N,N-dimethylacetamide (0.2 mL) was stirred at r.t. overnight. Additional tert-butyl 6-methyl-3,8-diazabicyclo[3.2.1]octane-8-carboxylate (5 mg) was added and the reaction mixture was stirred for 2 h. The reaction was evaporated under a stream of $N_2$ and chromatographed using reverse phase (C18, Gilson) eluting with 5-95% $MeCN/H_2O$+0.1% TFA as modifier. The desired fractions were freebased by partitioning between aqueous $Na_2CO_3$ and DCM. The first-eluted isomer was assigned as endo-(1R,5S,6R) (5 mg, 15%); and the second-eluted as exo-isomer (1R,5S,6S), (20 mg, 59%). LCMS (MM-ES+APCI, Pos): m/z 633.4 (M+H).

Step D. 7-(8-chloronaphthalen-1-yl)-4-((1R,5S,6R)-6-methyl-3,8-diazabicyclo[3.2.1]octan-3-yl)-2-(((S)-1-methylpyrrolidin-2-yl)methoxy)-5,6,7,8-tetrahydropyrido[3,4-d]pyrimidine. To a stirred solution of tert-butyl (1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-methyl-3,8-diazabicyclo[3.2.1]octane-8-carboxylate (5 mg, 0.00790 mmol) in dichloromethane (1 mL) was added trifluoroacetic acid (0.2 mL, 2.61 mmol). The reaction mixture was stirred for 1 h, diluted with DCM (5 mL) and quenched with 1M $Na_2CO_3$ (2.4 mL, 2.4 mmol). The organic phase was dried over $Na_2CO_3$, filtered, and evaporated in vacuo to yield the target compound (3.2 mg, 76%). LCMS (MM-ES+APCI, Pos): m/z 533.3 (M+H).

Example 88

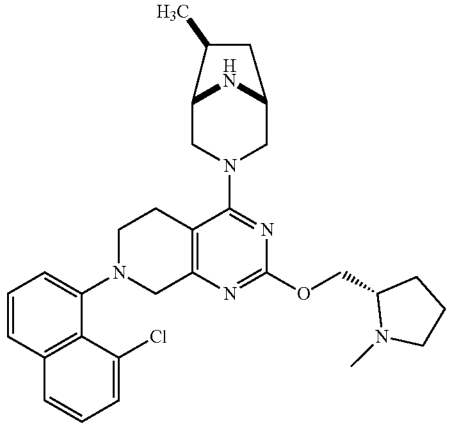

7-(8-chloronaphthalen-1-yl)-4-((1R,5S,6S)-6-methyl-3,8-diazabicyclo[3.2.1]octan-3-yl)-2-(((S)-1-methylpyrrolidin-2-yl)methoxy)-5,6,7,8-tetrahydropyrido[3,4-d]pyrimidine

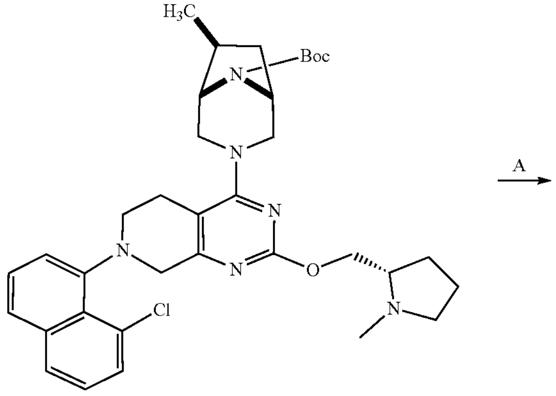

-continued

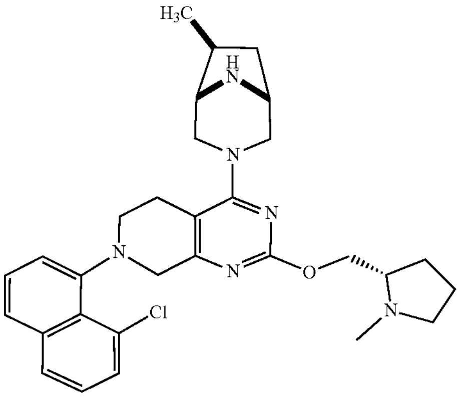

Step A. 7-(8-chloronaphthalen-1-yl)-4-((1R,5S,6S)-6-methyl-3,8-diazabicyclo[3.2.1]octan-3-yl)-2-(((S)-1-methylpyrrolidin-2-yl)methoxy)-5,6,7,8-tetrahydropyrido[3,4-d]pyrimidine. To a stirred solution of tert-butyl (1R,5S,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-methyl-3,8-diazabicyclo[3.2.1]octane-8-carboxylate (20 mg, 0.032 mmol, synthesized according to Example 87, Step A-C) in chloroform (1 mL) was added 2,2,2-trifluoroacetic acid (0.20 mL, 2.6 mmol). The reaction mixture was stirred at r.t. for 30 min., evaporated under vacuum, and chromatographed on the reverse phase (C18, Gilson) eluting with 5-95% $MeCN/H_2O$+0.1% TFA as modifier. The product was freebased by partitioning between $Na_2CO_3$, and DCM. The organics were dried under vacuum to give product (4.2 mg, 25%). LCMS (MM-ES+APCI, Pos): m/z 533.3 (M+H).

Example 89 and 90

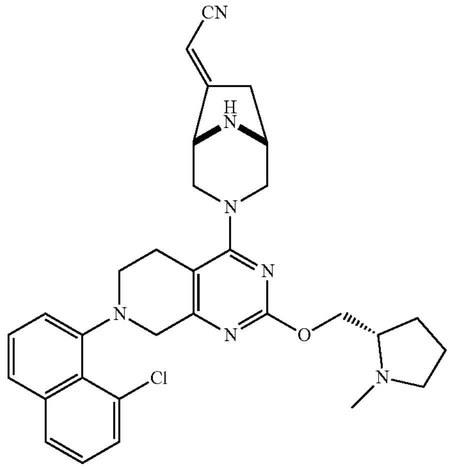

-continued

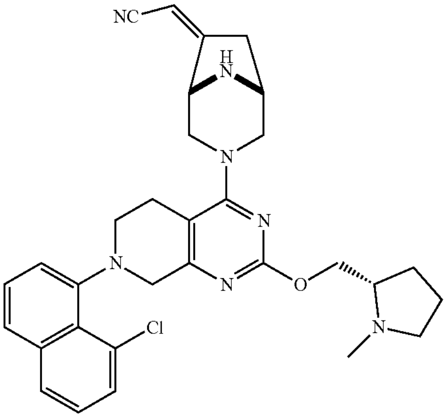

(E)-2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ylidene)acetonitrile and (Z)-2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ylidene)acetonitrile

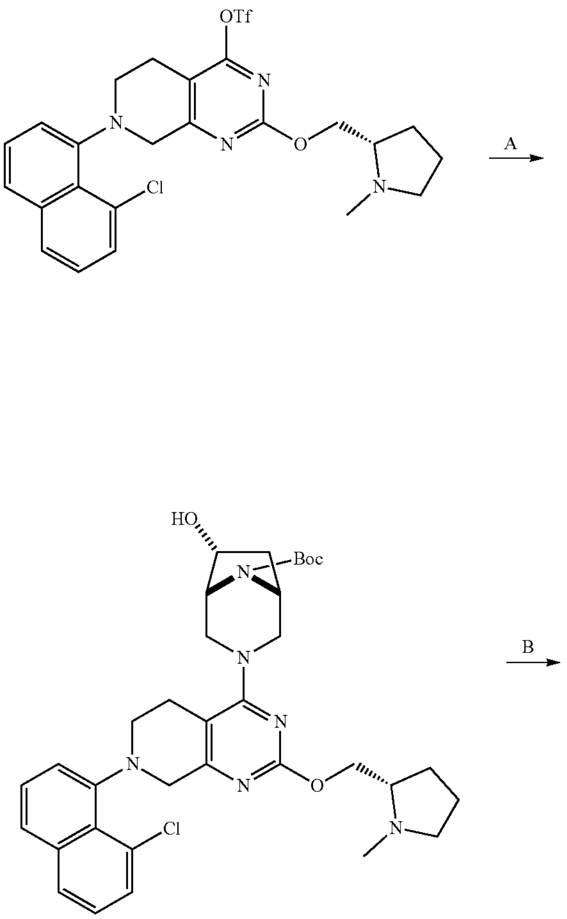

-continued

-continued

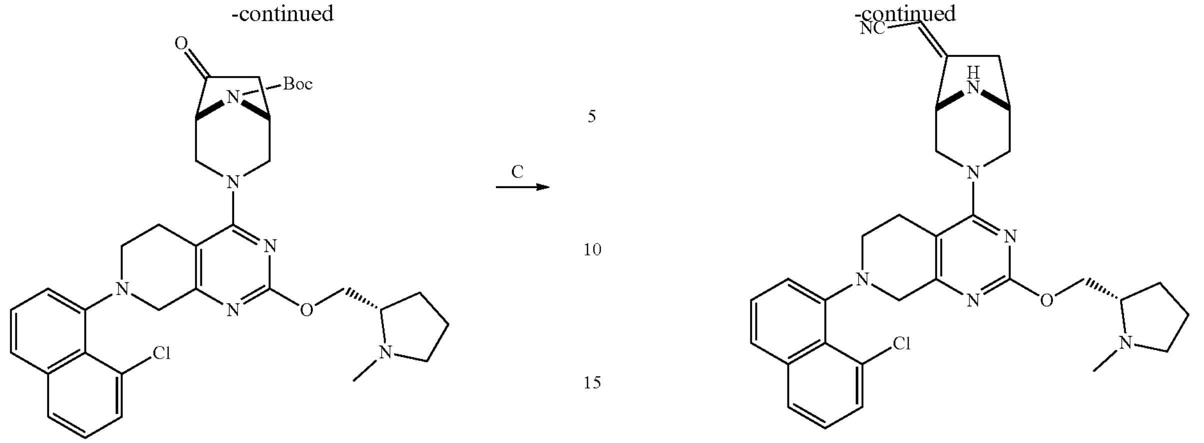

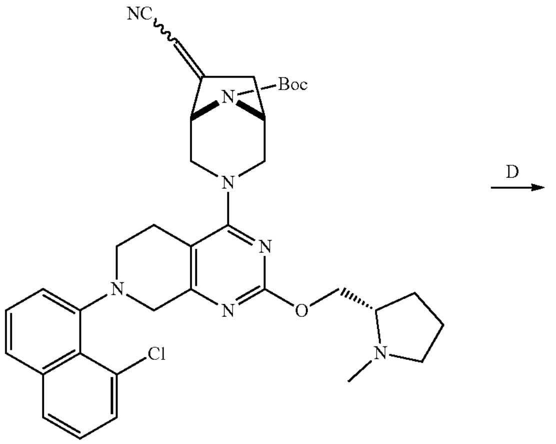

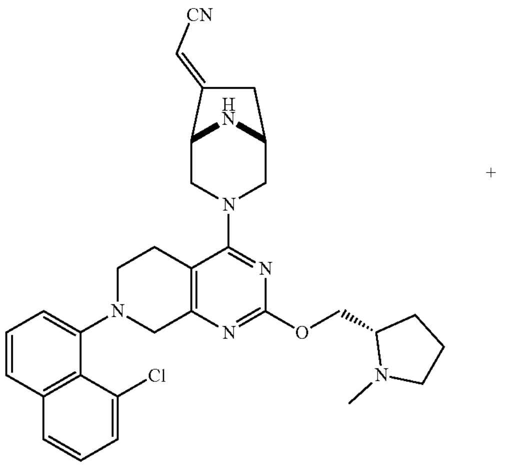

Step A. tert-butyl (1R,5R,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-hydroxy-3,8-diazabicyclo[3.2.1]octane-8-carboxylate. A solution of tert-butyl (1R,5R,6R)-6-hydroxy-3,8-diazabicyclo[3.2.1]octane-8-carboxylate (0.14 g, 0.53 mmol), (S)-7-(8-chloronaphthalen-1-yl)-2-((1-methylpyrrolidin-2-yl)methoxy)-5,6,7,8-tetrahydropyrido[3,4-d]pyrimidin-4-yl trifluoromethanesulfonate (0.30 g, 0.53 mmol) and triethylamine (0.11 mL, 0.80 mmol) in N,N-dimethylacetamide (1.1 mL) was stirred at r.t. overnight. Additional tert-butyl (1R,5R,6R)-6-hydroxy-3,8-diazabicyclo[3.2.1]octane-8-carboxylate (50 mg) was added and the reaction mixture was stirred for 2 h, evaporated under vacuum, and chromatographed on silica gel eluting with 4→6% MeOH/DCM+10% $NH_4OH$ as modifier to yield the desired product as brown solid (0.25 g, 74%). LCMS (MM-ES+APCI, Pos): m/z 635.3 (M+H).

Step B. tert-butyl (1R,5R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-oxo-3,8-diazabicyclo[3.2.1]octane-8-carboxylate. A mixture of tert-butyl (1R,5R,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-hydroxy-3,8-diazabicyclo[3.2.1]octane-8-carboxylate (50 mg, 0.079 mmol), 2-azaadamantane-N-oxyl (0.36 mg, 0.0024 mmol), copper (I) chloride (0.23 mg, 0.0024 mmol), 2,2'-dipyridyl (0.37 mg, 0.0024 mmol) and N,N-dimethylpyridin-4-amine (0.58 mg, 0.0047 mmol) in acetonitrile (0.5 mL) and DCM (1 mL) was stirred under an air atmosphere overnight. The reaction was concentrated in vacuo. The residue was diluted with MeCN/DCM (1:3 mixture, 1 mL) and stirred for another 5 hours. The mixture was evaporated under a stream of $N_2$ and used crude in the next reaction. LCMS (MM-ES+APCI, Pos): m/z 633.3 (M+H).

Step C. tert-butyl (1R,5S,E)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethylene)-3,8-diazabicyclo[3.2.1]octane-8-carboxylate. To a suspension of (cyanomethyl)trimethylphosphonium iodide (38 mg, 0.16 mmol) in tetrahydrofuran (0.8 mL) under $N_2$ was added 60% sodium hydride (9.5 mg, 0.24 mmol) and the mixture was stirred at r.t. for 1 hour. The mixture was added to a stirred solution of tert-butyl (1R,5R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-oxo-3,8-diazabicyclo[3.2.1]octane-8-carboxylate (50 mg, 0.079 mmol) in MTBE. The reaction mixture was stirred for 1 hour at r.t., diluted with MTBE (5 mL), filtered, evaporated in vacuo, and chromatographed on silica gel eluting with 4% MeOH/DCM+0.4% $NH_4OH$ as a modifier to give the desired product (48 mg, 93%). LCMS (MM-ES+APCI, Pos): m/z 656.3 (M+H).

Step D. (E)- and (Z)-2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ylidene)acetonitrile. To a stirred solution of tert-butyl (1R,5S,E)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(cyanomethylene)-3,8-diazabicyclo[3.2.1]octane-8-carboxylate (6 mg, 0.009 mmol) and triethylsilane (7.3 μL, 0.046 mmol) in dichloromethane (0.1 mL) was added 2,2,2-trifluoroacetic acid (18 μL, 0.0091 mmol). The solution was stirred at r.t. for 4 h, diluted with water (0.3 mL), and the organics evaporated under a stream of $N_2$. The aqueous phase was chromatographed on a reverse phase column (C18, Gilson) eluting with 5 to 95% MeCN/water+0.1% TFA as a modifier to yield the two compounds as TFA salts. The first-eluted isomer was assigned as (E)-2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ylidene)acetonitrile (1.9 mg, 36%) and the second-eluted peak as (Z)-2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ylidene)acetonitrile (3.0 mg, 59%). LCMS (MM-ES+APCI, Pos): m/z 556.3 (M+H).

Example 91

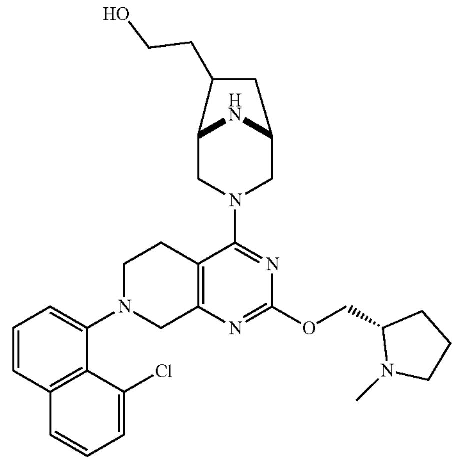

2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)ethan-1-ol

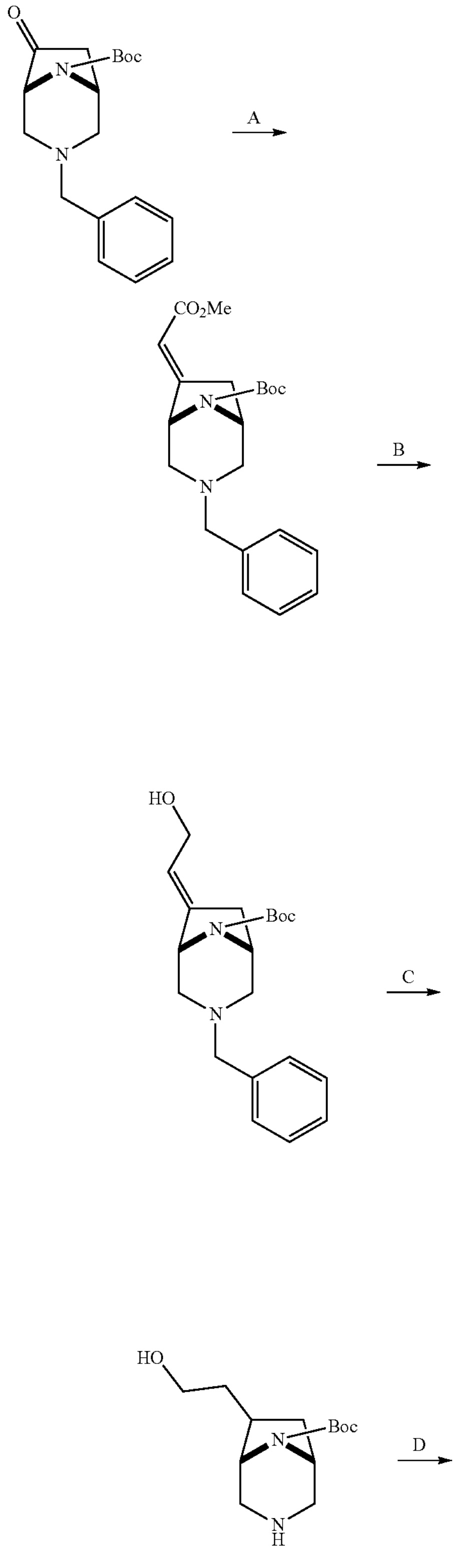

-continued

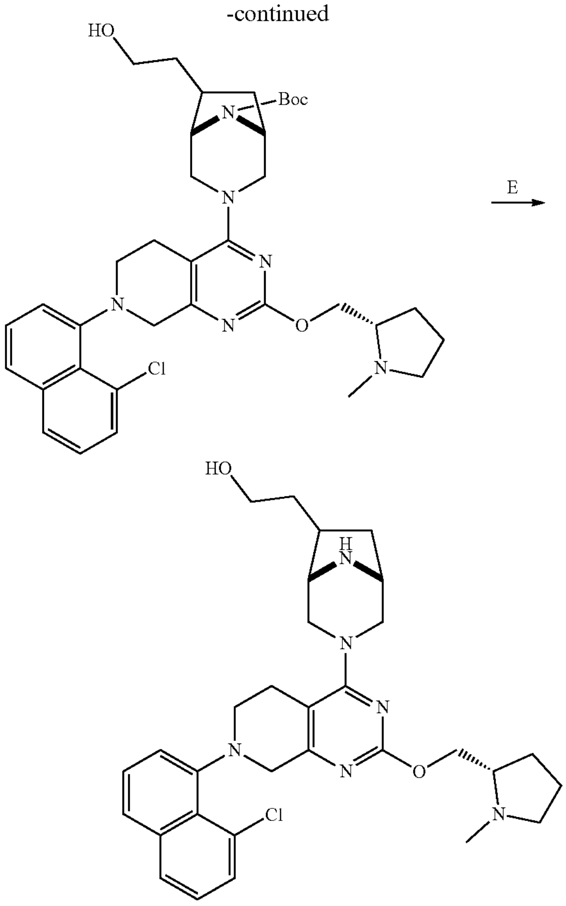

Step A. tert-butyl (1R,5S)-3-benzyl-6-(2-ethoxy-2-oxoethylidene)-3,8-diazabicyclo[3.2.1]octane-8-carboxylate.
To a stirred suspension of ethyl 2-(diethoxyphosphoryl) acetate (71 mg, 0.32 mmol) in tetrahydrofuran (1.6 mL) under $N_2$ was added sodium hydride (19 mg, 0.47 mmol) and the reaction mixture was stirred at r.t. for 2 hours. The solution was added to tert-butyl (1R,5R)-3-benzyl-6-oxo-3,8-diazabicyclo[3.2.1]octane-8-carboxylate (0.10 g, 0.32 mmol). The reaction mixture was stirred at r.t. for 1 hour, and divided between MTBE (15 mL) and 0.5M $NaHCO_3$ (5 mL). The layers were separated. The organic layer was dried over $Na_2SO_4$, evaporated in vacuo, and chromatographed on silica gel eluting with 20% EtOAc/hex to afford the desired product as a colorless oil (0.11 g, 93%). LCMS (MM-ES+APCI, Pos): m/z 387.3 (M+H).

Step B. tert-butyl (1R,5S)-3-benzyl-6-(2-hydroxyethylidene)-3,8-diazabicyclo[3.2.1]octane-8-carboxylate. A solution of tert-butyl (1R,5S)-3-benzyl-6-(2-methoxy-2-oxoethylidene)-3,8-diazabicyclo[3.2.1]octane-8-carboxylate (22 mg, 0.059 mmol) in ethoxyethane (0.6 mL) under $N_2$ was cooled to 0° C. and diisobutylaluminium hydride (84 mg, 0.15 mmol) was added dropwise. After 1 hour, the reaction mixture was diluted with MTBE (10 mL), washed with 1M NaOH and brine (3 mL each), and dried over $Na_2CO_3$. The solution was filtered through a silica gel plug using MTBE. The combined organics were evaporated under $N_2$ to give the target compound (19 mg, 93%), which was used crude in the next reaction. LCMS (MM-ES+APCI, Pos): m/z 345.3 (M+H).

Step C. Tert-butyl (1R,5S)-6-(2-hydroxyethyl)-3,8-diazabicyclo[3.2.1]octane-8-carboxylate. Synthesized according to Example 1, Step C, substituting tert-butyl (1R,5S)-3-benzyl-6-(2-hydroxyethylidene)-3,8-diazabicyclo[3.2.1]octane-8-carboxylate in place of tert-butyl (1R,5S)-3-(7-benzyl-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. LCMS (MM-ES+APCI, Pos): m/z 257.2 (M+H).

Step D. tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(2-hydroxyethyl)-3,8-diazabicyclo[3.2.1]octane-8-carboxylate. Synthesized according to Example 89, step A substituting tert-butyl (1R,5S)-6-(2-hydroxyethyl)-3,8-diazabicyclo[3.2.1]octane-8-carboxylate in place of tert-butyl (1R,5R,6R)-6-hydroxy-3,8-diazabicyclo[3.2.1]octane-8-carboxylate. The reaction mixture was concentrated under a stream of $N_2$, diluted with 1% of TFA in water (0.5 mL), filtered through Celite, and chromatographed using a reverse phase column (C18, Gilson) eluting with 0-50% $MeCN/H_2O$+0.1% TFA as a modifier. The target compound was isolated as the bis TFA (9.2 mg, 19%). LCMS (MM-ES+APCI, Pos): m/z 663.3 (M+H).

Step E. 2-((1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-yl)ethan-1-ol. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(2-hydroxyethyl)-3,8-diazabicyclo[3.2.1]octane-8-carboxylate bis(2,2,2-trifluoroacetate) (9.2 mg, 0.010 mmol) and triethylsilane (6.0 mg, 0.052 mmol) in dichloromethane (0.5 mL) was added 2,2,2-trifluoroacetic acid (95 μL, 1.2 mmol). The solution was stirred at r.t. for 4 hours and diluted with water (0.3 mL). The organic solvents were evaporated in a stream of $N_2$ and the aqueous phase was chromatographed on a reverse phase column (C18, Gilson) eluting with 5>95% MeCN/water+0.1% TFA as a modifier. The target compound was freebased by partitioning between aqueous $Na_2CO_3$ and DCM. The organics were concentrated and dried under vacuum to yield a colorless solid (1.9 mg, 33%). LCMS (MM-ES+APCI, Pos): m/z 563.3 (M+H).

Example 92

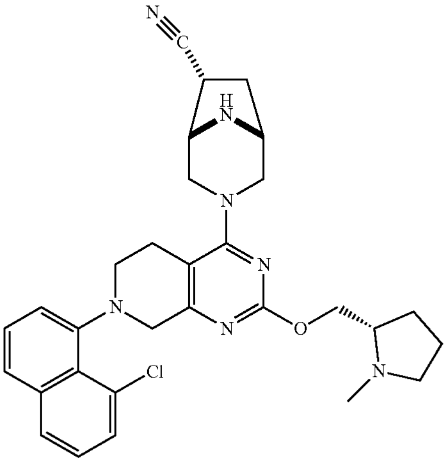

(1R,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-6-carbonitrile

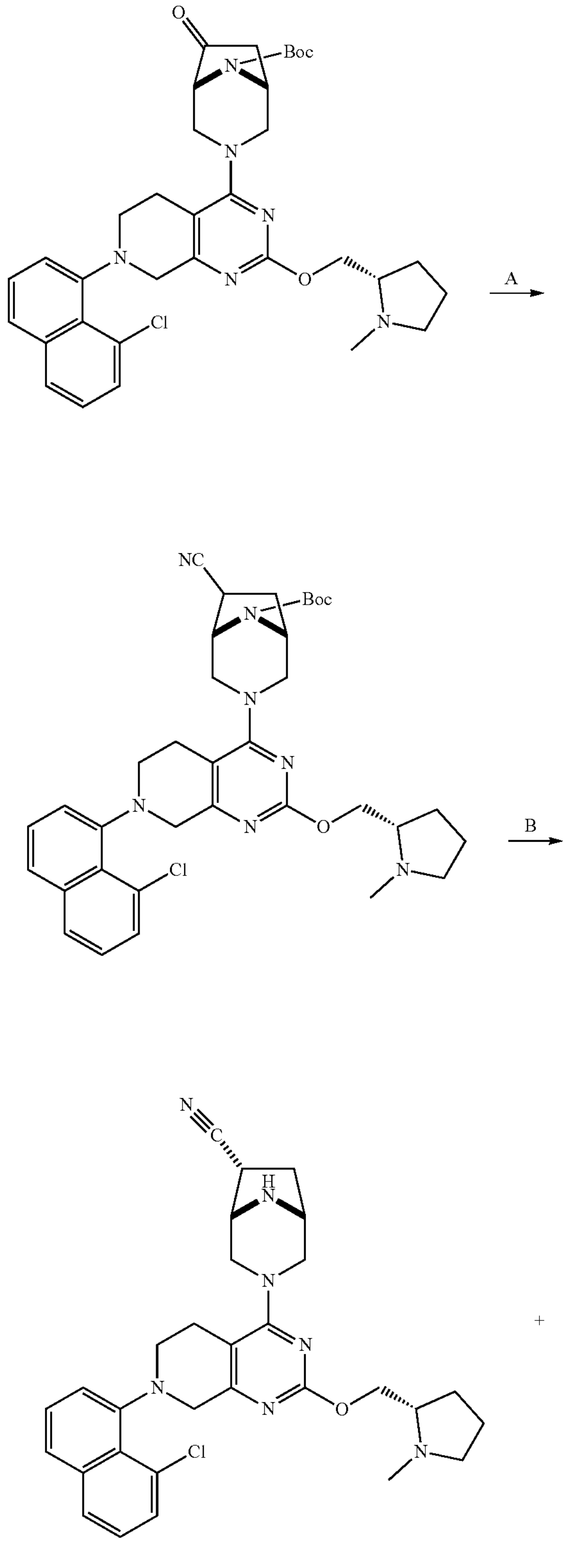

-continued

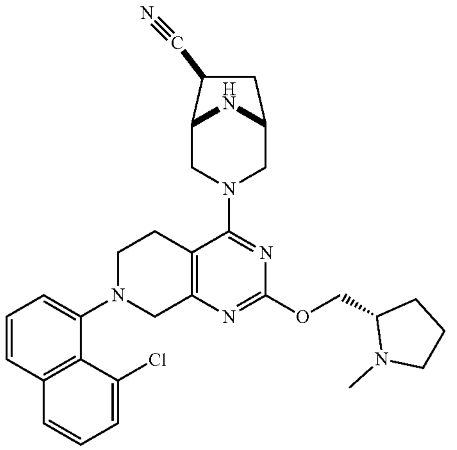

Step A. tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-cyano-3,8-diazabicyclo[3.2.1]octane-8-carboxylate. To a stirred solution of tert-butyl (1R,5R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-oxo-3,8-diazabicyclo[3.2.1]octane-8-carboxylate (50 mg, 0.079 mmol) in 1,2-dimethoxyethane (0.8 mL) at −20° C. were added ethanol (12 μL, 0.20 mmol) and potassium tert-butoxide (31 mg, 0.28 mmol) followed by tosylmethyl isocyanide (31 mg, 0.16 mmol). The reaction mixture was stirred while being warmed to r.t. over 4 hours. The mixture was suspended between EtOAc and 0.5M $NaHCO_3$ (10 mL each) and the layers were separated. The organic layer was washed with water and brine (5 mL each), dried over $Na_2SO_4$, and chromatographed on silica gel in 4% MeOH/DCM+0.4% $NH_4OH$ to give the desired product as a mixture of two isomers (16 mg, 32%). LCMS (MM-ES+APCI, Pos): m/z 644.3 (M+H).

Step B. (1R,5S,6R)-(endo-) and (1R,5S,6S)-(exo-) 3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-6-carbonitrile. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-cyano-3,8-diazabicyclo[3.2.1]octane-8-carboxylate (16 mg, 0.024 mmol) and triethylsilane (40 μL, 0.25 mmol) in DCM (0.05 mL) was added a solution of 2,2,2-trifluoroacetic acid (57 μL, 0.75 mmol) in dichloromethane (0.25 mL). The mixture was stirred at rt for 2 hours, diluted with chloroform (5 mL), cooled to −78° C., and evaporated under high vacuum. The residue was dissolved in 1:1 MeOH—$H_2O$ (1 mL), filtered through a cotton plug, and chromatographed using reverse phase chromatography (C18, Gilson) eluting with 0-50% MeCN/$H_2O$+0.1% TFA as a modifier to yield the target products as the TFA salt (5 mg, 26%) of each isomer. LCMS (MM-ES+APCI, Pos): m/z 544.3 (M+H).

Example 93 and 94
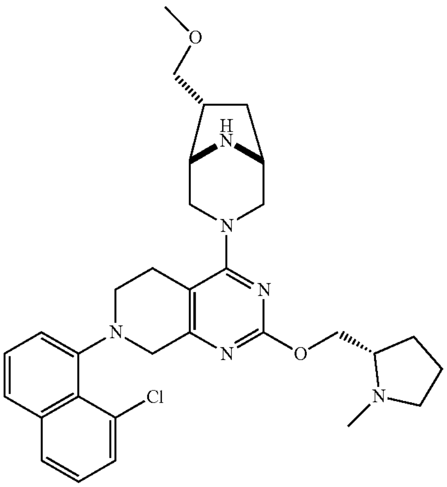
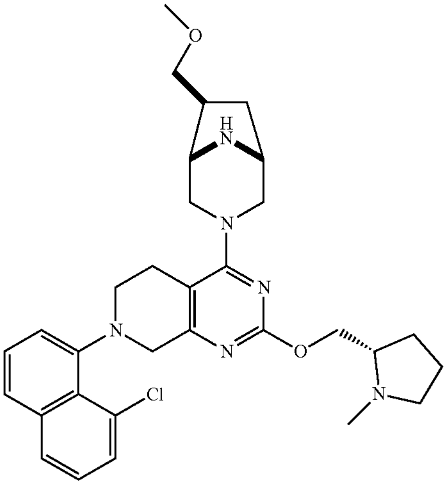
7-(8-chloronaphthalen-1-yl)-4-((1R,5S,6R)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine and 7-(8-chloronaphthalen-1-yl)-4-((1R,5S,6S)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine
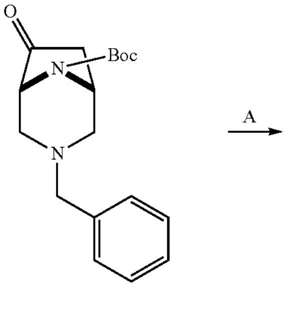
-continued
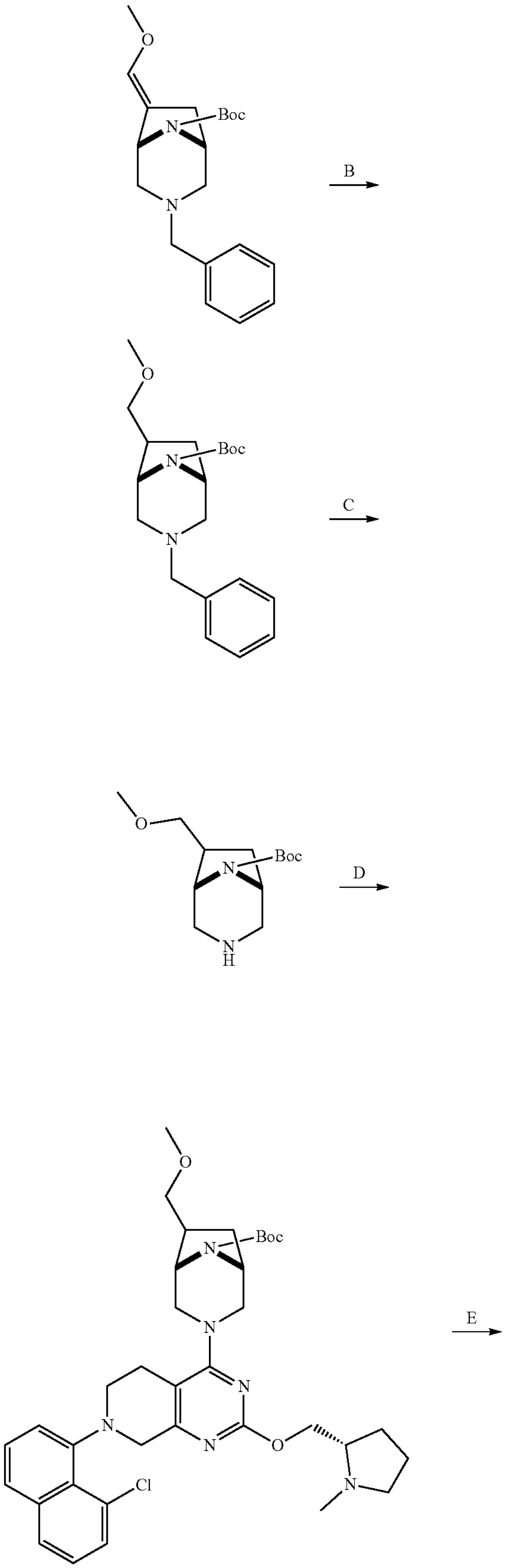

-continued

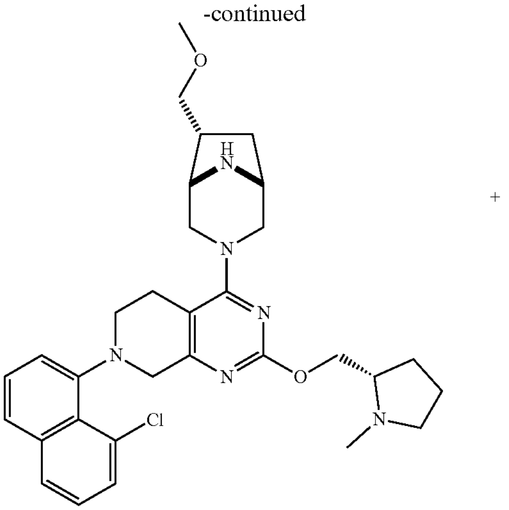

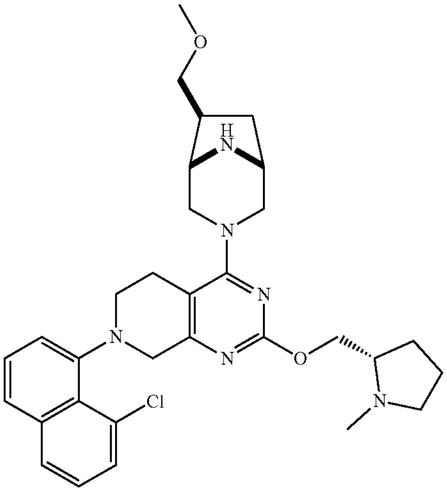

Step A. tert-butyl (1R,5S,E)-3-benzyl-6-(methoxymethylene)-3,8-diazabicyclo[3.2.1]octane-8-carboxylate. To a suspension of (methoxymethyl)triphenylphosphonium chloride (0.13 g, 0.38 mmol) in tetrahydrofuran (3 mL) at 0° C. under $N_2$ was added lithium diisopropylamide (0.19 mL, 0.38 mmol) and the suspension was stirred at 0° C. for 10 minutes. The phosphorane mixture was added dropwise over 5 minutes to a stirred solution of tert-butyl (1R,5R)-3-benzyl-6-oxo-3,8-diazabicyclo[3.2.1]octane-8-carboxylate (0.10 g, 0.32 mmol) in THE (2 mL) under $N_2$ at −78° C. The reaction mixture was warmed to 0° C. over 1 hour. The mixture was partitioned between EtOAc (15 mL) and water (10 mL), washed with brine, dried over $Na_2SO_4$, and evaporated in vacuum to give the title product which was used crude in the next reaction (0.11 g, 30%). LCMS (MM-ES+APCI, Pos): m/z 345.3 (M+H).

Step B. tert-butyl (1R,5S)-3-benzyl-6-(methoxymethyl)-3,8-diazabicyclo[3.2.1]octane-8-carboxylate. A stirred mixture of crude tert-butyl (1R,5S,E)-3-benzyl-6-(methoxymethylene)-3,8-diazabicyclo[3.2.1]octane-8-carboxylate (0.11 g, 0.095 mmol), methanol (0.5 mL), and 10% palladium on carbon (20 mg) was degassed and backfilled with $H_2$ by balloon. After stirring for 3 hours, 20% palladium (II) hydroxide on carbon (30 mg) was added and the reaction mixture was stirred under $H_2$ for 24 hours. The reaction mixture was filtered through Celite. The filtrate was treated with $NaBH_4$ (20 mg) and stirred for 2 hours. The mixture was concentrated in vacuo and partitioned between MTBE (15 mL) and water (5 mL). The organic layer was washed with brine, dried over $Na_2SO_4$, filtered through a cotton plug, and concentrated under a stream of $N_2$. The residue was chromatographed on silica gel eluting with 20% EtOAc/hexane to afford the target product as a colorless oil (8 mg, 24%). LCMS (MM-ES+APCI, Pos): m/z 347.3 (M+H).

Step C. tert-butyl (1R,5S)-3-benzyl-6-(methoxymethyl)-3,8-diazabicyclo[3.2.1]octane-8-carboxylate. A stirred mixture of tert-butyl (1R,5S)-3-benzyl-6-(methoxymethyl)-3,8-diazabicyclo[3.2.1]octane-8-carboxylate (8.0 mg, 0.023 mmol), methanol (2.5 mL) and 20% dihydroxypalladium on carbon (10 mg) was degassed and a hydrogen atmosphere was introduced via balloon. The reaction mixture was stirred at r.t. for 3 hours, filtered through Celite, and evaporated in vacuo. The residue was dissolved in MTBE (2 mL), filtered through a cotton plug, and concentrated under $N_2$ flow. The material was used crude in the next reaction. LCMS (MM-ES+APCI, Pos): m/z 257.3 (M+H).

Step D. tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(methoxymethyl)-3,8-diazabicyclo[3.2.1]octane-8-carboxylate. Synthesized according to Example 89, step A substituting tert-butyl (1R,5S)-6-(methoxymethyl)-3,8-diazabicyclo[3.2.1]octane-8-carboxylate in place of tert-butyl (1R,5R,6R)-6-hydroxy-3,8-diazabicyclo[3.2.1]octane-8-carboxylate. The crude compound was purified by reverse phase chromatography (C18, Gilson) eluting with 5>95% MeCN/$H_2O$+0.1% TFA as a modifier. The material was freebased by partitioning between aqueous $Na_2CO_3$ and DCM to yield the desired product (11 mg, 50%). LCMS (MM-ES+APCI, Pos): m/z 663.3 (M+H).

Step E. 7-(8-chloronaphthalen-1-yl)-4-((1R,5S,6R)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine and 7-(8-chloronaphthalen-1-yl)-4-((1R,5S,6S)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine. To a solution of tert-butyl (1R,5S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-(methoxymethyl)-3,8-diazabicyclo[3.2.1]octane-8-carboxylate (11 mg, 0.017 mmol) in dichloromethane (1 mL) was added 2,2,2-trifluoroacetic acid (0.2 mL). The mixture was stirred at r.t. for 2 hours, diluted with $CHCl_3$ (5 mL), cooled to −78° C. and evaporated in vacuo. The residue was purified by reverse phase chromatography (C18, Gilson) eluting with 0-50% MeCN/$H_2O$+0.1% TFA as a modifier to yield two separate isomers. The isomers were freebased by partitioning between aqueous $Na_2CO_3$ and DCM. The organics were concentrated in vacuo to yield the target products. The first-eluted isomer was assigned as 7-(8-chloronaphthalen-1-yl)-4-((1R,5S,6R)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine (2.4 mg, 26%) and the second-eluted isomer as 7-(8-chloronaphthalen-1-yl)-4-((1R,5S,6S)-6-(methoxymethyl)-3,8-diazabicyclo[3.2.1]octan-3-yl)-2-(((S)-1-methylpyrrolidin-2-yl)methoxy)-5,6,7,8-tetrahydropyrido[3,4-d]pyrimidine (1.0 mg, 11%). LCMS (MM-ES+APCI, Pos): m/z 563.5 (M+H).

Example 95

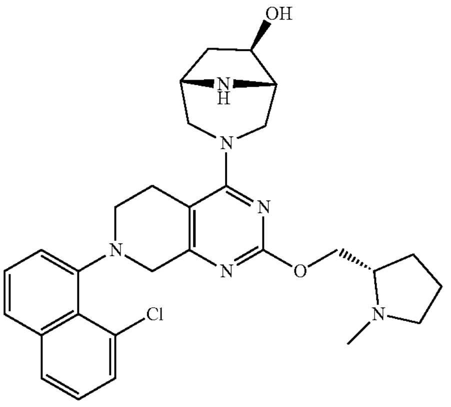 [SMILES: CN1CCC[C@H]1COc1nc2c(c(N3C[C@@H]4C[C@@H](O)[C@H](C3)N4)n1)CCN(c1cccc3cccc(Cl)c13)C2]

(1S,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol (1S,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol. Synthesized according to Example 39, step A substituting tert-butyl (1S,5S,6R)-6-hydroxy-3,8-diazabicyclo[3.2.1]octane-8-carboxylate for tert-butyl (1R,5S)-6-(cyanomethylene)-3,8-diazabicyclo[3.2.1]octane-8-carboxylate hydrochloride while also using step D substituting tert-butyl (1S,5S,6R)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-hydroxy-3,8-diazabicyclo[3.2.1]octane-8-carboxylate for tert-butyl (1R,5S,6R)-6-(2-aminoethyl)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (4.6 mg, 26%). LCMS (MM-ES+APCI, Pos): m/z 535.3 (M+H).

Example 96

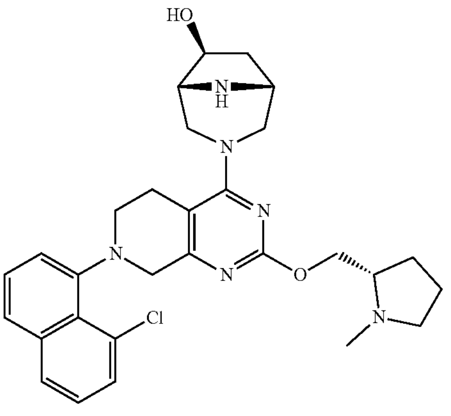 [SMILES: CN1CCC[C@H]1COc1nc2c(c(N3C[C@H]4C[C@H](O)[C@@H](C3)N4)n1)CCN(c1cccc3cccc(Cl)c13)C2]

(1R,5R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol (1R,5R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octan-6-ol. Synthesized according to Example 39, step A substituting tert-butyl (1R,5R,6S)-6-hydroxy-3,8-diazabicyclo[3.2.1]octane-8-carboxylate for tert-butyl (1R,5S)-6-(cyanomethylene)-3,8-diazabicyclo[3.2.1]octane-8-carboxylate hydrochloride while also using step D substituting tert-butyl (1R,5R,6S)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-6-hydroxy-3,8-diazabicyclo[3.2.1]octane-8-carboxylate for tert-butyl (1R,5S,6R)-6-(2-aminoethyl)-3-(7-(8-chloronaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (5.2 mg, 92%). LCMS (MM-ES+APCI, Pos): m/z 535.3 (M+H).

Example 97

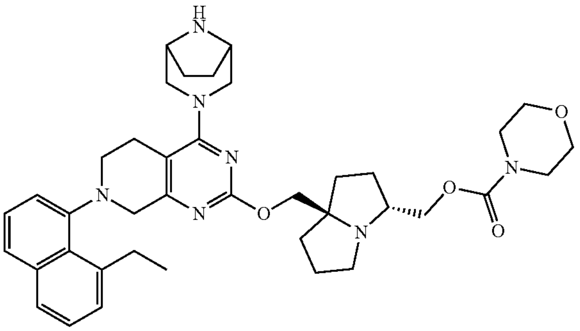 [SMILES: CCc1cccc2cccc(N3CCc4c(nc(OC[C@]56CCCN5[C@@H](COC(=O)N5CCOCC5)CC6)nc4N4CC5CCC(C4)N5)C3)c12]

((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate

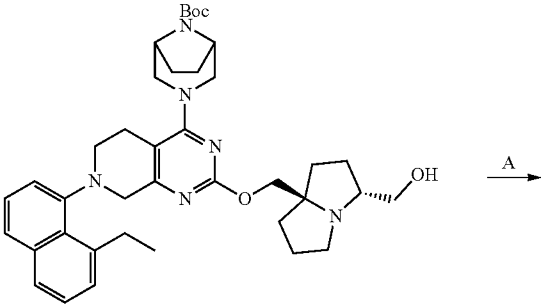

-continued

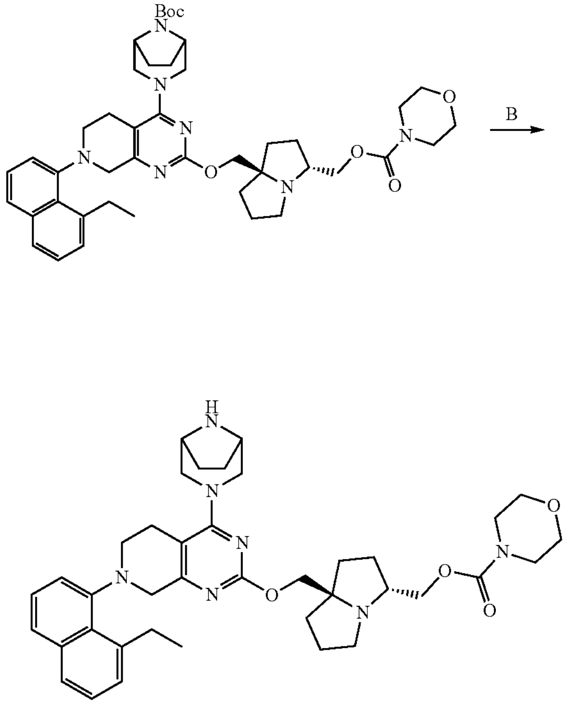

Step A. ((3R,7aR)-7a-(((4-((1R,5S)-8-(tert-butoxycarbonyl)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate. Synthesized according to Example 18, Step E substituting morpholine in place of 2.0 M methylamine in THE to afford ((3R,7aR)-7a-(((4-((1R,5S)-8-(tert-butoxycarbonyl)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate (13 mg, 65%). LCMS (MM-ES+APCI, Pos): m/z 782.7 [M+H].

Step B. ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate. Synthesized according to Example 18, Step F substituting ((3R,7aR)-7a-(((4-((1R,5S)-8-(tert-butoxycarbonyl)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate in place of tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate (4.5 mg, 39%). LCMS (MM-ES+APCI, Pos): m/z 682.4 [M+H].

Example 98

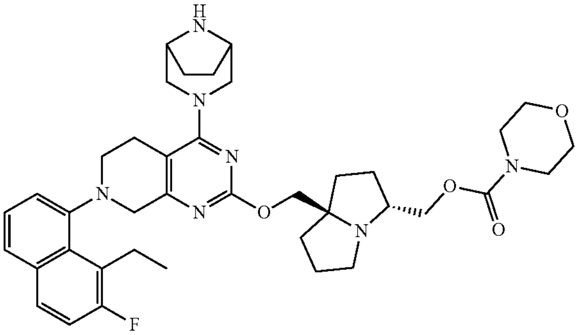 [SMILES: CCc1c(F)ccc2cccc(N3CCc4c(nc(OC[C@]56CCCN5[C@@H](COC(=O)N5CCOCC5)CC6)nc4N4CC5CCC(C4)N5)C3)c12]

((3R,7aR)-7a-(((4-((1R,5S)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate

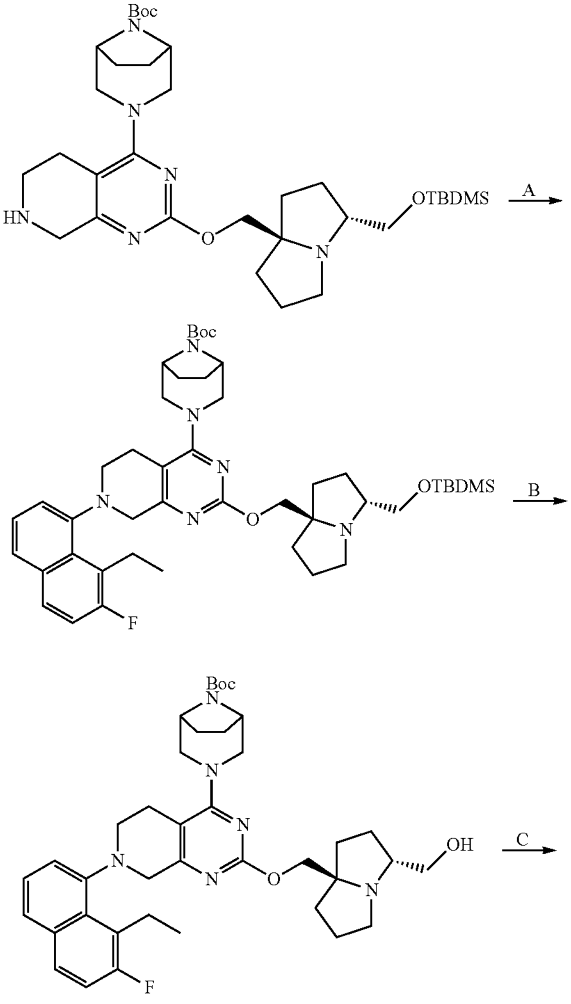

-continued

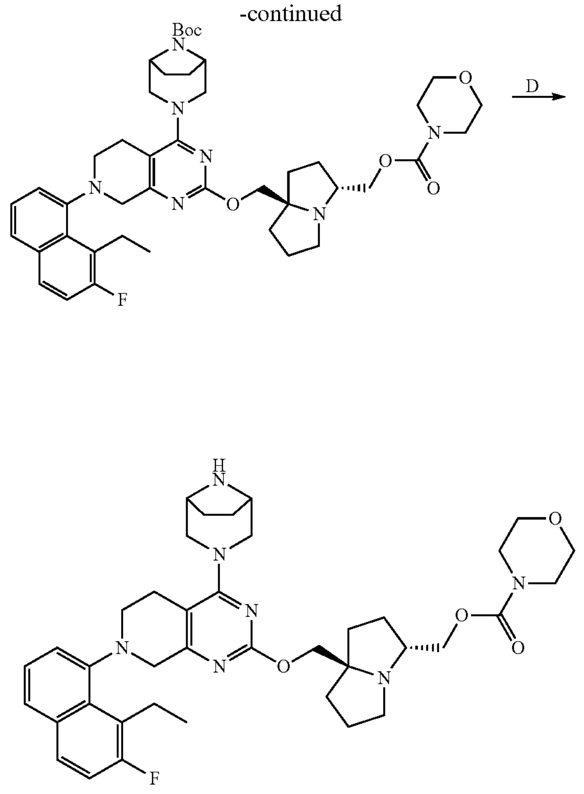

Step A. tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethyl-7-fluoronaphthalen-1-yl)-5,6,7,8-tetrahydropyrido[3,4-d]pyrimidin-4-yl)-3,8-diazabicyclo[3.2.1]octane-8-carboxylate. Synthesized according to Example 18, Step C substituting 8-ethyl-7-fluoronaphthalen-1-yl trifluoromethanesulfonate in place of 1-bromo-8-ethylnaphthalene to afford tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethyl-7-fluoronaphthalen-1-yl)-5,6,7,8-tetrahydropyrido[3,4-d]pyrimidin-4-yl)-3,8-diazabicyclo[3.2.1]octane-8-carboxylate (80 mg, 55%). LCMS (MM-ES+APCI, Pos): m/z 801.6 [M+H].

Step B. tert-butyl (1R,5S)-3-(7-(8-ethyl-7-fluoronaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 18, Step D substituting tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethyl-7-fluoronaphthalen-1-yl)-5,6,7,8-tetrahydropyrido[3,4-d]pyrimidin-4-yl)-3,8-diazabicyclo[3.2.1]octane-8-carboxylate in place of tert-butyl (1R,5S)-3-(2-(((3R,7aR)-3-(((tert-butyldimethylsilyl)oxy)methyl)tetrahydro-1H-pyrrolizin-7a(5H)-yl)methoxy)-7-(8-ethylnaphthalen-1-yl)-5,6,7,8-tetrahydropyrido[3,4-d]pyrimidin-4-yl)-3,8-diazabicyclo[3.2.1]octane-8-carboxylate to afford tert-butyl (1R,5S)-3-(7-(8-ethyl-7-fluoronaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (58 mg, 84%). LCMS (MM-ES+APCI, Pos): m/z 687.4 [M+H].

Step C. ((3R,7aR)-7a-(((4-((1R,5S)-8-(tert-butoxycarbonyl)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate. Synthesized according to Example 18, Step E substituting tert-butyl (1R,5S)-3-(7-(8-ethyl-7-fluoronaphthalen-1-yl)-2-(((3R,7aR)-3-(hydroxymethyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate and morpholine in place of 2.0 M methylamine in THE to afford ((3R,7aR)-7a-(((4-((1R,5S)-8-(tert-butoxycarbonyl)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate (14 mg, 56%). LCMS (MM-ES+APCI, Pos): m/z 800.4 [M+H].

Step D. ((3R,7aR)-7a-(((4-((1R,5S)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate. Synthesized according to Example 18, Step F substituting ((3R,7aR)-7a-(((4-((1R,5S)-8-(tert-butoxycarbonyl)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate in place of tert-butyl (1R,5S)-3-(7-(8-ethylnaphthalen-1-yl)-2-(((3R,7aR)-3-(((methylcarbamoyl)oxy)methyl) tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford ((3R,7aR)-7a-(((4-((1R,5S)-3,8-diazabicyclo[3.2.1]octan-3-yl)-7-(8-ethyl-7-fluoronaphthalen-1-yl)-5,6,7,8-tetrahydropyrido[3,4-d]pyrimidin-2-yl)oxy)methyl)hexahydro-1H-pyrrolizin-3-yl)methyl morpholine-4-carboxylate as a white solid (4.9 mg, 38%). LCMS (MM-ES+APCI, Pos): m/z 700.4 [M+H].

Example 99

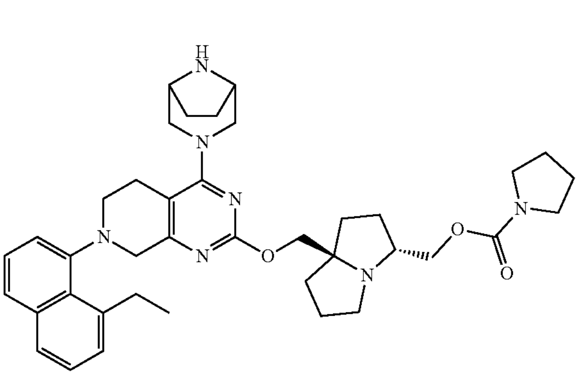 [SMILES: CCc1cccc2cccc(N3CCc4c(nc(OC[C@]56CCCN5[C@@H](COC(=O)N5CCCC5)CC6)nc4N4CC5CCC(C4)N5)C3)c12]

((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl pyrrolidine-1-carboxylate

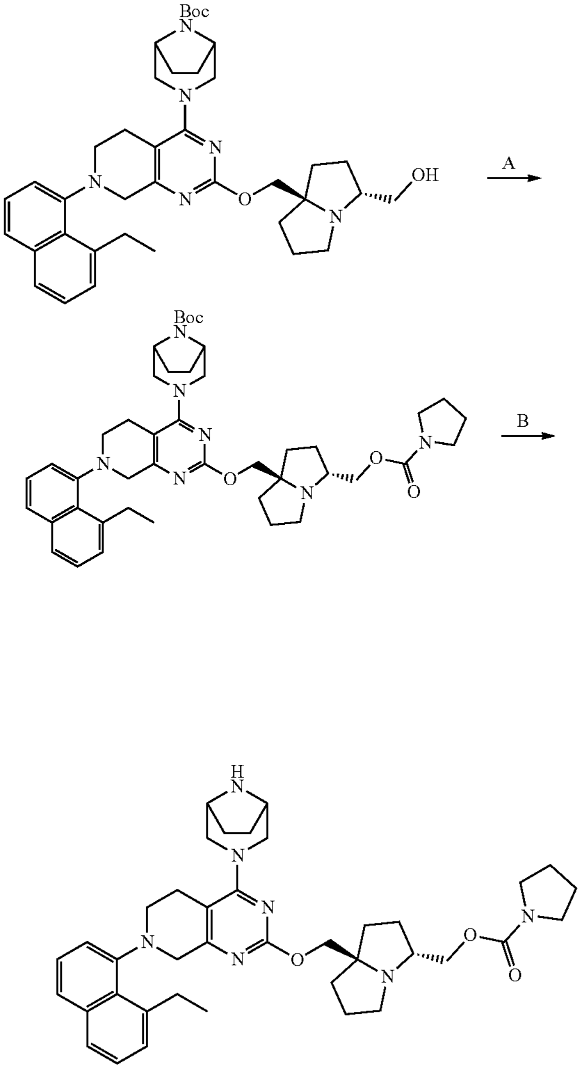

Step A. tert-butyl (1R,5S)-3-(7-(8-ethylnaphthalen-1-yl)-2-(((3R,7aR)-3-(((pyrrolidine-1-carbonyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 18, Step E substituting pyrrolidine in place of 2.0 M methylamine in THF to afford tert-butyl (1R,5S)-3-(7-(8-ethylnaphthalen-1-yl)-2-(((3R,7aR)-3-(((pyrrolidine-1-carbonyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (9.4 mg, 55%). LCMS (MM-ES+APCI, Pos): m/z 766.5 [M+H].

Step B. ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl pyrrolidine-1-carboxylate. Synthesized according to Example 18, Step F substituting tert-butyl (1R,5S)-3-(7-(8-ethylnaphthalen-1-yl)-2-(((3R,7aR)-3-(((pyrrolidine-1-carbonyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(8-ethylnaphthalen-1-yl)-2-(((3R,7aR)-3-(((methylcarbamoyl)oxy) methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford ((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl pyrrolidine-1-carboxylate as an off-white (4.8 mg, 59%). LCMS (MM-ES+APCI, Pos): m/z 666.4 [M+H].

Example 100

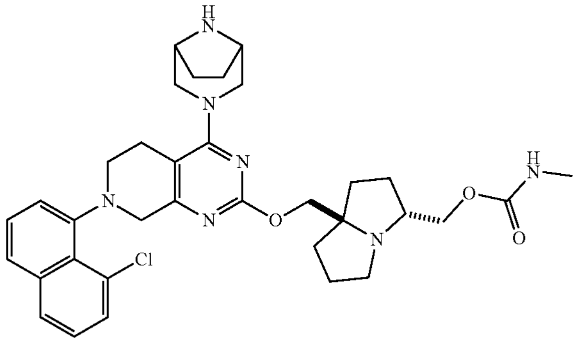

(7a-(((4-((1R,5S)-3,8-diazabicyclo[3.2.1]octan-3-yl)-7-(8-chloronaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers)

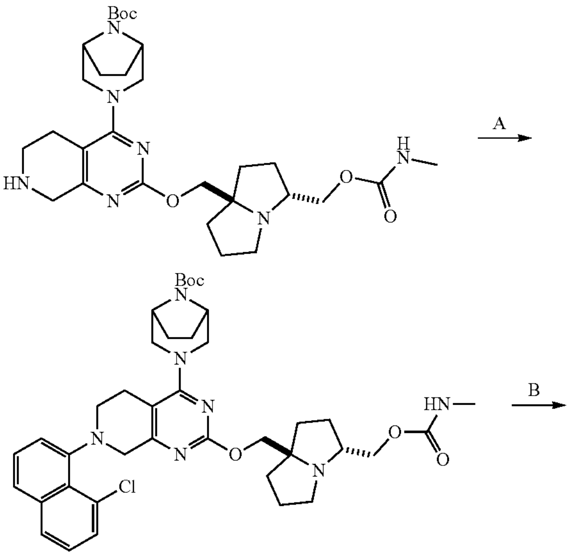

-continued

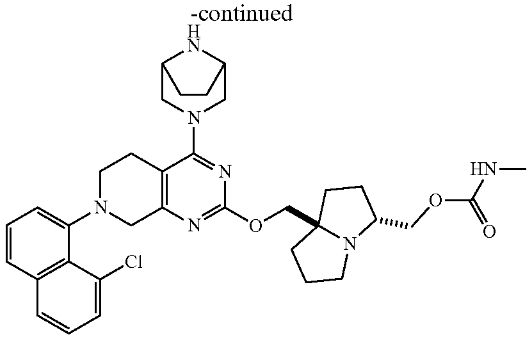

Step A. tert-butyl (1R,5S)-3-(7-(8-chloronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. tert-butyl (1R,5S)-3-(2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (44 mg, 0.08 mmol, synthesized according to Example 21, Step A-D), tris(dibenzylideneacetone)dipalladium (0) (11 mg, 0.012 mmol), racemic-2,2'-bis(diphenylphosphino)-1,1'-binaphthyl (16 mg, 0.025 mmol) and toluene (0.3 mL) were added to a vial with a stir bar and septa cap. The vial was sparged with $N_2$ for 10 minutes and heated to 100° C. for 15 minutes. Sodium tert-butoxide was added followed by 1-bromo-8-chloronaphthalene. The vial was degassed and purged with $N_2$ 3 times. The reaction was heated to 100° C. for 17 hours. The reaction was diluted with water and extracted with DCM 3 times. The DCM layers were combined, dried with $Na_2SO_4$, filtered, and concentrated. The residue was purified via flash chromatography (0-20% MeOH in DCM) to yield tert-butyl (1R,5S)-3-(7-(8-chloronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a brown solid. (56 mg, 17%). LCMS (MM-ES+APCI, Pos): m/z 732.4 [M+H].

Step B. (7a-(((4-((1R,5S)-3,8-diazabicyclo[3.2.1]octan-3-yl)-7-(8-chloronaphthalen-1-yl)-5,6,7,8-tetrahydropyrido[3,4-d]pyrimidin-2-yl)oxy)methyl)hexahydro-1H-pyrrolizin-3-yl)methyl methylcarbamate (trans enantiomers). Synthesized according to Example 21, Step F substituting tert-butyl (1R,5S)-3-(7-(8-chloronaphthalen-1-yl)-2-((3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(2-((3-(((methylcarbamoyl)oxy)methyl)tetrahydro-1H-pyrrolizin-7a(5H)-yl)methoxy)-7-(8-methylnaphthalen-1-yl)-5,6,7,8-tetrahydropyrido[3,4-d]pyrimidin-4-yl)-3,8-diazabicyclo[3.2.1]octane-8-carboxylate to afford (7a-(((4-((1R,5S)-3,8-diazabicyclo[3.2.1]octan-3-yl)-7-(8-chloronaphthalen-1-yl)-5,6,7,8-tetrahydropyrido[3,4-d]pyrimidin-2-yl)oxy)methyl)hexahydro-1H-pyrrolizin-3-yl)methyl methylcarbamate as the TFA salt (1.6 mg, 14%). LCMS (MM-ES+APCI, Pos): m/z 632.5 [M+H].

Example 101

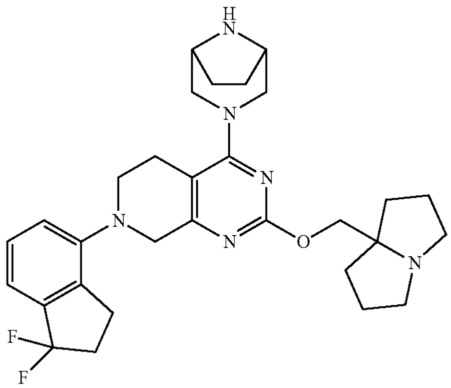 [SMILES: FC1(F)CCc2c(N3CCc4c(nc(OCC56CCCN5CCC6)nc4N4CC5CCC(C4)N5)C3)cccc21]

4-((1R,5S)-3,8-diazabicyclo[3.2.1]octan-3-yl)-7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidine

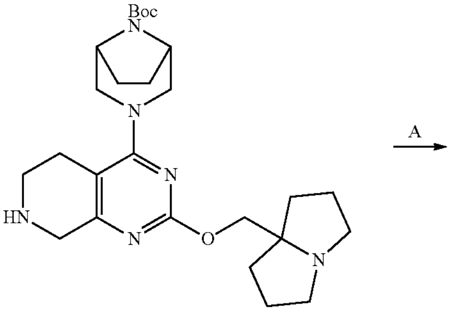

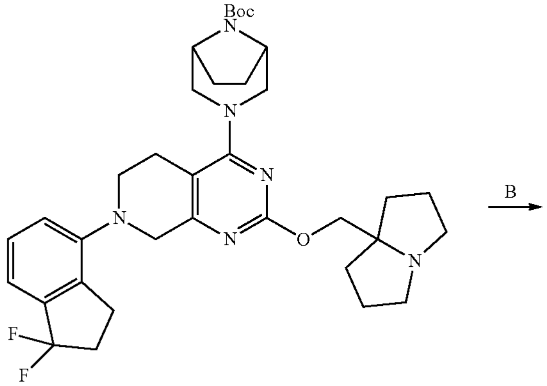

-continued

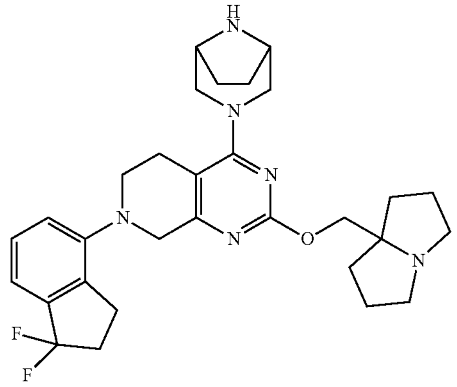

Step A. tert-butyl (1R,5S)-3-(7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Tert-butyl (1R,5S)-3-(2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (24 mg, 0.05 mmol), 4-bromo-1,1-difluoro-2,3-dihydro-1H-indene (17 mg, 0.075 mmol), tris(dibenzylideneacetone)dipalladium (0) (4.6 mg, 0.005 mmol), 9,9-dimethyl-4,5-bis(dipheylphosphino)xanthene (5.8 mg, 0.01 mmol), $Cs_2CO_3$ (65 mg, 0.20 mmol) and dioxane (0.3 mL) were added to a vial with a stir bar and septa cap. The vial was sparged with $N_2$ for 10 minutes and heated to 100° C. for 18 hours. The reaction was diluted with water and extracted with DCM 3 times. The DCM layers were combined, dried with $Na_2SO_4$, filtered, and concentrated. The residue was purified via flash chromatography (0-20% MeOH in DCM with 2% $NH_4OH$) to yield tert-butyl (1R,5S)-3-(7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate as a pale orange oil (8.1 mg, 25%). LCMS (MM-ES+APCI, Pos): m/z 637.4 [M+H].

Step B. 4-((1R,5S)-3,8-diazabicyclo[3.2.1]octan-3-yl)-7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidine. Tert-butyl (1R,5S)-3-(7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (8.1 mg, 0.013 mmol) was added to a round bottom flask with a stir bar. DCM (1.0 mL) and TFA (0.5 mL) were added. The reaction was stirred at room temperature for 30 minutes before being concentrated to dryness. The residue was purified via a reverse phase column 0-80% MeCN/water with 0.1% TFA as modifier. The fractions containing the product were combined, frozen, and lyophilized to yield the TFA salt of 4-((1R,5S)-3,8-diazabicyclo[3.2.1]octan-3-yl)-7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidine as a white solid (1.0 mg, 13% yield). LCMS (MM-ES+APCI, Pos): m/z 537.4 [M+H].

Example 102

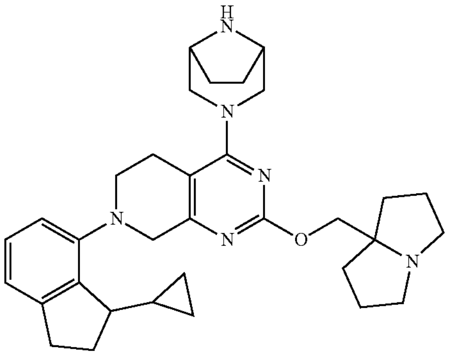 [SMILES: c1cc2c(c(N3CCc4c(nc(OCC56CCCN5CCC6)nc4N4CC5CCC(C4)N5)C3)c1)C(C1CC1)CC2]

4-((1R,5S)-3,8-diazabicyclo[3.2.1]octan-3-yl)-7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidine

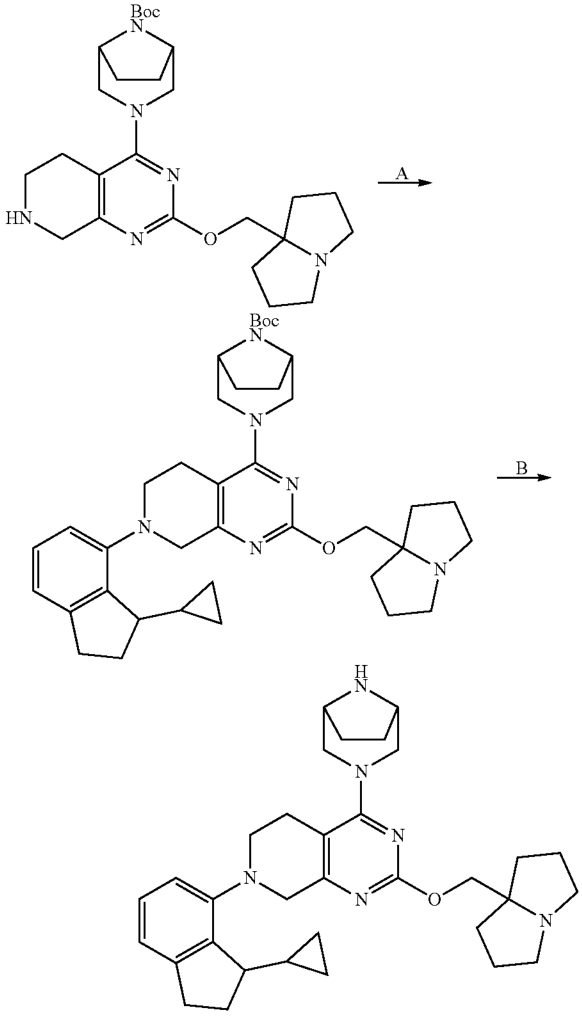

Step A. tert-butyl (1R,5S)-3-(7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 101, Step A substituting 7-bromo-1-cyclopropyl-2,3-dihydro-1H-indene in place of 4-bromo-1,1-difluoro-2,3-dihydro-1H-indene to afford tert-butyl (1R,5S)-3-(7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (12 mg, 28%). LCMS (MM-ES+APCI, Pos): m/z 641.4 [M+H].

Step B. 4-((1R,5S)-3,8-diazabicyclo[3.2.1]octan-3-yl)-7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidine. Synthesized according to Example 101, Step B substituting tert-butyl (1R,5S)-3-(7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford the TFA salt of 4-((1R,5S)-3,8-diazabicyclo[3.2.1]octan-3-yl)-7-(3-cyclopropyl-2,3-dihydro-1H-inden-4-yl)-2-((tetrahydro-1H-pyrrolizin-7a(5H)-yl)methoxy)-5,6,7,8-tetrahydropyrido[3,4-d]pyrimidine as a white solid (4.2 mg, 38%). LCMS (MM-ES+APCI, Pos): m/z 541.4 [M+H].

Example 103

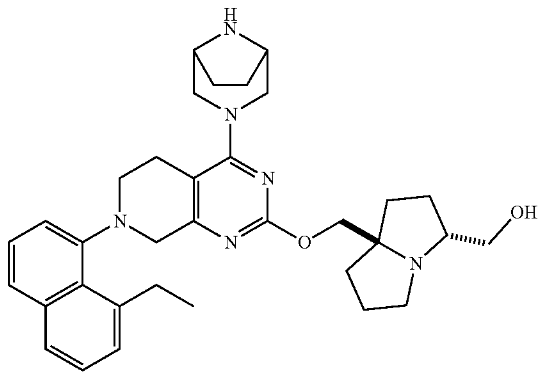

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methanol (trans enantiomers)

Synthesized according to Example 18, Step F substituting (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methanol in place of tert-butyl (1R,5S)-3-(7-(8-ethylnaphthalen-1-yl)-2-(((3R,7aR)-3-(((methylcarbamoyl)oxy)methyl)tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methanol (trans enantiomers) (3.4 mg, 11%). LCMS (MM-ES+APCI, Pos): m/z 569.4 [M+H].

Example 104

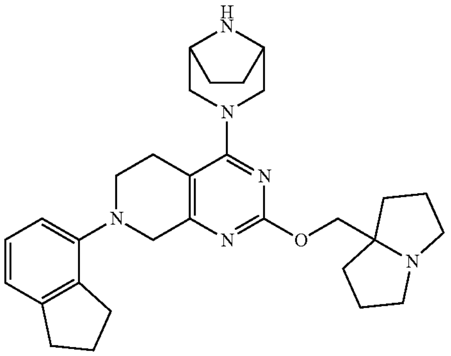 [SMILES: c1cc2c(c(N3CCc4c(nc(OCC56CCCN5CCC6)nc4N4CC5CCC(C4)N5)C3)c1)CCC2]

4-((1R,5S)-3,8-diazabicyclo[3.2.1]octan-3-yl)-7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidine

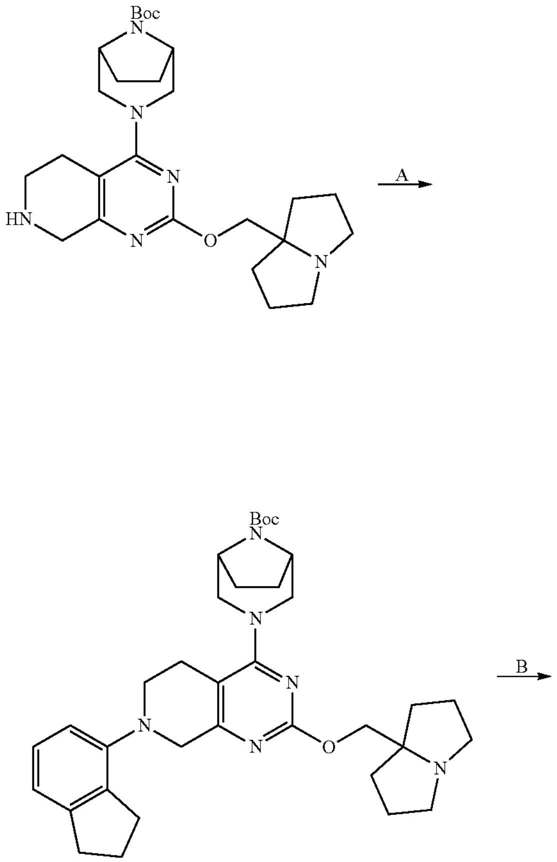

-continued

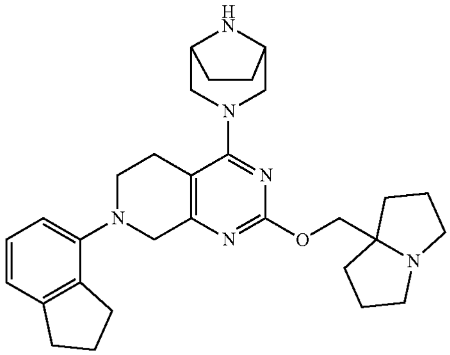

Step A. tert-butyl (1R,5S)-3-(7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate. Synthesized according to Example 101, Step A substituting 4-bromo-2,3-dihydro-1H-indene in place of 4-bromo-1,1-difluoro-2,3-dihydro-1H-indene to afford tert-butyl (1R,5S)-3-(7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate (11 mg, 35%). LCMS (MM-ES+APCI, Pos): m/z 601.4 [M+H].

Step B. 4-((1R,5S)-3,8-diazabicyclo[3.2.1]octan-3-yl)-7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidine. Synthesized according to Example 101, Step B substituting tert-butyl (1R,5S)-3-(7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(1,1-difluoro-2,3-dihydro-1H-inden-4-yl)-2-((tetrahydro-1H-pyrrolizin-7a(5H)-yl)methoxy)-5,6,7,8-tetrahydropyrido[3,4-d]pyrimidin-4-yl)-3,8-diazabicyclo[3.2.1]octane-8-carboxylate to afford the TFA salt of 4-((1R,5S)-3,8-diazabicyclo[3.2.1]octan-3-yl)-7-(2,3-dihydro-1H-inden-4-yl)-2-((tetrahydro-1H-pyrrolizin-7a(5H)-yl)methoxy)-5,6,7,8-tetrahydropyrido[3,4-d]pyrimidine as a tan solid (2.8 mg, 22%). LCMS (MM-ES+APCI, Pos): m/z 501.4 [M+H].

Example 105

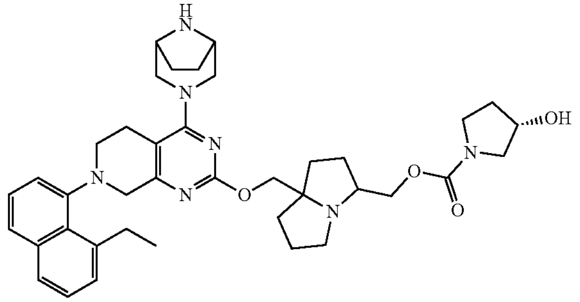 [SMILES: CCc1cccc2cccc(N3CCc4c(nc(OCC56CCCN5C(COC(=O)N5CC[C@H](O)C5)CC6)nc4N4CC5CCC(C4)N5)C3)c12]

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (3S)-3-hydroxypyrrolidine-1-carboxylate Synthesized according to Example 5 substituting (S)-3-pyrrolidinol in place of methylamine in step F to afford (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (3S)-3-hydroxypyrrolidine-1-carboxylate as the TFA salt (1.9 mg, 17% yield). LCMS (MM-ES+APCI, Pos): m/z 682.4 (M+H).

Example 106

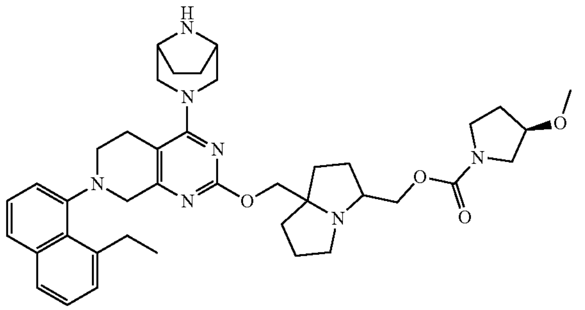 [SMILES: CCc1cccc2cccc(N3CCc4c(nc(OCC56CCCN5C(COC(=O)N5CC[C@@H](OC)C5)CC6)nc4N4CC5CCC(C4)N5)C3)c12]

(7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (3R)-3-methoxypyrrolidine-1-carboxylate (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (3R)-3-methoxypyrrolidine-1-carboxylate. Synthesized according to Example 5 substituting (R)-3-methoxypyrrolidine in place of methylamine in step F to afford (7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (3R)-3-methoxypyrrolidine-1-carboxylate as the TFA salt (4.4 mg, 40% yield). LCMS (MM-ES+APCI, Pos): m/z 696.5 (M+H).

Example 107

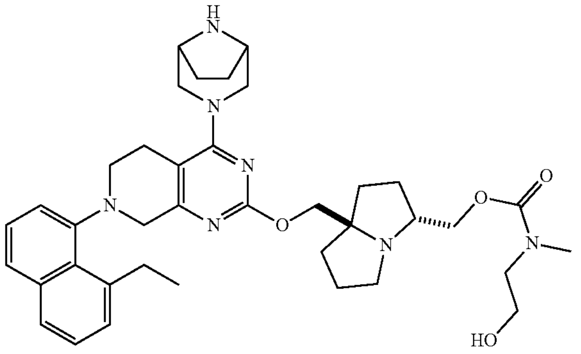

((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (2-hydroxyethyl)(methyl)carbamate (trans enantiomers)

Synthesized according to Example 5 substituting 2-(methylamino)ethan-1-ol in place of methylamine in Step F to give product as the TFA salt. LCMS (MM-ES+APCI, Pos): m/z 670.4 [M+H].

Example 108

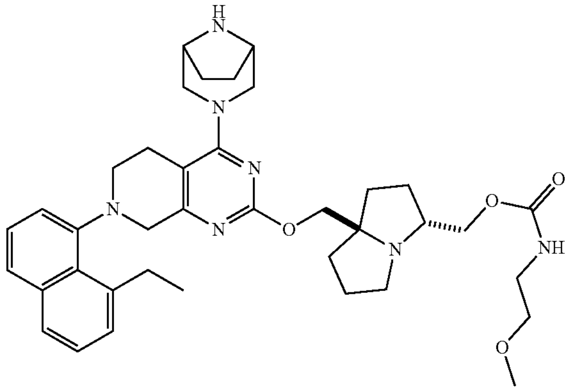

((3R,7aR)-7a-(((4-((1R,5S)-3,8-diazabicyclo[3.2.1]octan-3-yl)-7-(8-ethylnaphthalen-1-yl)-5,6,7,8-tetrahydropyrido[3,4-d]pyrimidin-2-yl)oxy)methyl)hexahydro-1H-pyrrolizin-3-yl)methyl (2-methoxyethyl)carbamate (trans enantiomers)

Synthesized according to Example 5 substituting 2-methoxyethan-1-amine in place of methylamine in Step F to give product as the TFA salt. LCMS (MM-ES+APCI, Pos): m/z 670.4 [M+H].

Example 109

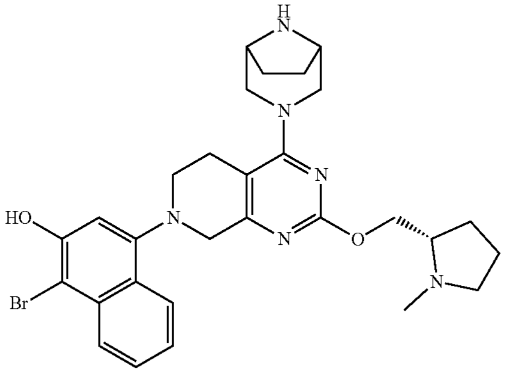 [SMILES: CN1CCC[C@H]1COc1nc2c(c(N3CC4CCC(C3)N4)n1)CCN(c1cc(O)c(Br)c3ccccc13)C2]

4-(4-((1R,5S)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)-1-bromonaphthalen-2-ol

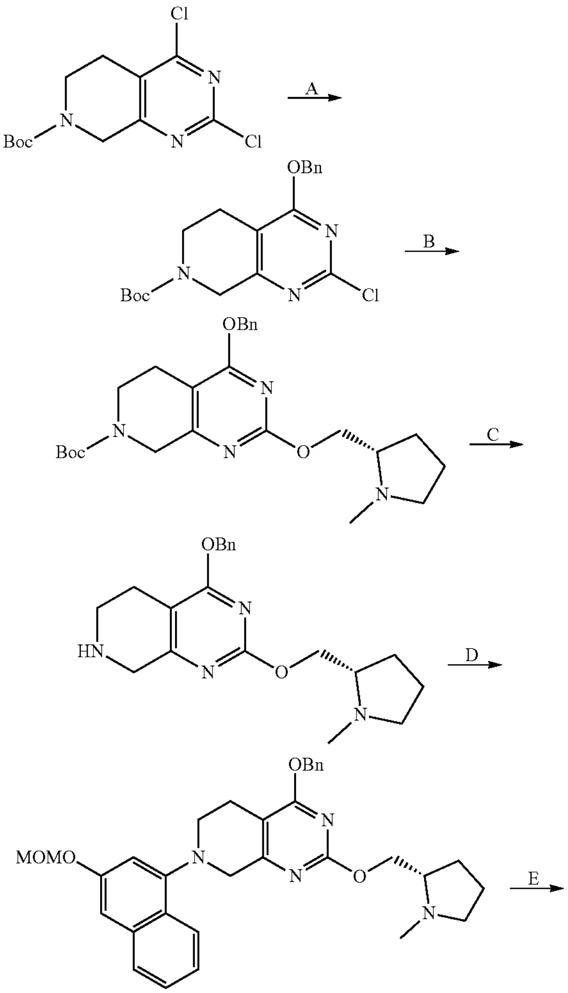

-continued

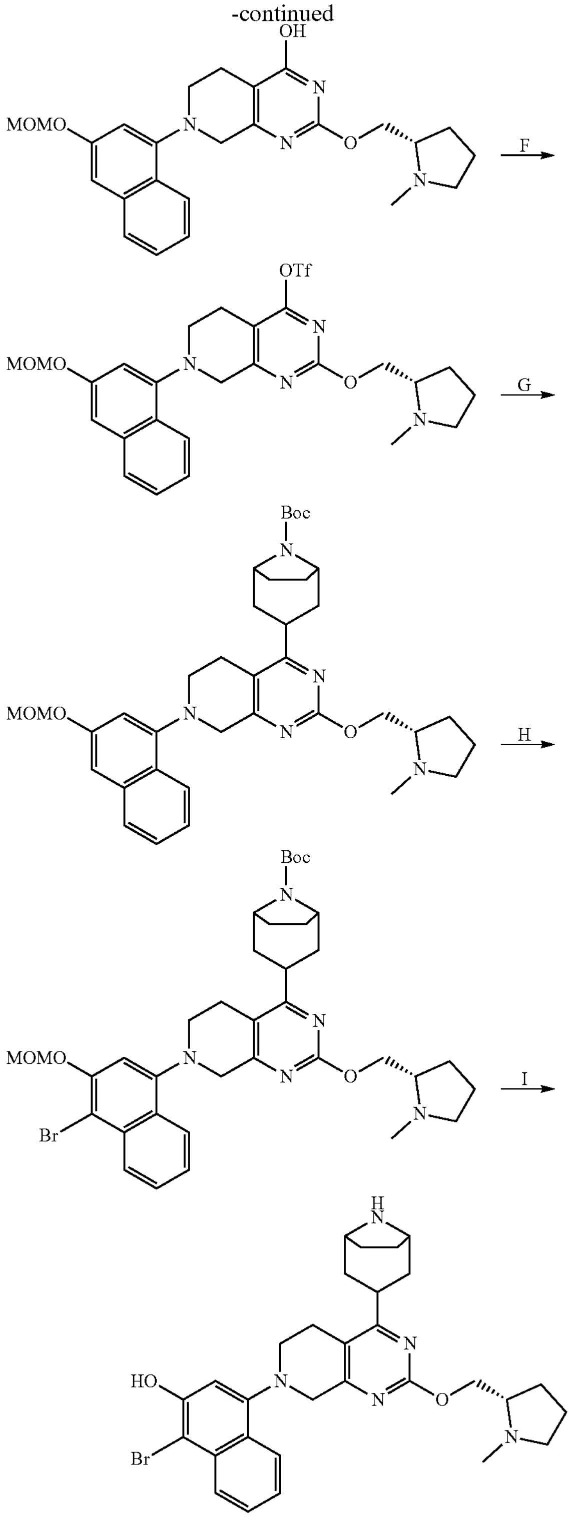

Step A: tert-butyl 4-(benzyloxy)-2-chloro-5,6-dihydropyrido[3,4-d]pyrimidine-7(8H)-carboxylate. To a solution of tert-butyl 2,4-dichloro-6,8-dihydro-5H-pyrido[3,4-d]pyrimidine-7-carboxylate (10.0 g, 32.9 mmol, 1.0 eq) in dioxane (100.0 mL) were added phenylmethanol (10.7 g, 98.6 mmol, 3.0 eq) and cesium carbonate (21.4 g, 65.8 mmol, 2.0 eq) at 25° C., and the reaction mixture was heated to 80° C. and stirred for 3 hr. Then the reaction mixture was cooled to 25° C., diluted with water (20.0 mL), and then extracted with ethyl acetate (20.0 mL×3). The combined organic layers were washed with brine (20.0 mL), and dried with $Na_2SO_4$. The mixture was filtered and concentrated to give a residue. The residue was purified by reversed phase flash [water (trifluoroacetic acid, 0.100%)/acetonitrile]. The desired fractions were collected and adjusted pH>7 by saturated sodium bicarbonate (5.00 mL). The mixture was extracted with ethyl acetate (3×50.0 mL). The organic layers were washed with brine (100 mL), dried over $Na_2SO_4$, then filtered and concentrated under vacuum to give title compound (7.60 g, 16.3 mmol, 49.7% yield). Colorless oil; $^1$H NMR (400 MHz, $CDCl_3$) δ=7.41-7.22 (m, 5H), 5.38 (s, 2H), 4.46 (s, 2H), 3.58 (br t, J=6.0 Hz, 2H), 2.60 (br t, J=5.6 Hz, 2H), 1.40 (s, 9H).

Step B: (S)-tert-butyl 4-(benzyloxy)-2-((1-methylpyrrolidin-2-yl)methoxy)-5,6-dihydropyrido[3,4-d]pyrimidine-7(8H)-carboxylate. To a solution of tert-butyl 4-benzyloxy-2-chloro-6,8-dihydro-5H-pyrido[3,4-d]pyrimidine-7-carboxylate (3.50 g, 9.31 mmol, 1.0 eq) and [(2S)-1-methylpyrrolidin-2-yl]methanol (2.15 g, 18.6 mmol, 2.0 eq) in toluene (35.0 mL) were added $Pd(OAc)_2$ (209 mg, 931 μmol, 0.1 eq), rac-BINAP (1.16 g, 1.86 mmol, 0.20 eq) and cesium carbonate (9.10 g, 27.9 mmol, 3.0 eq) under nitrogen atmosphere. The reaction mixture was stirred at 110° C. for 8 hours under nitrogen. The mixture was diluted with water (20.0 mL) and extracted with ethyl acetate (3×20.0 mL). The combined organic layers were washed with brine (30.0 mL), dried over $Na_2SO_4$, filtered, and concentrated under vacuum to give a residue. The residue was purified by column chromatography ($SiO_2$, Petroleum ether/Ethyl acetate=20/1 to 0:1) to give title compound (4.70 g, crude). Yellow oil; $^1$H NMR (400 MHz, $CDCl_3$) δ=7.38-7.23 (m, 5H), 5.36 (s, 2H), 4.41-4.30 (m, 3H), 4.13 (dd, J=6.4, 10.4 Hz, 1H), 3.57 (br t, J=6.0 Hz, 2H), 3.04 (br d, J=6.4 Hz, 1H), 2.68-2.48 (m, 3H), 2.42 (s, 3H), 2.23 (br d, J=7.6 Hz, 1H), 2.00 (br dd, J=3.2, 8.8 Hz, 1H), 1.97-1.93 (m, 1H), 1.84-1.74 (m, 1H), 1.70 (br dd, J=7.6, 10.4 Hz, 2H), 1.41 (s, 9H).

Step C: (S)-4-(benzyloxy)-2-((1-methylpyrrolidin-2-yl)methoxy)-5,6,7,8-tetrahydropyrido[3,4-d]pyrimidine. A solution of tert-butyl 4-benzyloxy-2-[[(2S)-1-methylpyrrolidin-2-yl]methoxy]-6,8-dihydro-5H-pyrido[3,4-d]pyrimidine-7-carboxylate (4.50 g, 9.90 mmol, 1.0 eq) in trifluoroacetic acid (20.0 mL, 270 mmol, 27.3 eq) and dichloromethane (20.0 mL) was stirred at 20° C. for one hour. The reaction mixture was concentrated under reduced pressure, and the residue was acidified with hydrochloric acid (20.0 mL, 1 mol/L) to pH=3. Then the residue was washed with ethyl acetate (3×100.0 mL). The aqueous phase was basified with saturated sodium bicarbonate (50.0 mL) to pH=9 and extracted with ethyl acetate (3×100.0 mL). The combined organic layers were washed with brine (100.0 mL) and dried with $Na_2SO_4$. The mixture was filtered and concentrated to give title compound (2.30 g, 65.6% yield). Yellow solid; $^1$H NMR (400 MHz, CDCl3) δ=7.44-7.32 (m, 5H), 5.44 (s, 2H), 4.40 (br dd, J=4.8, 10.6 Hz, 1H), 4.18 (br dd, J=6.8, 10.0 Hz, 1H), 3.88 (s, 2H), 3.10 (br t, J=6.0 Hz, 3H), 2.68 (br s, 1H), 2.58 (br t, J=5.6 Hz, 2H), 2.49 (s, 3H), 2.35-2.24 (m, 1H), 2.14-2.01 (m, 1H), 1.84 (br d, J=9.6 Hz, 1H), 1.76 (br d, J=5.2 Hz, 2H).

Step D: 4-benzyloxy-7-[3-(methoxymethoxy)-1-naphthyl]-2-[[(2S)-1-methylpyrrolidin-2-yl]methoxy]-6,8-dihydro-5H-pyrido[3,4-d]pyrimidine. To a solution of 4-benzyloxy-2-[[(2S)-1-methylpyrrolidin-2-yl]methoxy]-5,6,7,8-tetrahydropyrido[3,4-d]pyrimidine (3.0 g, 8.46 mmol, 1.0 eq) and 1-bromo-3-(methoxymethoxy)naphthalene (2.94 g, 11.0 mmol, 1.30 eq) in toluene (40.0 mL) were added $Pd_2(dba)_3$ (155 mg, 169 μmol, 0.02 eq), RuPhos (158 mg, 338 μmol, 0.04 eq) and sodium tert-butoxide (1.63 g, 16.9 mmol, 2.0 eq) under nitrogen atmosphere. The reaction mixture was stirred at 110° C. for 0.5 hours under nitrogen. The mixture was diluted with water (50.0 mL) and extracted with ethyl acetate (3×50.0 mL). The combined organic layers were washed with brine (50.0 mL), dried over $Na_2SO_4$, filtered and concentrated under vacuum to give a residue. The residue was purified by column chromatography (dichloromethane:methyl alcohol=20:1) to give title compound (4.0 g, 87.5% yield). Yellow solid; $^1$H NMR (400 MHz, $CDCl_3$) δ=7.99 (d, J=8.4 Hz, 1H), 7.66 (d, J=8.0 Hz, 1H), 7.43-7.22 (m, 7H), 7.07 (d, J=2.0 Hz, 1H), 6.79 (d, J=2.0 Hz, 1H), 5.41 (s, 2H), 5.22 (s, 2H), 4.49-4.33 (m, 1H), 4.20-4.09 (m, 3H), 3.46 (s, 3H), 3.41-3.27 (m, 2H), 3.05 (br s, 1H), 2.82 (br s, 2H), 2.65 (br s, 1H), 2.44 (s, 3H), 2.27 (br d, J=19.6 Hz, 1H), 2.02 (br d, J=7.6 Hz, 1H), 1.78 (br s, 1H), 1.71 (br s, 2H).

Step E: 7-[3-(methoxymethoxy)-1-naphthyl]-2-[[(2S)-1-methylpyrrolidin-2-yl]methoxy]-6,8-dihydro-5H-pyrido[3,4-d]pyrimidin-4-ol. To a solution of 4-benzyloxy-7-[3-(methoxymethoxy)-1-naphthyl]-2-[[(2S)-1-methylpyrrolidin-2-yl]methoxy]-6,8-dihydro-5H-pyrido[3,4-d]pyrimidine (4.0 g, 7.4 mmol, 1.0 eq) in tetrahydrofuran (80.0 mL) was added palladium on activated carbon (400 mg, 10% purity) under nitrogen, and the reaction mixture was stirred at 20° C. for 1 hour under hydrogen balloon (15.0 psi). The reaction mixture was filtered, and the filtrate was concentrated in vacuum affording the title compound (3.2 g, 83.7% yield). Yellow oil; $^1$H NMR (400 MHz, MeOD) δ=7.95 (d, J=8.4 Hz, 1H), 7.62 (d, J=8.4 Hz, 1H), 7.35-7.28 (m, 1H), 7.27-7.21 (m, 1H), 7.04 (d, J=2.0 Hz, 1H), 6.79 (d, J=2.0 Hz, 1H), 5.19 (s, 2H), 4.39-4.33 (m, 1H), 4.30-4.22 (m, 1H), 3.89 (s, 2H), 3.40 (s, 3H), 3.23 (br d, J=1.6 Hz, 2H), 3.15-3.08 (m, 1H), 2.83 (br s, 1H), 2.60 (br s, 2H), 2.51-2.37 (m, 4H), 2.07-1.94 (m, 1H), 1.83-1.59 (m, 3H); LCMS [M+1]: 451.

Step F: [7-[3-(methoxymethoxy)-1-naphthyl]-2-[[(2S)-1-methylpyrrolidin-2-yl]methoxy]-6,8-dihydro-5H-pyrido[3,4-d]pyrimidin-4-yl] trifluoromethanesulfonate. To a solution of 7-[3-(methoxymethoxy)-1-naphthyl]-2-[[(2S)-1-methylpyrrolidin-2-yl]methoxy]-6,8-dihydro-5H-pyrido[3,4-d]pyrimidin-4-ol (1.0 g, 2.0 mmol, 1.0 eq) in dichloromethane (20.0 mL) were added trifluoromethanesulfonic anhydride (620 mg, 2.2 mmol, 1.1 eq) and triethylamine (405 mg, 4.0 mmol, 2.0 eq) at −40° C. The mixture was stirred at −40° C. for 0.5 hr. The reaction mixture was quenched with water (12.0 mL) and extracted with dichloromethane (3×12.0 mL). The combined organic layers were washed with brine (12.0 mL), and then dried with $Na_2SO_4$. The mixture was filtered and concentrated to give a residue. The residue was purified by prep-TLC (dichloromethane:methyl alcohol=10:1) affording the title compound (1.00 g, 76.5% yield). Colorless oil; LCMS [M+1]: 583.

Step G: (1R,5S)-tert-butyl 3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of [7-[3-(methoxymethoxy)-1-naphthyl]-2-[[(2S)-1-methylpyrrolidin-2-yl]methoxy]-6,8-dihydro-5H-pyrido[3,4-d]pyrimidin-4-yl]trifluoromethanesulfonate (50.0 mg, 74.8 μmol, 1.0 eq), DIEA (19.3 mg, 150 μmol, 26.1 uL, 2.0 eq) in acetonitrile (1.0 mL) were added tert-butyl (1S,5R)-3,8-diazabicyclo[3.2.1]octane-8-carboxylate (31.8 mg, 150 μmol, 2.0 eq) at 20° C. The reaction mixture was heated to 80° C. and stirred for one hour. The reaction mixture was concentrated in vacuum to give a residue, and the residue was purified by prep-TLC (SiO2, DCM:MeOH=10:1) affording the title compound (58.0 mg, crude). Brown solid; LCMS [M+1]: 645.3.

Step H: (1R,5S)-tert-butyl 3-(7-(4-bromo-3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl 3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (46.0 mg, 71.3 μmol, 1.0 eq) in acetonitrile (2.0 mL) was added N-bromosuccinimide (12.7 mg, 71.3 μmol, 1.0 eq) at 10° C. under nitrogen atmosphere. The reaction mixture was stirred at 10° C. for 2 hours under nitrogen atmosphere. The reaction mixture was concentrated in vacuum to give a residue, and the residue was purified by prep-TLC (SiO2, DCM:MeOH=10:1) affording the title compound (10.0 mg, 19.4% yield). Brown solid; $^1$H NMR (400 MHz, MeOD-$d_4$) δ=8.05-8.17 (m, 2H) 7.43-7.51 (m, 1H) 7.31-7.39 (m, 1H) 7.08 (s, 1H) 5.14-5.32 (m, 2H) 4.30-4.49 (m, 2H) 4.22 (m, 2H) 3.94-4.08 (m, 3H) 3.40-3.50 (m, 3H) 3.24-3.40 (m, 3H) 3.14 (m, 2H) 2.68-2.88 (m, 5H) 2.30-2.56 (m, 1H) 2.08-2.22 (m, 1H) 1.74-1.97 (m, 7H) 1.35-1.44 (s, 9H) 1.11-1.21 (m, 2H); LCMS [M+1]: 723.2.

Step I: 4-(4-((1R,5S)-3,8-diazabicyclo[3.2.1]octan-3-yl)-2-(((S)-1-methylpyrrolidin-2-yl)methoxy)-5,6-dihydropyrido[3,4-d]pyrimidin-7(8H)-yl)-1-bromonaphthalen-2-ol. A solution of (1R,5S)-tert-butyl 3-(7-(4-bromo-3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (10.0 mg, 13.8 μmol, 1.0 eq) in HCl·MeOH (2.00 mL) was stirred at 15° C. for one hour. The reaction mixture was concentrated in vacuum to give a residue. The residue was purified by prep-HPLC (column: Phenomenex Synergi C18 150*25*10 um; mobile phase: [water(0.05% HCl)-ACN]; B %: 7%-27%, 11 min), and lyophilized affording the title compound (4.75 mg, 55% yield, HCl salt). Yellow solid; $^1$H NMR (400 MHz, MeOD-$d_4$) δ=8.14-8.23 (m, 2H) 7.58 (t, J=7.2 Hz, 1H) 7.39-7.46 (m, 1H) 7.03 (s, 1H) 4.97-5.03 (m, 1H) 4.88-4.94 (m, 2H) 4.26-4.39 (m, 4H) 4.04 (br d, J=5.6 Hz, 1H) 3.75-3.89 (m, 3H) 3.36-3.52 (m, 2H) 3.23-3.30 (m, 2H) 3.11 (s, 4H) 2.42-2.53 (m, 1H) 2.05-2.31 (m, 8H); LCMS [M+1]: 579.3.

Example 110

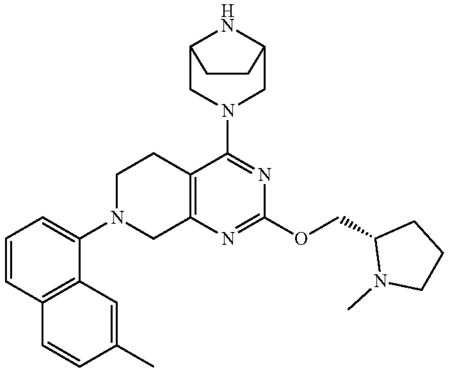 [SMILES: Cc1ccc2cccc(N3CCc4c(nc(OC[C@@H]5CCCN5C)nc4N4CC5CCC(C4)N5)C3)c2c1]

4-((1R,5S)-3,8-diazabicyclo[3.2.1]octan-3-yl)-7-(7-methylnaphthalen-1-yl)-2-(((S)-1-methylpyrrolidin-2-yl)methoxy)-5,6,7,8-tetrahydropyrido[3,4-d]pyrimidine

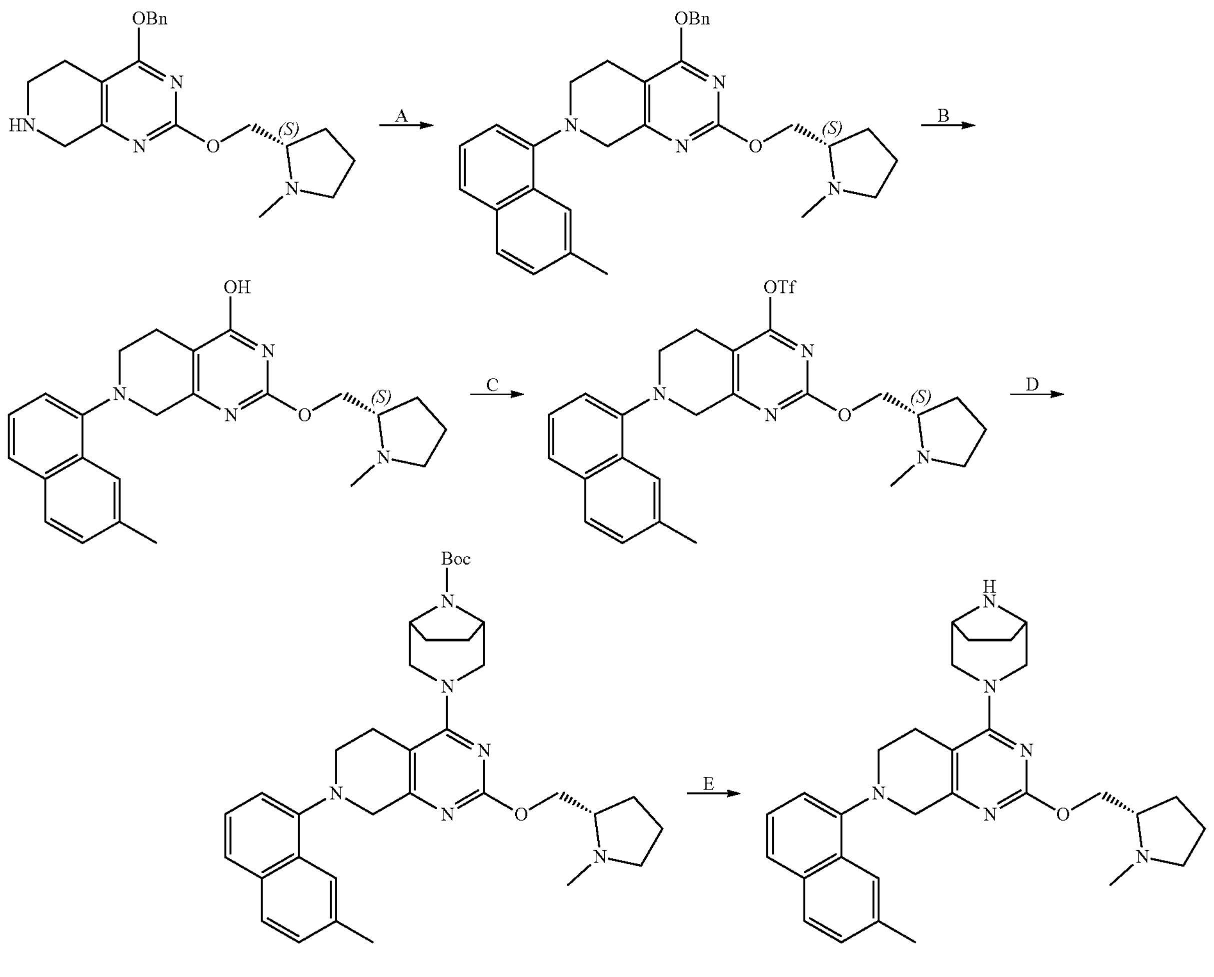

Step A: (S)-4-(benzyloxy)-7-(7-methylnaphthalen-1-yl)-2-((1-methylpyrrolidin-2-yl)methoxy)-5,6,7,8-tetrahydropyrido[3,4-d]pyrimidine. To a solution of 4-benzyloxy-2-[[(2S)-1-methylpyrrolidin-2-yl]methoxy]-5,6,7,8-tetrahydropyrido[3,4-d]pyrimidine (280 mg, 790 μmol, 1.0 eq.) and (7-methyl-1-naphthyl) trifluoromethanesulfonate (321 mg, 1.11 mmol, 1.40 eq) in toluene (5.0 mL) were added $Pd_2(dba)_3$ (72.3 mg, 79.0 μmol, 0.10 eq), RuPhos (73.7 mg, 158 μmol, 0.20 eq) and cesium carbonate (643 mg, 1.97 mmol, 2.50 eq) under nitrogen atmosphere. The reaction mixture was stirred at 110° C. for 3 hours under nitrogen. The mixture was diluted with water (20.0 mL) and extracted with ethyl acetate (3×20.0 mL). The combined organic layers were washed with brine (20.0 mL), dried over $Na_2SO_4$, filtered, and concentrated under vacuum to give a residue. The residue was purified by prep-TLC ($SiO_2$, Dichloromethane:Methyl alcohol=10:1) to give title compound (275 mg, 70.4% yield). Yellow oil; $^1H$ NMR (400 MHz, MeOD) δ=7.97 (s, 1H), 7.76 (d, J=8.4 Hz, 1H), 7.57 (d, J=8.0 Hz, 1H), 7.50 (d, J=7.2 Hz, 2H), 7.44-7.39 (m, 2H), 7.36 (dt, J=3.2, 7.6 Hz, 3H), 7.18 (d, J=7.6 Hz, 1H), 5.56 (s, 2H), 4.40 (d, J=5.6 Hz, 2H), 4.16-4.12 (m, 2H), 3.14 (td, J=4.8, 10.0 Hz, 1H), 2.89 (br d, J=6.8 Hz, 2H), 2.85-2.79 (m, 1H), 2.54 (s, 3H), 2.52 (s, 3H), 2.47-2.35 (m, 2H), 2.18-2.09 (m, 1H), 1.93-1.80 (m, 3H), 1.79-1.72 (m, 1H).

Step B: 7-(7-methyl-1-naphthyl)-2-[[(2S)-1-methylpyrrolidin-2-yl]methoxy]-6,8-dihydro-5H-pyrido[3,4-d]pyrimidin-4-ol. To a solution of 4-benzyloxy-7-(7-methyl-1-naphthyl)-2-[[(2S)-1-methylpyrrolidin-2-yl]methoxy]-6,8-dihydro-5H-pyrido[3,4-d]pyrimidine (260 mg, 526 μmol, 1.0 eq) in methanol (3.00 mL) was added palladium on activated carbon (10 mg, 10% purity) under nitrogen, and the reaction mixture was stirred at 20° C. for 2 hours under hydrogen balloon (15.0 psi). The reaction mixture was filtered, and the filtrate was concentrated under vacuum affording the title compound (272 mg, crude). Yellow oil; LCMS [M+1]: 405.4.

Step C: [7-(7-methyl-1-naphthyl)-2-[[(2S)-1-methylpyrrolidin-2-yl]methoxy]-6,8-dihydro-5H-pyrido[3,4-d]pyrimidin-4-yl] trifluoromethanesulfonate. To a solution of 7-(7-methyl-1-naphthyl)-2-[[(2S)-1-methylpyrrolidin-2-yl]methoxy]-6,8-dihydro-5H-pyrido[3,4-d]pyrimidin-4-ol (220 mg, 544 μmol, 1.0 eq) in dichloromethane (2.00 mL) were added trifluoromethanesulfonic anhydride (230 mg, 815 μmol, 1.5 eq) and triethylamine (165 mg, 1.63 mmol, 3.0 eq) at −5° C. The mixture was stirred at 20° C. for 3 hours. The mixture was concentrated to give a residue. The residue was purified by prep-TLC (SiO2, Dichloromethane:Methyl alcohol=10:1) affording the title compound (300 mg, 85.6% yield). Brown oil; LCMS [M+1]: 537.2.

Step D: (1R,5S)-tert-butyl 3-(7-(7-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of [7-(7-methyl-1-naphthyl)-2-[[(2S)-1-methylpyrrolidin-2-yl]methoxy]-6,8-dihydro-5H-pyrido[3,4-d]pyrimidin-4-yl] trifluoromethanesulfonate (100 mg, 155 μmol, 1.0 eq), diisopropylethylamine (40.1 mg, 310 μmol, 2.0 eq) in acetonitrile (2.00 mL) was added tert-butyl (1S,5R)-3,8-diazabicyclo[3.2.1]octane-8-carboxylate (65.9 mg, 310 μmol, 2.0 eq) at 20° C. The reaction mixture was heated to 80° C. and stirred for one hour. The reaction mixture was concentrated in vacuum to give a residue, and the residue was purified by prep-TLC (SiO2, DCM:MeOH=10:1) affording the title compound (61.0 mg, 49.2% yield, 75% purity). Brown oil; LCMS [M+1]: 599.4.

Step E: 4-((1R,5S)-3,8-diazabicyclo[3.2.1]octan-3-yl)-7-(7-methylnaphthalen-1-yl)-2-(((S)-1-methylpyrrolidin-2-yl)methoxy)-5,6,7,8-tetrahydropyrido[3,4-d]pyrimidine. A solution of (1R,5S)-tert-butyl 3-(7-(7-methylnaphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (60.0 mg, 75.2 μmol, 1.0 eq) in HCl·MeOH (1.00 mL) was stirred at 20° C. for one hour. The reaction mixture was concentrated in vacuum to give a residue. The residue was purified by prep-HPLC (column: Phenomenex Synergi C18 150*25*10 um; mobile phase: [water(0.1% TFA)-ACN]; B %: 12%-42%,2 min), and lyophilized affording the title compound (7.46 mg, 16% yield, $CF_3COOH$ salt). Orange solid; $^1$H NMR (400 MHz, MeOD) δ=8.02 (s, 1H), 7.79 (d, J=8.4 Hz, 1H), 7.61 (d, J=8.0 Hz, 1H), 7.42-7.35 (m, 2H), 7.21 (d, J=7.2 Hz, 1H), 4.79 (dd, J=3.2, 12.4 Hz, 1H), 4.61 (dd, J=7.2, 12.4 Hz, 1H), 4.36 (br s, 1H), 4.23 (br s, 4H), 3.98-3.87 (m, 1H), 3.82-3.71 (m, 1H), 3.62-3.52 (m, 2H), 3.37 (s, 2H), 3.26 (br d, J=8.8 Hz, 1H), 3.10 (s, 3H), 3.07-2.84 (m, 2H), 2.55 (s, 3H), 2.47-2.36 (m, 1H), 2.36-1.95 (m, 8H); LCMS [M+1]=499.3

Example 111

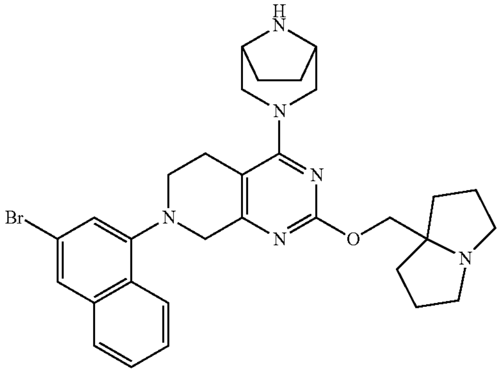 [SMILES: Brc1cc(N2CCc3c(nc(OCC45CCCN4CCC5)nc3N3CC4CCC(C3)N4)C2)c2ccccc2c1]

4-((1R,5S)-3,8-diazabicyclo[3.2.1]octan-3-yl)-7-(3-bromonaphthalen-1-yl)-2-((tetrahydro-1H-pyrrolizin-7a(5H)-yl)methoxy)-5,6,7,8-tetrahydropyrido[3,4-d]pyrimidine

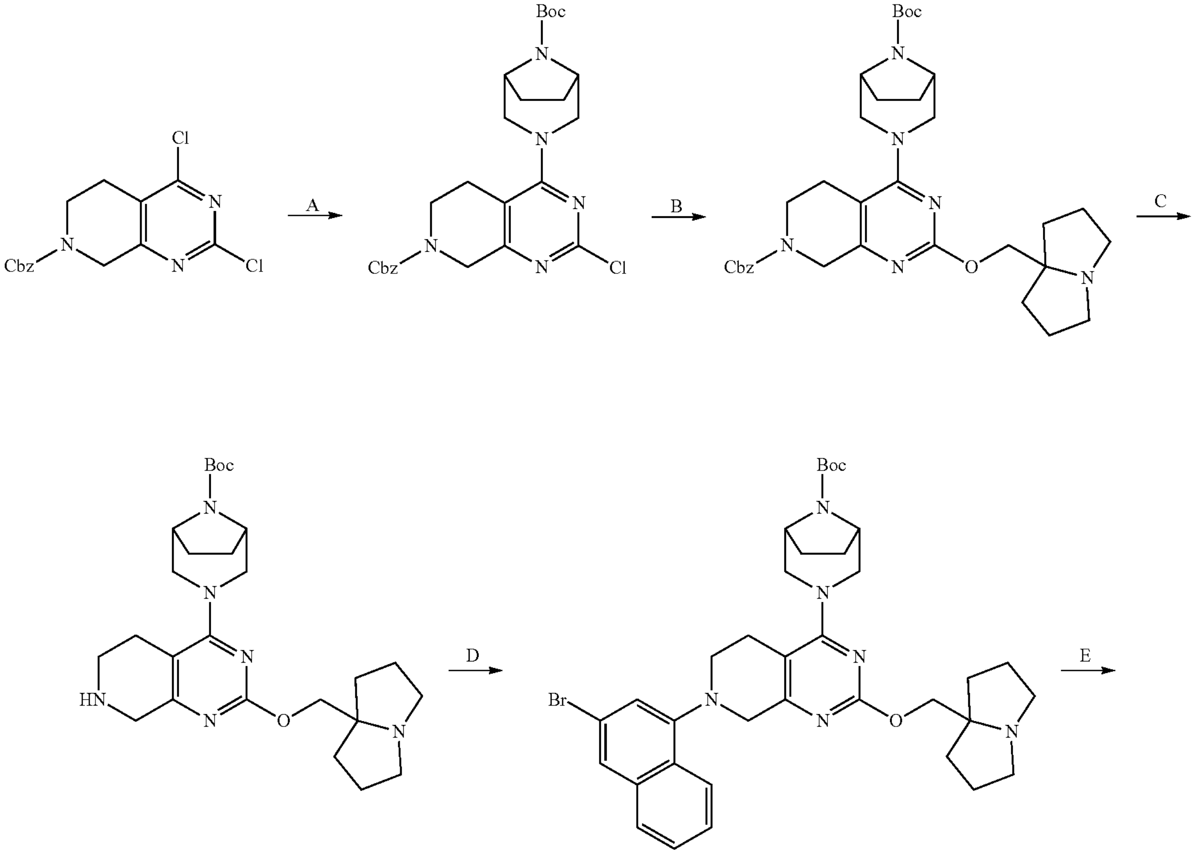

-continued

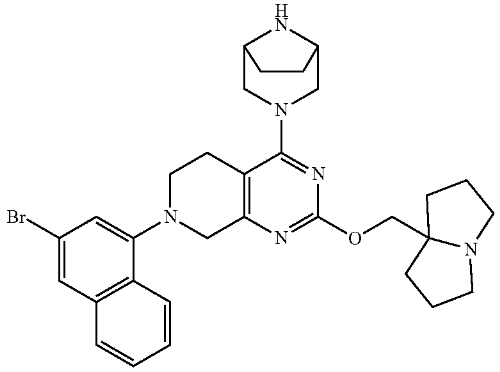

Step A: Benzyl 4-((1R,5S)-8-(tert-butoxycarbonyl)-3,8-diazabicyclo[3.2.1]octan-3-yl)-2-chloro-5,6-dihydropyrido[3,4-d]pyrimidine-7(8H)-carboxylate. To a solution of benzyl 2,4-dichloro-5,8-dihydropyrido[3,4-d]pyrimidine-7(6H)-carboxylate (1.00 g, 2.96 mmol, 1.0 eq), DIEA (764 mg, 5.91 mmol, 1.03 mL, 2.0 eq) in DCM (20.0 mL) was added tert-butyl 3,8-diazabicyclo[3.2.1]octane-3-carboxylate (628 mg, 2.96 mmol, 1.0 eq) at −40° C., and the reaction mixture was stirred at 25° C. for 12 hours. The reaction mixture was concentrated under vacuum to give a residue, and the residue was purified by silica gel chromatography (petroleum ether/ethyl acetate=10/1 to 2/1) affording the title compound (800 mg, 53% yield). Brown oil; $^1$H NMR (400 MHz, CDC13) δ=7.44-7.33 (m, 5H), 5.18 (s, 2H), 4.59 (br s, 2H), 4.38-4.22 (m, 2H), 3.87 (br d, J=12.4 Hz, 2H), 3.73-3.54 (m, 2H), 3.26 (br d, J=11.2 Hz, 2H), 2.66 (br s, 2H), 1.97-1.89 (m, 2H), 1.80-1.74 (m, 2H), 1.49 (s, 9H).

Step B: Benzyl 4-((1R,5S)-8-(tert-butoxycarbonyl)-3,8-diazabicyclo[3.2.1]octan-3-yl)-2-((hexahydro-1H-pyrrolizin-7a-yl)methoxy)-5,6-dihydropyrido[3,4-d]pyrimidine-7(8H)-carboxylate. To a solution of benzyl 4-((1R,5S)-8-(tert-butoxycarbonyl)-3,8-diazabicyclo[3.2.1]octan-3-yl)-2-chloro-5,6-dihydropyrido[3,4-d]pyrimidine-7(8H)-carboxylate (700 mg, 1.36 mmol, 1.0 eq) and (tetrahydro-1H-pyrrolizin-7a(5H)-yl)methanol (288 mg, 2.04 mmol, 1.5 eq) in toluene (10.0 mL) were added RuPhos (127 mg, 272 μmol, 0.2 eq), cesium carbonate (1.33 g, 4.09 mmol, 3.0 eq) and $Pd_2(dba)_3$ (125 mg, 136 μmol, 0.1 eq) under nitrogen atmosphere. The reaction mixture was stirred at 100° C. for 2 hours under nitrogen. The reaction mixture was filtered and concentrated in vacuum to give a residue, and the residue was purified by silica gel chromatography (petroleum ether/ethyl acetate=5/1 to dichloromethane/methanol=10/1) affording the title compound (800 mg, 95% yield). Brown oil; $^1$H NMR (400 MHz, $CDCl_3$) δ=7.42-7.33 (m, 5H), 5.17 (s, 2H), 4.54 (br s, 2H), 4.34-4.11 (m, 4H), 3.91-3.75 (m, 2H), 3.67-3.56 (m, 2H), 3.37-3.12 (m, 4H), 2.75-2.52 (m, 4H), 2.23-2.07 (m, 2H), 1.97-1.88 (m, 6H), 1.84-1.64 (m, 4H), 1.49 (s, 9H).

Step C: (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of benzyl 4-((1R,5S)-8-(tert-butoxycarbonyl)-3,8-diazabicyclo[3.2.1]octan-3-yl)-2-((hexahydro-1H-pyrrolizin-7a-yl)methoxy)-5,6-dihydropyrido[3,4-d]pyrimidine-7(8H)-carboxylate (800 mg, 1.29 mmol, 1.0 eq) in methanol (10.0 mL) was added palladium on activated carbon (100 mg, 10% purity) under nitrogen, and the reaction mixture was stirred at 25° C. for 1 hour under hydrogen balloon (15.0 psi). The reaction mixture was filtered, and the filtrate was concentrated in vacuum affording the title compound (520 mg, 83% yield). Brown solid; $^1$H NMR (400 MHz, $CDCl_3$) δ=4.39-4.17 (m, 2H), 4.04-3.92 (m, 3H), 3.91-3.80 (m, 2H), 3.32-2.92 (m, 5H), 2.74-2.48 (m, 4H), 2.15-2.01 (m, 2H), 1.96-1.71 (m, 10H), 1.68-1.59 (m, 2H), 1.50 (s, 9H).

Step D: (1R,5S)-tert-butyl3-(7-(3-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (200 mg, 413 μmol, 1.0 eq), 3-bromo-1-iodonaphthalene (165 mg, 495 μmol, 1.2 eq) in dioxane (4.00 mL) were added cesium carbonate (403 mg, 1.24 mmol, 3.0 eq) and rac-BINAP-Pd-G3 (20.5 mg, 20.6 μmol, 0.05 eq) under nitrogen, and the reaction mixture was stirred at 80° C. for 12 hours under nitrogen atmosphere. The reaction mixture was filtered and concentrated in vacuum to give a residue, and the residue was purified by prep-TLC (dichloromethane/methanol=10/1) affording the title compound (55.0 mg, crude). Brown oil; LCMS [ESI, M+1]: 689.0.

Step E: 4-((1R,5S)-3,8-diazabicyclo[3.2.1]octan-3-yl)-7-(3-bromonaphthalen-1-yl)-2-((hexahydro-1H-pyrrolizin-7a-yl)methoxy)-5,6,7,8-tetrahydropyrido[3,4-d]pyrimidine. A solution of (1R,5S)-tert-butyl3-(7-(3-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (50.0 mg, 72.5 μmol, 1.0 eq) in HCl·dioxane (2.00 mL) and acetonitrile (2.00 mL) was stirred at 25° C. for 0.5 hour. The reaction mixture was concentrated in vacuum to give a residue. The residue was purified by prep-HPLC (column: Phenomenex Synergi C18 150*25*10 um; mobile phase: [water (0.225% FA)-ACN]; B %: 23%-53%, 10 min), and the desired fractions were lyophilized affording the title compound (17.4 mg, 37% yield, HCOOH salt). Yellow gum; $^1$H NMR (400 MHz, $CDCl_3$) δ=8.13 (dd, J=3.2, 6.4 Hz, 1H), 7.78-7.73 (m, 2H), 7.53-7.48 (m, 2H), 7.18 (d, J=1.6 Hz, 1H), 4.49 (s, 2H), 4.23 (s, 2H), 4.01-3.94 (m, 2H), 3.90 (br s, 2H), 3.77-3.68 (m, 2H), 3.51-3.42 (m, 2H), 3.39-3.28 (m, 2H), 2.92-2.83 (m, 4H), 2.18-1.99 (m, 10H), 1.96-1.89 (m, 2H); LCMS [ESI, M+3]: 591.2.

Example 112

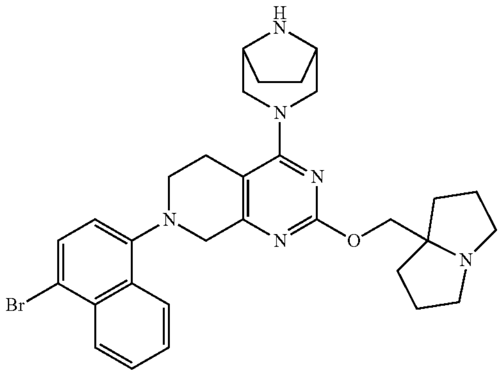 [SMILES: Brc1ccc(N2CCc3c(nc(OCC45CCCN4CCC5)nc3N3CC4CCC(C3)N4)C2)c2ccccc12]

4-((1R,5S)-3,8-diazabicyclo[3.2.1]octan-3-yl)-7-(4-bromonaphthalen-1-yl)-2-((hexahydro-1H-pyrrolizin-7a-yl)methoxy)-5,6,7,8-tetrahydropyrido[3,4-d]pyrimidine

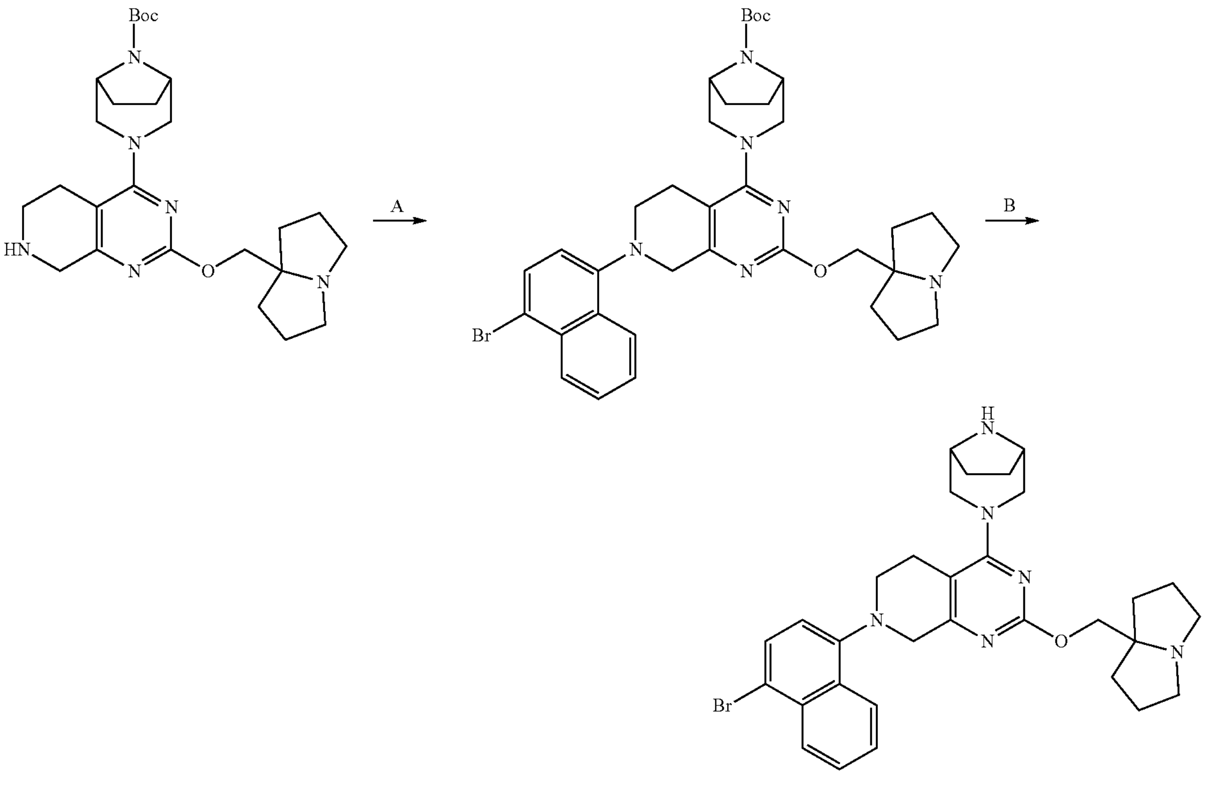

Step A: (1R,5S)-tert-butyl 3-(7-(4-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (200 mg, 413 μmol, 1.0 eq), 1,4-dibromonaphthalene (236 mg, 825 μmol, 2.0 eq) in dioxane (4.00 mL) were added cesium carbonate (403 mg, 1.24 mmol, 3.0 eq) and rac-BINAP-Pd-G3 (40.9 mg, 41.3 μmol, 0.10 eq) under nitrogen, and the reaction was stirred at 95° C. for 6 hours under nitrogen atmosphere. The reaction was filtered and concentrated in vacuum to give a residue. The residue was purified by reversed phase flash [water (FA, 0.1%)/acetonitrile] affording the title compound (91.0 mg, 29% yield). Yellow solid. $^1$H NMR (400 MHz, $CDCl_3$-d) δ=8.27-8.21 (m, 2H), 7.71 (d, J=8.0 Hz, 1H), 7.64-7.53 (m, 2H), 6.98 (d, J=8.0 Hz, 1H), 4.38-4.26 (m, 2H), 4.23 (br s, 2H), 4.05 (s, 2H), 4.03-3.89 (m, 2H), 3.40-3.20 (m, 4H), 3.15-3.07 (m, 2H), 2.95-2.75 (m, 2H), 2.64 (td, J=6.8, 10.0 Hz, 2H), 2.13-2.06 (m, 2H), 1.97-1.91 (m, 2H), 1.89-1.81 (m, 6H), 1.69-1.63 (m, 2H), 1.51 (s, 9H). LCMS [ESI, M+1]: 689, 691.

Step B: 4-((1R,5S)-3,8-diazabicyclo[3.2.1]octan-3-yl)-7-(4-bromonaphthalen-1-yl)-2-((hexahydro-1H-pyrrolizin-7a-yl)methoxy)-5,6,7,8-tetrahydropyrido[3,4-d]pyrimidine. A solution of (1R,5S)-tert-butyl 3-(7-(4-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (50.0 mg, 72.5 μmol, 1.0 eq) in HCl·dioxane (2.00 mL) and acetonitrile (1.00 mL) was stirred at 0° C. for 0.5 hour. The reaction mixture was concentrated in vacuum to give a residue. The residue was purified by prep-HPLC (column: Waters Xbridge 150*25 mm*5 um; mobile phase: [water (10 mM $NH_4HCO_3$)-ACN]; B %: 25%-55%, 10 min), and the desired fractions were lyophilized affording the title compound (21.1 mg, 49% yield, free base). White solid. $^1$H NMR (400 MHz, $CDCl_3$-d) δ=8.27-8.21 (m, 2H), 7.71 (d, J=8.0 Hz, 1H), 7.63-7.52 (m, 2H), 6.98 (d, J=8.4 Hz, 1H), 4.78 (br s, 2H), 4.69-4.45 (m, 1H), 4.21 (br d, J=4.8 Hz, 4H), 4.04-3.91 (m, 2H), 3.64-3.57 (m, 2H), 3.42-3.26 (m, 4H), 3.21 (br d, J=12.8 Hz, 2H), 2.91-2.78 (m, 2H), 2.78-2.70 (m, 2H), 2.23-2.14 (m, 2H), 2.05-1.91 (m, 8H). LCMS [ESI, M+1]: 589, 591.

Example 113

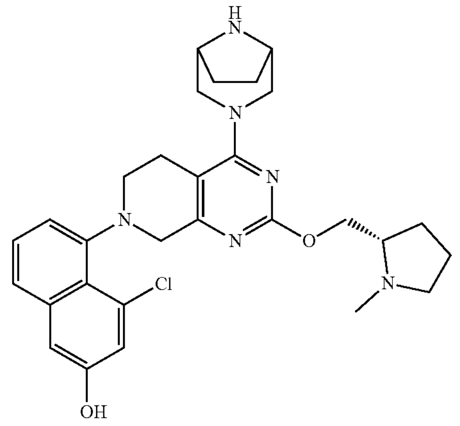 [SMILES: CN1CCC[C@H]1COc1nc2c(c(N3CC4CCC(C3)N4)n1)CCN(c1cccc3cc(O)cc(Cl)c13)C2]

5-(4-((1R,5S)-3,8-diazabicyclo[3.2.1]octan-3-yl)-2-(((S)-1-methylpyrrolidin-2-yl)methoxy)-5,6-dihydropyrido[3,4-d]pyrimidin-7(8H)-yl)-4-chloronaphthalen-2-ol Step A: (1R,5S)-tert-butyl 3-(7-(8-chloro-6-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl 3-(2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (300 mg, 654 μmol, 1.0 eq), 8-bromo-1-chloro-3-(methoxymethoxy)naphthalene (295 mg, 981 μmol, 1.5 eq) in toluene (6.00 mL) were added cesium carbonate (532 mg, 1.64 mmol, 2.5 eq), RuPhos (122 mg, 261 μmol, 0.40 eq) and $Pd_2(dba)_3$ (119 mg, 130 μmol, 0.20 eq) under nitrogen, and the reaction mixture was stirred at 90° C. for 12 hours under nitrogen atmosphere. The mixture was diluted with water (20.0 mL) and extracted with ethyl acetate (2×30.0 mL). The combined organic layers were washed with saturated brine (50.0 mL), and dried over anhydrous $Na_2SO_4$. The mixture was filtered and concentrated under vacuum. Then the residue was purified by column chromatography (SiO2, ethyl acetate/methanol=1/0 to 2/1) affording the title compound (50.0 mg, crude). Brown solid. LCMS [ESI, M+1]: 679.

Step B: 5-(4-((1R,5S)-3,8-diazabicyclo[3.2.1]octan-3-yl)-2-(((S)-1-methylpyrrolidin-2-yl)methoxy)-5,6-dihydropyrido[3,4-d]pyrimidin-7(8H)-yl)-4-chloronaphthalen-2-ol.

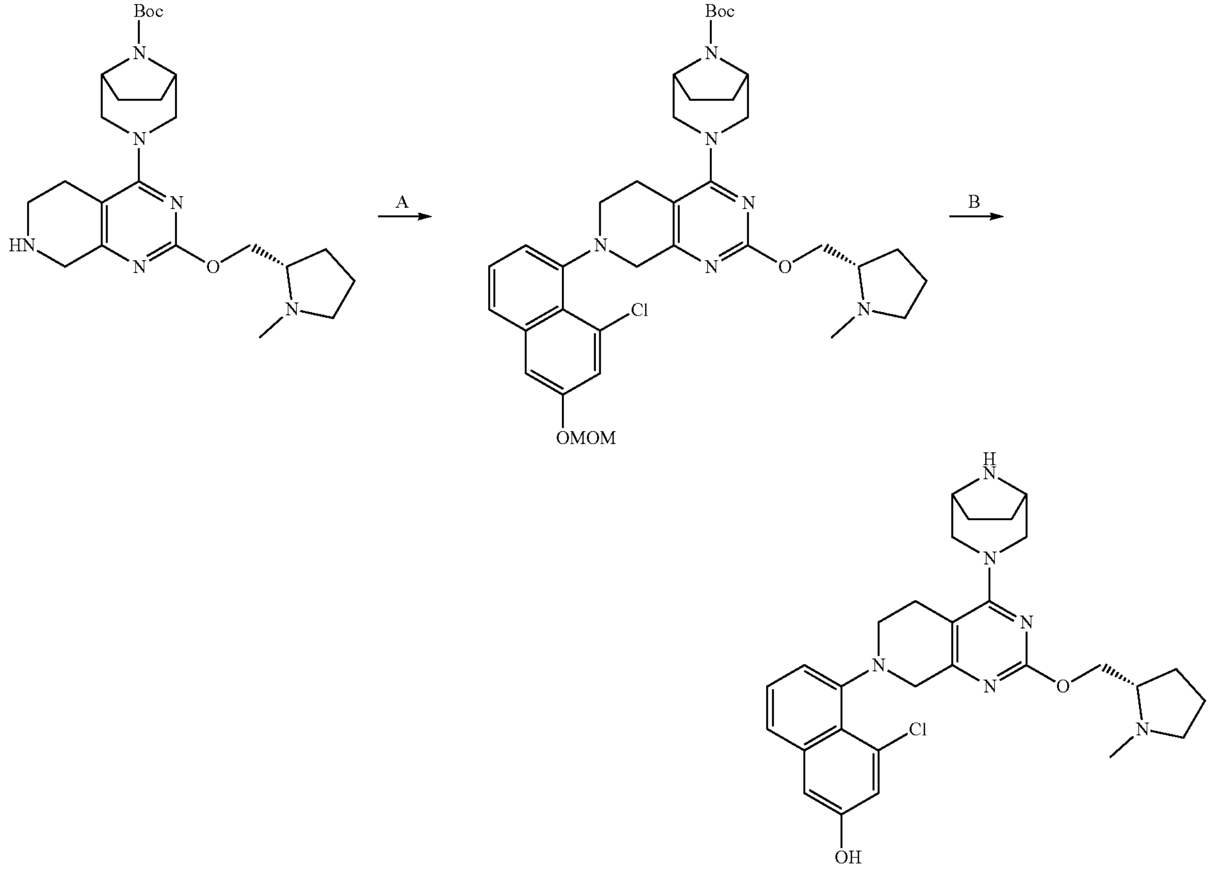

A solution of (1R,5S)-tert-butyl 3-(7-(8-chloro-6-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (50.0 mg, 73.6 μmol, 1.0 eq) in HCl·MeOH (0.50 mL) was stirred at 10° C. for one hour. The reaction mixture was concentrated under vacuum to give a residue. The residue was purified by prep-HPLC (column: Phenomenex luna C18 250*50 mm*10 um; mobile phase: [water (0.075% TFA)-ACN]; B %: 10%-40%, 9 min), and the desired fractions were lyophilized affording the title compound (5.20 mg, 9% yield, $CF_3COOH$ salt). Brown solid; $^1H$ NMR (400 MHz, Acetic-$d_3$) δ=7.50 (d, J=8.4 Hz, 1H), 7.38 (t, J=7.6 Hz, 1H), 7.25 (d, J=2.4 Hz, 1H), 7.18 (d, J=2.4 Hz, 1H), 7.12 (d, J=7.6 Hz, 1H), 4.98-4.76 (m, 3H), 4.52-4.35 (m, 4H), 4.15-3.73 (m, 5H), 3.57 (br d, J=10.0 Hz, 1H), 3.37-3.06 (m, 6H), 2.78-2.67 (m, 1H), 2.51-2.37 (m, 1H), 2.34-2.09 (m, 7H). LCMS [ESI, M+1]: 535. SFC analysis: Column: Chiralpak IC-3 50×4.6 mm I.D., 3 um; Mobile phase: Phase A for $CO_2$, and Phase B for MeOH+CAN (0.05% DEA); Gradient elution: 60% MeOH+CAN (0.05% DEA) in $CO_2$; Flow rate: 3 mL/min; Wavelength: 220 nm; Column Temp: 35C; Back Pressure: 100 Bar.

Example 114

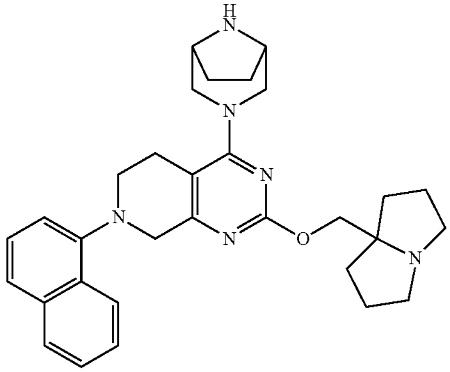 [SMILES: c1ccc2c(N3CCc4c(nc(OCC56CCCN5CCC6)nc4N4CC5CCC(C4)N5)C3)cccc2c1]

4-((1R,5S)-3,8-diazabicyclo[3.2.1]octan-3-yl)-2-((hexahydro-1H-pyrrolizin-7a-yl)methoxy)-7-(naphthalen-1-yl)-5,6,7,8-tetrahydropyrido[3,4-d]pyrimidine

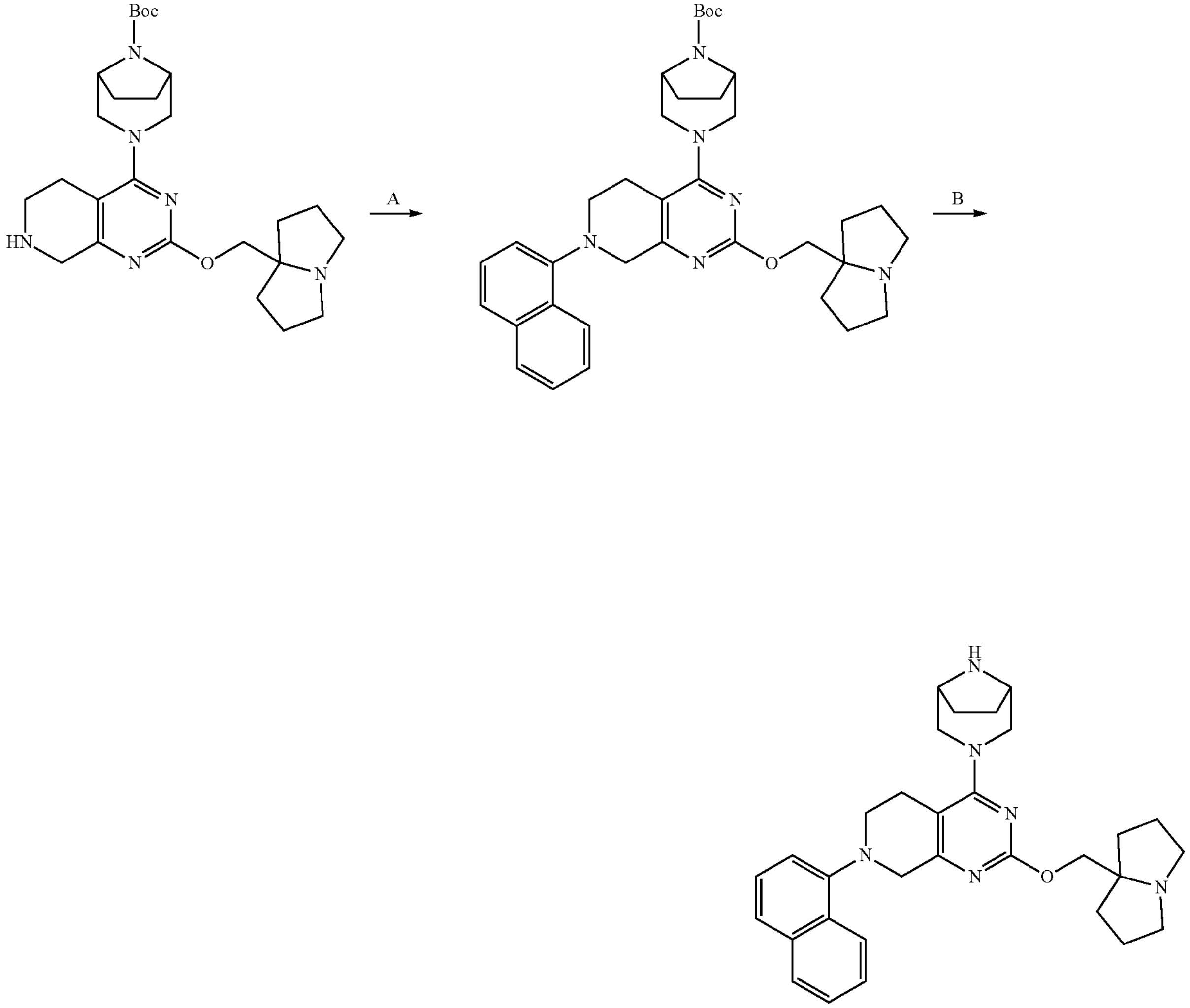

Step A: (1R,5S)-tert-butyl 3-(2-((hexahydro-1H-pyrrolizin-7a-yl)methoxy)-7-(naphthalen-1-yl)-5,6,7,8-tetrahydropyrido[3,4-d]pyrimidin-4-yl)-3,8-diazabicyclo[3.2.1]octane-8-carboxylate. To a solution of (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (200 mg, 413 μmol, 1.0 eq), 1-bromonaphthalene (171 mg, 825 μmol, 2.0 eq) in toluene (4.00 mL) were added cesium carbonate (403 mg, 1.24 mmol, 3.0 eq), $Pd_2(dba)_3$ (37.8 mg, 41.3 μmol, 0.10 eq) and RuPhos (38.5 mg, 82.5 μmol, 0.20 eq) under nitrogen, and the reaction mixture was stirred at 90° C. for 6 hours under nitrogen atmosphere. The mixture was diluted with water (10.0 mL) and extracted with ethyl acetate (2×10.0 mL). The combined organic layers were washed with saturated brine (10.0 mL), and dried over anhydrous $Na_2SO_4$. The mixture was filtered and concentrated under vacuum. Then the residue was purified by reversed phase flash [water (FA, 0.1%)/acetonitrile] affording the title compound (95.0 mg, 37% yield). Yellow solid. LCMS [ESI, M+1]: 611.

Step B: 4-((1R,5S)-3,8-diazabicyclo[3.2.1]octan-3-yl)-2-((hexahydro-1H-pyrrolizin-7a-yl)methoxy)-7-(naphthalen-1-yl)-5,6,7,8-tetrahydropyrido[3,4-d]pyrimidine. A solution of (1R,5S)-tert-butyl 3-(2-((hexahydro-1H-pyrrolizin-7a-yl)methoxy)-7-(naphthalen-1-yl)-5,6,7,8-tetrahydropyrido[3,4-d]pyrimidin-4-yl)-3,8-diazabicyclo[3.2.1]octane-8-carboxylate (105 mg, 172 μmol, 1.0 eq) in HCl·dioxane (2.00 mL) and acetonitrile (1.00 mL) was stirred at 0° C. for 0.5 hour. The reaction was concentrated in vacuum, then the pH value was adjusted to 9 with saturated $Na_2CO_3$ solution and the mixture was washed with methanol (2×8.0 mL). Then the mixture was filtered and concentrated under vacuum to give a residue. The residue was purified by prep-HPLC (column: Waters Xbridge 150*25 mm*5 um; mobile phase: [water (10 mM $NH_4HCO_3$)-ACN]; B %: 25%-55%, 10 min), and the desired fractions were lyophilized affording the title compound (44.1 mg, 50% yield, free base). White solid. $^1H$ NMR (400 MHz, $CDCl_3$-d) δ=8.24-8.18 (m, 1H), 7.87-7.81 (m, 1H), 7.58 (d, J=8.0 Hz, 1H), 7.52-7.45 (m, 2H), 7.42 (t, J=7.6 Hz, 1H), 7.12 (d, J=7.2 Hz, 1H), 4.25 (s, 2H), 4.04 (s, 2H), 4.01-3.89 (m, 2H), 3.57 (br s, 2H), 3.32 (br s, 2H), 3.19 (br d, J=12.0 Hz, 2H), 3.12-3.05 (m, 2H), 2.85 (br s, 2H), 2.62 (td, J=6.8, 10.0 Hz, 2H), 2.13-2.05 (m, 2H), 1.91-1.81 (m, 6H), 1.81-1.76 (m, 2H), 1.69-1.60 (m, 2H). LCMS [ESI, M/2+1, M+1]: 256, 511.

Example 115

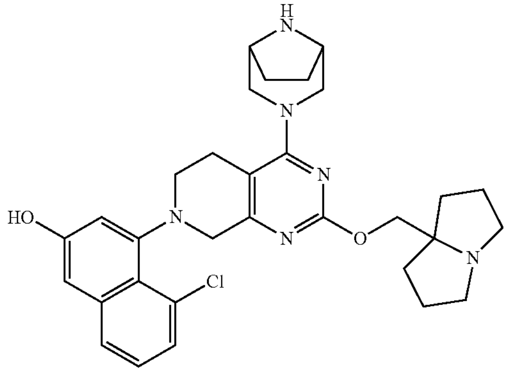 [SMILES: Oc1cc(N2CCc3c(nc(OCC45CCCN4CCC5)nc3N3CC4CCC(C3)N4)C2)c2c(Cl)cccc2c1]

4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-chloronaphthalen-2-ol

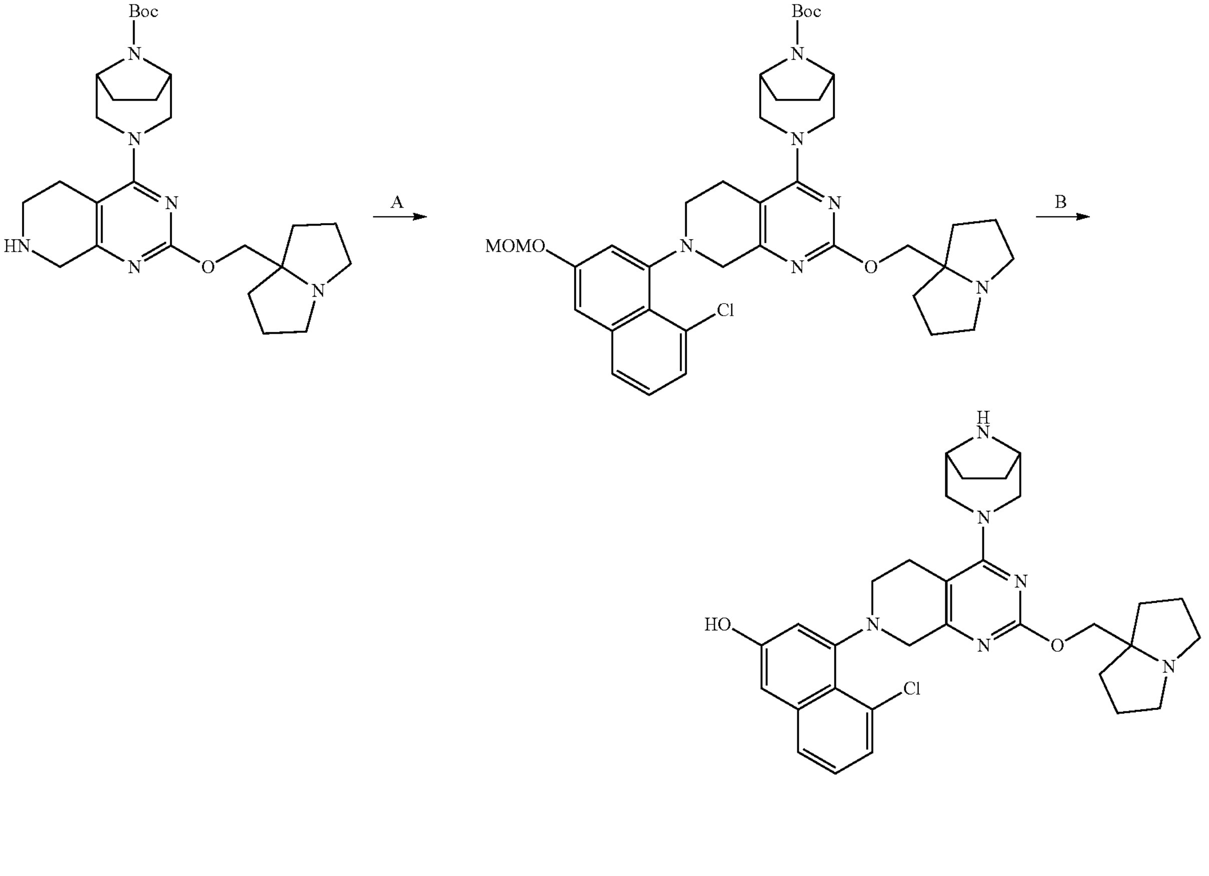

Step A: (1R,5S)-tert-butyl 3-(7-(4-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo [3.2.1]octane-8-carboxylate. To a solution of (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo [3.2.1]octane-8-carboxylate (1.30 g, 2.68 mmol, 1.0 eq), 1-bromo-8-chloro-3-(methoxymethoxy)naphthalene (1.21 g, 4.02 mmol, 1.5 eq) in toluene (25.0 mL) were added cesium carbonate (2.62 g, 8.05 mmol, 3.0 eq), $Pd_2(dba)_3$ (246 mg, 268 μmol, 0.1 eq) and RuPhos (250 mg, 536 μmol, 0.2 eq) under nitrogen, and the reaction mixture was stirred at 100° C. for 5 hours under nitrogen atmosphere. The mixture was filtered, and diluted with ethyl acetate (10.0 mL) and water (15.0 mL). The aqueous phase was extracted with ethyl acetate (10.0 mL), then the combined organic layer was washed with saturated brine (15.0 mL), and dried over $Na_2SO_4$. The mixture was filtered and concentrated under vacuum to give a residue. The residue was purified by reversed phase flash [water (FA, 0.1%)/acetonitrile] affording the title compound (930 mg, 49% yield). Brown solid; $^1H$ NMR (400 MHz, $CDCl_3$-d) δ=7.62 (dd, J=0.8, 8.0 Hz, 1H), 7.36 (dd, J=1.2, 7.6 Hz, 1H), 7.35-7.23 (m, 1H), 7.15 (d, J=2.0 Hz, 1H), 6.92 (d, J=2.4 Hz, 1H), 5.28 (s, 2H), 4.40 (br d, J=17.6 Hz, 1H), 4.35-4.25 (m, 2H), 4.13-4.03 (m, 3H), 3.83 (br d, J=17.6 Hz, 1H), 3.69 (br d, J=12.4 Hz, 1H), 3.52 (s, 3H), 3.43-3.32 (m, 1H), 3.21-3.02 (m, 5H), 2.72-2.63 (m, 2H), 2.16-2.07 (m, 2H), 2.00-1.72 (m, 12H), 1.50 (s, 9H); LCMS [ESI, M+1]: 705.

Step B: 4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-chloronaphthalen-2-ol. A solution of (1R,5S)-tert-butyl 3-(7-(4-bromonaphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo [3.2.1]octane-8-carboxylate (400 mg, 567 μmol, 1.0 eq) in HCl·MeOH (8.00 mL) was stirred at 0° C. for 0.5 hour. The reaction mixture was concentrated in vacuum to give a residue. The residue was purified by prep-HPLC (column: Phenomenex luna C18 150*40 mm*15 um; mobile phase: [water (0.225% FA)-ACN]; B %: 1%-30%, 9 min), and the desired fractions were lyophilized affording the title compound (219 mg, 68% yield, HCOOH salt). Yellow solid. $^1H$ NMR (400 MHz, $CDCl_3$-d) δ=8.52 (s, 2H), 7.57 (dd, J=1.6, 7.6 Hz, 1H), 7.28-7.21 (m, 2H), 6.97-6.87 (m, 2H), 4.48 (s, 2H), 4.41-4.30 (m, 2H), 4.09 (br s, 2H), 3.95 (br d, J=13.6 Hz, 1H), 3.72 (s, 1H), 3.66-3.53 (m, 4H), 3.29-3.20 (m, 3H), 3.20-3.07 (m, 2H), 2.64 (br d, J=14.4 Hz, 1H), 2.31-2.26 (m, 2H), 2.24-1.99 (m, 10H). LCMS [ESI, M/2+1, M+1]: 281, 561.

Example 116

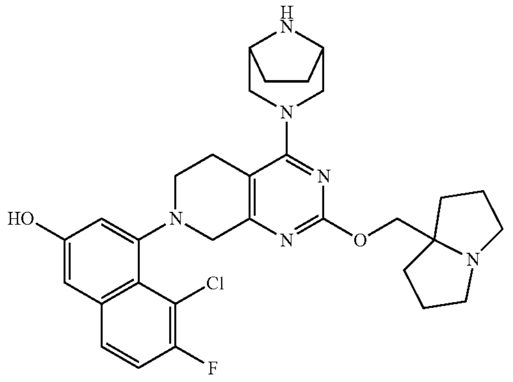 [SMILES: Oc1cc(N2CCc3c(nc(OCC45CCCN4CCC5)nc3N3CC4CCC(C3)N4)C2)c2c(Cl)c(F)ccc2c1]

4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-chloro-6-fluoronaphthalen-2-ol

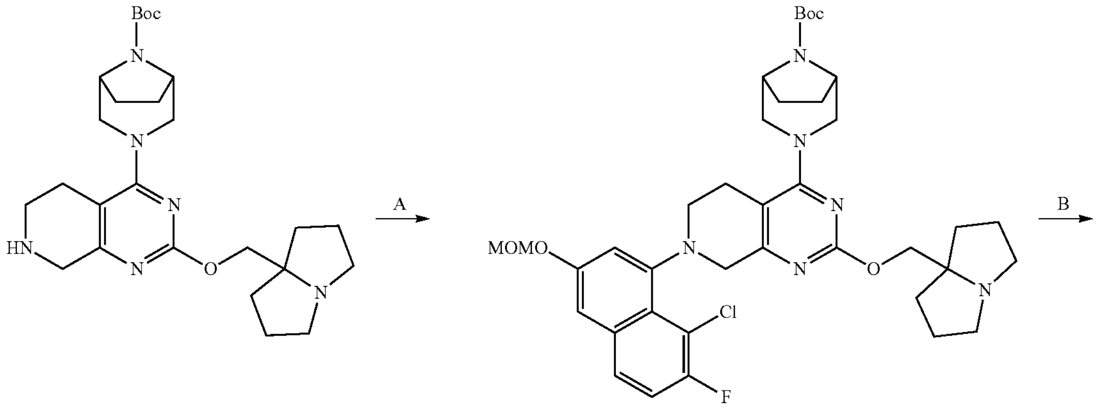

-continued

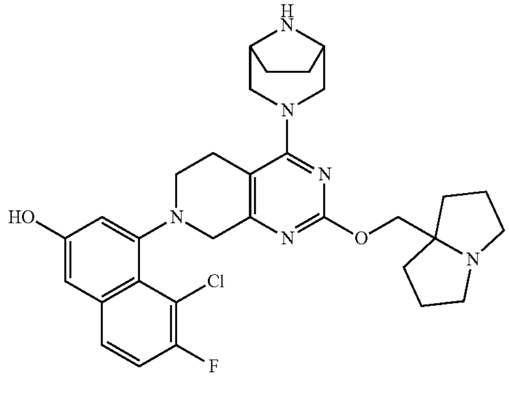

Step A: (1R,5S)-tert-butyl 3-(7-(8-chloro-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (170 mg, 437 μmol, 1.5 eq), 8-chloro-7-fluoro-3-(methoxymethoxy)naphthalen-1-yl trifluoromethanesulfonate (141 mg, 292 μmol, 1.0 eq) in toluene (8.0 mL) were added cesium carbonate (285 mg, 875 μmol, 3.0 eq), $Pd_2(dba)_3$ (26.7 mg, 29.2 μmol, 0.1 eq) and RuPhos (27.2 mg, 58.3 μmol, 0.2 eq) under nitrogen, and the reaction mixture was stirred at 100° C. for 9 hours under nitrogen atmosphere. The mixture was filtered, and diluted with ethyl acetate (60.0 mL) and water (30.0 mL). The organic layer was washed with saturated brine (15.0 mL), and dried over with $Na_2SO_4$. The mixture was filtered and concentrated under vacuum to give a residue. The residue was purified by column chromatography ($Al_2O_3$, Petroleum ether/Ethyl acetate=1/1 to 0/1) and reversed phase flash [water (FA 0.1%)/acetonitrile] affording the title compound (86.6 mg, 41% yield). Yellow solid. LCMS [ESI, M+1]: 723.

Step B: 4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-chloro-6-fluoronaphthalen-2-ol. A solution of (1R,5S)-tert-butyl 3-(7-(8-chloro-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (50.0 mg, 69.1 μmol, 1.0 eq) in HCl·MeOH (4.00 mL) was stirred at 0° C. for one hour. The reaction mixture was concentrated in vacuum to give a residue. The residue was purified by prep-HPLC (column: 3_Phenomenex Luna C18 75*30 mm*3 um; mobile phase: [water(0.225% FA)-ACN]; B %: 6%-26%,8 min), and the desired fractions were lyophilized affording the title compound (14.1 mg, 30% yield, FA salt). Off-white solid. $^1H$ NMR (400 MHz, Methanol-$d_4$) δ=8.52 (br s, 2H), 7.63 (br dd, J=5.6, 8.4 Hz, 1H), 7.28 (br t, J=8.8 Hz, 1H), 6.97 (s, 2H), 4.46 (br s, 2H), 4.41-4.27 (m, 2H), 4.04-3.90 (m, 3H), 3.72 (br d, J=17.6 Hz, 1H), 3.67-3.52 (m, 4H), 3.28-3.11 (m, 5H), 2.74-2.59 (m, 1H), 2.31-1.95 (m, 12H). LCMS [ESI, M+1]: 579.

Example 117

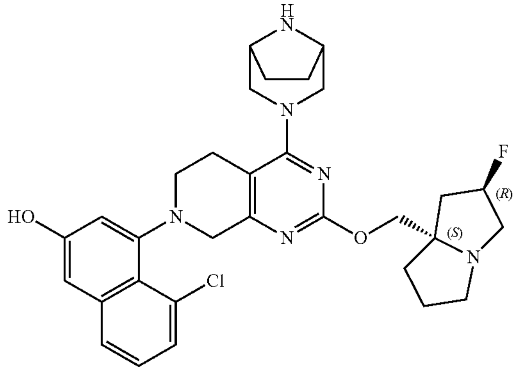

4-(4-((1R,5S)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidin-7(8H)-yl)-5-chloronaphthalen-2-ol

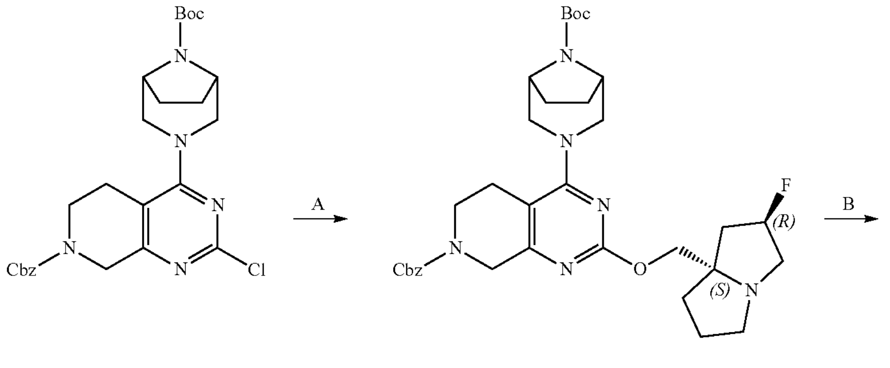

-continued

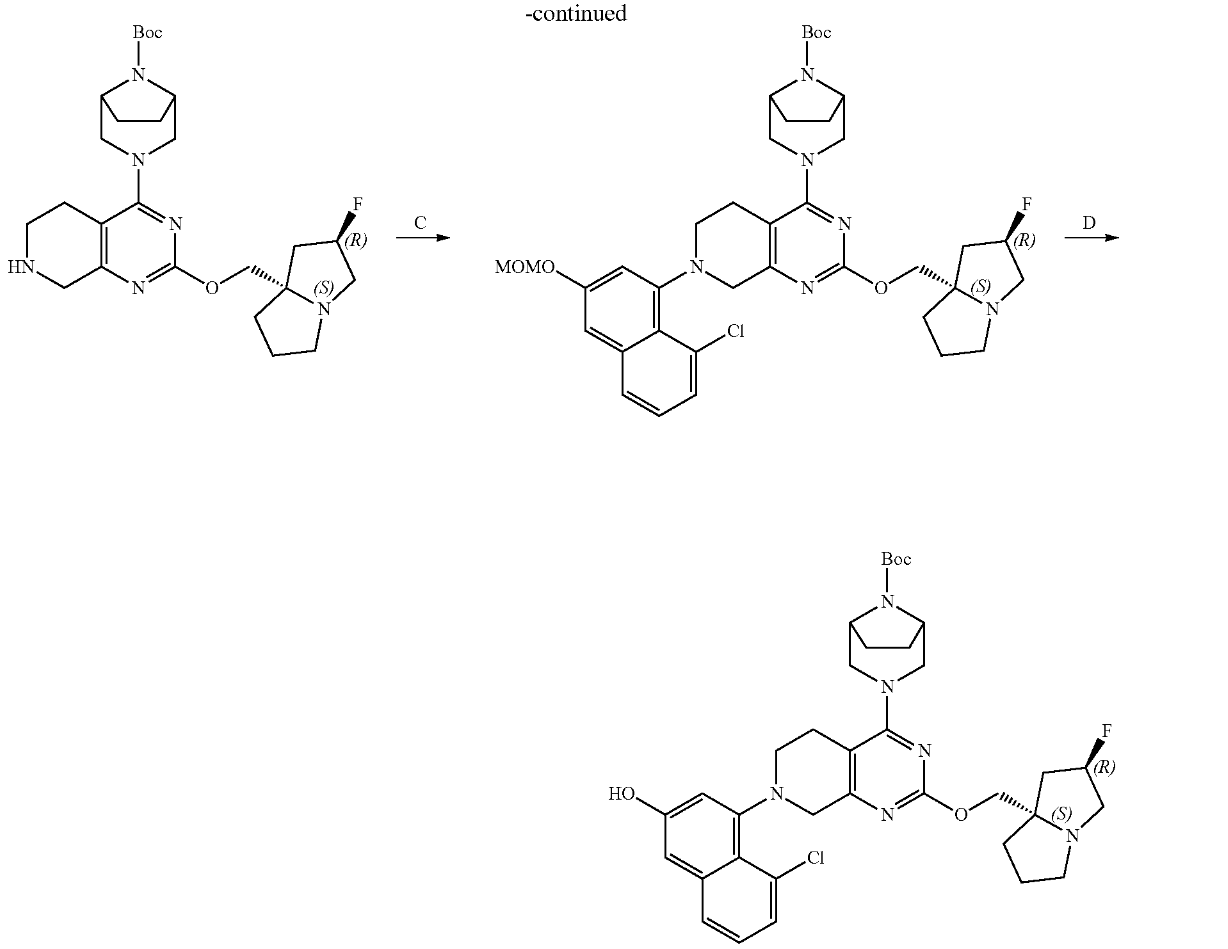

Step A: benzyl 4-((1R,5S)-8-(tert-butoxycarbonyl)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidine-7(8H)-carboxylate. To a solution of benzyl 4-((1R,5S)-8-(tert-butoxycarbonyl)-3,8-diazabicyclo[3.2.1]octan-3-yl)-2-chloro-5,6-dihydropyrido[3,4-d]pyrimidine-7(8H)-carboxylate (800 mg, 1.56 mmol, 1.0 eq) and [(2R,8S)-2-fluoro-1,2,3,5,6,7-hexahydropyrrolizin-8-yl]methanol (322 mg, 2.02 mmol, 1.3 eq) in toluene (20.0 mL) were added rac-BINAP (193 mg, 311 μmol, 0.2 eq), cesium carbonate (1.52 g, 4.67 mmol, 3.0 eq) and $Pd(OAc)_2$ (34.9 mg, 155 μmol, 0.1 eq) under nitrogen atmosphere. The reaction mixture was stirred at 110° C. for 3 hours under nitrogen. The reaction mixture was diluted with water (50.0 mL) and extracted with ethyl acetate (3×50.0 mL). The combined organic layers were washed with brine (50.0 mL), and then dried over with $Na_2SO_4$. The mixture was filtered and concentrated under reduced pressure to give a residue. The residue was purified by reversed phase flash [water (0.1% formic acid)/acetonitrile)] affording the title compound (750 mg, 75% yield). White solid; $^1H$ NMR (400 MHz, $CDCl_3$) δ=7.44-7.30 (m, 5H), 5.38-5.13 (m, 3H), 4.54 (br s, 2H), 4.27 (br s, 2H), 4.10-3.90 (m, 2H), 3.81 (br d, J=11.6 Hz, 2H), 3.62 (br s, 2H), 3.32-2.91 (m, 6H), 2.62 (br s, 2H), 2.34-2.07 (m, 3H), 1.99-1.76 (m, 7H), 1.50 (s, 9H). LCMS [ESI, M+1]: 637.

Step B: (1R,5S)-tert-butyl 3-(2-(((2R,7aS)-2-fluorohexahydro-1H-pyrrolizin-7a-yl) methoxy)-5,6,7,8-tetrahydropyrido[3,4-d]pyrimidin-4-yl)-3,8-diazabicyclo[3.2.1]octane-8-carboxylate. To a solution of benzyl 4-((1R,5S)-8-(tert-butoxycarbonyl)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidine-7(8H)-carboxylate (2.0 g, 3.14 mmol, 1.0 eq) in methanol (20.0 mL) and $NH_3$·MeOH (5 mL, 20% purity) was added palladium on activated carbon (500 mg, 10% purity) under nitrogen, and the reaction mixture was stirred at 30° C. for 1 hour under hydrogen balloon (15 psi). The reaction mixture was filtered, and the filtrate was concentrated in vacuum affording the title compound (1.6 g, crude). White solid; LCMS [ESI, M+1]: 503.

Step C: (1R,5S)-tert-butyl 3-(7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl 3-(2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (800 mg, 1.59 mmol, 1.0 eq), 1-bromo-8-chloro-3-(methoxymethoxy)naphthalene (575 mg, 1.91 mmol, 1.2 eq) in toluene (15.0 mL) were added cesium carbonate (1.30 g, 3.98 mmol, 2.5 eq), $Pd_2(dba)_3$ (291 mg, 318 μmol, 0.2 eq) and RuPhos (297 mg, 636 μmol, 0.4 eq) under nitrogen, and the reaction mixture was stirred at 90° C. for 5 hours under nitrogen atmosphere. The mixture was diluted with water (50.0 mL)

and extracted with ethyl acetate (3×50.0 mL). The combined organic layers were washed with saturated brine (50.0 mL), dried over with $Na_2SO_4$, filtered and concentrated under reduced pressure to give a residue. The residue was purified by column chromatography ($SiO_2$, ethyl acetate/methanol=1/0 to 10/1) affording the title compound (1.0 g, 70% yield). Yellow solid; LCMS [ESI, M+1]: 723.

Step D: 4-(4-((1R,5S)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidin-7(8H)-yl)-5-chloronaphthalen-2-ol. A solution of (1R,5S)-tert-butyl 3-(7-(8-chloro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (1.20 g, 1.66 mmol, 1.0 eq) in HCl·MeOH (25.0 mL) was stirred at 25° C. for 0.5 hour. The reaction mixture was concentrated in vacuum to give a residue. The residue was purified by prep-HPLC (column: Phenomenex luna C18 150*40 mm*15 um; mobile phase: [water (0.225% FA)-ACN]; B %: 5%-35%, 10 min), and the desired fractions were lyophilized affording the title compound (500 mg, 44% yield, HCOOH salt). Yellow solid. $^1$H NMR (400 MHz, methanol-$d_4$) 7.58 (dd, J=1.6, 7.6 Hz, 1H), 7.32-7.20 (m, 2H), 6.94 (d, J=2.4 Hz, 1H), 6.89 (d, J=2.4 Hz, 1H), 5.60-5.35 (m, 1H), 4.48-4.29 (m, 4H), 4.13 (br s, 2H), 3.97 (br d, J=14.0 Hz, 1H), 3.84-3.53 (m, 6H), 3.31-3.07 (m, 4H), 2.71-2.38 (m, 3H), 2.34-1.97 (m, 8H). LCMS [ESI, M+1]: 579.

Example 118

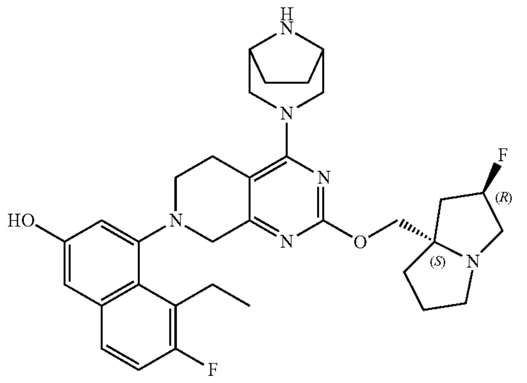

4-(4-((1R,5S)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol

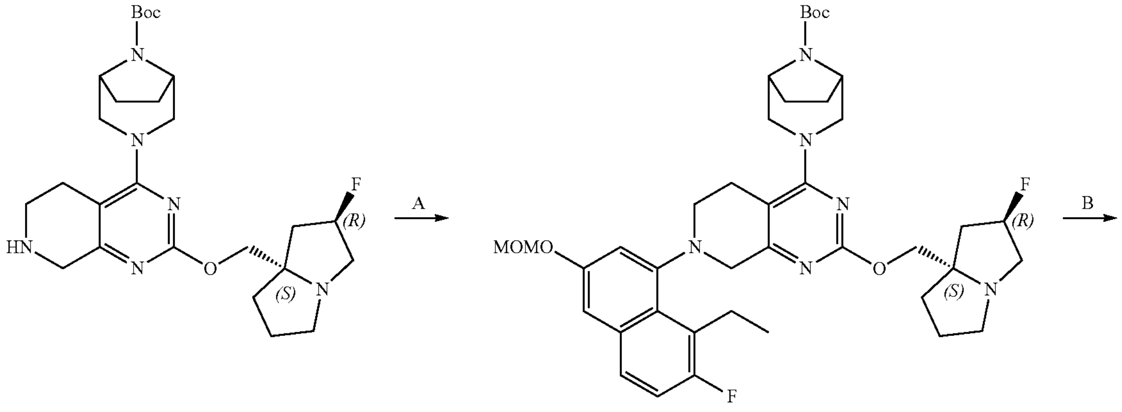

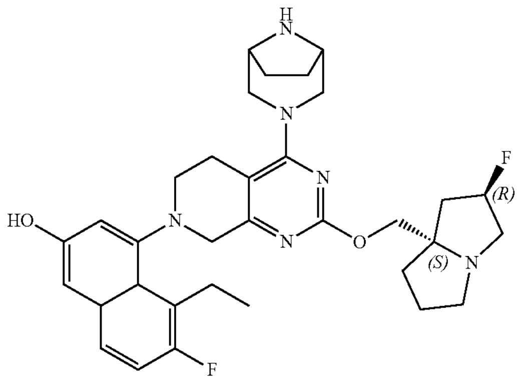

Step A: (1R,5S)-tert-butyl 3-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl 3-(2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (1.35 g, 2.69 mmol, 1.0 eq), 8-ethyl-7-fluoro-3-(methoxymethoxy)naphthalen-1-yl trifluoromethanesulfonate (1.54 g, 4.03 mmol, 1.5 eq) in toluene (20.0 mL) were added cesium carbonate (2.19 g, 6.71 mmol, 2.5 eq) and XantPhos Pd G3 (255 mg, 269 μmol, 0.1 eq) under nitrogen, and the reaction mixture was stirred at 110° C. for 16 hours under nitrogen atmosphere. The mixture was diluted with water (20.0 mL) and extracted with ethyl acetate (3×20.0 mL). The combined organic layers were washed with saturated brine (50.0 mL), dried over with $Na_2SO_4$, then filtered and concentrated under reduced pressure to give a residue. The residue was purified by reversed phase flash [water (FA, 0.1%)/acetonitrile] affording the title compound (1.4 g, 67% yield). Yellow solid; $^1H$ NMR (400 MHz, $CDCl_3$) δ=7.56 (dd, J=6.0, 9.2 Hz, 1H), 7.24-7.14 (m, 2H), 7.02 (s, 1H), 5.34-5.16 (m, 3H), 4.45-4.26 (m, 2H), 4.24-4.16 (m, 1H), 4.10-3.88 (m, 2H), 3.81-3.70 (m, 1H), 3.65 (br d, J=12.4 Hz, 1H), 3.53 (s, 3H), 3.50-3.32 (m, 4H), 3.28-3.23 (m, 1H), 3.22-3.18 (m, 1H), 3.17-3.01 (m, 4H), 3.00-2.90 (m, 1H), 2.57 (br d, J=14.0 Hz, 1H), 2.32-2.10 (m, 3H), 2.03-1.69 (m, 8H), 1.51 (s, 9H), 1.10 (t, J=7.2 Hz, 3H); LCMS [ESI, M+1]: 735.5.

Step B: 4-(4-((1R,5S)-3,8-diazabicyclo[3.2.1]octan-3-yl)-2-(((2R,7aS)-2-fluorohexahydro-1H-pyrrolizin-7a-yl)methoxy)-5,6-dihydropyrido[3,4-d]pyrimidin-7(8H)-yl)-5-ethyl-6-fluoronaphthalen-2-ol. A solution of (1R,5S)-tert-butyl 3-(7-(8-ethyl-7-fluoro-3-(methoxymethoxy)naphthalen-1-yl)-2-(((2R,7aS)-2-fluorohexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (1.70 g, 2.31 mmol, 1.0 eq) in HCl·MeOH (25.0 mL) and acetonitrile (5.0 mL) was stirred at 0° C. for 0.5 hour. The reaction mixture was concentrated in vacuum to give a residue. The residue was purified by prep-HPLC (column: Phenomenex luna C18 150*25 mm*10 um; mobile phase: [water (0.1% TFA)-ACN]; B %: 15%-45%, 10 min). The desired fractions were collected, concentrated, then added saturated $NaHCO_3$ aqueous solution (3.0 mL) and extracted with dichloromethane (3×5.0 mL). The organic layer was washed with saturated brine (15.0 mL). dried over $Na_2SO_4$, then filtered and concentrated affording the title compound (121 mg, 11% yield). Yellow solid; $^1H$ NMR (400 MHz, $CDCl_3$) δ=7.42 (dd, J=5.6, 8.8 Hz, 1H), 7.12 (td, J=2.0, 8.4 Hz, 1H), 6.94-6.89 (m, 1H), 6.88-6.83 (m, 1H), 5.35-5.10 (m, 1H), 4.22-3.93 (m, 4H), 3.80-3.61 (m, 2H), 3.54 (br d, J=13.6 Hz, 2H), 3.41-3.17 (m, 6H), 3.16-2.87 (m, 5H), 2.56-2.43 (m, 1H), 2.29-2.20 (m, 1H), 2.19-2.06 (m, 2H), 2.00-1.77 (m, 7H), 1.09 (t, J=7.2 Hz, 3H); LCMS [ESI, M+1]: 591.4

Example 119

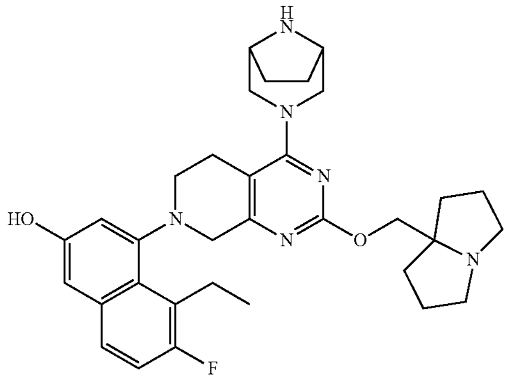 [SMILES: CCc1c(F)ccc2cc(O)cc(N3CCc4c(nc(OCC56CCCN5CCC6)nc4N4CC5CCC(C4)N5)C3)c12]

4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-ethyl-6-fluoronaphthalen-2-ol

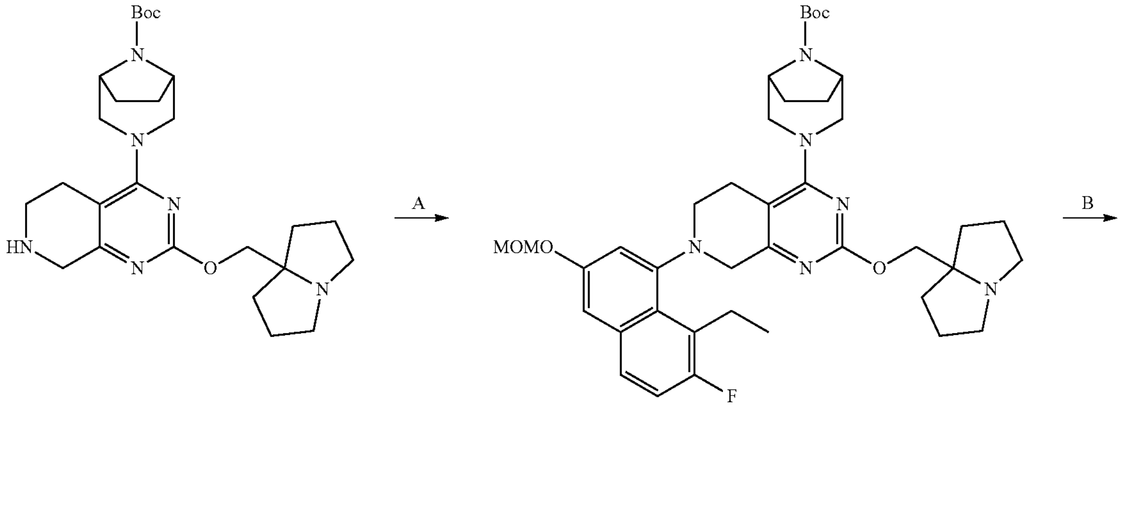

-continued

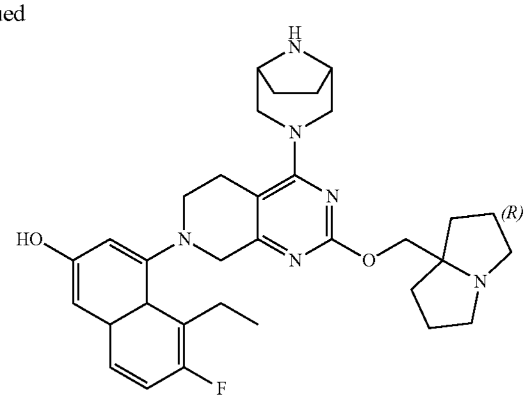

Step A: (1R,5S)-tert-butyl 3-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate. To a solution of (1R,5S)-tert-butyl 3-(2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (600 mg, 1.24 mmol, 1.0 eq), 8-ethyl-7-fluoro-3-(methoxymethoxy)naphthalen-1-yl trifluoromethanesulfonate (710 mg, 1.86 mmol, 1.5 eq) in toluene (15.0 mL) were added cesium carbonate (1.21 g, 3.71 mmol, 3.0 eq), 4 Å molecular sieve (200 mg), XantPhos (143 mg, 247 μmol, 0.2 eq) and XantPhos Pd G3 (176 mg, 186 μmol, 0.15 eq) under nitrogen, and the reaction mixture was stirred at 110° C. for 12 hours under nitrogen atmosphere. The mixture was filtered, and diluted with ethyl acetate (40.0 mL) and water (15.0 mL). The organic layer was washed with saturated brine (15.0 mL), and dried over $Na_2SO_4$. The mixture was filtered and concentrated under vacuum to give a residue. The residue was purified by reversed phase flash (FA 0.1%)/acetonitrile] affording the title compound (450 mg, 47% yield). Yellow solid; $^1H$ NMR (400 MHz, CDCl3) δ=7.56 (dd, J=5.2 Hz, 8.8 Hz, 1H), 7.23-7.15 (m, 2H), 7.02 (s, 1H), 5.28 (s, 2H), 4.40-4.12 (m, 4H) 4.10-3.95 (m, 2H), 3.81-3.71 (m, 1H), 3.70-3.62 (m, 1H), 3.54 (s, 3H), 3.50-3.30 (m, 4H), 3.15-3.08 (m, 5H), 2.66-2.52 (m, 3H), 2.12-2.05 (m, 2H), 2.01-1.91 (m, 3H), 1.90-1.75 (m, 5H), 1.69-1.56 (m, 2H), 1.52 (s, 9H), 1.12 (t, J=7.2 Hz, 3H). LCMS [ESI, M+1]: 717.5.

Step B: 4-(4-((1R,5S)-3,8-diazabicyclo[3.2.1]octan-3-yl)-2-((hexahydro-1H-pyrrolizin-7a-yl)methoxy)-5,6-dihydropyrido[3,4-d]pyrimidin-7(8H)-yl)-5-ethyl-6-fluoronaphthalen-2-ol. A solution of (1R,5S)-tert-butyl 3-(7-(8-ethyl-7-fluoro-3-(methoxymethoxy)naphthalen-1-yl)-2-((hexahydro-1H-pyrrolizin-7a-yl)methoxy)-5,6,7,8-tetrahydropyrido[3,4-d]pyrimidin-4-yl)-3,8-diazabicyclo[3.2.1]octane-8-carboxylate (200 mg, 279 μmol, 1.0 eq) in DCM (2.00 mL) was added TFA (2.00 mL, 27.0 mmol, 96.8 eq) in one portion at 15° C. under $N_2$. The reaction mixture was stirred at 15° C. for 0.5 hour. The reaction mixture was adjusted with saturated $NaHCO_3$ solution to pH=9 at 0° C., extracted with ethyl acetate (2×2.0 mL), and then dried over anhydrous sodium sulfate. The mixture was filtered and concentrated to give a residue. The residue was purified by prep-HPLC (column C18 150*25*10 um; mobile phase: [water(0.225% FA)-ACN]; B %: 12%-42%,8.5 min), and the desired fractions were lyophilized affording the title compound (28.4 mg, 15% yield, HCOOH salt). Yellow solid; $^1H$ NMR (400 MHz, $CDCl_3$) δ=7.52 (dd, J=6.00 Hz, 9.2 Hz, 1H), 7.15 (t, J=9.6 Hz, 1H), 6.95 (dd, J=2.8 Hz, 7.6 Hz, 2H), 4.47 (s, 2H), 4.39 (d, J=14.0 Hz, 1H), 4.16-4.05 (m, 3H), 3.95 (d, J=10.6 Hz, 1H), 3.75-3.71 (m, 1H), 3.67-3.50 (m, 4H), 3.43-3.34 (m, 2H), 3.28-3.15 (m, 4H), 2.77-2.66 (m, 1H), 2.33-1.95 (m, 13H), 1.10 (t, J=7.2 Hz, 3H). LCMS [ESI, M+1]: 573.3.

Example 120

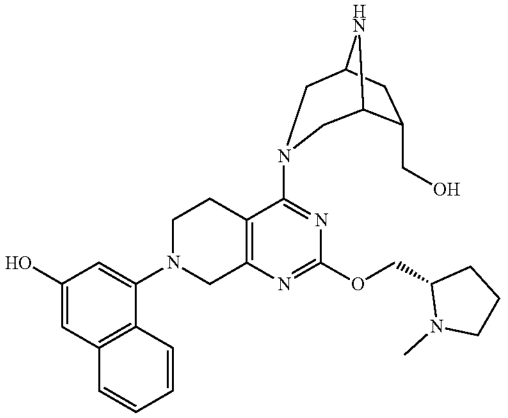 [SMILES: CN1CCC[C@H]1COc1nc2c(c(N3CC4CC(CO)C(C3)N4)n1)CCN(c1cc(O)cc3ccccc13)C2]

4-(4-((1S,5R,6S)-6-(hydroxymethyl)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol

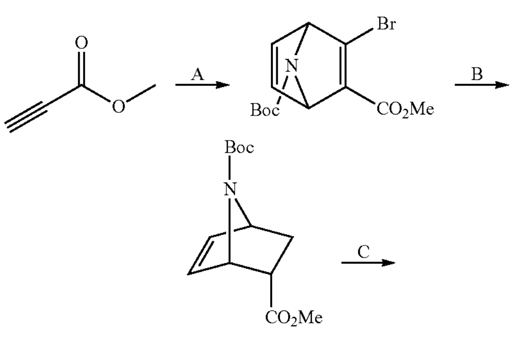

-continued

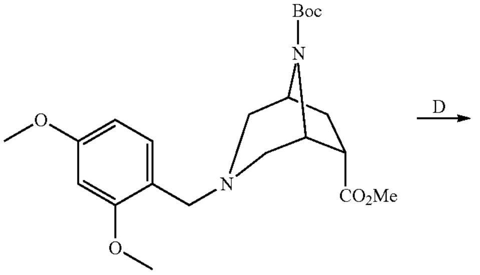

-continued

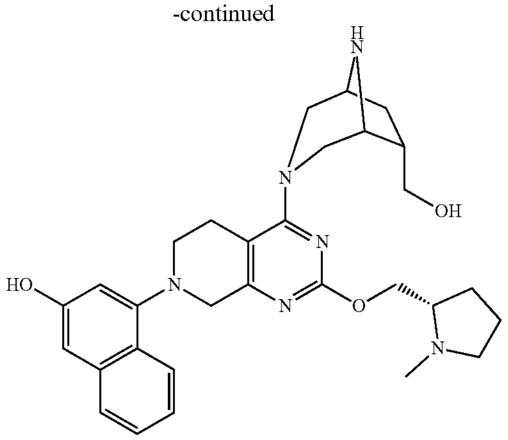

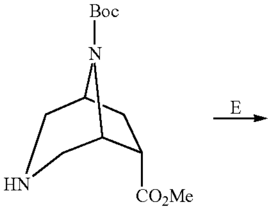

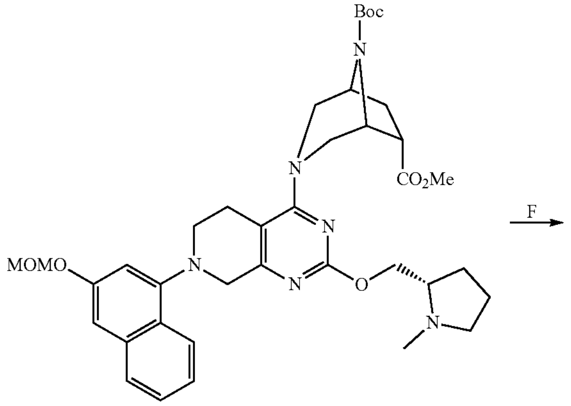

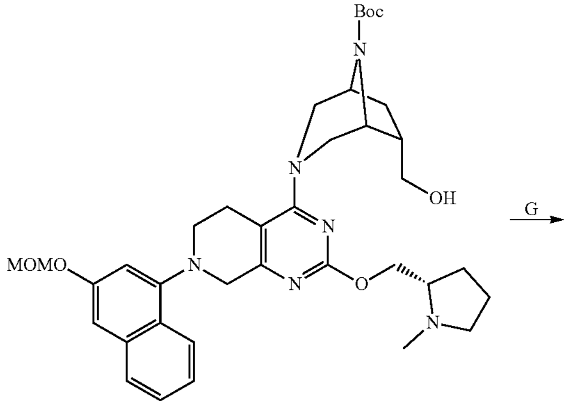

Step A. 7-(tert-butyl) 2-methyl 3-bromo-7-azabicyclo[2.2.1]hepta-2,5-diene-2,7-dicarboxylate. Silver nitrate (0.96 g, 5.7 mmol) and NBS (24 g, 140 mmol) were added to a solution of methyl propiolate (10 ml, 113 mmol) in acetone (120 ml), and the mixture was stirred at ambient temperature for 15 h. The reaction mixture was poured into water (200 mL) and extracted with dichloromethane (3×100 mL). The combined organic layers were washed with a saturated aqueous sodium bicarbonate solution (2×50 mL) and brine (50 mL), dried with sodium sulfate and concentrated under reduced pressure. To this crude material, tert-butyl 1H-pyrrole-1-carboxylate (19 g, 110 mmol) was added, and the mixture was stirred at 90° C. for 30 h. The mixture was cooled to ambient temperature, and the excess tert-butyl pyrrole-1-carboxylate was removed under reduced pressure (0.5 Torr, >90° C.). Column chromatography of the residue eluting with 1→7% ethyl acetate/n-hexane gave the title compound (11.8 g, 47%). LCMS (MM-ES+APCI, Pos): m/z 230.1, 232.1 $(M-Boc)^+$.

Step B. 7-(tert-butyl) 2-methyl (1S,2S,4S)-7-azabicyclo[2.2.1]hept-5-ene-2,7-dicarboxylate. To a solution of 7-(tert-butyl) 2-methyl 3-bromo-7-azabicyclo[2.2.1]hepta-2,5-diene-2,7-dicarboxylate (3.8 g, 11 mmol) in DMSO (29 ml, 11 mmol) and water (5.7 ml, 11 mmol) at −40° C. was added $NaBH_4$ (0.87 g, 23 mmol) and the mixture was stirred at −5° C. for 1 h. The reaction mixture was partitioned between EtOAc/brine and the aqueous layer was extracted 1× with EtOAc. The combined org layers were washed with brine (2×). The org layer was dried and concentrated. The residue was purified by column chromatography eluting with 0-75% EtoAc/Hex (no chromophore) TLC showed two bands, the less polar band was collected to give 7-(tert-butyl) 2-methyl (1S,2R,4S)-7-azabicyclo[2.2.1]hept-5-ene-2,7-dicarboxylate (2.2 g, 75%): $^1H$ NMR ($CDCl_3$, 400 MHz): δ 6.36-6.45 (m, 1H), 6.17-6.22 (m, 1H), 4.90 (br. s, 1H), 4.68 (br. s, 1H), 3.32 (s, 3H), 3.13-3.28 (m, 1H), 2.14-2.20 (m, 1H), 1.51-1.57 (m, 1H), 1.40 (s, 9H).

Step C. 8-(tert-butyl) 6-methyl (1S,5R,6S)-3-(2,4-dimethoxybenzyl)-3,8-diazabicyclo[3.2.1]octane-6,8-dicarboxylate. A solution of 7-(tert-butyl) 2-methyl (1S,2S,4S)-7-azabicyclo[2.2.1]hept-5-ene-2,7-dicarboxylate (0.78 g, 3.1 mmol) in DCM (15 ml) at −78° C. was sparged ozone gas. The mixture was stirred at −78° C. for 1 h. To this mixture was then added dimethyl sulfide (0.69 L, 9.2 mmol). The mixture was sparged with nitrogen and warmed to ambient temperature. To the mixture was added 2,4-dimethoxybenzyl amine (58 μl, 0.39 mmol) portion wise (8 portions) and $NaBH(OAc)_3$ (1.6 g, 7.7 mmol) in DCM (62 ml, 0.05 M).

The reaction mixture was stirred at RT overnight. The reaction mixture was purified directly by column chromatography eluting with 0→100% EtOAc/Hex collecting all fractions (product stains with KMnO4) to give 8-(tert-butyl) 6-methyl (1S,5R,6S)-3-(2,4-dimethoxybenzyl)-3,8-diazabicyclo[3.2.1]octane-6,8-dicarboxylate (260 mg, 20%) LCMS (MM-ES+APCI, Pos): m/z 421.4 $(M+H)^+$.

Step D. 8-(tert-butyl) 6-methyl (1S,5R,6S)-3,8-diazabicyclo[3.2.1]octane-6,8-dicarboxylate. A mixture of 8-(tert-butyl) 6-methyl (1S,5R,6S)-3-(2,4-dimethoxybenzyl)-3,8-diazabicyclo[3.2.1]octane-6,8-dicarboxylate (200 mg, 0.48 mmol) and palladium hydroxide (33 mg, 0.02 mmol) in MeOH (2.3 ml) was stirred under a balloon atmosphere of hydrogen for 2 h. The mixture was filtered and the filtrate was concentrated to give 8-(tert-butyl) 6-methyl (1S,5R,6S)-3,8-diazabicyclo[3.2.1]octane-6,8-dicarboxylate (129 mg, 100%): LCMS (MM-ES+APCI, Pos): m/z 271.3 $(M+H)^+$.

Step E. 8-(tert-butyl) 6-methyl (1S,5R,6S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-6,8-dicarboxylate. Made according to Example 4, step G substituting 8-(tert-butyl) 6-methyl (1S,5R,6S)-3,8-diazabicyclo[3.2.1]octane-6,8-dicarboxylate for tert-butyl 6-hydroxy-3,8-diazabicyclo[3.2.1]octane-8-carboxylate to give the desired product (130 mg, 44%). LCMS (MM-ES+APCI, Pos): m/z 703.4 $(M+H)^+$.

Step F. tert-butyl (1S,5R,6S)-6-(hydroxymethyl)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate. A solution of $LiBH_4$ (0.21 mL, 0.43 mmol) was added to 8-(tert-butyl) 6-methyl (1S,5R,6S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-6,8-dicarboxylate (100 mg, 0.142 mmol) in THE (0.8 mL). The mixture was stirred at RT for 5 h. The mixture was heated to 55° C. for 1 h and cooled. 10 equivalents of additional LiBH4 were added and the reaction was heated to 55° C. for 24 hrs. The reaction was poured into water and the aqueous layer extracted with ethyl acetate. The organics were concentrated in vacuo and the residue purified by column chromatography eluting with 0→10% MeOH/DCM to give tert-butyl (1S,5R,6S)-6-(hydroxymethyl)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate (12 mg, 13%). LCMS (MM-ES+APCI, Pos): m/z 675.4 $(M+H)^+$.

Step G. 4-(4-((1S,5R,6S)-6-(hydroxymethyl)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol. Made according to example 1, Step E substituting tert-butyl (1S,5R,6S)-6-(hydroxymethyl)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate in place of tert-butyl (1R,5S)-3-(7-(3-(methoxymethoxy)naphthalen-1-yl)-2-(((S)-1-methylpyrrolidin-2-yl)methoxy)-5,6,7,8-tetrahydropyrido[3,4-d]pyrimidin-4-yl)-3,8-diazabicyclo[3.2.1]octane-8-carboxylate to give 4-(4-((1S,5R,6S)-6-(hydroxymethyl)-3,8-diazabicyclo[3.2.1]octan-3-yl)-2-(((S)-1-methylpyrrolidin-2-yl)methoxy)-5,8-dihydropyrido[3,4-d]pyrimidin-7(6H)-yl)naphthalen-2-ol (3 mg, 47%). LCMS (MM-ES+APCI, Pos): m/z 531.3 $(M+H)^+$.

Example 121 and 122

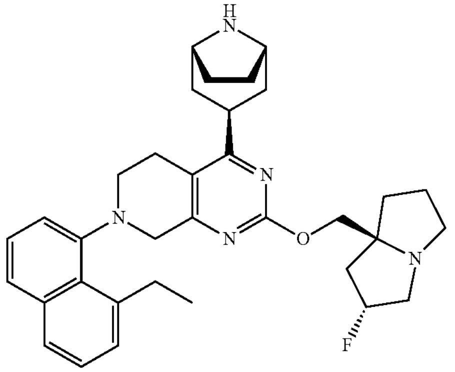

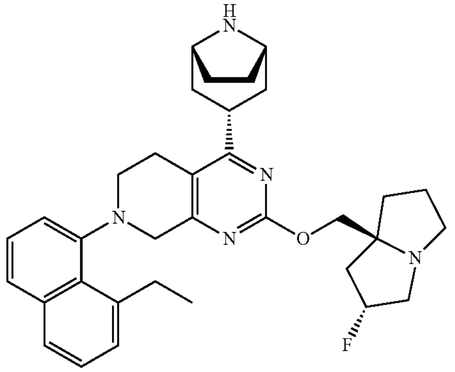

4-((1R,3r,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine and 4-((1R,3s,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine

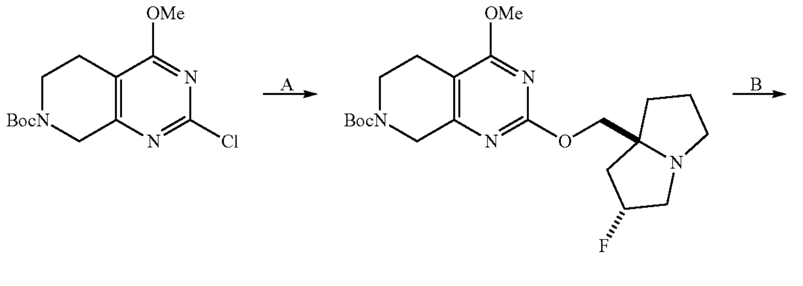

-continued

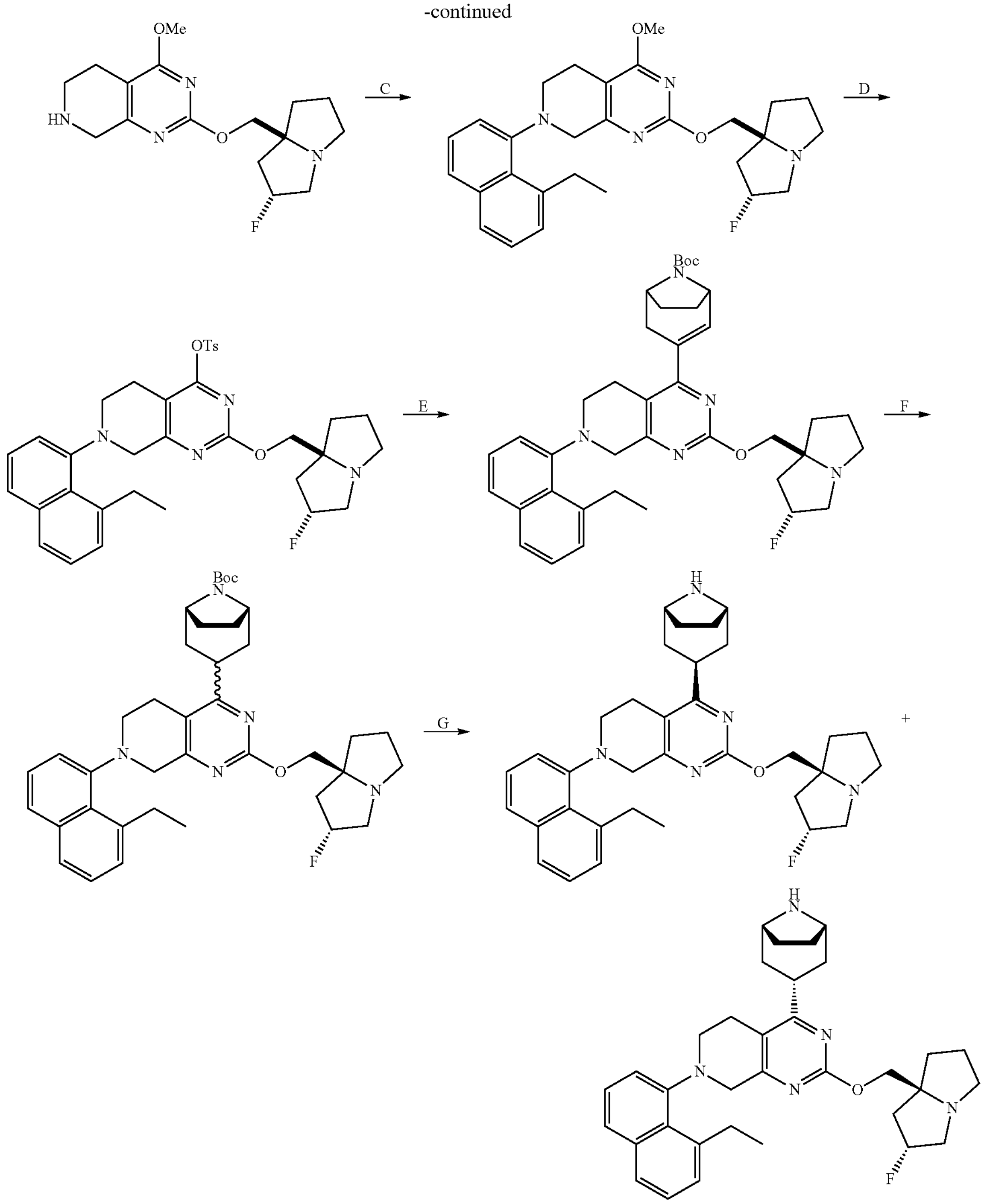

Step A. tert-butyl 2-(((2R,7aS)-2-fluorotetrahydro-1H-pyrrolizin-7a(5H)-yl)methoxy)-4-methoxy-5,8-dihydro-pyrido[3,4-d]pyrimidine-7(6H)-carboxylate. To a 100 ml flask equipped with a stir bar were sequentially added tert-butyl 2-chloro-4-methoxy-5,8-dihydropyrido[3,4-d]pyrimidine-7(6H)-carboxylate (4.5 g, 15 mmol), ((2R,7aS)-2-fluorotetrahydro-1H-pyrrolizin-7a(5H)-yl)methanol (3.6 g, 23 mmol), toluene (75 ml), 2,2'-bis(diphenylphosphanyl)-1,1'-binaphthalene (1.3 g, 2.1 mmol) and $Cs_2CO_3$ (9.8 g, 30. mmol). The mixture was purged with argon and $Pd(OAc)_2$ (0.23 g, 1.1 mmol) was added. The flask was closed with a septum and heated at 100° C. for 8.5 hours. The mixture was cooled to rt, diluted with EtOAc and filtered through a short pad of Celite. The filtrate was concentrated to dryness and the residue was purified by flash chromatography eluting with MeOH/DCM (0-10%) to give the title compound (2.9 g, 46%) as a gummy brown oil. LCMS (MM-ES+APCI, Pos): m/z 423.3 (M+H).

Step B. 2-(((2R,7aS)-2-fluorotetrahydro-1H-pyrrolizin-7a(5H)-yl)methoxy)-4-methoxy-5,6,7,8-tetrahydropyrido[3,4-d]pyrimidine. To a solution of tert-butyl 2-(((2R,7aS)-2-fluorotetrahydro-1H-pyrrolizin-7a(5H)-yl)methoxy)-4- methoxy-5,8-dihydropyrido[3,4-d]pyrimidine-7(6H)-carboxylate (2.8 g, 6.6 mmol) in DCM (33 ml) at rt was added TFA (13 ml). The mixture was stirred at rt for 20 min, concentrated to dryness and basified with $NaHCO_3$ (Sat.). The mixture was extracted with DCM/IPA (6:1). The extract was dried over $Na_2SO_4$ and concentrated to give the crude title compound (1.9 g, 92%) as a light brown oil. LCMS (MM-ES+APCI, Pos): m/z 323.1 (M+H).

Step C. 7-(8-ethylnaphthalen-1-yl)-2-(((2R,7aS)-2-fluorotetrahydro-1H-pyrrolizin-7a(5H)-yl)methoxy)-4-methoxy-5,6,7,8-tetrahydropyrido[3,4-d]pyrimidine. To a flask with a stir bar were charged 2-(((2R,7aS)-2-fluorotetrahydro-1H-pyrrolizin-7a(5H)-yl)methoxy)-4-methoxy-5,6,7,8-tetrahydropyrido[3,4-d]pyrimidine (0.97 g, 3.0 mmol), $Cs_2CO_3$ (2.0 g, 6.0 mmol), 1-bromo-8-ethylnaphthalene (1.2 g, 5.1 mmol) and 1,4-dioxane (30 ml). The mixture was sparged with $N_2$ for 1 min, followed by addition of $Pd_2dba_3$ (0.28 g, 0.30 mmol) and Xantphos (0.35 g, 0.60 mmol). The mixture was stirred at 95° C. for 15 h, cooled to rt, diluted with EtOAc and filtered. The filtrate was concentrated, and the residue was purified by flash chromatography eluting with MeOH/DCM (0-10%) to give the title compound (0.63 g, 44%) as a brown solid. LCMS (MM-ES+APCI, Pos): m/z 477.3 (M+H).

Step D. 7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate. To a flask with a stir bar were sequentially charged with 7-(8-ethylnaphthalen-1-yl)-2-(((2R,7aS)-2-fluorotetrahydro-1H-pyrrolizin-7a(5H)-yl)methoxy)-4-methoxy-5,6,7,8-tetrahydropyrido[3,4-d]pyrimidine (0.63 g, 1.3 mmol), NaSMe (0.19 g, 2.6 mmol) and DMA (6.6 ml). The mixture was stirred at 80° C. for 4 h under $N_2$. Additional NaSMe (0.19 g, 2.6 mmol) was added and the reaction was stirred at 80° C. for 3 h. The solution was cooled to rt, diluted with water (40 ml) and extracted with EtOAc (20 ml×5). The combined extract was washed with brine, dried over $Na_2SO_4$ and concentrated in vacuo. To the residue was added DCM (13 ml), triethylamine (0.27 ml, 1.9 mmol), DMAP (16 mg, 0.13 mmol), and 4-methylbenzenesulfonyl chloride (0.30 g, 1.6 mmol). The mixture was stirred at rt for 16 h, concentrated and the residue was purified by flash chromatography eluting with EtOAc/hexanes (0-100%) to give the title compound (0.59 g, 73%) as a light brown solid. LCMS (MM-ES+APCI, Pos): m/z 617.3 (M+H).

Step E. tert-butyl 3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]oct-2-ene-8-carboxylate. To a flask with a stir bar were charged 7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl 4-methylbenzenesulfonate (67 mg, 0.11 mmol), tert-butyl 3-(4,4,5,5-tetramethyl-1,3,2-dioxaborolan-2-yl)-8-azabicyclo[3.2.1]oct-2-ene-8-carboxylate (73 mg, 0.22 mmol), $Pd(PPh_3)_4$(19 mg, 0.016 mmol), $K_2CO_3$ (2.0 M, 0.16 ml, 0.32 mmol) and 1,4-dioxane (2.2 ml) under $N_2$. The flask was degassed and heated at 80° C. under $N_2$ for 2 h. The mixture was cooled to rt, and directly purified by flash chromatography eluting with EtOAc/hexanes (0-100%) to give the title compound (70 mg, 99%) as a white solid. LCMS (MM-ES+APCI, Pos): m/z 654.4 (M+H).

Step F. tert-butyl (1R,5S)-3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]octane-8-carboxylate. To a flask with a stir bar were added tert-butyl 3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]oct-2-ene-8-carboxylate (14 mg, 0.021 mmol), $Pd(OH)_2$ (20% on carbon, 4.5 mg, 0.0064 mmol) and methanol (2.1 ml). The flask was degassed and the mixture was stirred under a balloon of $H_2$ at rt for 16 h. The mixture was diluted with EtOAc and Celite added. The mixture was filtered, and the filter cake was further washed with EtOAc. The combined filtrate was concentrated to give the crude title compound (12 mg, 85%) as a mixture of isomers. LCMS (MM-ES+APCI, Pos): m/z 656.4 (M+H).

Step G. 4-((1R,3r,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine and 4-((1R,3s,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine. To a solution of tert-butyl (1R,5S)-3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]octane-8-carboxylate (12 mg, 0.018 mmol) in DCM (1.0 ml) was added TFA (0.50 ml). The solution was stirred at rt for 0.5 h, and concentrated to dryness. The residue was purified by preparative C18 HPLC (Gilson, 0-95% $CH_3CN$/$H_2O$ with 0.1% TFA). Fractions corresponding to the more polar peak were combined and lyophilized to give 4-((1R,3r,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine (2.8 mg, 20%, Example 121) as the TFA salt. LCMS (MM-ES+APCI, Pos): m/z 556.3 (M+H). Fractions corresponding to the less polar peak were combined and lyophilized to give 4-((1R,3s,5S)-8-azabicyclo[3.2.1]octan-3-yl)-7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidine (5.0 mg, 35%, Example 122) as the TFA salt. LCMS (MM-ES+APCI, Pos): m/z 556.4 (M+H).

Example 123

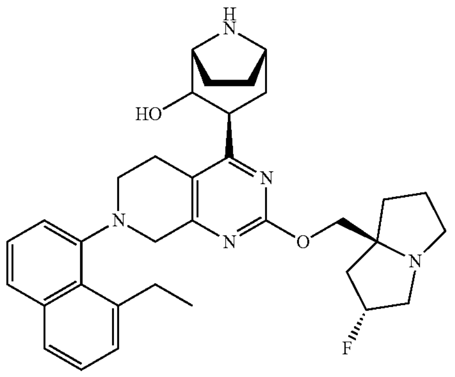

(1S,3R,5R)-3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]octan-2-ol

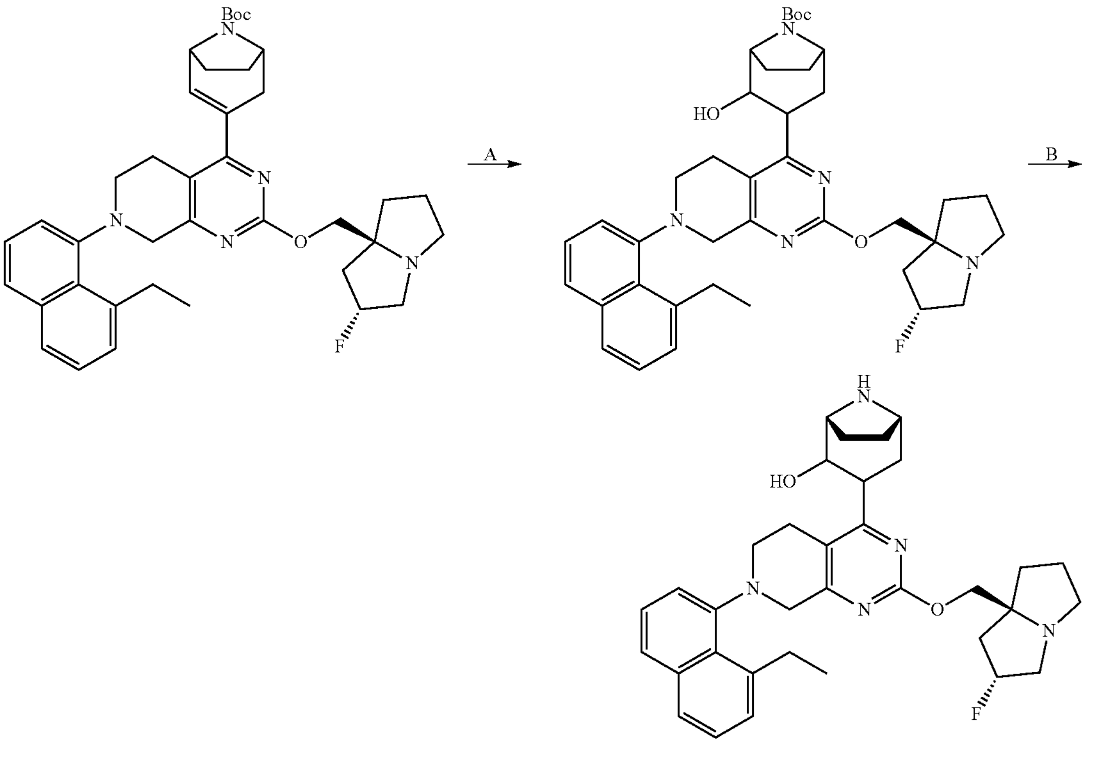

Step A. tert-butyl 3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-2-hydroxy-8-azabicyclo[3.2.1]octane-8-carboxylate. To a vial with a stir bar were added $K_2HPO_4$ (21 mg, 0.12 mmol), tert-butyl 3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]oct-2-ene-8-carboxylate (40 mg, 0.061 mmol), bis(pinacolato) diborane (31 mg, 0.12 mmol), $Cu_2O$ (1.9 mg, 0.024 mmol), and $PPh_3$ (6.4 mg, 0.024 mmol). The vial was closed with a septum and MeOH (0.61 ml) was added under $N_2$. The mixture was stirred at 50° C. for 3 h. The mixture was cooled to rt and recharged with $K_2HPO_4$ (21 mg, 0.12 mmol), bis (pinacolato) diborane (31 mg, 0.12 mmol), $Cu_2O$ (1.9 mg, 0.024 mmol), $PPh_3$ (6.4 mg, 0.024 mmol) under $N_2$. Stirring was continued at 50° C. for 5 h. The mixture was cooled to rt and filtered through a filtration disc. The filtrate was concentrated to dryness. The residue was dissolved in THE (0.61 ml) and treated with sodium perborate tetrahydrate (28 mg, 0.18 mmol) and water (0.61 ml) at rt for 5 h. The mixture was purified by preparative C18 HPLC (Gilson, 0-95% $CH_3CN/H_2O$ with 0.1% TFA). The desired fractions were combined, basified with $NaHCO_3$ (sat.) and extracted with EtOAc. The extract was dried over $Na_2SO_4$ and concentrated to give the title compound (15 mg, 37%) as a light-yellow oil. LCMS (MM-ES+APCI, Pos): m/z 672.4 (M+H).

Step B. (1S,3R,5R)-3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-8-azabicyclo[3.2.1]octan-2-ol bis(2,2,2-trifluoroacetate). To a solution of tert-butyl 3-(7-(8-ethylnaphthalen-1-yl)-2-(((2R,7aS)-2-fluorotetrahydro-1H-pyrrolizin-7a(5H)-yl)methoxy)-5,6,7,8-tetrahydropyrido[3,4-d]pyrimidin-4-yl)-2-hydroxy-8-azabicyclo[3.2.1]octane-8-carboxylate (15 mg, 0.022 mmol) in DCM (1.0 ml) was added TFA (0.5 ml). The solution was stirred at rt for 20 min, and concentrated to dryness. The residue was purified by preparative C18 HPLC (Gilson, 0-95% $CH_3CN/H_2O$ with 0.1% TFA). The desired fractions were combined and concentrated to give the title compound (4 mg, 22%) as the TFA salt. LCMS (MM-ES+APCI, Pos): m/z 572.3 (M+H).

Example A

KRas G12D Surface Plasmon Resonance (SPR) Binding Assay

This Example illustrates that exemplary compounds of the present invention bind to KRas G12D as measured by surface plasmon resonance (SPR).

Briefly, 1 L of 1.05xHBS-Mg buffer (262.5 mM BioUltra Hepes, pH 7.5, 157.5 mM NaCl, 105 mM $MgCl_2$, 0.525 mM TCEP, 0.0305% Brij-35) was prepared and filter sterilized using a 0.22 μm bottle top filter. Approximately 50 mL of 1.05xHBS-Mg buffer was removed and saved for future dilutions. A 50 mL aliquot of DMSO (Sigma Aldrich DMSO Lot. #SHBK2079) was added and continued to stir for 10 minutes, creating the final 1.0xHBS-Mg buffer (250 mM BioUltra Hepes pH 7.5, 150 mM NaCl, 100 mM $MgCl_2$, 0.5 mM TCEP, 0.03% Brij-35).

Biacore T200 instrument was primed using 1.0xHBS-Mg buffer before docking a GE Streptavidin (SA) chip and then primed two additional times prior to beginning the immobilization step. All immobilized protein mixtures were created using 3-5 mg/mL Biotinylated Avidin-tagged KRAS protein using the following immobilization settings: SA chip type, 1 flow cells per cycle, 720 second contact time, and 5 μL/min flow rate. Normalization of the detector was also performed during the immobilization step using the GE BiaNormalize solution.

All compounds were diluted to 10 mM in 100% DMSO prior to being diluted 20× in 1.05× buffer. Another 10× dilution was created using 1.0× buffer prior to performing a series of 3× dilutions to create a compound concentration curve using the following assay settings: 20 C analysis temperature, General Settings=10 Hz data collection rate and multi-detection; Assay Steps=all set to LMW kinetics; Cycle Types=LMW kinetics (60s contact time, 120s dissociation time, 100 μL/min flow rate, extra wash after injection with 50% DMSO, flow path 1,2,3,4); Flow path detection=2-1, 4-3). Data evaluation was performed using the Biacore T200 Evaluation software and data fit to 1:1 binding model.

The results for exemplary compounds of Formula (I) are shown in Table 1. ND=not determined.

TABLE 1

Determination of KRas G12D $K_D$ for Exemplary Compounds of Formula (I)

| Example No. | $K_D$ (nM) |
|---|---|
| 1 | 110.2 |
| 2 | 163.2 |
| 3 | 6365.7 |
| 4 | 1.5 |
| 22 | 302195.6 |
| 24 | 37.7 |
| 25 | 846.8 |
| 26 | 325.1 |
| 27 | 91.3 |
| 28 | >1000000 |
| 29 | 6.3 |
| 30 | 87.1 |
| 31 | 0.8 |
| 35 | 569626.2 |
| 36 | 24285.7 |
| 37 | 12793.7 |
| 38 | 2338.1 |
| 40 | 957.1 |
| 43 | 57.6 |
| 44 | 43.9 |
| 45 | 1.9 |
| 52 | 250128.2 |
| 53 | >1000000 |
| 54 | 500733.2 |
| 55 | 38684.4 |
| 56 | 89891.1 |
| 57 | 98461.5 |
| 58 | 438.1 |
| 59 | 597845.6 |
| 61 | 175.5 |
| 62 | 8.1 |
| 63 | 12.3 |
| 64 | 67.3 |
| 65 | 18.2 |
| 69 | 38443.4 |
| 70 | 2100.0 |
| 71 | 4217.1 |
| 72 | 922.5 |
| 73 | 3161.7 |
| 74 | 41604.3 |
| 75 | 170483.5 |
| 76 | 97014.9 |
| 77 | 264294.8 |
| 78 | 51441.4 |
| 79 | 1863.0 |
| 80 | 616.7 |
| 82 | 149.5 |

TABLE 1-continued

Determination of KRas G12D $K_D$ for Exemplary Compounds of Formula (I)

| Example No. | $K_D$ (nM) |
|---|---|
| 83 | 19926.5 |
| 84 | 8709.7 |
| 85 | 1509.8 |
| 86 | 33232.2 |
| 87 | 704.8 |
| 88 | 2102.1 |
| 89 | 27058.2 |
| 90 | 938.3 |
| 91 | 176.1 |
| 95 | 58.3 |
| 109 | 20.8 |
| 110 | 3231.1 |
| 120 | 1401.0 |

Example B

KRas G12D Binding Assay

This Example illustrates that exemplary compounds of the present invention bind to KRas G12D and are capable of displacing a labeled tracer ligand occupying the KRas G12D binding site.

The ability of a compound to bind to KRAS G12D was measured using a TR-FRET displacement assay. Biotinylated GDP-loaded recombinant human KRAS G12D (corresponding to amino acids 1:169, produced at Array BioPharma) was incubated with a custom-made Cy5 labelled tracer, europium labelled streptavidin and compound (2% DMSO final) in buffer (50 mM HEPES [pH 7.5], 5 mM $MgCl_2$, 0.005% Tween-20 & 1 mM DTT). After a 60 minute incubation at 22° C., the reaction was measured using a PerkinElmer EnVision multimode plate reader via TR-FRET dual wavelength detection, and the percent of control (POC) calculated using a ratiometric emission factor. 100 POC is determined using no test compound and 0 POC is determined using a concentration of control compound that completely inhibits binding of the tracer to KRAS. The POC values were fit to a 4-parameter logistic curve and the $IC_{50}$ value was determined as the concentration where the curve crosses 50 POC.

The results for exemplary compounds of Formula (I) are shown in Table 2 ND is not determined

TABLE 2

Binding to KRas G12D by Exemplary Compounds of Formula (I)

| Example No. | $IC_{50}$ (nM) |
|---|---|
| 1 | 48.9 |
| 2 | 266.5 |
| 3 | 1315.4 |
| 4 | 3.7 |
| 5 | 1.6 |
| 6 | 0.8 |
| 7 | 1.0 |
| 8 | 5.5 |
| 9 | 3.1 |
| 10 | 1.1 |
| 11 | 19.8 |
| 12 | 344.8 |
| 13 | 1.3 |
| 14 | 1.1 |
| 15 | 7904.6 |
| 16 | 1762.9 |
| 17 | 29.5 |
| 18 | 2.0 |

TABLE 2-continued

Binding to KRas G12D by Exemplary Compounds of Formula (I)

| Example No. | $IC_{50}$ (nM) |
|---|---|
| 19 | 1.8 |
| 20 | 2.8 |
| 21 | 12.3 |
| 22 | 7862.6 |
| 23 | 1.1 |
| 24 | 1362.6 |
| 25 | 6788.2 |
| 27 | 1601.7 |
| 28 | 1.2 |
| 29 | 2.5 |
| 30 | 16.8 |
| 31 | 3.8 |
| 32 | 1170.4 |
| 33 | 50.2 |
| 34 | 111.4 |
| 35 | >10000 |
| 36 | >10000 |
| 37 | 88.1 |
| 38 | 73.5 |
| 39 | 2694.4 |
| 40 | 63.9 |
| 41 | 3128.4 |
| 42 | 1799.0 |
| 43 | 90.1 |
| 44 | 43.5 |
| 45 | 2.6 |
| 46 | 4.4 |
| 47 | 1.0 |
| 48 | 5.5 |
| 49 | 0.5 |
| 50 | 7.1 |
| 51 | 16.9 |
| 52 | 361.4 |
| 53 | 5259.0 |
| 54 | 41.1 |
| 55 | 774.8 |
| 56 | >10000 |
| 57 | >10000 |
| 58 | 282.9 |
| 59 | 7500.0 |
| 60 | >10000 |
| 61 | 184.3 |
| 62 | 1.0 |
| 63 | 5.1 |
| 64 | 13.0 |
| 65 | 15.2 |
| 66 | 4.6 |
| 67 | 1.5 |
| 68 | 5.9 |
| 69 | >10000 |
| 70 | 1118.9 |
| 71 | 1780.0 |
| 72 | 226.3 |
| 73 | 1101.0 |
| 74 | >10000 |
| 75 | >10000 |
| 76 | >10000 |
| 77 | >10000 |
| 78 | >10000 |
| 79 | 485.5 |
| 81 | 710.2 |
| 82 | 61.0 |
| 83 | 6565.8 |
| 84 | 3688.9 |
| 86 | 2900.3 |
| 87 | 271.4 |
| 88 | 1088.1 |
| 89 | >10000 |
| 90 | 1462.9 |
| 91 | 78.4 |
| 92 | 5489.7 |
| 93 | 360.3 |
| 94 | 851.7 |
| 95 | 50.6 |
| 96 | 331.2 |
| 97 | 1.2 |

TABLE 2-continued

Binding to KRas G12D by Exemplary Compounds of Formula (I)

| Example No. | $IC_{50}$ (nM) |
|---|---|
| 98 | 0.7 |
| 99 | 2.7 |
| 100 | 9.7 |
| 101 | 2485.2 |
| 102 | 654.1 |
| 103 | 3.9 |
| 104 | 755.6 |
| 105 | 2.3 |
| 106 | 7.2 |
| 107 | 2.0 |
| 108 | 2.0 |
| 109 | 5.5 |
| 110 | 3174.0 |
| 111 | 1052.0 |
| 112 | 5456.6 |
| 113 | 806.6 |
| 114 | 34.2 |
| 115 | 0.6 |
| 116 | 0.5 |
| 117 | 0.7 |
| 118 | 2.1 |
| 119 | 1.6 |
| 121 | 8.7 |
| 122 | 234.2 |
| 123 | 508.3 |

Example C

Inhibition of KRas G12D-mediated Phosphorylation of ERK by Exemplary Compounds of Formula (I)

This Example illustrates that exemplary compounds of the present invention inhibit the phosphorylation of ERK downstream of KRAS G12D.

AGS cells (ATCC CRL-1739) expressing G12D were grown in DMEM medium supplemented with 10% fetal bovine serum, 10 mM HEPES, and Penicillin/Streptomycin. Cells were plated in tissue culture treated 96 well plates at a density of 40,000 cells/well and allowed to attach for 12-14 hours. Diluted compounds were then added in a final concentration of 0.5% DMSO. After 3 hours, the medium was removed, 150 μl of 4.0% formaldehyde was added and the plates incubated at room temperature for 20 minutes. The plates were washed with PBS, and permeabilized with 150 μL of ice cold 100% methanol for 10 minutes. Non-specific antibody binding to the plates was blocked using 100 μL Licor blocking buffer (Li-Cor Biotechnology, Lincoln NE) for 1 hour at room temperature.

The amount of phospho-ERK was determined using an antibody specific for the phosphorylated form of ERK and compared to the amount of GAPDH. Primary antibodies used for the detection were added as follows: Phospho-ERK (Cell Signaling cs-9101) diluted 1:500 and GAPDH(Millipore MAB374) diluted 1:5000 in Licor block+0.05% Tween 20. The plates were incubated for 2 hours at room temperature. The plates were washed with PBS+0.05% Tween 20.

Secondary antibodies used to visualize primary antibodies were added as follows: Anti-rabbit-680 diluted 1:1000 and Anti-mouse-800 diluted 1:1000 both in Licor block+0.05% Tween20, and were incubated for 1 hour at room temperature. The plates were washed with PBS+0.05% Tween 20. A 100 μl aliquot of PBS was added to each well and the plates were read on a Li-Cor Odyssey CLX plate reader.

The phospho-ERK(Thr202/Tyr204 signal was normalized to the GAPDH signal for each well and percent of DMSO control values were calculated. IC50 values were generated using a 4-parameter fit of the dose response curve.

The results for exemplary compounds of Formula (I) are shown in Table 3. ND is not determined.

TABLE 3

Inhibition of KRas G12D-mediated Phosphorylation of ERK by Exemplary Compounds of Formula (I)

| Example No. | $IC_{50}$ (nM) |
|---|---|
| 1 | 2349 |
| 2 | 16085 |
| 4 | 994 |
| 5 | 142 |
| 6 | 12 |
| 7 | 13 |
| 8 | 12570 |
| 9 | 1656 |
| 10 | 738 |
| 11 | >16667 |
| 13 | 261 |
| 14 | 21 |
| 17 | >16667 |
| 18 | 70 |
| 19 | 324 |
| 20 | 539 |
| 23 | 119 |
| 24 | >16667 |
| 26 | >16667 |
| 27 | 11111 |
| 28 | 361 |
| 29 | 4053 |
| 30 | 2611 |
| 31 | 1611 |
| 33 | 5556 |
| 34 | 3909 |
| 37 | 3849 |
| 38 | 5004 |
| 40 | >16667 |
| 43 | >16667 |
| 44 | 9030 |
| 45 | 1361 |
| 46 | 4570 |
| 47 | 537 |
| 48 | 5223 |
| 49 | 77 |
| 50 | >16667 |
| 51 | >16667 |
| 52 | 14931 |
| 54 | 1133 |
| 55 | 4876 |
| 56 | >16667 |
| 58 | >16667 |
| 61 | 6876 |
| 62 | 1936 |
| 63 | 6581 |
| 64 | >16667 |
| 65 | >16667 |
| 66 | 2209 |
| 67 | 150 |
| 68 | 1332 |
| 72 | >16667 |
| 75 | >16667 |
| 76 | >16667 |
| 80 | 11111 |
| 87 | 13438 |
| 91 | >16667 |
| 93 | >16667 |
| 95 | >16667 |
| 96 | >16667 |
| 97 | 187 |
| 98 | 50 |
| 99 | 559 |
| 100 | 1311 |
| 103 | 6216 |
| 105 | 561 |
| 106 | 5110 |
| 107 | 408 |
| 108 | 585 |

TABLE 3-continued

Inhibition of KRas G12D-mediated Phosphorylation of ERK by Exemplary Compounds of Formula (I)

| Example No. | $IC_{50}$ (nM) |
|---|---|
| 109 | 663 |
| 112 | >16667 |
| 114 | >16667 |
| 115 | 118 |
| 116 | 46 |
| 117 | 76 |
| 119 | 7 |
| 121 | 2359 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A compound of Formula (I):

Formula (I)

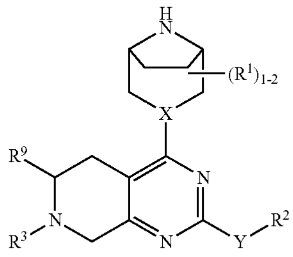

or a pharmaceutically acceptable salt thereof:

wherein:

each $R^1$ is independently hydrogen, hydroxy, halogen, C1-C3 alkyl, C1-C3 haloalkyl, C1-C3 alkoxy, (C1-C3 alkoxy)-C1-C3 alkyl-, C1-C3 alkyl-$N(R^5)_2$, cyano, C1-C3 cyanoalkyl, C2-C4 cyanoalkenyl, C1-C3 hydroxyalkyl, HC(═O)—, —$CO_2R^5$, or —$CO_2N(R^5)_2$;

X is N or $CR^5$;

Y is a bond, O or $NR^5$;

$R^2$ is hydrogen, —$N(R^5)_2$, heterocyclyl, C1-C6 alkyl, -L-heterocyclyl, -L-aryl, -L-heteroaryl, -L-cycloalkyl, -L-NHC(═NH)$NH_2$, -L-C(O)$N(R^5)_2$, -L-C1-C6 haloalkyl, -L-$OR^5$, -L-$(CH_2OR^5)(CH_2)_nOR^5$, -L-$NR^5C$(O)-aryl, or -L-COOH, wherein the heterocyclyl, the aryl portion of -L-$NR^5C$(O)-aryl, the heterocyclyl portion of -L-heterocyclyl and the cycloalkyl portion of -L-cycloalkyl is optionally substituted with one or more $R^6$, and wherein the aryl portion of -L-aryl and heteroaryl portion of -L-heteroaryl is optionally substituted with one or more $R^7$, wherein the heterocyclyl is hexahydro-1H-pyrrolizinyl, hexahydro-3H-pyrrolizin-3-one, hexahydro-1H-pyrrolo[2,1-c][1,4]oxazinyl, octahydroindolizinyl, hexahydropyrrolizine 4(1H)-oxide, azetidinyl, pyrrolidin-2-one, oxetanyl, piperidinyl, 1-azabicyclo[2.2.1]heptanyl, morpholinyl, oxa-5-azabicyclo[2.2.1]heptan- 5-yl, thiopyranyl, 6-oxa-2-azaspiro[3.4]octanyl, 7-oxa-2-azaspiro[3.5]nonanyl, 2',3'-dihydrospiro [cyclopropane-1,1'-indenyl], (2S)-1-azabicyclo[2.2.1] heptan-2-yl, or tetrahydrofuranyl;

$R^3$ is-L-aryl, aryl, -L-heteroaryl or heteroaryl, wherein the aryl or the heteroaryl is optionally substituted with one or more $R^8$;

each L is independently a C1-C4 alkylene optionally substituted with hydroxy, C1-C4 hydroxyalkyl or heteroaryl;

each $R^5$ is independently hydrogen, C1-C3 alkyl or C1-C3hydroxyalkyl, or two $R^5$ together with the atom to which they are both attached optionally join to form a heterocyclyl ring, wherein the heterocyclic ring formed by two $R^5$ is optionally substituted with one or more substituents independently selected from C1-C3 alkyl, hydroxy and C1-C3 alkoxy;

each $R^6$ is independently halogen, hydroxy, C1-C3 hydroxyalkyl, C1-C3 alkyl, C1-C3 haloalkyl, C1-C3 alkoxy, -Q-phenyl, -Q-phenyl$SO_2$F, —NHC(O)phenyl, —NHC(O)phenyl$SO_2$F, C1-C3 alkyl substituted pyrazolyl, araC1-C3 alkyl-, tert-butyldimethylsilyloxy$CH_2$—, —$N(R^5)_2$, (C1-C3 alkoxy)C1-C3 alkyl-, (C1-C3 alkyl)C(═O)—, oxo, (C1-C3 haloalkyl)C (═O)—, —$SO_2$F, (C1-C3 alkoxy)C1-C3 alkoxy, (C1-C3)alkyl-O(C═O)—$N(R^5)_2$ or (C1-C3)alkyl-O (C═O)—N($OR^5$)$R^5$;

Q is a bond or O;

each $R^7$ is independently halogen, hydroxy, HC(═O)—, C1-C4 alkyl, C1-C4 alkoxy, C1-C4 haloalkyl, C1-C4 hydroxyalkyl, or —$N(R^5)_2$;

each $R^8$ is independently halogen, cyano, hydroxy, C1-C4 alkyl, —S—C1-C3 alkyl, C2-C4 alkenyl, C2-C4 alkynyl, C2-C4 hydroxyalkynyl, C1-C3 cyanoalkyl, triazolyl, C1-C3 haloalkyl, —O—C1-C3 haloalkyl, cyclopropyl, $N(R_5)^2$, C1-C4hydroxyalkyl, —S—C1-C3 haloalkyl or —O—C1-C3alkyl; and $R^9$ is hydrogen or oxo.

2. The compound or pharmaceutically acceptable salt thereof of claim 1, wherein each $R^1$ is independently hydrogen, hydroxy, halogen, C1-C3 alkoxy, C1-C3alkyl-$N(R^5)_2$, C1-C3 cyanoalkyl, dihalo-C1-C3alkyl, C1-C3alkyl, cyano, C2-C4alkenyl-cyano, C1-C3 hydroxyalkyl, hydroxy or (C1-C3 alkoxy)-C1-C3alkyl.

3. The compound or pharmaceutically acceptable salt thereof of claim 2, wherein X is N.

4. The compound or pharmaceutically acceptable salt thereof of claim 1, wherein X is $CR^5$, $R^5$ is hydrogen or C1-C3 alkyl, and each $R^1$ is independently hydrogen or hydroxy.

5. The compound or pharmaceutically acceptable salt thereof of claim 1, wherein Y is O.

6. The compound or pharmaceutically acceptable salt thereof of claim 5, wherein $R^2$ is C1-C6 alkyl, heterocyclyl or -L-heterocyclyl.

7. The compound or pharmaceutically acceptable salt thereof of claim 6, wherein L, if present, is methylene optionally substituted with methyl, and $R^2$ is heterocyclyl optionally substituted with one or more $R^6$.

8. The compound or pharmaceutically acceptable salt thereof of claim 7, wherein the heterocyclyl is hexahydro-1H-pyrrolizinyl optionally substituted with one or more $R^6$.

9. The compound or pharmaceutically acceptable salt thereof of claim 8, wherein said one or more $R^6$ groups are each independently selected from halogen, hydroxy, C1-C3 hydroxyalkyl, C1-C3 alkyl, C1-C3 haloalkyl, C1-C3 alkoxy, (C1-C3 alkoxy)C1-C3 alkoxy, (C1-C3)alkyl-O(C═O)—$N(R^5)_2$ or (C1-C3)alkyl-O(C═O)—N($OR^5$)$R^5$.

10. The compound or pharmaceutically acceptable salt thereof of claim 9, wherein two $R^5$ join to form a heterocycle.

11. The compound or pharmaceutically acceptable salt thereof of claim 1, wherein $R^3$ is -L-aryl or aryl, wherein aryl is phenyl, naphthyl, 1,2,3,4-tetrahydronaphthalenyl or 2,3-dihydro-1H-indenyl, each optionally substituted with one or more $R^8$.

12. The compound or pharmaceutically acceptable salt thereof of claim 11, wherein each $R^8$ is independently halogen, hydroxy, C1-C4 alkyl, C1-C3 haloalkyl, —O—C1-C3 haloalkyl or cyclopropyl.

13. The compound or pharmaceutically acceptable salt thereof of claim 1, wherein $R^3$ is-L-heteroaryl or heteroaryl, wherein heteroaryl is isoquinoline or quinazoline, each optionally substituted with one or more $R^8$.

14. The compound or pharmaceutically acceptable salt thereof of claim 13, wherein each $R^8$ is independently halogen, hydroxy, C1-C4 alkyl, C1-C3 haloalkyl, —O—C1-C3 haloalkyl or cyclopropyl.

15. The compound of claim 1, wherein the compound is selected from:

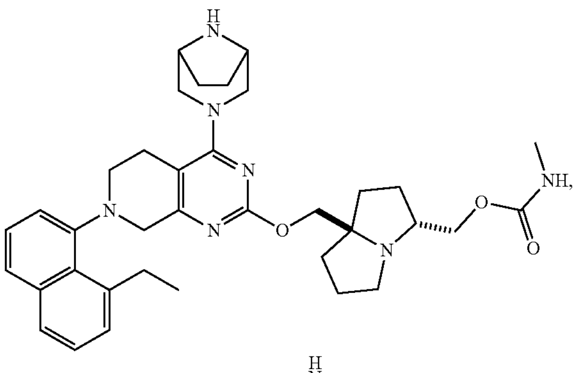

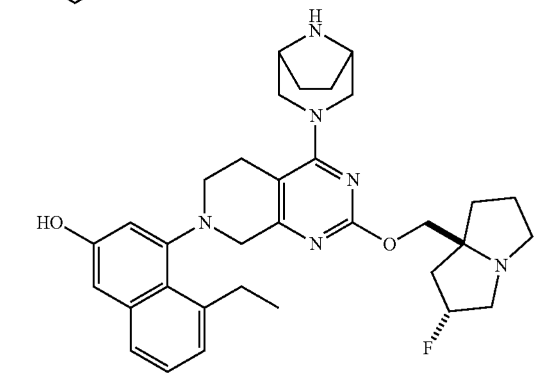

,

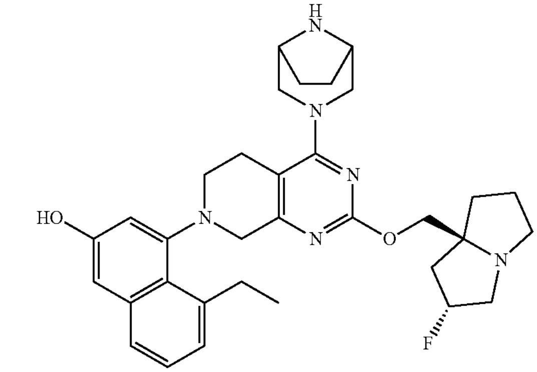

,

-continued
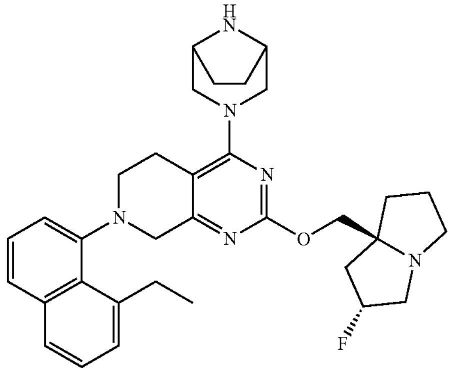
,
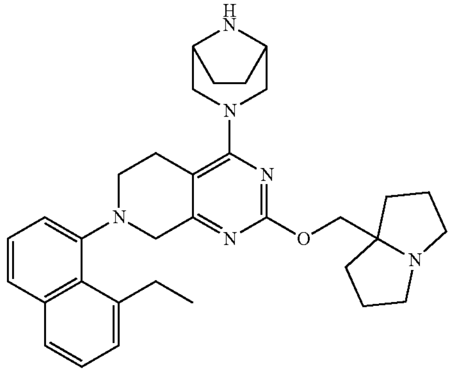
,
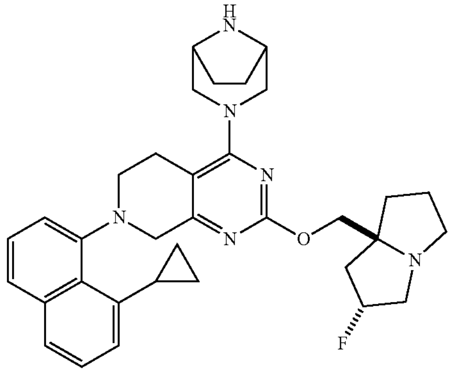
,
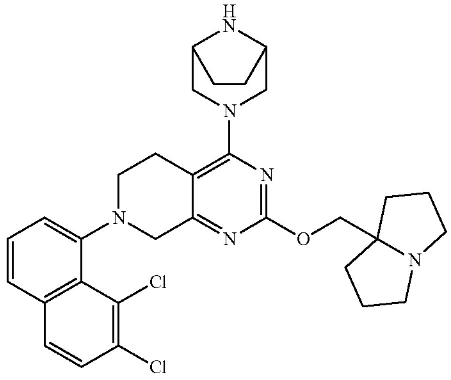
,
-continued
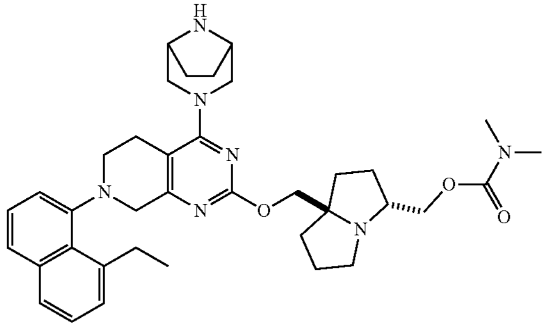
,
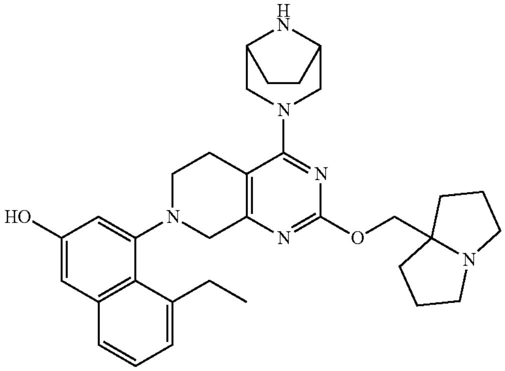
,
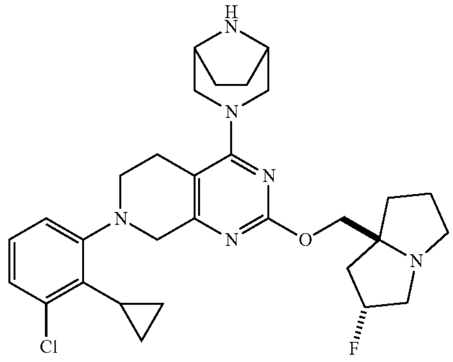
,
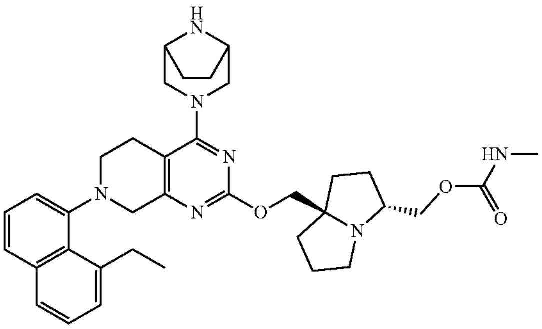
, -continued
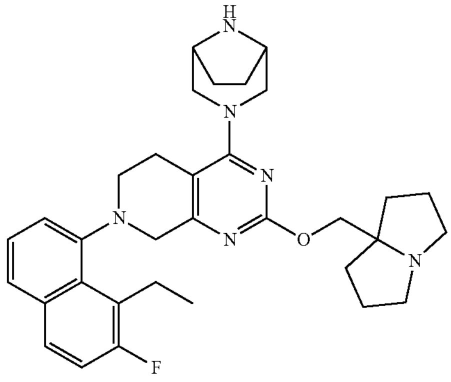
,
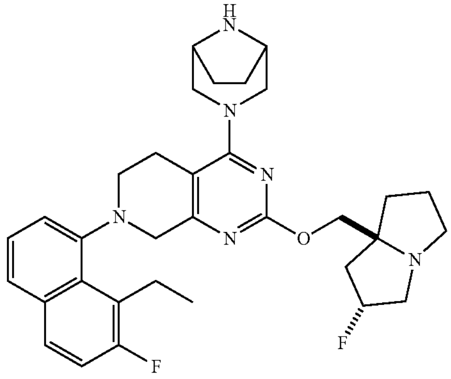
,
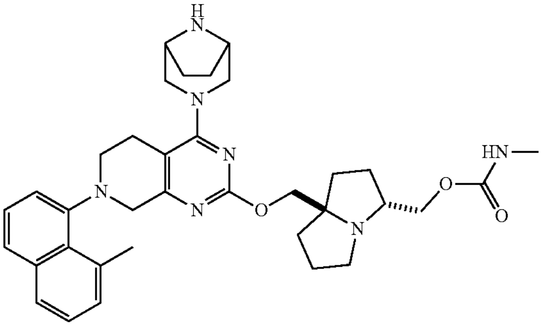
,
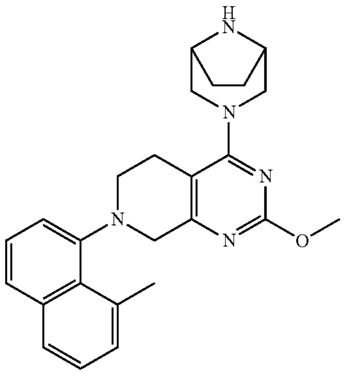
,
-continued
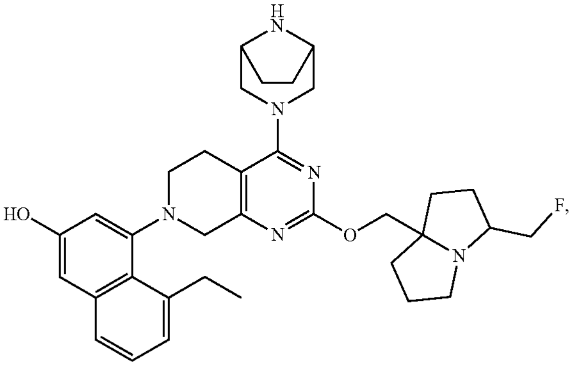
,
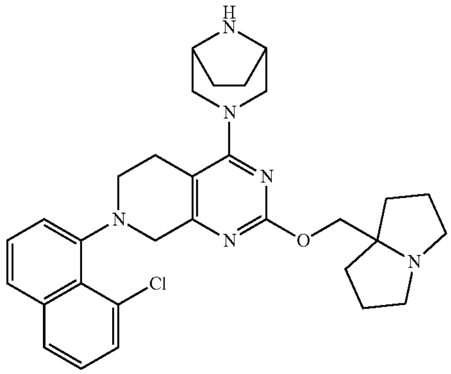
,
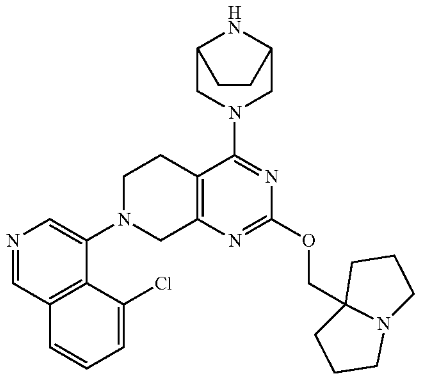
,
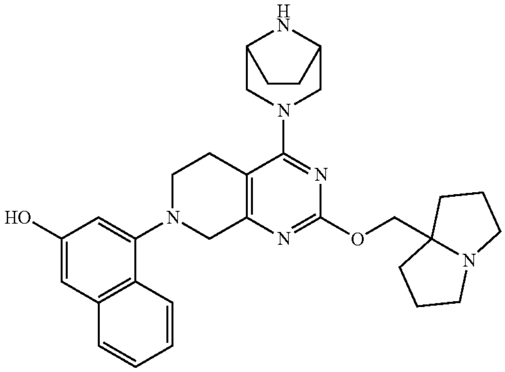
,

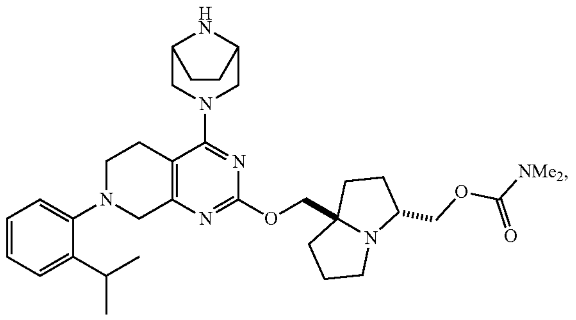
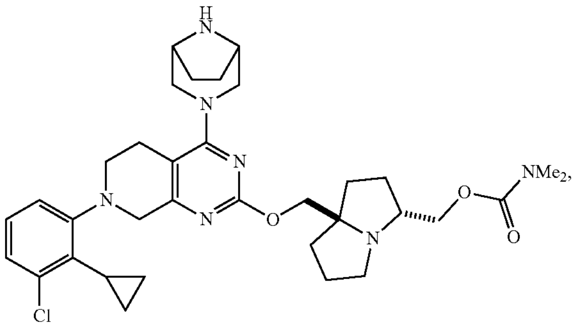
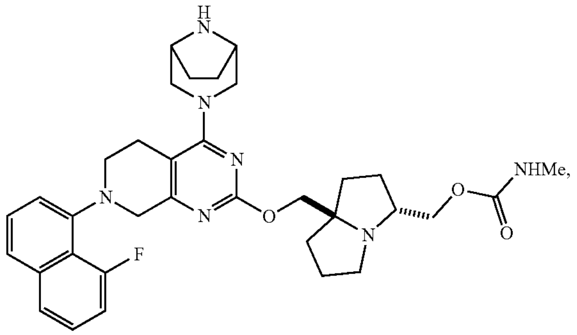
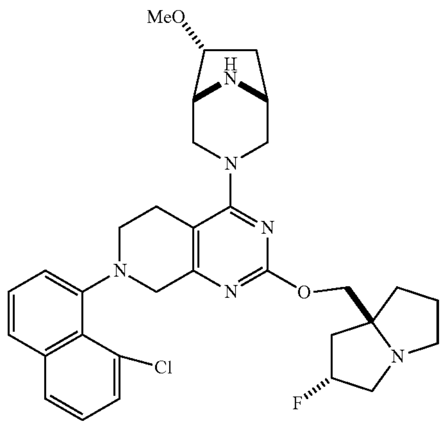
,
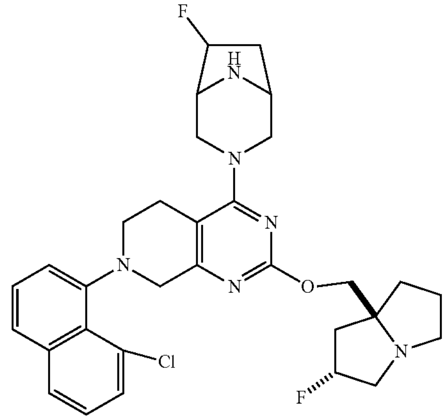
,
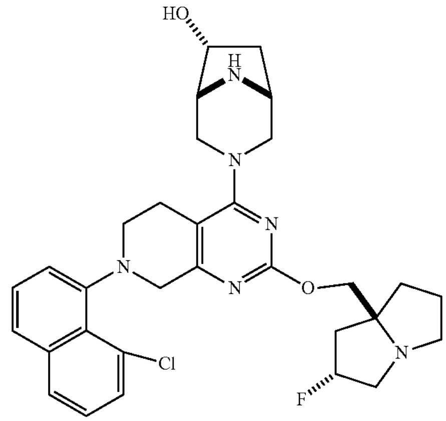
,
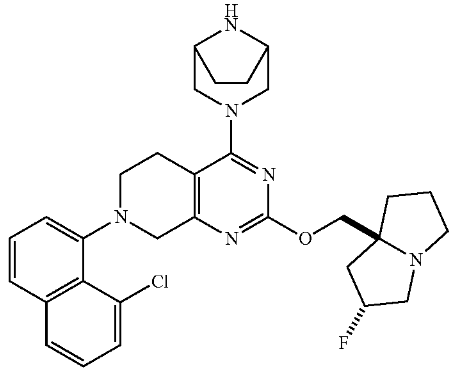
,
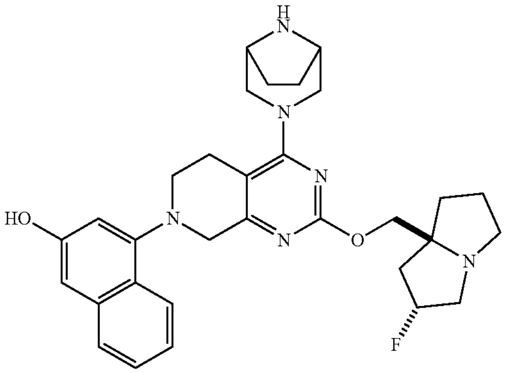
, -continued
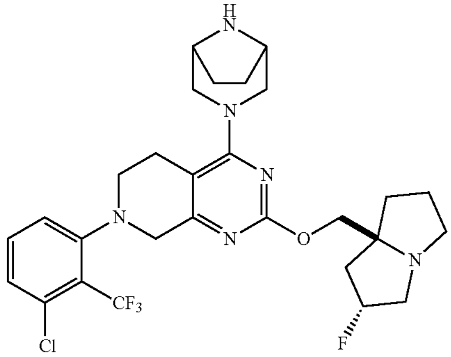
,
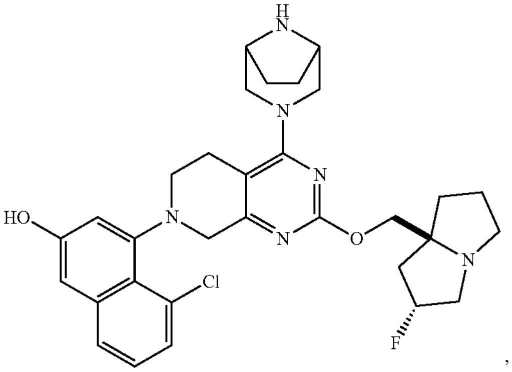
,
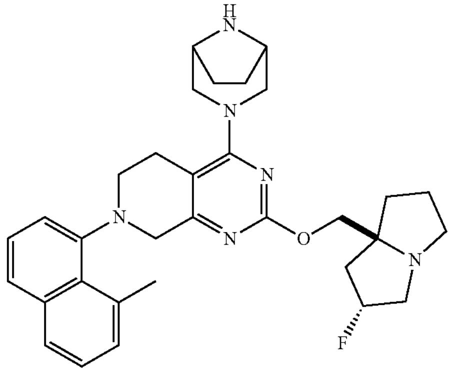
,
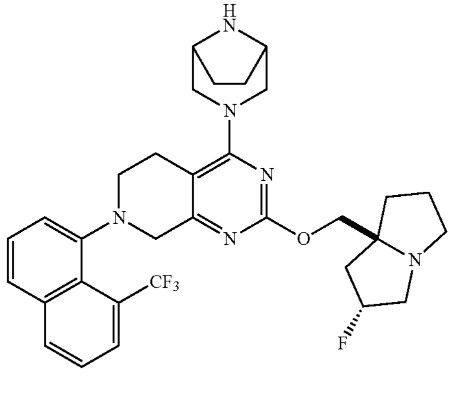
,
-continued
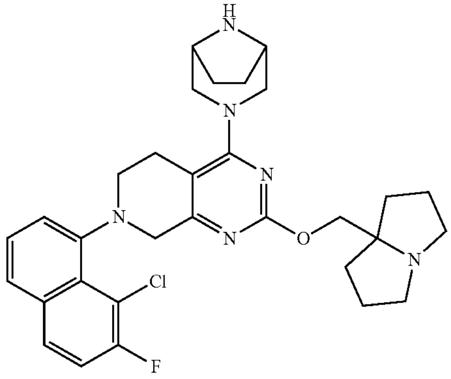
,
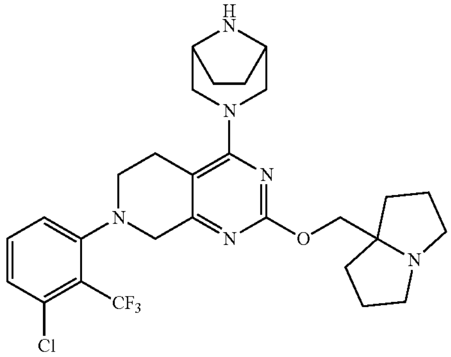
,
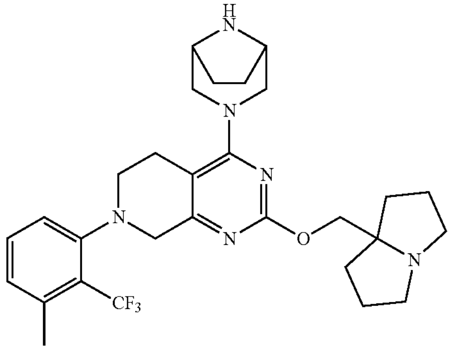
,
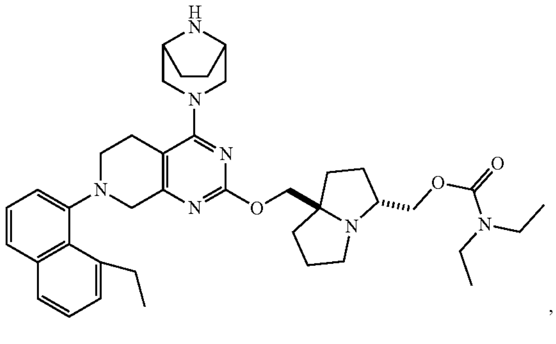
, -continued
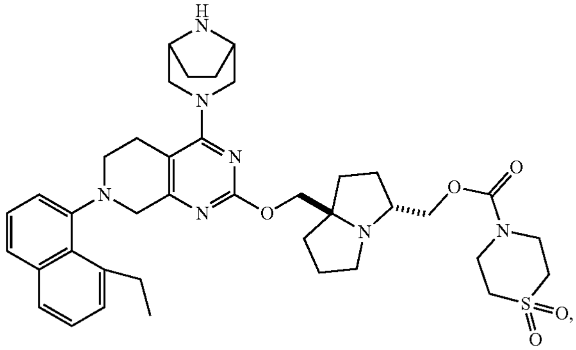
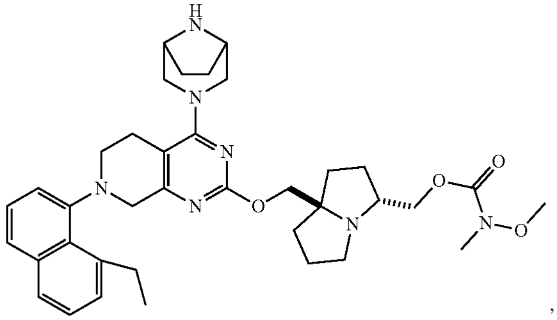
,
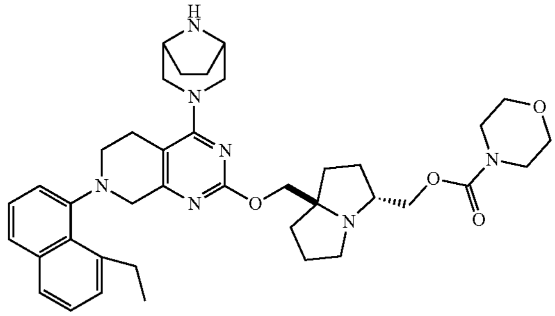
,
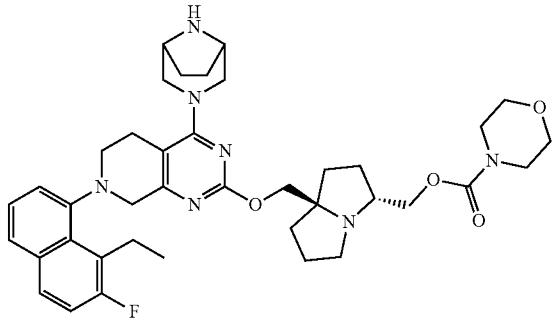
,
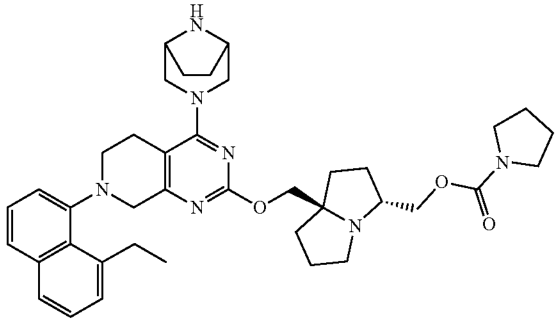
,
-continued
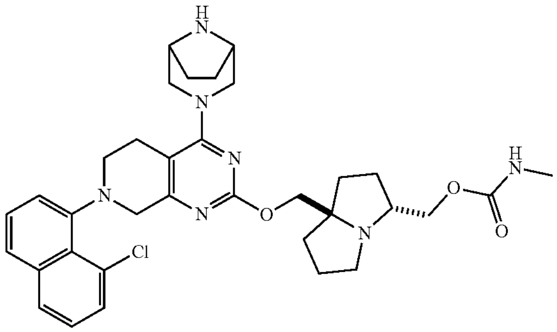
,
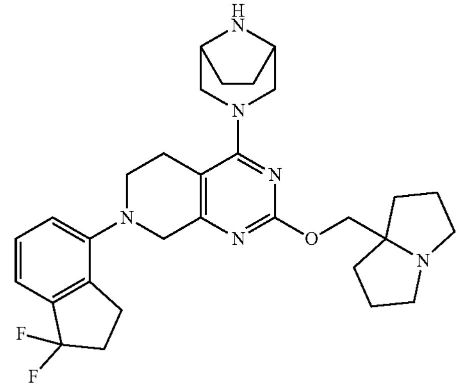
,
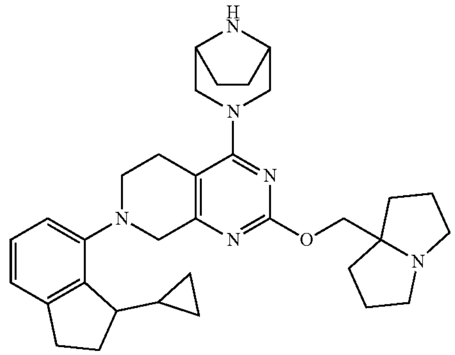
,
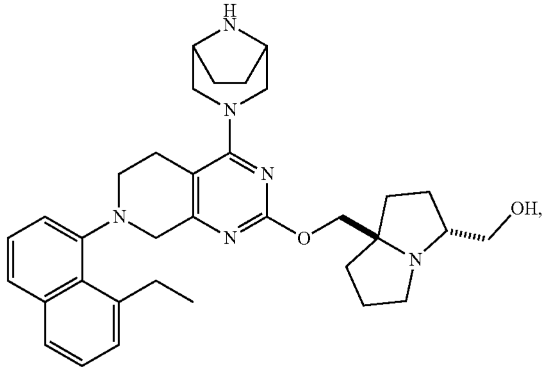

-continued
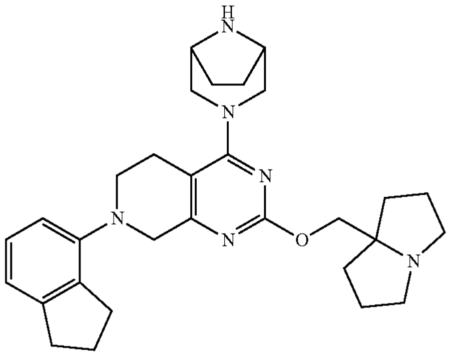
,
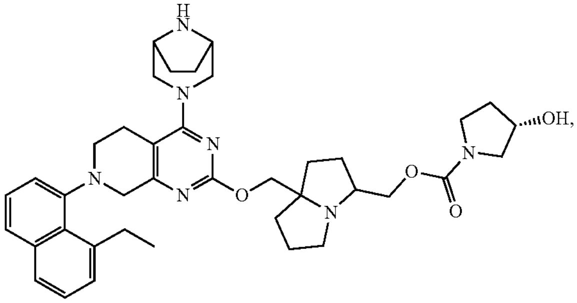
,
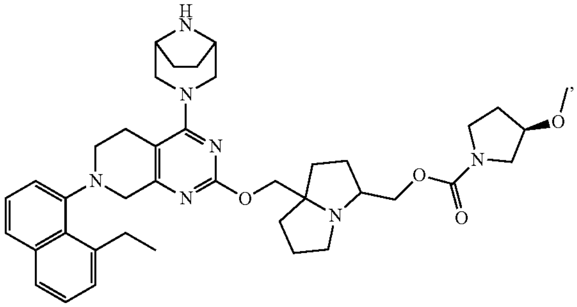
,
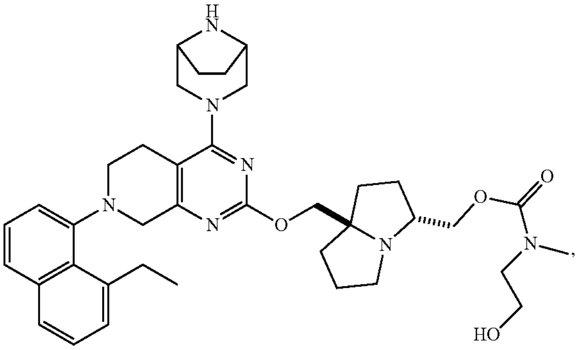
,
-continued
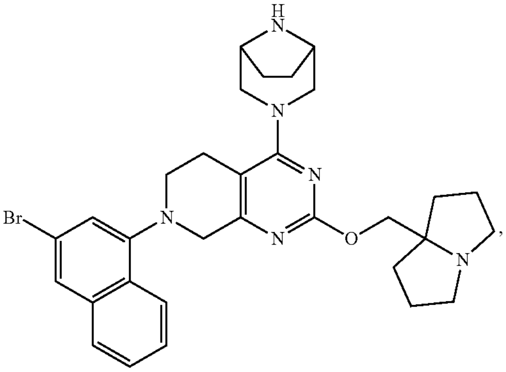
,
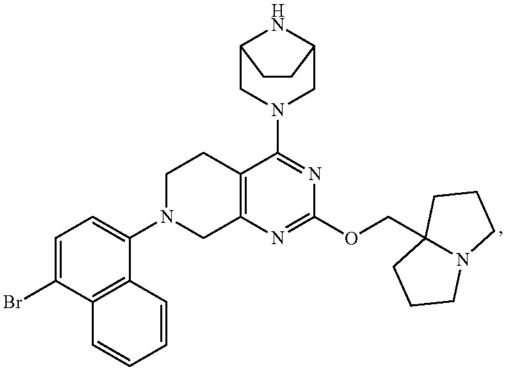
,
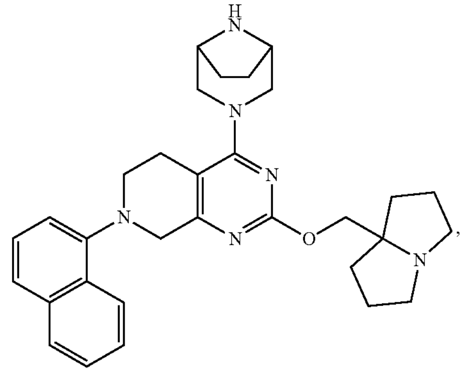
,
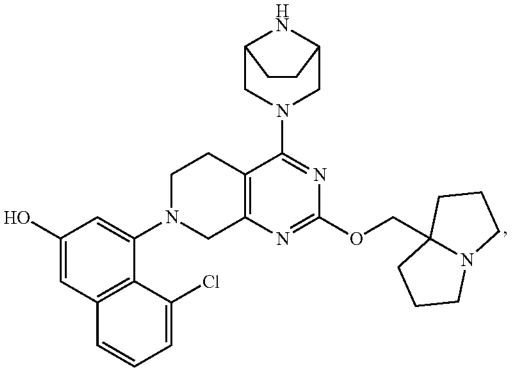
, -continued

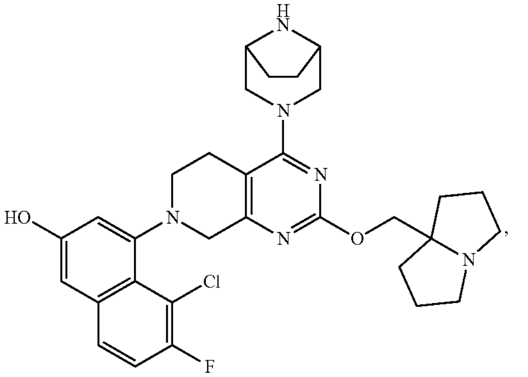

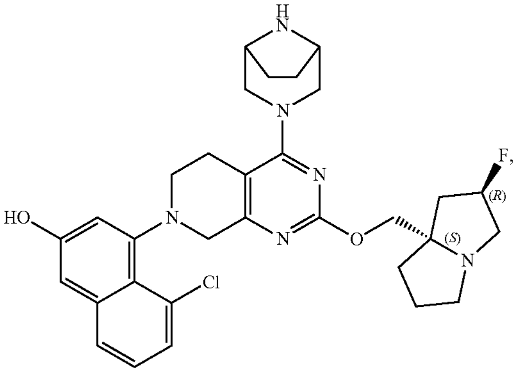

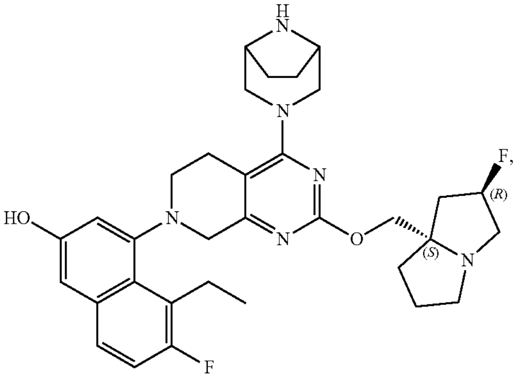

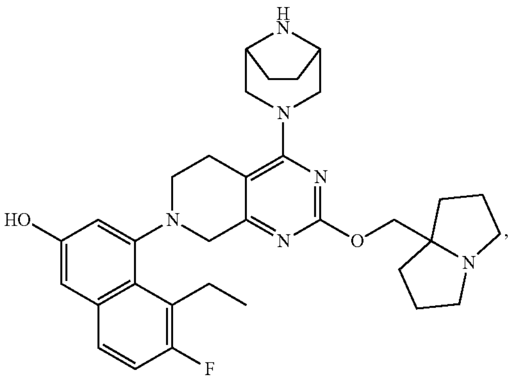

-continued

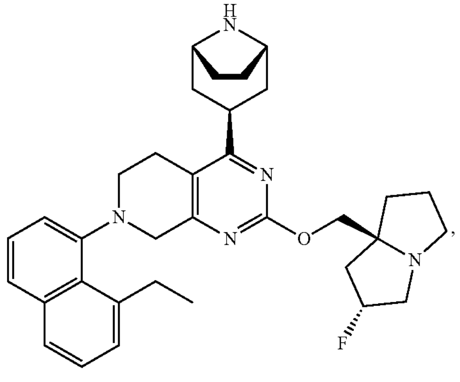

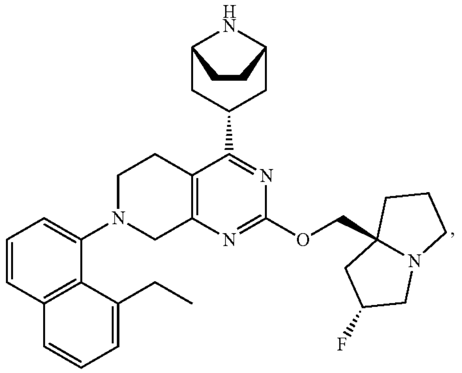

and

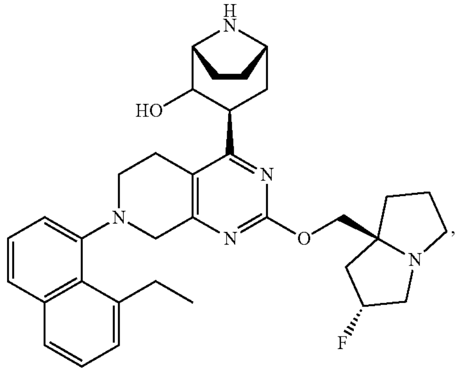

or a pharmaceutically acceptable salt thereof.

16. A pharmaceutical composition, comprising a therapeutically effective amount of a compound of claim 1 or a pharmaceutically acceptable salt thereof, and a pharmaceutically acceptable excipient.

17. A method for inhibiting KRas G12D activity in a cell, comprising contacting the cell in which inhibition of KRas G12D activity is desired with an effective amount of a compound of according to claim 1 or a pharmaceutically acceptable salt thereof.

18. A method for treating a KRas G12D-associated cancer comprising administering to a patient having a KRas G12D-associated cancer a therapeutically effective amount of a compound according to claim 1 or a pharmaceutically acceptable salt thereof.

19. The method of claim 18, wherein the KRas G12D-associated cancer is selected from the group consisting of Cardiac: sarcoma myxoma, rhabdomyoma, fibroma, lipoma and teratoma; Lung: bronchogenic carcinoma, alveolar carcinoma, bronchiolar carcinoma, bronchial adenoma, sarcoma, lymphoma, chondromatous hamartoma, mesothelioma; Gastrointestinal: esophagus squamous cell carcinoma, esophagus adenocarcinoma, esophagus leiomyosarcoma, esophagus lymphoma, stomach carcinoma, stomach lymphoma, stomach leiomyosarcoma, pancreas ductal adenocarcinoma, pancreas insulinoma, pancreas glucagonoma, pancreas gastrinoma, pancreas carcinoid tumors, pancreas vipoma, small bowel adenocarcinoma, small bowel lymphoma, small bowel carcinoid tumors, small bowel Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma; Genitourinary tract: kidney adenocarcinoma, Wilm's tumor, nephroblastoma, kidney lymphoma, kidney leukemia, bladder and urethra squamous cell carcinoma, bladder and urethra transitional cell carcinoma, bladder and urethra adenocarcinoma, prostate adenocarcinoma, prostate sarcoma, testicular seminoma, testicular teratoma, testicular embryonal carcinoma, testicular teratocarcinoma, testicular choriocarcinoma, testicular sarcoma, testicular interstitial cell carcinoma, testicular fibroma, testicular fibroadenoma, testicular adenomatoid tumors, testicular lipoma; Liver: hepatoma, liver cholangiocarcinoma, hepatoblastoma, liver angiosarcoma, hepatocellular adenoma, liver hemangioma; Biliary tract: gall bladder carcinoma, ampullary carcinoma, biliary tract cholangiocarcinoma; Bone: osteogenic sarcoma, bone fibrosarcoma, bone malignant fibrous histiocytoma, bone chondrosarcoma, Ewing's sarcoma, bone malignant lymphoma, bone reticulum cell sarcoma, bone multiple myeloma, malignant giant cell tumor chordoma, osteochondroma, osteocartilaginous exostoses, benign chondroma, chondroblastoma, chondromyxofibroma, osteoid osteoma and giant cell tumors; Nervous system: skull osteoma, skull hemangioma, skull granuloma, skull xanthoma, skull osteitis deformans, meningioma, meningiosarcoma, gliomatosis, brain astrocytoma, brain medulloblastoma, brain glioma, brain ependymoma, brain germinoma brain pinealoma, brain glioblastoma multiform, brain oligodendroglioma, brain schwannoma, brain retinoblastoma, brain congenital tumors, spinal cord neurofibroma, spinal cord meningioma, spinal cord glioma, spinal cord sarcoma; Gynecological: uterus endometrial carcinoma, uterus serous cystadenocarcinoma, uterus mucinous cystadenocarcinoma, uterus unclassified carcinoma, granulosa-thecal cell tumors, Sertoli-Leydig cell tumors, dysgerminoma, malignant teratoma, vulva squamous cell carcinoma, vulva intraepithelial carcinoma, vulva adenocarcinoma, vulva fibrosarcoma, vulva melanoma, vagina clear cell carcinoma, vagina squamous cell carcinoma, vagina botryoid sarcoma, vagina embryonal rhabdomyosarcoma, fallopian tube carcinoma; Hematologic: acute myeloid leukemia, chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma; Skin: skin malignant melanoma, basal cell carcinoma, skin squamous cell carcinoma, skin Kaposi's sarcoma, moles dysplastic nevi, lipoma, angioma, dermatofibroma, keloids, psoriasis; and Adrenal glands: neuroblastoma.

20. A compound selected from:

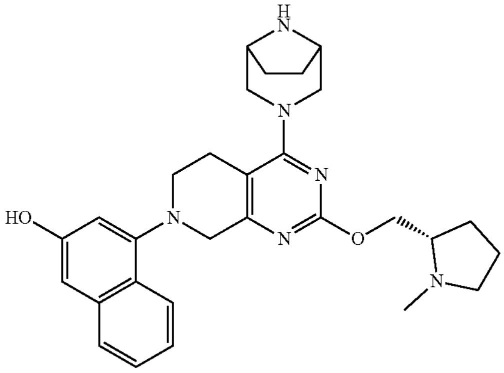

,

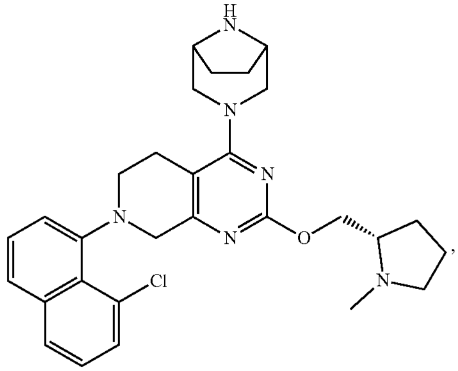

,

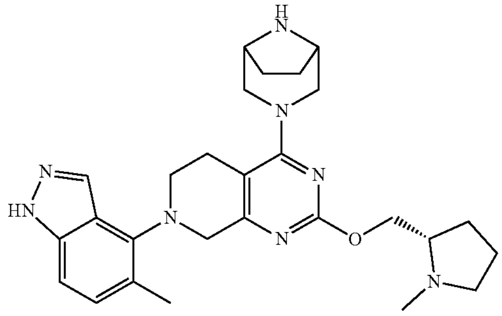

,

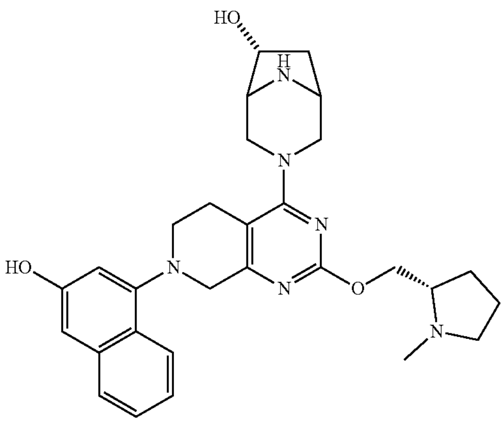

,

-continued
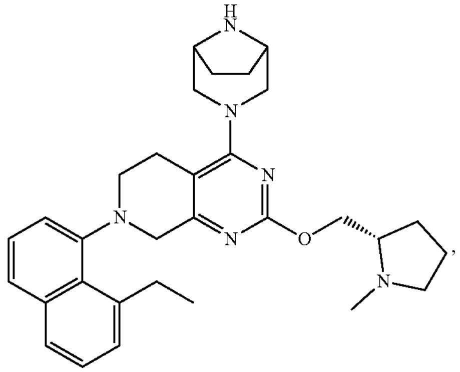,
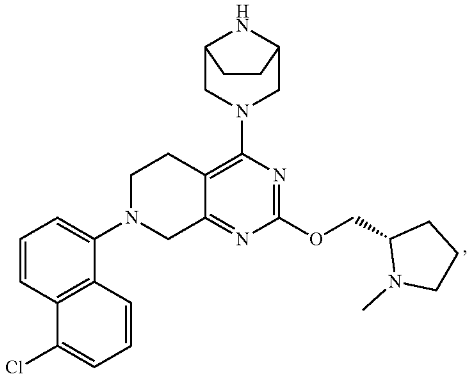,
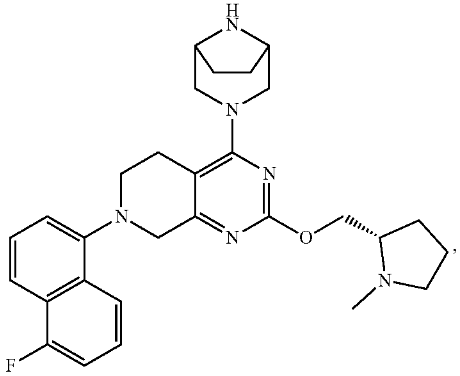,
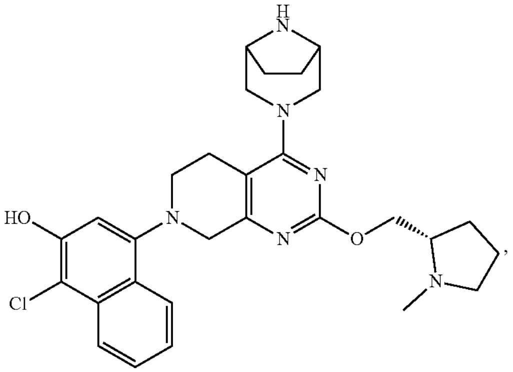,
-continued
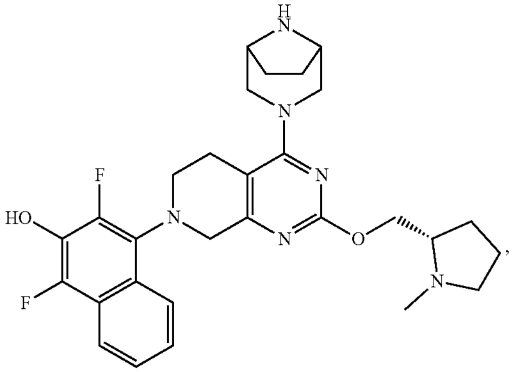,
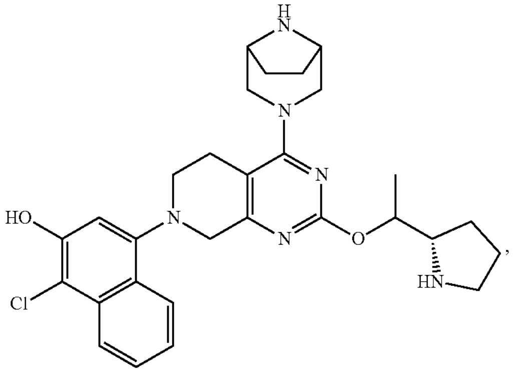,
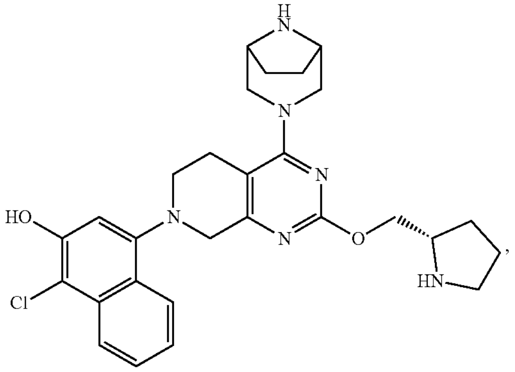,
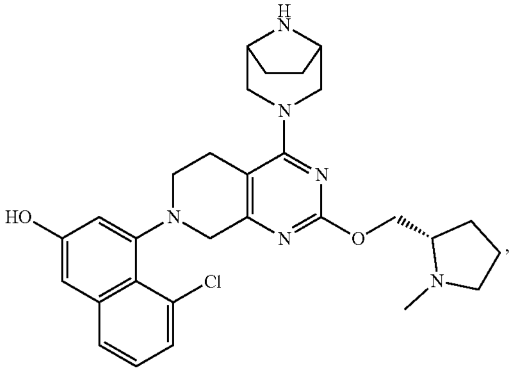, -continued
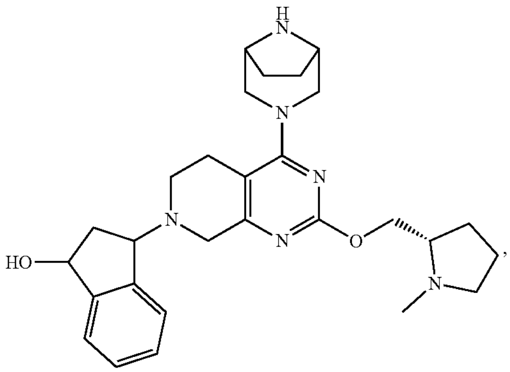
,
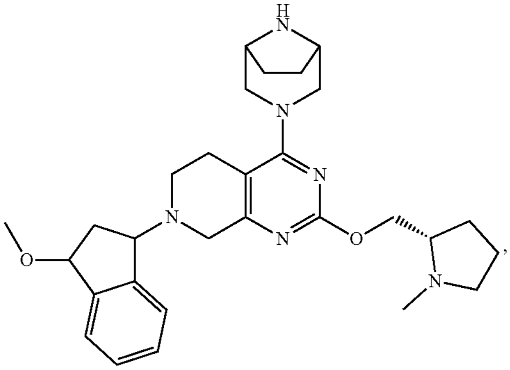
,
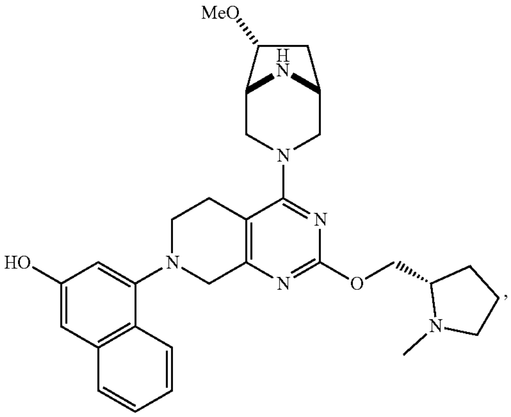
,
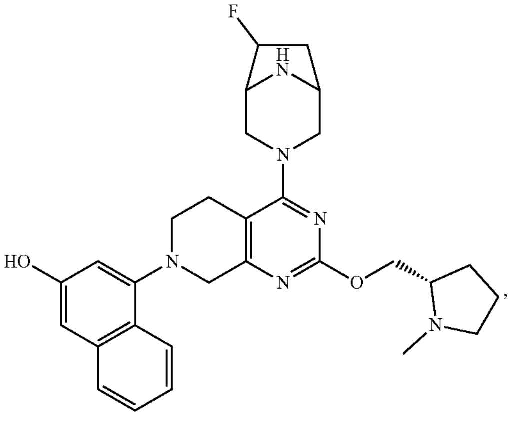
,
-continued
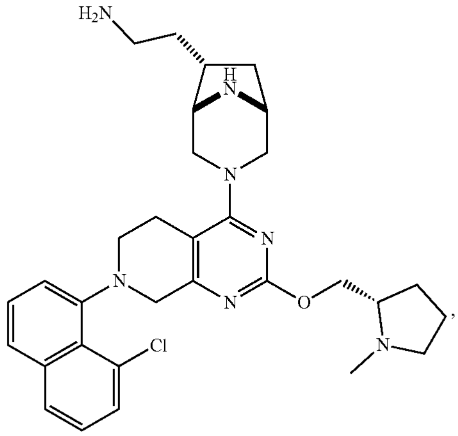
,
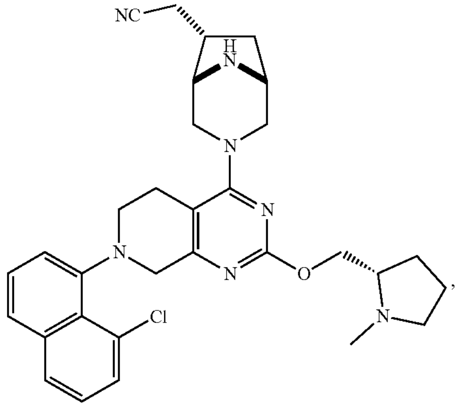
,
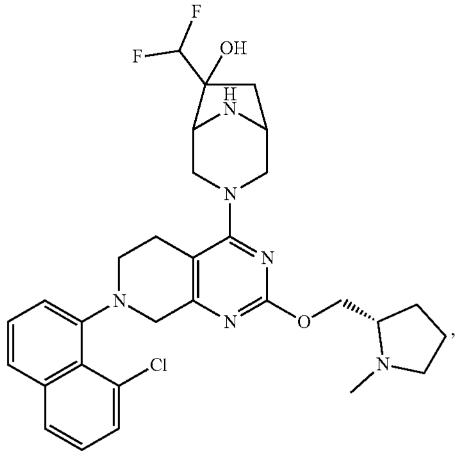
,
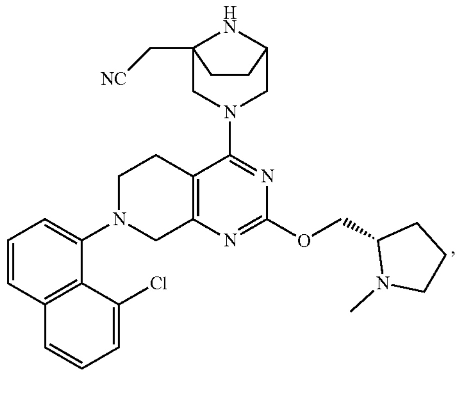
, -continued
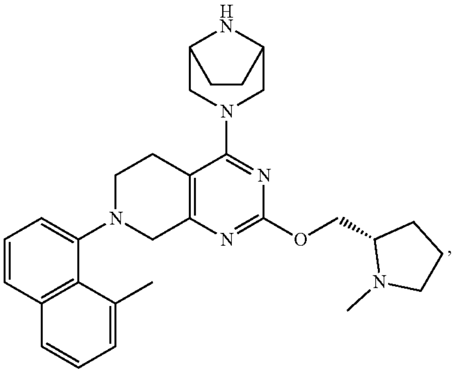
,
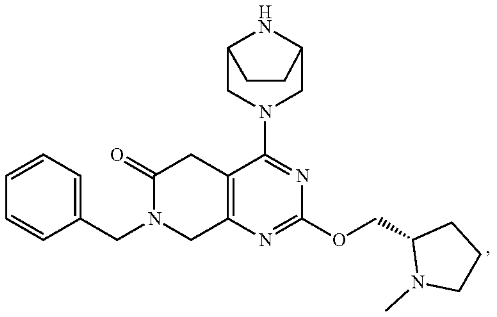
,
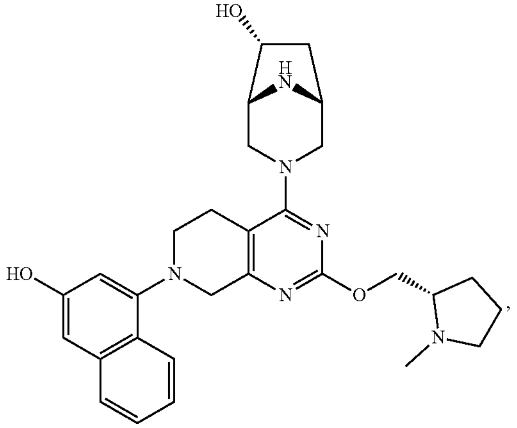
,
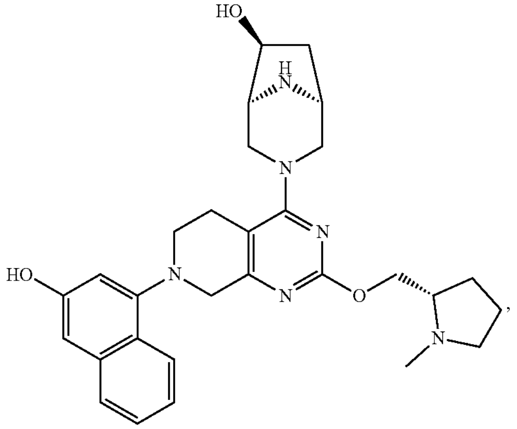
,
-continued
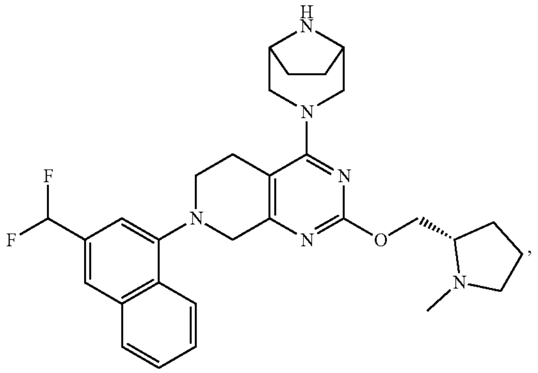
,
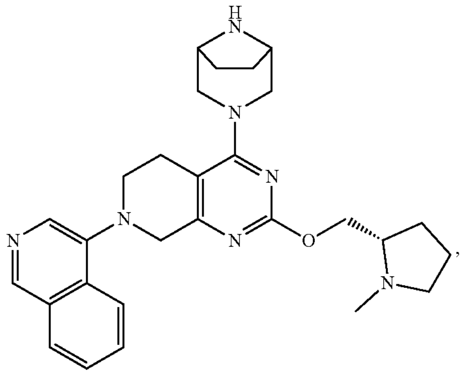
,
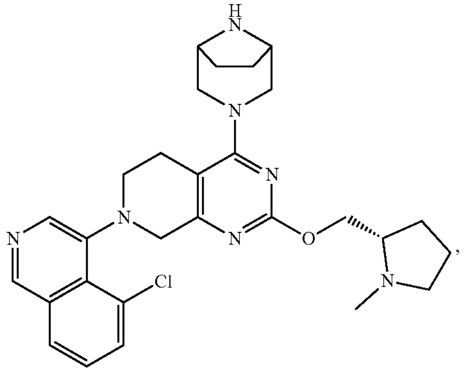
,
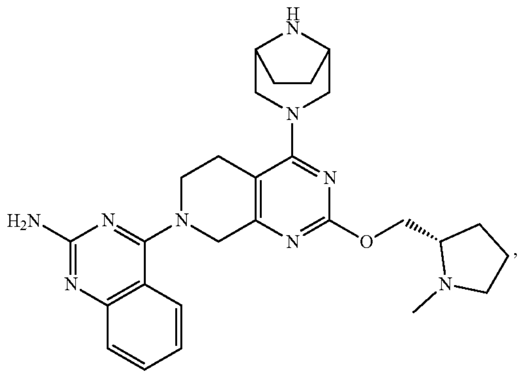
, -continued
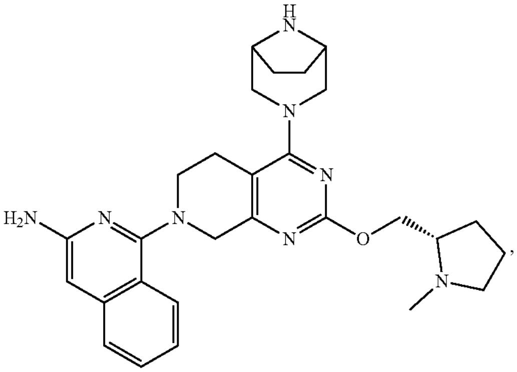
,
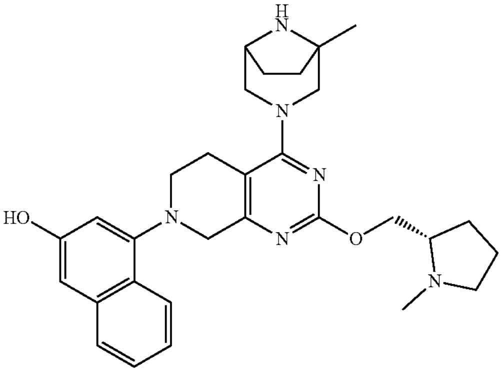
,
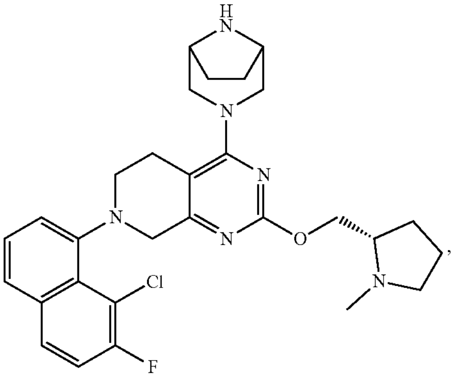
,
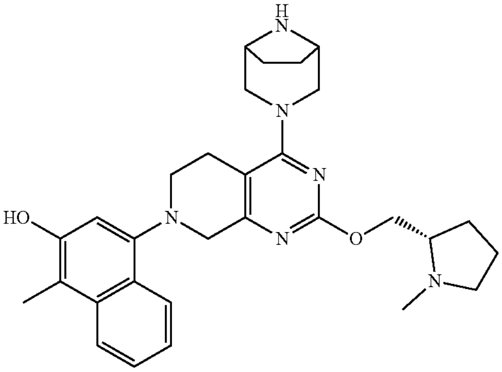
,
-continued
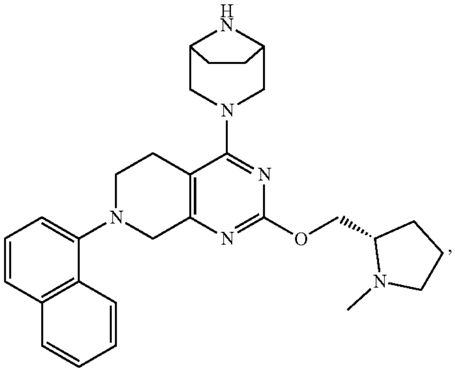
,
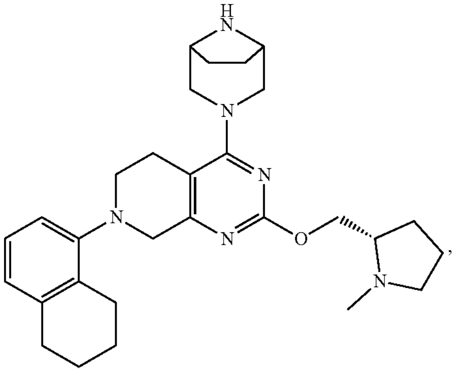
,
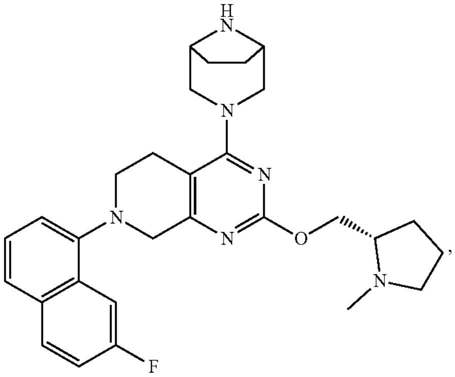
,
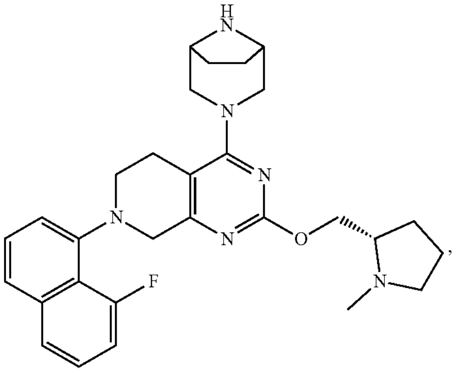
, -continued
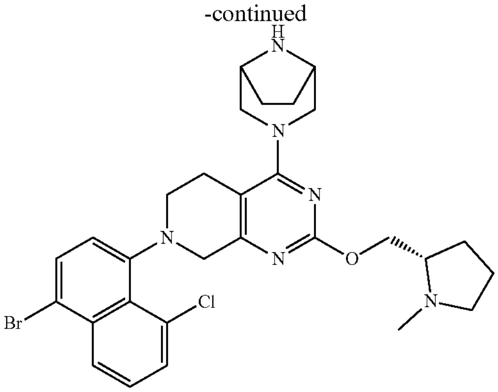
,
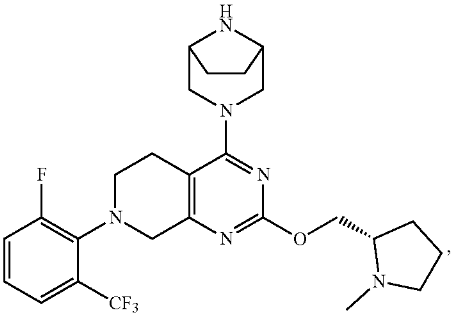
,
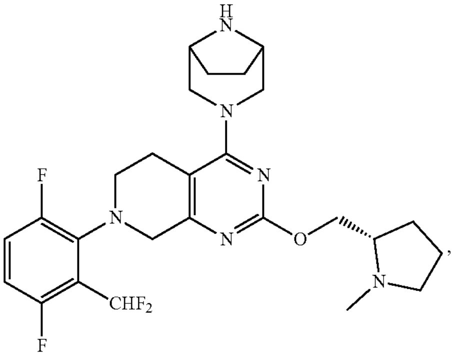
,
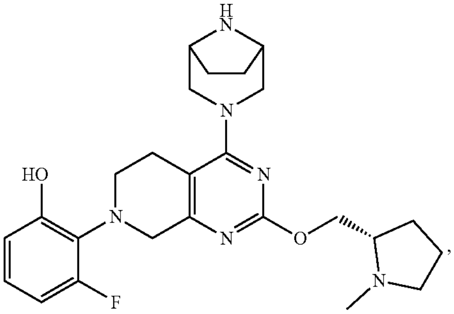
,
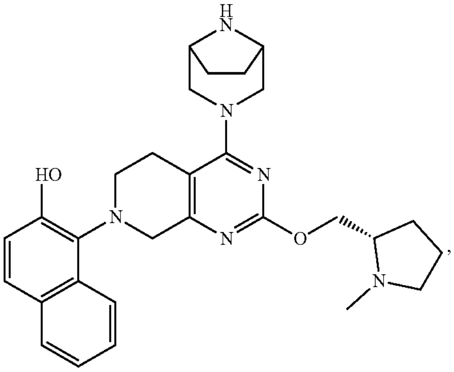
,
-continued
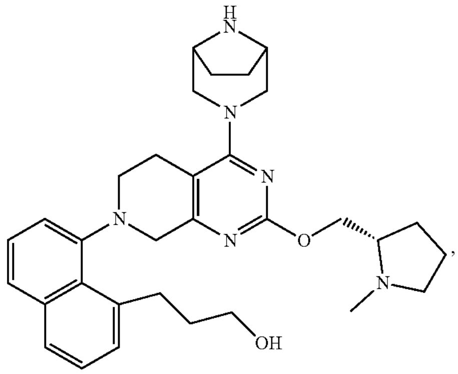
,
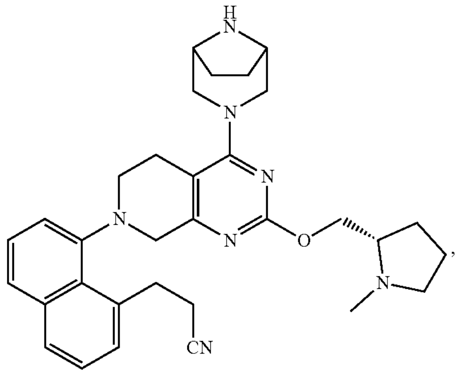
,
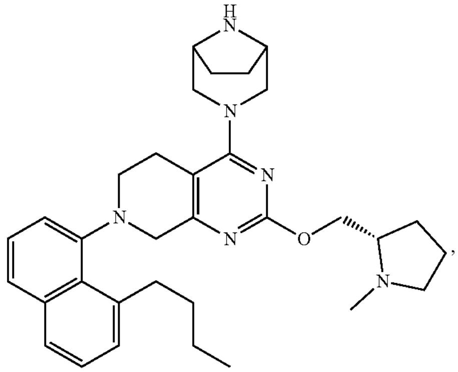
,
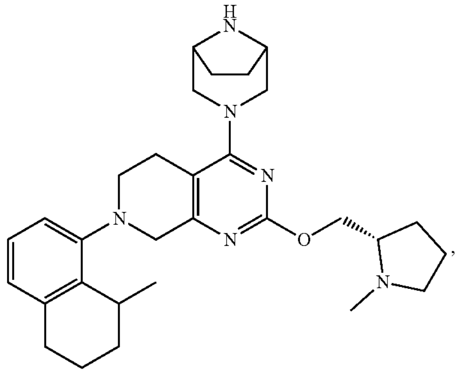
,

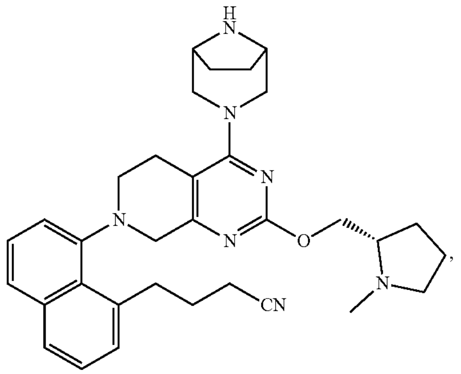
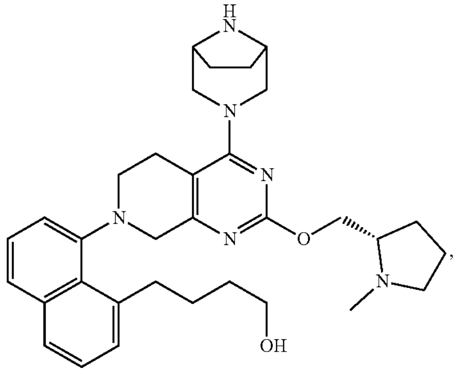
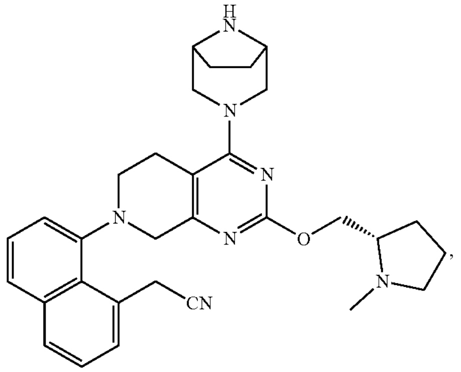
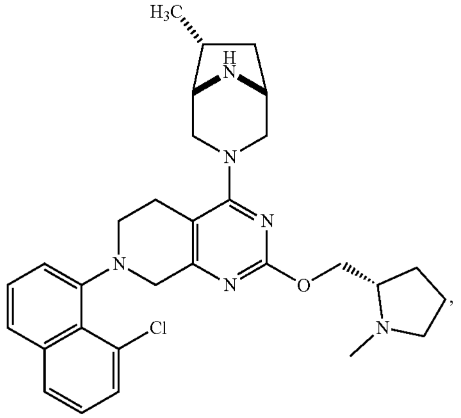
-continued
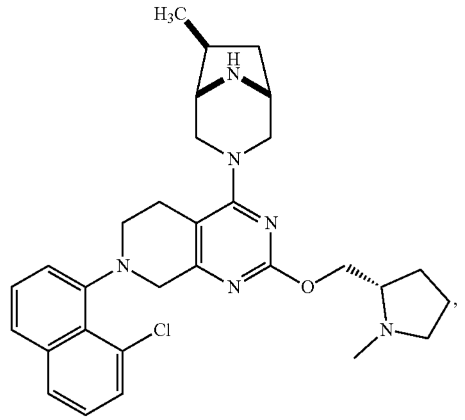
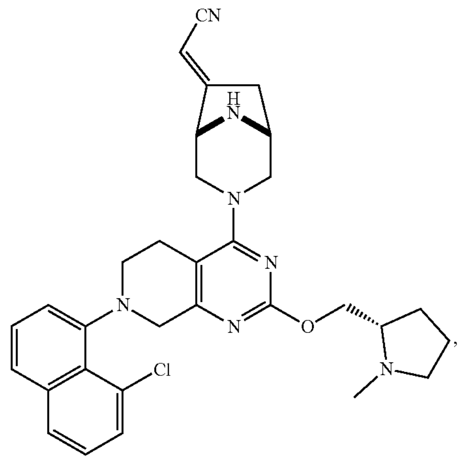
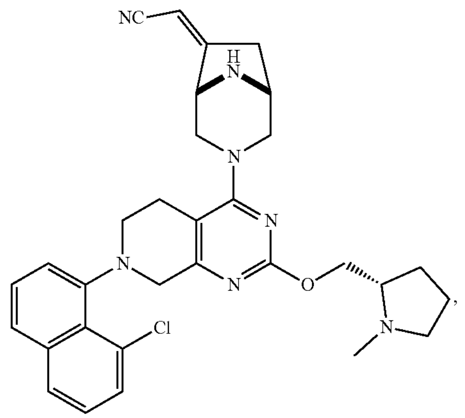

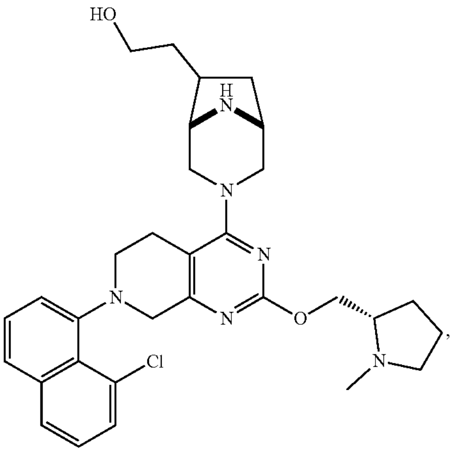
,
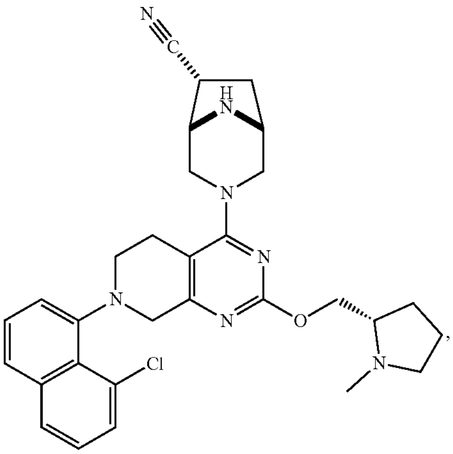
,
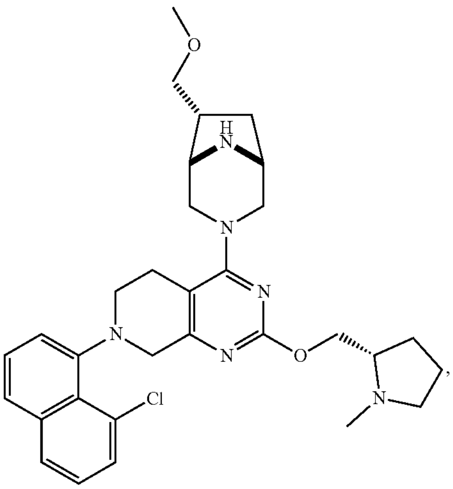
,
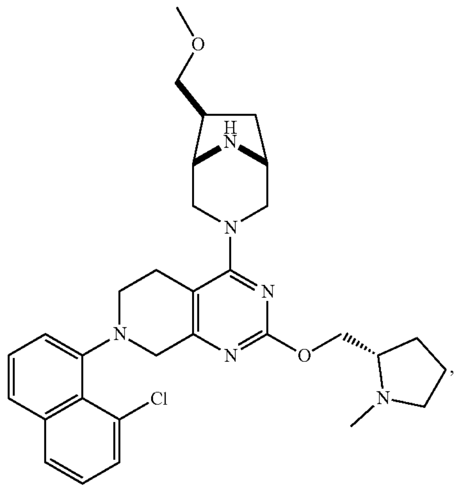
,
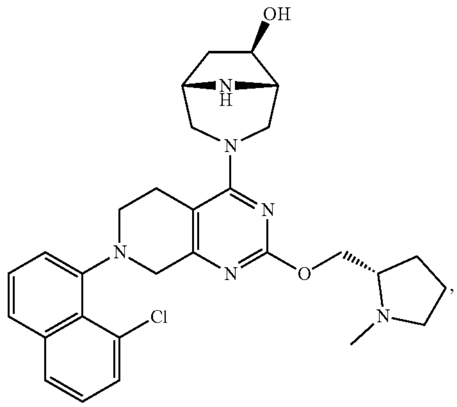
,
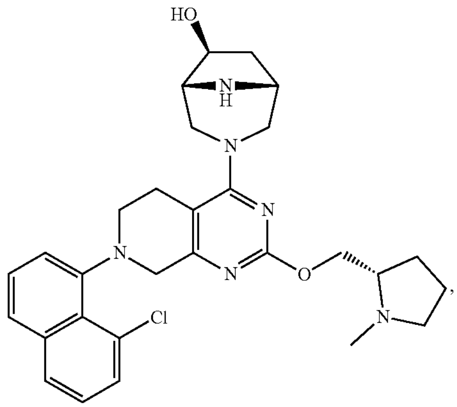
, -continued

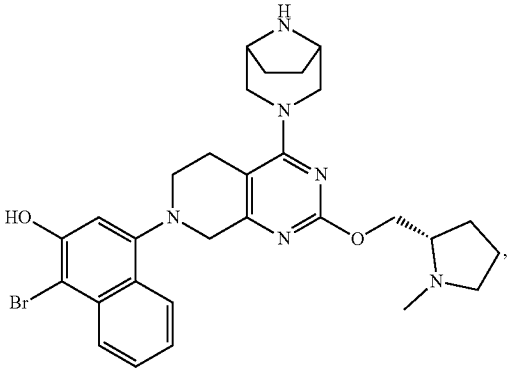

,

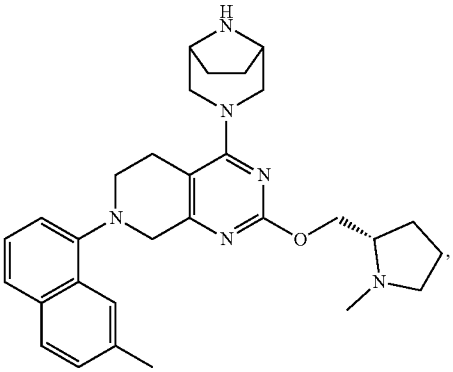

,

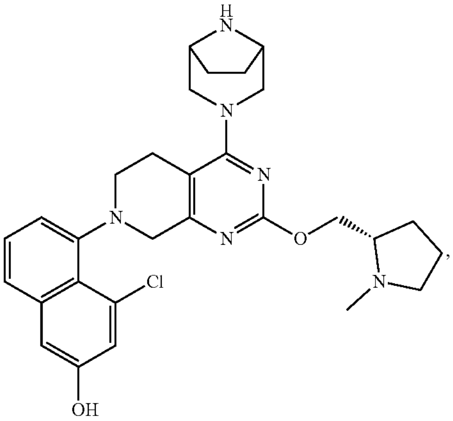

,

-continued

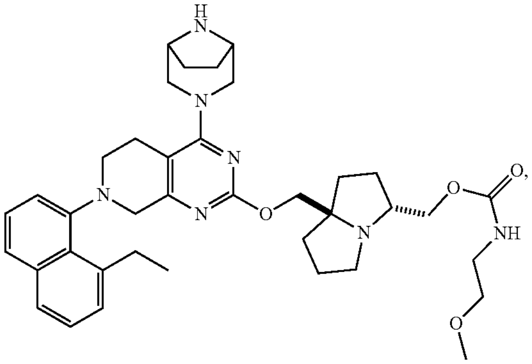

, and

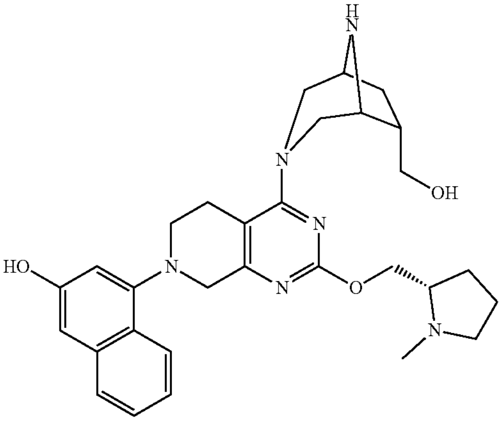

or a pharmaceutically acceptable salt thereof.

21. The method of claim 18, wherein the cancer is selected from the group consisting of cardiac, lung, esophagus, stomach, pancreas, small bowel, large bowel, kidney, bladder, urethra, prostate, testis, liver, biliary tract, bone, skull, meninges, brain, spinal cord, uterus, vulva, vagina, fallopian tubes, blood, skin, and adrenal gland cancer.

22. The method of claim 18, wherein the cancer is selected from the group consisting of cardiac angiosarcoma, cardiac fibrosarcoma, cardiac rhabdomyosarcoma, cardiac liposarcoma, squamous cell bronchogenic carcinoma, undifferentiated small cell bronchogenic carcinoma, undifferentiated large cell bronchogenic carcinoma, and bronchogenic adenocarcinoma.

* * * * *